(12) United States Patent
Gray et al.

(10) Patent No.: US 11,142,507 B2
(45) Date of Patent: Oct. 12, 2021

(54) INHIBITORS OF CYCLIN-DEPENDENT KINASES

(71) Applicant: Dana-Farber Cancer Institute, Inc., Boston, MA (US)

(72) Inventors: Nathanael S. Gray, Boston, MA (US); Tinghu Zhang, Brookline, MA (US); Nicholas Paul Kwiatkowski, Brookline, MA (US); Mingfeng Hao, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 369 days.

(21) Appl. No.: 15/758,982

(22) PCT Filed: Sep. 9, 2016

(86) PCT No.: PCT/US2016/051118
§ 371 (c)(1),
(2) Date: Mar. 9, 2018

(87) PCT Pub. No.: WO2017/044858
PCT Pub. Date: Mar. 16, 2017

(65) Prior Publication Data
US 2018/0362483 A1 Dec. 20, 2018
US 2020/0172499 A9 Jun. 4, 2020

Related U.S. Application Data

(60) Provisional application No. 62/216,271, filed on Sep. 9, 2015.

(51) Int. Cl.
| | | |
|---|---|---|
| C07D 277/46 | (2006.01) |
| C07D 417/04 | (2006.01) |
| C07D 417/12 | (2006.01) |
| C07D 417/14 | (2006.01) |
| A61P 35/00 | (2006.01) |
| A61P 25/00 | (2006.01) |
| A61K 31/497 | (2006.01) |

(52) U.S. Cl.
CPC .......... *C07D 277/46* (2013.01); *A61K 31/497* (2013.01); *A61P 25/00* (2018.01); *A61P 35/00* (2018.01); *C07D 417/04* (2013.01); *C07D 417/12* (2013.01); *C07D 417/14* (2013.01)

(58) Field of Classification Search
CPC .................................................... C07D 277/46
USPC ...................................................... 514/236.8
See application file for complete search history.

(56) References Cited

U.S. PATENT DOCUMENTS

| | | |
|---|---|---|
| 4,231,938 A | 11/1980 | Monaghan et al. |
| 4,270,537 A | 6/1981 | Romaine et al. |
| 4,596,556 A | 6/1986 | Morrow et al. |
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |

(Continued)

FOREIGN PATENT DOCUMENTS

| | | |
|---|---|---|
| CA | 2486101 A1 | 11/2003 |
| CA | 2503646 A1 | 5/2004 |

(Continued)

OTHER PUBLICATIONS

Extended European Search Report for EP 15773870.7, dated Oct. 17, 2018.
Extended European Search Report for EP 16845194.6, dated Mar. 1, 2019.
Partial Supplementary Search Report for EP 16808476.2, dated Mar. 7, 2019.
Extended European Search Report for EP 16808476.2, dated Jun. 14, 2019.
Extended European Search Report for EP 19168422.4, dated Aug. 13, 2019.
Bai et al., Design, synthesis and anticancer activity of 1-acyl-3-amino-1,4,5,6-tetrahydropyrrolo[3,4-c]pyrazole derivatives. Bioorg Med Chem Lett. Nov. 15, 2012;22(22):6947-51. Suppl. Info, 46 pages. doi: 10.1016/j.bmcl.2012.08.117. Epub Sep. 8, 2012.

(Continued)

*Primary Examiner* — Kahsay Habte
(74) *Attorney, Agent, or Firm* — Wolf, Greenfield & Sacks, P.C.

(57) ABSTRACT

The present invention provides novel compounds of Formulae (I'), (I), (II'), and (II), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating and/or preventing proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, ovarian cancer, neuroblastoma, lung cancer, colorectal cancer), benign neoplasms, diseases associated with angiogenesis, inflammatory diseases, autoinflammatory diseases, and autoimmune diseases) in a subject. Treatment of a subject with a proliferative disease using a compound or composition of the invention may inhibit the aberrant activity of a kinase, such as a cyclin-dependent kinase (CDK) (e.g., CDK7, CDK12, or CDK13), and therefore, induce cellular apoptosis and/or inhibit transcription in the subject.

26 Claims, 11 Drawing Sheets

Specification includes a Sequence Listing.

(56) References Cited

U.S. PATENT DOCUMENTS

| | | |
|---|---|---|
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna, Jr. et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,214,852 B1 | 4/2001 | Kim et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,273,765 B2 | 9/2012 | Fancelli et al. |
| 8,394,818 B2 | 3/2013 | Gray et al. |
| 8,765,747 B2 | 7/2014 | Choi et al. |
| 8,877,761 B2 | 11/2014 | Li |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,758,522 B2 | 9/2017 | Gray et al. |
| 9,814,709 B2 | 11/2017 | Liu et al. |
| 9,862,688 B2 | 1/2018 | Gray et al. |
| 9,879,003 B2 | 1/2018 | Gray et al. |
| 10,000,483 B2 | 6/2018 | Gray et al. |
| 10,017,477 B2 | 7/2018 | Gray et al. |
| 10,047,070 B2 | 8/2018 | Gray et al. |
| 10,112,927 B2 | 10/2018 | Gray et al. |
| 10,144,730 B2 | 12/2018 | Gray et al. |
| 10,336,760 B2 * | 7/2019 | Marineau ............. A61K 31/519 |
| 10,550,121 B2 | 2/2020 | Gray et al. |
| RE48,175 E | 8/2020 | Gray et al. |
| 2003/0139416 A1 | 7/2003 | Buchanan et al. |
| 2004/0106634 A1 | 6/2004 | Satoh et al. |
| 2004/0126359 A1 | 7/2004 | Lamb et al. |
| 2004/0209878 A1 | 10/2004 | Guzi et al. |
| 2005/0026914 A1 | 2/2005 | Buchanan et al. |
| 2005/0197338 A1 | 9/2005 | Huang et al. |
| 2005/0228031 A1 | 10/2005 | Bilodeau et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0060546 A1 | 3/2007 | Ruat et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0275963 A1 | 11/2007 | Guzi et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2009/0156582 A1 | 6/2009 | Tsukamoto et al. |
| 2010/0056524 A1 | 3/2010 | Mciver et al. |
| 2010/0197688 A1 | 8/2010 | Nantermet et al. |
| 2010/0254905 A1 | 10/2010 | Honigberg et al. |
| 2011/0039873 A1 | 2/2011 | Gaeta et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0196865 A1 | 8/2012 | Ruat et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2013/0184287 A1 | 7/2013 | Gray et al. |
| 2014/0187772 A1 | 7/2014 | Bebbington et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2015/0274728 A1 | 10/2015 | Gray et al. |
| 2016/0046636 A1 | 2/2016 | Gray et al. |
| 2016/0122323 A1 | 5/2016 | Gray et al. |
| 2016/0264551 A1 | 9/2016 | Ciblat et al. |
| 2016/0264554 A1 | 9/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |
| 2017/0204096 A1 | 7/2017 | Gelin et al. |
| 2018/0093990 A1 | 4/2018 | Gray et al. |
| 2018/0169097 A1 | 6/2018 | Hammerman et al. |
| 2018/0319801 A1 | 11/2018 | Gray et al. |
| 2019/0015411 A9 | 1/2019 | Hammerman et al. |
| 2019/0031642 A1 | 1/2019 | Gray et al. |
| 2019/0055248 A1 | 2/2019 | Gray et al. |
| 2019/0241541 A1 | 8/2019 | Ciblat et al. |
| 2019/0248778 A1 | 8/2019 | Gray et al. |
| 2019/0315747 A9 | 10/2019 | Gray et al. |
| 2020/0017475 A9 | 1/2020 | Gray et al. |
| 2020/0024271 A9 | 1/2020 | Gray et al. |
| 2020/0277292 A1 | 9/2020 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| CN | 1701073 | 11/2005 |
| CN | 1735614 | 2/2006 |
| CN | 100482665 | 5/2006 |
| CN | 1784410 | 6/2006 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 1 935 890 A1 | 6/2008 |
| EP | 2 311 842 A2 | 4/2011 |
| EP | 16773870.7 | 10/2018 |
| EP | 16808476.2 | 3/2019 |
| EP | 16845194.6 | 3/2019 |
| EP | 16808476.2 | 6/2019 |
| EP | 19168422.1 | 8/2019 |
| GB | 796524 A | 6/1958 |
| JP | H11-514336 | 12/1999 |

(56) References Cited

FOREIGN PATENT DOCUMENTS

| | | |
|---|---|---|
| JP | 2000-515550 | 11/2000 |
| JP | 2001-522842 | 11/2001 |
| JP | 2002-537300 | 11/2002 |
| JP | 2003-503481 A | 1/2003 |
| JP | 2003-509342 | 3/2003 |
| JP | 2003-516981 | 5/2003 |
| JP | 2003-516987 | 5/2003 |
| JP | 2004-505977 | 2/2004 |
| JP | 2004-516326 | 6/2004 |
| JP | 2004-517075 | 6/2004 |
| JP | 2004-529140 A | 9/2004 |
| JP | 2005-501860 A | 1/2005 |
| JP | 2005-505535 A | 2/2005 |
| JP | 2005-506950 | 3/2005 |
| JP | 2005-530711 A | 10/2005 |
| JP | 2005-533808 | 11/2005 |
| JP | 2005-534635 A | 11/2005 |
| JP | 2005-538100 A | 12/2005 |
| JP | 2006-502163 | 1/2006 |
| JP | 2006-502184 | 1/2006 |
| JP | 2006-514026 | 4/2006 |
| JP | 2006-518368 | 8/2006 |
| JP | 2006-521394 A | 9/2006 |
| JP | 2007-500226 A | 1/2007 |
| JP | 2007-500725 A | 1/2007 |
| JP | 2007-509130 | 4/2007 |
| JP | 2007-522220 | 8/2007 |
| JP | 2008-500320 A | 1/2008 |
| JP | 2008-501669 A | 1/2008 |
| JP | 2008-502610 A | 1/2008 |
| JP | 2008-538749 | 11/2008 |
| JP | 2009-510110 A | 3/2009 |
| JP | 2009-511483 | 3/2009 |
| JP | 2009-520805 | 5/2009 |
| JP | 2009-538304 | 11/2009 |
| JP | 2010-505905 | 2/2010 |
| JP | 2010-511655 A | 4/2010 |
| JP | 2010-514686 | 5/2010 |
| JP | 2010-518069 | 5/2010 |
| JP | 2010-521487 A | 6/2010 |
| JP | 2010-523643 | 7/2010 |
| JP | 2010-529140 | 8/2010 |
| JP | 2011-516533 A | 5/2011 |
| JP | 2012-529519 | 11/2012 |
| JP | 2012-530071 A | 11/2012 |
| JP | 2016-533379 A | 10/2016 |
| JP | 2017-504651 A | 2/2017 |
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/26412 A1 | 10/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/17861 A1 | 6/1996 |
| WO | WO 96/21456 A1 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 00/44777 A1 | 8/2000 |
| WO | WO 00/50032 A1 | 8/2000 |
| WO | WO 00/61186 A1 | 10/2000 |
| WO | WO 01/02369 A2 | 1/2001 |
| WO | WO 01/019829 A2 | 3/2001 |
| WO | WO 2001/053267 A1 | 7/2001 |
| WO | WO 02/076986 A1 | 10/2002 |
| WO | WO 02/079197 A1 | 10/2002 |
| WO | WO 02/080926 A1 | 10/2002 |
| WO | WO 2002/083653 A1 | 10/2002 |
| WO | WO 02/096905 A1 | 12/2002 |
| WO | WO 02/102800 A1 | 12/2002 |
| WO | WO 2003/018021 A1 | 3/2003 |
| WO | WO 2003/018022 A1 | 3/2003 |
| WO | WO 2003/026664 A1 | 4/2003 |
| WO | WO 2003/051847 A1 | 6/2003 |
| WO | WO 2003/078403 A2 | 9/2003 |
| WO | WO 2003/097610 A1 | 11/2003 |
| WO | WO 2004/000214 A2 | 12/2003 |
| WO | WO 2004/002948 A1 | 1/2004 |
| WO | WO 2004/005283 A1 | 1/2004 |
| WO | WO 2004/009601 A1 | 1/2004 |
| WO | WO 2004/010995 A1 | 2/2004 |
| WO | WO 2004/022561 | 3/2004 |
| WO | WO 2004/026229 | 4/2004 |
| WO | WO 2004/039796 A1 | 5/2004 |
| WO | WO 2004/046118 A2 | 6/2004 |
| WO | WO 2004/074283 A1 | 9/2004 |
| WO | WO 2004/076458 | 9/2004 |
| WO | WO 2004/078757 A2 | 9/2004 |
| WO | WO 2004/081013 | 9/2004 |
| WO | WO 2004/087699 A2 | 10/2004 |
| WO | WO 2004/087707 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/012256 A1 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2006/093247 A1 | 9/2006 |
| WO | WO 2006/124731 A1 | 11/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/044420 | 4/2007 |
| WO | WO 2007/048070 A2 | 4/2007 |

(56) References Cited

FOREIGN PATENT DOCUMENTS

| WO | WO 2007/056023 A2 | 5/2007 | |
| WO | WO 2007/072153 A2 | 6/2007 | |
| WO | WO 2007/075869 A2 | 7/2007 | |
| WO | WO 2007/076161 A2 | 7/2007 | |
| WO | WO 2007/086584 A1 | 8/2007 | |
| WO | WO 2007/129195 A2 | 11/2007 | |
| WO | WO 2007/138277 A1 | 12/2007 | |
| WO | WO 2008/049856 A1 | 5/2008 | |
| WO | WO 2008/063888 A2 | 5/2008 | |
| WO | WO 2008/068171 A1 | 6/2008 | |
| WO | WO 2008/074749 A1 | 6/2008 | |
| WO | WO 2008/080015 A2 | 7/2008 | |
| WO | WO 2008/112913 A1 | 9/2008 | |
| WO | WO 2008/124393 A1 | 10/2008 | |
| WO | WO 2008/144253 A1 | 11/2008 | |
| WO | WO 2008/151183 A1 | 12/2008 | |
| WO | WO 2008/151304 | 12/2008 | |
| WO | WO 2009/017822 A2 | 2/2009 | |
| WO | WO 2009/028655 A1 | 3/2009 | |
| WO | WO 2009/032694 A1 | 3/2009 | |
| WO | WO 2009/036016 A1 | 3/2009 | |
| WO | WO 2009/145360 A1 | 12/2009 | |
| WO | WO 2009/152027 A1 | 12/2009 | |
| WO | WO 2009/155017 A2 | 12/2009 | |
| WO | WO 2010/001166 A1 | 1/2010 | |
| WO | WO 2010/008847 A2 | 1/2010 | |
| WO | WO 2010/044885 A2 | 4/2010 | |
| WO | WO 2010/051781 A1 | 5/2010 | |
| WO | WO 2010/125799 A1 | 11/2010 | |
| WO | WO 2010/144909 A1 | 12/2010 | |
| WO | WO 2011/079231 A1 | 6/2011 | |
| WO | WO 2011/115725 A2 | 9/2011 | |
| WO | WO 2012/066061 A1 | 5/2012 | |
| WO | WO 2012/090219 A2 | 7/2012 | |
| WO | WO 2013/014162 A1 | 1/2013 | |
| WO | WO 2013/040436 A1 | 3/2013 | |
| WO | WO 2013/074986 A1 | 5/2013 | |
| WO | WO 2013/154778 A1 | 10/2013 | |
| WO | WO 2014/063061 A1 | 4/2014 | |
| WO | WO 2014/063068 A1 | 4/2014 | |
| WO | WO 2014/147021 A2 | 9/2014 | |
| WO | WO 2014/149164 A1 | 9/2014 | |
| WO | WO 2015/013635 A2 | 1/2015 | |
| WO | WO 2015/025197 A1 | 2/2015 | |
| WO | WO 2015/058126 A1 | 4/2015 | |
| WO | WO 2015/058140 A1 | 4/2015 | |
| WO | WO 2015/117087 A1 | 8/2015 | |
| WO | WO 2015/154022 A1 | 10/2015 | |
| WO | WO 2015/154038 A1 | 10/2015 | |
| WO | WO 2015/164604 A1 | 10/2015 | |
| WO | WO 2015/164614 A1 | 10/2015 | |
| WO | WO-2015154022 A1 * | 10/2015 | ......... A61K 31/4545 |
| WO | WO 2016/014542 A1 | 1/2016 | |
| WO | WO 2016/014551 A1 | 1/2016 | |
| WO | WO 2016/058544 A1 | 4/2016 | |
| WO | WO 2016/068287 A1 | 5/2016 | |
| WO | WO 2016/105528 A2 | 6/2016 | |
| WO | WO 2016/142855 A2 | 9/2016 | |
| WO | WO 2016/201370 A1 | 12/2016 | |
| WO | WO 2017/037576 A1 | 3/2017 | |

OTHER PUBLICATIONS

Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013. Author manuscript.

Bogoyevitch et al., c-Jun N-terminal kinase (JNK) signaling: recent advances and challenges. Biochim Biophys Acta. Mar. 2010;1804(3):463-75. doi: 10.1016/j.bbapap.2009.11.002. Epub Nov. 10, 2009.

Brasca et al., 6-Substituted pyrrolo[3,4-c]pyrazoles: an improved class of CDK2 inhibitors. ChemMedChem. Jun. 2007;2(6):841-52.

Chène, Challenges in design of biochemical assays for the identification of small molecules to target multiple conformations of protein kinases. Drug Discov Today. Jun. 2008;13(11-12):522-9. doi: 10.1016/j.drudis.2008.03.023. Epub May 5, 2008.

Database Registry [Online] Retrieved from STN, 2011月12年4日, search date : Oct. 7, 2019; RN 1350102-23-6, 1349782-05-3, 1349471-31-3, 1349357-86-3, 1349106-33-7, 1348397-56-7, 1348192-23-3, 1348088-42-5.

Dent et al. Synergistic combinations of signaling pathway inhibitors: mechanisms for improved cancer therapy. Drug Resist Updat. Jun. 2009;12(3):65-73. doi: 10.1016/j.drup.2009.03.001.

Fancelli et al., Potent and selective Aurora inhibitors identified by the expansion of a novel scaffold for protein kinase inhibition. J Med Chem. Apr. 21, 2005;48(8):3080-4.

Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258.

Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.

Girotti et al., No longer an untreatable disease: How targeted and immunotherapies have changed the management of melanoma patients. Mol Oncol. Sep. 2014; 8(6): 1140-1158. Published online Aug. 15, 2014. doi: 10.1016/j.molonc.2014.07.027.

Katt et al., Dissemination from a Solid Tumor: Examining the Multiple Parallel Pathways. Trends Cancer. Jan. 2018;4(1):20-37. doi: 10.1016/j.trecan.2017.12.002. Epub Jan. 10, 2018. Author manuscript.

Kooistra et al., Kinase-Centric Computational Drug Development, In 50 Annual Reports in Medicinal Chemistry. 2017;197-236.

Li et al., Identification of novel pyrrolopyrazoles as protein kinase C β II inhibitors. Bioorg Med Chem Lett. Jan. 1, 2011;21(1):584-7. doi: 10.1016/j.bmcl.2010.10.032. Epub Oct. 13, 2010.

McAuley et al., CARMA3 Is a Critical Mediator of G Protein-Coupled Receptor and Receptor Tyrosine Kinase-Driven Solid Tumor Pathogenesis. Front Immunol. Aug. 15, 2018;9:1887. doi: 10.3389/fimmu.2018.01887. eCollection 2018.

Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012.

Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.

Patani et al., Bioisosterism: A Rational Approach in Drug Design. Chem Rev. 1996;96:3147-3176.

Patel et al., Discovery of dual leucine zipper kinase (DLK, MAP3K12) inhibitors with activity in neurodegeneration models. J Med Chem. Jan. 8, 2015;58(1):401-18. doi: 10.1021/jm5013984. Epub Oct. 23, 2014.

Peifer et al., Small-molecule inhibitors of PDK1. ChemMedChem. Dec. 2008;3(12):1810-38. doi: 10.1002/cmdc.200800195.

Pevarello et al., 3-Amino-1,4,5,6-tetrahydropyrrolo[3,4-c]pyrazoles: A new class of CDK2 inhibitors. Bioorg Med Chem Lett. Feb. 15, 2006;16(4):1084-90.

Powell et al., Regulation of immune responses by mTOR. Annu Rev Immunol. 2012;30:39-68. doi:10.1146/annurev-immunol-020711-075024. Epub Nov. 29, 2011.

Sánchez-Martínez et al., Cyclin dependent kinase (CDK) inhibitors as anticancer drugs. Bioorg Med Chem Lett. Sep. 1, 2015;25(17):3420-35. doi: 10.1016/j.bmcl.2015.05.100. Epub Jun. 6, 2015.

Sidow et al., Concepts in solid tumor evolution. Trends Genet. Apr. 2015;31(4):208-14. doi: 10.1016/j.tig.2015.02.001. Epub Feb. 27, 2015. Author manuscript.

Tian et al., mTOR Signaling in Cancer and mTOR Inhibitors in Solid Tumor Targeting Therapy. Int J Mol Sci. Feb. 11, 2019;20(3). pii: E755. doi: 10.3390/ijms20030755.

Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.

(56) References Cited

OTHER PUBLICATIONS

Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Wu et al., FDA-approved small-molecule kinase inhibitors. Trends Pharmacol Sci. Jul. 2015;36(7):422-39. doi: 10.1016/j.tips.2015.04.005. Epub May 12, 2015.
Zeng et al. Targeting MYC dependency in ovarian cancer through inhibition of CDK7 and CDK12/13. Elife. 2018;7:e39030. Published Nov. 13, 2018. doi:10.7554/eLife.39030.
Zhang et al. CDK7 Inhibition Potentiates Genome Instability Triggering Anti-tumor Immunity in Small Cell Lung Cancer. Cancer Cell. 2020;37(1):37-54.e9. doi:10.1016/j.cce11.2019.11.003.
Zhang et al., Etk/Bmx transactivates vascular endothelial growth factor 2 and recruits phosphatidylinositol 3-kinase to mediate the tumor necrosis factor-induced angiogenic pathway. J Biol Chem. Dec. 19, 2003;278(51):51267-76. Epub Oct. 7, 2003.
Zompi et al., Animal models of dengue virus infection. Viruses. Jan. 2012;4(1):62-82. doi: 10.3390/v4010062. Epub Jan. 9, 2012.
U.S. Appl. No. 16/179,833, filed Nov. 2, 2018, Gray et al.
U.S. Appl. No. 14/921,894, filed Jun. 4, 2020, Gray et al.
U.S. Appl. No. 16/780,268, filed Feb. 3, 2020, Gray et al.
Partial European Search Report for EP 16773870.7, dated Jul. 12, 2018.
U.S. Appl. No. 14/358,606, filed May 15, 2014, Gray et al.
U.S. Appl. No. 15/188,545, filed Jun. 21, 2016, Gray et al.
U.S. Appl. No. 14/436,496, filed Apr. 17, 2015, Gray et al.
U.S. Appl. No. 14/436,387, filed Apr. 16, 2015, Gray et al.
U.S. Appl. No. 14/436,657, filed Apr. 17, 2015, Gray et al.
U.S. Appl. No. 15/699,948, filed Sep. 8, 2017, Gray et al.
U.S. Appl. No. 15/305,801, filed Oct. 21, 2016, Gray et al.
U.S. Appl. No. 15/305,845, filed Oct. 21, 2016, Gray et al.
U.S. Appl. No. 13/376,539, filed Dec. 6, 2011, Choi et al.
U.S. Appl. No. 14/321,242, filed Jul. 1, 2014, Gray et al.
U.S. Appl. No. 13/519,826, filed Nov. 1, 2012, Gray et al.
U.S. Appl. No. 14/552,229, filed Nov. 24, 2014, Gray et al.
U.S. Appl. No. 14/921,894, filed Oct. 23, 2015, Gray et al.
U.S. Appl. No. 15/538,763, filed Jun. 22, 2017, Gray et al.
U.S. Appl. No. 15/735,532, filed Dec. 11, 2017, Hammerman et al.
U.S. Appl. No. 15/561,729, filed Sep. 26, 2017, Gray et al.
U.S. Appl. No. 13/583,974, filed Dec. 5, 2012, Gray et al.
PCT/US2012/065618, Mar. 19, 2013, International Search Report and Written Opinion.
PCT/US2012/065618, May 30, 2014, International Preliminary Report on Patentability.
PCT/US2013/065708, Feb. 4, 2014, International Search Report and Written Opinion.
PCT/US2013/065708, Apr. 30, 2015, International Preliminary Report on Patentability.
PCT/US2013/065689, Mar. 4, 2014, International Search Report and Written Opinion.
PCT/US2013/065689, Apr. 30, 2015, International Preliminary Report on Patentability.
PCT/US2013/065698, Feb. 20, 2014, International Search Report and Written Opinion.
PCT/US2013/065698, Apr. 30, 2015, International Preliminary Report on Patentability.
PCT/US2014/061232, Dec. 23, 2014, International Search Report and Written Opinion.
PCT/2015/027312, Jul. 10, 2015, International Search Report and Written Opinion.
PCT/US2015/027312, Nov. 3, 2016, International Preliminary Report on Patentability.
PCT/US2015/027294, Jul. 10, 2015, International Search Report and Written Opinion.
PCT/US2015/027294, Nov. 3, 2016, International Preliminary Report on Patentability.
PCT/US2010/038518, Dec. 22, 2011, International Preliminary Report on Patentability.
PCT/US2010/038518, Aug. 6, 2010, International Search Report and Written Opinion.
EP 10786967.9, Oct. 23, 2012, Extended European Search Report.
EP 10844280.7, Apr. 17, 2013, Extended European Search Report.
EP 15160591.2, Jul. 14, 2015, Partial European Search Report.
EP 15160591.2, Nov. 2, 2015, Partial European Search Report.
PCT/US2010/062310, Oct. 4, 2011, International Search Report and Written Opinion.
PCT/US2010/062310, Jul. 12, 2012, International Preliminary Report on Patentability.
PCT/US2015/000297, Mar. 4, 2016, International Search Report and Written Opinion.
PCT/US2015/000297, Jul. 6, 2017, International Preliminary Report on Patentability.
PCT/US2016/037086, Sep. 2, 2016, International Search Report and Written Opinion.
PCT/US2016/037086, Dec. 21, 2017, International Preliminary Report on Patentability.
PCT/US2016/024345, Aug. 9, 2016, Invitation to Pay Additional Fees.
PCT/US2016/024345, Oct. 6, 2016, International Search Report and Written Opinion.
PCT/US2016/024345, Oct. 12, 2017, International Preliminary Report on Patentability.
PCT/US2016/051118, Dec. 1, 2016, Invitation to Pay Additional Fees.
PCT/US2016/051118, Mar. 13, 2017, International Search Report and Written Opinion.
PCT/US2011/025423, May 31, 2011, Invitation to Pay Additional Fees.
PCT/US2011/025423, Nov. 5, 2012, International Search Report and Written Opinion.
PCT/US2011/025423, Nov. 29, 2012, International Preliminary Report on Patentability.
PCT/US2016/051118, Mar. 22, 2018, International Preliminary Report on Patentability.
International Search Report and Written Opinion for PCT/US2019/068835, dated May 27, 2020.
Dranchak et al., Profile of the GSK published protein kinase inhibitor set across ATP-dependent and-independent luciferases: implications for reporter-gene assays. PLoS One. 2013;8(3):e57888. doi:10.1371/journal.pone.0057888.
Sun et al., Inhibition of the transcriptional kinase CDK7 overcomes therapeutic resistance in HER2-positive breast cancers. *Oncogene*. 2020;39(1):50-63. doi:10.1038/s41388-019-0953-9.
Zarei et al., Tumors with TSC mutations are sensitive to CDK7 inhibition through NRF2 and glutathione depletion. *J. Exp. Med.* 2019;216(11):2635-2652. doi:10.1084/jem.20190251.
Liu et al., Discovery of MFH290: A Potent and Highly Selective Covalent Inhibitor for Cyclin-Dependent Kinase 12/13. *J Med Chem.* Jul. 9, 2020;63(13):6708-6726. doi: 10.1021/acs.jmedchem.9b01929. Epub Jun. 25, 2020. PMID: 32502343.
U.S. Appl. No. 16/883,954, filed May 26, 2020, Hammerman et al.
U.S. Appl. No. 16/462,892, filed May 21, 2019, Gray et al.
PCT/US2019/068835, dated May 27, 2020, International Search Report and Written Opinion.
International Search Report and Written Opinion for PCT/US2012/065618, dated Mar. 19, 2013.
International Preliminary Report on Patentability for PCT/US2012/065618, dated May 30, 2014.
International Search Report and Written Opinion for PCT/US2013/065708, dated Feb. 4, 2014.
International Preliminary Report on Patentability for PCT/US2013/065708, dated Apr. 30, 2015.
International Search Report and Written Opinion for PCT/US2013/065689, dated Mar. 4, 2014.
International Preliminary Report on Patentability for PCT/US2013/065689, dated Apr. 30, 2015.
International Search Report and Written Opinion for PCT/US2013/065698, dated Feb. 20, 2014.
International Preliminary Report on Patentability for PCT/US2013/065698, dated Apr. 30, 2015.

(56) References Cited

OTHER PUBLICATIONS

International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
International Search Report and Written Opinion for PCT/US2015/027294, dated Jul. 10, 2015.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Partial European Search Report for EP 15160591.2, dated Jul. 14, 2015.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
International Search Report and Written Opinion for PCT/US2015/000297, dated Mar. 4, 2016.
International Preliminary Report on Patentability PCT/US2015/000297, dated Jul. 6, 2017.
International Search Report and Written Opinion for PCT/US2016/037086, dated Sep. 2, 2016.
International Preliminary Report on Patentability for PCT/US/2016/037086, dated Dec. 21, 2017.
Invitation to Pay Additional Fees for PCT/US2016/024345, dated Aug. 9, 2016.
International Search Report and Written Opinion for PCT/US2016/024345, dated Oct. 6, 2016.
International Preliminary Report on Patentability for PCT/US2016/024345, dated Oct. 12, 2017.
Invitation to Pay Additional Fees for PCT/US2016/051118, dated Dec. 1, 2016.
International Search Report and Written Opinion for PCT/US2016/051118, dated Mar. 13, 2017.
International Preliminary Report on Patentability for PCT/US2016/051118, dated Mar. 22, 2018.
Invitation to Pay Additional Fees for PCT/US2011/025423, dated May 31, 2011.
International Search Report and Written Opinion from PCT/US2011/025423, dated Nov. 5, 2012.
International Preliminary Report on Patentability for PCT/US2011/025423, dated Nov. 29, 2012.
CAS Registry No. 916173-61-0, STN Entry Date Dec. 21, 2006.
CAS Registry No. 769961-42-4, STN Entry Date Oct. 27, 2004.
CAS Registry No. 769961-59-3, STN Entry Date Oct. 27, 2004.
CAS Registry No. 1334419-59-8, STN Entry Date Dec. 30, 2013.
GenBank Accession No. M80629. Lapidot-Lifson et al., Dec. 31, 1994. 2 pages.
GenBank Accession No. NP_001790. Yang et al., Oct. 6, 2016. 4 pages.
PubChem-CID-68365059. Available at https://pubchem.ncbi.nlm.nih.gov/compound/68365059. Accessed Jun. 17, 2016.
Uniprot No. Q9NYV4. Last modified Mar. 15, 2017. 14 pages.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Akira et al., Toll-like receptor signalling. Nat Rev Immunol. Jul. 2004;4(7):499-511.
Attoub et al., The c-kit tyrosine kinase inhibitor STI571 for colorectal cancer therapy. Cancer Res. Sep. 1, 2002;62(17):4879-83.

Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Berge et al., Pharmaceutical salts. J. Pharmaceutical Sciences 1977 66:1-19.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Bosken et al., The structure and substrate specificity of human Cdk12/Cyclin K. Nat Commun. Mar. 24, 2014;5:3505. doi: 10.1038/ncomms4505.
Brower et al., Tumor Angiogenesis: New drugs on the block. Nature Biotechnology 1999;17:963-8.
Brunton et al., eds., Chemotherapy of Neoplastic Diseases. In Goodman & Gilman's the Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Carvajal et al., KIT as a therapeutic target in metastatic melanoma. JAMA. Jun. 8, 2011;305(22):2327-34. doi: 10.1001/jama.2011.746.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chiarugi et al., Cox-2, iNOS and p53 as play-makers of tumor angiogenesis. International Journal of Molecular Medicine 1998;2:715-9.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.

(56) References Cited

OTHER PUBLICATIONS

Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation EMBO J. Jul. 16, 2001;20(14):3716-27.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fan et al., Dual leucine zipper-bearing kinase (DLK) activates p46SAPK and p38mapk but not ERK2. J Biol Chem. Oct. 4, 1996;271(40):24788-93.
Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.
Fernandez et al., Neovascularization produced by angiotensin I.Journal of Laboratory and Clinical Medicine 1985;105(2):141-5.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hirai et al., The c-Jun N-terminal kinase activator dual leucine zipper kinase regulates axon growth and neuronal migration in the developing cerebral cortex. J Neurosci. Nov. 15, 2006;26(46):11992-2002.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kanakaraj et al., Interleukin (IL)-1 receptor-associated kinase (IRAK) requirement for optimal induction of multiple IL-1 signaling pathways and IL-6 production. J Exp Med. Jun. 15, 1998;187(12):2073-9.
Kantarjian et al., Dasatinib versus imatinib in newly diagnosed chronic-phase chronic myeloid leukemia. N Engl J Med. Jun. 17, 2010;362(24):2260-70.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Discovery of pyrrolopyridine-pyridone based inhibitors of Met kinase: synthesis, X-ray crystallographic analysis, and biological activities. J Med Chem. Sep. 11, 2008;51(17):533041. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.

(56) References Cited

OTHER PUBLICATIONS

Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Larochelle et al., Requirements for Cdk7 in the assembly of Cdk1/cyclin B and activation of Cdk2 revealed by chemical genetics in human cells. Mol Cell. Mar/ 23. 2007;25(6):839-50.
Lavis et al., Bright ideas for chemical biology. ACS Chem Biol. Mar. 20. 2008;3(3):142-55. doi: 10.1021/cb700248m.
Lee et al., BRAF mutations in non-Hodgkin's lymphoma. Br J Cancer. Nov. 17, 2003;89(10):1958-60.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Lorenzo et al., Expression of proto-oncogene c-kit in high risk prostate cancer. Eur J Surg Oncol. Nov. 2004;30(9):987-92.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Marelli et al., Tumor targeting via integrin ligands. Front. Oncol., Aug. 30, 2013. https://doi.org/10.3389/fonc.2013.00222.
Marques et al., A new subfamily of high molecular mass CDC2-related kinases with PITAI/VRE motifs. Biochem Biophys Res Commun. Dec. 29, 2000;279(3):832-7.
Matsuyama et al., Activation of Discoidin Domain Receptor 1 Isoform b with Collagen Up-Regulates Chemokine Production in Human Macrophages: Role of p38 Mitogen-Activated Protein Kinase and NF-κB. J Immunol Feb. 15, 2004, 172 (4) 2332-2340; DOI: https://doi.org/10.4049/jimmunol.172.4.2332.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.

Obenauf et al., Therapy-induced tumour secretomes promote resistance and tumour progression. Nature. Apr. 16, 2015;520(7547):368-72. doi: 10.1038/nature14336. Epub Mar. 25, 2015.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
Roberts et al., Antiangiogenic and antitumor activity of a selective PDGFR tyrosine kinase inhibitor, CP-673,451. Cancer Res. Feb. 1, 2005;65(3):957-66.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Rubin et al., KIT activation is a ubiquitous feature of gastrointestinal stromal tumors. Cancer Res. Nov. 15, 2001;61(22):8118-21.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Serizawa et al., Association of Cdk-activating kinase subunits with transcription factor TFIIH. Nature. Mar. 16, 1995;374(6519):280-2.
Sharma et al., A chromatin-mediated reversible drug-tolerant state in cancer cell subpopulations. Cell. Apr. 2, 2010;141(1):69-80.
Shiekhattar et al., Cdk-activating kinase complex is a component of human transcription factor TFIIH. Nature. Mar. 16, 1995;374(6519):283-7.
Shin et al., Dual leucine zipper kinase is required for retrograde injury signaling and axonal regeneration. Neuron. Jun. 21, 2012;74(6):1015-22. doi: 10.1016/j.neuron.2012.04.028.
Smith et al., Recent advances in the research and development of RAF kinase inhibitors. Curr. Top Med. Chem. 2006; 6(11):1071-89.
Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.
Stanovnik et al., The Tautomerism of Heterocycles: Substituent Tautomerism of Six-Membered Ring Heterocycles. Advances in Heterocyclic Chemistry. 2006;91:1-134.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;21(3):390-404.
Takemori et al., Inactivation of HDACS by SIK1 in AICAR-treated C2C12 myoblasts. Endocr J. 2009;56(1):121-30. Epub Oct. 22, 2008.
Terai et al., Activation of the FGF2-FGFR1 autocrine pathway: a novel mechanism of acquired resistance to gefitinib in NSCLC. Mol Cancer Res. Jul. 2013;11(7):759-67.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.

(56) References Cited

OTHER PUBLICATIONS

Wang et al., IRAK-4 inhibitors for inflammation. Curr Top Med Chem. 2009;9(8):724-37.

Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.

Wang et al., Mathematical modeling in cancer drug discovery. Drug Discov Today. Feb. 2014;19(2):145-50. doi: 10.1016/j.drudis.2013.06.015. Epub Jul. 4, 2013.

Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.

Wellbrock et al., The RAF proteins take centre stage Nat Rev Mol Cell Biol. Nov. 2004;5(11):875-85.

Wietek et al., IRAK-4: a new drug target in inflammation, sepsis, and autoimmunity. Mol Interv. Jul. 2002;2(4):212-5.

Wilen et al., Strategies in optical resolutions. Tetrahedron 33:2725 (1977).

Xin et al., Peroxisome proliferator-activated receptor gamma ligands are potent inhibitors of angiogenesis in vitro and in vivo. Journal of Biological Chemistry 1996;274(13):9116-21.

Yalpani, Cholesterol Lowering Drugs. Chemistry and Industry Feb. 1996;3:85-89.

Yasuda et al., The stem cell factor/c-kit receptor pathway enhances proliferation and invasion of pancreatic cancer cells. Mol Cancer. Oct. 18, 2006;5:46.

Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.

Zang et al., Genetic and structural variation in the gastric cancer kinome revealed through targeted deep sequencing. Cancer Res. Jan. 1, 2011;71(1):29-39. doi: 10.1158/0008-5472.CAN-10-749. Epub Nov. 19, 2010.

Zebisch et al., Back to the roots: the remarkable RAF oncogene story Cell Mol Life Sci. Jun. 2006;63(11):1314-30.

Zhang et al., Discovery of potent and selective covalent inhibitors of JNK. Chem Biol. Jan. 27, 2012;19(1):140-54. doi: 10.1016/j.chembiol.2011.11.010.

Zhou et al., Novel mutant-selective EGFR kinase inhibitors against EGFR T790M. Nature. Dec. 24, 2009;462(7276):1070-4.

Ziche et al., Role of prostaglandin E1 and copper in angiogenesis. Journal of the National Cancer Institute 1982;69(2):475.

* cited by examiner

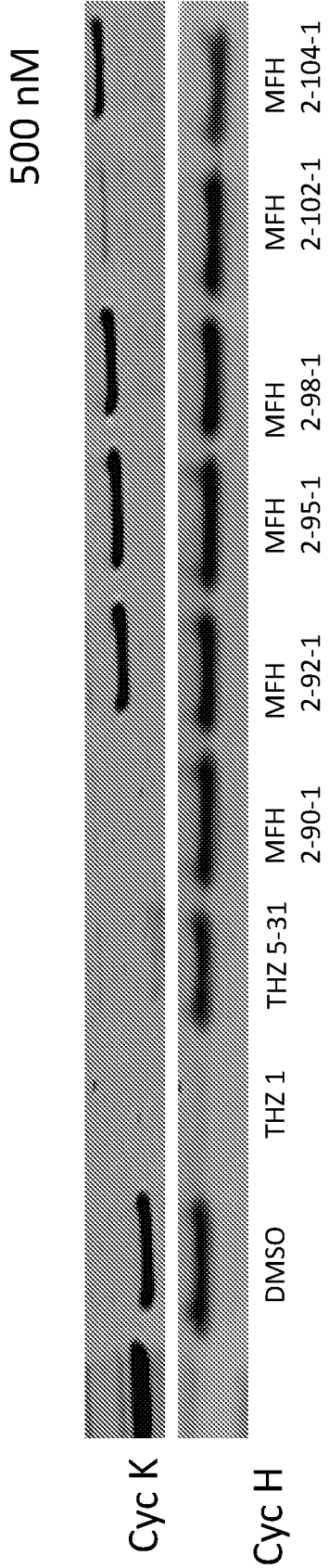
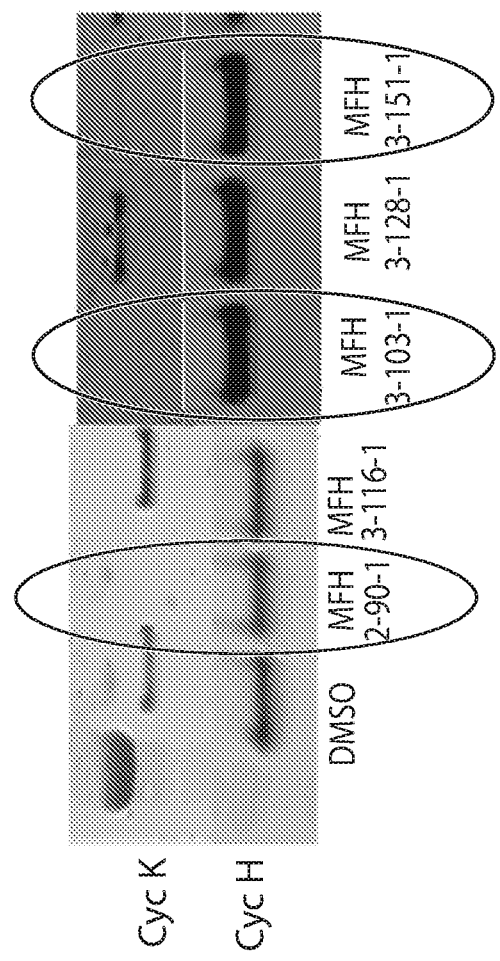
Figure 7A
Figure 7B

SEQUENCE LISTING

```
<160> NUMBER OF SEQ ID NOS: 5

<210> SEQ ID NO 1
<211> LENGTH: 346
<212> TYPE: PRT
<213> ORGANISM: Homo sapiens

<400> SEQUENCE: 1

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
            20                  25                  30

Asn Thr Asn Gln Ile Val Ala Ile Lys Lys Ile Lys Leu Gly His Arg
        35                  40                  45

Ser Glu Ala Lys Asp Gly Ile Asn Arg Thr Ala Leu Arg Glu Ile Lys
    50                  55                  60

Leu Leu Gln Glu Leu Ser His Pro Asn Ile Ile Gly Leu Leu Asp Ala
65                  70                  75                  80

Phe Gly His Lys Ser Asn Ile Ser Leu Val Phe Asp Phe Met Glu Thr
                85                  90                  95

Asp Leu Glu Val Ile Ile Lys Asp Asn Ser Leu Val Leu Thr Pro Ser
            100                 105                 110

His Ile Lys Ala Tyr Met Leu Met Thr Leu Gln Gly Leu Glu Tyr Leu
        115                 120                 125

His Gln His Trp Ile Leu His Arg Asp Leu Lys Pro Asn Asn Leu Leu
    130                 135                 140

Leu Asp Glu Asn Gly Val Leu Lys Leu Ala Asp Phe Gly Leu Ala Lys
145                 150                 155                 160

Ser Phe Gly Ser Pro Asn Arg Ala Tyr Thr His Gln Val Val Thr Arg
                165                 170                 175
```

```
Trp Tyr Arg Ala Pro Glu Leu Leu Phe Gly Ala Arg Met Tyr Gly Val
            180                 185                 190

Gly Val Asp Met Trp Ala Val Gly Cys Ile Leu Ala Glu Leu Leu Leu
        195                 200                 205

Arg Val Pro Phe Leu Pro Gly Asp Ser Asp Leu Asp Gln Leu Thr Arg
    210                 215                 220

Ile Phe Glu Thr Leu Gly Thr Pro Thr Glu Glu Gln Trp Pro Asp Met
225                 230                 235                 240

Cys Ser Leu Pro Asp Tyr Val Thr Phe Lys Ser Phe Pro Gly Ile Pro
                245                 250                 255

Leu His His Ile Phe Ser Ala Ala Gly Asp Asp Leu Leu Asp Leu Ile
            260                 265                 270

Gln Gly Leu Phe Leu Phe Asn Pro Cys Ala Arg Ile Thr Ala Thr Gln
        275                 280                 285

Ala Leu Lys Met Lys Tyr Phe Ser Asn Arg Pro Gly Pro Thr Pro Gly
    290                 295                 300

Cys Gln Leu Pro Arg Pro Asn Cys Pro Val Glu Thr Leu Lys Glu Gln
305                 310                 315                 320

Ser Asn Pro Ala Leu Ala Ile Lys Arg Lys Arg Thr Glu Ala Leu Glu
                325                 330                 335

Gln Gly Gly Leu Pro Lys Lys Leu Ile Phe
            340                 345

<210> SEQ ID NO 2
<211> LENGTH: 1490
<212> TYPE: PRT
<213> ORGANISM: Homo sapiens

<400> SEQUENCE: 2

Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Leu Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205
```

```
Ser Tyr Lys Thr Val Asp Ser Pro Lys Arg Arg Ser Arg Ser Pro His
    210                 215                 220
Arg Lys Trp Ser Asp Ser Ser Lys Gln Asp Asp Ser Pro Ser Gly Ala
225                 230                 235                 240
Ser Tyr Gly Gln Asp Tyr Asp Leu Ser Pro Ser Arg Ser His Thr Ser
                    245                 250                 255
Ser Asn Tyr Asp Ser Tyr Lys Lys Ser Pro Gly Ser Thr Ser Arg Arg
            260                 265                 270
Gln Ser Val Ser Pro Pro Tyr Lys Glu Pro Ser Ala Tyr Gln Ser Ser
        275                 280                 285
Thr Arg Ser Pro Ser Pro Tyr Ser Arg Arg Gln Arg Ser Val Ser Pro
    290                 295                 300
Tyr Ser Arg Arg Arg Ser Ser Ser Tyr Glu Arg Ser Gly Ser Tyr Ser
305                 310                 315                 320
Gly Arg Ser Pro Ser Pro Tyr Gly Arg Arg Ser Ser Ser Pro Phe
                    325                 330                 335
Leu Ser Lys Arg Ser Leu Ser Arg Ser Pro Leu Pro Ser Arg Lys Ser
                340                 345                 350
Met Lys Ser Arg Ser Arg Ser Pro Ala Tyr Ser Arg His Ser Ser Ser
            355                 360                 365
His Ser Lys Lys Lys Arg Ser Ser Arg Ser Arg His Ser Ser Ile
    370                 375                 380
Ser Pro Val Arg Leu Pro Leu Asn Ser Ser Leu Gly Ala Glu Leu Ser
385                 390                 395                 400
Arg Lys Lys Lys Glu Arg Ala Ala Ala Ala Ala Ala Lys Met Asp
                    405                 410                 415
Gly Lys Glu Ser Lys Gly Ser Pro Val Phe Leu Pro Arg Lys Glu Asn
            420                 425                 430
Ser Ser Val Glu Ala Lys Asp Ser Gly Leu Glu Ser Lys Lys Leu Pro
        435                 440                 445
Arg Ser Val Lys Leu Glu Lys Ser Ala Pro Asp Thr Glu Leu Val Asn
    450                 455                 460
Val Thr His Leu Asn Thr Glu Val Lys Asn Ser Ser Asp Thr Gly Lys
465                 470                 475                 480
Val Lys Leu Asp Glu Asn Ser Glu Lys His Leu Val Lys Asp Leu Lys
                    485                 490                 495
Ala Gln Gly Thr Arg Asp Ser Lys Pro Ile Ala Leu Lys Glu Glu Ile
            500                 505                 510
Val Thr Pro Lys Glu Thr Glu Thr Ser Glu Lys Glu Thr Pro Pro Pro
        515                 520                 525
Leu Pro Thr Ile Ala Ser Pro Pro Leu Pro Thr Thr Thr Pro
    530                 535                 540
Pro Pro Gln Thr Pro Pro Leu Pro Pro Leu Pro Ile Pro Ala Leu
545                 550                 555                 560
Pro Gln Gln Pro Pro Leu Pro Ser Gln Pro Ala Phe Ser Gln Val
                    565                 570                 575
Pro Ala Ser Ser Thr Ser Thr Leu Pro Pro Ser Thr His Ser Lys Thr
            580                 585                 590
Ser Ala Val Ser Ser Gln Ala Asn Ser Gln Pro Pro Val Gln Val Ser
        595                 600                 605
Val Lys Thr Gln Val Ser Val Thr Ala Ala Ile Pro His Leu Lys Thr
    610                 615                 620
```

-continued

Ser Thr Leu Pro Pro Leu Pro Leu Pro Pro Leu Pro Gly Asp Asp
625                 630                 635                 640

Asp Met Asp Ser Pro Lys Glu Thr Leu Pro Ser Lys Pro Val Lys Lys
                645                 650                 655

Glu Lys Glu Gln Arg Thr Arg His Leu Leu Thr Asp Leu Pro Leu Pro
            660                 665                 670

Pro Glu Leu Pro Gly Gly Asp Leu Ser Pro Pro Asp Ser Pro Glu Pro
        675                 680                 685

Lys Ala Ile Thr Pro Pro Gln Gln Pro Tyr Lys Lys Arg Pro Lys Ile
    690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Ile Gly Ile Ile Gly Glu Gly
                725                 730                 735

Thr Tyr Gly Gln Val Tyr Lys Ala Lys Asp Lys Asp Thr Gly Glu Leu
            740                 745                 750

Val Ala Leu Lys Lys Val Arg Leu Asp Asn Glu Lys Glu Gly Phe Pro
        755                 760                 765

Ile Thr Ala Ile Arg Glu Ile Lys Ile Leu Arg Gln Leu Ile His Arg
    770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
            820                 825                 830

Glu Asp His Ile Lys Ser Phe Met Lys Gln Leu Met Glu Gly Leu Glu
        835                 840                 845

Tyr Cys His Lys Lys Asn Phe Leu His Arg Asp Ile Lys Cys Ser Asn
    850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Gly Glu Glu Arg
            900                 905                 910

Tyr Thr Pro Ala Ile Asp Val Trp Ser Cys Gly Cys Ile Leu Gly Glu
        915                 920                 925

Leu Phe Thr Lys Pro Ile Phe Gln Ala Asn Leu Glu Leu Ala Gln
    930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
                965                 970                 975

Gln Tyr Arg Arg Arg Leu Arg Glu Phe Ser Phe Ile Pro Ser Ala
            980                 985                 990

Ala Leu Asp Leu Leu Asp His Met Leu Thr Leu Asp Pro Ser Lys Arg
        995                 1000                1005

Cys Thr Ala Glu Gln Thr Leu Gln Ser Asp Phe Leu Lys Asp Val
    1010                1015                1020

Glu Leu Ser Lys Met Ala Pro Pro Asp Leu Pro His Trp Gln Asp
        1025                1030                1035

Cys His Glu Leu Trp Ser Lys Lys Arg Arg Arg Gln Arg Gln Ser

-continued

```
                1040                1045                1050
Gly Val Val Val Glu Glu Pro Pro Ser Lys Thr Ser Arg Lys
    1055                1060                1065
Glu Thr Thr Ser Gly Thr Ser Thr Glu Pro Val Lys Asn Ser Ser
    1070                1075                1080
Pro Ala Pro Pro Gln Pro Ala Pro Gly Lys Val Glu Ser Gly Ala
    1085                1090                1095
Gly Asp Ala Ile Gly Leu Ala Asp Ile Thr Gln Gln Leu Asn Gln
    1100                1105                1110
Ser Glu Leu Ala Val Leu Leu Asn Leu Leu Gln Ser Gln Thr Asp
    1115                1120                1125
Leu Ser Ile Pro Gln Met Ala Gln Leu Leu Asn Ile His Ser Asn
    1130                1135                1140
Pro Glu Met Gln Gln Gln Leu Glu Ala Leu Asn Gln Ser Ile Ser
    1145                1150                1155
Ala Leu Thr Glu Ala Thr Ser Gln Gln Gln Asp Ser Glu Thr Met
    1160                1165                1170
Ala Pro Glu Glu Ser Leu Lys Glu Ala Pro Ser Ala Pro Val Ile
    1175                1180                1185
Leu Pro Ser Ala Glu Gln Thr Thr Leu Glu Ala Ser Ser Thr Pro
    1190                1195                1200
Ala Asp Met Gln Asn Ile Leu Ala Val Leu Leu Ser Gln Leu Met
    1205                1210                1215
Lys Thr Gln Glu Pro Ala Gly Ser Leu Glu Glu Asn Asn Ser Asp
    1220                1225                1230
Lys Asn Ser Gly Pro Gln Gly Pro Arg Arg Thr Pro Thr Met Pro
    1235                1240                1245
Gln Glu Glu Ala Ala Ala Cys Pro Pro His Ile Leu Pro Pro Glu
    1250                1255                1260
Lys Arg Pro Pro Glu Pro Pro Gly Pro Pro Pro Pro Pro Pro Pro
    1265                1270                1275
Pro Pro Leu Val Glu Gly Asp Leu Ser Ser Ala Pro Gln Glu Leu
    1280                1285                1290
Asn Pro Ala Val Thr Ala Ala Leu Leu Gln Leu Leu Ser Gln Pro
    1295                1300                1305
Glu Ala Glu Pro Pro Gly His Leu Pro His Glu His Gln Ala Leu
    1310                1315                1320
Arg Pro Met Glu Tyr Ser Thr Arg Pro Arg Pro Asn Arg Thr Tyr
    1325                1330                1335
Gly Asn Thr Asp Gly Pro Glu Thr Gly Phe Ser Ala Ile Asp Thr
    1340                1345                1350
Asp Glu Arg Asn Ser Gly Pro Ala Leu Thr Glu Ser Leu Val Gln
    1355                1360                1365
Thr Leu Val Lys Asn Arg Thr Phe Ser Gly Ser Leu Ser His Leu
    1370                1375                1380
Gly Glu Ser Ser Ser Tyr Gln Gly Thr Gly Ser Val Gln Phe Pro
    1385                1390                1395
Gly Asp Gln Asp Leu Arg Phe Ala Arg Val Pro Leu Ala Leu His
    1400                1405                1410
Pro Val Val Gly Gln Pro Phe Leu Lys Ala Glu Gly Ser Ser Asn
    1415                1420                1425
Ser Val Val His Ala Glu Thr Lys Leu Gln Asn Tyr Gly Glu Leu
    1430                1435                1440
```

-continued

```
Gly Pro Gly Thr Thr Gly Ala Ser Ser Ser Ala Gly Leu His
    1445                1450                1455

Trp Gly Gly Pro Thr Gln Ser Ser Ala Tyr Gly Lys Leu Tyr Arg
    1460                1465                1470

Gly Pro Thr Arg Val Pro Pro Arg Gly Gly Arg Gly Arg Gly Val
    1475                1480                1485

Pro Tyr
    1490

<210> SEQ ID NO 3
<211> LENGTH: 1512
<212> TYPE: PRT
<213> ORGANISM: Homo sapiens

<400> SEQUENCE: 3

Met Pro Ser Ser Ser Asp Thr Ala Leu Gly Gly Gly Gly Leu Ser
1               5                   10                  15

Trp Ala Glu Lys Lys Leu Glu Glu Arg Arg Lys Arg Arg Arg Phe Leu
                20                  25                  30

Ser Pro Gln Gln Pro Pro Leu Leu Leu Pro Leu Leu Gln Pro Gln Leu
            35                  40                  45

Leu Gln Pro Pro Pro Pro Pro Pro Leu Leu Phe Leu Ala Ala Pro
    50                  55                  60

Gly Thr Ala Ala Ala Ala Ala Ala Ala Ala Ser Ser Ser Cys
65                  70                  75                  80

Phe Ser Pro Gly Pro Pro Leu Glu Val Lys Arg Leu Ala Arg Gly Lys
                85                  90                  95

Arg Arg Ala Gly Gly Arg Gln Lys Arg Arg Gly Pro Arg Ala Gly
            100                 105                 110

Gln Glu Ala Glu Lys Arg Arg Val Phe Ser Leu Pro Gln Pro Gln Gln
        115                 120                 125

Asp Gly Gly Gly Gly Ala Ser Ser Gly Gly Gly Val Thr Pro Leu Val
    130                 135                 140

Glu Tyr Glu Asp Val Ser Ser Gln Ser Glu Gln Gly Leu Leu Leu Gly
145                 150                 155                 160

Gly Ala Ser Ala Ala Thr Ala Ala Thr Ala Ala Gly Gly Thr Gly Gly
                165                 170                 175

Ser Gly Gly Ser Pro Ala Ser Ser Ser Gly Thr Gln Arg Arg Gly Glu
            180                 185                 190

Gly Ser Glu Arg Arg Pro Arg Arg Asp Arg Arg Ser Ser Gly Arg
        195                 200                 205

Ser Lys Glu Arg His Arg Glu His Arg Arg Arg Asp Gly Gln Arg Gly
    210                 215                 220

Gly Ser Glu Ala Ser Lys Ser Arg Ser Arg His Ser His Ser Gly Glu
225                 230                 235                 240

Glu Arg Ala Glu Val Ala Lys Ser Gly Ser Ser Ser Ser Gly Gly
                245                 250                 255

Arg Arg Lys Ser Ala Ser Ala Thr Ser Ser Ser Ser Ser Arg Lys
            260                 265                 270

Asp Arg Asp Ser Lys Ala His Arg Ser Arg Thr Lys Ser Ser Lys Glu
        275                 280                 285

Pro Pro Ser Ala Tyr Lys Glu Pro Pro Lys Ala Tyr Arg Glu Asp Lys
    290                 295                 300

Thr Glu Pro Lys Ala Tyr Arg Arg Arg Arg Ser Leu Ser Pro Leu Gly
```

```
                305                 310                 315                 320
Gly Arg Asp Asp Ser Pro Val Ser His Arg Ala Ser Gln Ser Leu Arg
                    325                 330                 335
Ser Arg Lys Ser Pro Ser Pro Ala Gly Gly Ser Ser Pro Tyr Ser
                340                 345                 350
Arg Arg Leu Pro Arg Ser Pro Ser Pro Tyr Ser Arg Arg Ser Pro
            355                 360                 365
Ser Tyr Ser Arg His Ser Ser Tyr Glu Arg Gly Asp Val Ser Pro
    370                 375                 380
Ser Pro Tyr Ser Ser Ser Trp Arg Arg Ser Arg Ser Pro Tyr Ser
385                 390                 395                 400
Pro Val Leu Arg Arg Ser Gly Lys Ser Arg Ser Arg Ser Pro Tyr Ser
                405                 410                 415
Ser Arg His Ser Arg Ser Arg Ser Arg His Arg Leu Ser Arg Ser Arg
                420                 425                 430
Ser Arg His Ser Ser Ile Ser Pro Ser Thr Leu Thr Leu Lys Ser Ser
                435                 440                 445
Leu Ala Ala Glu Leu Asn Lys Asn Lys Lys Ala Arg Ala Ala Glu Ala
    450                 455                 460
Ala Arg Ala Ala Glu Ala Ala Lys Ala Ala Glu Ala Thr Lys Ala Ala
465                 470                 475                 480
Glu Ala Ala Lys Ala Ala Lys Ala Ser Asn Thr Ser Thr Pro Thr
                485                 490                 495
Lys Gly Asn Thr Glu Thr Ser Ala Ser Ala Ser Gln Thr Asn His Val
                500                 505                 510
Lys Asp Val Lys Lys Ile Lys Ile Glu His Ala Pro Ser Pro Ser Ser
                515                 520                 525
Gly Gly Thr Leu Lys Asn Asp Lys Ala Lys Thr Lys Pro Pro Leu Gln
                530                 535                 540
Val Thr Lys Val Glu Asn Asn Leu Ile Val Asp Lys Ala Thr Lys Lys
545                 550                 555                 560
Ala Val Ile Val Gly Lys Glu Ser Lys Ser Ala Ala Thr Lys Glu Glu
                565                 570                 575
Ser Val Ser Leu Lys Glu Lys Thr Lys Pro Leu Thr Pro Ser Ile Gly
                580                 585                 590
Ala Lys Glu Lys Glu Gln His Val Ala Leu Val Thr Ser Thr Leu Pro
                595                 600                 605
Pro Leu Pro Leu Pro Pro Met Leu Pro Glu Asp Lys Glu Ala Asp Ser
    610                 615                 620
Leu Arg Gly Asn Ile Ser Val Lys Ala Val Lys Lys Glu Val Glu Lys
625                 630                 635                 640
Lys Leu Arg Cys Leu Leu Ala Asp Leu Pro Leu Pro Pro Glu Leu Pro
                645                 650                 655
Gly Gly Asp Asp Leu Ser Lys Ser Pro Glu Glu Lys Lys Thr Ala Thr
                660                 665                 670
Gln Leu His Ser Lys Arg Arg Pro Lys Ile Cys Gly Pro Arg Tyr Gly
                675                 680                 685
Glu Thr Lys Glu Lys Asp Ile Asp Trp Gly Lys Arg Cys Val Asp Lys
                690                 695                 700
Phe Asp Ile Ile Gly Ile Ile Glu Gly Thr Tyr Gly Gln Val Tyr
705                 710                 715                 720
Lys Ala Arg Asp Lys Asp Thr Gly Glu Met Val Ala Leu Lys Lys Val
                725                 730                 735
```

-continued

Arg Leu Asp Asn Glu Lys Gly Phe Pro Ile Thr Ala Ile Arg Glu
                740                 745                 750

Ile Lys Ile Leu Arg Gln Leu Thr His Gln Ser Ile Asn Met Lys
            755                 760                 765

Glu Ile Val Thr Asp Lys Glu Asp Ala Leu Asp Phe Lys Lys Asp Lys
770                 775                 780

Gly Ala Phe Tyr Leu Val Phe Glu Tyr Met Asp His Asp Leu Met Gly
785                 790                 795                 800

Leu Leu Glu Ser Gly Leu Val His Phe Asn Glu Asn His Ile Lys Ser
                805                 810                 815

Phe Met Arg Gln Leu Met Glu Gly Leu Asp Tyr Cys His Lys Lys Asn
            820                 825                 830

Phe Leu His Arg Asp Ile Lys Cys Ser Asn Ile Leu Leu Asn Asn Arg
        835                 840                 845

Gly Gln Ile Lys Leu Ala Asp Phe Gly Leu Ala Arg Leu Tyr Ser Ser
850                 855                 860

Glu Glu Ser Arg Pro Tyr Thr Asn Lys Val Ile Thr Leu Trp Tyr Arg
865                 870                 875                 880

Pro Pro Glu Leu Leu Leu Gly Glu Glu Arg Tyr Thr Pro Ala Ile Asp
                885                 890                 895

Val Trp Ser Cys Gly Cys Ile Leu Gly Glu Leu Phe Thr Lys Lys Pro
            900                 905                 910

Ile Phe Gln Ala Asn Gln Glu Leu Ala Gln Leu Glu Leu Ile Ser Arg
        915                 920                 925

Ile Cys Gly Ser Pro Cys Pro Ala Val Trp Pro Asp Val Ile Lys Leu
    930                 935                 940

Pro Tyr Phe Asn Thr Met Lys Pro Lys Lys Gln Tyr Arg Arg Lys Leu
945                 950                 955                 960

Arg Glu Glu Phe Val Phe Ile Pro Ala Ala Ala Leu Asp Leu Phe Asp
                965                 970                 975

Tyr Met Leu Ala Leu Asp Pro Ser Lys Arg Cys Thr Ala Glu Gln Ala
            980                 985                 990

Leu Gln Cys Glu Phe Leu Arg Asp Val Glu Pro Ser Lys Met Pro Pro
        995                 1000                1005

Pro Asp Leu Pro Leu Trp Gln Asp Cys His Glu Leu Trp Ser Lys
    1010                1015                1020

Lys Arg Arg Arg Gln Lys Gln Met Gly Met Thr Asp Asp Val Ser
    1025                1030                1035

Thr Ile Lys Ala Pro Arg Lys Asp Leu Ser Leu Gly Leu Asp Asp
    1040                1045                1050

Ser Arg Thr Asn Thr Pro Gln Gly Val Leu Pro Ser Ser Gln Leu
    1055                1060                1065

Lys Ser Gln Gly Ser Ser Asn Val Ala Pro Val Lys Thr Gly Pro
    1070                1075                1080

Gly Gln His Leu Asn His Ser Glu Leu Ala Ile Leu Leu Asn Leu
    1085                1090                1095

Leu Gln Ser Lys Thr Ser Val Asn Met Ala Asp Phe Val Gln Val
    1100                1105                1110

Leu Asn Ile Lys Val Asn Ser Glu Thr Gln Gln Gln Leu Asn Lys
    1115                1120                1125

Ile Asn Leu Pro Ala Gly Ile Leu Ala Thr Gly Glu Lys Gln Thr
    1130                1135                1140

Asp Pro Ser Thr Pro Gln Gln Glu Ser Ser Lys Pro Leu Gly Gly
1145                1150                1155

Ile Gln Pro Ser Ser Gln Thr Ile Gln Pro Lys Val Glu Thr Asp
    1160                1165                1170

Ala Ala Gln Ala Ala Val Gln Ser Ala Phe Ala Val Leu Leu Thr
    1175                1180                1185

Gln Leu Ile Lys Ala Gln Gln Ser Lys Gln Lys Asp Val Leu Leu
    1190                1195                1200

Glu Glu Arg Glu Asn Gly Ser Gly His Glu Ala Ser Leu Gln Leu
    1205                1210                1215

Arg Pro Pro Glu Pro Ser Thr Pro Val Ser Gly Gln Asp Asp
    1220                1225                1230

Leu Ile Gln His Gln Asp Met Arg Ile Leu Glu Leu Thr Pro Glu
    1235                1240                1245

Pro Asp Arg Pro Arg Ile Leu Pro Pro Asp Gln Arg Pro Pro Glu
    1250                1255                1260

Pro Pro Glu Pro Pro Val Thr Glu Glu Asp Leu Asp Tyr Arg
    1265                1270                1275

Thr Glu Asn Gln His Val Pro Thr Thr Ser Ser Leu Thr Asp
    1280                1285                1290

Pro His Ala Gly Val Lys Ala Ala Leu Leu Gln Leu Leu Ala Gln
    1295                1300                1305

His Gln Pro Gln Asp Asp Pro Lys Arg Glu Gly Gly Ile Asp Tyr
    1310                1315                1320

Gln Ala Gly Asp Thr Tyr Val Ser Thr Ser Asp Tyr Lys Asp Asn
    1325                1330                1335

Phe Gly Ser Ser Ser Phe Ser Ala Pro Tyr Val Ser Asn Asp
    1340                1345                1350

Gly Leu Gly Ser Ser Ala Pro Pro Leu Glu Arg Arg Ser Phe
    1355                1360                1365

Ile Gly Asn Ser Asp Ile Gln Ser Leu Asp Asn Tyr Ser Thr Ala
    1370                1375                1380

Ser Ser His Ser Gly Gly Pro Pro Gln Pro Ser Ala Phe Ser Glu
    1385                1390                1395

Ser Phe Pro Ser Ser Val Ala Gly Tyr Gly Asp Ile Tyr Leu Asn
    1400                1405                1410

Ala Gly Pro Met Leu Phe Ser Gly Asp Lys Asp His Arg Phe Glu
    1415                1420                1425

Tyr Ser His Gly Pro Ile Ala Val Leu Ala Asn Ser Ser Asp Pro
    1430                1435                1440

Ser Thr Gly Pro Glu Ser Thr His Pro Leu Pro Ala Lys Met His
    1445                1450                1455

Asn Tyr Asn Tyr Gly Gly Asn Leu Gln Glu Asn Pro Ser Gly Pro
    1460                1465                1470

Ser Leu Met His Gly Gln Thr Trp Thr Ser Pro Ala Gln Gly Pro
    1475                1480                1485

Gly Tyr Ser Gln Gly Tyr Arg Gly His Ile Ser Thr Ser Thr Gly
    1490                1495                1500

Arg Gly Arg Gly Arg Gly Leu Pro Tyr
    1505                1510

<210> SEQ ID NO 4
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 4
ggcaggattg ccatgagttg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
ggcaagattg tcatgagtta                                              20
```

INHIBITORS OF CYCLIN-DEPENDENT KINASES

RELATED APPLICATIONS

This application is a national stage filing under 35 U.S.C. § 371 of international PCT application, PCT/US2016/051118, filed Sep. 9, 2016, which claims priority under 35 U.S.C. § 119(e) to U.S. Provisional Application, U.S. Ser. No. 62/216,271, filed Sep. 9, 2015, each of which is incorporated herein by reference.

GOVERNMENT SUPPORT

This invention was made with government support under grant number 1 R01 CA179483-01A1 awarded by the National Institutes of Health. The government has certain rights in the invention.

BACKGROUND OF THE INVENTION

The members of the cyclin-dependent kinase (CDK) family play critical regulatory roles in cell proliferation. There are currently twenty known mammalian CDKs. While CDK7 to CDK13 have been linked to transcription, CDK1, 2, 4, and 6 show demonstrable association with the cell cycle.

Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., "Effects of phosphorylation by CAK on cyclin binding by CDC2 and CDK2." *Mol. Cell Biol.* 15, 345-350 (1995); Kaldis et al., "Analysis of CAK activities from human cells." *Eur. J. Biochem.* 267, 4213-4221 (2000); Larochelle et al., "Requirements for CDK7 in the assembly of CDK1/cyclin B and activation of CDK2 revealed by chemical genetics in human cells." *Mol. Cell* 25, 839-850 (2007)). In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation (Serizawa. et al., "Association of CDK-activating kinase subunits with transcription factor TFIIH." Nature 374, 280-282 (1995); Shiekhattar et al., "CDK-activating kinase complex is a component of human transcription factor TFIIH." *Nature* 374, 283-287 (1995); Drapkin et al., "Human cyclin-dependent kinase-activating kinase exists in three distinct complexes." Proc. Natl. Acad. Sci. U.S.A. 93, 6488-6493 (1996); Liu. et al., "Two cyclin-dependent kinases promote RNA polymerase II transcription and formation of the scaffold complex." Mol. Cell Biol. 24, 1721-1735 (2004); Akhtar et al., "TFIIH kinase places bivalent marks on the carboxy-terminal domain of RNA polymerase II." Mol. Cell 34, 387-393 (2009); Glover-Cutter et al., "TFIIH-associated CDK7 kinase functions in phosphorylation of C-terminal domain Ser7 residues, promoter-proximal pausing, and termination by RNA polymerase II." Mol. Cell Biol. 29, 5455-5464 (2009)). Together, the two functions of CDK7, i.e., CAK and CTD phosphorylation, support critical facets of cellular proliferation, cell cycling, and transcription.

CDK12 and CDK13 were identified in cDNA screens for cell cycle regulators. Because their cyclin partners were not yet known, they were initially named CRKRS and CDC2L5 (Ko et al., J. Cell Sci., 2001, 114, 2591-2603; Marques et al., *Biochem Biophys Res Commun.*, 2000, 279(3):832-837), respectively. They were found to be 1490- and 1512-amino acid proteins, respectively, with a conserved central CTD kinase domain and degenerate RS domains identified in their N- and C-terminal regions (Even et al., *J Cell Biochem.*, 2006, 99(3), 890-904).

Evidence has shown CDK12 and CDK13 play an important role in cancer development. A comprehensive genomic approach identified CDK12 to be one of the most frequently somatically mutated genes in high-grade serous ovarian cancer, the most fatal form of the disease (Erratum, Nature, 2011, 474(7353), 609-615). Several identified point mutations in the kinase domain point to the critical importance of the kinase activity of CDK12 for the development/progression of this disease. CDK12 has also been found to contribute to the development of breast cancer. Notably, CDK12 is located on chromosome 17, within the 17921 locus that contains several candidate genes for breast cancer susceptibility (Kauraniemi et al., *Cancer Res.*, 2001, 61(22), 8235-8240), and it is co-amplified with the tyrosine kinase receptor ERBB2, a protein amplified and overexpressed in about 20% of breast tumors. Gene fusion between CDK12 and ERBB2 was also detected in gastric cancer (Zang et al., *Cancer Res.*, 2011, 71(1), 29-39). CDK12 is also implicated in the modification of tamoxifen sensitivity in estrogen-positive breast cancer via the modulation of the mitogen-activated protein kinase pathway (Iorns et al., *Carcinogenesis,* 2009, 30(10):1696-1701).

Due to the important regulatory functions of kinases, such as CDK7, CDK12, and CDK13, in cell cycle control, cell proliferation, differentiation, and apoptosis, it is important to develop modulators of the activities of these kinases, including selective modulators, for use as research tools as well as therapeutic agents in the treatment of diseases.

SUMMARY OF THE INVENTION

Cyclin dependent kinases (CDKs), e.g., CDK7, CDK12, and CDK13, are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. Most CDKs require the phosphorylation of a threonine residue located in the T-loop to achieve full kinase activity. This threonine residue is conserved in all CDKs that function in cell cycle regulation. The enzyme responsible for this phosphorylation is therefore termed CDK-activating-kinase or CAK. CAK complexes have been found to be composed of CDK7, CDK12, CDK13, cyclin H, and MAT1. Besides its CAK function, CDK7, CDK12, and CDK13 also play a role in transcription and possibly in DNA repair. This suggests that the CDK7, CDK12, and CDK13 enzyme complexes are involved in multiple functions in the cell, e.g., cell cycle control, apoptosis, transcription regulation, and DNA repair.

The present invention provides compounds of Formulae (I'), (II'), (I), (II), and pharmaceutically acceptable salts, solvates, hydrates, polymorphs, co-crystals, tautomers, stereoisomers, isotopically labeled derivatives, prodrugs, and compositions thereof. The compounds of Formulae (I'), (II'), (I), (II), and pharmaceutically acceptable salts, solvates, hydrates, polymorphs, co-crystals, tautomers, stereoisomers, isotopically labeled derivatives, prodrugs, and compositions thereof, may inhibit the activity of a kinase. The compounds described herein may in certain embodiments selectively inhibit specific CDK subtypes, for example, CDK7, CDK12, or CDK13. In certain embodiments, the compounds of Formulae (I'), (II'), (I), and (II) are selective for CDK7 compared to other kinases. In certain embodiments, the compounds of Formulae (I'), (II'), (I), and (II) are selective for CDK12 and/or CDK13 compared to other kinases. The present invention also provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK7, CDK12, and/or CDK13) and as therapeutics for the prevention and/or treatment of diseases associated with the overexpression and/or aberrant activity of a kinase (e.g., CDK7, CDK12, and/or CDK13). In certain embodiments, the inventive compounds are used for the prevention and/or treatment of proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject.

Since the discovery of selective inhibitors of CDK7, CDK12, and CDK13 has been hampered by the high sequence and structural similarities of the kinase domain of CDK family members, the development of selective inhibitors of the transcriptional cyclin-dependent kinases (tCDKs) will allow dissection of their individual contributions to the regulation of transcription and evaluation of their therapeutic potential. Without wishing to be bound by any particular theory, the inventive compounds' selectivity for CDK7, CDK12, and/or CDK13 may be due to the compounds' ability to covalently modify a specific cysteine residue of these kinases (e.g., Cys312 of CDK7, Cys1039 of CDK12, Cys1017 of CDK13).

In one aspect, the present invention provides compounds of Formula (I'):

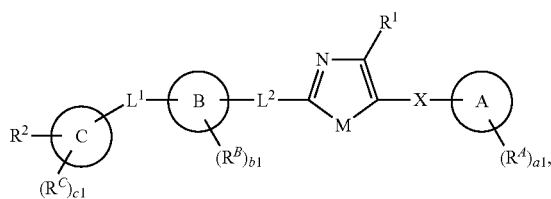

and pharmaceutically acceptable salts, solvates, hydrates, polymorphs, co-crystals, tautomers, stereoisomers, isotopically labeled derivatives, and prodrugs thereof, wherein $R^1$, $R^2$, $R^A$, $R^B$, $R^C$, Ring A, Ring B, Ring C, $L^1$, $L^2$, X, a1, b1, and c1 are as defined herein.

In one aspect, the present invention provides compounds of Formula (I):

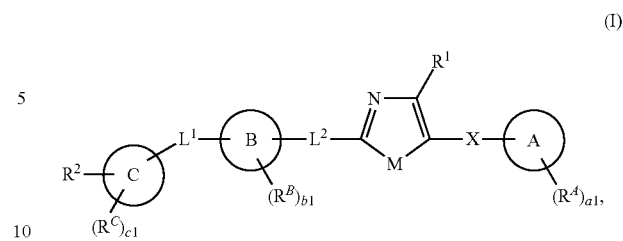

and pharmaceutically acceptable salts, solvates, hydrates, polymorphs, co-crystals, tautomers, stereoisomers, isotopically labeled derivatives, and prodrugs thereof, wherein $R^1$, $R^2$, $R^A$, $R^B$, $R^C$, Ring A, Ring B, Ring C, $L^1$, $L^2$, X, a1, b1, and c1 are as defined herein.

In one aspect, the present invention provides compounds of Formula (II'):

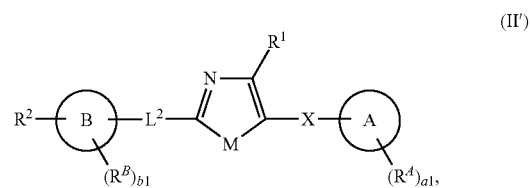

and pharmaceutically acceptable salts, solvates, hydrates, polymorphs, co-crystals, tautomers, stereoisomers, isotopically labeled derivatives, and prodrugs thereof, wherein $R^1$, $R^2$, $R^A$, $R^B$, Ring A, Ring B, $L^2$, X, a1, and b1 are as defined herein.

In one aspect, the present invention provides compounds of Formula (II):

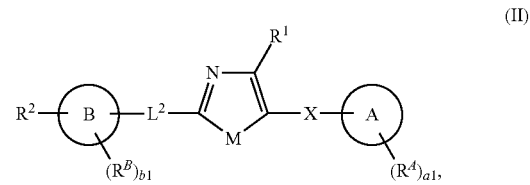

and pharmaceutically acceptable salts, solvates, hydrates, polymorphs, co-crystals, tautomers, stereoisomers, isotopically labeled derivatives, and prodrugs thereof, wherein $R^1$, $R^2$, $R^A$, $R^B$, Ring A, Ring B, $L^2$, X, a1, and b1 are as defined herein.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, inhibiting the activity of a protein kinase in a subject, biological sample, tissue, or cell, and/or inducing apoptosis in a cell. In certain embodiments, the proliferative disease is an inflammatory disease. In certain embodiments, the inflammatory disease is rheumatoid arthritis, Crohn's disease, or fibrosis.

In another aspect, the present invention provides methods for treating and/or preventing a proliferative disease. Exemplary proliferative diseases which may be treated include cancer, benign neoplasms, diseases associated with angiogenesis, inflammatory diseases, autoinflammatory diseases, and autoimmune diseases. In certain embodiments, the cancer is selected from the group consisting of pancreatic cancer, lung cancer (e.g., small cell lung cancer (SCLC), and non-small cell lung cancer), prostate cancer, breast cancer, ovarian cancer, kidney cancer, liver cancer, Ewing's sarcoma, osteosarcoma, brain cancer, neuroblastoma, and colorectal cancer.

Another aspect of the invention relates to methods of inhibiting the activity of a kinase (e.g., CDK (e.g., CDK7, CDK12, CDK13)) using a compound described herein in a biological sample or subject. In certain embodiments, the method involves the selective inhibition of CDK7. In certain embodiments, the method involves the selective inhibition of CDK12. In certain embodiments, the method involves the selective inhibition of CDK13.

Also provided by the present invention are methods of inhibiting the transcription of one or more genes in the cell of a biological sample or subject using a compound described herein. The transcription of genes affected by the activity of CDK7 may be inhibited by a compound of the invention. In certain embodiments, these genes are one or more selected from the group consisting of MYC, RUNX1, MYB, TAL1, GATA3, KLF2, HNRPDL, p21, ASCL1, MYCN, INSM1, NEUROD1, NEUROG1, FOXG1, FOXA1, SOX2, SOX4, BCL11A, OTX2, GAT2, PHOX2B, PLK2, TAF1, CTGF, WEE1, SDIM, JUN, PIM1, IL8, and FOS1. The transcription of genes affected by the activity of CDK12 may be inhibited by a compound of the invention. In certain embodiments, these genes are one or more selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI. The transcription of genes affected by the activity of CDK13 may be inhibited by a compound of the invention. In certain embodiments, the gene is SNORA38.

The present invention also provides methods of inhibiting cell growth in a biological sample or subject. In still another aspect, the present invention provides methods of inducing apoptosis of a cell in a biological sample or subject.

The present invention provides methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent. The methods described herein may further include performing radiotherapy, immunotherapy, and/or transplantation on the subject.

In yet another aspect, the present invention provides compounds of Formulae (I'), (II'), (I), (II), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a proliferative disease such as cancer) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency such as the U.S. Food and Drug Administration (FDA).

The details of one or more embodiments of the invention are set forth herein. Other features, objects, and advantages of the invention will be apparent from the Detailed Description, Examples, Figures, and Claims.

BRIEF DESCRIPTION OF THE DRAWINGS

The accompanying drawing, which are incorporated in and constitute a part of this specification, illustrate several embodiments of the invention and together with the description, serve to explain the principles of the invention.

FIG. 7 shows the binding of intracellular CDK12 and CDK13-associated cyclin K complexes by exemplified compounds. Jurkat cells were treated with each compound at a concentration of 500 nM for 6 hours, followed by lysing and pull down with biotin-THZ1, and subsequent western blotting for cyclin K (Cyc K) and cyclin H (Cyc H). Compounds that decrease the pull down efficiency of CDK12 and CDK13-associated cyclin K complexes indicate those compounds successfully targeted intracellular CDK12 and CDK13-associated cyclin K complexes and therefore were able to block biotin-THZ1 pull down of these complexes. In FIG. 7A, compounds MFH 2-90-1 and MFH 2-102-1, show a loss in cyclin K pulldown by biotin-THZ1, indicating that these compounds were able to bind intracellular CDK12 and CDK13-associated cyclin K complexes and block pull down by biotin-THZ1. In FIG. 7B, compounds MFH 2-90-1, MFH 3-103-1, and MFH 3-151-1, show a loss in cyclin K pulldown by biotin-THZ1, indicating that these compounds were able to bind intracellular CDK12 and CDK13-associated cyclin K complexes and thus block pull down by biotin-THZ1.

FIG. 8 shows the binding of intracellular CDK12 and CDK13-associated cyclin K complexes by exemplified compounds. Jurkat cells were treated with each compound at a concentration of 500 nM for 6 hours, followed by lysing and pull down with biotin-THZ1, and subsequent western blotting for cyclin K (Cyc K) and cyclin H (Cyc H). Compounds that decrease the pull down efficiency of CDK12 and CDK13-associated cyclin K complexes indicate those compounds successfully targeted intracellular CDK12 and CDK13-associated cyclin K complexes and therefore were able to block biotin-THZ1 pull down of these complexes.

FIG. 9 shows the binding of intracellular CDK12 and CDK13-associated cyclin K complexes by exemplified compounds. Jurkat cells were treated with each compound at a concentration of 500 nM for 4 hours, followed by lysing and pull down with biotin-THZ1, and subsequent western blotting for cyclin K (Cyc K) and cyclin H (Cyc H). Compounds that decrease the pull down efficiency of CDK12 and CDK13-associated cyclin K complexes indicate those compounds successfully targeted intracellular CDK12 and CDK13-associated cyclin K complexes and therefore were able to block biotin-THZ1 pull down of these complexes.

DEFINITIONS

Figure 1:
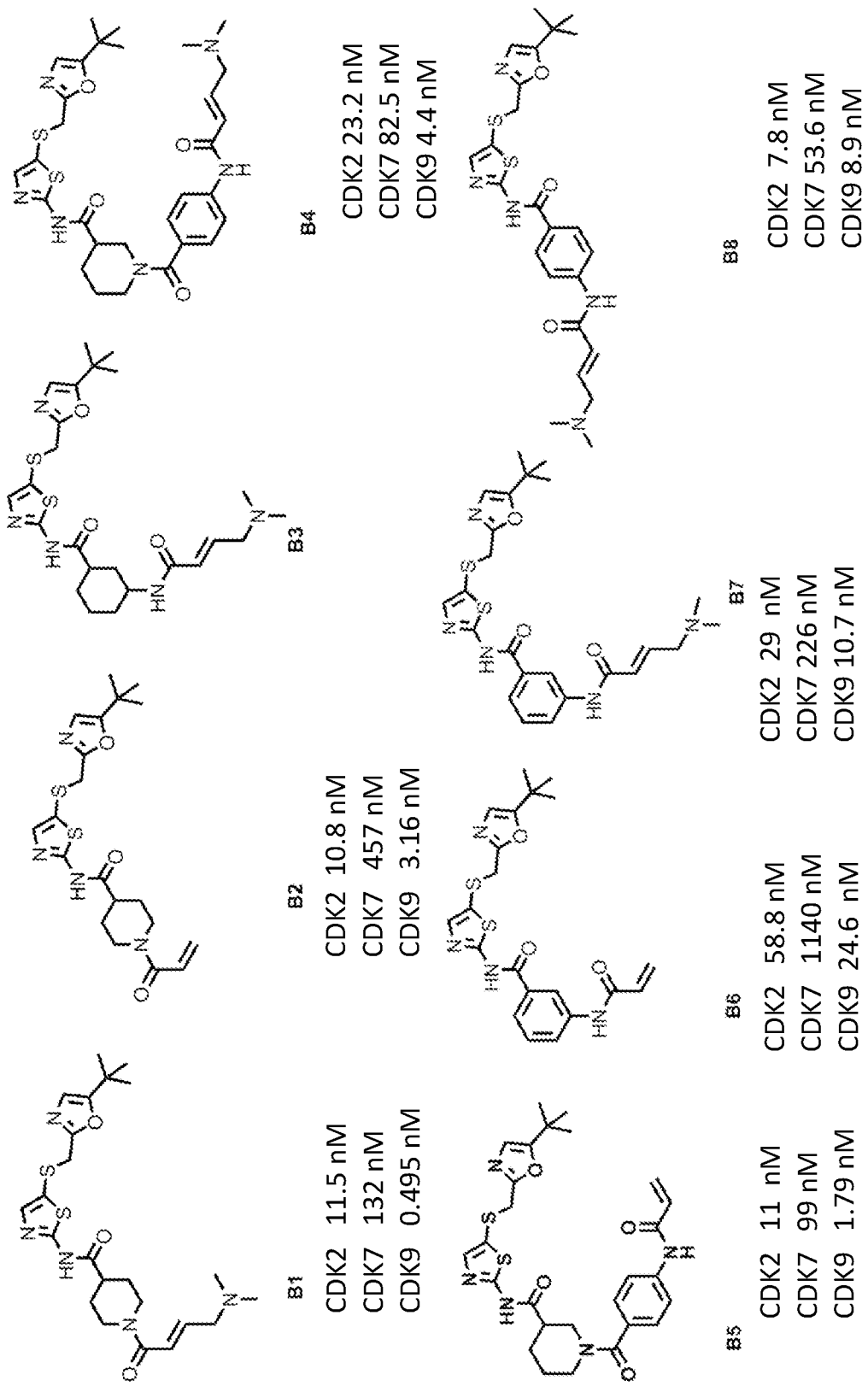
FIG. 1 shows the chemical structures of exemplary compounds described herein and the $IC_{50}$ values of the exemplary compounds in inhibiting select cyclin-dependent kinases.
Figure 1:
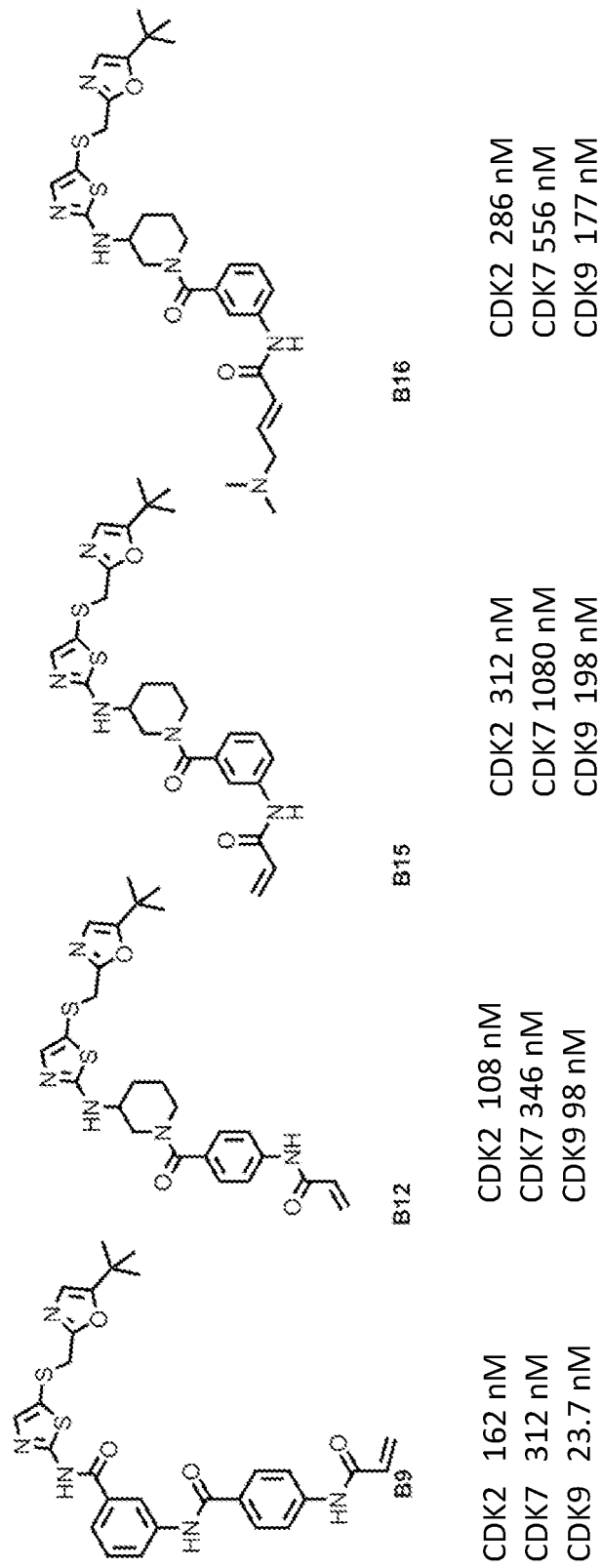
Figure 2A:
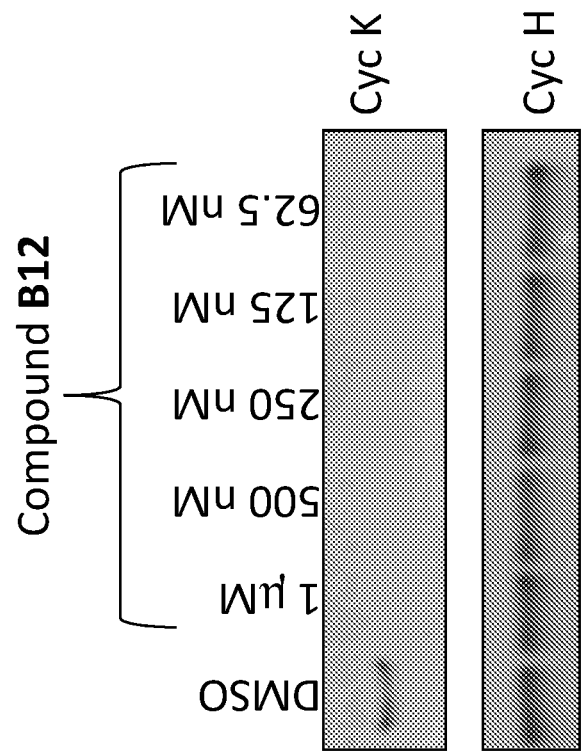
FIG. 2A shows that compound B12 exhibits binding of intracellular CDK12 and CDK13 at concentrations between 62.5 nM to 1 µM treatment. Jurkat cells treated with compound B12 for 6 hours show decreased pulldown of CDK12 and CDK13-associated cyclin K by biotin-THZ1 relative to DMSO-treated cells. These data indicate that B12 cellular treatment blocks biotin-THZ1 from binding CDK12 and CDK13-associated cyclin K complexes by successful binding of these complexes in cells at these concentrations. Cyclin H (Cyc H) pulldown was not affected, indicating that CDK7 binding is not affected.
Figure 2B:
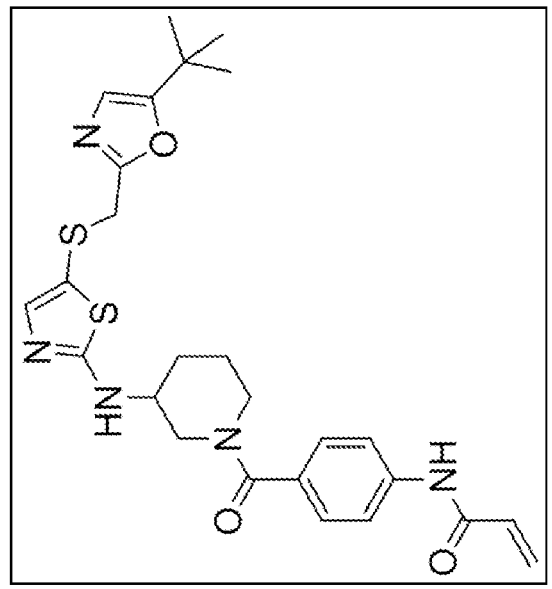
FIG. 2B shows the structure of compound B12.
Figure 3:
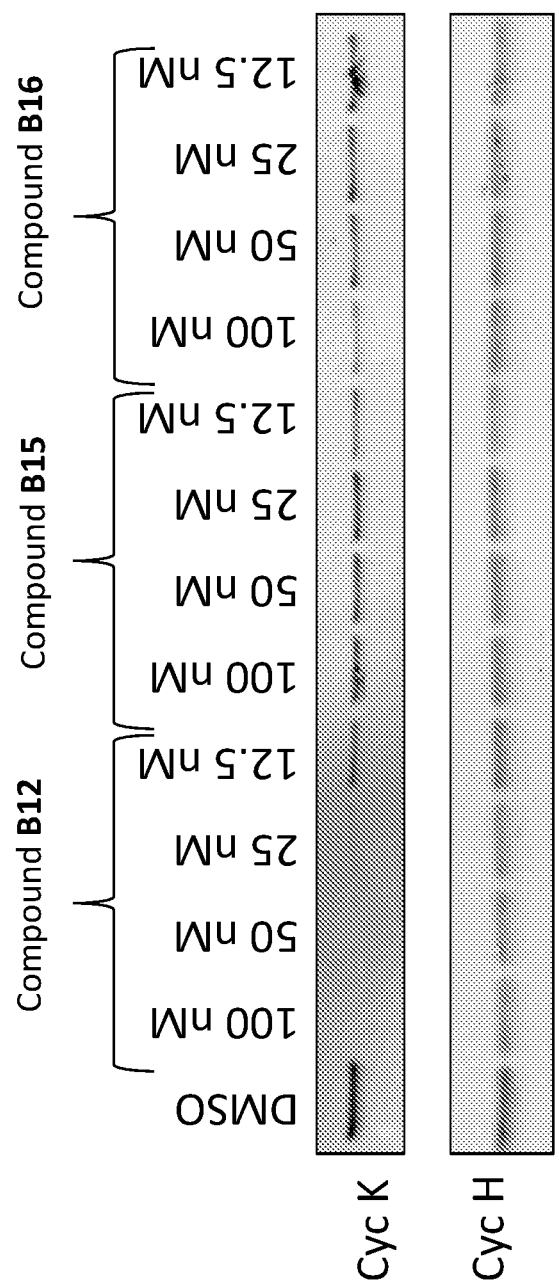
FIG. 3 shows the binding of compounds B12, B15, and B16 (relative to DMSO control) to CDK12 and CDK13-associated cyclin K at concentrations of 100 nM, 50 nM, 25 nM, and 12.5 nM. Jurkat cells were treated with each compound (or DMSO) for 6 hours, followed by lysis and pulldown with biotin-THZ1, and subsequent western blotting for cyclin K (Cyc K) and cyclin H (Cyc H). Compound B12 exhibits binding to CDK12 and CDK13-associated cyclin K, while compounds B15 and B16 do not. Compound B12 is able to block pulldown of CDK12 and CDK13-associated cyclin K down to 25 nM treatment, while compounds B15 and B16 show very little effect on cyclin K pulldown. These results indicate that at concentrations as low as 25 nM B12 successfully targets intracellular CDK12 and CDK13-associated cyclin K complexes.
Figure 4:
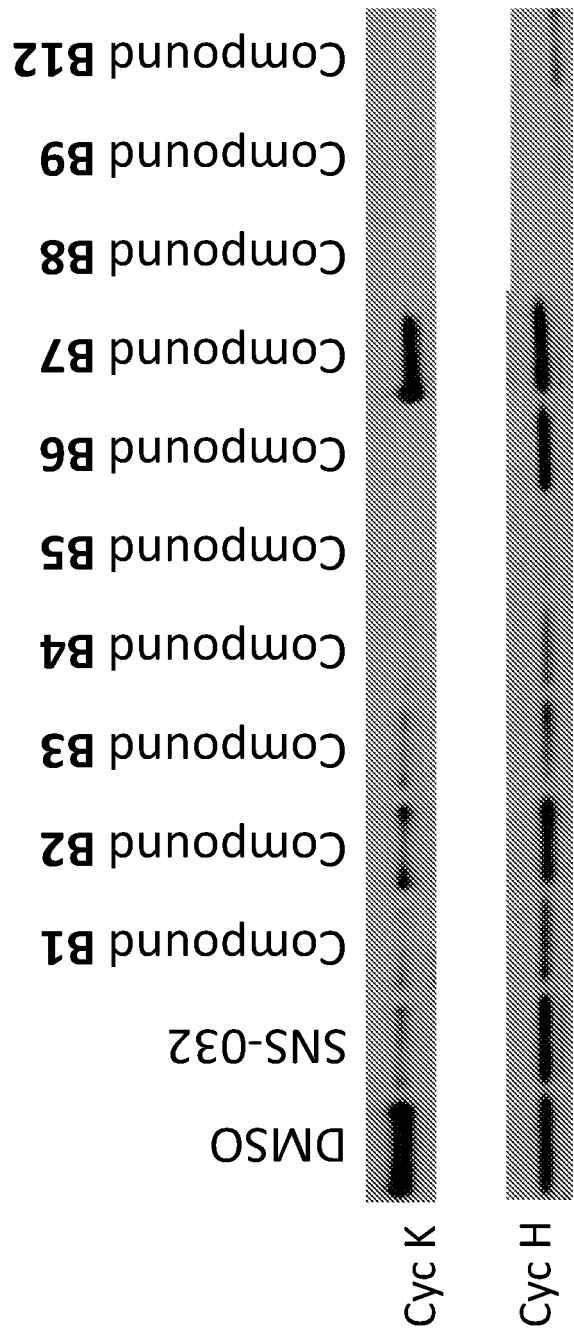
FIG. 4 shows binding of intracellular CDK12 and CDK13-associated cyclin K complexes by exemplified compounds. Jurkat cells were treated with each compound at a concentration of 500 nM for 6 hours, followed by lysing and pulldown with biotin-THZ1, and subsequent western blotting for cyclin K (Cyc K) and cyclin H (Cyc H). Compounds B1, B3, B4, B5, B6, B8, B9, and B12 show a loss in CDK12 and CDK13-associated cyclin K pulldown, indicating that these compounds successfully bind CDK12 and CDK13-associated cyclin K complexes in cells thus blocking biotin-THZ1 pull down, while compounds B5, B8, and B9 show a more pronounced loss of cyclin H pulldown, indicating that these compounds successfully target CDK7-cyclin H complexes in cells and interfere with biotin-THZ1 pull down.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein.

Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al, *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of CM alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl (C9), cyclononenyl (C9), cyclodecyl ($C_{10}$), cyclodecenyl ($C_{10}$), octahydro-1H-indenyl (C9), decahydronaphthalenyl ($C_{10}$), spiro[4.5]decanyl (C10), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("C510 cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered, non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-4}$aryl"; e.g., anthracyl). "Aryl" also includes ring systems wherein the aryl ring, as defined above, is fused with one or more carbocyclyl or heterocyclyl groups, wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered, monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent linking groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P (=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1,2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1,2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1,2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC (=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O) (OR$^{66}$)$_2$, —P(=O)(R$^{ee}$)$_2$, —OP(=O)(R$^{ee}$)$_2$, —OP(=O) (OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1,2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1,2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-f-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-f-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, r-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, A-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluencsulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, A-methylamine, A-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2J-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[2-pyridyl)mesityl]methyleneamine, N—(N', N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine A-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —N($R^{bb}$)$_2$, —C(=O)S$R^{aa}$, —C(=O)

R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), f-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), f-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), r-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl 5-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

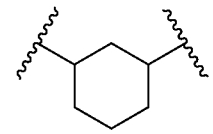 [SMILES: *C1CCCC(*)C1]

is a C$_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

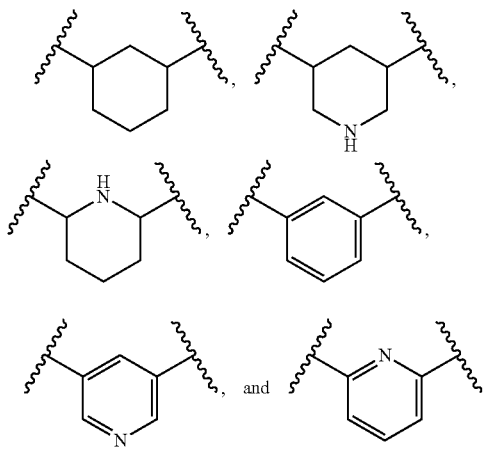

are all examples of a hydrocarbon chain. In contrast, in certain embodiments,

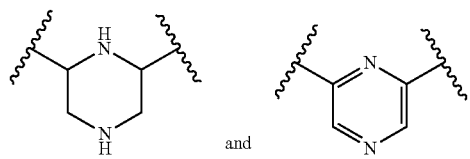 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

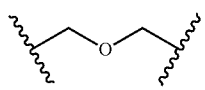 [SMILES: *COC*]

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds described herein include those derived from suitable inorganic and organic acids and bases. Examples of pharmaceutically acceptable, non-toxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal may contain a compound of the present invention and one or more other component, including but not limited to, atoms, ions, molecules, or solvent molecules. In certain embodiments, a co-crystal may contain a compound of the present invention and one or more components related to said compound, including not limited to, an isomer, tautomer, salt, solvate, hydrate, synthetic precursor, synthetic derivative, fragment or impurity of said compound.

The term "isotopically labeled derivative" or "isotopically labeled" refers to a compound wherein one or more atoms in the compound (or in an associated ion or molecule of a salt, hydrate, or solvate) has been replaced with an isotope of the same element. For the given element or position in the molecule the isotope will be enriched, or present in a higher percentage of all atoms of the element or of all atoms at the position in the molecule in a sample, relative to an unlabeled variant. In certain embodiments, the enriched isotope will be a stable isotope. In certain embodiments, the enriched isotope will be an unstable or radioactive isotope (e.g., a radionuclide). In certain embodiments, the enriched isotope may be detected by a measurement technique, including but not limited to nuclear magnetic resonance, mass spectrometry, infrared spectroscopy, or a technique that measures radioactive decay.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process (e.g., CDK kinase activity)) in a cell relative to vehicle.

When a compound, pharmaceutical composition, method, use, or kit is referred to as "selectively," "specifically," or "competitively" binding a first protein kinase, the compound, pharmaceutical composition, method, use, or kit binds the first protein kinase (e.g., CDK) with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or second chromatin that is different from the first protein and the first chromatin.

When a compound, pharmaceutical composition, method, use, or kit is referred to as "selectively," "specifically," or "competitively" modulating (e.g., increasing or inhibiting) the activity of a first protein kinase, the compound, pharmaceutical composition, method, use, or kit modulates the activity of the first protein kinase (e.g., CDK) to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of a second protein kinase that is different from the first protein kinase.

The term "aberrant activity" refers to activity deviating from normal activity, that is, abnormal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from another biological sample.

The terms "administer," "administering," or "administration" refers to implanting, absorbing, ingesting, injecting, inhaling, or otherwise introducing a compound described herein, or a composition thereof, into, in, or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated as in the growth of normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedmcm's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological malignancy" refers to tumors that affect blood, bone marrow, and/or lymph nodes. Exemplary hematological malignancies include, but are not limited to, leukemia, such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenstrom's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis *nodosa*, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "kinase" is a class of enzyme that transfers a phosphate group from a high energy donor molecules, such as ATP, to a specific substrate, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. Exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYR03, TYR03ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "SRC family kinase" refers to a family of non-receptor tyrosine protein kinases that includes nine members: SRCA subfamily that includes c-SRC (proto-oncogene tyrosine-protein kinase SRC), YES (proto-oncogene tyrosine-protein kinase Yes), FYN (proto-oncogene tyrosine-protein kinase FYN), and FGR (Gardner-Rasheed feline sarcoma viral (v-FGR) oncogene homolog); SRCB subfamily that includes LCK (lymphocyte-specific protein tyrosine kinase), HCK (tyrosine-protein kinase HCK, hemopoietic cell kinase), BLK (tyrosine-protein kinase BLK), and LYN (tyrosine-protein kinase LYN); and FRK (Fyn-related kinase).

The term "CDK" refers to a cyclin-dependent kinase. A CDK binds a cyclin (e.g., Cyclin H), which is a regulatory protein. CDKs phosphorylate their substrates at serines and threonines. The consensus sequence for the phosphorylation site in the amino acid sequence of a CDK substrate is [S/T*]PX[K/R], where S/T* is the phosphorylated serine or threonine, P is proline, X is any amino acid, K is lysine, and R is arginine. CDKs include CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19. and CDK20.

CDK7, cyclin-dependent kinase 7, is a CDK, wherein the substrate is Cyclin H, MAT1 (e.g., MNAT1), or Cyclin H and MAT1. CDK7 is alternatively referred to as CAK1, HCAK, MO15, STK1, CDKN7, and p39MO15. Non-limiting examples of the nucleotide and protein sequences for human CDK7 are described in GenBank Accession Number: NP_001790, incorporated herein by reference. The amino acid sequence of this CDK7 is as follows:

```
                                          (SEQ ID NO: 1)
MALDVKSRAKRYEKLDFLGEGQFATVYKARDKNTNQIVAIKKIKLGHRSE

AKDGINRTALREIKLLQELSHPNIIGLLDAFGHKSNISLVEDFMETDLEV

IIKDNSLVLTPSHIKAYMLMTLQGLEYLHQHWILHRDLKPNNLLLDENGV

LKLADFGLAKSFGSPNRAYTHQVVTRWYRAPELLFGARMYGVGVDMWAVG

CILAELLLRVPFLPGDSDLDQLTRIFETLGTPTEEQWPDMCSLPDYVTFK

SFPGIPLHHIFSAAGDDLLDLIQGLFLFNPCARITATQALKMKYFSNRPG

PTPGCQLPRPNCPVETLKEQSNPALAIKRKRTEALEQGGLPKKLIF
```

CDK12, cyclin-dependent kinase 12, is a CDK, wherein the substrate is Cyclin K or flavopiridol. CDK12 is alternatively referred to as Cdc2-related kinase, CDC2-related protein kinase 7, Cell division cycle 2-related protein kinase 7, Cell division protein kinase 12, CRK7, CRKR, CRKRS, cyclin-dependent kinase 12, or KIAA0904. Non-limiting examples of the nucleotide and protein sequences for human CDK12 are described in Uniprot Number: Q9NYV4, which is incorporated herein by reference. The amino acid sequence of this CDK12 is as follows:

```
                                          (SEQ ID NO 2)
MPNSERHGGKKDGSGGASGTLQPSSGGGSSNSRERHRLVSKHKRHKSKHS

KDMGLVTPEAASLGTVIKPLVEYDDISSDSDTFSDDMAFKLDRRENDERR

GSDRSDRLHKHRHHQHRRSRDLLKAKQTEKEKSQEVSSKSGSMKDRISGS
```

```
SKRSNEETDDYGKAQVAKSSSKESRSSKLHKEKTRKERELKSGHKDRSKS

HRKRETPKSYKTVDSPKRRSRSPHRKWSDSSKQDDSPSGASYGQDYDLSP

SRSHTSSNYDSYKKSPGSTSRRQSVSPPYKEPSAYQSSTRSPSPYSKRQR

SVSPYSRRRSSSYERSGSYSGRSPSPYGRRRSSSPFLSKRSLSRSPLPSR

KSMKSRSRSPAYSRHSSSHSKKKRSSSRSRHSSISPVRLPLNSSLGAELS

RKKKERAAAAAAAKMDGKESKGSPVFLPRKENSSVEAKDSGLESKKLPRS

VKLEKSAPDTELVNVTHLNTEVKNSSDTGKVKLDENSEKHLVKDLKAQGT

RDSKPIALKEEIVTPKETETSEKETPPPLPTIASPPPPLPTTTPPPQTPP

LPPLPPIPALPQQPPLPPSQPAFSQVPASSTSTLPPSTHSKTSAVSSQAN

SQPPVQVSVKTQVSVTAAIPHLKTSTLPPLPLPPLLPGDDDMDSPKETLP

SKPVKKEKEQRTRHLLTDLPLPPELPGGDLSPPDSPEPKAITPPQQPYKK

RPKICCPRYGERRQTESDWGKRCVDKFDIIGIIGEGTYGQVYKAKDKDTG

ELVALKKVRLDNEKEGFPITAIREIKILRQLIHRSVVNMKEIVTDKQDAL

DFKKDKGAFYLVFEYMDHDLMGLLESGLVHFSEDHIKSFMKQLMEGLEYC

HKKNFLHRDIKCSNILLNNSGQIKLADEGLARLYNSEESRPYTNKVITLW

YRPPELLLGEERYTPAIDVWSCGCILGELFTKKPIFQANLELAQLELISR

LCGSPCPAVWPDVIKLPYFNTMKPKKQTRRRLREEFSFIPSAALDLLDHM

LTLDPSKRCTAEQTLQSDFLKDVELSKMAPPDLPHWQDCHELWSKKRRRQ

RQSGVVVEEPPPSKTSPKETTSGTSTEPVKNSSPAPPQPAPGKVESGAGD

AIGLADITQQLNQSELAVLLNLLQSQTDLSIPQMAQLLNIHSNPEMQQQL

EALNQSISALTEATSQQQDSETMAPEESLKEAPSAPVILPSAEQTTLEAS

STPADMQNILAVLLSQLMKTQEPAGSLEENNSDKNSGPQGPRRTPTMPQE

EAAACPPHILPPEKRPPEPPGPPPPPPPPPLVEGDLSSAPQELNPAVTAA

LLQLLSQPEAEPPGHLPHEHQALRPMEYSTRPRPNRTYGNTDGPETGESA

IDTDERNSGPALTESLVQTLVKNRTFSGSLSHLGESSSYQGTGSVQFPGD

QDLRFARVPLALHPVVGQPFLKAEGSSNSVVHAETKLQNYGELGPGTTGA

SSSSGAGLHWGGPTQSSAYGKLYRGPTRVPPRGGRGRGVPY
```

CDK13, cyclin-dependent kinase 13, is a CDK, wherein the relevant cyclin is cyclin K and a reference inhibitor is the pan-CDK inhibitor flavopiridol and the c-terminal domain (CTD) of RNA-polymerase II is a physiological substrate. CDK13 is alternatively referred to as CHED; CDC2L; CDC2L5; or hCDK13. Non-limiting examples of the nucleotide and protein sequences for human CDK12 are described in GenBank Accession Number M80629, which is incorporated herein by reference. The amino acid sequence of this CDK13 is as follows:

```
                                               (SEQ ID NO: 3)
MPSSSDTALGGGGGLSWAEKKLEERRKRRRFLSPQQPPLLLPLLQPQLLQ

PPPPPPPLLFLAAPGTAAAAAAAAASSSCFSPGPPLEVKRLARGKRRAG

GRQKRRRGPRAGQEAEKRRVFSLPQPQQDGGGGASSGGGVTPLVEYEDVS

SQSEQGLLLGGASAATAATAAGGTGGSGGSPASSSGTQRRGEGSERRPRR

DRRSSSGRSKERHREHRRRDGQRGGSEASKSRSRESHSGEERAEVAKSGS

SSSSGGRRKSASATSSSSSSRKDRDSKAHRSRTKSSKEPPSAYKEPPKAY

REDKTEPKAYRRRRSLSPLGGRDDSPVSHRASQSLRSRKSPSPAGGGSSP

YSRRLPRSPSPYSRRRSPSYSRHSSYERGGDVSPSPYSSSSWRRSRSPYS

PVLRRSGKSRSRSPYSSRHSRSRSRHRLSRSRSRHSSISPSTLTLKSSLA

AELNKNKKARAAEAARAAEAAKAAEATKAAEAAAKAAKASNTSTPTKGNT

ETSASASQTNHVKDVKKIKIEHAPSPSSGGTLKNDKAKTKPPLQVTKVEN

NLIVDKATKYAVIVGKESKSAATKEESVSLKEKTKPLTPSIGAKEKEQHV

ALVTSTLPPLPLPPMLPEDKEADSLRGNISVKAVKKEVEKKLRCLLADLP

LPPELPGGDDLSKSPEEKKTATQLHSKRRPKICGPPYGETKEKDIDWGKR

CVDKFDISGIIGEGTYGQVYKARDKDTGEMVALKKVRLDNEKEGFPITAI

REIKILRQLTHQSIINMKEIVTDKEDALDFKKDKGAFYLVFEYMDHDLMG

LLESGLVHFNENHIKSFMRQLMEGLDYCHKKNFLHRDIKCSNILLNNRGQ

IKLADFGLARLYSSEESRPYTNKVITLWYRPPELLLGEERYTPAIDVWSC

GCILGELFTKKPIFQANQELAQLELISRICGSPCPAVWPDVIKLPYFNTM

KPKKQYRRKLREEFVFIPAAALDLFDYMLALDPSKRCTAEQALQCEFLRD

VEPSKMPPPDLPLWQDCHELWSKKRRRQKQMGMTDDVSTIKAPRKDLSLG

LDDSRTNTPQGVLPSSQLKSQGSSNVAPVKTGPGQHLNHSELAILLNLLQ

SKTSVNMADFVQVLNIKVNSETQQQLNKINLPAGILATGEKQTDPSTPQQ

ESSKPLGGIQPSSQTIQPKVETDAAQAAVQSAFAVLLTQLIKAQQSKQKD

VLLEERENGSGHEASLQLRPPPEPSTPVSGQDDLIQHQDMRILELTPEPD

RPRILPPDQRPPEPPEPPPVTEEDLDYRTENQHVPTTSSSLTDPHAGVKA

ALLQLLAQHQPQDDPKREGGIDYQAGDTYVSTSDYKDNFGSSSFSSAPYV

SNDGLGSSSAPPLERRSFIGNSDIQSLDNYSTASSHSGGPPQPSAFSESF

PSSVAGYGDIYLNAGPMLFSGDKDHRFEYSHGPIAVLANSSDPSTGPEST

HPLPAKMHNYNYGGNLQENPSGPSLMHGQTWTSPAQGPGYSQGYRGHIST

STGRGRGRGLPY
```

DETAILED DESCRIPTION OF CERTAIN EMBODIMENTS OF THE INVENTION

Cyclin dependent kinases (CDKs) are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. CDK7 plays a critical role in the regulation of RNA polymerase II-mediated transcription of protein-encoding genes. Disruption of CDK7, CDK12, and/or CDK13 signaling causes defects in transcription. However, a complete understanding of how these disruptions affect global transcription is lacking. Furthermore, the absence of selective inhibitors of CDK7, CDK12, and CDK13 has hindered investigation of the transcriptional and functional consequences of acute and long-term inhibition of these kinases under normal and pathological conditions. The present invention provides selective CDK7, CDK12, and/or CDK13 inhibitors, which covalently modify a cysteine residue located outside of the canonical kinase domain (i.e., Cys312 of CDK7, Cys1039 of CDK12, and Cys1017 of CDK13). Selective covalent inhibitors of these kinases may be useful in the treatment of various proliferative diseases including cancer.

The present invention provides compounds, which inhibit the activity of a kinase, for the prevention and/or treatment of a subject with a proliferative disease. In certain embodiments, the inventive compounds inhibit the activity of a cyclin-dependent kinase (CDK). In certain embodiments, the inventive compounds inhibit the activity of a cyclin-dependent kinase 7 (CDK7). In certain embodiments, the inventive compounds inhibit the activity of a cyclin-dependent kinase 12 (CDK12). In certain embodiments, the inventive compounds inhibit the activity of a cyclin-dependent kinase 13 (CDK13). The present invention also provides methods of using the compounds described herein, e.g., as biological probes to study the inhibition of the activity of a kinase (e.g., CDK (e.g. CDK7, CDK12, and/or CDK13)), and as therapeutics, e.g., in the prevention and/or treatment of diseases associated with the overexpression and/or aberrant activity of a kinase (e.g., CDK (e.g. CDK7, CDK12, and/or CDK13)). In certain embodiments, the diseases are proliferative diseases. The proliferative diseases that may be treated and/or prevented include, but are not limited to, cancers (e.g., breast cancer, leukemia, melanoma, multiple myeloma), benign neoplasms, diseases associated with angiogenesis, inflammatory diseases, autoinflammatory diseases, and autoimmune diseases. Also provided by the present disclosure are pharmaceutical compositions, kits, methods, and uses including a compound of Formulae (I'), (II'), (I), and (II) as described herein.

Compounds

Aspects of the present disclosure relate to the compounds described herein. The compounds described herein may be useful in treating and/or preventing proliferative diseases in a subject, inhibiting the activity of a protein kinase (e.g., CDK) in a subject or biological sample, and inducing apoptosis of a cell. In certain embodiments, a compound described herein is a compound of any one of Formulae (I'), (II'), (I), (II), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I'), or a pharmaceutically acceptable salt thereof. In certain embodiments, a compound described herein is a compound of Formula (I), or a pharmaceutically acceptable salt thereof. In certain embodiments, a compound described herein is a compound of Formula (II'), or a pharmaceutically acceptable salt thereof. In certain embodiments, a compound described herein is a compound of Formula (II), or a pharmaceutically acceptable salt thereof.

In certain embodiments, a compound described herein is of Formula (I'):

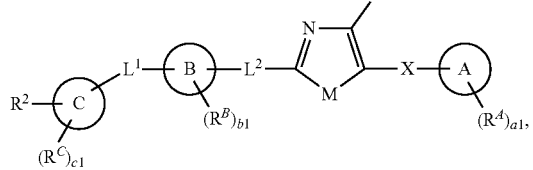

(I')

or a pharmaceutically acceptable salt thereof, wherein:

$R^1$ is hydrogen, halogen, or optionally substituted alkyl;
M is O, S, or $NR^M$;
$R^M$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group;

Ring A is optionally substituted monocyclic carbocyclyl, optionally substituted monocyclic heterocyclyl, optionally substituted phenyl, or optionally substituted monocyclic heteroaryl;

Ring B is optionally substituted monocyclic carbocyclyl, optionally substituted monocyclic heterocyclyl, optionally substituted phenyl, or optionally substituted monocyclic heteroaryl;

Ring C is optionally substituted monocyclic carbocyclyl, optionally substituted monocyclic heterocyclyl, optionally substituted monocyclic or bicyclic aryl, or optionally substituted monocyclic or bicyclic heteroaryl;

each instance of $R^A$, $R^B$, and $R^C$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^a$, $-N(R^a)_2$, $-SR^a$, $-CN$, $-SCN$, $-NO_2$, $-N_3$, or optionally substituted acyl;

each instance of $R^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

each of a1, b1, and c1 is independently 0, 1, 2, 3, 4, 5, or 6, as valency permits;

$L^1$ is $-CH_2-$, $^{lc}-S(=O)_2-^{lb}$, $-O-$, $-S-$, $-NR^{L1}-$, $-C(=O)-$, $^{lc}-NR^{L1}C(=O)-^{lb}$, $^{lc}-C(=O)NR^{L1}-^{lb}$, $^{lc}-OC(=O)-^{lb}$, or $^{lc}-C(=O)O-^{lb}$; wherein $^{lb}$ indicates the point of attachment is to Ring B; and $^{lc}$ indicates the point of attachment is to Ring C;

$L^2$ is $-O-$, $-S-$, $-NR^{L2}-$, $^{lb}-NR^{L2}C(=O)-^{lm}$, $^{lb}-C(=O)NR^{L2}-^{lm}$; wherein $^{lb}$ indicates the point of attachment is to Ring B; and $^{lm}$ indicates the point of attachment is to the heteroaryl ring with M;

X is $^{xm}-CH_2CH_2-^{xa}$, $^{xm}-CH=CH-^{xa}$, $^{xm}-CH_2-NR^{LX}-^{xa}$, $^{xm}-CH_2-O-CH_2-^{xa}$, $^{xm}-CH_2-NR^{LX}-CH_2-^{xa}$, $-O-$, $-S-$, $-NR^{LX}-$, $^{xm}-O-CH_2-^{xa}$, $^{xm}-S-CH_2-^{xa}$, $^{xm}-S-C(=O)CH_2-^{xa}$, or $^{xm}-NR^{LX}-CH_2-^{xa}$; wherein $^{xa}$ indicates the point of attachment is to Ring A; and $^{xm}$ indicates the point of attachment is to the heteroaryl ring with M;

each of $R^{L1}$, $R^{L2}$, and $R^{LX}$ is independently hydrogen, optionally substituted $C_{1-6}$ alkyl, or a nitrogen protecting group;

$R^2$ is any of Formulae (i-1)-(i-41):

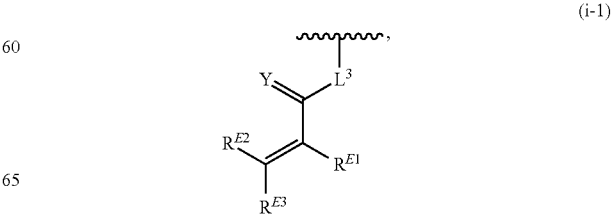

(i-1)

-continued
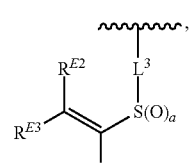 (i-2)
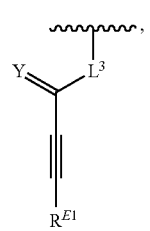 (i-3)
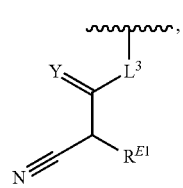 (i-4)
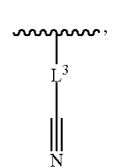 (i-5)
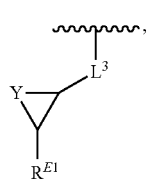 (i-6)
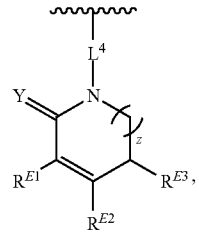 (i-7)
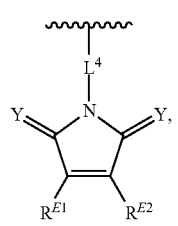 (i-8)
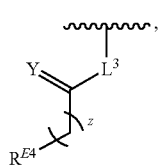 (i-9)
-continued
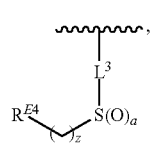 (i-10)
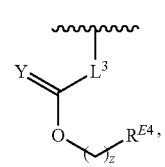 (i-11)
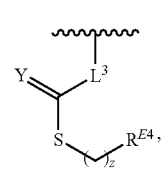 (i-12)
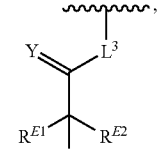 (i-13)
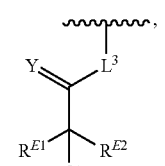 (i-14)
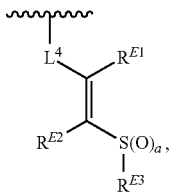 (i-15)
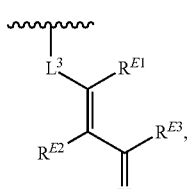 (i-16)
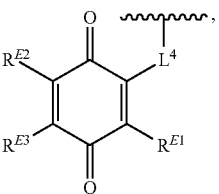 (i-17)

-continued
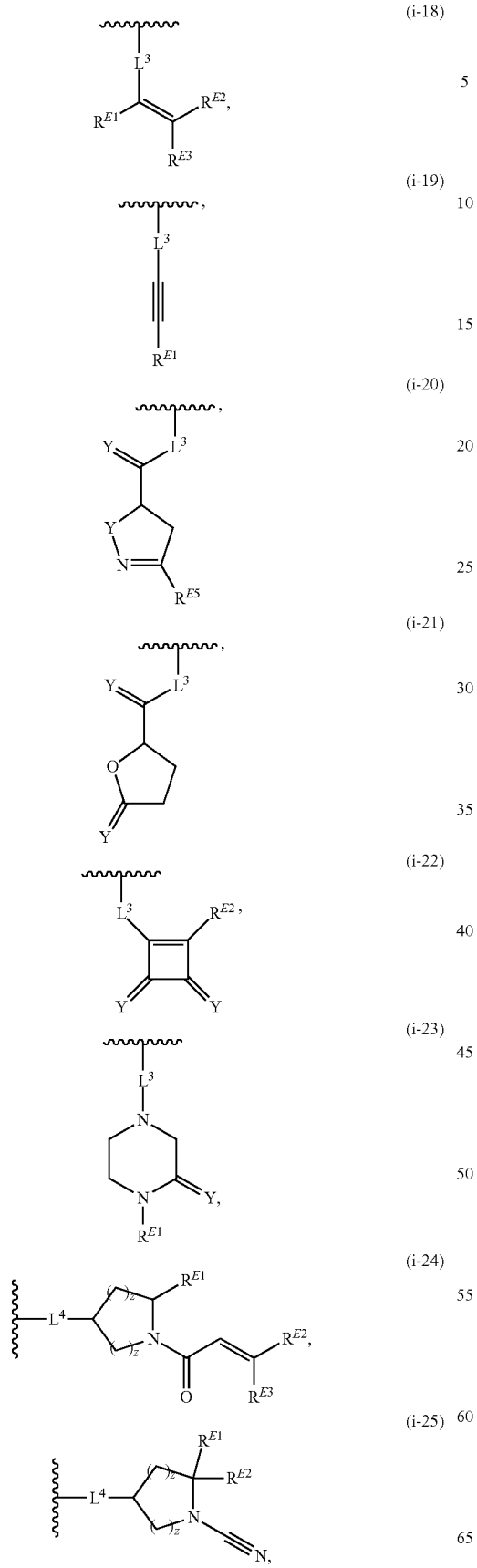
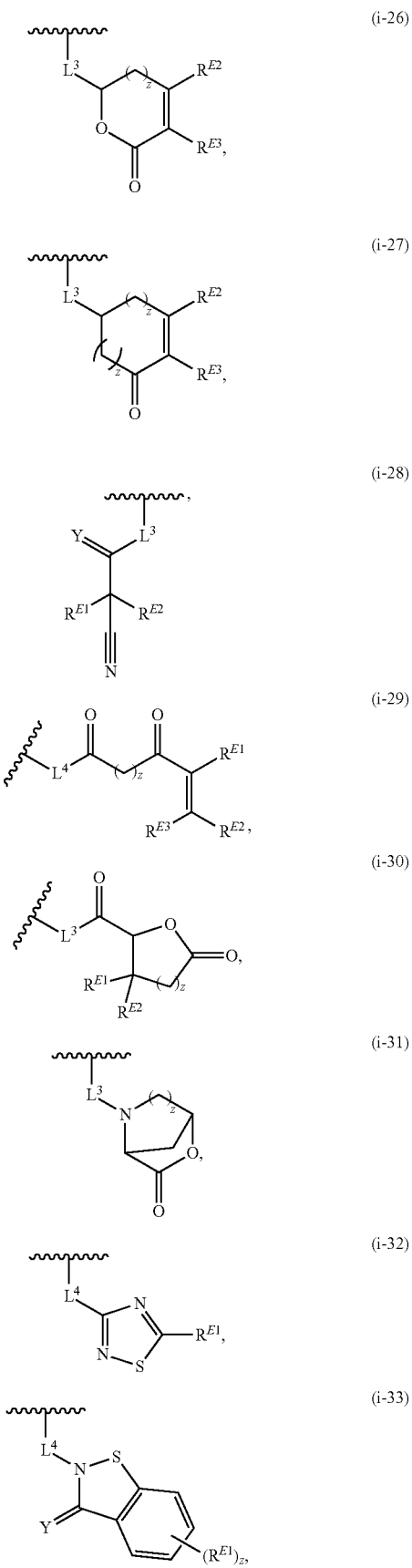

-continued

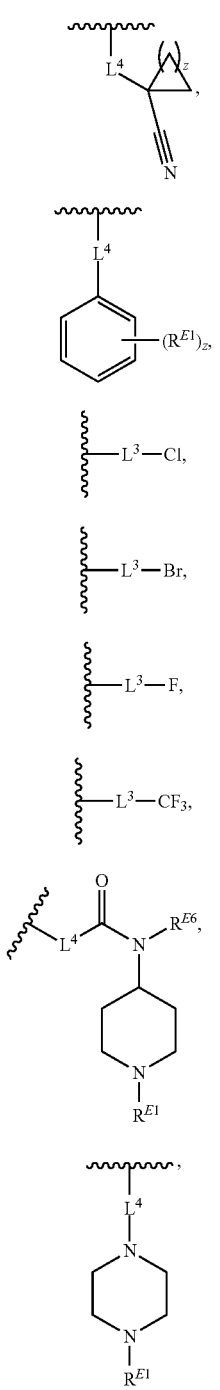

(i-34)

(i-35)

(i-36)

(i-37)

(i-38)

(i-39)

(i-40)

(i-41)

wherein:
L³ is a bond or an optionally substituted C₁₋₄ hydrocarbon chain, optionally wherein one or more carbon units of the hydrocarbon chain are independently replaced with —C(=O)—, —O—, —S—, —NR^{L3a}—, —NR^{L3a}C(=O)—, —C(=O)NR^{L3a}—, —SC(=O)—, —C(=O)S—, —OC(=O)—, —C(=O)O—, —NR^{L3a}C(=S)—, —C(=S)NR^{L3a}—, trans-CR^{L3b}=CR^{L3b}—, cis-CR^{L3b}=CR^{L3b}—, —C≡C—, —S(=O)—, —S(=O)O—, —OS(=O)—, —S(=O)NR^{L3a}—, —NR^{L3a}S(=O)—, —S(=O)₂—, —S(=O)₂O—, —OS(=O)₂—, —S(=O)₂NR^{L3a}—, or —NR^{L3a}S(=O)₂—, wherein R^{L3a} is hydrogen, optionally substituted C₁₋₆ alkyl, or a nitrogen protecting group, and wherein each occurrence of R^{L3b} is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R^{L3b} groups are joined to form an optionally substituted carbocyclic or optionally substituted heterocyclic ring;

L⁴ is a bond or an optionally substituted, branched or unbranched C₁₋₆ hydrocarbon chain;

each of R^{E1}, R^{E2}, and R^{E3} is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR^{EE}, —CH₂N(R^{EE})₂, —CH₂SR^{EE}, —OR^{EE}, —N(R^{EE})₂, —Si(R^{EE})₃, and —SR^{EE}, wherein each occurrence of R^{EE} is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R^{EE} groups are joined to form an optionally substituted heterocyclic ring;

or R^{E1} and R^{E3}, or R^{E2} and R^{E3}, or R^{E1} and R^{E2} are joined to form an optionally substituted carbocyclic or optionally substituted heterocyclic ring;

R^{E4} is a leaving group;
R^{E5} is halogen;
R^{E6} is hydrogen, optionally substituted C₁₋₆ alkyl, or a nitrogen protecting group;
each instance of Y is independently O, S, or NR^{E7}, wherein R^{E7} is hydrogen, optionally substituted C₁₋₆ alkyl, or a nitrogen protecting group;
a is 1 or 2; and
each instance of z is independently 0, 1, 2, 3, 4, 5, or 6, as valency permits.

In certain embodiments, a compound described herein is of Formula (I):

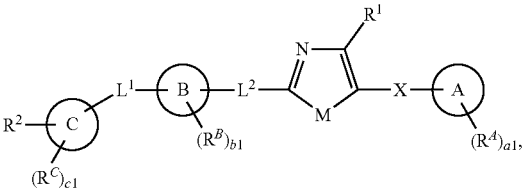

(I)

or a pharmaceutically acceptable salt thereof, wherein:
R¹ is hydrogen, halogen, or optionally substituted alkyl;
M is O, S, or NR^{M};
R^{M} is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group;
Ring A is optionally substituted monocyclic carbocyclyl, optionally substituted monocyclic heterocyclyl, optionally substituted phenyl, or optionally substituted monocyclic heteroaryl;

Ring B is optionally substituted monocyclic carbocyclyl, optionally substituted monocyclic heterocyclyl, optionally substituted phenyl, or optionally substituted monocyclic heteroaryl;

Ring C is optionally substituted monocyclic carbocyclyl, optionally substituted monocyclic heterocyclyl, optionally substituted phenyl, or optionally substituted monocyclic heteroaryl;

each instance of $R^A$, $R^B$, and $R^C$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^a$, —$N(R^a)_2$, —$SR^a$, —CN, —SCN, —$NO_2$, —$N_3$, or optionally substituted acyl;

each instance of $R^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

each of a1, b1, and c1 is independently 0, 1, 2, 3, 4, 5, or 6, as valency permits;

$L^1$ is —O—, —S—, —$NR^{L1}$—, —C(=O)—, $^{lc}$—$NR^{L1}$C(=O)—$^{lb}$, $^{lc}$—C(=O)$NR^{L1}$—$^{lb}$, $^{lc}$—OC(=O)—$^{lb}$, or $^{lc}$—C(=O)O—$^{lb}$; wherein $^{lb}$ indicates the point of attachment is to Ring B; and $^{lc}$ indicates the point of attachment is to Ring C;

$L^2$ is —O—, —S—, —$NR^{L2}$—, $^{lb}$—$NR^{L2}$C(=O)—$^{lm}$, $^{lb}$—C(=O)$NR^{L2}$—$^{lm}$; wherein $^{lb}$ indicates the point of attachment is to Ring B; and $^{lm}$ indicates the point of attachment is to the heteroaryl ring with M;

X is —O—, —S—, —$NR^{LX}$—, $^{nm}$—O—$CH_2$—$^{xa}$, $^{xm}$—S—$CH_2$—$^{xa}$, or $^{xm}$—$NR^{LX}$—$CH_2$—$^{xa}$; wherein $^{xa}$ indicates the point of attachment is to Ring A; and $^{xm}$ indicates the point of attachment is to the heteroaryl ring with M;

each of $R^{L1}$, $R^{L2}$, and $R^{LX}$ is independently hydrogen, optionally substituted $C_{1-6}$ alkyl, or a nitrogen protecting group;

$R^2$ is any of Formulae (i-1)-(i-46):

(i-1)

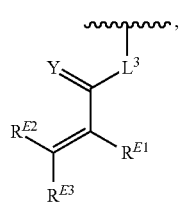

(i-2)

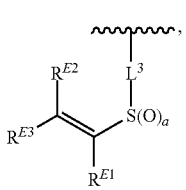

(i-3)

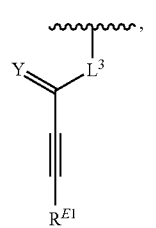

(i-4)

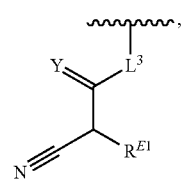

(i-5)

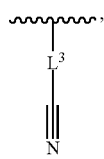

(i-6)

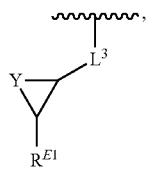

(i-7)

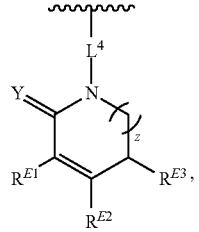

(i-8)

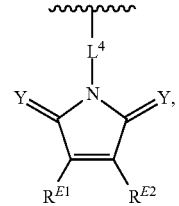

(i-9)

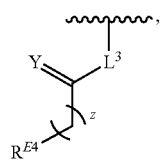

(i-10)

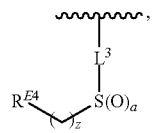

-continued
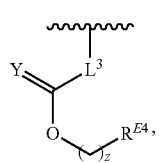 (i-11)
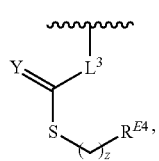 (i-12)
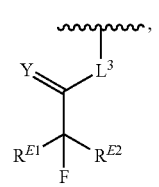 (i-13)
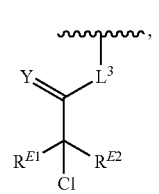 (i-14)
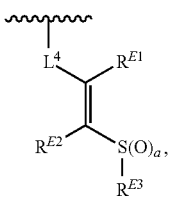 (i-15)
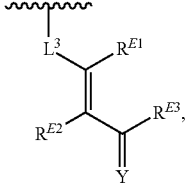 (i-16)
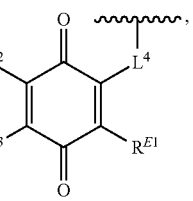 (i-17)
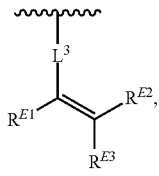 (i-18)
-continued
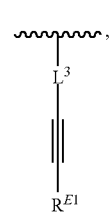 (i-19)
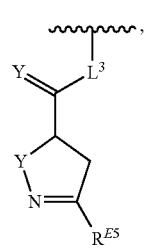 (i-20)
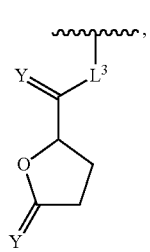 (i-21)
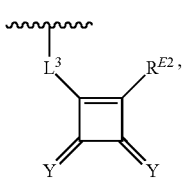 (i-22)
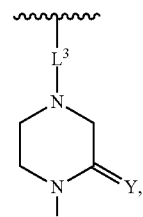 (i-23)
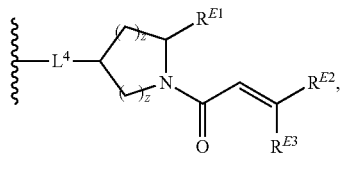 (i-24)
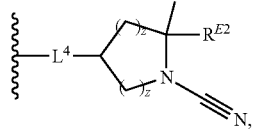 (i-25)

-continued

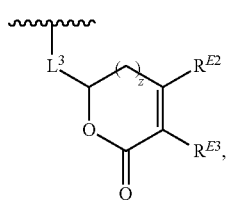
(i-26)

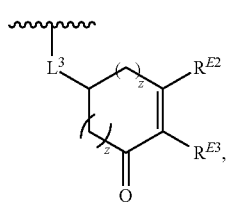
(i-27)

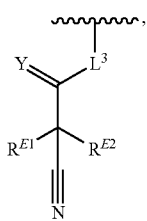
(i-28)

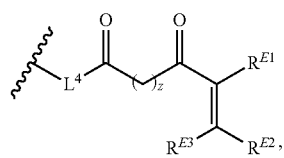
(i-29)

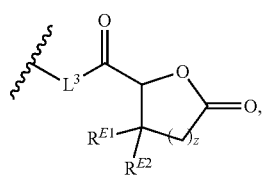
(i-30)

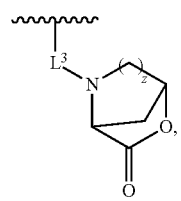
(i-31)

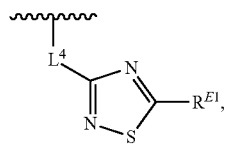
(i-32)

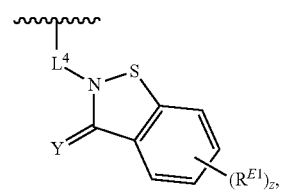
(i-33)

-continued

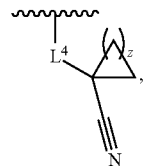
(i-34)

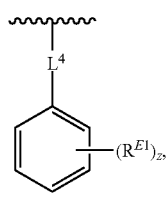
(i-35)

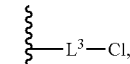
(i-36)

(i-37)

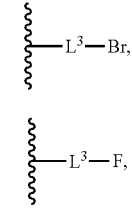
(i-38)

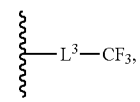
(i-39)

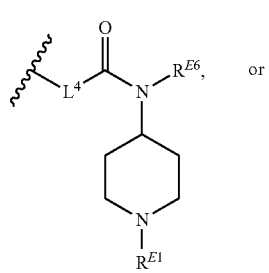
(i-40)

or

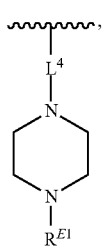
(i-41)

$L^3$ is a bond or an optionally substituted $C_{1-4}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of $R^{E1}$, $R^{E2}$, and $R^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two $R^{EE}$ groups are joined to form an optionally substituted heterocyclic ring; or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

$R^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

In certain embodiments, a compound described herein is of Formula (II'):

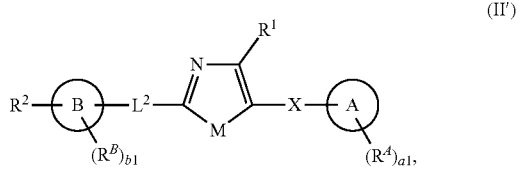

(II')

$R^1$ is hydrogen, halogen, or optionally substituted alkyl;

M is O, S, or NR$^M$;

$R^M$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group;

Ring A is optionally substituted monocyclic carbocyclyl, optionally substituted monocyclic heterocyclyl, optionally substituted phenyl, or optionally substituted monocyclic heteroaryl;

Ring B is optionally substituted monocyclic carbocyclyl, optionally substituted monocyclic heterocyclyl, optionally substituted phenyl, or optionally substituted monocyclic heteroaryl;

each instance of $R^A$ and $R^B$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

each of a1 and b1 is independently 0, 1, 2, 3, 4, 5, or 6, as valency permits;

$L^2$ is —O—, —S—, —NR$^{L2}$—, $^{lb}$—NR$^{L2}$C(=O)—$^{lm}$, $^{lb}$—C(=O)NR$^{L2}$—$^{lm}$; wherein $^{lb}$ indicates the point of attachment is to Ring B; and $^{lm}$ indicates the point of attachment is to the heteroaryl ring with M;

X is a bond, —O—, —S—, —NR$^{LX}$, $^{xm}$—O—CH$_2$—$^{xa}$, $^{xm}$—S—CH$_2$—$^{xa}$, or $^{xm}$—NR$^{LX}$—CH$_2$—$^{xa}$; wherein $^{xa}$ indicates the point of attachment is to Ring A; and $^{xm}$ indicates the point of attachment is to the heteroaryl ring with M;

each of $R^{L2}$ and $R^{LX}$ is independently hydrogen, optionally substituted $C_{1-6}$ alkyl, or a nitrogen protecting group;

$R^2$ is any of Formulae (i-1)-(i-41):

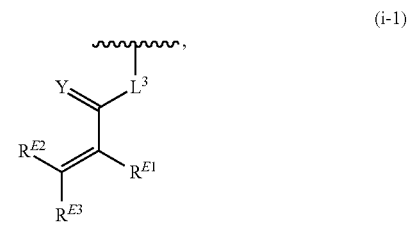

(i-1)

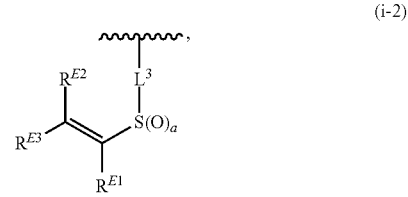

(i-2)

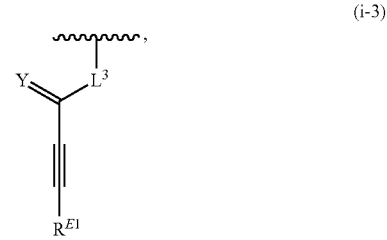

(i-3)

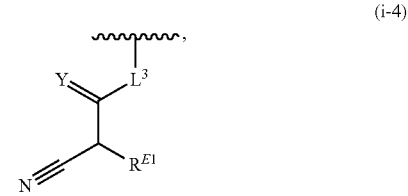

(i-4)

-continued
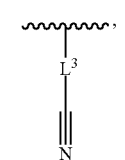 (i-5)
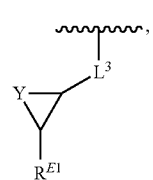 (i-6)
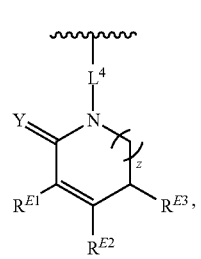 (i-7)
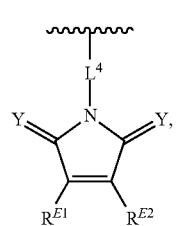 (i-8)
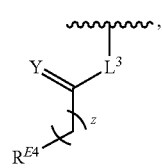 (i-9)
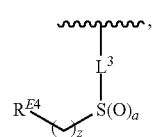 (i-10)
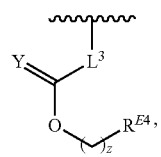 (i-11)
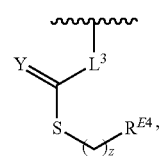 (i-12)
-continued
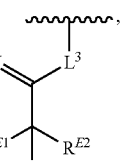 (i-13)
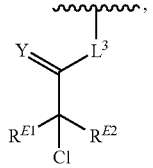 (i-14)
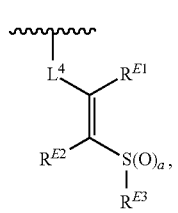 (i-15)
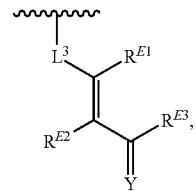 (i-16)
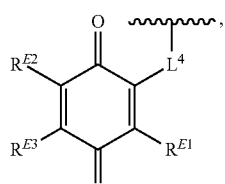 (i-17)
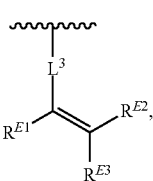 (i-18)
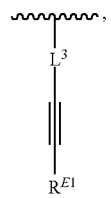 (i-19)
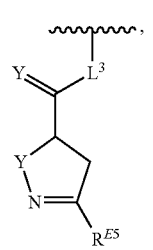 (i-20)

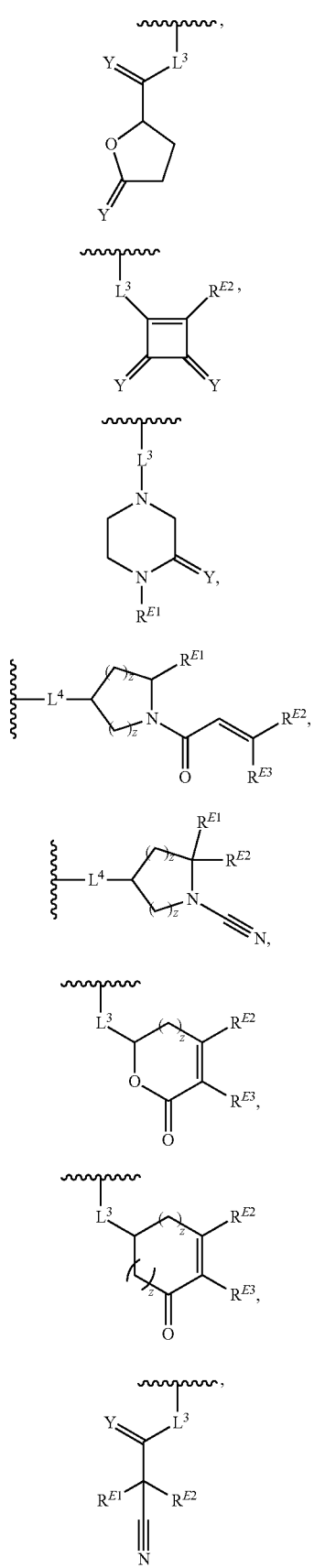
(i-21)
(i-22)
(i-23)
(i-24)
(i-25)
(i-26)
(i-27)
(i-28)
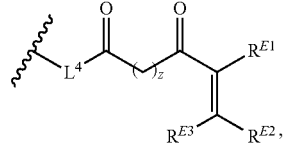
(i-29)
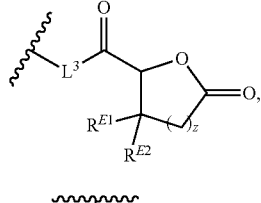
(i-30)
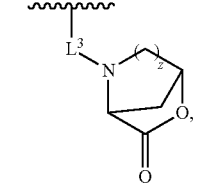
(i-31)
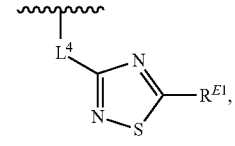
(i-32)
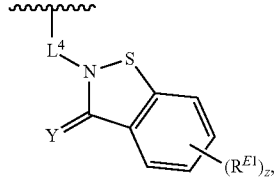
(i-33)
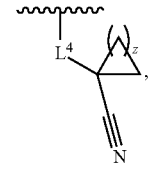
(i-34)
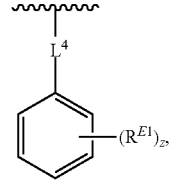
(i-35)
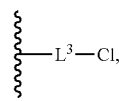
(i-36)
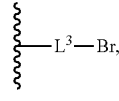
(i-37)
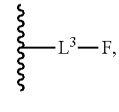
(i-38)

-continued

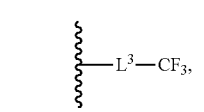
(i-39)

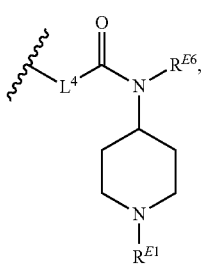
(i-40)

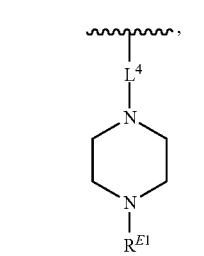
(i-41)

wherein:
L³ is a bond or an optionally substituted $C_{1-4}$ hydrocarbon chain, optionally wherein one or more carbon units of the hydrocarbon chain are independently replaced with —C(=O)—, —O—, —S—, —$NR^{L3a}$—, —$NR^{L3a}$C(=O)—, —C(=O)$NR^{L3a}$—, —SC(=O)—, —C(=O)S—, —OC(=O)—, —C(=O)O—, —$NR^{L3a}$C(=S)—, —C(=S)$NR^{L3a}$—, trans-$CR^{L3b}$=$CR^{L3b}$—, cis-$CR^{L3b}$=$CR^{L3b}$—, —C≡C—, —S(=O)—, —S(=O)O—, —OS(=O)—, —S(=O)$NR^{L3a}$—, —$NR^{L3a}$S(=O)—, —S(=O)$_2$—, —S(=O)$_2$O—, —OS(=O)$_2$—, —S(=O)$_2NR^{L3a}$—, or —$NR^{L3a}$S(=O)$_2$—, wherein $R^{L3a}$ is hydrogen, optionally substituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring;
L⁴ is a bond or an optionally substituted, branched or unbranched $C_{1-6}$ hydrocarbon chain;
each of $R^{E1}$, $R^{E2}$, and $R^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{EE}$, —$CH_2N(R^{EE})_2$, —$CH_2SR^{EE}$, —$OR^{EE}$, —$N(R^{ee})_2$, —$Si(R^{EE})_3$, and —$SR^{EE}$, wherein each occurrence of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two $R^{EE}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;
$R^{E4}$ is a leaving group;
$R^{E5}$ is halogen;
$R^{E6}$ is hydrogen, optionally substituted $C_{1-6}$ alkyl, or a nitrogen protecting group;
each instance of Y is independently O, S, or $NR^{E7}$, wherein $R^{E7}$ is hydrogen, optionally substituted $C_{1-6}$ alkyl, or a nitrogen protecting group;
a is 1 or 2; and
each instance of z is independently 0, 1, 2, 3, 4, 5, or 6, as valency permits.

In certain embodiments, a compound described herein is of Formula (II):

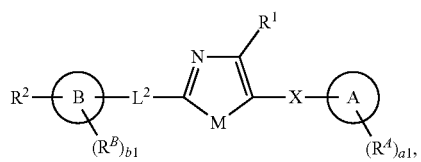

(II)

or a pharmaceutically acceptable salt thereof, wherein:
$R^1$ is hydrogen, halogen, or optionally substituted alkyl;
M is O, S, or $NR^m$;
$R^M$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group;
Ring A is optionally substituted monocyclic carbocyclyl, optionally substituted monocyclic heterocyclyl, optionally substituted phenyl, or optionally substituted monocyclic heteroaryl;
Ring B is optionally substituted monocyclic carbocyclyl, optionally substituted monocyclic heterocyclyl, optionally substituted phenyl, or optionally substituted monocyclic heteroaryl;
each instance of $R^A$ and $R^B$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;
each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;
each of a1 and b1 is independently 0, 1, 2, 3, 4, 5, or 6, as valency permits;

$L^2$ is —O—, —S—, —NR$^{L2}$~, $^{lb}$—NR$^{L2}$C(=O)—$^{lm}$, $^{lb}$—C(=O)NR$^{L2}$—$^{lm}$; wherein $^{lb}$ indicates the point of attachment is to Ring B; and $^{lm}$ indicates the point of attachment is to the heteroaryl ring with M;

X is —O—, —S—, —NR$^{LX}$~, $^{xm}$—O—CH$_2$—$^{xa}$, $^{xm}$—S—CH$_2$—$^{xa}$, or $^{xm}$—NR$^{LX}$—CH$_2$—$^{xa}$; wherein $^{xa}$ indicates the point of attachment is to Ring A; and $^{xm}$ indicates the point of attachment is to the heteroaryl ring with M;

each of R$^{L2}$ and R$^{LX}$ is independently hydrogen, optionally substituted C$_{1-6}$ alkyl, or a nitrogen protecting group;

R$^2$ is any of Formulae (i-1)-(i-46):

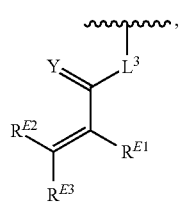 (i-1)

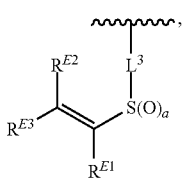 (i-2)

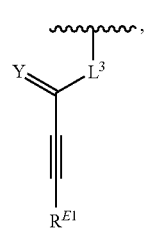 (i-3)

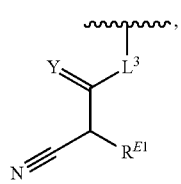 (i-4)

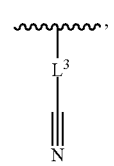 (i-5)

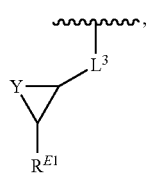 (i-6)

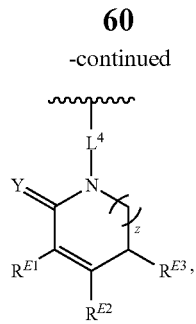 (i-7)

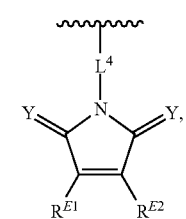 (i-8)

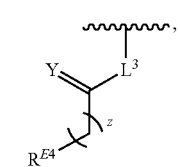 (i-9)

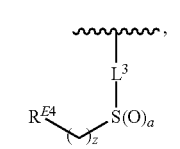 (i-10)

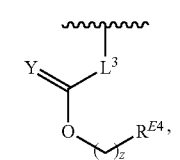 (i-11)

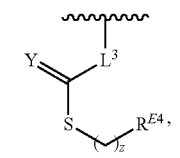 (i-12)

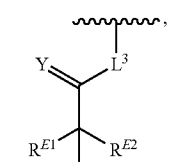 (i-13)

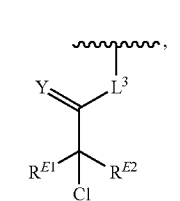 (i-14)

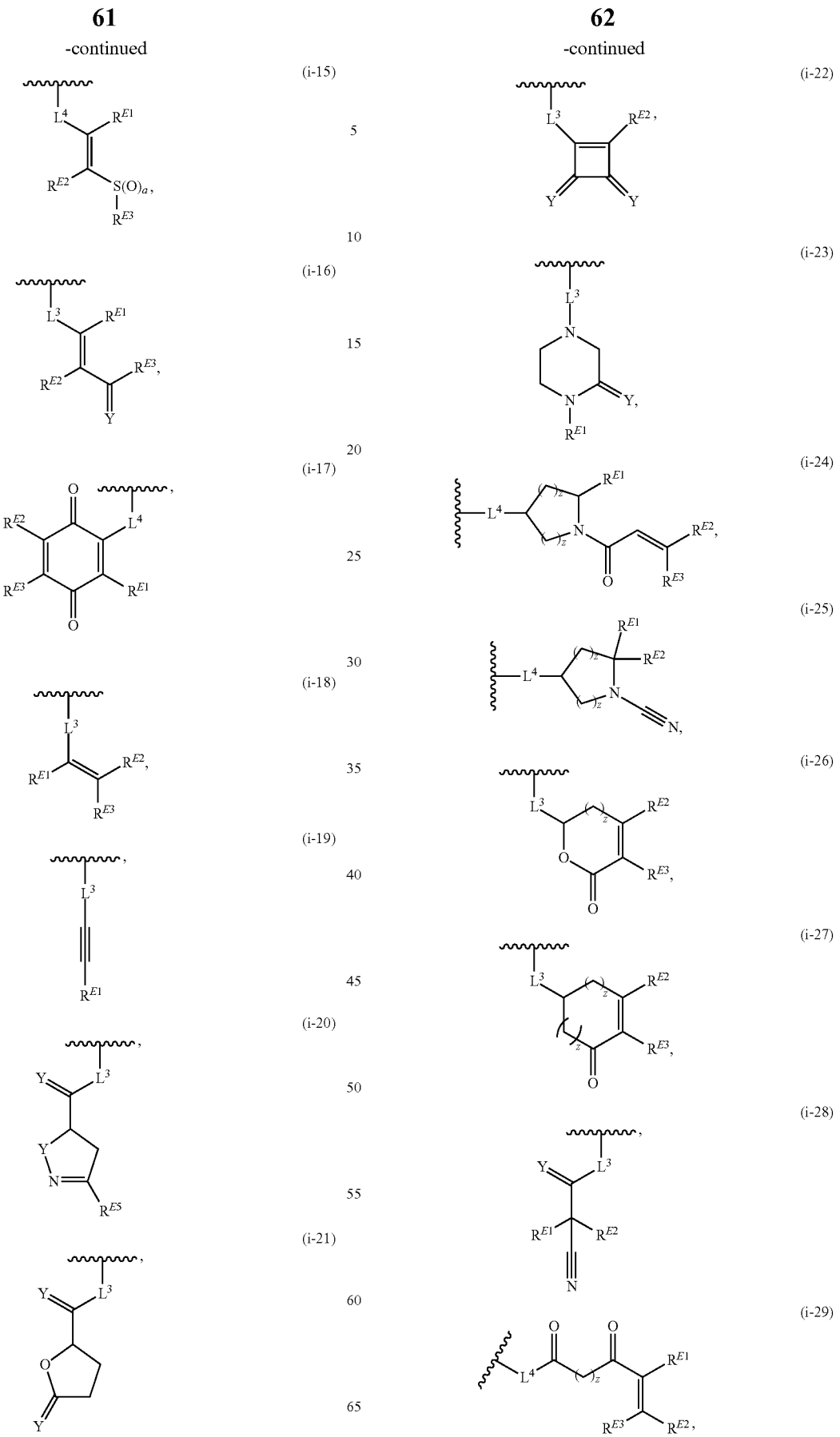

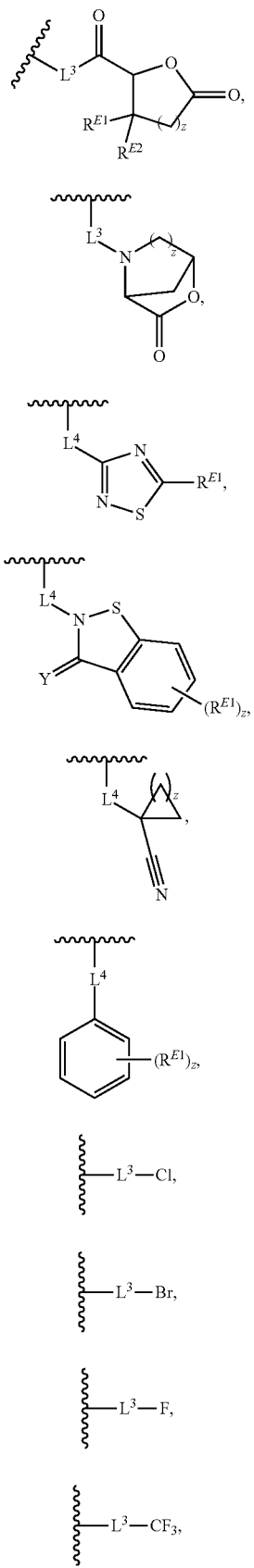

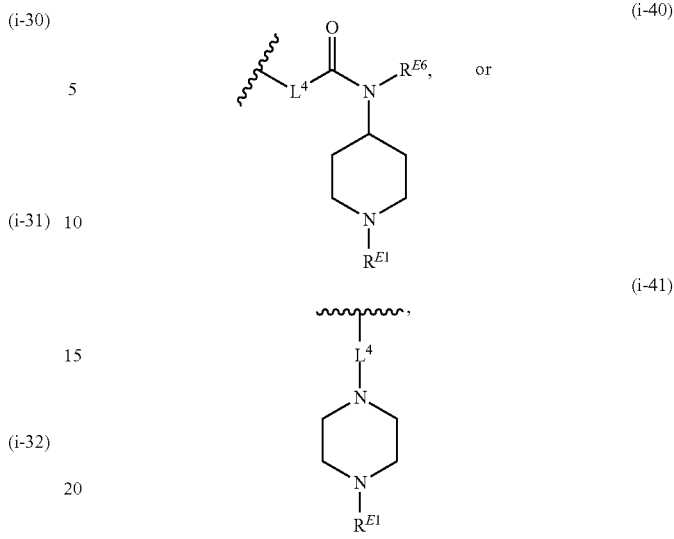

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{ee}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{64}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or $NR^{E7}$, wherein $R^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

As generally defined herein in Formulae (I'), (II'), (I), and (II), $R^1$ is hydrogen, halogen, or optionally substituted alkyl. As generally defined herein in Formulae (I)-(II), $R^1$ is hydrogen, halogen, or optionally substituted alkyl. In certain embodiments, $R^1$ is hydrogen. In certain embodiments, $R^1$ is halogen. In certain embodiments, $R^1$ is F. In certain embodiments, $R^1$ is Cl. In certain embodiments, $R^1$ is Br. In certain embodiments, $R^1$ is I. In certain embodiments, $R^1$ is optionally substituted alkyl. In certain embodiments, $R^1$ is unsubstituted alkyl. In certain embodiments, $R^1$ is unsubstituted $C_{1-6}$alkyl. In certain embodiments, $R^1$ is methyl. In certain embodiments, $R^1$ is substituted alkyl. In certain embodiments, $R^1$ is substituted $C_{1-6}$alkyl.

In certain embodiments, M is O. In certain embodiments, M is S. In certain embodiments, M is $NR^M$, wherein $R^M$ is as defined herein. In certain embodiments, M is NH. In certain embodiments, M is $NR^M$, wherein $R^M$ is optionally substituted alkyl. In certain embodiments, M is $NR^M$, wherein $R^M$ is unsubstituted alkyl. In certain embodiments, M is $NCH_3$. In certain embodiments, M is NAc.

Compounds of any one of Formulae (I'), (II'), (I), and (II) include Ring A attached to linker X. Compounds of any one of Formulae (I)-(II) include Ring A attached to linker X. Ring A may be optionally substituted monocyclic carbocyclyl, optionally substituted monocyclic heterocyclyl, optionally substituted phenyl, or optionally substituted monocyclic heteroaryl. In certain embodiments, Ring A is optionally substituted monocyclic carbocyclyl. In certain embodiments, Ring A is optionally substituted cyclohexyl. In certain embodiments, Ring A is optionally substituted monocyclic heterocyclyl. In certain embodiments, Ring A is optionally substituted piperidinyl. In certain embodiments, Ring A is optionally substituted piperizinyl. In certain embodiments, Ring A is optionally substituted tetrahydropyranyl. In certain embodiments, Ring A is optionally substituted phenyl. In certain embodiments, Ring A is phenyl substituted with only X. In certain embodiments, Ring A is optionally substituted monocyclic heteroaryl. In certain embodiments, Ring A is optionally substituted 5-membered heteroaryl. In certain embodiments, Ring A is optionally substituted 6-membered heteroaryl. In certain embodiments, Ring A is optionally substituted pyridine. In certain embodiments, Ring A is optionally substituted pyrimidine.

In certain embodiments, Ring A is of Formula (x-i):

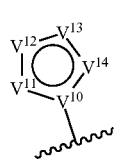

(x-i)

wherein:

each of $V^{10}$, $V^{11}$, $V^{12}$, $V^{13}$, and $V^{14}$ is independently O, S, N, $NR^{A1}$, C, or $CR^{A2}$, as valency permits;

each instance of $R^{A1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, and a nitrogen protecting group;

each instance of $R^{A2}$ is independently selected from the group consisting of hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —$OR^{A2a}$, —$N(R^{A2a})_2$, and —$SR^{A2a}$; and each occurrence of $R^{A2a}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two $R^{A2a}$ groups are joined to form a substituted or unsubstituted heterocyclic ring.

In certain embodiments, only one of $V^{10}$, $V^{11}$, $V^{12}$, $V^{13}$, and $V^{14}$ is selected from the group consisting of O, S, N, and $NR^{A1}$. In certain embodiments, Ring A is of the formula:

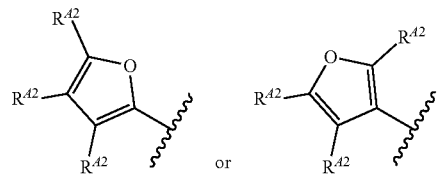

In certain embodiments, Ring A is of the formula:

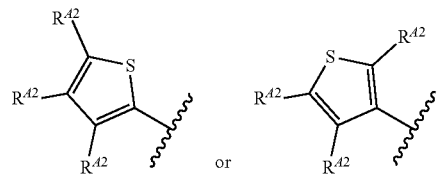

In certain embodiments, Ring A is of the formula:

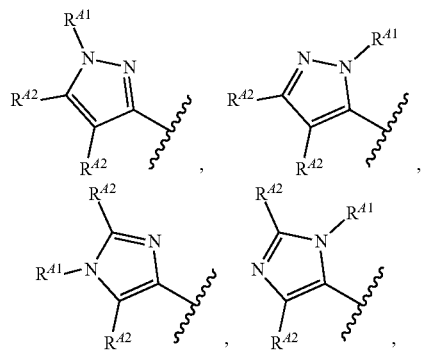

-continued

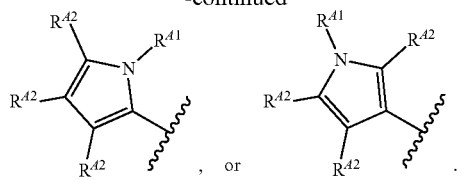

In certain embodiments, only two of $V^{10}$, $V^{11}$, $V^{12}$, $V^{13}$, and $V^{14}$ are each independently selected from the group consisting of O, S, N, and $NR^{A1}$. In certain embodiments, Ring A is of the formula:

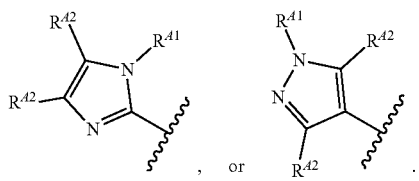

In certain embodiments, Ring A is of the formula:

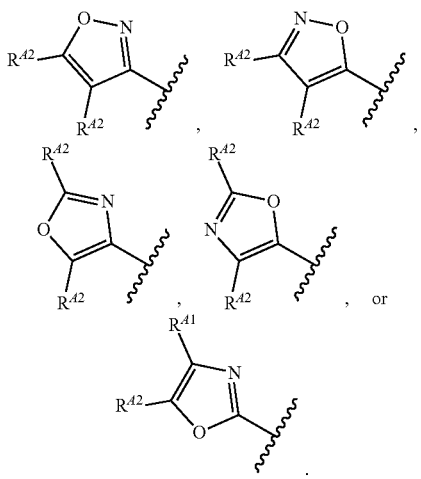

In certain embodiments, Ring A is of Formula (x-ii):

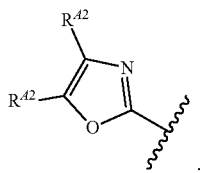
(x-ii)

In certain embodiments, Ring A is of the formula:

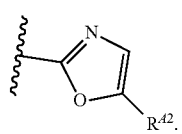

In certain embodiments, Ring A is of the formula:

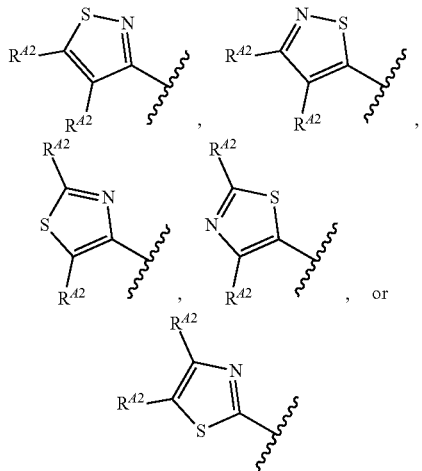

In certain embodiments, Ring A is of the formula:

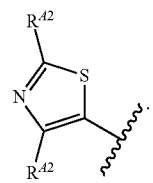

In certain embodiments, Ring A is of the formula:

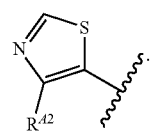

In certain embodiments, Ring A is of the formula:

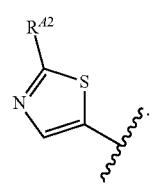

In certain embodiments, Ring A is of the formula:

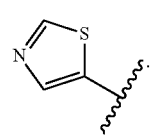

In certain embodiments, only three of $V^{10}$, $V^{11}$, $V^{12}$, $V^{13}$, and $V^{14}$ are each independently selected from the group consisting of O, S, N, and $NR^{A1}$. In certain embodiments, Ring A is of the formula:

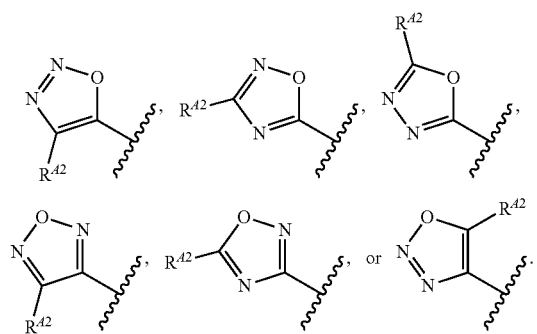

In certain embodiments, Ring A is of the formula:

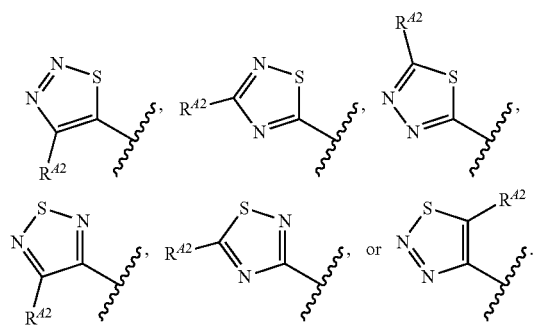

In certain embodiments, Ring A is of the formula:

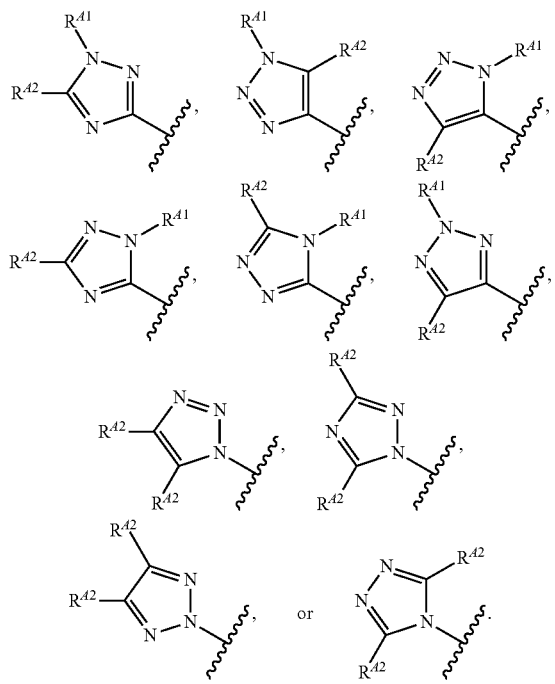

In certain embodiments, only four of $V^{10}$, $V^{11}$, $V^{12}$, $V^{13}$, and $V^{14}$ are each independently selected from the group consisting of N and $NR^{A1}$. In certain embodiments, Ring A is of the formula:

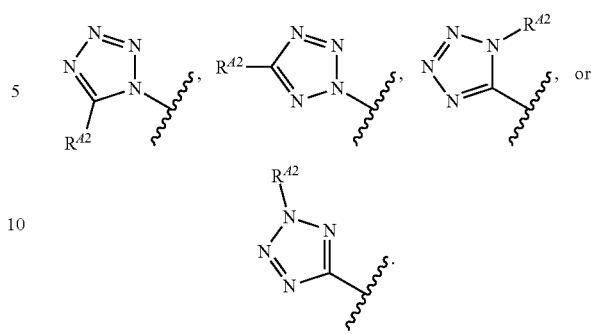

In certain embodiments, Ring A may also be a substituted or unsubstituted 6-membered heteroaryl ring. In certain embodiments, Ring A is of the formula:

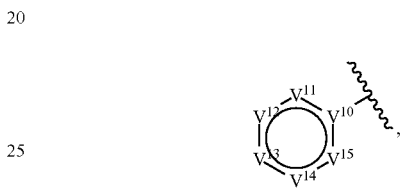

wherein each of $V^{10}$, $V^{11}$, $V^{12}$, $V^{13}$, $V^{14}$, and $V^{15}$ is independently N, C, or $CR^{A2}$, as valency permits, wherein $R^{A2}$ is as defined herein. In certain embodiments, only one of $V^{10}$, $V^{11}$, $V^{12}$, $V^{13}$, $V^{14}$, and $V^{15}$ is N. In certain embodiments, Ring A is of the formula:

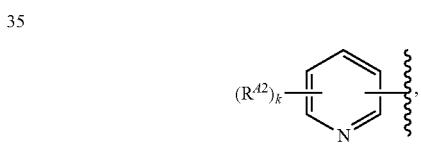

wherein k is 0, 1, 2, 3, or 4, and $R^{A2}$ is as defined herein. In certain embodiments, Ring A is of the formula:

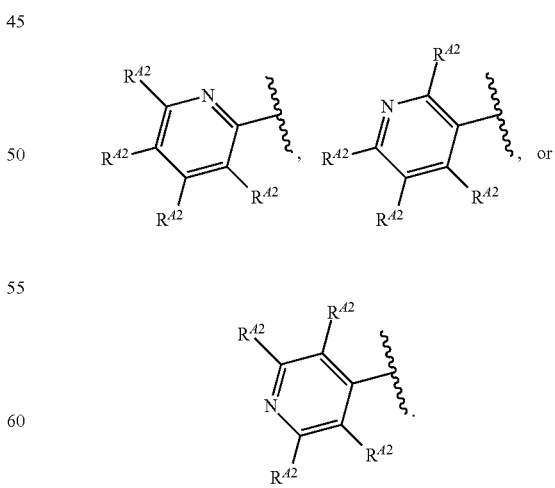

In certain embodiments, only two of $V^{10}$, $V^{11}$, $V^{12}$, $V^{13}$, $V^{14}$, and $V^{15}$ are N. In certain embodiments, Ring A is of the formula:

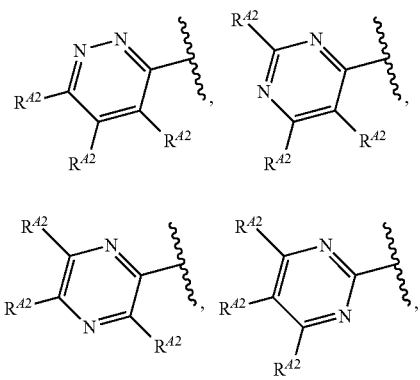

In certain embodiments, only three of $V^{10}$, $V^{11}$, $V^{12}$, $V^{13}$, $V^{14}$, and $V^{15}$ are N. In certain embodiments, Ring A is of the formula:

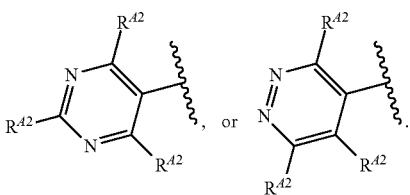

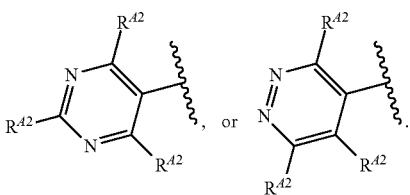

In certain embodiments, Ring A is of the formula:

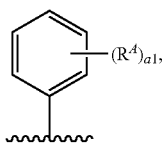

wherein $R^A$ and a1 are as defined herein.

In certain embodiments, a1 is 1; and Ring A is one of the formulae:

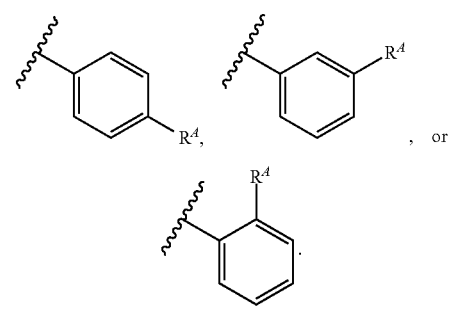

In certain embodiments, a1 is 2; and Ring A is one of the formulae:

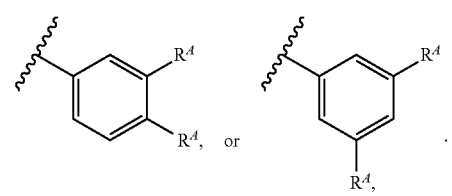

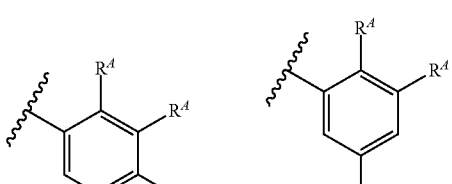

In certain embodiments, a2 is 3; and $R_{61}$ is one of the formulae:

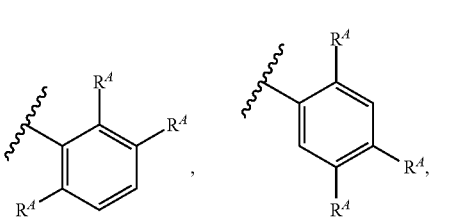

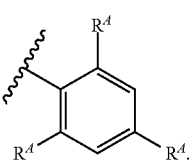

In certain embodiments, a2 is 4; and $R_{61}$ is one of the formulae:

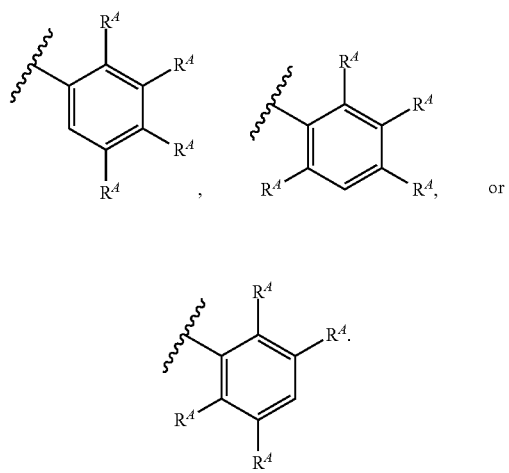

In certain embodiments, a2 is 5; and $R_{61}$ is of the formula

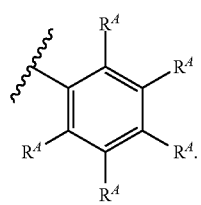

In certain embodiments, Ring A is of the formula:

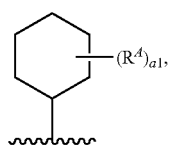

wherein $R^A$ and a1 are as defined herein.

In certain embodiments, a1 is 1; and Ring A is one of the formulae:

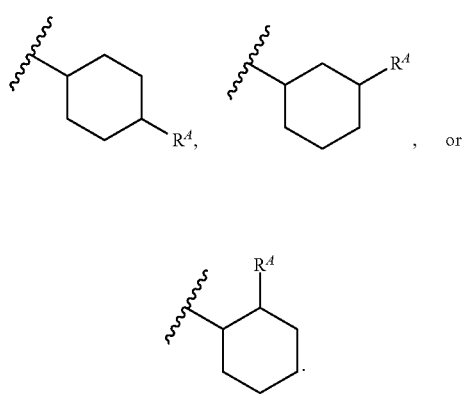

In certain embodiments, a1 is 2; and Ring A is one of the formulae:

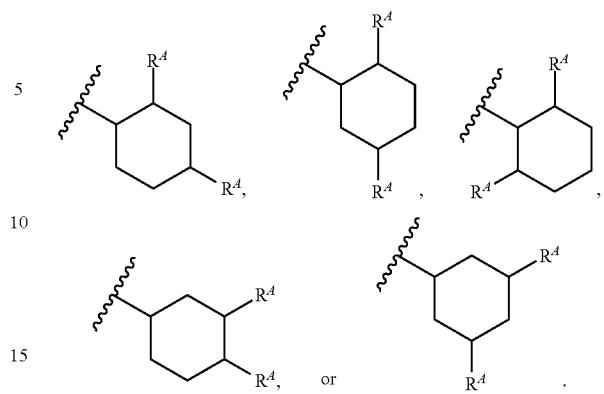

In certain embodiments, a2 is 3; and $R_{61}$ is one of the formulae:

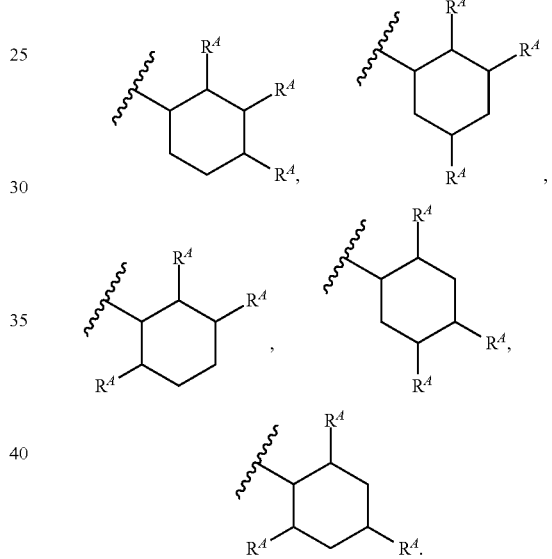

In certain embodiments, a2 is 4; and $R_{61}$ is one of the formulae:

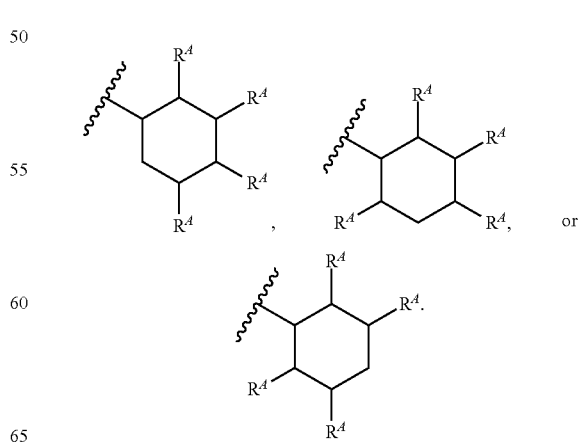

In certain embodiments, a2 is 5; and $R_{61}$ is of the formula

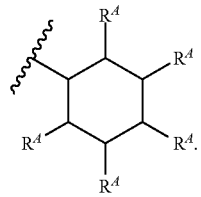

In certain embodiments, Ring A is optionally substituted monocyclic heterocyclyl. In certain embodiments, Ring A is optionally substituted 5-membered heterocyclyl. In certain embodiments, Ring A is optionally substituted 6-membered heterocyclyl. In certain embodiments, Ring A is optionally substituted 6-membered heterocyclyl with one heteroatom selected from the group of S, O, and N.

In certain embodiments, Ring A is of the formula:

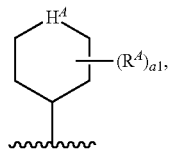

wherein $H^A$ is S, O, or $NR^{HA}$; $R^{HA}$ is hydrogen, optionally substituted alkyl, or a nitrogen protecting group; and $R^A$ and a1 are as defined herein.

In certain embodiments, Ring A is of the formula:

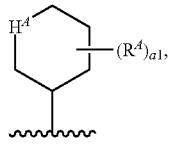

wherein $H^A$, $R^A$ and a1 are as defined herein.

In certain embodiments, Ring A is of the formula:

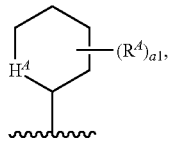

wherein $H^A$, $R^A$ and a1 are as defined herein.

In certain embodiments, $H^A$ is S. In certain embodiments, $H^A$ is O. In certain embodiments, $H^A$ is $NR^{HA}$.

In certain embodiments, Ring A is of the formula:

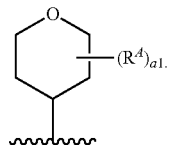

In certain embodiments, Ring A is of the formula:

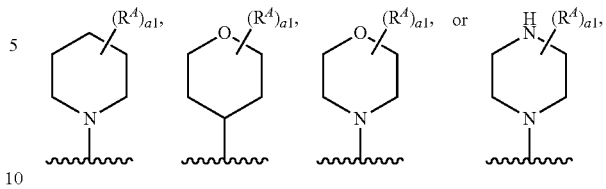

wherein $R^{HA}$ is hydrogen, optionally substituted alkyl, or a nitrogen protecting group; and $R^A$ and a1 are as defined herein. In certain embodiments, Ring A is of the formula:

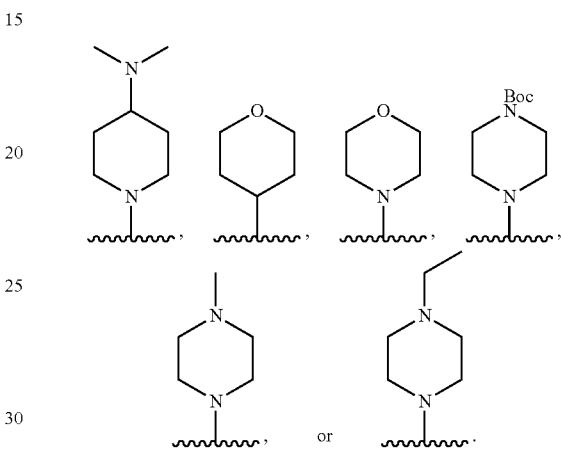

In certain embodiments, $R^A$ is hydrogen. In certain embodiments, $R^A$ is halogen. In certain embodiments, $R^A$ is F. In certain embodiments, $R^A$ is Cl. In certain embodiments, $R^A$ is Br. In certain embodiments, $R^A$ is I. In certain embodiments, $R^A$ is optionally substituted alkyl. In certain embodiments, $R^A$ is unsubstituted alkyl. In certain embodiments, $R^A$ is methyl, ethyl, n-propyl, i-propyl, n-butyl, 5-butyl, i-butyl, n-pentyl, i-pentyl, neo-pentyl, i-pentyl, 5-pentyl, or 3-pentyl. In certain embodiments, $R^A$ is i-butyl. In certain embodiments, $R^A$ is substituted alkyl. In certain embodiments, $R^A$ is haloalkyl. In certain embodiments, $R^A$ is —$CF_3$, —$CHF_2$, or —$CH_2F$. In certain embodiments, $R^A$ is optionally substituted alkenyl. In certain embodiments, $R^A$ is optionally substituted alkynyl. In certain embodiments, $R^A$ is optionally carbocyclyl. In certain embodiments, $R^A$ is optionally substituted heterocyclyl. In certain embodiments, $R^A$ is optionally substituted aryl. In certain embodiments, $R^A$ is optionally substituted heteroaryl. In certain embodiments, $R^A$ is —$OR^a$, wherein $R^a$ is as defined herein. In certain embodiments, $R^A$ is —OH. In certain embodiments, $R^A$ is —$OR^a$, wherein $R^a$ is optionally substituted alkyl or an oxygen protecting group. In certain embodiments, $R^A$ is —$OR^a$, wherein $R^a$ is unsubstituted alkyl. In certain embodiments, $R^A$ is —$OCH_3$. In certain embodiments, $R^A$ is —$N(R^a)_2$, wherein $R^a$ is as defined herein. In certain embodiments, $R^A$ is —$NH_2$. In certain embodiments, $R^A$ is —$N(R^a)_2$, wherein each instance of $R^a$ is optionally substituted alkyl or a nitrogen protecting group. In certain embodiments, $R^A$ is —$N(CH_3)_2$. In certain embodiments, $R^A$ is —$NHR^a$, wherein $R^a$ is optionally substituted alkyl or a nitrogen protecting group. In certain embodiments, $R^A$ is —$NHCH_3$.

In certain embodiments, at least one instance of $R^{A1}$ is H (hydrogen). In certain embodiments, at least one instance of $R^{A1}$ is halogen. In certain embodiments, at least one instance of $R^{A1}$ is F (fluorine). In certain embodiments, at least one instance of $R^{A1}$ is Cl (chlorine). In certain embodiments, at least one instance of $R^{41}$ is Br (bromine). In certain embodiments, at least one instance of $R^{41}$ is I (iodine). In certain embodiments, at least one instance of $R^{41}$ is substituted acyl. In certain embodiments, at least one instance of $R^{41}$ is unsubstituted acyl. In certain embodiments, at least one instance of $R^{41}$ is acetyl. In certain embodiments, at least one instance of $R^{41}$ is substituted acetyl. In certain embodiments, at least one instance of $R^{41}$ is substituted alkyl. In certain embodiments, at least one instance of $R^{41}$ is unsubstituted alkyl. In certain embodiments, at least one instance of $R^{41}$ is $C_{1-6}$ alkyl. In certain embodiments, at least one instance of $R^{41}$ is methyl. In certain embodiments, at least one instance of $R^{41}$ is ethyl. In certain embodiments, at least one instance of $R^{41}$ is propyl. In certain embodiments, at least one instance of $R^{41}$ is butyl. In certain embodiments, at least one instance of $R^{41}$ is substituted alkenyl. In certain embodiments, at least one instance of $R^{41}$ is unsubstituted alkenyl. In certain embodiments, at least one instance of $R^{41}$ is vinyl. In certain embodiments, at least one instance of $R^{41}$ is substituted alkynyl. In certain embodiments, at least one instance of $R^{41}$ is unsubstituted alkynyl. In certain embodiments, at least one instance of $R^{41}$ is ethynyl. In certain embodiments, at least one instance of $R^{41}$ is substituted carbocyclyl. In certain embodiments, at least one instance of $R^{41}$ is unsubstituted carbocyclyl. In certain embodiments, at least one instance of $R^{41}$ is substituted heterocyclyl. In certain embodiments, at least one instance of $R^{41}$ is unsubstituted heterocyclyl. In certain embodiments, at least one instance of $R^{41}$ is substituted aryl. In certain embodiments, at least one instance of $R^{41}$ is unsubstituted aryl. In certain embodiments, at least one instance of $R^{41}$ is substituted phenyl. In certain embodiments, at least one instance of $R^{41}$ is unsubstituted phenyl. In certain embodiments, at least one instance of $R^{41}$ is substituted heteroaryl. In certain embodiments, at least one instance of $R^{41}$ is unsubstituted heteroaryl. In certain embodiments, at least one instance of $R^{41}$ is substituted pyridyl. In certain embodiments, at least one instance of $R^{41}$ is unsubstituted pyridyl. In certain embodiments, at least one instance of $R^{41}$ is a nitrogen protecting group. In certain embodiments, at least one instance of $R^{41}$ is BOC.

In certain embodiments, at least one $R^{41}$ is hydrogen, substituted or unsubstituted $C_{1-6}$ alkyl, or a nitrogen protecting group. In certain embodiments, all instances of $R^{41}$ are each independently hydrogen, substituted or unsubstituted $C_{1-6}$ alkyl, or a nitrogen protecting group. In certain embodiments, all instances of $R^{41}$ are hydrogen.

In certain embodiments, at least one $R^{42}$ is H. In certain embodiments, at least one $R^{42}$ is halogen. In certain embodiments, at least one $R^{42}$ is F. In certain embodiments, at least one $R^{42}$ is Cl. In certain embodiments, at least one $R^{42}$ is Br. In certain embodiments, at least one $R^{42}$ is I (iodine). In certain embodiments, at least one $R^{42}$ is substituted acyl. In certain embodiments, at least one $R^{42}$ is unsubstituted acyl. In certain embodiments, at least one $R^{42}$ is acetyl. In certain embodiments, at least one $R^{42}$ is substituted acetyl. In certain embodiments, at least one $R^{42}$ is substituted alkyl. In certain embodiments, at least one $R^{42}$ is unsubstituted alkyl. In certain embodiments, at least one $R^{42}$ is $C_{1-6}$ alkyl. In certain embodiments, at least one $R^{42}$ is methyl. In certain embodiments, at least one $R^{42}$ is ethyl. In certain embodiments, at least one $R^{42}$ is propyl. In certain embodiments, at least one $R^{42}$ is butyl. In certain embodiments, at least one $R^{42}$ is substituted alkenyl. In certain embodiments, at least one $R^{42}$ is unsubstituted alkenyl. In certain embodiments, at least one $R^{42}$ is vinyl. In certain embodiments, at least one $R^{42}$ is substituted alkynyl. In certain embodiments, at least one $R^{42}$ is unsubstituted alkynyl. In certain embodiments, at least one $R^{42}$ is ethynyl. In certain embodiments, at least one $R^{42}$ is substituted carbocyclyl. In certain embodiments, at least one $R^{42}$ is unsubstituted carbocyclyl. In certain embodiments, at least one $R^{42}$ is substituted heterocyclyl. In certain embodiments, at least one $R^{42}$ is unsubstituted heterocyclyl. In certain embodiments, at least one $R^{42}$ is substituted aryl. In certain embodiments, at least one $R^{42}$ is unsubstituted aryl. In certain embodiments, at least one $R^{42}$ is substituted phenyl. In certain embodiments, at least one $R^{42}$ is unsubstituted phenyl. In certain embodiments, at least one $R^{42}$ is substituted heteroaryl. In certain embodiments, at least one $R^{42}$ is unsubstituted heteroaryl. In certain embodiments, at least one $R^{42}$ is substituted pyridyl. In certain embodiments, at least one $R^{42}$ is unsubstituted pyridyl. In certain embodiments, at least one $R^{42}$ is $-OR^{42a}$, wherein $R^{42a}$ is as defined herein. In certain embodiments, at least one $R^{42}$ is $-OR^{42a}$, wherein $R^{42a}$ is hydrogen. In certain embodiments, at least one $R^{42}$ is $-OR^{42a}$, wherein $R^{42a}$ is substituted or unsubstituted $C_{1-6}$ alkyl. In certain embodiments, at least one $R^{42}$ is $-OR^{42a}$, wherein $R^{42a}$ is unsubstituted $C_{1-6}$ alkyl. In certain embodiments, at least one $R^{42}$ is $-OCH_3$. In certain embodiments, at least one $R^{42}$ is $-N(R^{42a})_2$. In certain embodiments, at least one $R^{42}$ is $-SR^{42a}$. In certain embodiments, all instances of $R^{42}$ are hydrogen.

In certain embodiments, all $R^{41}$ and $R^{42}$ are hydrogen. In certain embodiments, $R^{41}$ is hydrogen; and at least one $R^{42}$ is substituted or unsubstituted alkyl. In certain embodiments, $R^{41}$ is hydrogen; and at least one $R^{42}$ is unsubstituted alkyl. In certain embodiments, $R^{41}$ is hydrogen; and at least one $R^{42}$ is methyl, ethyl, or n-propyl. In certain embodiments, $R^{41}$ is hydrogen; and at least one $R^{42}$ is-$OR^{42a}$, wherein $R^{42a}$ is as defined herein. In certain embodiments, $R^{41}$ is hydrogen; and at least one $R^{42}$ is-$OR^{42a}$, wherein $R^{42a}$ is substituted or unsubstituted $C_{1-6}$ alkyl. In certain embodiments, $R^{41}$ is hydrogen; and at least one $R^{42}$ is-$OR^{42a}$, wherein $R^{42a}$ is unsubstituted $C_{1-6}$ alkyl. In certain embodiments, $R^{41}$ is hydrogen; and at least one $R^{42}$ is $-OCH_3$.

In certain embodiments, Ring A is of the formula:

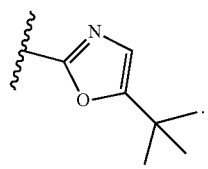 [SMILES: *c1ncc(C(C)(C)C)o1]

In certain embodiments, Ring A is of the formula:

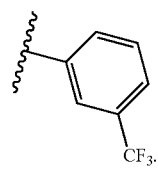 [SMILES: *c1cccc(C(F)(F)F)c1]

In certain embodiments, Ring A is of the formula:

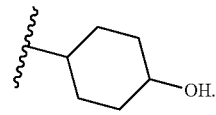 [SMILES: *C1CCC(O)CC1]

In certain embodiments, Ring A is of one of the formula:

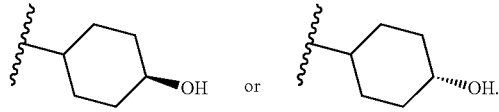

In certain embodiments, Ring A is of the formula:

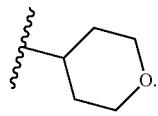 [SMILES: *C1CCOCC1]

Compounds of any one of Formulae (I'), (II'), (I), and (II) include Ring B between linker $L^1$ and linker $L^2$. Compounds of any one of Formulae (I)-(II) include Ring B between linker $L^1$ and linker $L^2$. Ring B may be optionally substituted monocyclic carbocyclyl, optionally substituted monocyclic heterocyclyl, optionally substituted phenyl, or optionally substituted monocyclic heteroaryl. In certain embodiments, Ring B is optionally substituted monocyclic carbocyclyl. In certain embodiments, Ring B is optionally substituted monocyclic heterocyclyl. In certain embodiments, Ring B is optionally substituted pyrrolidinyl. In certain embodiments, Ring B is optionally substituted phenyl. In certain embodiments, Ring B is optionally substituted monocyclic heteroaryl. In certain embodiments, Ring B is phenyl substituted with only $L^1$ and $L^2$. In certain embodiments, Ring B is optionally substituted cyclohexyl. In certain embodiments, Ring B is optionally substituted piperidinyl. In certain embodiments, Ring B is optionally substituted piperizinyl. In certain embodiments, Ring B is optionally substituted pyridinyl. In certain embodiments, Ring B is optionally substituted pyrimidinyl.

In certain embodiments of Formulae (I'), (II'), (I), and (II), Ring B is

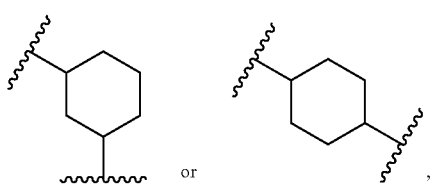 [SMILES: *C1CCCC(*)C1 ; *C1CCC(*)CC1]

wherein each ring atom is optionally substituted. In certain embodiments, Ring B is

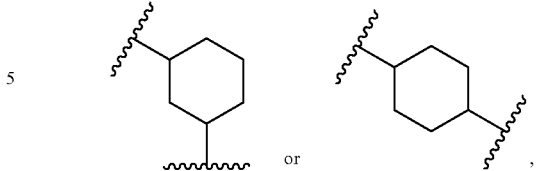

wherein each ring atom is optionally substituted. In certain embodiments, Ring B is

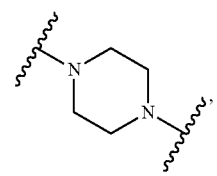 [SMILES: *N1CCN(*)CC1]

wherein each ring atom is optionally substituted. In certain embodiments, Ring B is

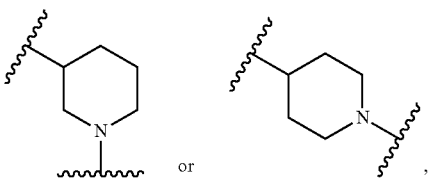 [SMILES: *C1CCCN(*)C1 ; *C1CCN(*)CC1]

wherein each ring atom is optionally substituted, and $L^1$ and $L^2$ may attach to Ring B at either indicated position. In certain embodiments, Ring B is

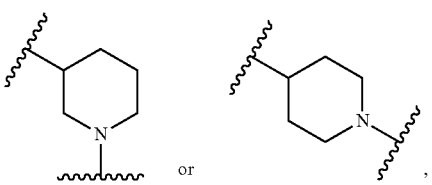 [SMILES: *C1CCCN(*)C1 ; *C1CCN(*)CC1]

wherein each ring atom is optionally substituted, and $L^2$ and $R^2$ may attach to Ring B at either indicated position. In certain embodiments, Ring B is

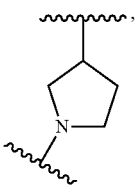 [SMILES: *C1CCN(*)C1]

wherein each ring atom is optionally substituted, and $L^2$ and $R^2$ is attached to Ring B at either position indicated. In certain embodiments, Ring B is

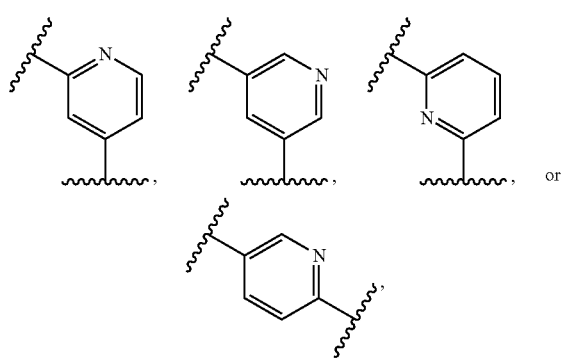

wherein each ring atom is optionally substituted, and L¹ and L² may attach to Ring B at either indicated position. In certain embodiments, Ring B is

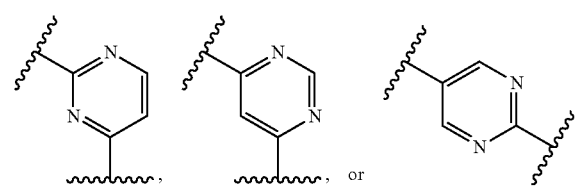

wherein each ring atom is optionally substituted, and L¹ and L² may attach to Ring B at either indicated position.

Compounds of Formula (I') and (I) include Ring C between linker L¹ and R². Ring C may be optionally substituted monocyclic carbocyclyl, optionally substituted monocyclic heterocyclyl, optionally substituted phenyl, or optionally substituted monocyclic heteroaryl. In certain embodiments, Ring C is optionally substituted monocyclic carbocyclyl. In certain embodiments, Ring C is optionally substituted monocyclic heterocyclyl. In certain embodiments, Ring C is optionally substituted monocyclic aryl. In certain embodiments, Ring C is optionally substituted phenyl. In certain embodiments, Ring C is optionally substituted bicyclic aryl. In certain embodiments, Ring C is optionally substituted 2,3-dihydro-1H-indene. In certain embodiments, Ring C is optionally substituted naphthalene. In certain embodiments, Ring C is:

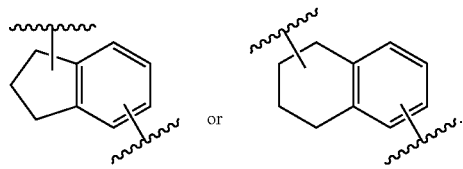

In certain embodiments, Ring C is:

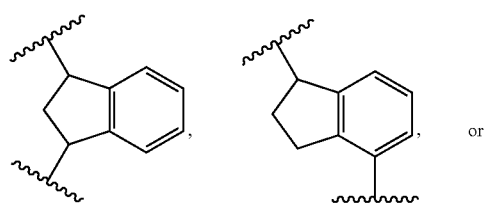

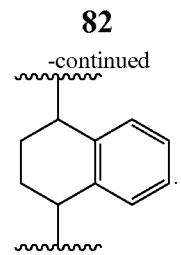

In certain embodiments, Ring C is optionally substituted monocyclic heteroaryl. In certain embodiments, Ring C is phenyl substituted with only L¹ and R². In certain embodiments, Ring C is optionally substituted cyclohexyl. In certain embodiments, Ring C is optionally substituted pyridinone. In certain embodiments, Ring C is:

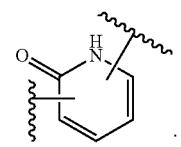

In certain embodiments, Ring C is:

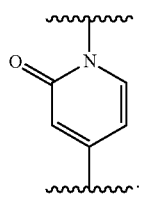

In certain embodiments, Ring C is optionally substituted piperidinyl. In certain embodiments, Ring C is optionally substituted piperizinyl. In certain embodiments, Ring C is optionally substituted pyridinyl. In certain embodiments, Ring C is optionally substituted pyrimidinyl. In certain embodiments, Ring C is optionally substituted bicyclic heteroaryl. In certain embodiments, Ring C is optionally substituted indolyl. In certain embodiments, Ring C is optionally substituted indolinyl. In certain embodiments, Ring C is:

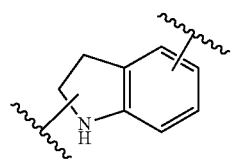

In certain embodiments, Ring C is:

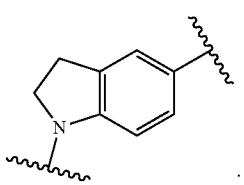 [SMILES: *c1ccc2c(c1)CCN2*]

In certain embodiments, for Formula (I'), $L^1$ is —CH$_2$—. In certain embodiments, for Formula (I'), $L^1$ is $^{lc}$—S(=O)$_2$—$^{lb}$. In certain embodiments, $L^1$ is —O—. In certain embodiments, $L^1$ is —S—. In certain embodiments, $L^1$ is —NR$^{L1}$—. In certain embodiments, $L^1$ is —C(=O)—. In certain embodiments, $L^1$ is —NR$^{L1}$—. In certain embodiments, $L^1$ is $^{lc}$—OC(=O)—$^{lb}$. In certain embodiments, $L^1$ is $^{lc}$—C(=O)O—$^{lb}$. In certain embodiments, $L^1$ is $^{lc}$—NR$^{L1}$C(=O)—$^{lb}$. In certain embodiments, $L^1$ is $^{lc}$—C(=O)NR$^{L1}$—$^{lb}$. As used herein, $^{lb}$ indicates the point of attachment is to Ring B; and $^{lc}$ indicates the point of attachment is to Ring C.

In certain embodiments, $R^{L1}$ is hydrogen. In certain embodiments, $R^{L1}$ is optionally substituted $C_{1-6}$ alkyl. In certain embodiments, $R^{L1}$ is unsubstituted $C_{1-6}$ alkyl. In certain embodiments, $R^{L1}$ is methyl. In certain embodiments, $R^{L1}$ is substituted $C_{1-6}$ alkyl. In certain embodiments, $R^{L1}$ is a nitrogen protecting group.

In certain embodiments, $L^2$ is —O—. In certain embodiments, $L^2$ is —S—. In certain embodiments, $L^2$ is —NR$^{L2}$—. In certain embodiments, $L^2$ is $^{lb}$—NR$^{L2}$C(=O)—$^{lm}$. In certain embodiments, $L^2$ is $^{lb}$—C(=O)NR$^{L2}$—$^{lm}$. As used herein, $^{lb}$ indicates the point of attachment is to Ring B; and $^{lm}$ indicates the point of attachment is to the heteroaryl ring with M.

In certain embodiments, $R^{L2}$ is hydrogen. In certain embodiments, $R^{12}$ is optionally substituted $C_{1-6}$ alkyl. In certain embodiments, $R^{L2}$ is unsubstituted $C_{1-6}$ alkyl. In certain embodiments, $R^{L2}$ is methyl. In certain embodiments, $R^{L2}$ is substituted $C_{1-6}$ alkyl. In certain embodiments, $R^{L2}$ is a nitrogen protecting group.

In certain embodiments, for Formula (II'), X is a bond. In certain embodiments, for Formula (I'), X is $^{xm}$—CH$_2$CH$_2$—$^{xa}$. In certain embodiments, for Formula (I'), X is $^{xm}$—CH=CH—$^{xa}$. In certain embodiments, for Formula (I'), X is $^{xm}$—CH$_2$—NR$^{LX}$—$^{xa}$. In certain embodiments, for Formula (I'), X is $^{xm}$—CH$_2$—NH—$^{xa}$. In certain embodiments, for Formula (I'), X is $^{xm}$—CH$_2$—O—CH$_2$—$^{xa}$. In certain embodiments, for Formula (I'), X is $^{xm}$—CH$_2$—NH—CH$_2$—$^{xa}$. In certain embodiments, X is —O—. In certain embodiments, X is —S—. In certain embodiments, X is $^{xm}$—S—C(=O)CH$_2$—$^{xa}$. In certain embodiments, X is —NR$^{LX}$—. In certain embodiments, X is —O—CH$_2$—. In certain embodiments, X is —S—CH$_2$—. In certain embodiments, X is —NR$^{LX}$—CH$_2$—. In certain embodiments, X is —NH—CH$_2$—.

In certain embodiments, a1 is 1. In certain embodiments, a1 is 2. In certain embodiments, a1 is 3.

In certain embodiments, b1 is 1. In certain embodiments, b1 is 2. In certain embodiments, b1 is 3.

In certain embodiments, c1 is 1. In certain embodiments, c1 is 2. In certain embodiments, c1 is 3.

In certain embodiments, $R^B$ is optionally substituted alkyl. In certain embodiments, $R^B$ is optionally substituted $C_1$-$C_6$ alkyl. In certain embodiments, $R^B$ is unsubstituted $C_1$-$C_6$ alkyl. In certain embodiments, $R^B$ is methyl or ethyl. In certain embodiments, $R^B$ is substituted $C_1$-$C_6$ alkyl. In certain embodiments, $R^B$ is hydroxy $C_1$-$C_6$ alkyl. In certain embodiments, $R^B$ is —CH$_2$OH. In certain embodiments, $R^B$ is —CH$_2$CH$_2$OH. In certain embodiments, $R^B$ is —N(R$^a$)$_2$, wherein $R^a$ is as defined herein. In certain embodiments, $R^B$ is —NHR$^a$, wherein $R^a$ is as defined herein. In certain embodiments, $R^B$ is —NHR$^a$, wherein $R^a$ is hydrogen or optionally substituted $C_1$-$C_6$ alkyl. In certain embodiments, $R^B$ is —NH2. In certain embodiments, $R^B$ is —NHR$^a$, wherein $R^a$ is optionally substituted $C_1$-$C_6$ alkyl. In certain embodiments, $R^B$ is —NHR$^a$, wherein $R^a$ is unsubstituted $C_1$-$C_6$ alkyl. In certain embodiments, $R^B$ is —NHR$^a$, wherein $R^a$ is methyl or ethyl. In certain embodiments, $R^B$ is —NHCH$_3$. In certain embodiments, $R^B$ is —NHR$^a$ wherein $R^a$ is a nitrogen protecting group. In certain embodiments, $R^B$ is —N(CH$_3$)R$^a$, wherein $R^a$ is optionally substituted $C_1$-$C_6$ alkyl. In certain embodiments, $R^B$ is —N(CH$_3$)R$^a$, wherein $R^a$ is unsubstituted $C_1$-$C_6$ alkyl. In certain embodiments, $R^B$ is —N(CH$_3$)R$^a$, wherein $R^a$ is methyl or ethyl. In certain embodiments, $R^B$ is —N(CH$_3$)$_2$. In certain embodiments, $R^B$ is —N(CH$_3$)R$^a$, wherein $R^a$ is a nitrogen protecting group.

In certain embodiments, $R^c$ is optionally substituted alkyl. In certain embodiments, $R^c$ is optionally substituted $C_1$-$C_6$ alkyl. In certain embodiments, $R^c$ is unsubstituted $C_1$-$C_6$ alkyl. In certain embodiments, $R^c$ is methyl or ethyl. In certain embodiments, $R^c$ is substituted $C_1$-$C_6$ alkyl. In certain embodiments, $R^c$ is hydroxy $C_1$-$C_6$ alkyl. In certain embodiments, $R^c$ is —CH$_2$OH. In certain embodiments, $R^c$ is —CH$_2$CH$_2$OH. In certain embodiments, $R^c$ is —N(R$^a$)$_2$, wherein $R^a$ is as defined herein. In certain embodiments, $R^c$ is —NHR$^a$, wherein $R^a$ is as defined herein. In certain embodiments, $R^c$ is —NHR$^a$, wherein $R^a$ is hydrogen or optionally substituted $C_1$-$C_6$ alkyl. In certain embodiments, $R^c$ is —NH2. In certain embodiments, $R^c$ is —NHR$^a$, wherein $R^a$ is optionally substituted $C_1$-$C_6$ alkyl. In certain embodiments, $R^c$ is —NHR$^a$, wherein $R^a$ is unsubstituted $C_1$-$C_6$ alkyl. In certain embodiments, $R^c$ is —NHR$^a$, wherein $R^a$ is methyl or ethyl. In certain embodiments, $R^C$ is —NHCH$_3$. In certain embodiments, $R^C$ is —NHR$^a$, wherein $R^a$ is a nitrogen protecting group. In certain embodiments, $R^C$ is —N(CH$_3$)R$^a$, wherein $R^a$ is optionally substituted $C_1$-$C_6$ alkyl. In certain embodiments, $R^C$ is —N(CH$_3$)R$^a$, wherein $R^a$ is unsubstituted $C_1$-$C_6$ alkyl. In certain embodiments, $R^C$ is —N(CH$_3$)R$^a$, wherein $R^a$ is methyl or ethyl. In certain embodiments, $R^C$ is —N(CH$_3$)$_2$. In certain embodiments, $R^C$ is —N(CH$_3$)R$^a$, wherein $R^a$ is a nitrogen protecting group.

Compounds of Formula (I') include $R^2$ attached to Ring C. Compounds of Formula (I) include $R^2$ attached to Ring C. Compounds of Formula (I) include $R^2$ attached to Ring B. Compounds of Formula (I') include $R^2$ attached to Ring B. In certain embodiments, $R^2$ comprises an electrophilic moiety. In certain embodiments, $R^2$ comprises a Michael acceptor moiety. The electrophilic moiety (e.g., Michael acceptor moiety) may react with a cysteine residue of a kinase (e.g., CDK (e.g., CDK7)) to allow for covalent attachment of the compound to the kinase. In certain embodiments, the electrophilic moiety (e.g., Michael acceptor moiety) may react with a cysteine residue of a kinase (e.g., CDK (e.g., CDK7)). In certain embodiments, the electrophilic moiety (e.g., Michael acceptor moiety) may react with the Cys312 residue of CDK7. In certain embodiments, the covalent attachment is irreversible. In certain embodiments, the covalent attachment is reversible.

As generally defined herein in Formulae (I'), (II'), (I), and (II), $R^2$ may be any one of Formulae (i-1)-(i-41). In certain embodiments, $R^2$ is of Formula (i-1):

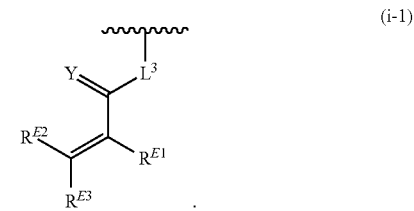

(i-1)

In certain embodiments, $R^2$ is of Formula (i-2):

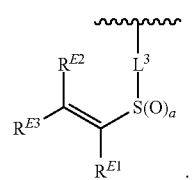 (i-2)

In certain embodiments, $R^2$ is of Formula (i-3):

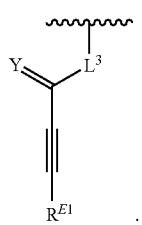 (i-3)

In certain embodiments, $R^2$ is of Formula (i-4):

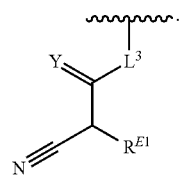 (i-4)

In certain embodiments, $R^2$ is of Formula (i-5):

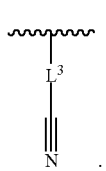 (i-5)

In certain embodiments, $R^2$ is of Formula (i-6):

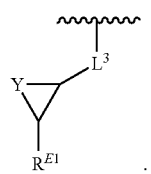 (i-6)

In certain embodiments, $R^2$ is of Formula (i-7):

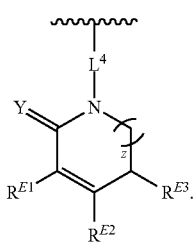 (i-7)

In certain embodiments, $R^2$ is of Formula (i-8):

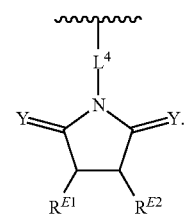 (i-8)

In certain embodiments, $R^2$ is of Formula (i-9):

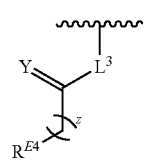 (i-9)

In certain embodiments, $R^2$ is of Formula (i-10):

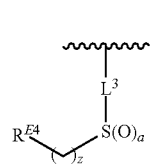 (i-10)

In certain embodiments, $R^2$ is of Formula (i-11):

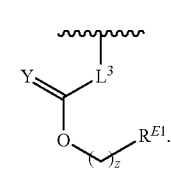 (i-11)

In certain embodiments, $R^2$ is of Formula (i-12):

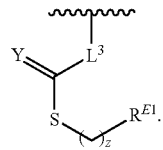
(i-12)

In certain embodiments, $R^2$ is of Formula (i-13):

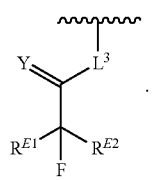
(i-13)

In certain embodiments, $R^2$ is of Formula (i-14):

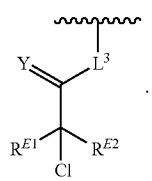
(i-14)

In certain embodiments, $R^2$ is of Formula (i-15):

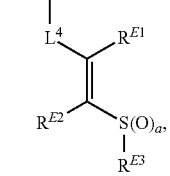
(i-15)

In certain embodiments, $R^2$ is of Formula (i-16):

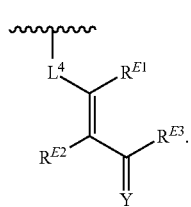
(i-16)

In certain embodiments, $R^2$ is of Formula (i-17):

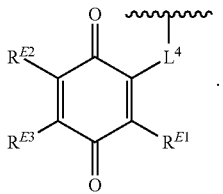
(i-17)

In certain embodiments, $R^2$ is of Formula (i-18):

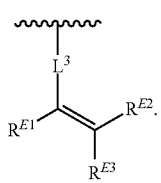
(i-18)

In certain embodiments, $R^2$ is of Formula (i-19):

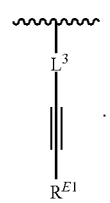
(i-19)

In certain embodiments, $R^2$ is of Formula (i-20):

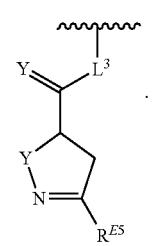
(i-20)

In certain embodiments, $R^2$ is of Formula (i-21):

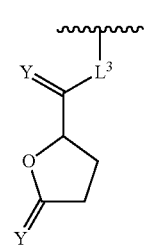
(i-21)

In certain embodiments, $R^2$ is of Formula (i-22):

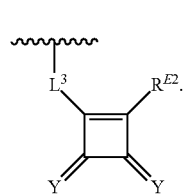

(i-22)

In certain embodiments, $R^2$ is of Formula (i-23):

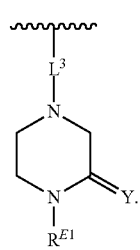

(i-23)

In certain embodiments, $R^2$ is of Formula (i-24):

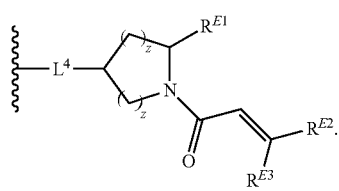

(i-24)

In certain embodiments, $R^2$ is of Formula (i-25):

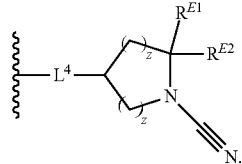

(i-25)

In certain embodiments, $R^2$ is of Formula (i-26):

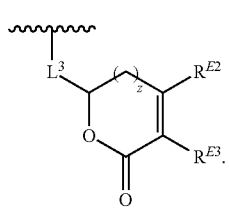

(i-26)

In certain embodiments, $R^2$ is of Formula (i-27):

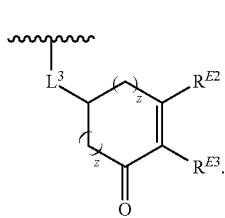

(i-27)

In certain embodiments, $R^2$ is of Formula (i-28):

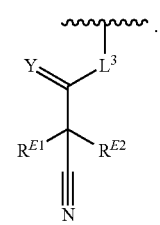

(i-28)

In certain embodiments, $R^2$ is of Formula (i-29):

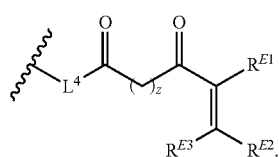

(i-29)

In certain embodiments, $R^2$ is of Formula (i-30):

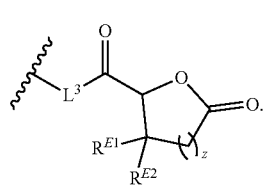

(i-30)

In certain embodiments, $R^2$ is of Formula (i-31):

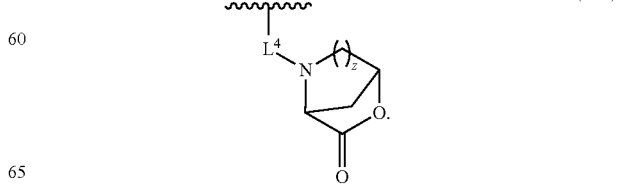

(i-31)

In certain embodiments, $R^2$ is of Formula (i-32):

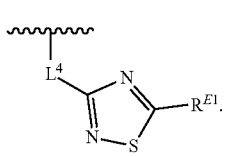
(i-32)

In certain embodiments, $R^2$ is of Formula (i-33):

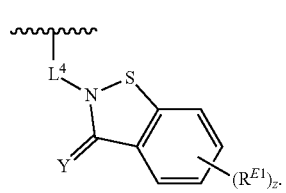
(i-33)

In certain embodiments, $R^2$ is of Formula (i-34):

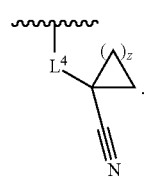
(i-34)

In certain embodiments, $R^2$ is of Formula (i-35):

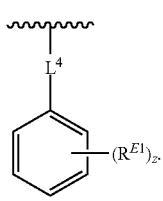
(i-35)

In certain embodiments, $R^2$ is of Formula (i-36):

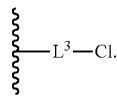
(i-36)

In certain embodiments, $R^2$ is of Formula (i-37):

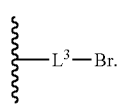
(i-37)

In certain embodiments, $R^2$ is of Formula (i-38):

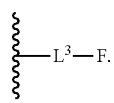
(i-38)

In certain embodiments, $R^2$ is of Formula (i-39):

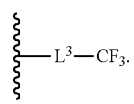
(i-39)

In certain embodiments, $R^2$ is of Formula (i-40):

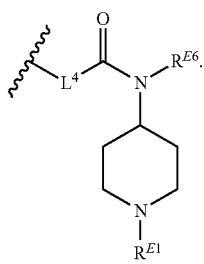
(i-40)

In certain embodiments, $R^2$ is of Formula (i-41):

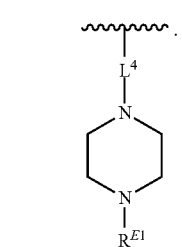
(i-41)

In certain embodiments, $R^2$ is of Formula (i-1a):

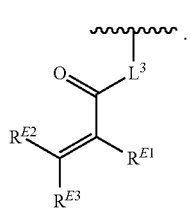
(i-1a)

In certain embodiments, $R^2$ is of Formula (i-1b):

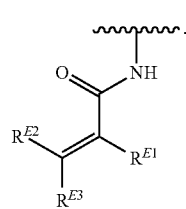

(i-1b)

In certain embodiments, $R^2$ is of Formula (i-1c):

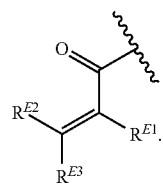

(i-1c)

In certain embodiments, $R^2$ is of Formula (i-1d):

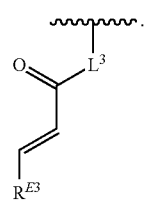

(i-1d)

In certain embodiments, $R^2$ is of Formula (i-1e):

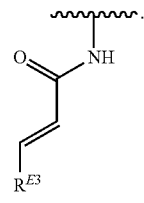

(i-1e)

In certain embodiments, $R^2$ is of Formula (i-1f):

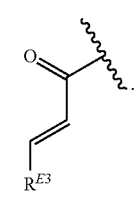

(i-1f)

In certain embodiments, $R^2$ is of Formula (i-1g):

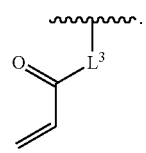

(i-1g)

In certain embodiments, $R^2$ is

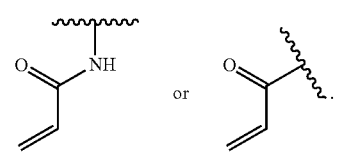

or

In certain embodiments, $R^2$ is

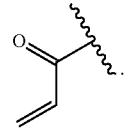

In certain embodiments, $R^2$ is

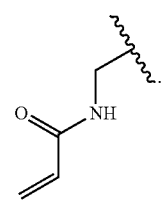 [SMILES: *CNC(=O)C=C]

In certain embodiments, $R^2$ is of Formula (i-1h):

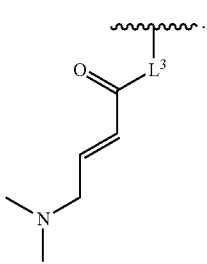

(i-1h)

In certain embodiments, $R^2$ is

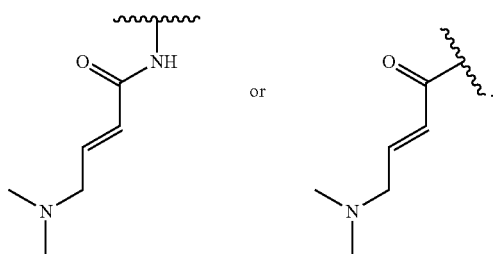 or

In certain embodiments, $R^2$ is of Formula (i-1a):

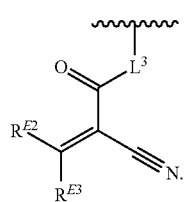
(i-1a)

In certain embodiments, $R^2$ is of Formula (i-1b):

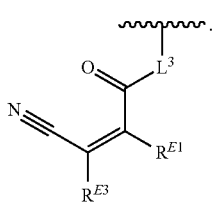
(i-1b)

In certain embodiments, $R^2$ is of Formula (i-1c):

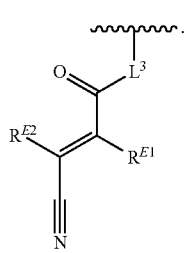
(i-1c)

In certain embodiments, $R^2$ is of Formula (i-18a):

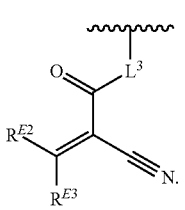
(i-18a)

In certain embodiments, $R^2$ is of Formula (i-18b):

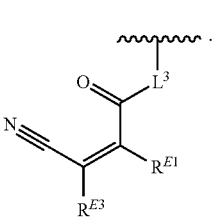
(i-18b)

In certain embodiments, $R^2$ is of Formula (i-18c):

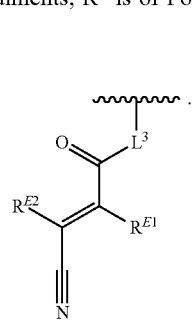
(i-18c)

In certain embodiments, $R^2$ is of Formula (i-15a):

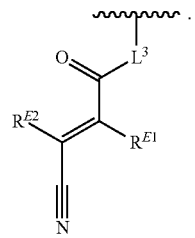
(i-15a)

In certain embodiments, $R^2$ is of Formula (i-15b):

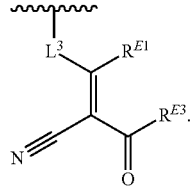
(i-15b)

In certain embodiments, $R^2$ is of Formula (i-15c):

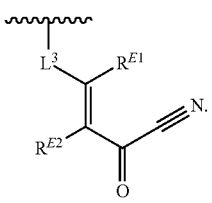
(i-15c)

$R^2$ may contain linker $L^3$ or $L^4$. In certain embodiments, $L^3$ is a bond. $L^3$ is an optionally substituted $C_{1-4}$ hydrocarbon chain. In certain embodiments, $L^3$ is an optionally substi tuted $C_{1-4}$ hydrocarbon chain, wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{Ua}$—, or —NR$^{L3a}$S(=O)$_2$—. In certain embodiments, L$^3$ is an optionally substituted $C_{1-4}$ hydrocarbon chain, wherein one carbon unit of the hydrocarbon chain is replaced with —NR$^{L3a}$— (e.g., —NH—). In certain embodiments, L$^3$ is of the formula: —(CH$_2$)$_{1-4}$—NR$^{L3a}$— (e.g., —(CH$_2$)$_{1-4}$—NH—) or —NR$^{L3a}$—CH$_2$)$_{1-4}$— (e.g., —NH—CH$_2$)$_{1-4}$—). In certain embodiments, L$^3$ is —NR$^{L3a}$—. In certain embodiments, L$^3$ is —NR$^{L3a}$(C=O)—. In certain embodiments, L$^3$ is —(C=O)NR$^{L3a}$—. In certain embodiments, L$^3$ is —NH—. In certain embodiments, L$^3$ is —(C=O)—. In certain embodiments, L$^3$ is —NH(C=O)—. In certain embodiments, L$^3$ is —(C=O)NH—. In certain embodiments, L$^3$ is —O—. In certain embodiments, L$^3$ is —S—. In certain embodiments, L$^4$ is a bond. In certain embodiments, L$^4$ is an optionally substituted $C_{1-4}$ hydrocarbon chain.

Linker L$^3$ may contain groups R$^{L3a}$ or R$^{L3b}$. In certain embodiments, R$^{L3a}$ is hydrogen. In certain embodiments, at least one instance of R$^{L3b}$ is hydrogen. In certain embodiments, each instance of R$^{L3b}$ is hydrogen. In certain embodiments, at least one instance of R$^{L3b}$ is —Cl, —Br, or —I. In certain embodiments, each instance of R$^{L3b}$ is —Cl, —Br, or —I. In certain embodiments, at least one instance of R$^{L3b}$ is —F. In certain embodiments, each instance of R$^{L3b}$ is —F. In certain embodiments, at least one instance of R$^{L3b}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, two R$^{L3b}$ groups are joined to form an optionally substituted carbocyclic or optionally substituted heterocyclic ring.

R$^2$ may contain groups R$^{E1}$, R$^{E2}$, and/or R$^{E3}$. In certain embodiments, R$^{E1}$ is hydrogen. In certain embodiments, R$^{E2}$ is hydrogen. In certain embodiments, R$^{E3}$ is hydrogen. In certain embodiments, R$^{E1}$ is —Cl, —Br, or —I. In certain embodiments, R$^{E2}$ is —Cl, —Br, or —I. In certain embodiments, R$^{E3}$ is —Cl, —Br, or —I. In certain embodiments, R$^{E1}$ is —F. In certain embodiments, R$^{E2}$ is —F. In certain embodiments, R$^{E3}$ is —F. In certain embodiments, R$^{E1}$ is optionally substituted alkyl (e.g., substituted or unsubstituted $C_{1-6}$ alkyl). In certain embodiments, R$^{E2}$ is optionally substituted alkyl (e.g., substituted or unsubstituted $C_{1-6}$ alkyl). In certain embodiments, R$^{E3}$ is optionally substituted alkyl (e.g., substituted or unsubstituted $C_{1-6}$ alkyl). In certain embodiments, R$^{E1}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, R$^{E2}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, R$^{E3}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, R$^{E1}$ is —N(R$^{EE}$)$_2$. In certain embodiments, R$^{E2}$ is —N(R$^{EE}$)$_2$. In certain embodiments, R$^{E3}$ is —N(R$^{EE}$)$_2$. In certain embodiments, R$^{E1}$ is —N(CH$_3$)$_2$. In certain embodiments, R$^{E2}$ is —N(CH$_3$)$_2$. In certain embodiments, R$^{E3}$ is —N(CH$_3$)$_2$. In certain embodiments, R$^{E1}$ is —CH$_2$N(R$^{ee}$)$_2$. In certain embodiments, R$^{E2}$ is —CH$_2$N(R$^{EE}$)$_2$. In certain embodiments, R$^{E3}$ is —CH$_2$N(R$^{EE}$)$_2$. In certain embodiments, R$^{E1}$ is —CH$_2$N(CH$_3$)$_2$. In certain embodiments, R$^{E2}$ is —CH$_2$N(CH$_3$)$_2$. In certain embodiments, R$^{E3}$ is —CH$_2$N(CH$_3$)$_2$. In certain embodiments, R$^{E1}$ is —CN. In certain embodiments, R$^{E2}$ is —CN. In certain embodiments, R$^{E3}$ is —CN.

In certain embodiments, R$^{E1}$ and R$^{E3}$ are joined to form an optionally substituted carbocyclic ring. In certain embodiments, R$^{E1}$ and R$^{E3}$ are joined to form an optionally substituted heterocyclic ring. In certain embodiments, R$^{E2}$ and R$^{E3}$ are joined to form an optionally substituted carbocyclic ring. In certain embodiments, R$^{E2}$ and R$^{E3}$ are joined to form an optionally substituted heterocyclic ring. In certain embodiments, R$^{E1}$ and R$^{E2}$ are joined to form an optionally substituted carbocyclic ring. In certain embodiments, R$^{E1}$ and R$^{E2}$ are joined to form an optionally substituted heterocyclic ring.

R$^2$ may contain group R$^{E4}$, where R$^{E4}$ is a leaving group. In certain embodiments, R$^{E4}$ is —Cl, —Br, or —I. In certain embodiments, R$^{E4}$ is —F. In certain embodiments, R$^{E4}$ is —OS(=O)R$^{E4a}$ or —OS(=O)$_2$R$^{E4a}$, wherein R$^{E4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, R$^{E4}$ is —OR$^{E4a}$. In certain embodiments, R$^{E4}$ is —OMs, —OTf, —OTs, —OBs, or 2-nitrobenzenesulfonyloxy. In certain embodiments, R$^{E4}$ is —OR$^{E4a}$. In certain embodiments, R$^{E4}$ is —OMe, —OCF$_3$, or —OPh. In certain embodiments, R$^{E4}$ is —OC(=O)R$^{E4a}$. In certain embodiments, R$^{E4}$ is —OC(=O)Me, —OC(=O)CF$_3$, —OC(=O)Ph, or —OC(=O)Cl. In certain embodiments, R$^{B4}$ is —OC(=O)OR$^{E4a}$. In certain embodiments, R$^{E4}$ is —OC(=O)OMe or —OC(=O)O(t-Bu).

R$^2$ may contain group R$^{E5}$, where R$^{E5}$ is a halogen. In certain embodiments, R$^{E5}$ is —Cl, —Br, or —I. In certain embodiments, R$^{E5}$ is —F.

R$^2$ may contain group R$^{E6}$. In certain embodiments, R$^{E6}$ is hydrogen. In certain embodiments, R$^{E6}$ is substituted or unsubstituted $C_1$-$C_6$ alkyl. In certain embodiments, R$^{E6}$ is a nitrogen protecting group.

In certain embodiments, a is 1. In certain embodiments, a is 2.

In certain embodiments, z is 0. In certain embodiments, z is 1. In certain embodiments, z is 2. In certain embodiments, z is 3, 4, 5, or 6.

R$^2$ may contain group Y. In certain embodiments, Y is O. In certain embodiments, Y is S. In certain embodiments, Y is NR$^{E7}$. In certain embodiments, Y is NH. In certain embodiments, a compound of Formula (I') is of Formula (I).

In certain embodiments, the compound of Formula (I) is the formula:

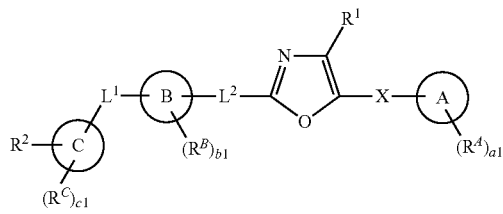

or a pharmaceutically acceptable salt, solvate, hydrate, polymorph, co-crystal, tautomer, stereoisomer, isotopically labeled derivative, or prodrug thereof.

In certain embodiments, the compound of Formula (I) is the formula:

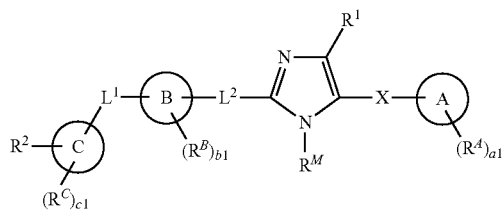

or a pharmaceutically acceptable salt, solvate, hydrate, polymorph, co-crystal, tautomer, stereoisomer, isotopically labeled derivative, or prodrug thereof.

In certain embodiments, the compound of Formula (I) is the formula:

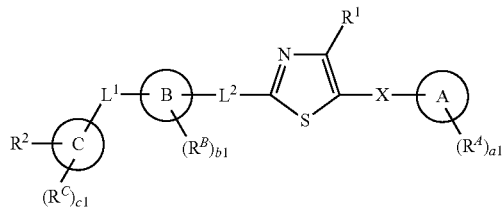

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of Formula (I-i):

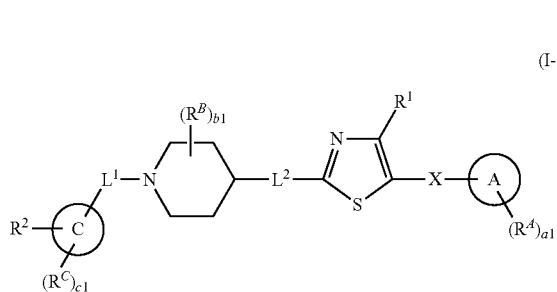

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, Ring C, $R^1$, $R^2$, $R^A$, $R^B$, $R^C$, a1, b1, and c1 are as defined herein.

In certain embodiments, a compound of Formula (I) is of Formula (I-ii):

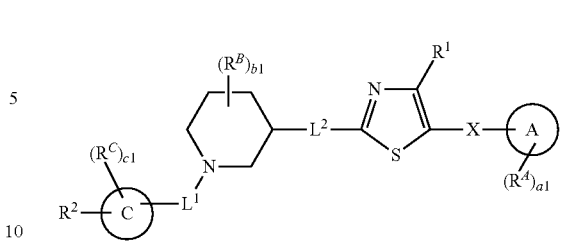

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, Ring C, $R^1$, $R^2$, $R^A$, $R^B$, $R^C$, a1, b1, and c1 are as defined herein.

In certain embodiments, a compound of Formula (I) is of Formula (I-ii-a):

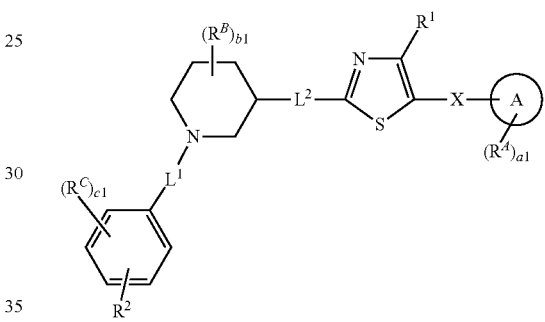

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^a$, $R^b$, $R^C$, a1, b1, and c1 are as defined herein.

In certain embodiments, a compound of Formula (I) is of the formula:

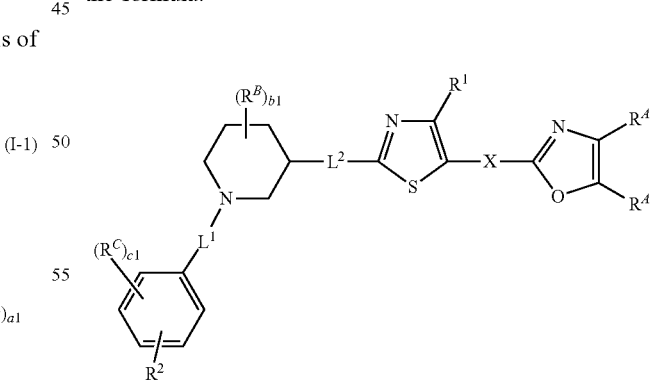

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^a$, $R^b$, $R^C$, a1, b1, and c1 are as defined herein.

In certain embodiments, a compound of Formula (I) is of the formula:

101

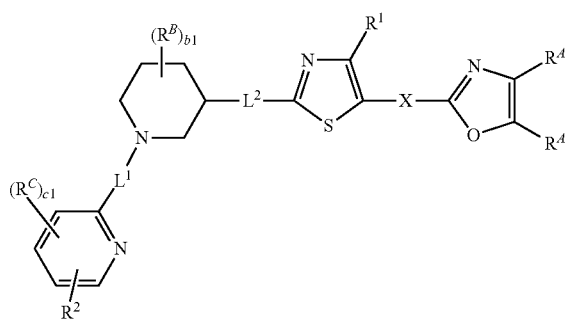

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^b$, $R^C$, a1, b1, and c1 are as defined herein.

In certain embodiments, a compound of Formula (I) is of the formula:

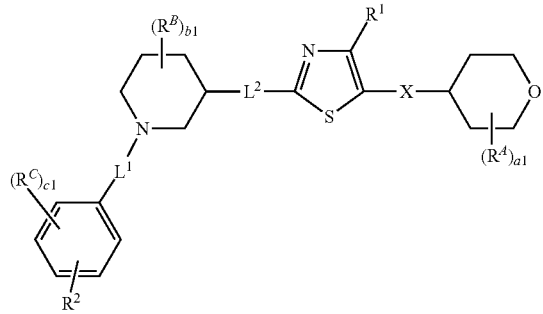

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^a$, $R^B$, $R^C$, a1, b1, and c1 are as defined herein.

In certain embodiments, a compound of Formula (I) is of the formula:

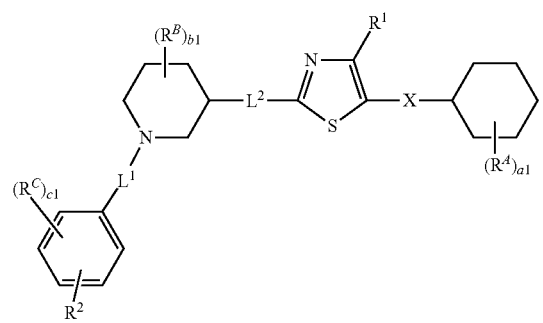

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of the formula:

102

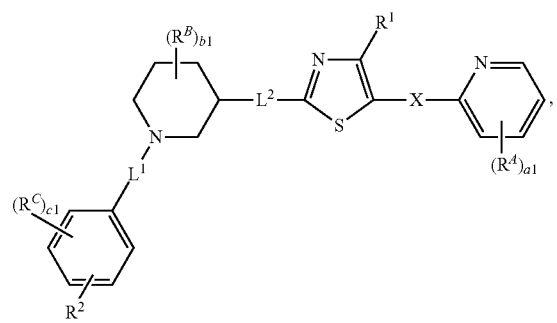

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of the formula:

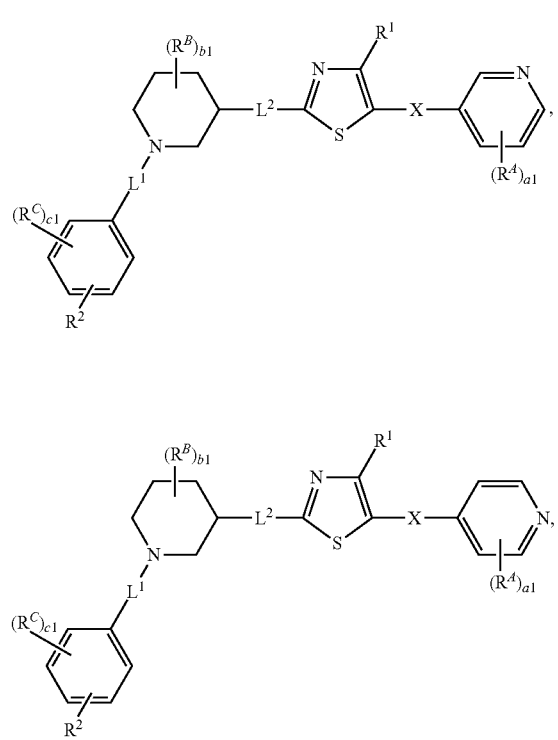

-continued

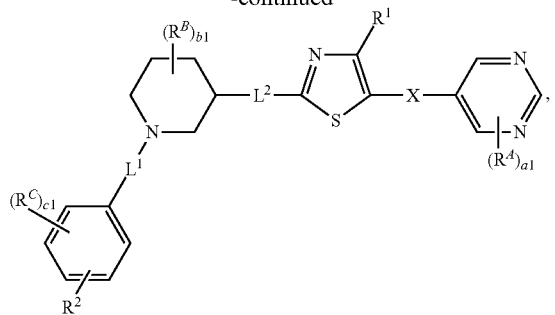

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of Formula (I-ii-b):

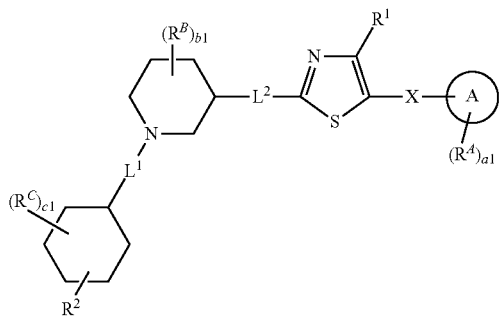

(I-ii-b)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I) is of the formula:

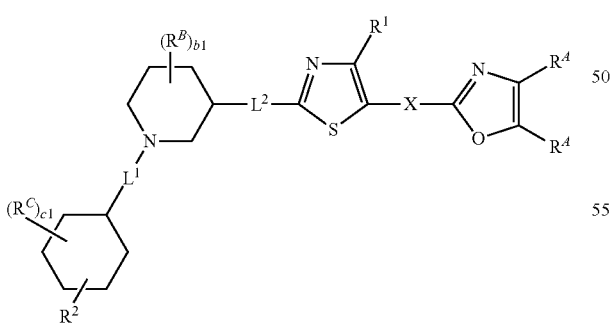

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of Formula (I-ii-c):

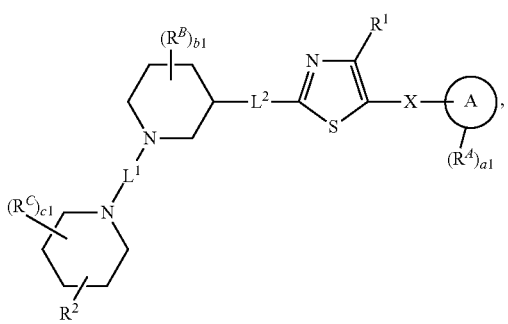

(I-ii-c)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I) is of the formula:

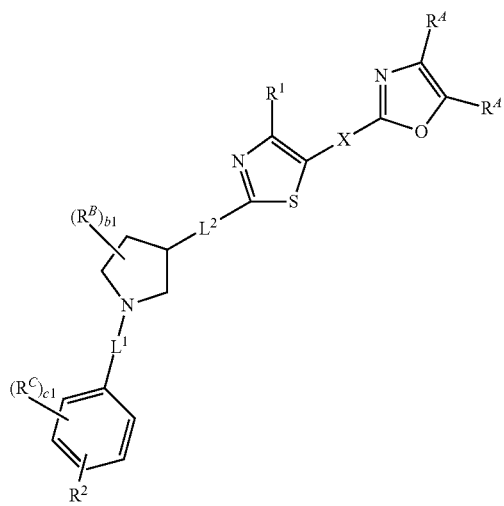

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of Formula (I-ii-A):

(I-ii-A)

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, b1, and c1 are as defined herein.

In certain embodiments, a compound of Formula (I) is of Formula (I-iii):

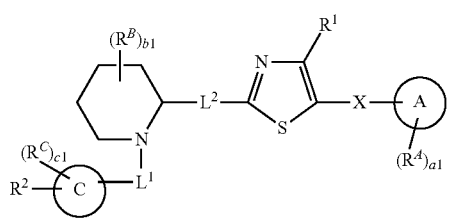

(I-iii)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, Ring C, $R^1$, $R^2$, $R^A$, $R^B$, $R^C$, a1, b1, and c1 are as defined herein.

In certain embodiments, a compound of Formula (I) is of Formula (I-iv):

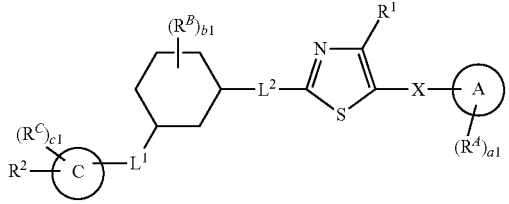

(I-iv)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, Ring C, $R^1$, $R^2$, $R^A$, $R^B$, $R^C$, a1, b1, and c1 are as defined herein.

In certain embodiments, a compound of Formula (I) is of Formula (I-iv-a):

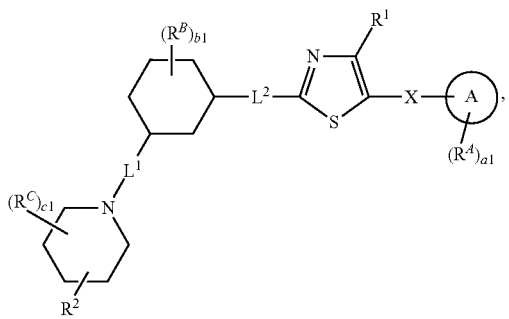

(I-iv-a)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I) is of the formula:

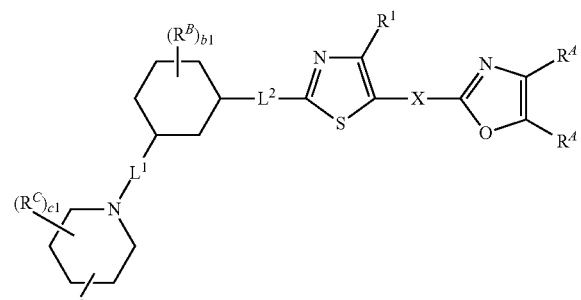

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of Formula (I-iv-b):

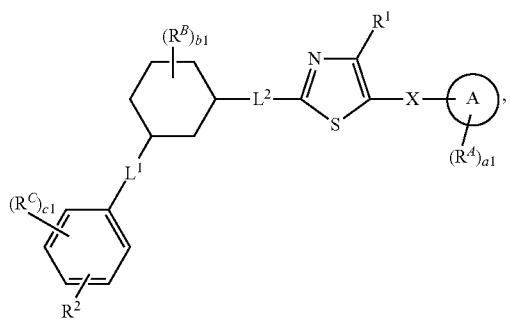

(I-iv-b)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I) is of the formula:

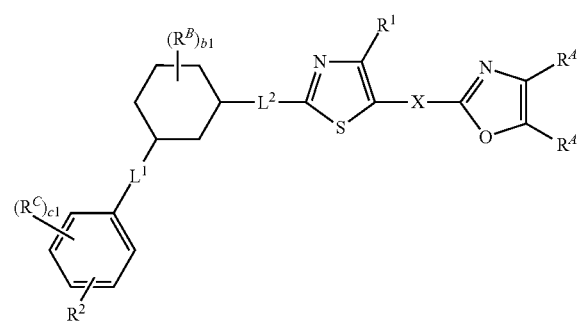

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of Formula (I-v):

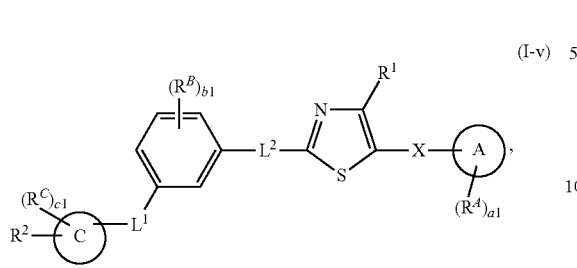
(I-v)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, Ring C, $R^1$, $R^2$, $R^A$, $R^B$, $R^C$, a1, b1, and c1 are as defined herein.

In certain embodiments, a compound of Formula (I) is of Formula (I-v-a):

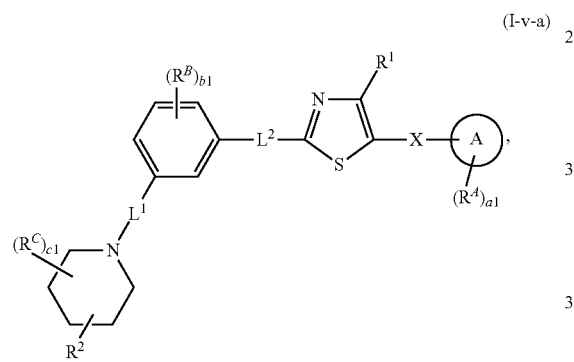
(I-v-a)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I) is of the formula:

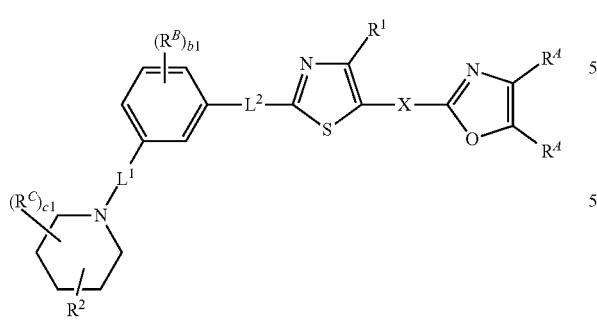

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I) is of Formula (I-v-b):

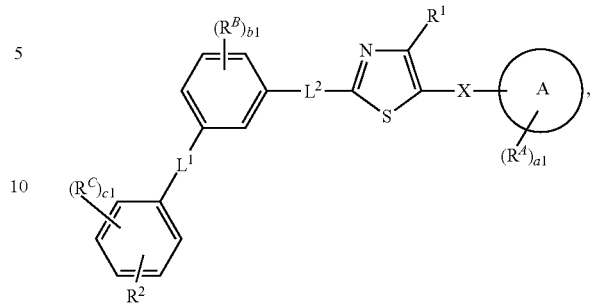
(I-v-b)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I) is of the formula:

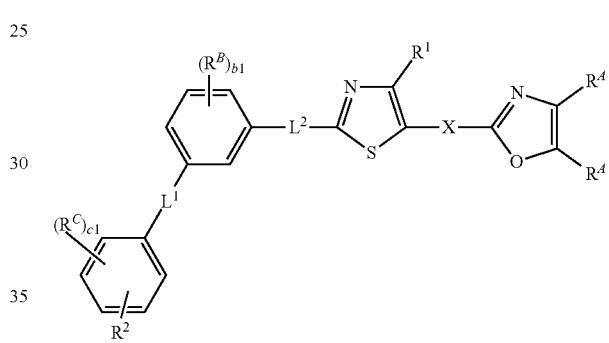

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, a1, b1, and c1 are as defined herein.

In certain embodiments, a compound of Formula (I') is of Formula (I'-A):

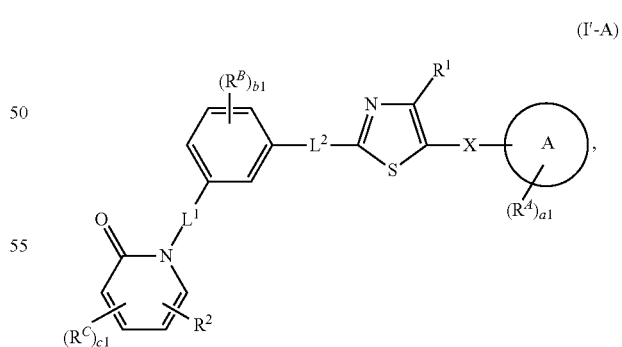
(I'-A)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^b$, $R^C$, a1, b1, and c1 are as defined herein.

In certain embodiments, a compound of Formula (I') is of the formula:

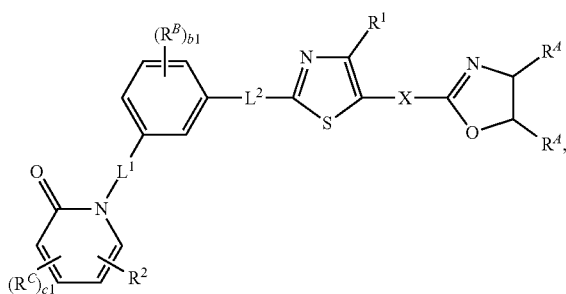

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, b1, and c1 are as defined herein.

In certain embodiments, a compound of Formula (I') is of Formula (I'-i):

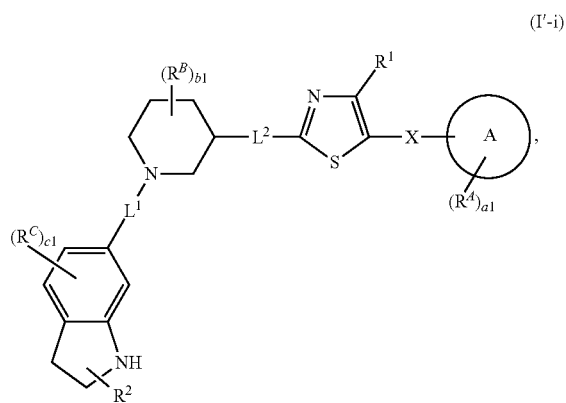

(I'-i)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I') is of Formula (I'-ii):

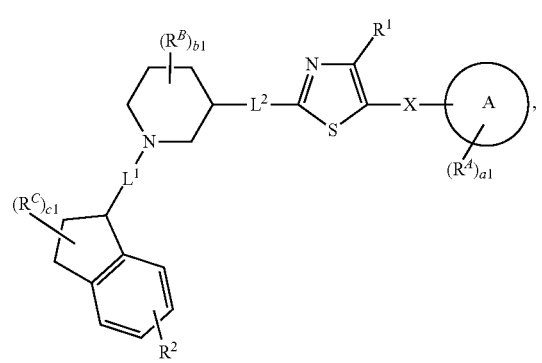

(I'-ii)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I') is of of Formula (I'-iii):

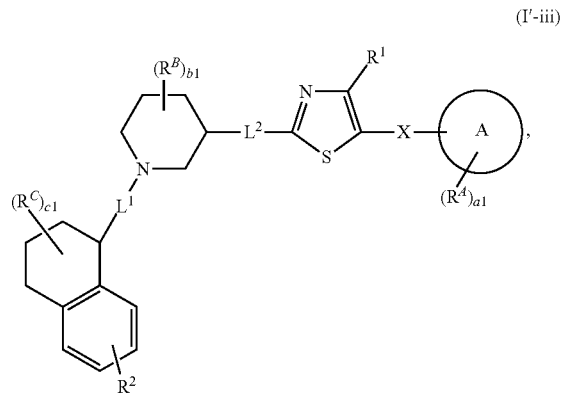

(I'-iii)

or a pharmaceutically acceptable salt, solvate, hydrate, polymorph, co-crystal, tautomer, stereoisomer, isotopically labeled derivative, or prodrug thereof, wherein $L^1$, $L^2$, X, Ring A, $R^1$, $R^2$, $R^A$, $R^B$, $R^C$, a1, b1, and c1 are as defined herein.

In certain embodiments, a compound of Formula (I') is of the formula:

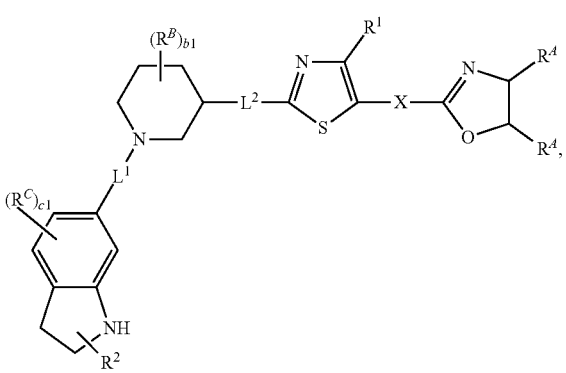

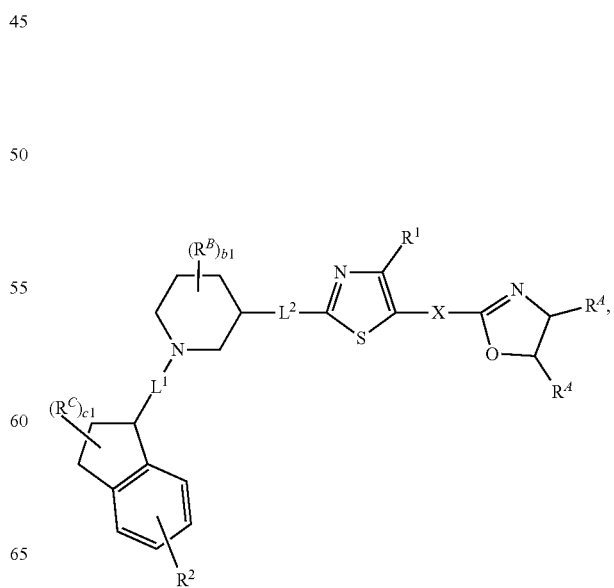

-continued

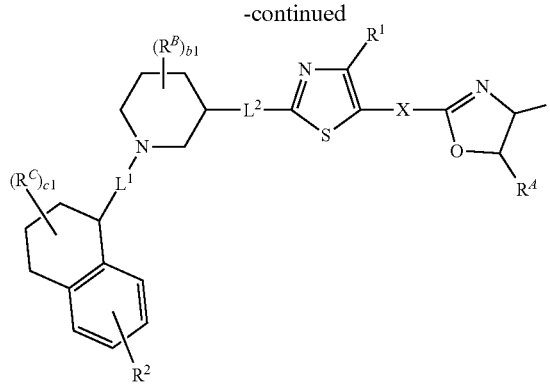

or a pharmaceutically acceptable salt, solvate, hydrate, polymorph, co-crystal, tautomer, stereoisomer, isotopically labeled derivative, or prodrug thereof, wherein $L^1$, $L^2$, X, $R^1$, $R^2$, $R^A$, $R^B$, $R^C$, b1, and c1 are as defined herein.

In certain embodiments, a compound of Formula (II') is of Formula (II).

In certain embodiments, the compound of Formula (II) is the formula:

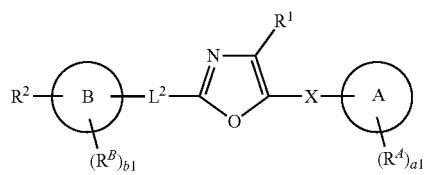

or a pharmaceutically acceptable salt, solvate, hydrate, polymorph, co-crystal, tautomer, stereoisomer, isotopically labeled derivative, or prodrug thereof.

In certain embodiments, the compound of Formula (II) is the formula:

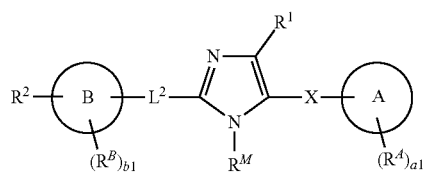

or a pharmaceutically acceptable salt, solvate, hydrate, polymorph, co-crystal, tautomer, stereoisomer, isotopically labeled derivative, or prodrug thereof.

In certain embodiments, the compound of Formula (II) is the formula:

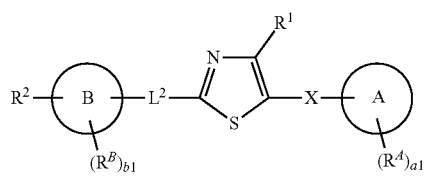

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of Formula (II-i):

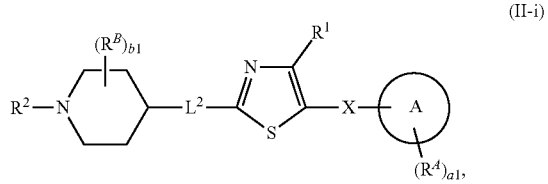

(II-i)

or a pharmaceutically acceptable salt, solvate, hydrate, polymorph, co-crystal, tautomer, stereoisomer, isotopically labeled derivative, or prodrug thereof, wherein $L^2$, X, Ring A, $R^1$, $R^2$, $R^A$, $R^B$, a1, and b1 are as defined herein.

In certain embodiments, a compound of Formula (II) is of the formula:

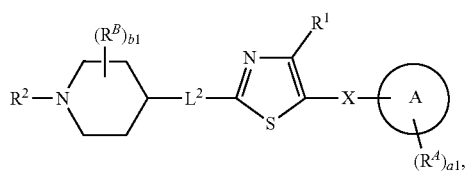

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

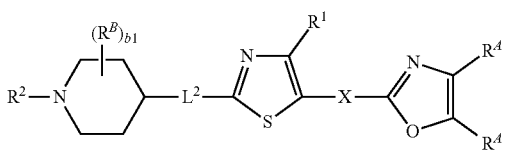

or a pharmaceutically acceptable salt, solvate, hydrate, polymorph, co-crystal, tautomer, stereoisomer, isotopically labeled derivative, or prodrug thereof.

In certain embodiments, a compound of Formula (II') is of Formula (II'-i):

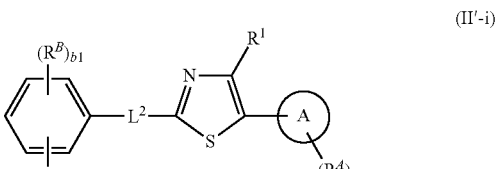

(II'-i)

or a pharmaceutically acceptable salt, solvate, hydrate, polymorph, co-crystal, tautomer, stereoisomer, isotopically labeled derivative, or prodrug thereof, wherein $L^2$, X, Ring A, $R^1$, $R^2$, $R^A$, $R^B$, and b1 are as defined herein.

In certain embodiments, the compound of Formula (II') is of the formula:

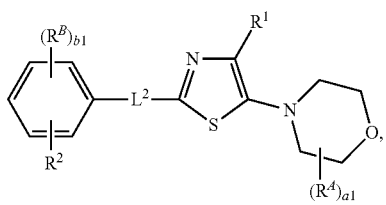

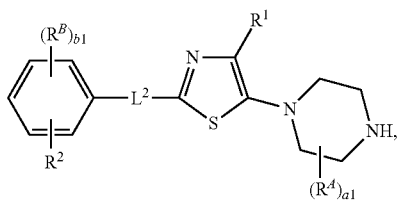

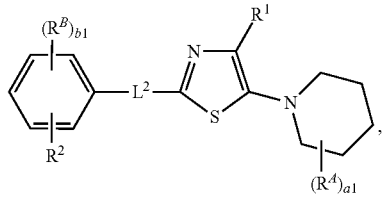

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of Formula (II-ii).

(II-ii)

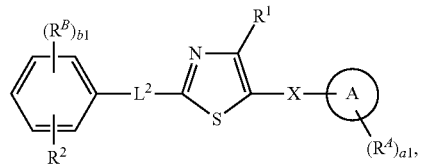

or a pharmaceutically acceptable salt, solvate, hydrate, polymorph, co-crystal, tautomer, stereoisomer, isotopically labeled derivative, or prodrug thereof, wherein $L^2$, X, Ring A, $R^1$, $R^2$, $R^A$, $R^B$, a1, and b1 are as defined herein.

In certain embodiments, a compound of Formula (II) is of the formula.

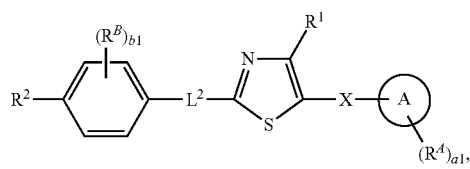

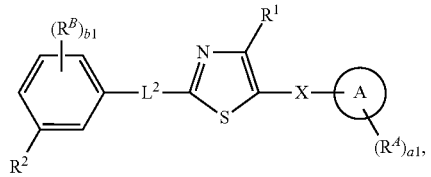

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

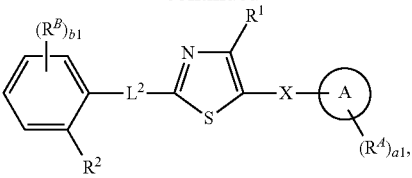

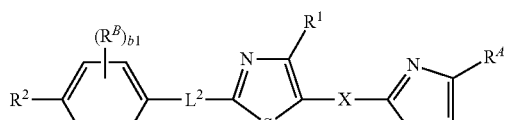

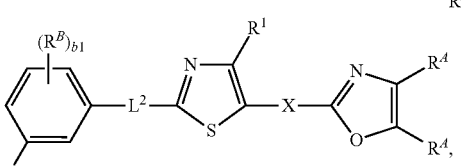

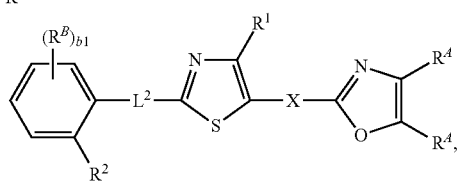

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of Formula (II-iii):

(II-iii)

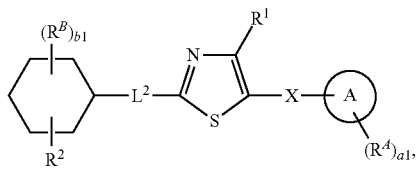

or a pharmaceutically acceptable salt, solvate, hydrate, polymorph, co-crystal, tautomer, stereoisomer, isotopically labeled derivative, or prodrug thereof, wherein $L^2$, X, Ring A, $R^1$, $R^2$, $R^A$, $R^B$, a1, and b1 are as defined herein.

In certain embodiments, a compound of Formula (II) is of the formula:

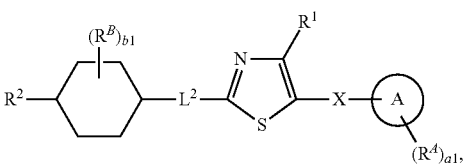

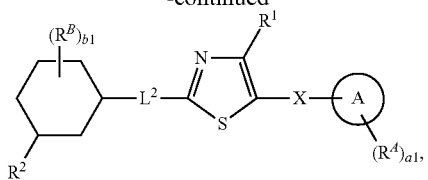

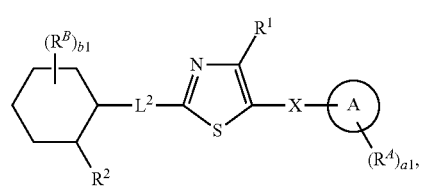

or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

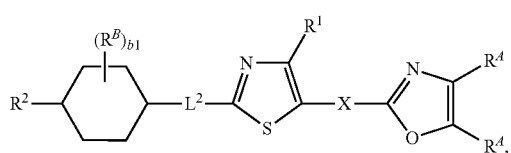

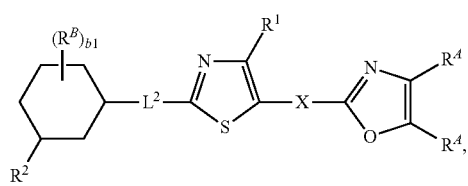

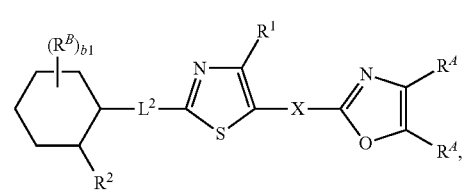

or a pharmaceutically acceptable salt, solvate, hydrate, polymorph, co-crystal, tautomer, stereoisomer, isotopically labeled derivative, or prodrug thereof.

In certain embodiments, a compound of Formula (I') is of the formula:

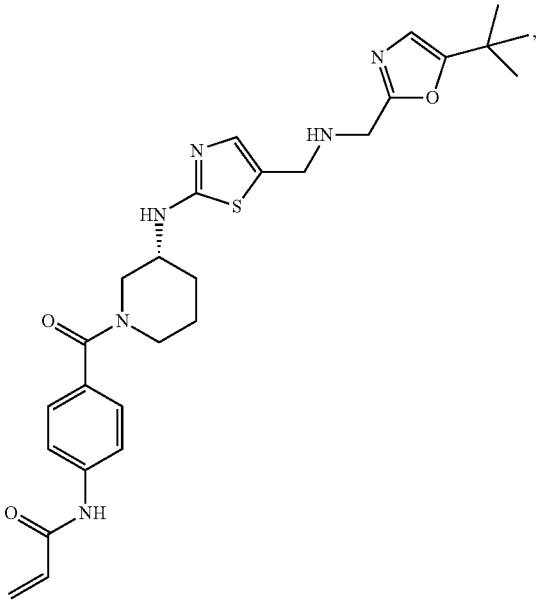

MFH-3-137-1

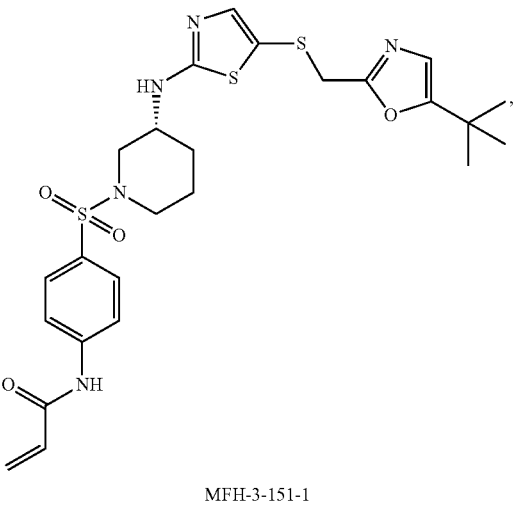

MFH-3-151-1

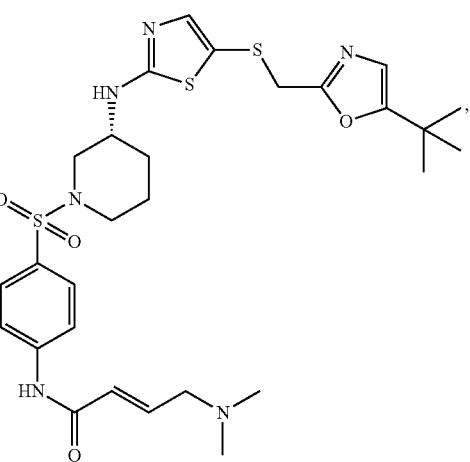

MFH-4-40-1

117
-continued
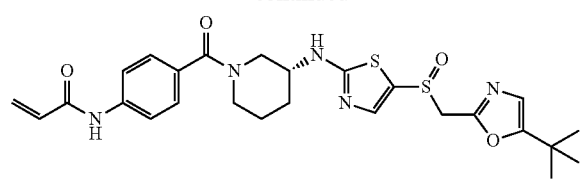
YLIU-01-007-1
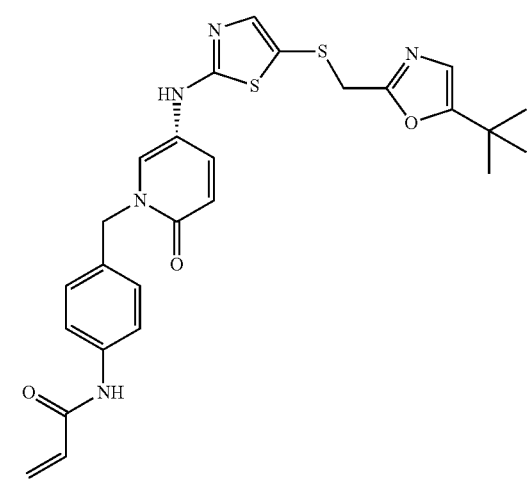
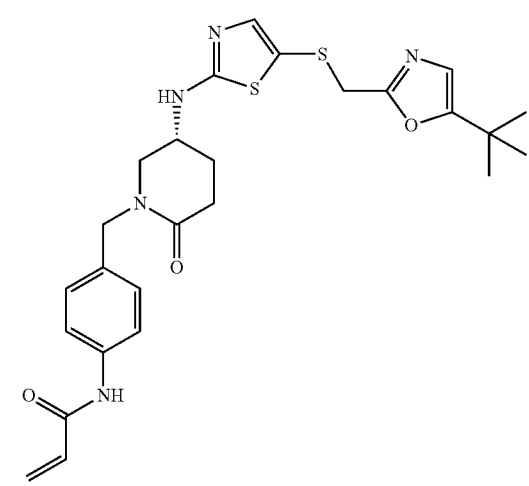
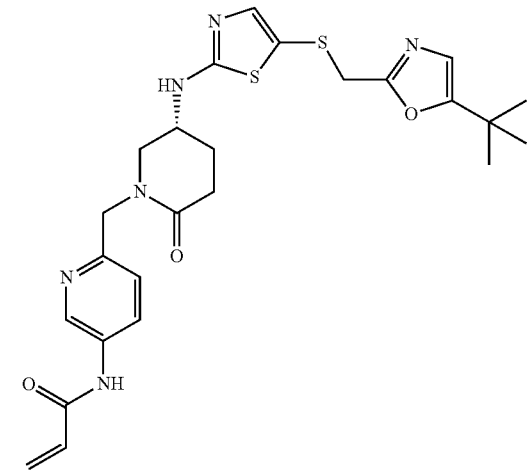
118
-continued
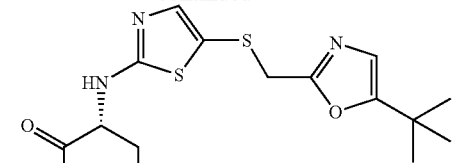
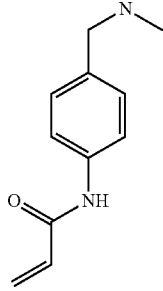
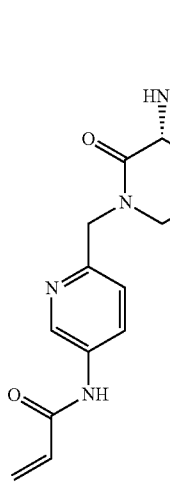
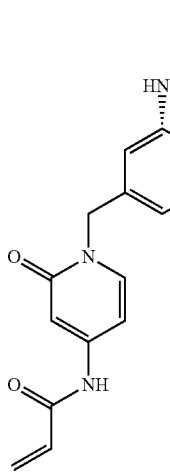

119
-continued
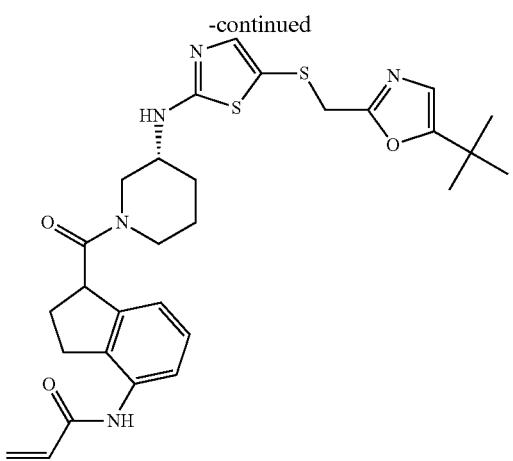
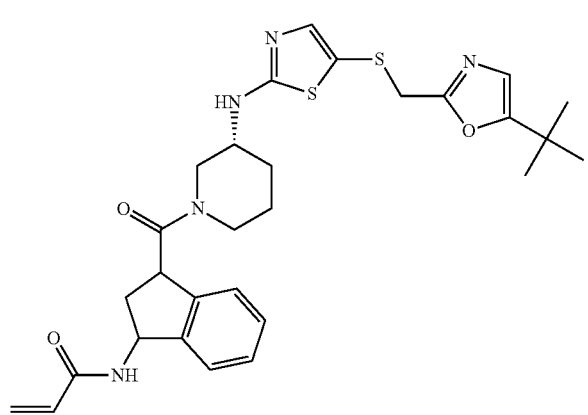
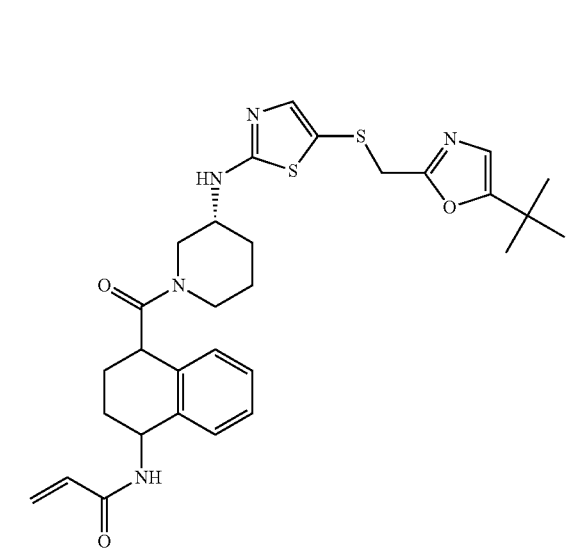
120
-continued
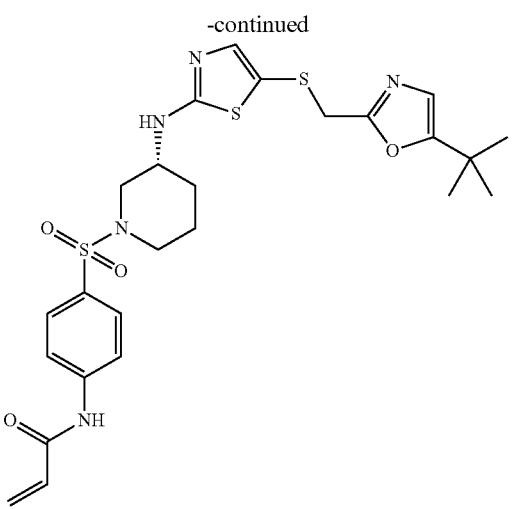
MFH-3-151-1
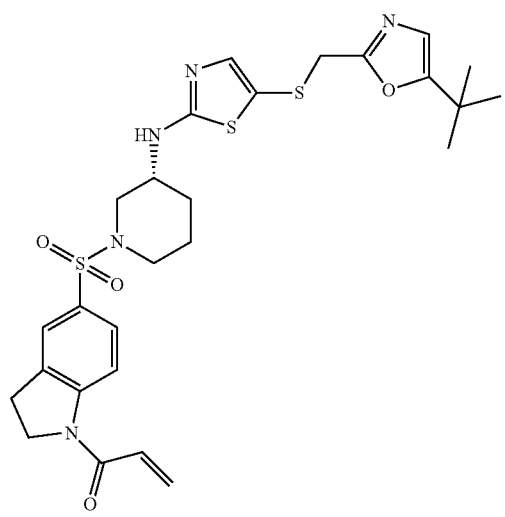
MFH-3-128-1
MFH-3-168-1

121
-continued
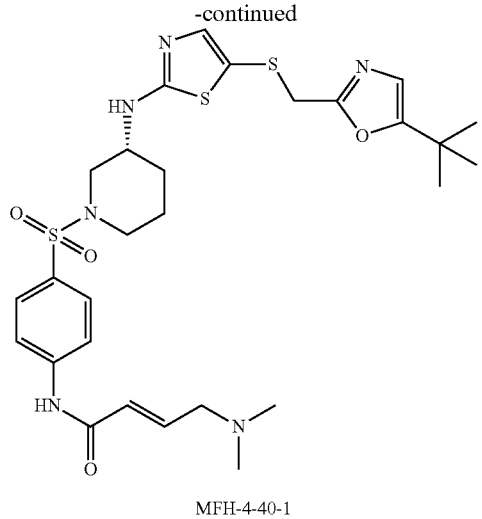
MFH-4-40-1
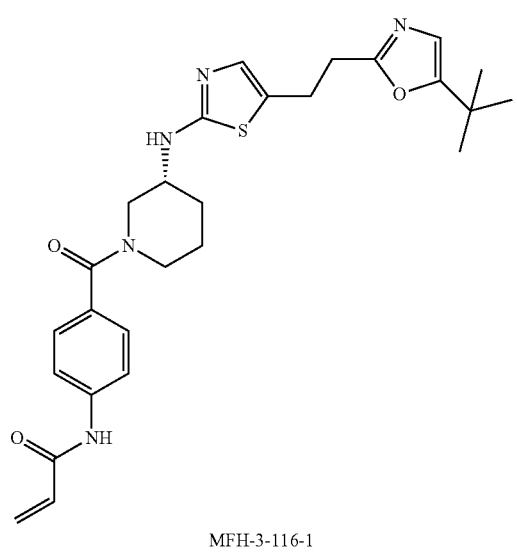
MFH-3-116-1
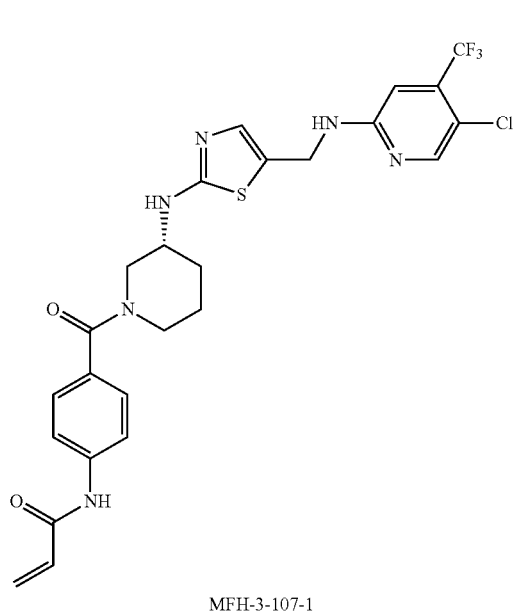 [SMILES: C=CC(=O)Nc1ccc(C(=O)N2CCC[C@@H](Nc3ncc(CNc4cc(C(F)(F)F)c(Cl)cn4)s3)C2)cc1]
MFH-3-107-1
122
-continued
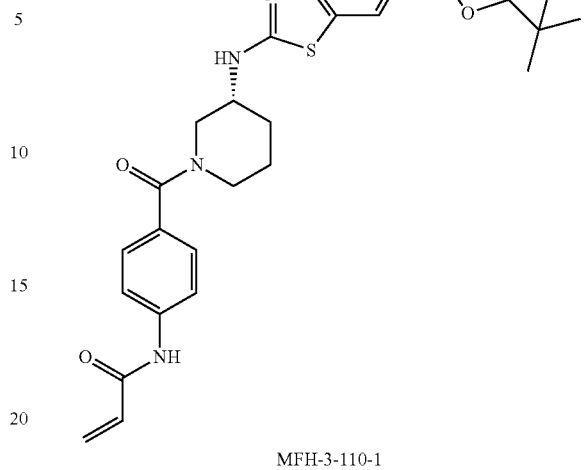
MFH-3-110-1
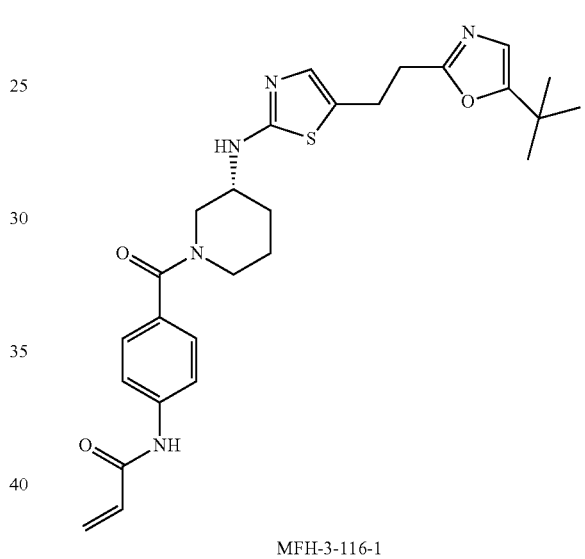
MFH-3-116-1
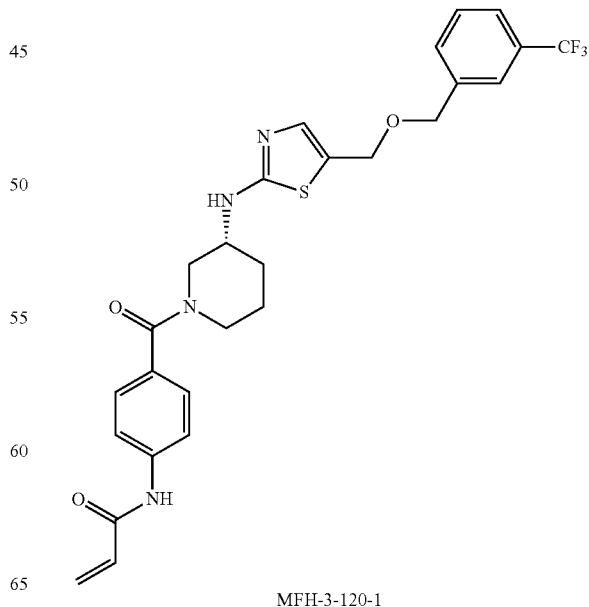
MFH-3-120-1

123
-continued
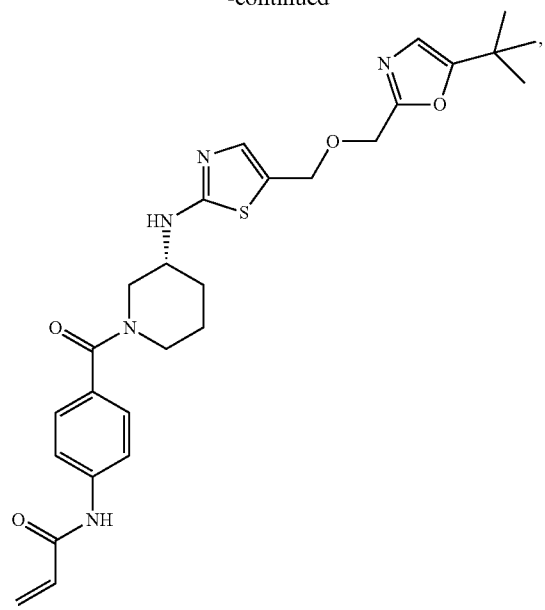
MFH-3-123-1
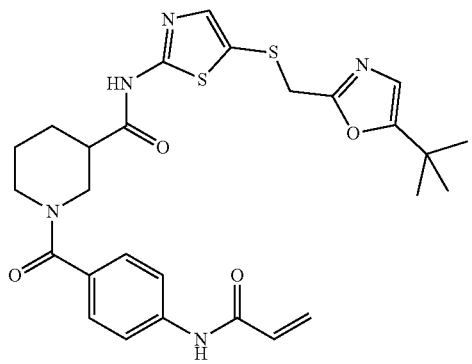
MFH-3-168-1
or a pharmaceutically acceptable salt, solvate, hydrate, polymorph, co-crystal, tautomer, stereoisomer, isotopically labeled derivative, or prodrug thereof.
In certain embodiments, a compound of Formula (I) is of the formula:
124
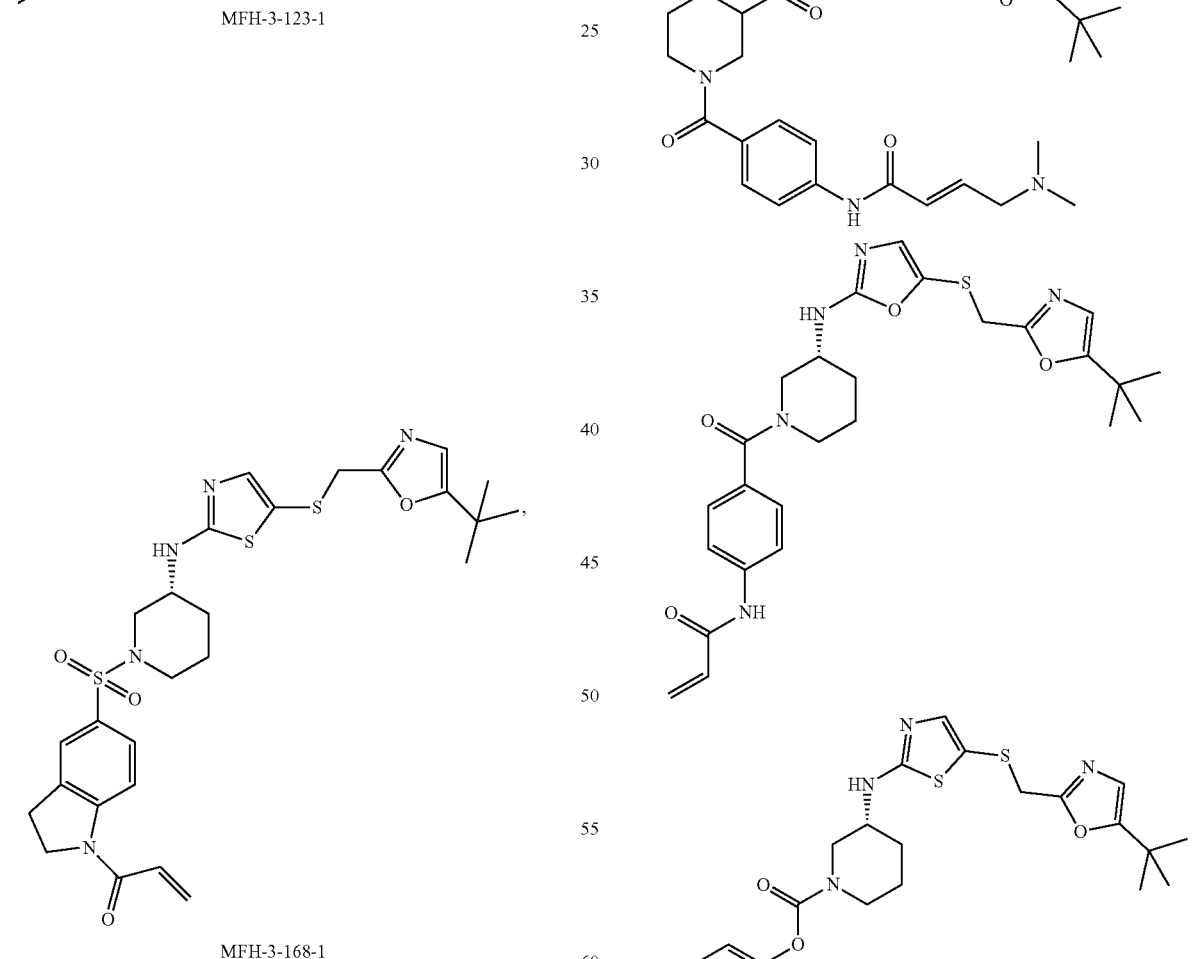

125
-continued
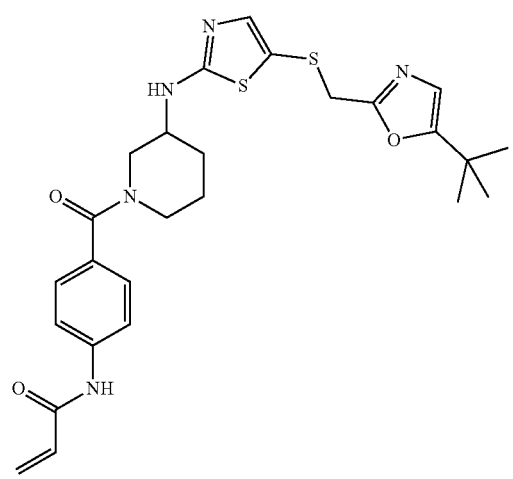
B12
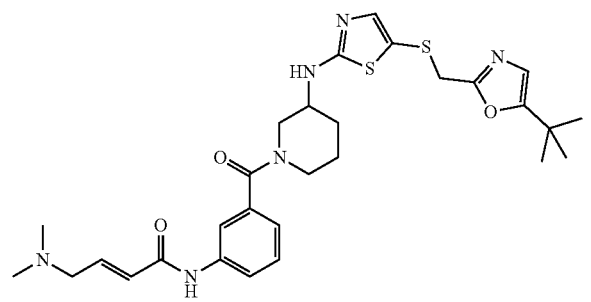
B16
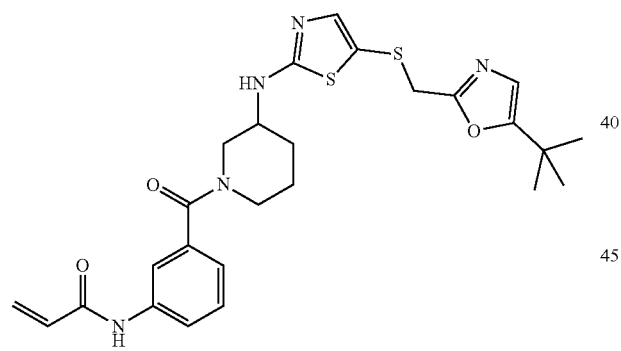
B15
126
-continued
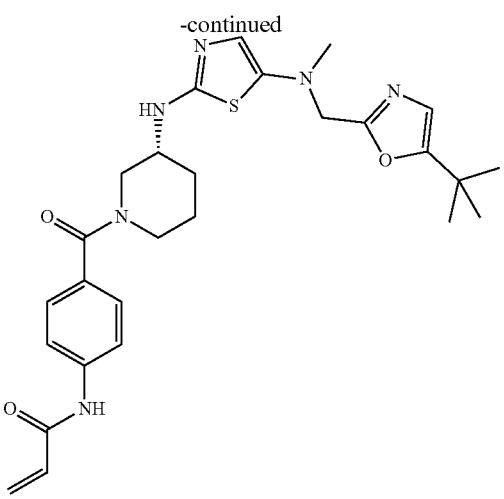
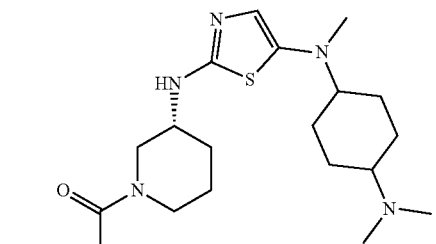
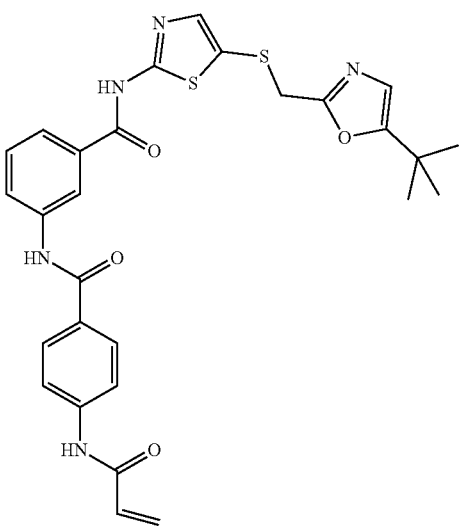
B9

-continued
127
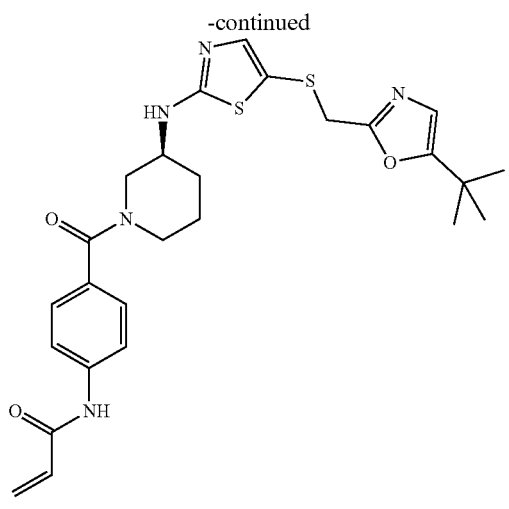
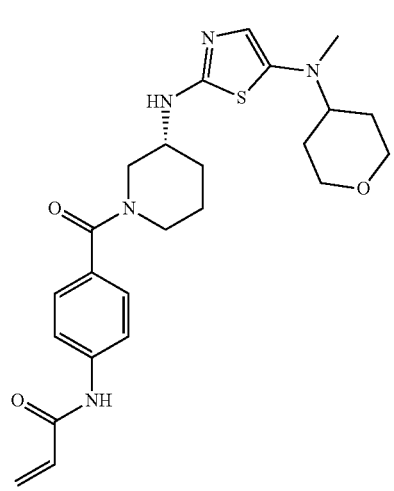
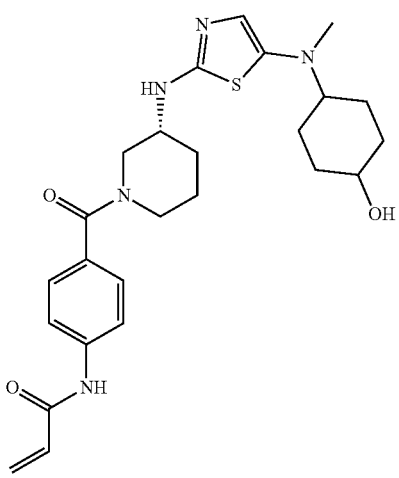
128
-continued
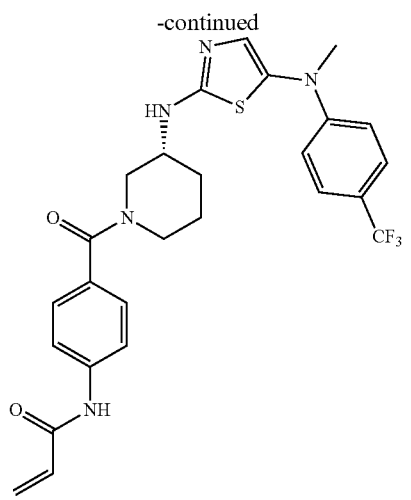
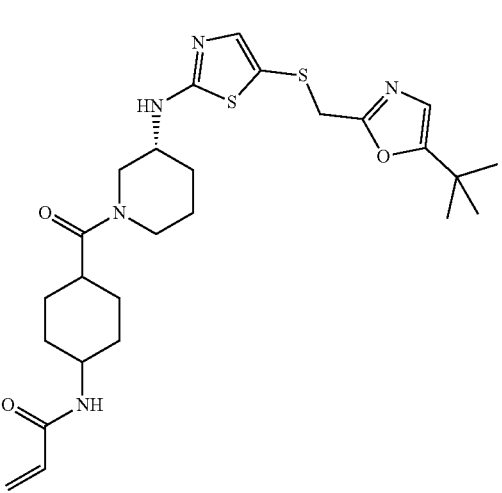
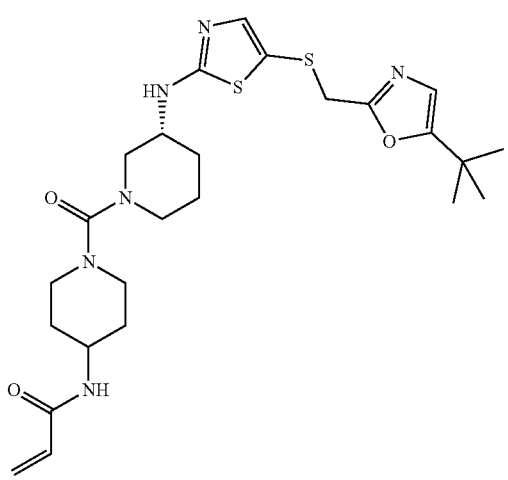

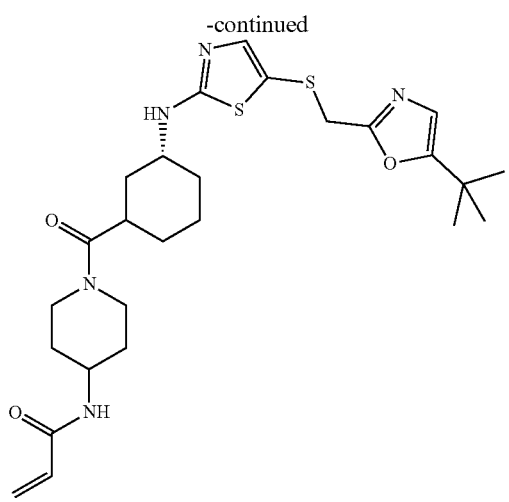
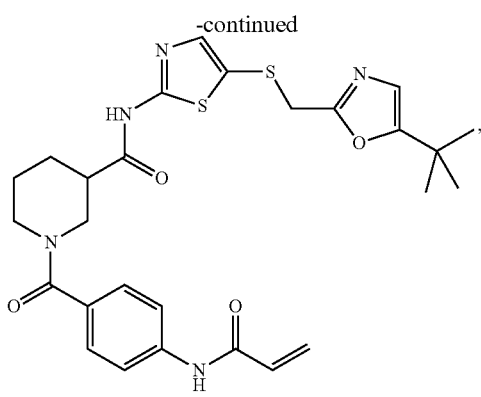
THZ-CE-B-5
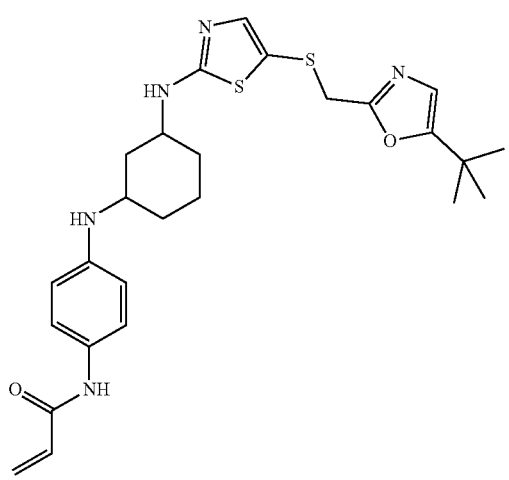
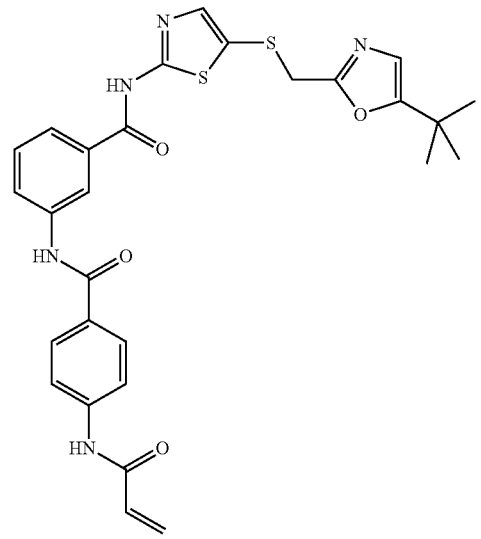
THZ-CE-B-9
or a pharmaceutically acceptable salt, solvate, hydrate, polymorph, co-crystal, tautomer, stereoisomer, isotopically labeled derivative, or prodrug thereof.
In certain embodiments, a compound of Formula (I) is of the formula:
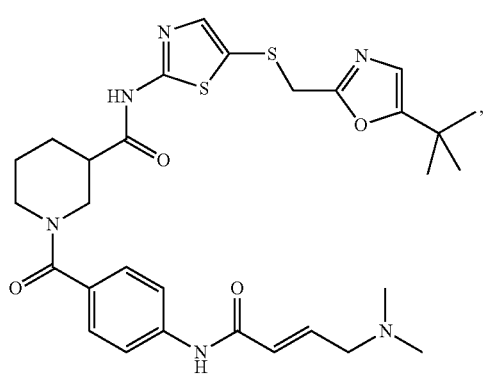
THZ-CE-B-4
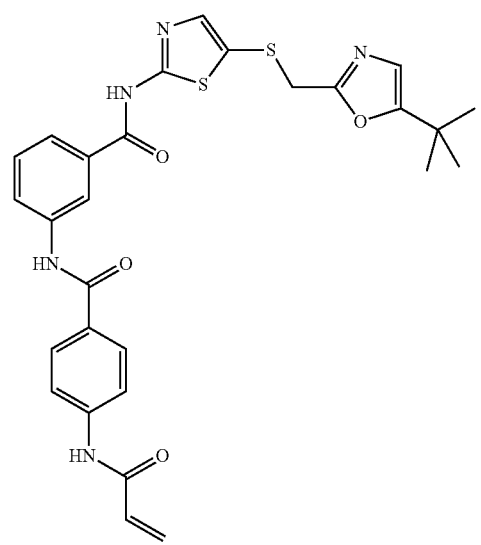
THZ-CE-B-5

-continued
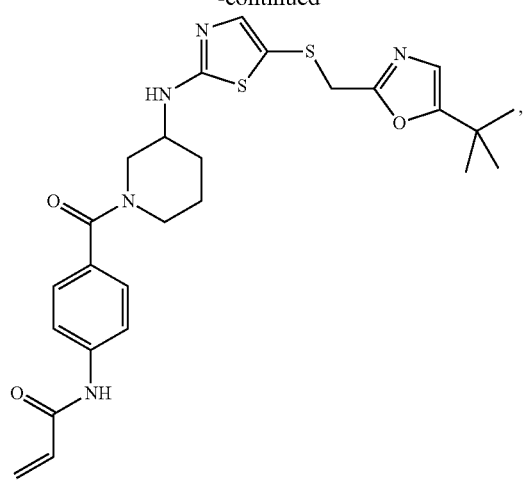
THZ-CE-B-12
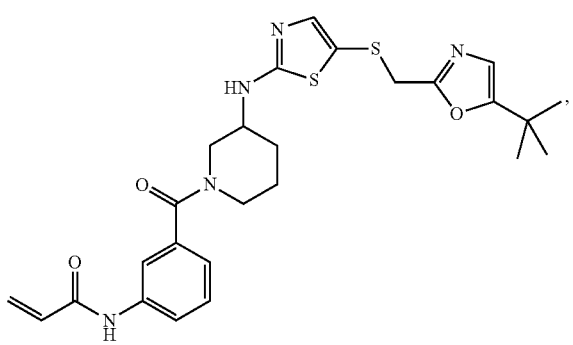
THZ-CE-B-15
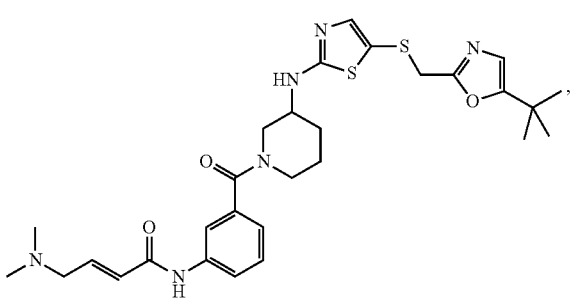
THZ-CE-B-16
-continued
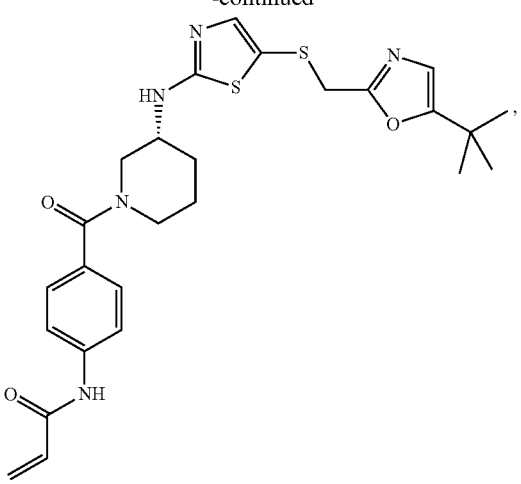
MFH-2-90-1
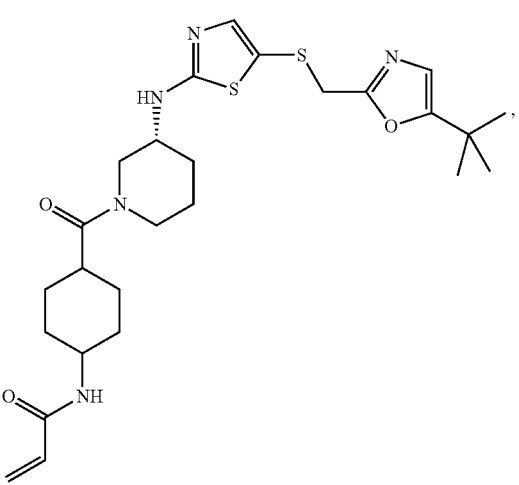
MFH-2-95-1
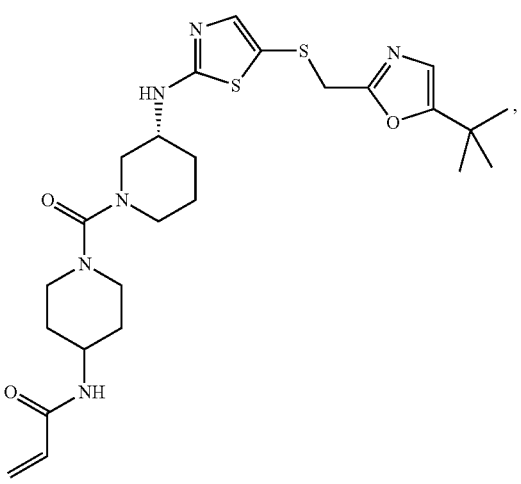
MFH-2-104-1

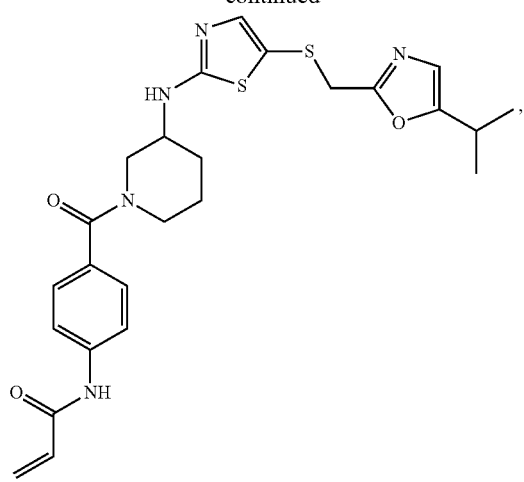
MFH-2-92-1
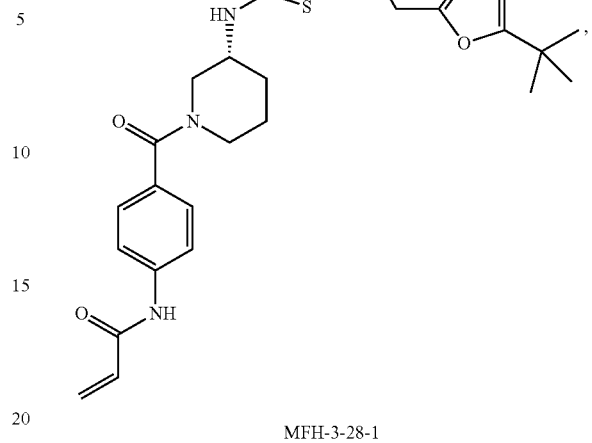
MFH-3-28-1
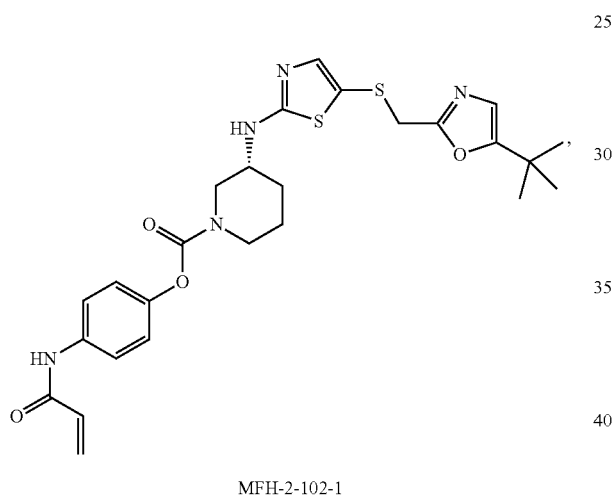
MFH-2-102-1
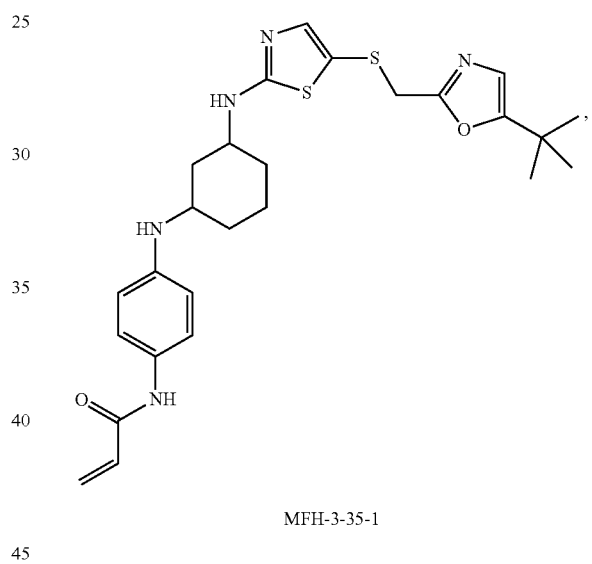
MFH-3-35-1
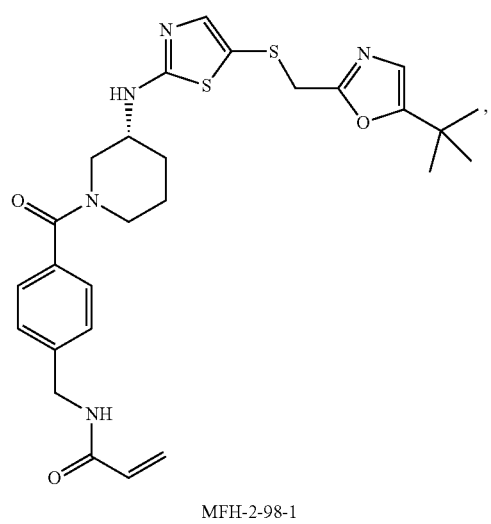
MFH-2-98-1
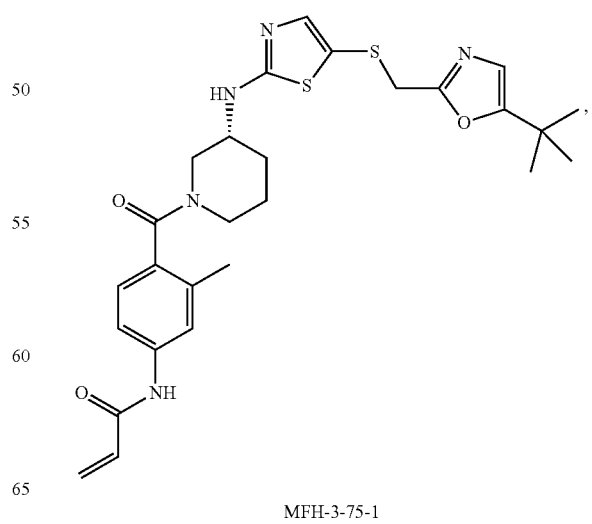
MFH-3-75-1

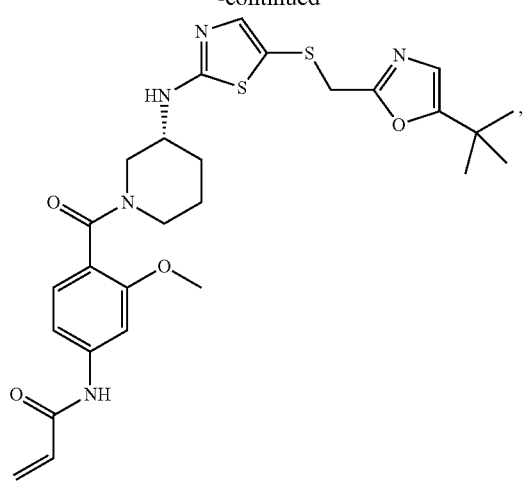
MFH-3-81-1
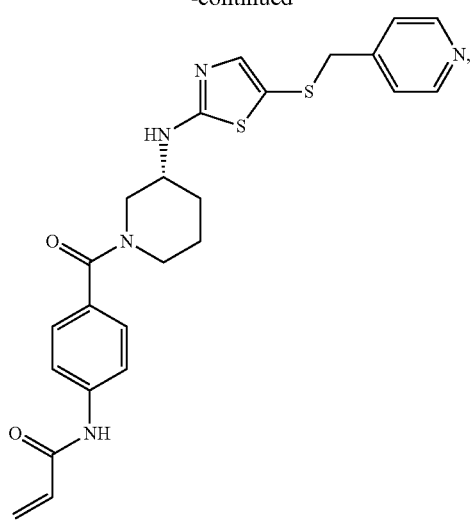
MFH-3-179-1
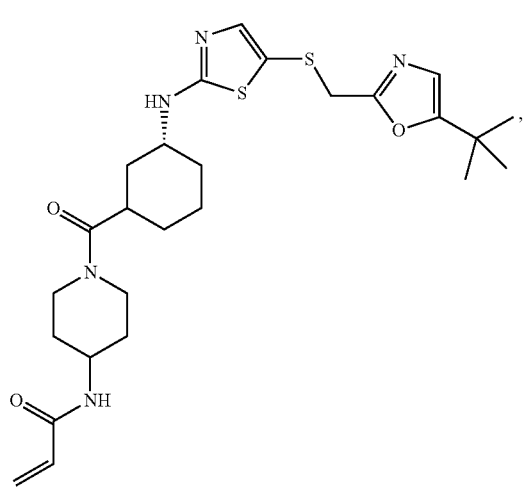
MFH-3-88-1
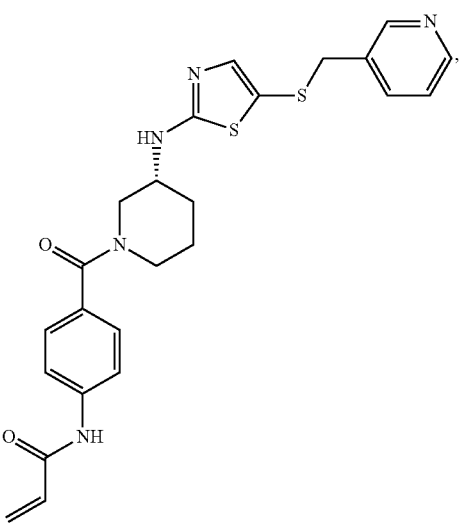
MFH-3-191-1
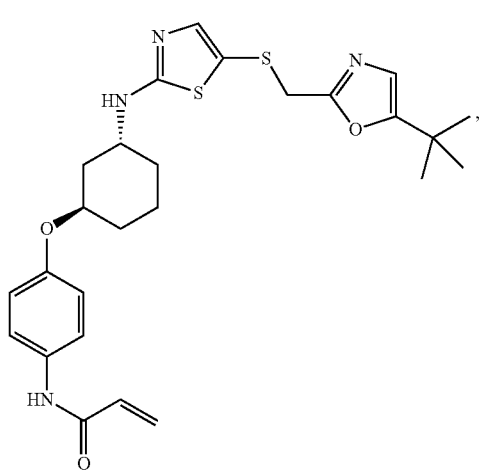
MFH-3-103-1
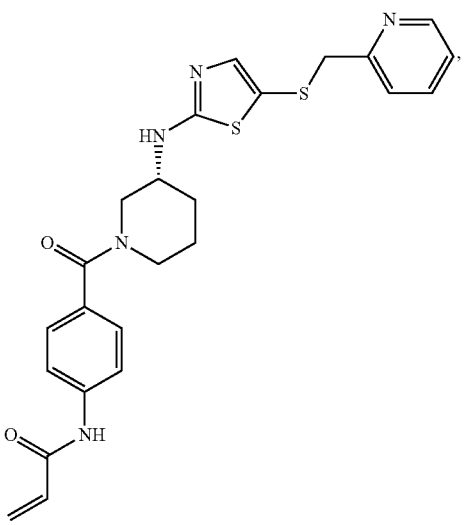
MFH-3-203-1

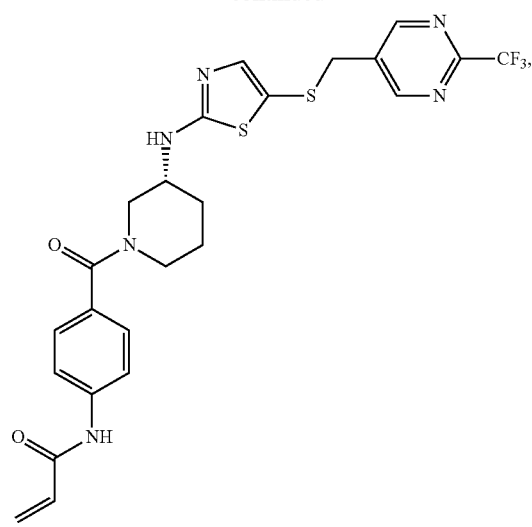
MFH-3-201-1
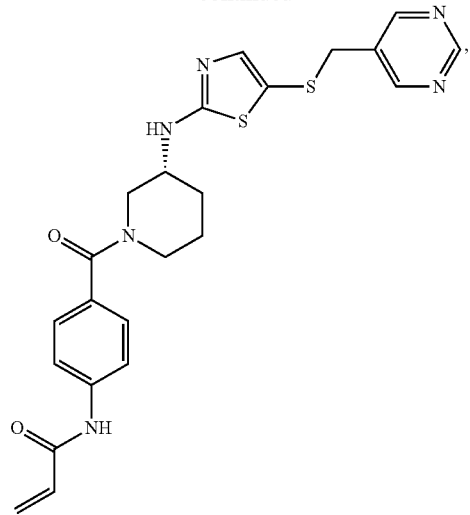
MFH-4-10-1
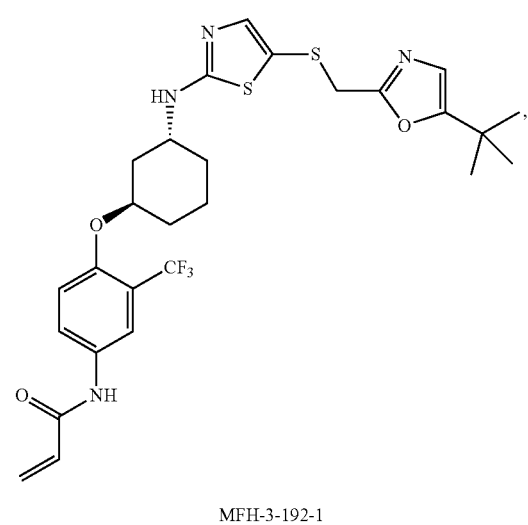
MFH-3-192-1
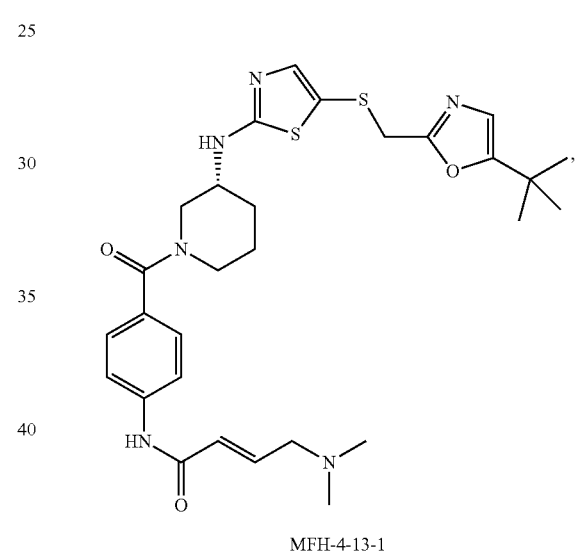
MFH-4-13-1
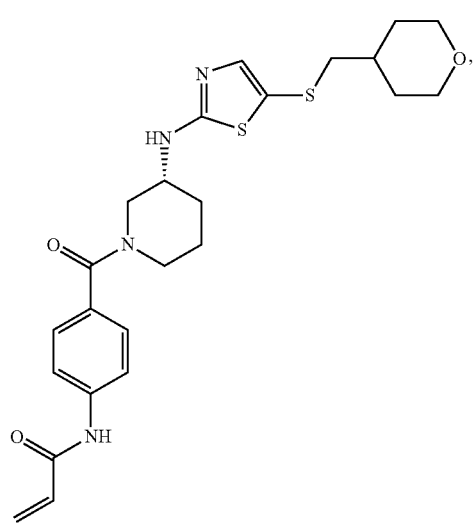
MFH-4-4-1
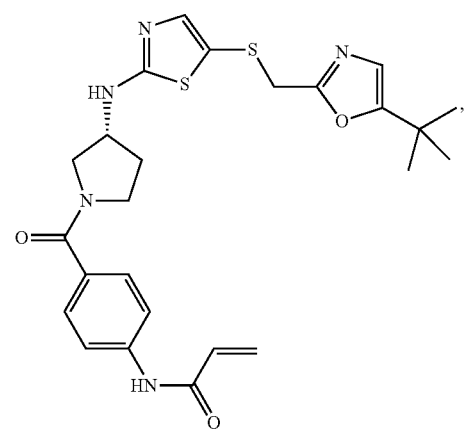
MFH-4-70-1

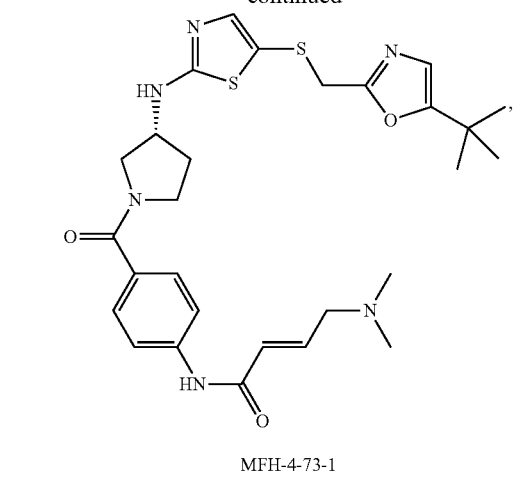
MFH-4-73-1
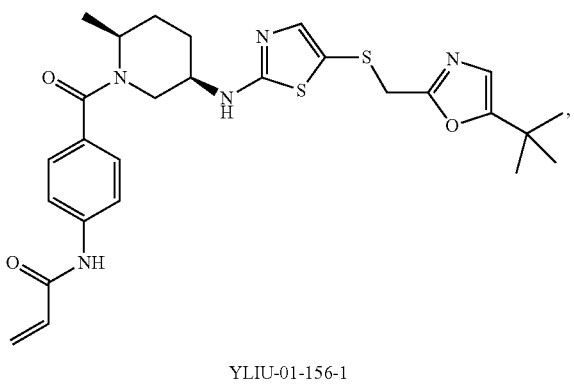
YLIU-01-156-1
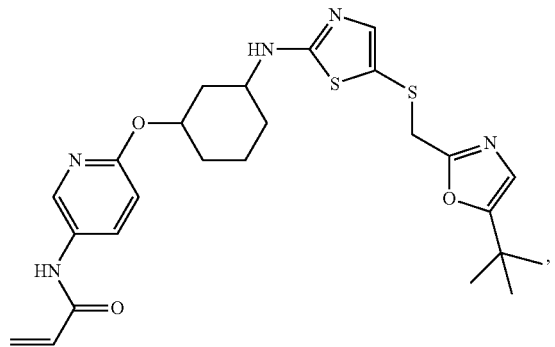
YLIU-01-163-1
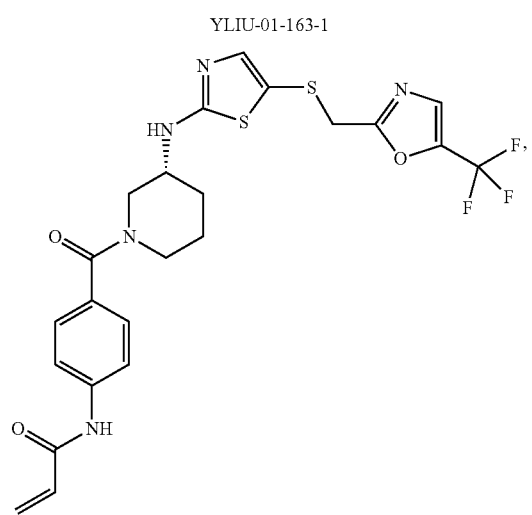
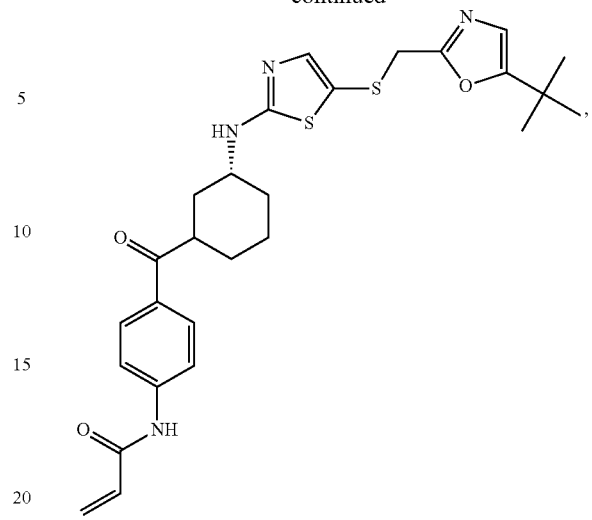
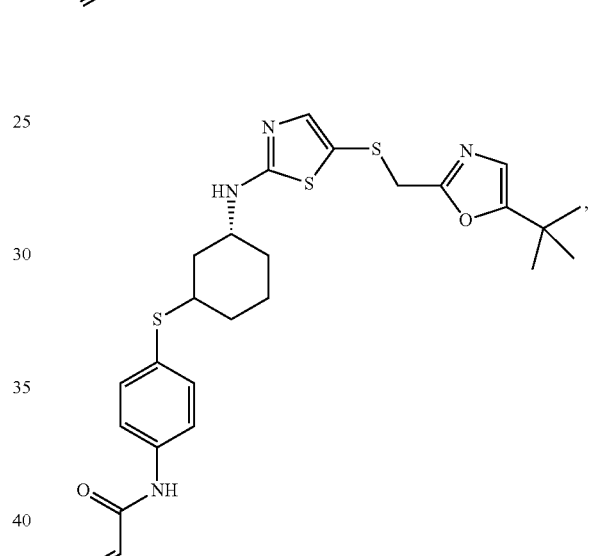
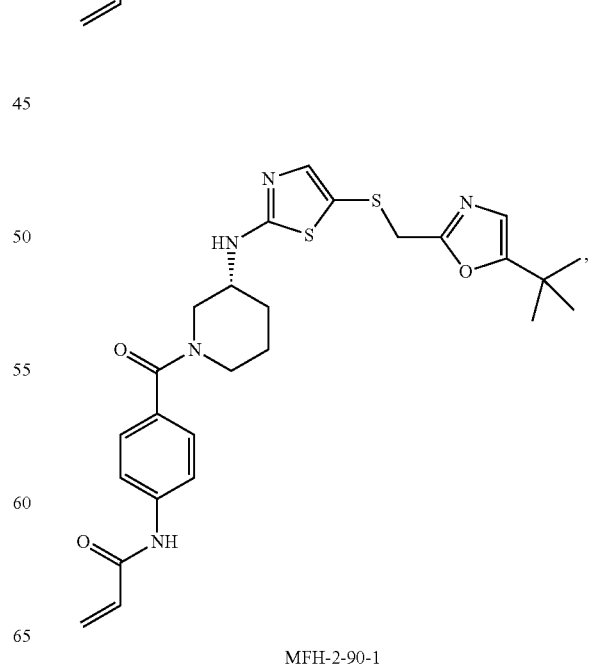
MFH-2-90-1

141
-continued
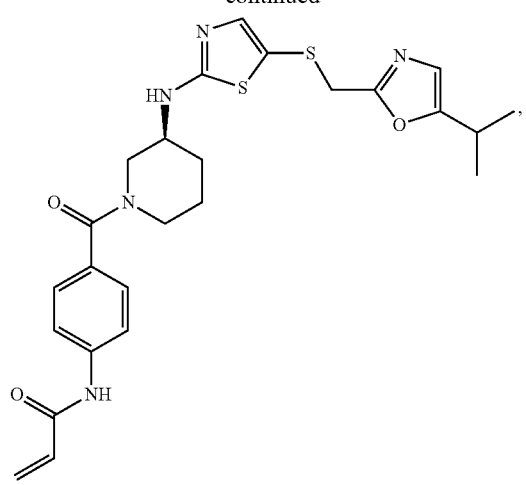
MFH-2-92-1
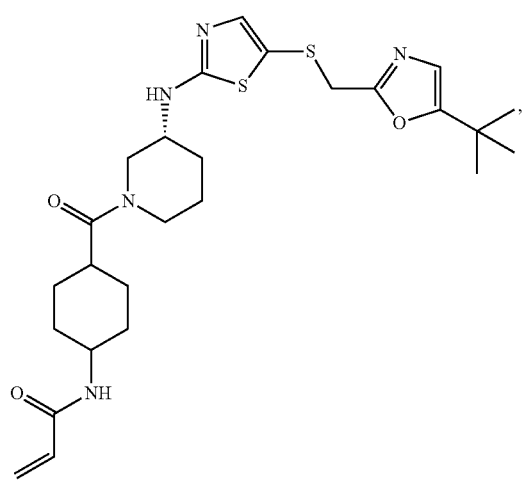
MFH-2-95-1
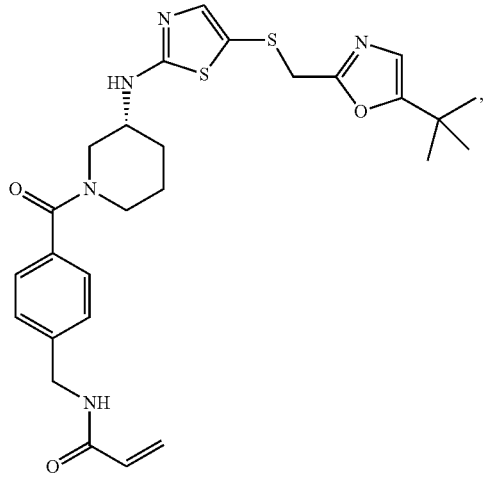
MFH-2-98-1
142
-continued
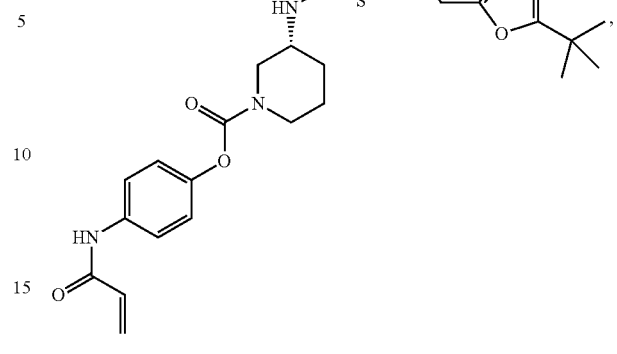
MFH-2-102-1
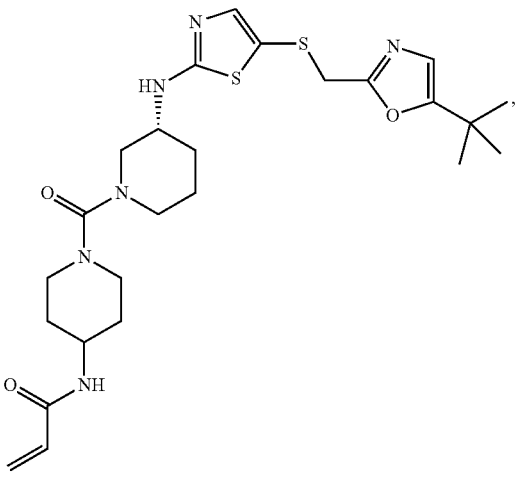
MFH-2-104-1
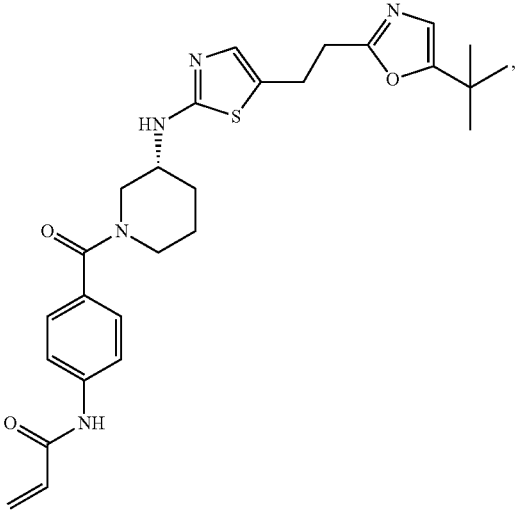
MFH-3-116-1

143
-continued
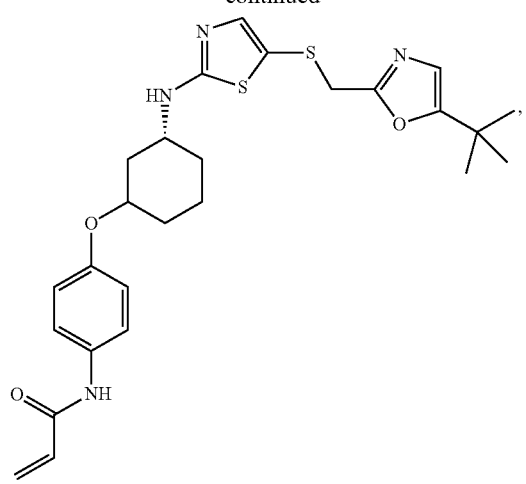
MFH-3-103-1
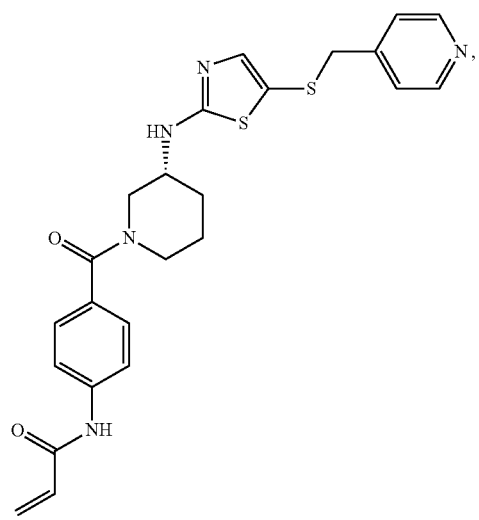
MFH-3-179-1
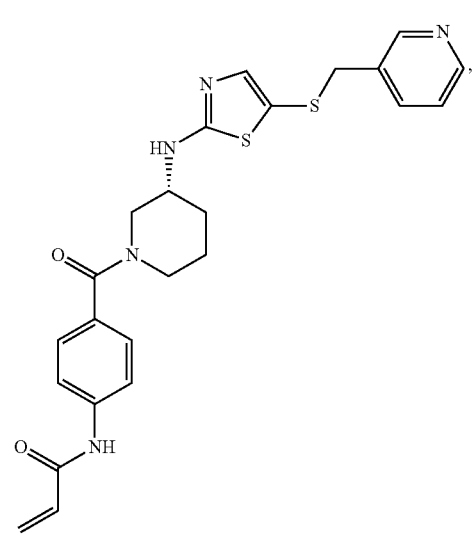
MFH-3-191-1
144
-continued
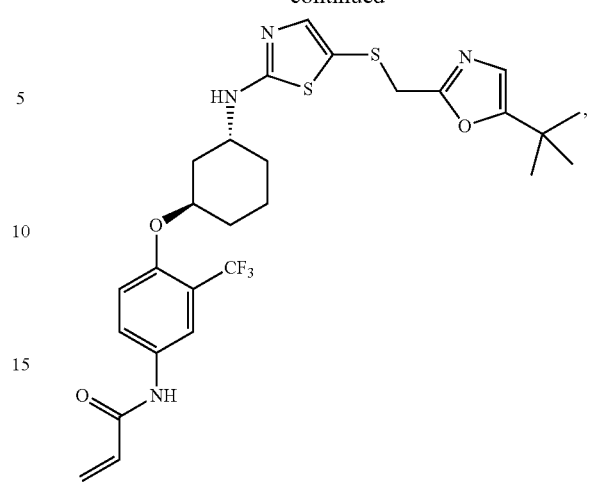
MFH-3-192-1
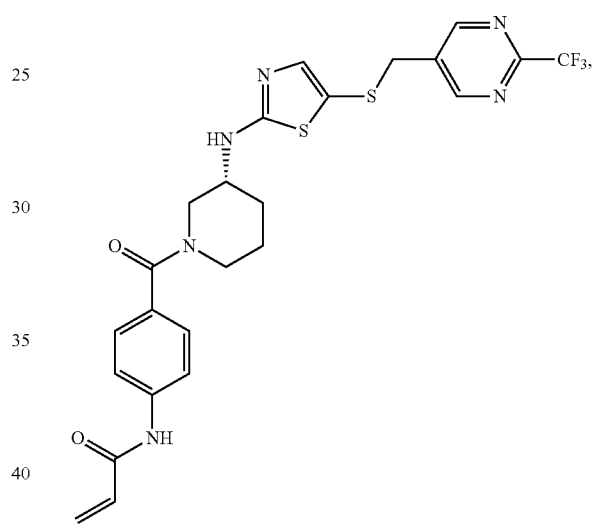
MFH-3-201-1
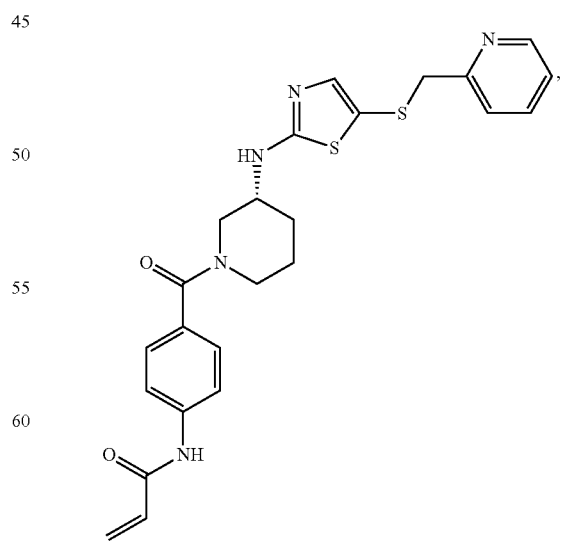
MFH-3-203-1

-continued
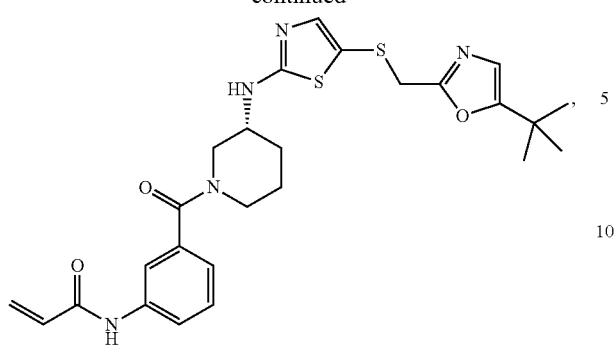
THZ-CE-B-15
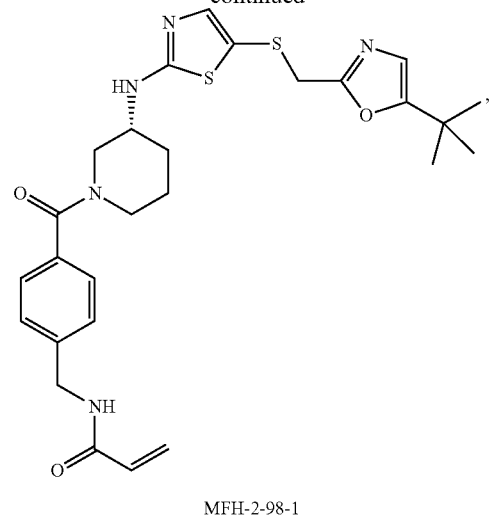
MFH-2-98-1
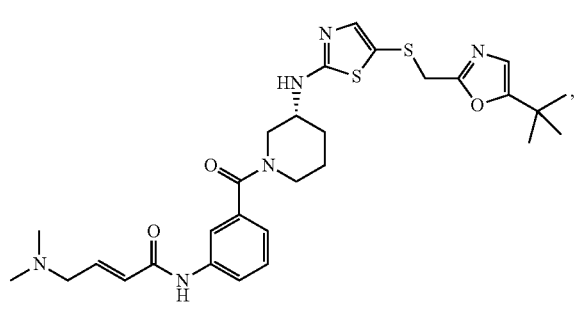
THZ-CE-B-16
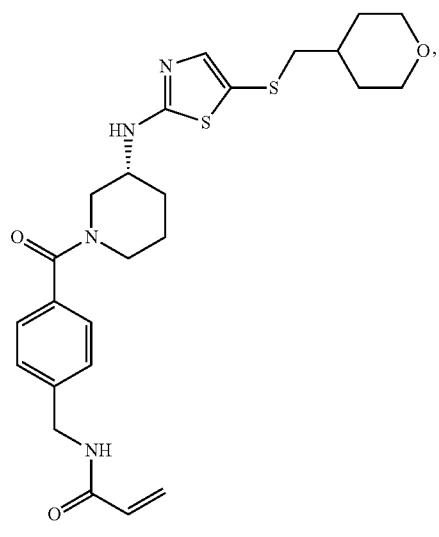
MFH-4-4-1
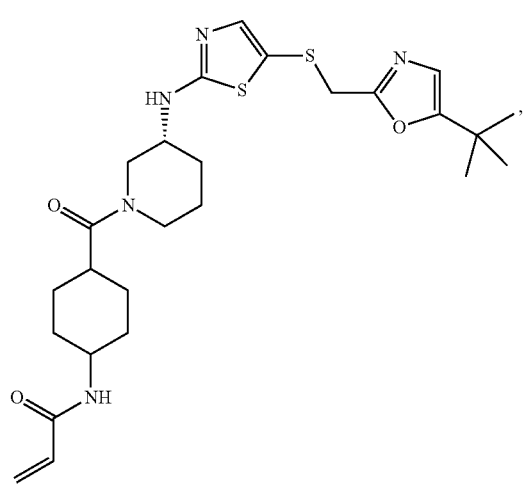
MFH-2-95-1
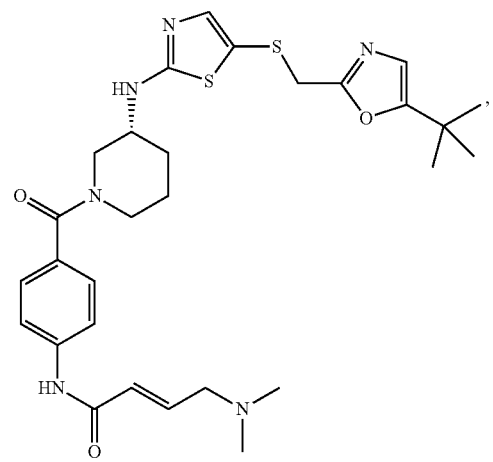
MFH-4-13-1

147
-continued
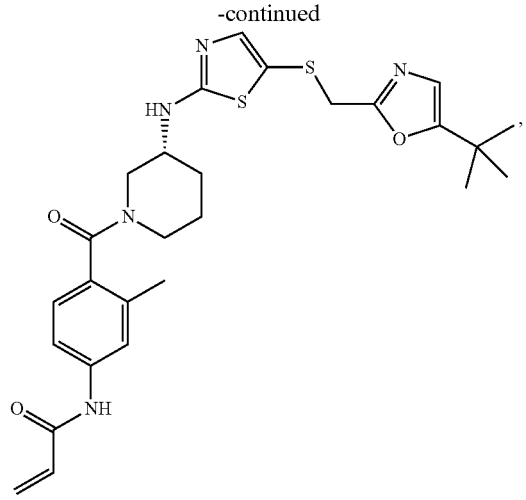
MFH-3-75-1
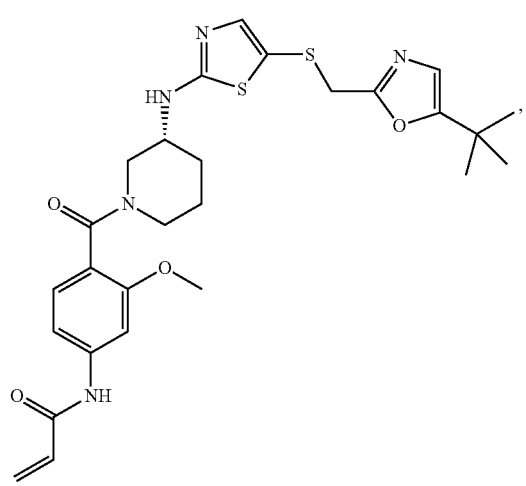
MFH-3-81-1
MFH-3-88-1
148
-continued
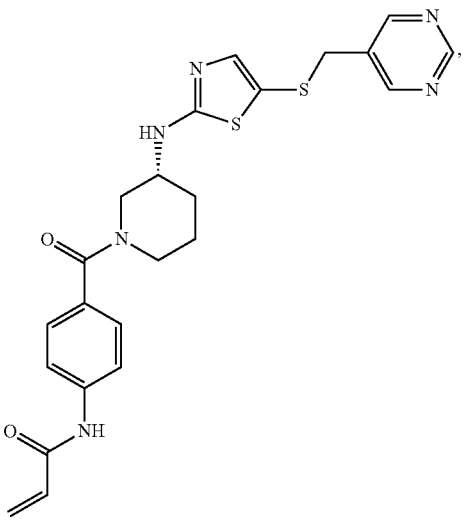
MFH-4-10-1
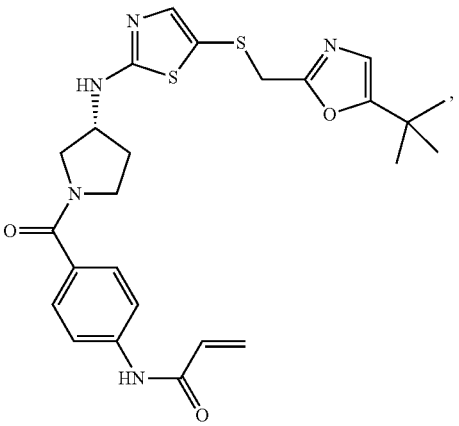
MFH-4-70-1
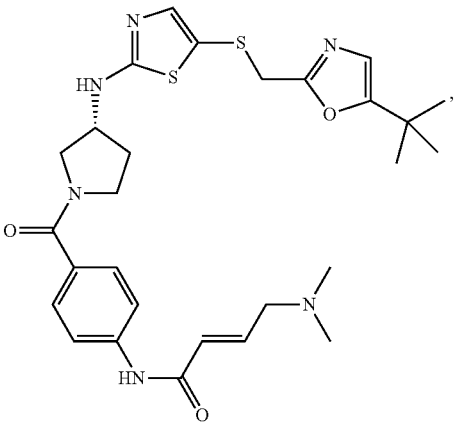
MFH-4-73-1
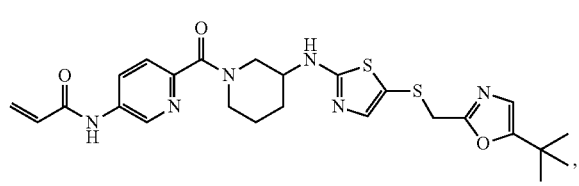
YLIU-01-067-1

-continued

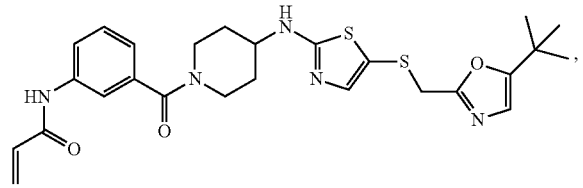
YLIU-01-078-1

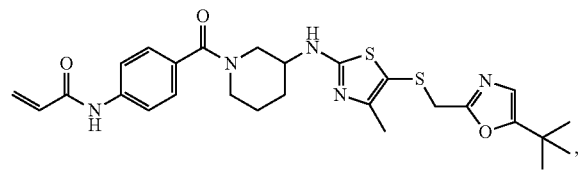
YLIU-01-099-1

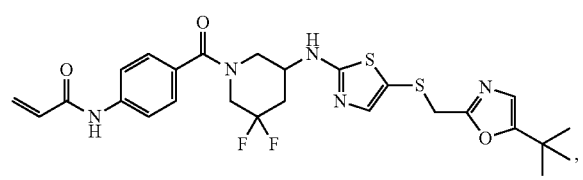
YLIU-01-114-1

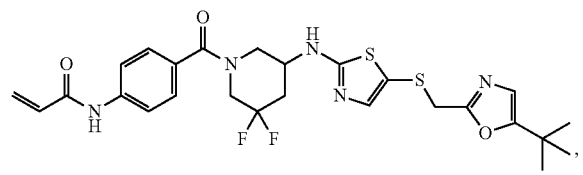
YLIU-01-114-1

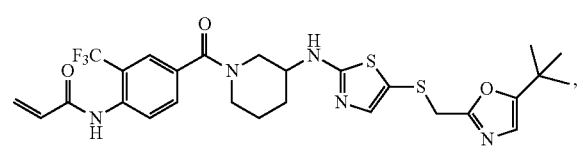
YLIU-01-121-1

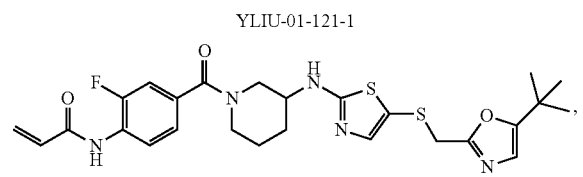
YLIU-01-123-1

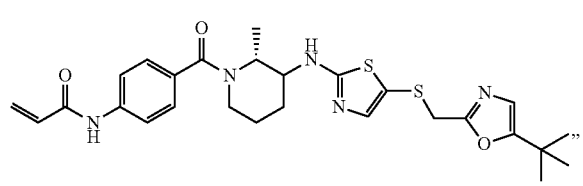
YLIU-01-126-1 or a pharmaceutically acceptable salt, solvate, hydrate, polymorph, co-crystal, tautomer, stereoisomer, isotopically labeled derivative, or prodrug thereof.

In certain embodiments, a compound of Formula (II') is of the formula:

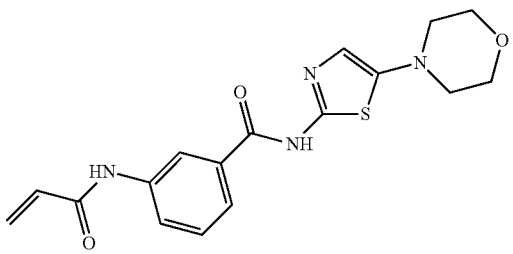
THZ-CE-B-17

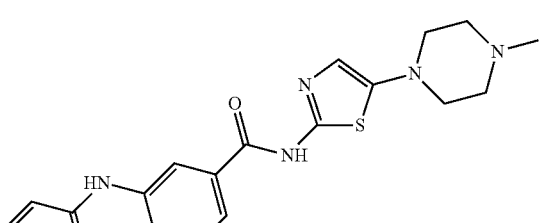
THZ-CE-B-18

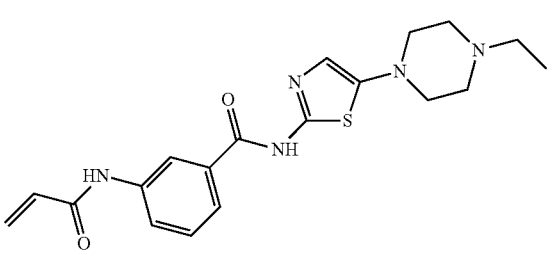
THZ-CE-B-19

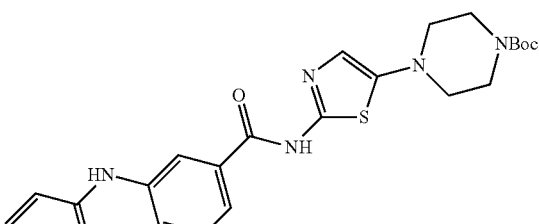
THZ-CE-B-20

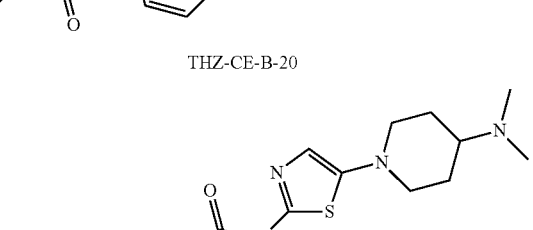
THZ-CE-B-22 or a pharmaceutically acceptable salt, solvate, hydrate, polymorph, co-crystal, tautomer, stereoisomer, isotopically labeled derivative, or prodrug thereof.

In certain embodiments, a compound of Formula (II) is of the formula:

B1
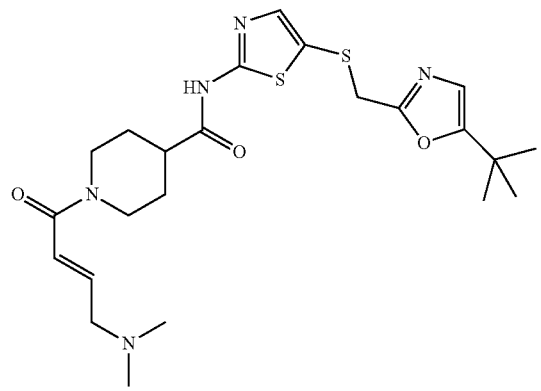

B2
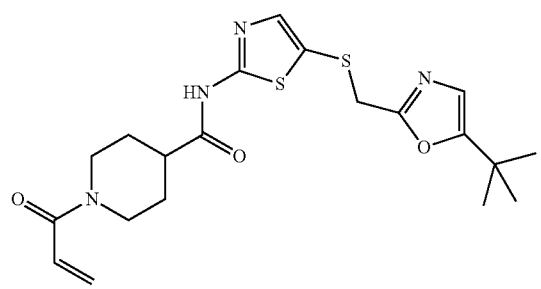

B3
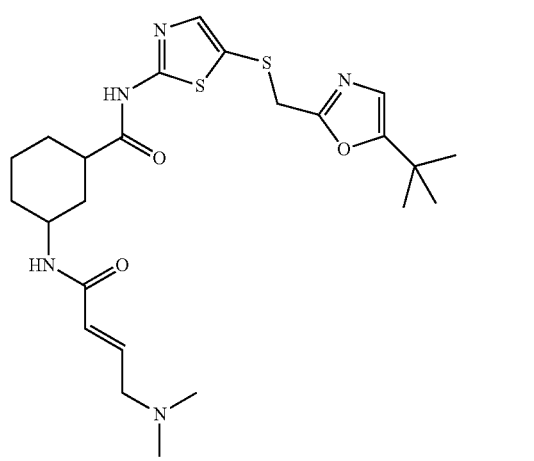

B8
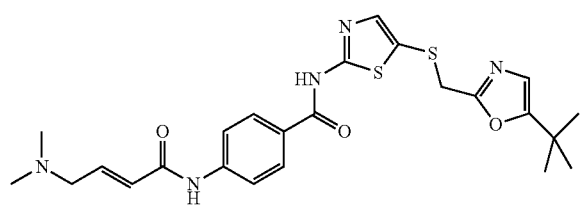

B6
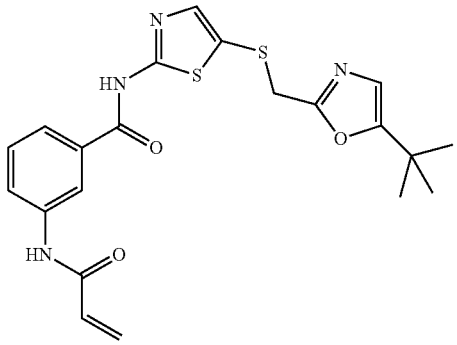

B7
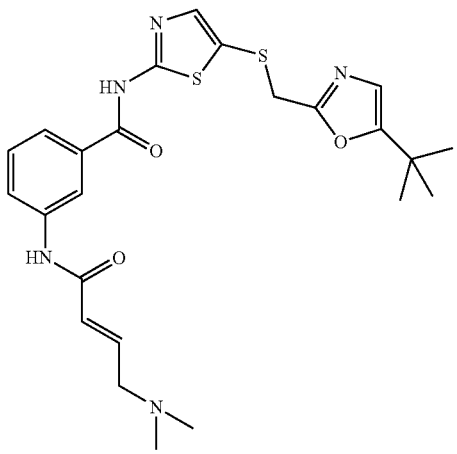

or a pharmaceutically acceptable salt, solvate, hydrate, polymorph, co-crystal, tautomer, stereoisomer, isotopically labeled derivative, or prodrug thereof.

Pharmaceutical Compositions and Administration

The pharmaceutical compositions described herein may be useful in treating and/or preventing proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject. The compositions described herein may also be useful for inhibiting the activity of a protein kinase (e.g., CDK (e.g., CDK7, CDK12, and/or CDK13)) in a subject, biological sample, tissue, or cell. The compositions described herein may also be useful for inducing apoptosis in a cell.

The present disclosure provides pharmaceutical compositions comprising a compound described herein (e.g., a compound of any one of Formulae (I'), (II'), (I), (II), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical composition of the invention comprises a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. In certain embodiments, the compound described herein, or a pharmaceutically acceptable salt, solvate, hydrate, polymorph, co-crystal, tautomer, stereoisomer, isotopically labeled derivative, or prodrug thereof, is provided in an effective amount in the pharmaceutical composition.

In certain embodiments, the effective amount is a therapeutically effective amount (e.g., amount effective for treating a proliferative disease in a subject in need thereof). In certain embodiments, the effective amount is an amount effective for inhibiting the activity of a protein kinase (e.g., CDK (e.g., CDK7, CDK12, and/or CDK13)) in a subject in need thereof. In certain embodiments, the effective amount is an amount effective for inhibiting the activity of a protein kinase (e.g., CDK (e.g., CDK7, CDK12, and/or CDK13)) in a cell. In certain embodiments, the effective amount is an amount effective for inducing apoptosis in a cell. In certain embodiments, the effective amount is a prophylactically effective amount (e.g., amount effective for preventing a proliferative disease in a subject in need thereof and/or for keeping a subject in need thereof in remission of a proliferative disease).

In certain embodiments, the protein kinase being inhibited is a CDK. In certain embodiments, the protein kinase being inhibited is CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19, or CDK20. In certain embodiments, the protein kinase being inhibited is CDK7. In certain embodiments, the protein kinase being inhibited is CDK12. In certain embodiments, the protein kinase being inhibited is CDK13. In certain embodiments, the protein kinase being inhibited is a Src family kinase. In certain embodiments, the protein kinase being inhibited is SRC. In certain embodiments, the protein kinase being inhibited is FGR. In certain embodiments, the protein kinase being inhibited is BUB IB. In certain embodiments, the protein kinase being inhibited is CHEK2. In certain embodiments, the protein kinase being inhibited is HIPK4. In certain embodiments, the protein kinase being inhibited is PRKCQ. In certain embodiments, the protein kinase being inhibited is RET. In certain embodiments, the protein kinase being inhibited is MELK. In certain embodiments, the protein kinase being inhibited is IRAK1, ERAK4, BMX, or PI3K. In certain embodiments, the protein kinase being inhibited is ABL, ARG, BLK, CSK, EphB1, EphB2, FGR, FRK, FYN, SRC, YES, LCK, LYN, MAP2K5, NLK, p38a, SNRK, or TEC. In certain embodiments, the protein kinase being inhibited is ABL1(H396P)-phosphorylated, ABL1-phosphorylated, BLK, EPHA4, EPHB2, EPHB3, EPHB4, FGR, JAK3(JH1 domain-catalytic), KIT, KIT (L576P), KIT(V559D), PDGFRB, SRC, YES, ABL1 (H396P)-nonphosphorylated, ABL1(Y253F)-phosphorylated, ABL1-nonphosphorylated, FRK, LYN, ABL1 (Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1 (F317L)-nonphosphorylated, FYN, LCK, EPHA2, ABL1 (M351T)-phosphorylated, TXK, EGFR(L858R), EGFR (L861Q), ERBB2, ERBB3, EPHA5, ABL1(F317I)-nonphosphorylated, EGFR(L747-E749del, A750P), CSK, EPHA1, ABL1(F317L)-phosphorylated, BRAF(V600E), EGFR, KIT-autoinhibited, or EGFR(E746-A750del). In certain embodiments, the protein kinase being inhibited is ABL1(F317L)-nonphosphorylated, ABL1 (H396P)-nonphosphorylated, ABL1 (H396P)-phosphorylated, ABL1-phosphorylated, BLK, EPHA4, EPHB2, EPHB3, EPHB4, JAK3(JH1domain-catalytic), KIT, KIT(L576P), KIT (V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1 (Q252H)-nonphosphorylated, ABL2, FYN, EPHB1, ABL1 (E255K)-phosphorylated, ABL1(F317L)-phosphorylated, EPHA1, ABL1 (M351 T)-phosphorylated, ERBB4, TXK, LCK, EPHA8, SIK, EPHA5, EGFR(L861Q), CSF1R-autoinhibited, BRAF(V600E), BRK, CSK, KIT(D816V), KIT-autoinhibited, EGFR(L747-T751del,Sins), EGFR(L858R), EGFR(L747-E749del, A750P), or CSF1R.

In certain embodiments, the effective amount is an amount effective for inhibiting the activity of a protein kinase (e.g., CDK (e.g., CDK7, CDK12, and/or CDK13)) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a protein kinase (e.g., CDK (e.g., CDK7, CDK12, and/or CDK13)) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a protein kinase (e.g., CDK (e.g., CDK7, CDK12, and/or CDK13)) by a range between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between about 0.1% and about 100% (w/w) of the active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose for an adult human whose body weight is approximately 70 kg.

A compound or composition, as described herein, may be administered in combination with one or more additional pharmaceutical agents (e.g., therapeutically and/or prophylactically active agents) useful in treating and/or preventing a proliferative disease. The compounds or compositions can be administered in combination with additional pharmaceutical agents that improve their activity (e.g., activity (e.g., potency and/or efficacy) in treating a proliferative disease in a subject in need thereof, in preventing a proliferative disease in a subject in need thereof, and/or in inhibiting the activity of a protein kinase (e.g., CDK (e.g., CDK7, CDK12, and/or CDK13)) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which are different from the compound or composition and may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent useful in inhibiting the activity of a protein kinase (e.g., CDK (e.g., CDK7, CDK12, and/or CDK13)) in a subject, biological sample, tissue, or cell. In certain embodiments, the additional pharmaceutical agent is a pharmaceutical agent useful in inducing apoptosis in a cell. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agent(s) may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is a cytotoxic agent. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine 1131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELEX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VLADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a kinase inhibitor. In certain embodiments, the additional pharmaceutical agent is a protein kinase inhibitor (e.g., tyrosine protein kinase inhibitor). In certain embodiments, the additional pharmaceutical agent is an inhibitor of a Src family kinase. In certain embodiments, the additional pharmaceutical agent is a CDK inhibitor. In certain embodiments, the additional pharmaceutical agent is a CDK7 inhibitor. In certain embodiments, the additional pharmaceutical agent is a CDK12 inhibitor. In certain embodiments, the additional pharmaceutical agent is a CDK13 inhibitor. In certain embodiments, the additional pharmaceutical agent is an inhibitor of one or more protein kinases selected from the group consisting of IRAK1, IRAK4, BMX, and PI3K. In certain embodiments, the additional pharmaceutical agent is an inhibitor of one or more protein kinases selected from the group consisting of BUB1B, CDK2, CDK9, CHEK2, FGR, HIPK4, PRKCQ, RET, SRC, and MELK. In certain embodiments, the additional pharmaceutical agent is an inhibitor of one or more protein kinases selected from the group consisting of ABL, ARG, BLK, CSK, EphB1, EphB2, FGR, FRK, FYN, SRC, YES, LCK, LYN, MAP2K5, NLK, p38a, SNRK, and TEC. In certain embodiments, the additional pharmaceutical agent is an inhibitor of one or more protein kinases selected from the group consisting of ABL1(H396P)-phosphorylated, ABL1-phosphorylated, BLK, EPHA4, EPHB2, EPHB3, EPHB4, FGR, JAK3(JH1domain-catalytic), KIT, KIT (L576P), KIT(V559D), PDGFRB, SRC, YES, ABL1 (H396P)-nonphosphorylated, ABL1(Y253F)-phosphorylated, ABL1-nonphosphorylated, FRK, LYN, ABL1 (Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1 (F317L)-nonphosphorylated, FYN, LCK, EPHA2, ABL1 (M351T)-phosphorylated, TXK, EGFR(L858R), EGFR (L861Q), ERBB2, ERBB3, EPHA5, ABL1(F317I)-nonphosphorylated, EGFR(L747-E749del, A750P), CSK, EPHA1, ABL1(F317L)-phosphorylated, BRAF(V600E), EGFR, KIT-autoinhibited, and EGFR(E746-A750del). In certain embodiments, the additional pharmaceutical agent is an inhibitor of one or more protein kinases selected from the group consisting of ABL1(F317L)-nonphosphorylated, ABL1 (H396P)-nonphosphorylated, ABL1 (H396P)-phosphorylated, ABL1-phosphorylated, BLK, EPHA4, EPHB2, EPHB3, EPHB4, JAK3(JHldomain-catalytic), KIT, KIT (L576P), KIT(V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1 (Q252H)-phosphorylated, MEK5, ABL1(Q252H)-nonphosphorylated, ABL2, FYN, EPHB1, ABL1(E255K)-phosphorylated, ABL1(F317L)-phosphorylated, EPHA1, ABL1(M351T)-phosphorylated, ERBB4, TXK, LCK, EPHA8, SIK, EPHA5, EGFR(L861Q), CSF1R-autoinhibited, BRAF(V600E), BRK, CSK, KIT (D816V), KIT-autoinhibited, EGFR(L747-T751del,Sins), EGFR(L858R), EGFR(L747-E749del, A750P), and CSF1R. In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered or used in combination with an anti-cancer therapy including, but not limited to, transplantation (e.g., bone marrow transplantation, stem cell transplantation), surgery, radiation therapy, immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Methods of Treatment and Uses

The present invention also provides methods for the treatment or prevention of a proliferative disease (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases).

The compounds described herein may exhibit kinase inhibitory activity; the ability to inhibit cyclin-dependent kinase (CDK); the ability to inhibit cyclin-dependent kinase 7 (CDK7); the ability to inhibit cyclin-dependent kinase 7 (CDK7), without inhibiting another cyclin-dependent kinase (CDK); the ability to inhibit cyclin-dependent kinase 12 (CDK12); the ability to inhibit cyclin-dependent kinase 12 (CDK12), without inhibiting another cyclin-dependent kinase (CDK); the ability to inhibit cyclin-dependent kinase 13 (CDK13); the ability to inhibit cyclin-dependent kinase 13 (CDK13), without inhibiting another cyclin-dependent kinase (CDK); the ability to inhibit cyclin-dependent kinases 12 and 13 (CDK12 and CDK13); the ability to inhibit cyclin-dependent kinases 12 and 13 (CDK12 and CDK13), without inhibiting another cyclin-dependent kinase (CDK); a therapeutic effect and/or preventative effect in the treatment of cancers; a therapeutic effect and/or preventative effect in the treatment of Myc-dependent cancers; and/or a therapeutic profile (e.g., optimum safety and curative effect) that is superior to existing chemotherapeutic agents.

Without wishing to be bound by any particular theory, the compounds described herein are able to bind (e.g., covalently modify) the protein kinase being inhibited. In certain embodiments, the $R^2$ group of a compound described herein is able to bind (e.g., covalently modify) to the protein kinase. In certain embodiments, the $R^2$ group of a compound described herein is able to covalently bind a cysteine residue of the protein kinase. In certain embodiments, the compound is capable of covalently modifying CDK7 (e.g., Cys312 of CDK7). In certain embodiments, the $R^2$ group of a compound described herein is able to covalently modify residue Cys312 of CDK7. In certain embodiments, the compound is capable of covalently modifying CDK12 (e.g., Cys1039 of CDK12). In certain embodiments, the $R^2$ group of a compound described herein is able to covalently modify residue Cys1039 of CDK12. In certain embodiments, the compound is capable of covalently modifying CDK13 (e.g., Cys1017 of CDK13). In certain embodiments, the $R^2$ group of a compound described herein is able to covalently modify residue Cys1017 of CDK13.

In another aspect, the present disclosure provides methods of inhibiting the activity of a protein kinase in a subject, the methods comprising administering to the subject an effective amount (e.g., therapeutically effective amount) of a compound, or pharmaceutical composition thereof, as described herein.

In another aspect, the present disclosure provides methods of inhibiting the activity of a protein kinase in a biological sample, the methods comprising contacting the biological sample with an effective amount of a compound, or pharmaceutical composition thereof, as described herein.

In another aspect, the present disclosure provides methods of inhibiting the activity of a protein kinase in a tissue, the methods comprising contacting the tissue with an effective amount of a compound, or pharmaceutical composition thereof, as described herein.

In another aspect, the present disclosure provides methods of inhibiting the activity of a protein kinase in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the biological sample being contacted with the compound or composition is breast tissue, bone marrow, lymph node, lymph tissue, spleen, or blood.

In certain embodiments, the cell being contacted with the compound or composition is in vitro. In certain embodiments, the cell being contacted with the compound or composition is in vivo. In certain embodiments, the cell being contacted with the compound or composition is ex vivo. In certain embodiments, the cell being contacted with the compound or composition is a malignant cell (e.g., malignant blood cell). In certain embodiments, the cell being contacted with the compound or composition is a malignant hematopoietic stem cell (e.g., malignant myeloid cell or malignant lymphoid cell). In certain embodiments, the cell being contacted with the compound or composition is a malignant lymphocyte (e.g., malignant T-cell or malignant B-cell). In certain embodiments, the cell being contacted with the compound or composition is a malignant red blood cell, malignant white blood cell, or malignant platelet. In certain embodiments, the cell being contacted with the compound or composition is a malignant neutrophil, malignant macrophage, or malignant plasma cell. In certain embodiments, the cell being contacted with the compound or composition is a carcinoma cell. In certain embodiments, the cell being contacted with the compound or composition is a carcinoma breast cell. In certain embodiments, the cell being contacted with the compound or composition is a sarcoma cell. In certain embodiments, the cell being contacted with the compound or composition is a sarcoma cell from breast tissue.

The proliferative disease to be treated or prevented using the compounds described herein may be associated with overexpression of a kinase, such as cyclin-dependent kinase (CDK). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins.

Modulation of the expression levels, degradation rates, protein levels, and activity levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, i.e., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

CDK7, a member of the CDK family, was originally isolated as the catalytic subunit of the trimeric CDK-activating kinase (CAK) complex. This complex, consisting of CDK7, cyclin H, and MAT1, is responsible for activation of the mitotic promoting factor in vitro. The discovery that CDK7 was also a component of the basal transcription repair factor IIH (TFIIH) implicated a dual role for CDK7 in transcription as part of TFIIH and in the control of the cell cycle as the trimeric CAK complex. TFIIH is a multi-subunit protein complex identified as a factor required for RNA polymerase II (RNAP II)-catalyzed transcription, and subsequently this complex was found to play a key role in nucleotide excision repair. CDK7 is a component of at least three complexes, i.e., the trimeric CAK complex, the quaternary complex with the XPD (or ERCC2, a protein involved in transcription-coupled nucleotide excision repair), and the nine-subunit TFIIH complex. The two functions of CDK7 in CAK and CTD phosphorylation support critical facets of cellular proliferation, cell cycling, and transcription. Overexpression of CDK7 may inhibit apoptosis, promote transcription and cell proliferation, and/ or disrupt DNA repair, and therefore, cause proliferative diseases. In certain embodiments, the proliferative disease to be treated or prevented using the compounds described herein may be associated with overexpression of a CDK (e.g., CDK7).

Cdk12 and Cdk13 are Cdc2-related proteins that share 92% identity in their kinase domains (Chen et al., *Exp. Neurol.*, 2014, 261, 10-21). CDK12 plays a critical role in cell processes, for example, regulating transcription and splicing machinery by stabilizing the RNAPII and DNA interaction, and regulating DNA damage response (DDR) and maintenance of genomic stability by modulating the expression of DDR genes. Overexpression of CDK12 has been found to correlate, both at the transcriptional and protein level, with pathological parameters of breast cancer disease.

A proliferative disease may be associated with aberrant activity of a CDK (e.g., CDK7, CDK12, and/or CDK13). Aberrant activity of a CDK (e.g., CDK7, CDK12, and/or CDK13) may be an elevated and/or an inappropriate activity of the CDK. Deregulation of cell cycle progression is a characteristic of a proliferative disease, and a majority of proliferative diseases have abnormalities in some component of CDK (e.g., CDK7, CDK12, and/or CDK13) activity, frequently through elevated and/or inappropriate CDK activation. Inhibition of the catalytic activity of CDK7, CDK12, and/or CDK13 would be expected to inhibit cell cycle progression by blocking the phosphorylation of cell cycle CDKs, and would additionally inhibit transcription of effectors of cell division. In certain embodiments, CDK7 is not overexpressed, and the activity of CDK7 is elevated and/or inappropriate. In certain other embodiments, CDK7 is overexpressed, and the activity of CDK7 is elevated and/or inappropriate. In certain embodiments, CDK12 is not overexpressed, and the activity of CDK12 is elevated and/or inappropriate. In certain embodiments, CDK12 is overexpressed, and the activity of CDK12 is elevated and/or inappropriate. In certain other embodiments, CDK13 is not overexpressed, and the activity of CDK13 is elevated and/or inappropriate. In certain other embodiments, CDK13 is overexpressed, and the activity of CDK13 is elevated and/or inappropriate. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of CDK7 and be useful in treating and/or preventing proliferative diseases. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of CDK12 and/or CDK13 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Apoptosis is the process of programmed cell death. Inhibition of apoptosis may result in uncontrolled cell proliferation and, therefore, may cause proliferative diseases. The cell cycle CDKs (CDK1,2, 4, and 6) are activated by phosphorylation by CDK7/cyclin H (also called CAK). Inhibition of CDK7 would therefore result in cell-cycle arrest at multiple points in the cell cycle due to failure to activate the cell cycle CDKs. CDK 7 activates transcription by phosphorylating the CTD of RNAPII. Inhibition of CTD phosphorylation has been shown to inhibit transcription and reduce expression of short lived proteins, including those involved in apoptosis regulation. It is appreciated in the art that stalling of RNA polymerase may activate p53 (also known as protein 53 or tumor protein 53, a tumor suppressor protein that is encoded in humans by the TP53 gene), leading to apoptosis. Thus, inhibition of the activity of CDK7 are expected to cause cytotoxicity by inducing apoptosis. The compounds described herein, and pharmaceutically acceptable salts, solvates, hydrates, polymorphs, co-crystals, tautomers, stereoisomers, isotopically labeled derivatives, prodrugs, and compositions thereof, may induce apoptosis, and therefore, be useful in treating and/or preventing proliferative diseases.

The CycK/Cdk12 complex regulates phosphorylation of Ser2 in the C-terminal domain of RNA polymerase II and expression of a small subset of human genes, as revealed in expression microarrays. Through regulation of expression of DNA damage response genes (i.e. oncogenes), CycK/Cdk12 protects cells from genomic instability. In certain embodiments, the DNA damage response genes are BRCA1, BRCA2, HER1, HER2, ATR, FANCI, or FANCD2. In certain embodiments, the DNA damage response genes are BRCA1, HER2, ATR, FANCI, and FANCD2. In certain embodiments, the DNA damage response genes are BRCA1. In certain embodiments, the DNA damage response genes are HER2.

In certain embodiments, the proliferative disease to be treated or prevented using the compounds described herein is cancer. All types of cancers disclosed herein or known in the art are contemplated as being within the scope of the invention. In certain embodiments, the proliferative disease is a cancer associated with BCL-2 anti-apoptotic proteins (e.g., MCL-1 and/or XIAP) (e.g., cancer associated with dependence on BCL-2 anti-apoptotic proteins). In certain embodiments, the proliferative disease is a cancer associated with overexpression of MYC (a gene that codes for a transcription factor). In certain embodiments, the cancer is a MYC-dependent cancer. In certain embodiments, the proliferative disease is a cancer associated with amplification of BRCA1. In certain embodiments, the proliferative disease is a cancer associated with amplification of HER2. In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2-breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis.

In certain embodiments, the proliferative disease is an acute inflammatory disease. In certain embodiments, the acute inflammatory disease is rheumatoid arthritis, chron's disease, or fibrosis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

Another aspect of the invention relates to methods of inhibiting the activity of a kinase in a biological sample, tissue, cell, or subject. In certain embodiments, the kinase is a CDK. In certain embodiments, the kinase is CDK7. In certain embodiments, the kinase is CDK12. In certain embodiments, the kinase is CDK13. In certain embodiments, the activity of the kinase is aberrant activity of the kinase. In certain embodiments, the activity of the kinase is increased activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound described herein to the kinase.

Also provided in the present invention are methods of inhibiting transcription of genes in a biological sample or subject. In certain embodiments, the transcription of genes affected by the activity of CDK7 may be inhibited by a compound of the invention. In certain embodiments, the genes which may have their transcription inhibited by the activity of CDK7 are one or more selected from the group consisting of MYC, RUNX1, MYB, TAL1, GATA3, KLF2, HNRPDL, p21, ASCL1, MYCN, INSM1, NEUROD1, NEUROG1, FOXG1, FOXA1, SOX2, SOX4, BCL11A, OTX2, GAT2, PHOX2B, PLK2, TAF1, CTGF, WEE1, SDIM, JUN, PIM1, IL8, and FOS1. In certain embodiments, the genes which may have their transcription inhibited by the activity of CDK7 include MYC, KLF2, E2F2, CDK6, CCND3, E2F3, HNRPDL, TET1, IL7R, BRCA1, BRCA2, HER1, and HER2. In certain embodiments, the transcription of genes affected by the activity of CDK12 may be inhibited by a compound of the invention. In certain embodiments, the genes which may have their transcription inhibited by the activity of CDK12 are one or more selected from the group consisting of BRCA1, FANCI, ATR, FANCD2, APEX1, NEK9, CHEK1, CHEK2, ATM, RAD51C, RAD51D, ORC3L, MDC1, TERF2, ERCC4, FANCF, PARP9, RUNX1, MYB, TAL1, MCL1, MYC, BCL2, ETS1, and EWS-FLI. In certain embodiments, the transcription of genes affected by the activity of CDK13 may be inhibited by a compound of the invention. In certain embodiments, the gene is SNORA38.

The present invention also provides methods of inhibiting cell growth in a biological sample, tissue, cell, or subject.

In still another aspect, the present invention provides methods of inducing apoptosis of a cell in a biological sample, tissue, cell, or subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of a CDK. In certain embodiments, the additional pharmaceutical agent is an inhibitor of CDK7. In certain embodiments, the additional pharmaceutical agent is a selective inhibitor of CDK7. In certain embodiments, the additional pharmaceutical agent is a nonselective inhibitor of CDK7. In certain embodiments, the additional pharmaceutical agent is an inhibitor of CDK12. In certain embodiments, the additional pharmaceutical agent is a selective inhibitor of CDK12. In certain embodiments, the additional pharmaceutical agent is a nonselective inhibitor of CDK12. In certain embodiments, the additional pharmaceutical agent is an inhibitor of CDK13. In certain embodiments, the additional pharmaceutical agent is a selective inhibitor of CDK13. In certain embodiments, the additional pharmaceutical agent is a nonselective inhibitor of CDK13. In certain embodiments, the additional pharmaceutical agent is an inhibitor of another CDK. In certain embodiments, the additional pharmaceutical agent is a selective inhibitor of another CDK. In certain embodiments, the additional pharmaceutical agent is a nonselective inhibitor of another CDK. In certain embodiments, the additional pharmaceutical agent is flavopiridol, triptolide, SNS-032 (BMS-387032), PHA-767491, PHA-793887, BS-181, (S)—CR8, (R)—CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a calmodulin-dependent kinase (CaM Kinase). In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase.

In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In some embodiments, the additional pharmaceutical agent is etoposide, obatoclax, or navitoclax, and the disease to be treated is breast cancer, e.g., triple-negative breast cancer, HER2 positive breast cancer, HER2 negative breast cancer, ER-positive breast cancer, ER-negative breast cancer, or ER/PR-positive breast cancer. In some embodiments, the additional pharmaceutical agent is etoposide, JIB04, or cisplatin, and the disease to be treated is Ewing's sarcoma. In some embodiments, the additional pharmaceutical agent is JQ1 or NVP2, and the disease to be treated is leukemia, e.g., acute myelogenous leukemia, myeloblastic leukemia, promyelocytic leukemia, myelomonocytic leukemia, monocytic leukemia, monoblastic leukemia, or megakaryoblastic leukemia. In certain embodiments, a pharmaceutical composition described herein further comprises a combination of the additional pharmaceutical agents described herein.

The inventive compounds or compositions may synergistically augment inhibition of CDK7 induced by the additional pharmaceutical agent(s) in the biological sample or subject. The inventive compounds or compositions may synergistically augment inhibition of CDK12 induced by the additional pharmaceutical agent(s) in the biological sample or subject. The inventive compounds or compositions may synergistically augment inhibition of CDK12 and/or CDK13 induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In some embodiments, the activity of a protein kinase is non-selectively inhibited by the compounds or pharmaceutical compositions described herein. In some embodiments, the activity of the protein kinase being inhibited is selectively inhibited by the compounds or pharmaceutical compositions described herein, compared to the activity of a different protein (e.g., a different protein kinase). In certain embodiments, the activity of CDK (e.g., CDK7, CDK12, or CDK13) is selectively inhibited by a compound or pharmaceutical composition described herein, compared to the activity of a different protein. In certain embodiments, the activity of CDK7 is selectively inhibited by a compound or pharmaceutical composition described herein, compared to the activity of a different CDK protein. In certain embodiments, the activity of CDK7 is selectively inhibited by a compound or pharmaceutical composition described herein, compared to the activity of CDK12. In certain embodiments, the activity of CDK7 is selectively inhibited by a compound or pharmaceutical composition described herein, compared to the activity of CDK13. In certain embodiments, the activity of CDK7 is selectively inhibited by a compound or pharmaceutical composition described herein, compared to the activity of CDK12 and the activity of CDK13. In certain embodiments, the activity of CDK12 is selectively inhibited by a compound or pharmaceutical composition described herein, compared to the activity of CDK7. In certain embodiments, the activity of CDK13 is selectively inhibited by a compound or pharmaceutical composition described herein, compared to the activity of CDK7. In certain embodiments, the activity of CDK12 and the activity of CDK13 are selectively inhibited by a compound or pharmaceutical composition described herein, compared to the activity of CDK7.

The selectivity of a compound or pharmaceutical composition described herein in inhibiting the activity of a protein kinase over a different protein (e.g., a different protein kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the protein kinase. The selectivity of a compound or pharmaceutical composition described herein for a protein kinase over a different protein may also be measured by the quotient of the $K_d$ value of an adduct of the compound or pharmaceutical composition and the different protein over the $K_d$ value of an adduct of the compound or pharmaceutical composition and the protein kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

In certain embodiments, a kit described herein includes a first container comprising a compound or pharmaceutical composition described herein. In certain embodiments, a kit described herein is useful in treating a proliferative disease (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject in need thereof, preventing a proliferative disease in a subject in need thereof, inhibiting the activity of a protein kinase (e.g., CDK (e.g., CDK7, CDK12, or CDK13)) in a subject, biological sample, tissue, or cell, and/or inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a proliferative disease in a subject in need thereof, inhibiting the activity of a protein kinase (e.g., CDK (e.g., CDK7, CDK12, or CDK13)) in a subject, biological sample, tissue, or cell, and/or inducing apoptosis in a cell. A kit described herein may include one or more additional pharmaceutical agents described herein as a separate composition.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Pulldown Assay (FIGS. 2-4 and 7-9)

Jurkat cells were treated with DMSO or concentration of compound indicated. 6 hours after treatment, cells were washed and harvested by resuspending in lysis buffer (50 mM Hepes pH 7.4, 150 mM NaCl, 1% NP-40, 5 mM EDTA, protease and phosphatase inhibitors) and lysing on ice 30 minutes. Lysates were cleared by centrifugation at 15,000 rpm 30 minutes. Biotin-labeled THZ1 was added to 1 µM to lysates and rotated at 4° C. overnight. Streptavidin-agarose beads were washed and 30 µL slurry was added to each lysate and rotated for 1 hour at 4° C. Beads were washed 5 times with lysis buffer and 50 µL 2xLDS buffer was added to each sample. Samples were boiled and equal volume of protein was loaded onto gel. Gel was transferred to nitrocellulose and blotted for Cyclin K and Cyclin H.

Interpretation of Results

We conclude that pre-treatment of cells with several of the compounds, but not DMSO, blocks biotin-THZ1 from being able to bind to CDK12, which blocks the pulldown of CDK12 and CDK13-associated Cyclin K. This indicates that active compounds are able to engage CDK12 and CDK13-associated cyclin K complexes in cells and block binding of these complexes by bio-THZ1. We do not see a similar loss of pulldown of Cyclin H, indicating that these compounds are not able to bind to CDK7-associated cyclin H complexes and block its association with biotin-THZ1.

Figure 5:
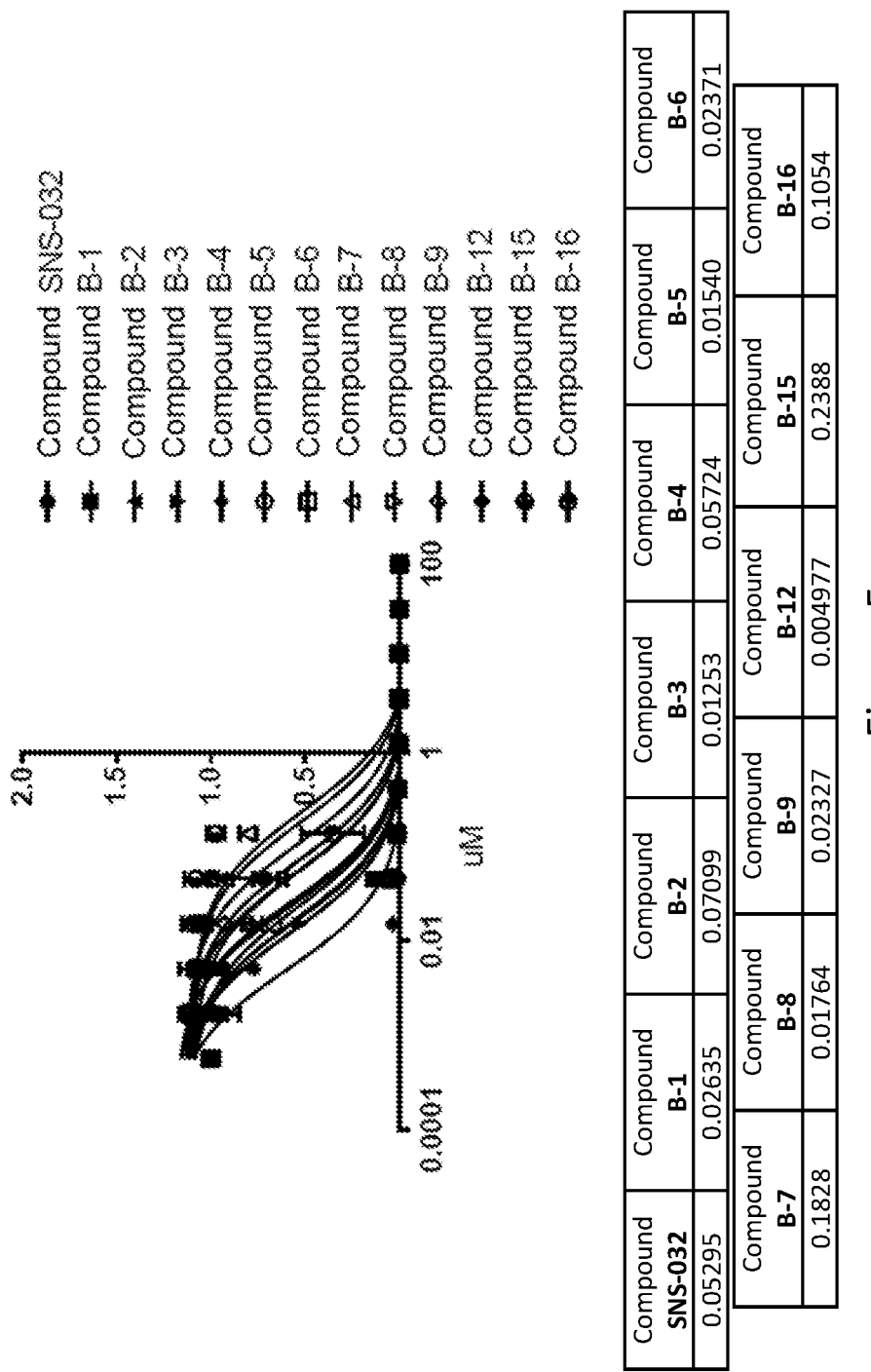
FIG. 5 shows exemplary results of growth assays of select compounds described herein. Jurkat cells were plated at 30,000 cells/well and treated with a titration of compounds indicated. Cells were allowed to grow for 72 hours. Cells were assayed using CELLTITER GLO (Promega) to determine cell viability by measuring the amount of ATP present, which is an indicator of cell metabolic activity. Top panel: luminescent values (y-axis); concentration in μM (uM) (x-axis); the curves are generated using PRISM. Bottom panel: $IC_{50}$ values in μM. Error bars indicate +/− standard deviation. All compounds tested showed anti-proliferative effects to varying extents.
Figure 6:
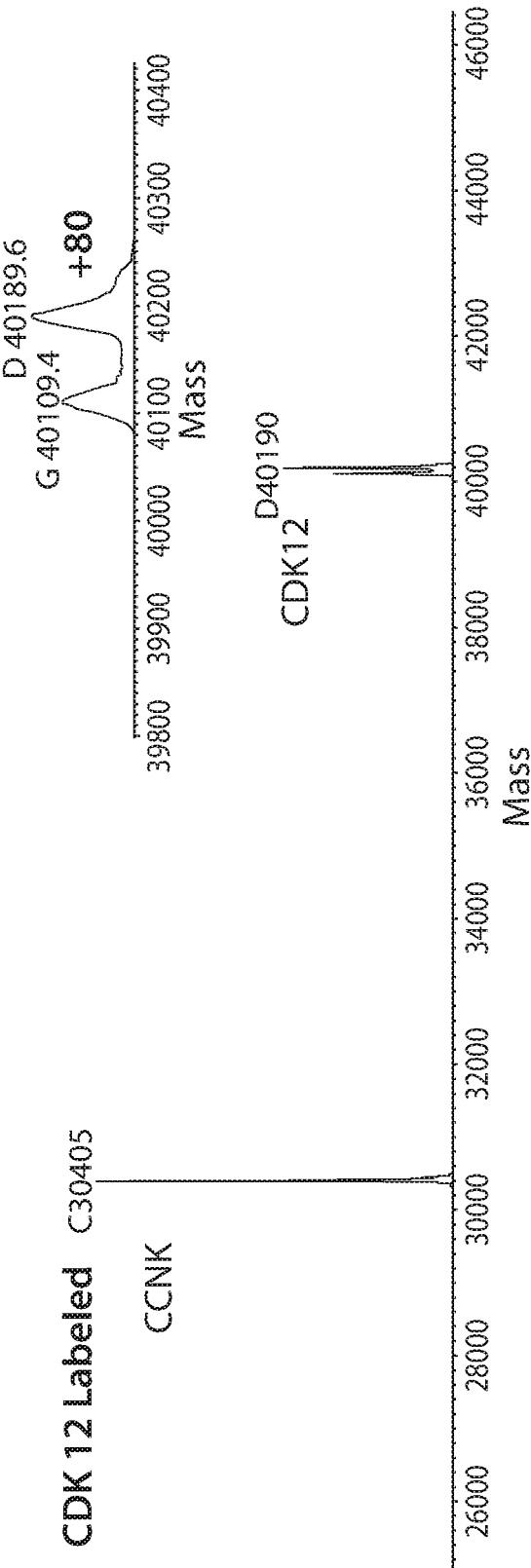
FIG. 6 shows exemplary mass spectrum labeling of CDK12 with compound B12. Compound B12 is able to label CDK12 once treated with a 5-fold excess of compound B12 for 1 hour at 4° C.
Figure 6:
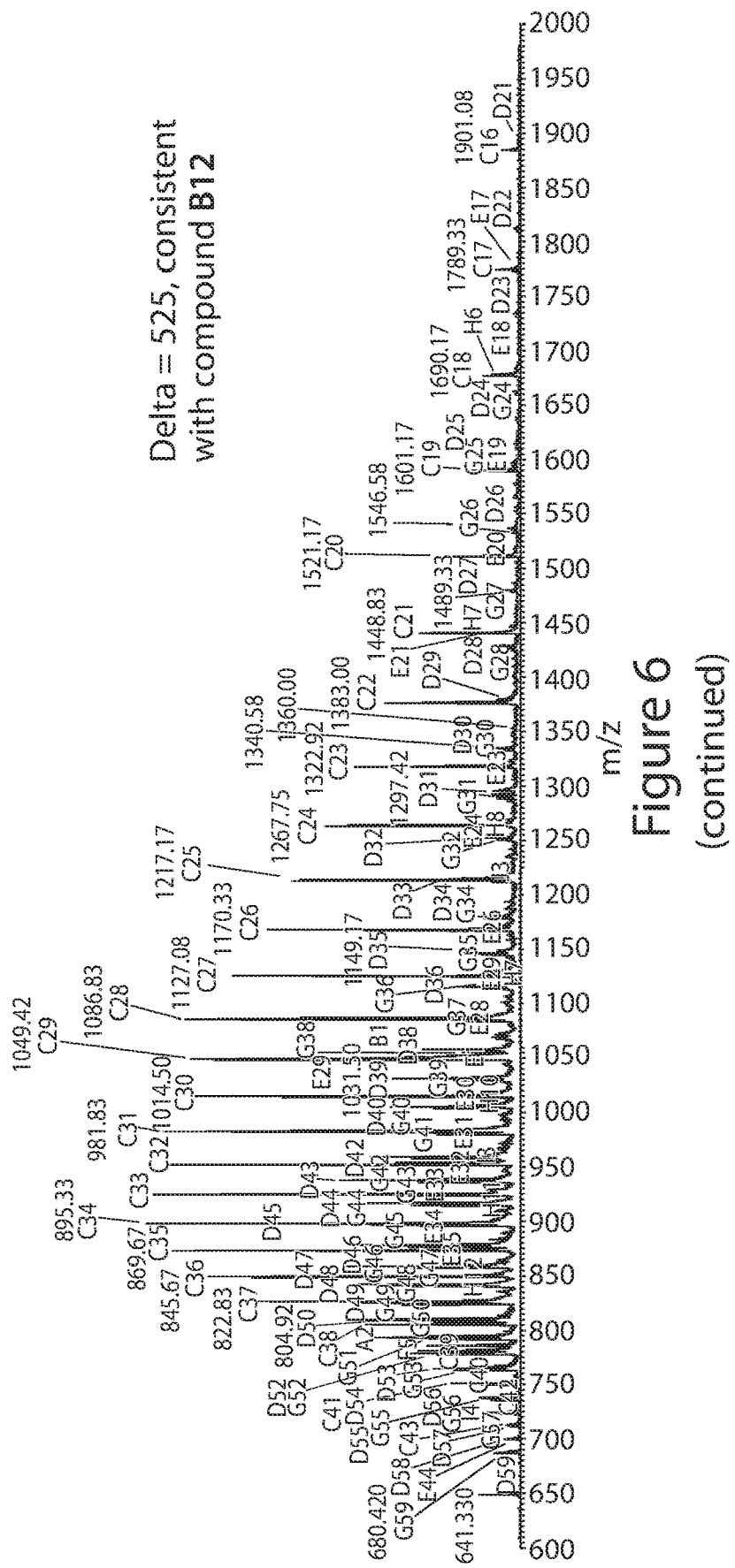
Figure 8A:
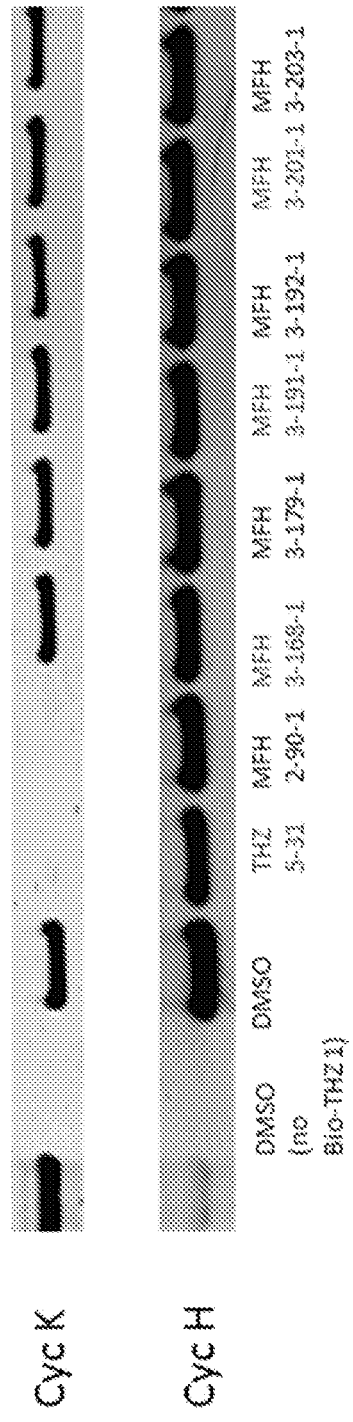
In FIG. 8A, compound THZ 5-31 and MFH 2-90-1 show a loss in cyclin K pulldown by biotin-THZ1, indicating that these compounds successfully targeted CDK12 and CDK13-associated complexes in cells and block biotin-THZ1 binding.
Figure 8B:
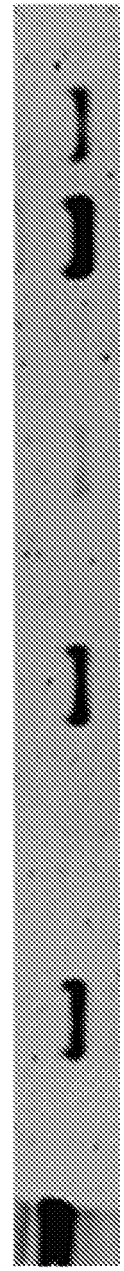
In FIG. 8B, compounds THZ 5-31, MFH 2-90-1, THZ-CE B-15, and THZ-CE B-16, show a loss in cyclin K pull down by biotin-THZ1, indicating that these compounds successfully targeted CDK12 and CDK13-associated complexes in cells and block biotin-THZ1 binding.
Figure 8B:
Figure 9A:
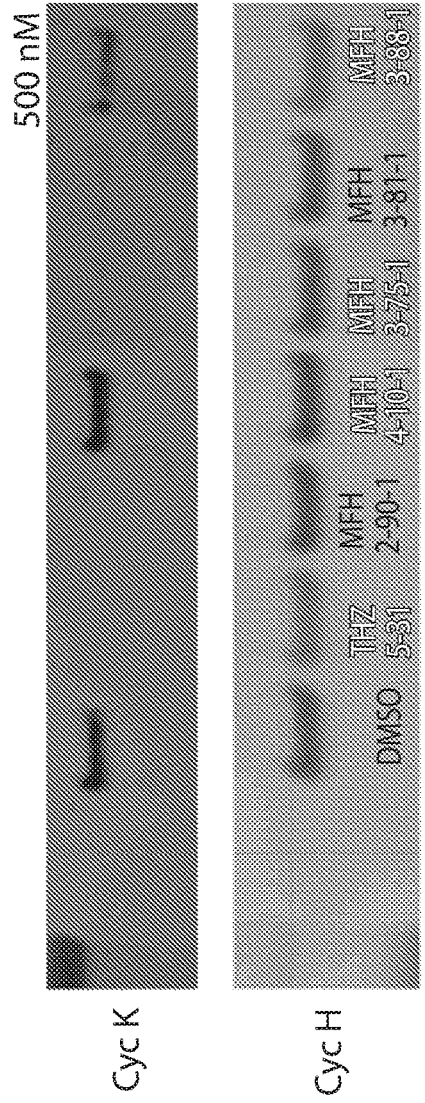
In FIG. 9A, compounds THZ 5-31, MFH 2-90-1, MFH 3-75-1, and MFH 3-81-1 show a loss in cyclin K pull down by biotin-THZ1, indicating that these compounds successfully targeted CDK12 and CDK13-associated complexes in cells and block biotin-THZ1 binding.
Figure 9B:
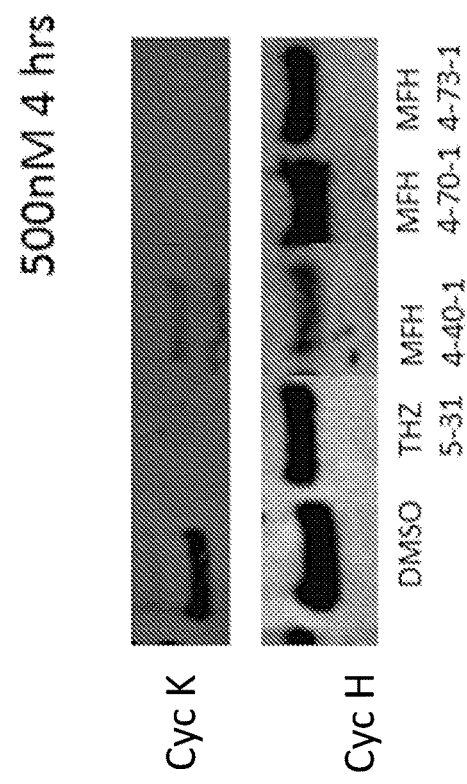
In FIG. 9B, compounds THZ 5-31, MFH 4-70-1, and MFH 4-70-1 show a loss in cyclin K pull down, by biotin-THZ1, indicating that these compounds successfully targeted CDK12 and CDK13-associated complexes in cells and block biotin-THZ1 binding.

Growth Assay (FIG. 5)

Jurkat cells were plated at 30,000 cells/well and treated with a titration of compounds indicated. Cells were allowed to grow for 72 hours. Cells were assayed using CELLTITER GLO (Promega) to determine cell viability by measuring the amount of ATP present, which is an indicator of cell metabolic activity. Results are graphed as luminescent values. Curves were generated using PRISM and an $IC_{50}$ value was determined.

Interpretation of Results

We can conclude that several of the compounds generated and tested are more potent against cell growth than the parent SNS-032 compound in Jurkat cells.

Synthesis of the Compounds

The compounds provided herein can be prepared from readily available starting materials using the following general methods and procedures. Reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 (Xm particle size): solvent gradient=95% A at 0 min, 0% A at 5 min; solvent A=0.5% TFA in Water; solvent B=Methanol; flow rate: 1.5 mL/min. Purification of reaction products was carried out by flash chromatography using CombiFlash® Rf with Teledyne Isco RediSep® Rf High Performance Gold or Silicycle SiliaSe/?™ High Performance columns (4 g, 12 g, 24 g, 40 g, 80 g or 120 g) or by Waters preparative HPLC system with a C18 column: solvent gradient=100% A at 0 min, 0% A at 15 min; solvent A=0.5% TFA in Water; solvent B=Methanol; flow rate: 20 mL/min. The purity of all compounds was over 95% and was analyzed with Waters LCMS system. $^1$H NMR and $^{13}$C NMR spectra were obtained using a Varian Inova-600 or 400 MHz spectrometer. Chemical shifts are reported relative to chloroform (<5=7.24) for $^1$H NMR or dimethyl sulfoxide (δ=2.50) for $^1$H NMR and dimethyl sulfoxide (δ=39.51) for $^{13}$C NMR. Data are reported as (br=broad, s=singlet, d=doublet, t=triplet, q=quartet, m=multiplet).

MFH-2-90-1

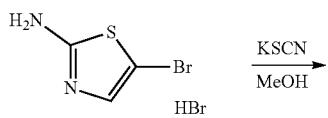

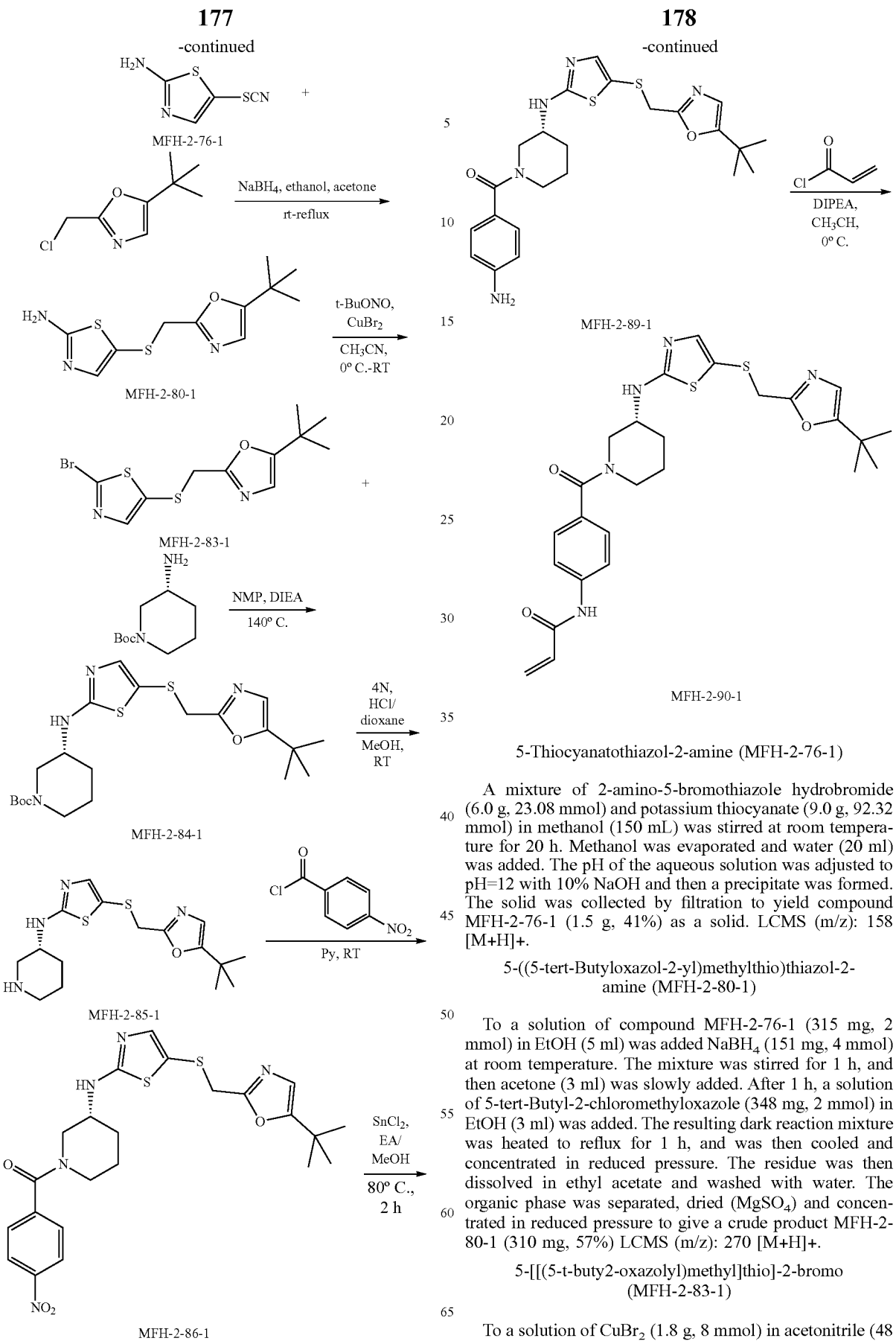

5-Thiocyanatothiazol-2-amine (MFH-2-76-1)

A mixture of 2-amino-5-bromothiazole hydrobromide (6.0 g, 23.08 mmol) and potassium thiocyanate (9.0 g, 92.32 mmol) in methanol (150 mL) was stirred at room temperature for 20 h. Methanol was evaporated and water (20 ml) was added. The pH of the aqueous solution was adjusted to pH=12 with 10% NaOH and then a precipitate was formed. The solid was collected by filtration to yield compound MFH-2-76-1 (1.5 g, 41%) as a solid. LCMS (m/z): 158 [M+H]+.

5-((5-tert-Butyloxazol-2-yl)methylthio)thiazol-2-amine (MFH-2-80-1)

To a solution of compound MFH-2-76-1 (315 mg, 2 mmol) in EtOH (5 ml) was added NaBH$_4$ (151 mg, 4 mmol) at room temperature. The mixture was stirred for 1 h, and then acetone (3 ml) was slowly added. After 1 h, a solution of 5-tert-Butyl-2-chloromethyloxazole (348 mg, 2 mmol) in EtOH (3 ml) was added. The resulting dark reaction mixture was heated to reflux for 1 h, and was then cooled and concentrated in reduced pressure. The residue was then dissolved in ethyl acetate and washed with water. The organic phase was separated, dried (MgSO$_4$) and concentrated in reduced pressure to give a crude product MFH-2-80-1 (310 mg, 57%) LCMS (m/z): 270 [M+H]+.

5-[[(5-t-buty2-oxazolyl)methyl]thio]-2-bromo (MFH-2-83-1)

To a solution of CuBr$_2$ (1.8 g, 8 mmol) in acetonitrile (48 mL) at 0° C. was added t-BuONO (827 mg, 8 mmol)

followed by compound MFH-2-80-1 (1.8 g, 6.68 mmol). The mixture was stirred at 0° C. for 1 h and then was warmed up to room temperature. Ethyl acetate was added and the organic mixture washed with hydrochloric acid (50 mL), dried over magnesium sulfate, filtered through a pad of silica gel, and concentrated in reduced pressure. The residue was purified by chromatographed on silica gel to give product. MFH-2-83-1 (1.5g, 67%). LCMS (m/z): 334 [M+H]+.

(R)-tert-butyl3-(5-((5-tert-butyloxazol-2-yl)methyl-thio)thiazol-2-ylamino)piperidine-1-carboxylate (MFH-2-84-1)

The mixture of MFH-2-83-1 (1.5g, 4.5 mmol), (R)-tert-butyl 3-aminopiperidine-1-carboxylate (1.6 g, 8.1 mmol) and DIEA (1.5 g, 11.25 mmol) in NMP (5 mL) was stirred at 140° C. for overnight. The residue was extracted with chloroform and iso-propanol (4:1). The organic phase was washed with brine (50 mL) and dried over $Na_2SO_4$. After removal of the solvent, the residue was purified by silica gel (MeOH/DCM=0-20%) to obtain MFH-2-84-1 (1.36 g, yield 66.8%). LCMS (m/z): 453 [M+H]$^+$.

(R)-5-((5-tert-butyloxazol-2-yl)methylthio)-N-(piperidin-3-yl)thiazol-2-amine (MFH-2-85-1)

To a solution of MFH-2-85-1 (1.36 g, 3 mmol) in methanol (18 mL) was added 4N HCl/dioxane (18 mL). The solution was then stirred for 3 h at room temperature and the solvent was removed under reduced pressure to provide a crude which was directly used in the next step. LCMS (m/z): 353 [M+H]$^+$.

(R)-(3-(5-((5-tert-butyloxazol-2-yl)methylthio)thi-azol-2-ylamino)piperidin-1-yl)(4-nitrophenyl)metha-none (MFH-2-86-1)

The mixture of MFH-2-85-1 (250 mg, 0.643 mmol), 4-nitrobenzoyl chloride (132 mg, 0.71 mmol) in pyridine (3 mL) was stirred for overnight at room temperature. Then the reaction mixture was concentrated under reduced pressure and the residue was directly used in the next step. LCMS (m/z): 502 [M+H]$^+$.

(R)-(4-aminophenyl)(3-(5-((5-tert-butyloxazol-2-yl) methylthio)thiazol-2-ylamino)piperidin-1-yl)metha-none (MFH-2-89-1)

To a solution of MFH-2-86-1 (270 mg, 0.54 mmol) in ethyl acetate and methanol (1:1) were added Tin (II) chloride dehydrate (1.2 g, 5.4 mmol) and conc. HCl (0.2 mL). After stirring for 3 h at 80° C., the reaction mixture was diluted with chloroform and iso-propanol (4:1), neutralized with saturated $NaHCO_3$ and filtered. The filtrate was extracted with chloroform and iso-propanol (4:1), concentrated under reduced pressure and the resulting residue was purified by silica gel column chromatography (MeOH/DCM=0-20%) to give MFH-2-89-1 (140 mg, yield 55%). LCMS (m/z): 472 [M+H]+.

(R)—N-(4-(3-(5-((5-tert-butyloxazol-2-yl)methyl-thio)thiazol-2-ylamino)piperidine-1-carbonyl)phe-nyl)acrylamide (MFH-2-90-1)

To a solution of MFH-2-89-1 (140 mg, 0.30 mmol) and DIPEA (0.2 mL) in $CH_3CN$ (2 mL) was added acryloyl chloride (35 mg, 0.39 mmol) in DCM (0.8 mL) dropwise. The mixture was then stirred at 0° C. for 1 h. The solution was then concentrated under reduced pressure and the residue was purified by prep-HPLC (MeOH/$H_2O$, 0.05% TFA) to provide MFH-2-90-1 (24.7 mg, yield 16%). LCMS (m/z): 526 [M+H]+ 0.1H NMR (500 MHz, DMSO) δ 10.27 (s, 1H), 7.97 (s, 1H), 7.67 (s, 2H), 7.35 (d, J=6.7 Hz, 2H), 6.87 (d, J=26.3 Hz, 1H), 6.70 (s, 1H), 6.43 (dd, J=17.0, 10.1 Hz, 1H), 6.27 (dd, J=17.0, 1.8 Hz, 1H), 5.77 (dd, J=10.1, 1.8 Hz, 1H), 3.94 (s, 2H), 3.79 (s, 1H), 3.63 (d, J=23.9 Hz, 2H), 3.14 (d, J=65.1 Hz, 2H), 1.95 (s, 1H), 1.76 (s, 1H), 1.52 (d, J=7.8 Hz, 2H), 1.17 (s, 9H).

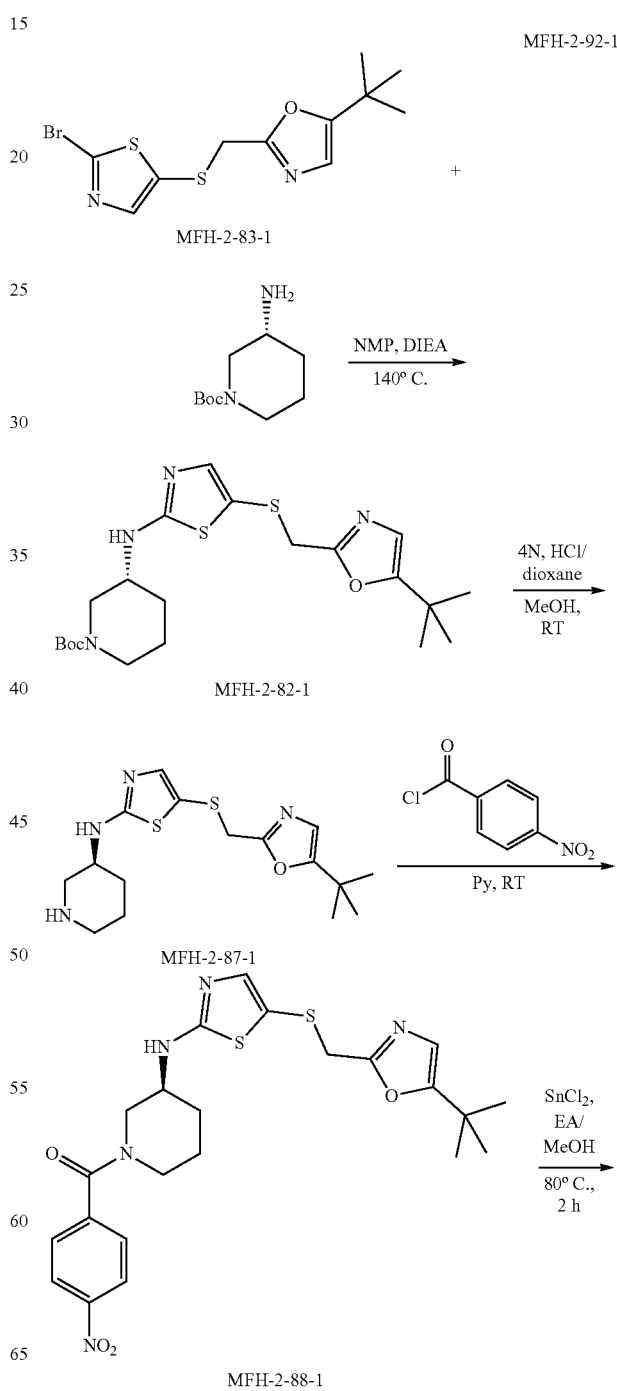

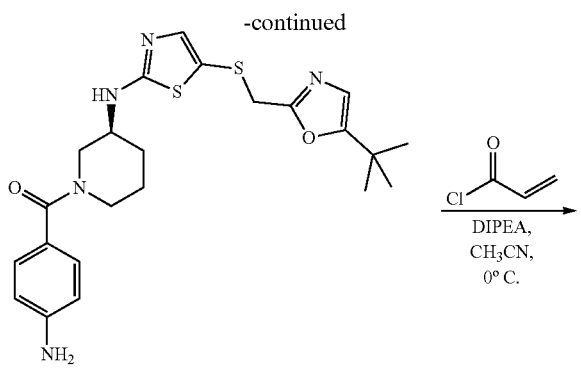

MFH-2-91-1

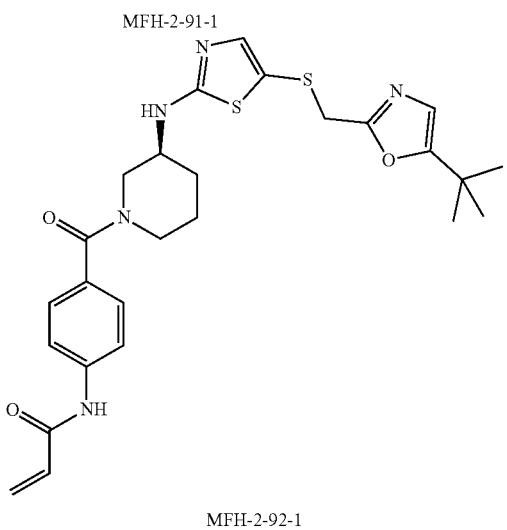

MFH-2-92-1

(S)-tert-butyl3-(5-((5-tert-butyloxazol-2-yl)methyl-thio)thiazol-2-ylamino)piperidine-1-carboxylate (MFH-2-82-1)

The mixture of MFH-2-83-1 (150 mg, 0.45 mmol), (S)-tert-butyl 3-aminopiperidine-1-carboxylate (160 mg, 0.81 mmol) and DIEA (150 mg, 1.13 mmol) in NMP (1 mL) was stirred at 140° C. for overnight. The residue was extracted with chloroform and iso-propanol (4:1). The organic phase was washed with brine (20 mL) and dried over Na$_2$SO$_4$. After removal of the solvent, the residue was purified by silica gel (MeOH/DCM=0-20%) to obtain MFH-2-82-1 (136 mg, yield 67%). LCMS (m/z): 453 [M+H]$^+$.

(S)-5-((5-tert-butyloxazol-2-yl)methylthio)-N-(piperidin-3-yl)thiazol-2-amine (MFH-2-87-1)

To a solution of MFH-2-82-1 (136 mg, 0.3 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 353 [M+H]$^+$.

(S)-(3-(5-((5-tert-butyloxazol-2-yl)methylthio)thi-azol-2-ylamino)piperidin-1-yl)(4-nitrophenyl)metha-none (MFH-2-88-1)

The mixture of MFH-2-87-1 (250 mg, 0.643 mmol), 4-nitrobenzoyl chloride (132 mg, 0.71 mmol) in pyridine (3 mL) was stirred for overnight at room temperature. Then the reaction mixture was concentrated under reduced pressure and the residue was directly used in the next step. LCMS (m/z): 502 [M+H]$^+$.

(S)-(4-aminophenyl)(3-(5-((5-tert-butyloxazol-2-yl)methylthio)thiazol-2-ylamino)piperidin-1-yl)metha-none (MFH-2-91-1)

To a solution of MFH-2-88-1 (270 mg, 0.54 mmol) in ethyl acetate and methanol (1:1) were added Tin(II) chloride dehydrate (1.2 g, 5.4 mmol) and conc. HCl (0.2 mL). After stirring for 3 h at 80° C., the reaction mixture was diluted with chloroform and iso-propanol (4:1), neutralized with saturated NaHCO$_3$ and filtered. The filtrate was extracted with chloroform and iso-propanol (4:1), concentrated under reduced pressure and the resulting residue was purified by silica gel column chromatography (MeOH/DCM=0-20%) to give MFH-2-91-1 (140 mg, yield 55%). LCMS (m/z): 472 [M+H]+.

(S)—N-(4-(3-(5-((5-tert-butyloxazol-2-yl)methyl-thio)thiazol-2-ylamino)piperidine-1-carbonyl)phe-nyl)acrylamide (MFH-2-92-1)

To a solution of MFH-2-91-1 (30 mg, 0.06 mmol) and DIPEA (0.2 mL) in CH$_3$CN (2 mL) was added acryloyl chloride (8 mg, 0.08 mmol) in DCM (0.5 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-2-92-1 (11 mg, yield 33%). LCMS (m/z): 526 [M+H]+. 1H NMR (500 MHz, DMSO) δ 10.30 (s, 1H), 8.07 (s, 1H), 7.65 (s, 2H), 7.35 (d, J=6.7 Hz, 2H), 6.88 (d, J=37.7 Hz, 1H), 6.70 (s, 1H), 6.43 (dd, J=16.9, 10.1 Hz, 1H), 6.27 (dd, J=17.0, 1.6 Hz, 1H), 5.77 (dd, J=10.2, 1.7 Hz, 1H), 3.95 (s, 2H), 3.79 (s, 1H), 3.63 (d, J=23.9 Hz, 2H), 3.14 (d, J=65.1 Hz, 2H), 1.92 (s, J=18.7 Hz, 1H), 1.76 (s, 1H), 1.52 (d, J=6.6 Hz, 2H), 1.17 (s, 9H).

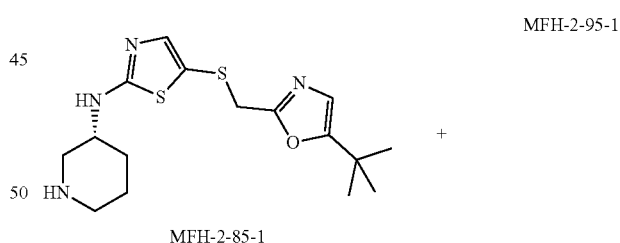

MFH-2-85-1

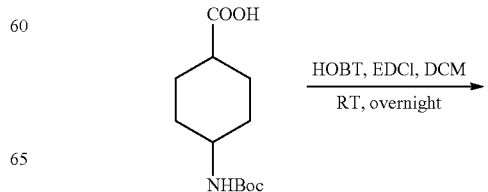

-continued

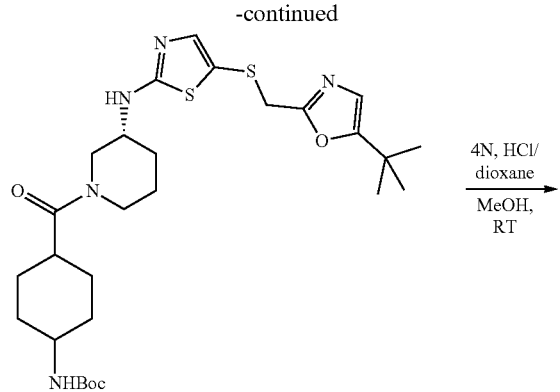

MFH-2-93-1

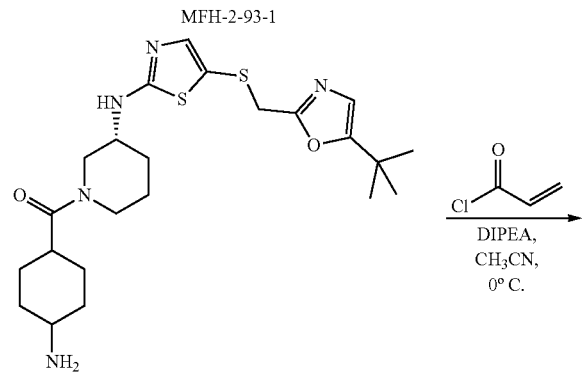

MFH-2-94-1

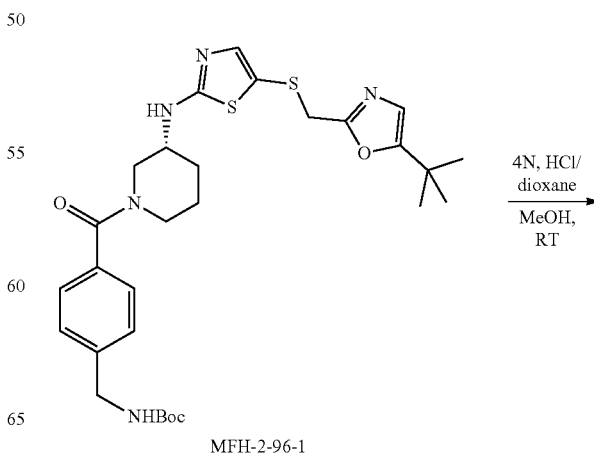

MFH-2-95-1

(R)-tert-butyl4-(3-(5-((5-tert-butyloxazol-2-yl)methylthio)thiazol-2-ylamino)piperidine-1-carbonyl)cyclohexylcarbamate (MFH-2-93-1)

The mixture of MFH-2-85-1 (116 mg, 0.33 mmol), 4-(tert-butoxycarbonylamino)cyclohexanecarboxylic acid (120 mg, 0.5 mmol), HOBT (68 mg, 0.5 mmol) and EDCI (96 mg, 0.5 mmol) in DCM (10 ml) was stirred for overnight. The reaction mixture was diluted with DCM (25 ml). The organic phase was washed with saturated $Na_2CO_3$ and brine (20 mL) and dried over $Na_2SO_4$. After removal of the solvent, the residue was purified by silica gel (MeOH/DCM=0-20%) to obtain MFH-2-93-1 (80 mg, yield 42%). LCMS (m/z): 578 [M+H]+.

(R)-(4-aminocyclohexyl)(3-(5-((5-tert-butyloxazol-2-yl)methylthio)thiazol-2-ylamino)piperidin-1-yl)methanone (MFH-2-94-1)

To a solution of MFH-2-93-1 (80 mg, 0.14 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 478 [M+H]+.

(R)—N-(4-(3-(5-((5-tert-butyloxazol-2-yl)methylthio)thiazol-2-ylamino)piperidine-1-carbonyl)cyclohexyl)acrylamide (MFH-2-95-1)

To a solution of MFH-2-94-1 (30 mg, 0.06 mmol) and DIPEA (0.2 mL) in $CH_3CN$ (2 mL) was added acryloyl chloride (8 mg, 0.08 mmol) in DCM (0.5 mL) dropwise. The mixture was then stirred at 0° C. for 1 h. The solution was then concentrated under reduced pressure and the residue was purified by prep-HPLC (MeOH/$H_2O$, 0.05% TFA) to provide MFH-2-95-1 (15.9 mg, yield 48%). LCMS (m/z): 532 [M+H]+.

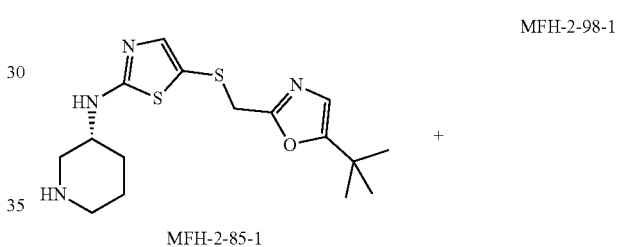

MFH-2-85-1

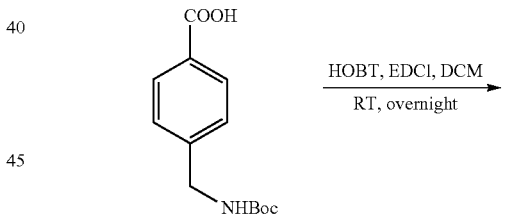

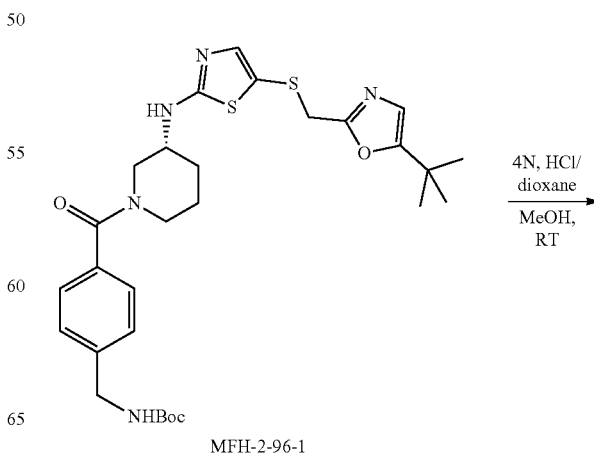

MFH-2-96-1

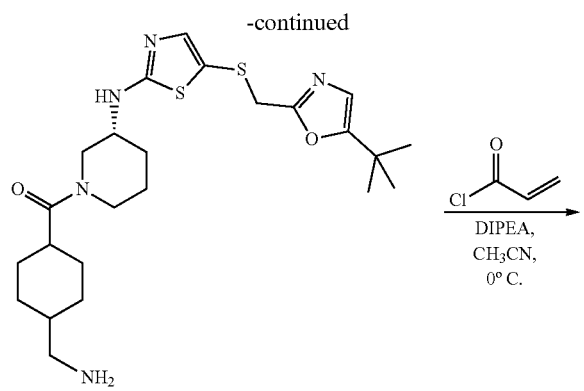

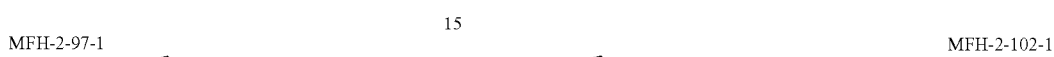

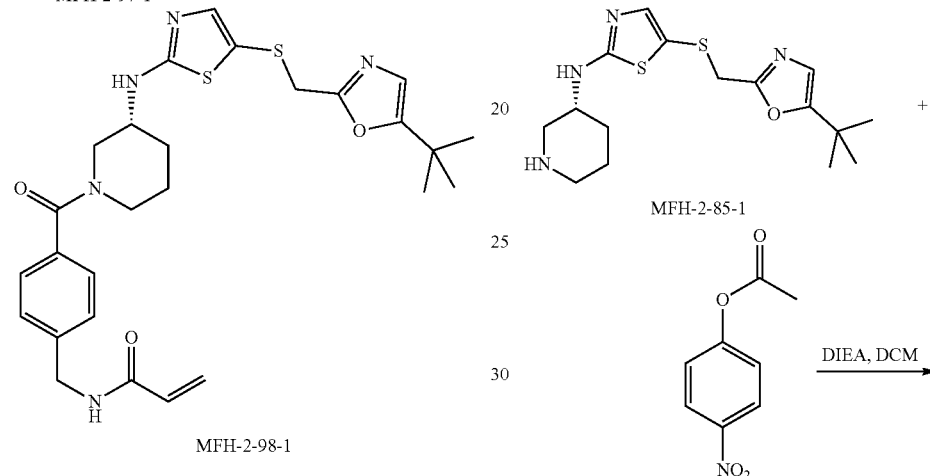

chloride (12 mg, 0.13 mmol) in DCM (0.5 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-2-98-1 (16.4 mg, yield 30%). LCMS (m/z): 540 [M+H]+. $^1$H NMR (500 MHz, DMSO) δ 8.62 (s, 1H), 8.08 (d, J=54.5 Hz, 1H), 7.28 (d, J=31.4 Hz, 4H), 6.91 (d, J=65.2 Hz, 1H), 6.72 (s, 1H), 6.28 (dd, J=17.1, 10.2 Hz, 1H), 6.13 (dd, J=17.1, 2.2 Hz, 1H), 5.62 (dd, J=10.2, 1.9 Hz, 1H), 4.36 (s, 2H), 3.95 (s, 2H), 3.67-3.62 (m, 2H), 3.33 (s, 1H), 3.14-2.83 (m, 2H), 1.94 (s, 1H), 1.74 (d, J=65.1 Hz, 1H), 1.53 (s, 2H), 1.20 (s, 9H).

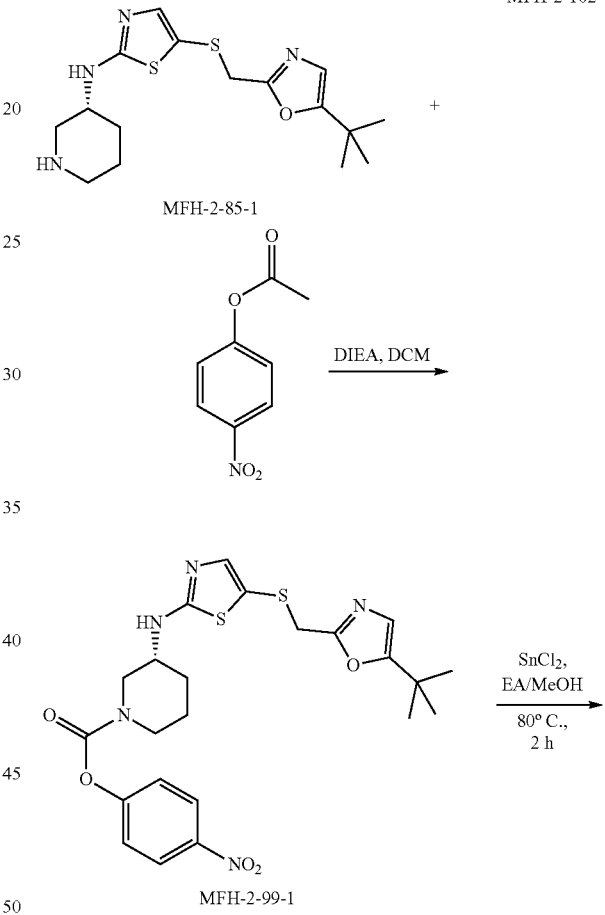

(R)-tert-butyl4-(3-(5-((5-tert-butyloxazol-2-yl)methylthio)thiazol-2-ylamino)piperidine-1-carbonyl)benzylcarbamate (MFH-2-96-1)

The mixture of MFH-2-85-1 (88 mg, 0.25 mmol), 4-((tert-butoxycarbonylamino)methyl)benzoic acid (94 mg, 0.38 mmol), HOBT (51 mg, 0.38 mmol) and EDCI (72 mg, 0.38 mmol) in DCM (8 ml) was stirred for overnight. The reaction mixture was diluted with DCM (25 ml). The organic phase was washed with saturated Na$_2$CO$_3$ and brine (20 mL) and dried over Na$_2$SO$_4$. After removal of the solvent, the residue was purified by silica gel (MeOH/DCM=0-20%) to obtain MFH-2-96-1 (125 mg, yield 85%). LCMS (m/z): 586 [M+H]+.

(R)-(4-(aminomethyl)phenyl)(3-(5-((5-tert-butyloxazol-2-yl)methylthio)thiazol-2-ylamino)piperidin-1-yl)methanone (MFH-2-97-1)

To a solution of MFH-2-96-1 (125 mg, 0.21 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 486 [M+H]$^+$.

(R)—N-(4-(3-(5-((5-tert-butyloxazol-2-yl)methylthio)thiazol-2-ylamino)piperidine-1-carbonyl)benzyl)acrylamide (MFH-2-98-1)

To a solution of MFH-2-97-1 (50 mg, 0.1 mmol) and DIPEA (0.2 mL) in CH$_3$CN (2 mL) was added acryloyl

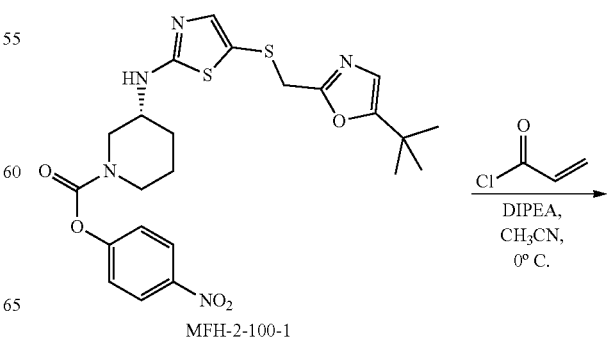

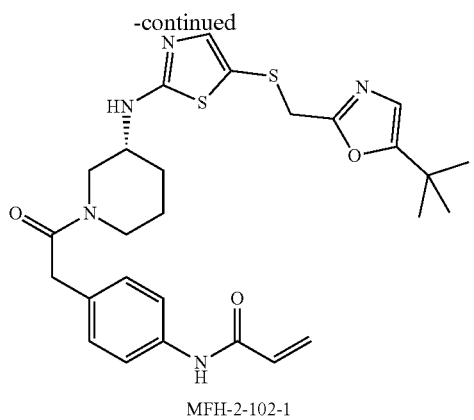

MFH-2-102-1

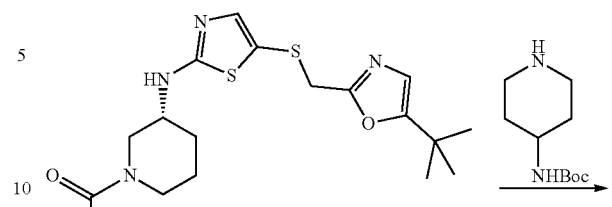

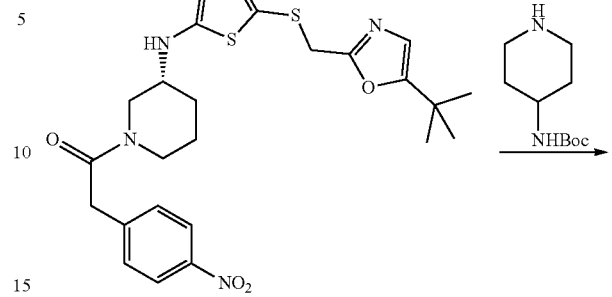

(R)-4-nitrophenyl 3-(5-((5-tert-butyloxazol-2-yl)methylthio)thiazol-2-ylamino)piperidine-1-carboxylate (MFH-2-99-1)

To a solution of MFH-2-85-1 (210 mg, 0.6 mmol) and DIPEA (116 mg, 0.9 mmol) in DCM (8 mL) was added 4-nitrophenyl chloroformate (133 mg, 0.66 mmol) in DCM (1 mL) dropwise. The mixture was then stirred at 0° C. for 1 h. The solution was then concentrated under reduced pressure and the residue was purified by silica gel (MeOH/DCM=0-20%) to obtain MFH-2-99-1 (283 mg, yield 91%). LCMS (m/z): 518 [M+H]+.

(R)-4-aminophenyl 3-(5-((5-tert-butyloxazol-2-yl)methylthio)thiazol-2-ylamino)piperidine-1-carboxylate (MFH-2-100-1)

To a solution of MFH-2-99-1 (106 mg, 0.21 mmol) in ethyl acetate and methanol (1:1) were added Tin(II) chloride dehydrate (462 mg, 2.1 mmol) and conc. HCl (0.1 mL). After stirring for 3 h at 80° C., the reaction mixture was diluted with chloroform and iso-propanol (4:1), neutralized with saturated $NaHCO_3$ and filtered. The filtrate was extracted with chloroform and iso-propanol (4:1), concentrated under reduced pressure and the resulting residue was purified by silica gel column chromatography (MeOH/DCM=0-20%) to give MFH-2-100-1 (60 mg, yield 60%). LCMS (m/z): 488 [M+H]+.

(R)-4-acrylamidophenyl 3-(5-((5-tert-butyloxazol-2-yl)methylthio)thiazol-2-ylamino)piperidine-1-carboxylate (MFH-2-102-1)

To a solution of MFH-2-100-1 (60 mg, 0.12 mmol) and DIPEA (0.2 mL) in $CH_3CN$ (2 mL) was added acryloyl chloride (15 mg, 0.16 mmol) in DCM (0.5 mL) dropwise. The mixture was then stirred at 0° C. for 1 h. The solution was then concentrated under reduced pressure and the residue was purified by prep-HPLC (MeOH/$H_2O$, 0.05% TFA) to provide MFH-2-102-1 (18.1 mg, yield 27%). LCMS (m/z): 542 [M+H]+. $^1$H NMR (500 MHz, DMSO) δ 10.17 (s, 1H), 8.13 (d, J=14.2 Hz, 1H), 7.64 (s, 2H), 7.08 (s, 1H), 7.01 (d, J=9.0 Hz, 1H), 6.95 (s, 1H), 6.72 (dd, J=11.3, 7.1 Hz, 1H), 6.42 (dd, J=16.9, 10.1 Hz, 1H), 6.25 (dd, J=17.0, 1.7 Hz, 1H), 5.82-5.68 (m, 1H), 3.94 (s, 2H), 3.84 (s, 1H), 3.74 (s, 1H), 3.26 (d, J=44.4 Hz, 2H), 2.93 (s, 1H), 1.92 (d, J=13.1 Hz, 1H), 1.79 (d, J=6.3 Hz, 1H), 1.52 (s, 2H), 1.21 (s, 9H).

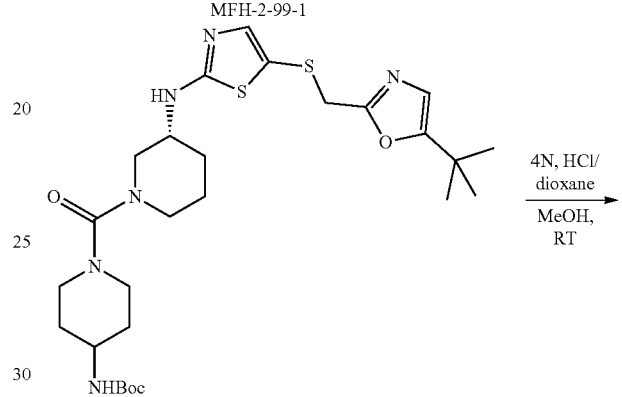

MFH-2-99-1

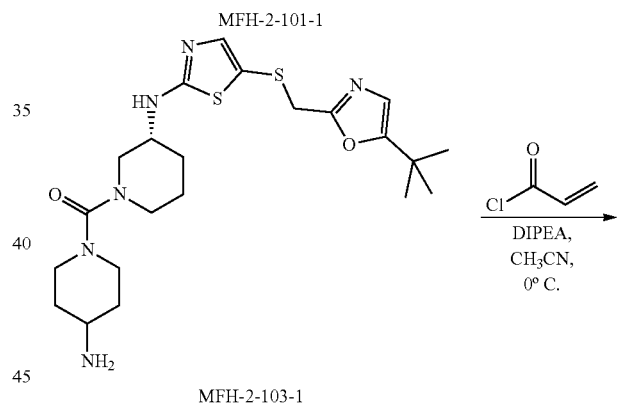

MFH-2-101-1

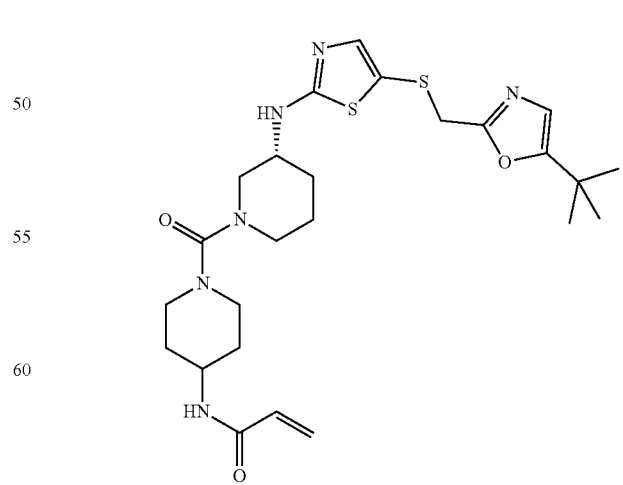

MFH-2-103-1

MFH-2-104-1

(R)-tert-butyl1-(3-(5-((5-tert-butyloxazol-2-yl)methylthio)thiazol-2-ylamino)piperidine-1-carbonyl)piperidin-4-ylcarbamate (MFH-2-101-1)

The mixture of MFH-2-99-1 (177 mg, 0.34 mmol) and tert-butyl piperidin-4-ylcarbamate (89 mg, 0.44 mmol) in DMSO (3 mL) was stirred at 60° C. overnight. The residue was extracted with chloroform and iso-propanol (4:1). The organic phase was washed with brine (20 mL) and dried over $Na_2SO_4$. After removal of the solvent, the residue was purified by silica gel (MeOH/DCM=0-20%) to obtain MFH-2-101-1 (150 mg, yield 76%). LCMS (m/z): 579 [M+H]+.

(R)-(4-aminopiperidin-1-yl)(3-(5-((5-tert-butyloxazol-2-yl)methylthio)thiazol-2-ylamino)piperidin-1-yl)methanone (MFH-2-103-1)

To a solution of MFH-2-101-1 (150 mg, 0.26 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 479 [M+H]+.

(R)—N-(1-(3-(5-((5-tert-butyloxazol-2-yl)methylthio)thiazol-2-ylamino)piperidine-1-carbonyl)piperidin-4-yl)acrylamide (MFH-2-104-1)

To a solution of MFH-2-103-1 (30 mg, 0.06 mmol) and DIPEA (0.2 mL) in $CH_3CN$ (2 mL) was added acryloyl chloride (8 mg, 0.08 mmol) in DCM (0.5 mL) dropwise. The mixture was then stirred at 0° C. for 1 h. The solution was then concentrated under reduced pressure and the residue was purified by prep-HPLC (MeOH/$H_2O$, 0.05% TFA) to provide MFH-2-104-1 (10.2 mg, yield 30%). LCMS (m/z): 533 [M+H]+. $^1$H NMR (500 MHz, DMSO) δ 8.13 (s, 1H), 8.07 (d, J=7.7 Hz, 1H), 6.97 (s, 1H), 6.70 (d, J=5.5 Hz, 1H), 6.18 (dd, J=17.1, 10.1 Hz, 1H), 6.07 (dd, J=17.1, 2.2 Hz, 1H), 5.57 (dd, J=10.1, 2.2 Hz, 1H), 3.94 (s, 2H), 3.81-3.71 (m, 2H), 3.48 (s, 2H), 3.34-3.24 (m, 2H), 2.79 (t, J=11.6 Hz, 3H), 2.70 (dd, J=13.2, 9.5 Hz, 1H), 1.89 (d, J=10.4 Hz, 1H), 1.71 (d, J=13.1 Hz, 3H), 1.43 (dd, J=16.4, 8.5 Hz, 2H), 1.32 (m, 2H), 1.18 (s, 9H).

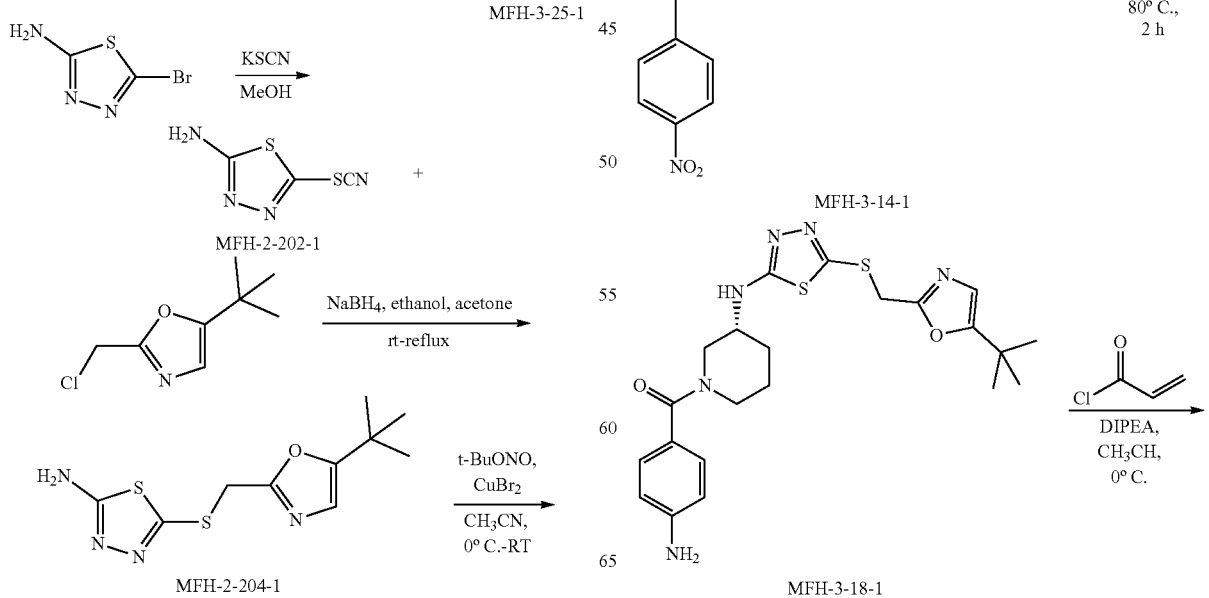

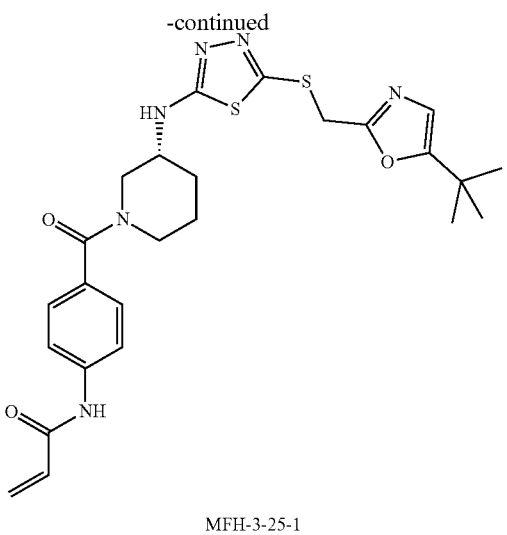

MFH-3-25-1

5-thiocyanato-1,3,4-thiadiazol-2-amine (MFH-2-202-1)

A mixture of 5-bromo-1,3,4-thiadiazol-2-amine (1.5 g, 8.3 mmol) and potassium thiocyanate (3.2 g, 33.3 mmol) in methanol (30 mL) was stirred at room temperature for 20 h. Methanol was evaporated and water (10 ml) was added. The pH of the aqueous solution was adjusted to pH=12 with 10% NaOH and precipitate formed. The solid was collected by filtration to yield compound MFH-2-202-1 (600 mg, 46%) as solid. LCMS (m/z): 159 [M+H]+.

5-((5-tert-butyloxazol-2-yl)methylthio)-1,3,4-thiadiazol-2-amine (MFH-2-204-1)

To a solution of compound MFH-2-202-1 (315 mg, 2 mmol) in EtOH (5 ml) was added NaBH$_4$ (151 mg, 4 mmol) at room temperature. The mixture was stirred for 1 h, and then acetone (3 ml) was slowly added. After 1 h, a solution of 5-tert-Butyl-2-chloromethyloxazole (348 mg, 2 mmol) in EtOH (3 ml) was added. The resulting reaction mixture was heated to reflux for 1 h and then was cooled followed by concentration in reduced pressure. The residue was dissolved in ethyl acetate. The organic phase was washed with brine (30 mL) and then the solvent was removed after drying with MgSO$_4$. The crude product was then obtained MFH-2-204-1 (310 mg, 57%) as solid LCMS (m/z): 271 [M+H]+.

2-((5-bromo-1,3,4-thiadiazol-2-ylthio)methyl)-5-tert-butyloxazole (MFH-2-208-1)

To a solution of CuBr$_2$ (594 mg, 2.66 mmol) in acetonitrile (8 mL) at 0° C. was added t-BuONO (275 mg, 2.66 mmol) followed by compound MFH-2-204-1 (600 mg, 2.22 mmol). The mixture was stirred at 0° C. for 1 h and then was warmed up to room temperature. After stirring for 1 h, ethyl acetate was added and the organic mixture washed with hydrochloric acid (50 mL), dried over magnesium sulfate, filtered through a pad of silica gel, and concentrated in reduced pressure. The residue was chromatographed on silica gel to give the MFH-2-208-1 (700 mg, 94%). LCMS (m/z): 335 [M+H]+.

(R)-tert-butyl 3-(5-((5-tert-butyloxazol-2-yl)methylthio)-1,3,4-thiadiazol-2-ylamino)piperidine-1-carboxylate (MFH-3-2-1)

The mixture of MFH-2-208-1 (250 mg, 0.75 mmol), (R)-tert-butyl 3-aminopiperidine-1-carboxylate (225 mg, 1.12 mmol) and DIEA (242 mg, 1.87 mmol) in NMP (1 mL) was stirred at 140° C. overnight. The residue was extracted with chloroform and iso-propanol (4:1). The organic phase was washed with brine (50 mL) and dried over Na$_2$SO$_4$. After removal of the solvent, the residue was purified by silica gel (MeOH/DCM=0-20%) to obtain MFH-3-2-1 (180 mg, yield 53%). LCMS (m/z): 454 [M+H]+.

(R)-5-((5-tert-butyloxazol-2-yl)methylthio)-N-(piperidin-3-yl)-1,3,4-thiadiazol-2-amine (MFH-3-11-1)

To a solution of MFH-3-2-1 (250 mg, 0.55 mmol) in methanol (5 mL) was added 4N HCl/dioxane (5 mL). The solution was then stirred for 3 h at room temperature and the solvent was removed under reduced pressure to provide a crude which was directly used in the next step. LCMS (m/z): 354 [M+H]+.

(R)-(3-(5-((5-tert-butyloxazol-2-yl)methylthio)-1,3,4-thiadiazol-2-ylamino)piperidin-1-yl)(4-nitrophenyl)methanone (MFH-3-14-1)

The mixture of MFH-3-11-1 (140 mg, 0.4 mmol), 4-nitrobenzoyl chloride (88 mg, 0.48 mmol) in pyridine (3 mL) was stirred overnight at room temperature. Then the reaction mixture was concentrated under reduced pressure and the residue was directly used in the next step. LCMS (m/z): 503 [M+H]+.

(R)-(4-aminophenyl)(3-(5-((5-tert-butyloxazol-2-yl)methylthio)-1,3,4-thiadiazol-2-ylamino)piperidin-1-yl)methanone (MFH-3-18-1)

To a solution of MFH-3-14-1 (200 mg, 0.4 mmol) in ethyl acetate and methanol (1:1) were added Tin(II) chloride dehydrate (904 mg, 4 mmol) and conc. HCl (0.2 mL). After stirring for 3 h at 80° C., the reaction mixture was diluted with chloroform and iso-propanol (4:1), neutralized with saturated NaHCO$_3$ and filtered. The filtrate was extracted with chloroform and iso-propanol (4:1), concentrated under reduced pressure and the resulting residue was purified by silica gel column chromatography (MeOH/DCM=0-20%) to give MFH-3-18-1 (45 mg, yield 24%). LCMS (m/z): 473 [M+H]+.

(R)—N-(4-(3-(5-((5-tert-butyloxazol-2-yl)methylthio)-1,3,4-thiadiazol-2-ylamino)piperidine-1-carbonyl)phenyl)acrylamide (MFH-3-25-1)

To a solution of MFH-3-18-1 (22 mg, 0.05 mmol) and DIPEA (0.2 mL) in CH$_3$CN (2 mL) was added acryloyl chloride (6 mg, 0.06 mmol) in DCM (0.2 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-3-25-1 (8.8 mg, yield 36%). LCMS (m/z): 527 [M+H]+. $^1$H NMR (500 MHz, DMSO) δ 10.29 (s, 1H), 8.02 (d, J=5.0 Hz, 1H), 7.68 (s, 2H), 7.35 (s, 2H), 6.75 (s, 1H), 6.44 (dd, J=17.0, 10.1 Hz, 1H), 6.28 (d, J=16.9 Hz, 1H), 5.86-5.70 (m, 1H), 4.33 (s, 2H), 3.74 (s, 1H), 3.60 (s, 2H), 3.21 (d, J=32.1 Hz, 2H), 1.99 (s, 1H), 1.77 (s, 1H), 1.58 (dd, J=22.4, 11.7 Hz, 2H), 1.29 (s, 9H).

193

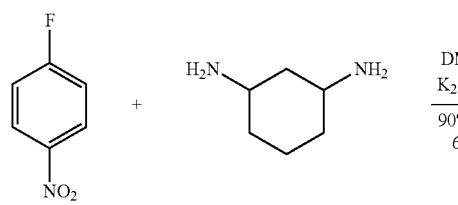

MFH-3-35-1

DMF, K₂CO₃
90° C., 6 h

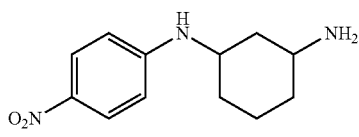

MFH-3-26-1

+

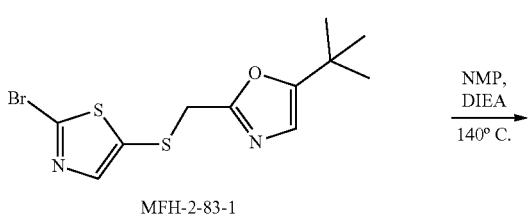

MFH-2-83-1

NMP,
DIEA
140° C.

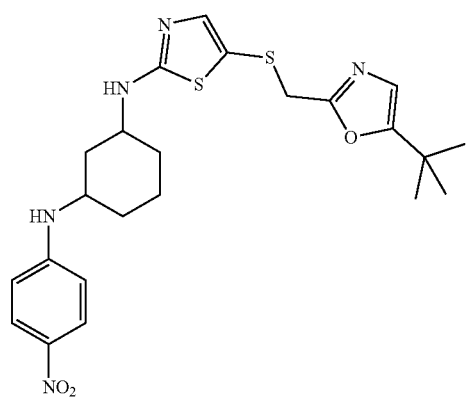

MFH-3-29-1

SnCl₂,
EA/
MeOH
80° C.,
2 h

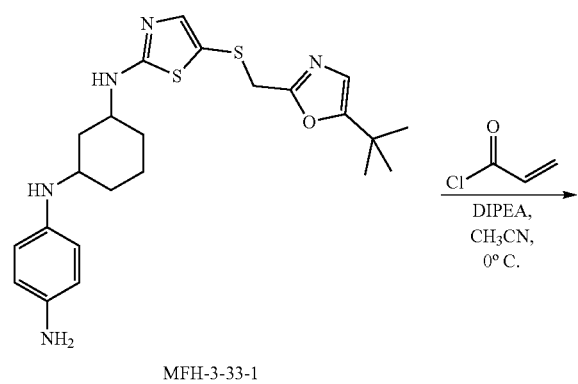

MFH-3-33-1

DIPEA,
CH₃CN,
0° C.

194

-continued

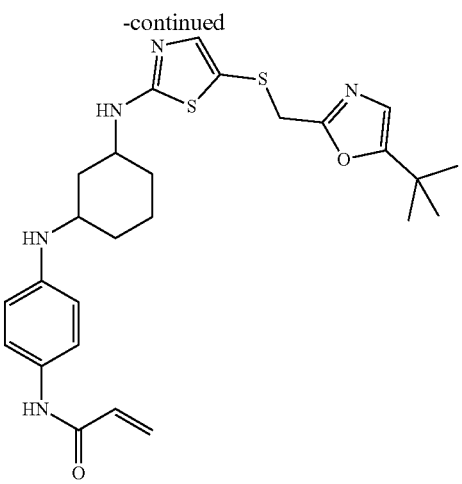

MFH-3-33-1

N1-(4-nitrophenyl)cyclohexane-1,3-diamine (MFH-3-26-1)

The mixture of 1-fluoro-4-nitrobenzene (200 mg, 1.42 mmol), cyclohexane-1,3-diamine (485 mg, 4.25 mmol) and K₂CO₃ (587 mg, 4.25 mmol) in DMF (3 mL) was stirred at 90° C. for 6 h. The solution was then diluted with chloroform and iso-propanol (4:1). The organic phase was washed with brine (50 mL) and dried over Na₂SO₄. After removal of the solvent, the residue was purified by silica gel (MeOH/DCM=0-20%) to obtain MFH-3-26-1 (230 mg, yield 69%). LCMS (m/z): 236 [M+H]⁺.

(5-((5-tert-butyloxazol-2-yl)methylthio)thiazol-2-yl)-N3-(4-nitrophenyl)cyclohexane-1,3-diamine (MFH-3-29-1)

The mixture of MFH-2-83-1 (272 mg, 0.82 mmol), MFH-3-26-1 (230 mg, 0.98 mmol) and DIEA (316 mg, 2.46 mmol) in NMP (2 mL) was stirred at 140° C. overnight. The solution was diluted with chloroform and iso-propanol (4:1). The organic phase was washed with brine (50 mL) and dried over Na₂SO₄. After removal of the solvent, the residue was purified by silica gel (MeOH/DCM=0-20%) to obtain MFH-3-29-1 (80 mg, yield 20%). LCMS (m/z): 458 [M+H]⁺.

N1-(3-(5-((5-tert-butyloxazol-2-yl)methylthio)thiazol-2-ylamino)cyclohexyl)benzene-1,4-diamine (MFH-3-33-1)

To a solution of MFH-3-29-1 (80 mg, 0.16 mmol) in ethyl acetate and methanol (1:1) were added Tin(II) chloride dehydrate (370 mg, 1.6 mmol) and conc. HCl (0.1 mL). After stirring for 3 h at 80° C., the reaction mixture was diluted with chloroform and iso-propanol (4:1), neutralized with saturated NaHCO₃ and filtered. The filtrate was extracted with chloroform and iso-propanol (4:1), concentrated under reduced pressure and the resulting residue was purified by silica gel column chromatography (MeOH/DCM=0-20%) to give MFH-3-33-1 (20 mg, yield 27%). LCMS (m/z): 458 [M+H]+.

N-(4-(3-(5-((5-tert-butyloxazol-2-yl)methylthio)thiazol-2-ylamino)cyclohexylamino)phenyl)acrylamide (MFH-3-35-1)

To a solution of MFH-3-33-1 (20 mg, 0.04 mmol) and DIPEA (0.1 mL) in CH₃CN (2 mL) was added acryloyl chloride (4 mg, 0.04 mmol) in DCM (0.2 mL) dropwise. The mixture was then stirred at −40° C. for 1 h. The solution was then concentrated under reduced pressure and the residue was purified by prep-HPLC (MeOH/H₂O, 0.05% TFA) to provide MFH-3-35-1 (9.3 mg, yield 41%). LCMS (m/z): 512 [M+H]+.

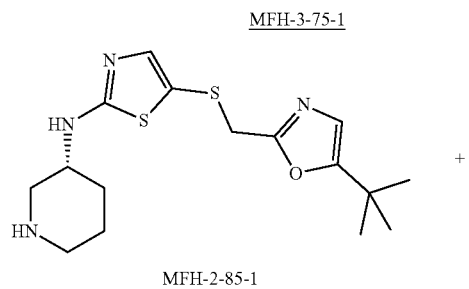

MFH-2-85-1

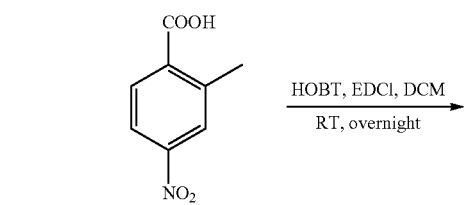

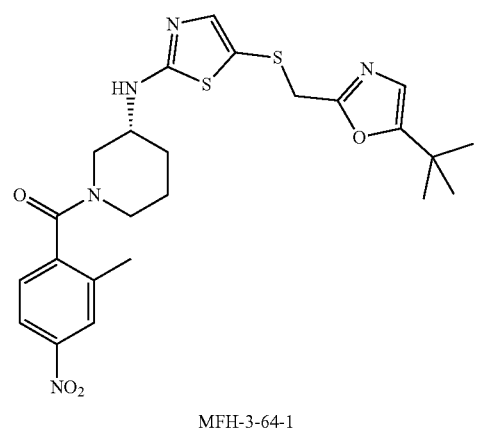

MFH-3-64-1

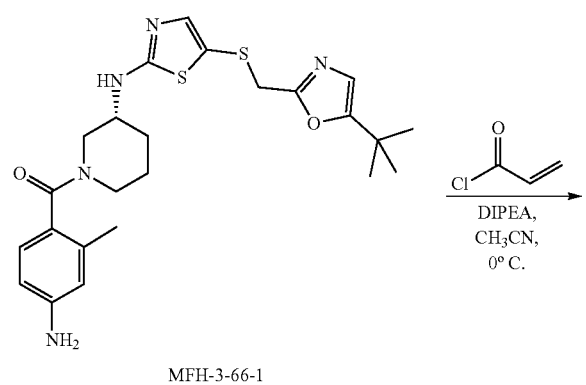

MFH-3-66-1

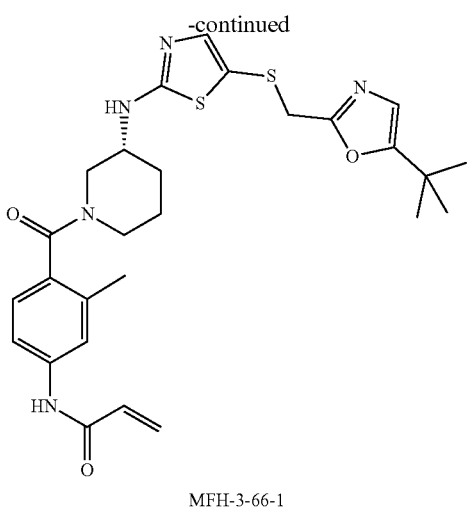

MFH-3-66-1

(R)-(3-(5-((5-tert-butyloxazol-2-yl)methylthio)thiazol-2-ylamino)piperidin-1-yl)(2-methyl-4-nitrophenyl)methanone (MFH-3-64-1)

The mixture of MFH-2-85-1 (44 mg, 0.13 mmol), 4-((tert-butoxycarbonylamino)methyl)benzoic acid (47 mg, 0.19 mmol), HOBT (25 mg, 0.19 mmol) and EDCI (36 mg, 0.19 mmol) in DCM (3 ml) was stirred for overnight. The reaction mixture was diluted with DCM (25 ml). The organic phase was washed with saturated Na₂CO₃ and brine (20 mL) and dried over Na₂SO₄. After removal of the solvent, the residue was purified by silica gel (MeOH/DCM=0-20%) to obtain MFH-3-64-1 (63 mg, yield 94%). LCMS (m/z): 516 [M+H]+.

(R)-(4-amino-2-methylphenyl)(3-(5-((5-tert-butyloxazol-2-yl)methylthio)thiazol-2-ylamino)piperidin-1-yl)methanone (MFH-3-66-1)

To a solution of MFH-3-64-1 (63 mg, 0.12 mmol) in ethyl acetate and methanol (1:1) were added Tin(II) chloride dehydrate (138 mg, 0.61 mmol) and conc. HCl (0.1 mL). After stirring for 3 h at 80° C., the reaction mixture was diluted with chloroform and iso-propanol (4:1), neutralized with saturated NaHCO₃ and filtered. The filtrate was extracted with chloroform and iso-propanol (4:1), concentrated under reduced pressure and the resulting residue was purified by silica gel column chromatography (MeOH/DCM=0-20%) to give MFH-3-66-1 (20 mg, yield 34%). LCMS (m/z): 486 [M+H]+.

(R)—N-(4-(3-(5-((5-tert-butyloxazol-2-yl)methylthio)thiazol-2-ylamino)piperidine-1-carbonyl)-3-methylphenyl)acrylamide (MFH-3-75-1)

To a solution of MFH-3-66-1 (20 mg, 0.04 mmol) and DIPEA (0.1 mL) in CH₃CN (2 mL) was added acryloyl chloride (4 mg, 0.04 mmol) in DCM (0.2 mL) dropwise. The mixture was then stirred at 0° C. for 1 h. The solution was then concentrated under reduced pressure and the residue was purified by prep-HPLC (MeOH/H₂O, 0.05% TFA) to provide MFH-3-75-1 (9.4 mg, yield 41%). LCMS (m/z): 540 [M+H]+. ¹H NMR (500 MHz, DMSO) δ 10.16 (d, J=35.4 Hz, 1H), 8.03 (d, J=59.1 Hz, 1H), 7.54 (d, J=9.3 Hz, 1H), 7.24-7.08 (m, 1H), 7.00 (d, J=9.0 Hz, 1H), 6.75 (d, J=10.5 Hz, 1H), 6.69 (s, 1H), 6.43 (dt, 7=17.0, 10.5 Hz, 1H), 6.32-6.20 (m, 1H), 5.76 (t, 7=11.0 Hz, 1H), 3.96 (s, 7=11.8 Hz, 2H), 3.59 (d, J=52.3 Hz, 4H), 3.00 (s, 1H), 2.19 (s, 3H), 1.92 (dd, J=59.5, 33.2 Hz, 2H), 1.57 (d, J=57.5 Hz, 2H), 1.20 (s, 9H).

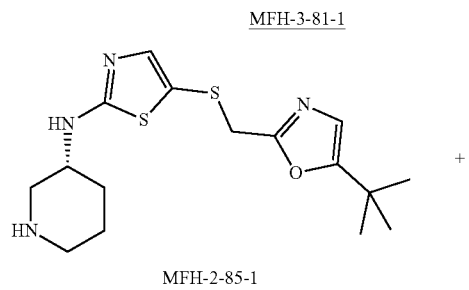

MFH-2-85-1

+

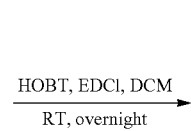

HOBT, EDCl, DCM
RT, overnight
→

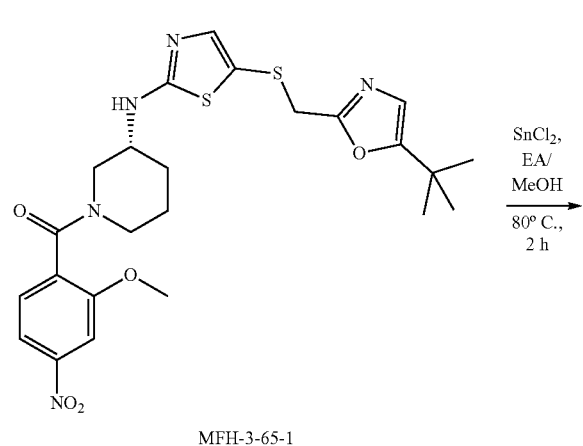

MFH-3-65-1

SnCl₂,
EA/
MeOH
────────
80° C.,
2 h

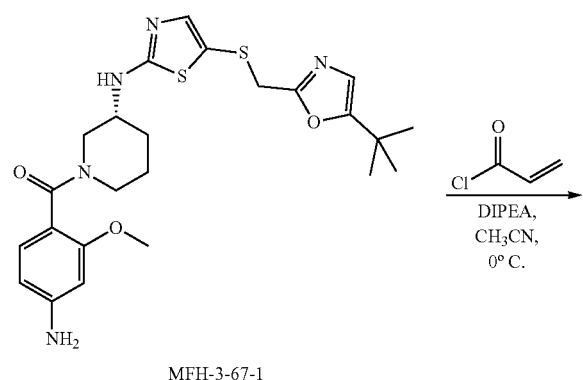

MFH-3-67-1

DIPEA,
CH₃CN,
0° C.

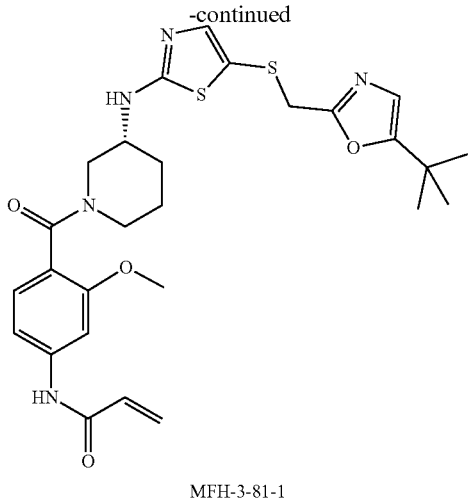

MFH-3-81-1

(R)-(3-(5-((5-tert-butyloxazol-2-yl)methylthio)thiazol-2-ylamino)piperidin-1-yl)(2-methoxy-4-nitrophenyl)methanone (MFH-3-65-1)

The mixture of MFH-2-85-1 (44 mg, 0.13 mmol), 4-((tert-butoxycarbonylamino)methyl)benzoic acid (47 mg, 0.19 mmol), HOBT (25 mg, 0.19 mmol) and EDCI (36 mg, 0.19 mmol) in DCM (3 ml) was stirred overnight. The reaction mixture was diluted with DCM (25 ml). The organic phase was washed with saturated Na₂CO₃ and brine (20 mL) and dried over Na₂SO₄. After removal of the solvent, the residue was purified by silica gel (MeOH/DCM=0-20%) to obtain MFH-3-64-1 (71 mg, yield 100%). LCMS (m/z): 532 [M+H]+.

(R)-(4-amino-2-methoxyphenyl)(3-(5-((5-tert-butyloxazol-2-yl)methylthio)thiazol-2-ylamino)piperidin-1-yl)methanone (MFH-3-67-1)

To a solution of MFH-3-64-1 (71 mg, 0.13 mmol) in ethyl acetate and methanol (1:1) were added Tin(II) chloride dehydrate (151 mg, 0.67 mmol) and conc. HCl (0.1 mL). After stirring for 3 h at 80° C., the reaction mixture was diluted with chloroform and iso-propanol (4:1), neutralized with saturated NaHCO₃ and filtered. The filtrate was extracted with chloroform and iso-propanol (4:1), concentrated under reduced pressure and the resulting residue was purified by silica gel column chromatography (MeOH/DCM=0-20%) to give MFH-3-67-1 (30 mg, yield 45%). LCMS (m/z): 502 [M+H]+.

(R)—N-(4-(3-(5-((5-tert-butyloxazol-2-yl)methylthio)thiazol-2-ylamino)piperidine-1-carbonyl)-3-methoxyphenyl)acrylamide (MFH-3-81-1)

To a solution of MFH-3-67-1 (30 mg, 0.06 mmol) and DIPEA (0.1 mL) in CH₃CN (2 mL) was added acryloyl chloride (7 mg, 0.08 mmol) in DCM (0.2 mL) dropwise. The mixture was then stirred at 0° C. for 1 h. The solution was then concentrated under reduced pressure and the residue was purified by prep-HPLC (MeOH/H₂O, 0.05% TFA) to provide MFH-3-81-1 (11.8 mg, yield 35%). LCMS (m/z): 556 [M+H]+. ¹H NMR (500 MHz, DMSO) δ 10.36-10.15 (m, 1H), 8.16-7.83 (m, 1H), 7.49 (d, J=14.3 Hz, 1H), 7.15 (dd, J=19.9, 7.7 Hz, 1H), 7.04-6.94 (m, 1H), 6.74 (dd, J=28.4, 22.6 Hz, 2H), 6.43 (dt, J=18.7, 9.3 Hz, 1H), 6.27 (ddd, J=17.0, 9.5, 1.8 Hz, 1H), 5.83-5.72 (m, 1H), 3.91 (s, 2H), 3.78 (s, 3H), 3.73 (s, 1H), 3.45 (d, J=13.3 Hz, 1H), 3.24 (t, J=32.2 Hz, 1H), 2.88 (dd, J=34.4, 22.2 Hz, 2H), 1.97 (d, J=18.3 Hz, 1H), 1.78 (s, 1H), 1.46 (s, 2H), 1.20 (s, 9H).

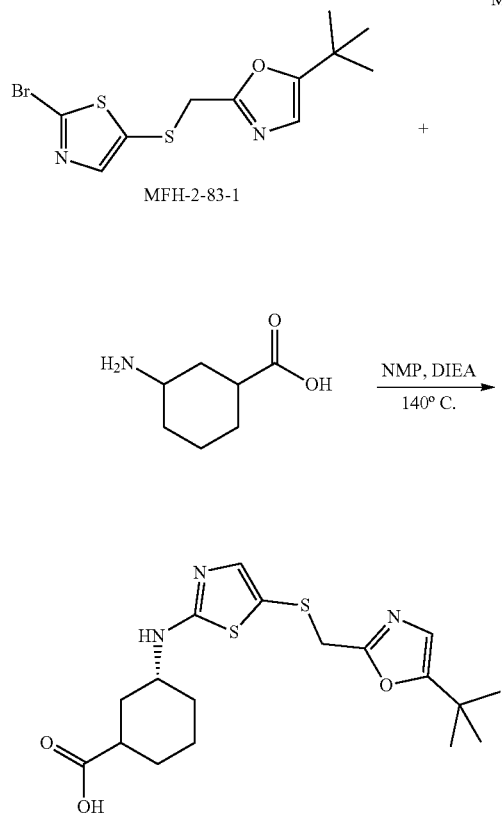

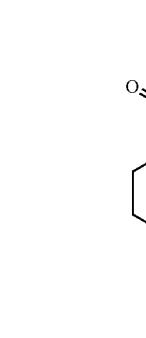

(1R,3S)-3-(5-((5-tert-butyloxazol-2-yl)methylthio) thiazol-2-ylamino)cyclohexanecarboxylic acid (MFH-3-79-1)

The mixture of MFH-2-83-1 (200 mg, 0.6 mmol), 3-aminocyclohexanecarboxylic acid (138 mg, 0.96 mmol) and DIEA (233 mg, 1.8 mmol) in NMP (1 mL) was stirred at 140° C. for overnight. The residue was extracted with chloroform and iso-propanol (4:1). The organic phase was washed with brine (50 mL) and dried over Na₂SO₄. After removal of the solvent, the residue was purified by silica gel (MeOH/DCM=0-20%) to obtain MFH-3-79-1 (60 mg, yield 26%). LCMS (m/z): 396 [M+H]⁺.

tert-butyl1-((1R,3S)-3-(5-((5-tert-butyloxazol-2-yl) methylthio)thiazol-2-ylamino)cyclohexanecarbonyl) piperidin-4-ylcarbamate (MFH-3-83-1)

The mixture of MFH-3-79-1 (60 mg, 0.15 mmol), tert-butyl piperidin-4-ylcarbamate (46 mg, 0.23 mmol), HOBT (31 mg, 0.23 mmol) and EDCI (44 mg, 0.23 mmol) in DCM (6 ml) was stirred for overnight. The reaction mixture was diluted with DCM (25 ml). The organic phase was washed with saturated Na₂CO₃ and brine (20 mL) and dried over Na₂SO₄. After removal of the solvent, the residue was purified by silica gel (MeOH/DCM=0-20%) to obtain MFH-3-83-1 (80 mg, yield 91%). LCMS (m/z): 578 [M+H]+.

(4-aminopiperidin-1-yl)((1R,3S)-3-(5-((5-tert-butyloxazol-2-yl)methylthio)thiazol-2-ylamino)cyclohexyl)methanone (MFH-3-85-1)

To a solution of MFH-3-83-1 (80 mg, 0.14 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 478 [M+H]⁺.

N-(1-((1R,3S)-3-(5-((5-tert-butyloxazol-2-yl)methylthio)thiazol-2-ylamino)cyclohexanecarbonyl)piperidin-4-yl)acrylamide (MFH-3-88-1)

To a solution of MFH-3-85-1 (20 mg, 0.04 mmol) and DIPEA (0.1 mL) in CH₃CN (2 mL) was added acryloyl chloride (5 mg, 0.05 mmol) in DCM (0.1 mL) dropwise. The mixture was then stirred at 0° C. for 1 h. The solution was then concentrated under reduced pressure and the residue was purified by prep-HPLC (MeOH/H₂O, 0.05% TFA) to provide MFH-3-88-1 (3.7 mg, yield 17%). LCMS (m/z): 532 [M+H]+.

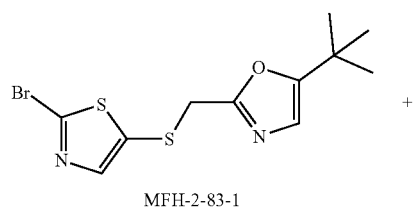

MFH-2-83-1

+

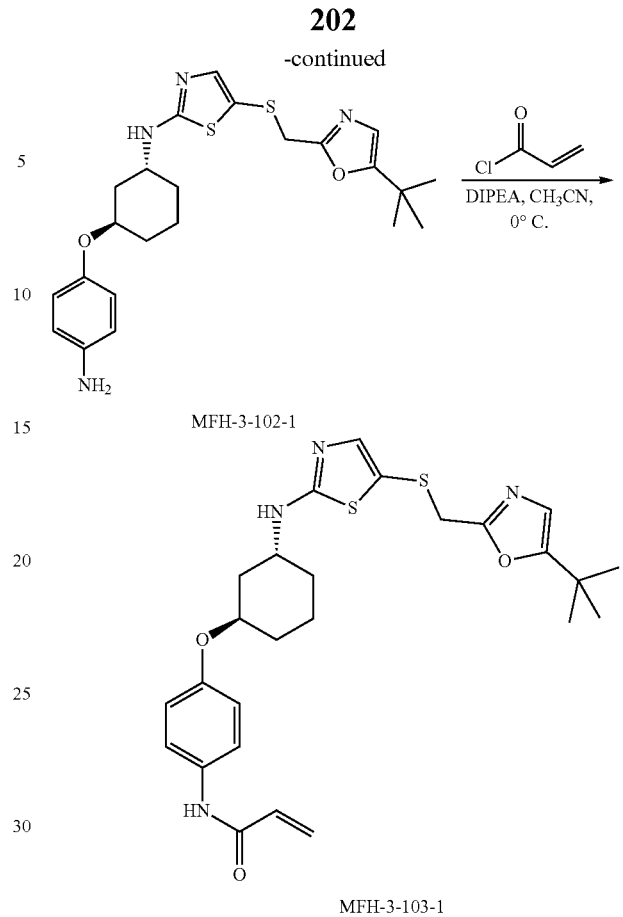

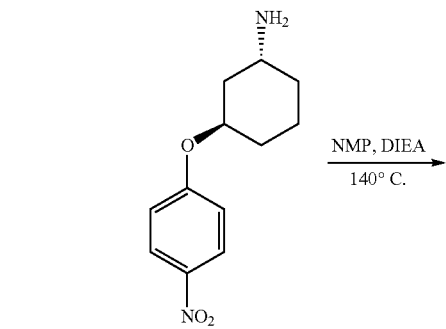

MFH-3-97-1

5-((5-tert-butyloxazol-2-yl)methylthio)-N-((1R,3R)-3-(4-nitrophenoxy)cyclohexyl)thiazol-2-amine (MFH-3-97-1)

The mixture of MFH-2-83-1 (180 mg, 0.54 mmol), (1R,3R)-3-(4-nitrophenoxy)cyclohexanamine (204 mg, 0.86 mmol) and DIEA (140 mg, 1.1 mmol) in NMP (1 mL) was stirred at 140° C. for overnight. The residue was extracted with chloroform and iso-propanol (4:1). The organic phase was washed with brine (50 mL) and dried over Na₂SO₄. After removal of the solvent, the residue was purified by silica gel (MeOH/DCM=0-20%) to obtain MFH-3-97-1 (80 mg, yield 30%). LCMS (m/z): 489 [M+H]⁺.

N-((1R,3R)-3-(4-aminophenoxy)cyclohexyl)-5-((5-tert-butyloxazol-2-yl)methylthio)thiazol-2-amine (MFH-3-102-1)

To a solution of MFH-3-97-1 (80 mg, 0.16 mmol) in ethyl acetate and methanol (1:1) were added Tin(II) chloride dehydrate (300 mg, 1.3 mmol) and conc. HCl (0.1 mL). After stirring for 3 h at 80° C., the reaction mixture was diluted with chloroform and iso-propanol (4:1), neutralized with saturated NaHCO₃ and filtered. The filtrate was extracted with chloroform and iso-propanol (4:1), concentrated under reduced pressure and the resulting residue was purified by silica gel column chromatography (MeOH/DCM=0-20%) to give MFH-3-102-1 (40 mg, yield 54%). LCMS (m/z): 459 [M+H]+.

N-(4-((1R,3R)-3-(5-((5-tert-butyloxazol-2-yl)methylthio)thiazol-2-ylamino)cyclohexyloxy)phenyl) acrylamide (MFH-3-103-1)

To a solution of MFH-3-102-1 (40 mg, 0.09 mmol) and DIPEA (0.1 mL) in CH$_3$CN (2 mL) was added acryloyl chloride (10 mg, 0.11 mmol) in DCM (0.2 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-3-103-1 (9.6 mg, yield 21%). LCMS (m/z): 513 [M+H]+. $^1$H NMR (500 MHz, DMSO) δ 10.00 (s, 1H), 8.04 (d, J=7.3 Hz, 1H), 7.56 (d, J=9.0 Hz, 2H), 6.94 (s, 1H), 6.93-6.89 (m, 2H), 6.71 (s, 1H), 6.39 (dd, J=17.0, 10.1 Hz, 1H), 6.21 (dd, J=17.0, 2.0 Hz, 1H), 5.71 (dd, J=10.1, 2.0 Hz, 1H), 4.66 (s, 1H), 3.94 (s, 2H), 3.83 (s, 1H), 2.01 (d, J=13.3 Hz, 1H), 1.85 (s, 1H), 1.74-1.54 (m, 5H), 1.34 (dd, J=21.1, 11.1 Hz, 1H), 1.18 (s, 9H).

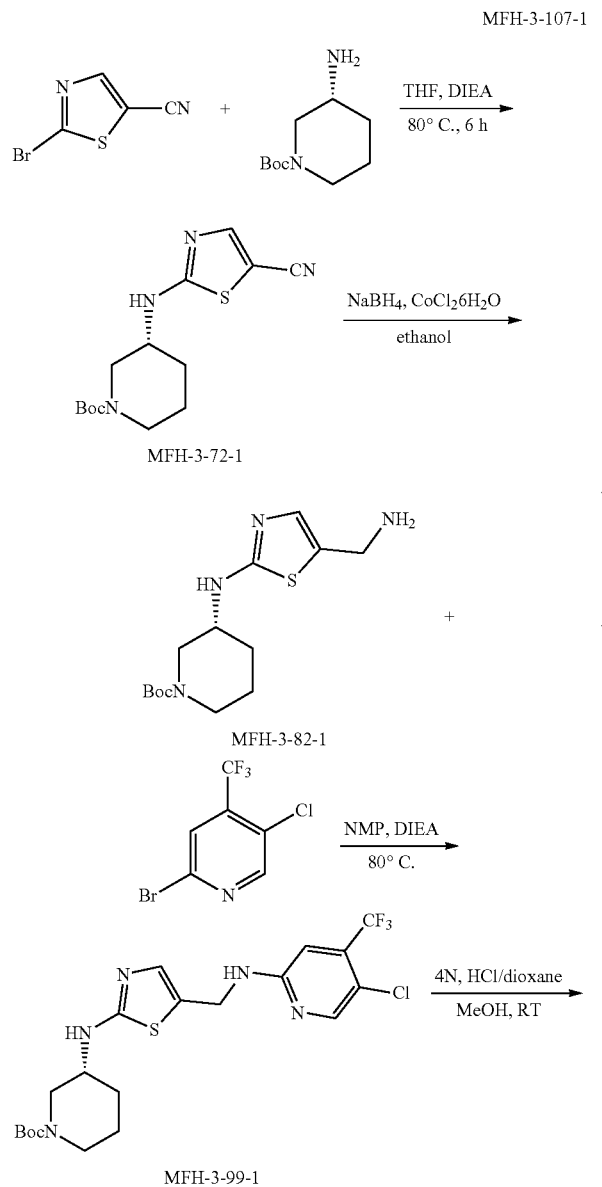

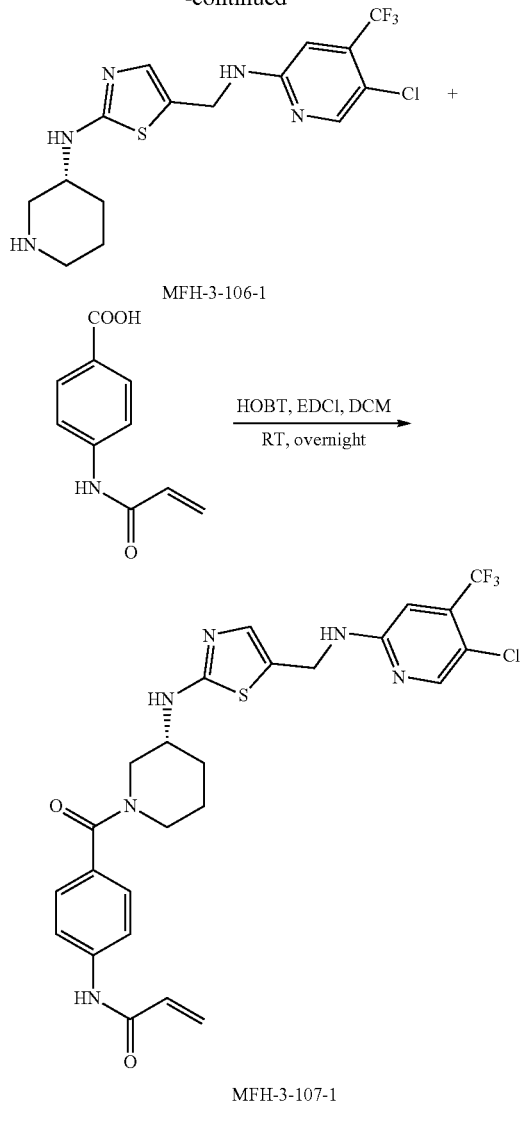

(R)-tert-butyl 3-(5-cyanothiazol-2-ylamino)piperidine-1-carboxylate (MFH-3-72-1)

The mixture of 2-bromothiazole-5-carbonitrile (800 mg, 4.23 mmol), (R)-tert-butyl 3-aminopiperidine-1-carboxylate (1.1 g, 5.5 mmol) and DIEA (820 mg, 6.35 mmol) in THF (15 mL) was stirred at 80° C. for 6 h. The residue was extracted with chloroform and iso-propanol (4:1). The organic phase was washed with brine (50 mL×2) and dried over Na$_2$SO$_4$. After removal of the solvent, the residue was purified by silica gel (MeOH/DCM=0-20%) to obtain MFH-3-72-1 (1.3 g, yield 100%). LCMS (m/z): 309 [M+H]+.

(R)-tert-butyl 3-(5-(aminomethyl)thiazol-2-ylamino)piperidine-1-carboxylate (MFH-3-82-1)

To a solution of MFH-3-72-1 (300 mg, 1 mmol) and CoCl$_2$ 6H$_2$O (232 mg, 1 mmol) in ethanol (8 mL) was added NaBH$_4$ (110 mg, 3 mmol) at room temperature. The vial was sealed and stirred at room temperature for 3 h and then was quenched with water. The obtained mixture was extracted with chloroform and iso-propanol (4:1). The organic phase

(R)-tert-butyl3-(5-((5-chloro-4-(trifluoromethyl) pyridin-2-ylamino)methyl)thiazol-2-ylamino)piperidine-1-carboxylate (MFH-3-99-1)

The mixture of MFH-2-82-1 (175 mg, 0.56 mmol), 2-bromo-5-chloro-4-(trifluoromethyl)pyridine (146 mg, 0.56 mmol) and DIEA (108 mg, 0.84 mmol) in NMP (1 mL) was stirred at 80° C. for overnight. The residue was extracted with chloroform and iso-propanol (4:1). The organic phase was washed with brine (50 mL×2) and dried over Na₂SO₄. After removal of the solvent, the residue was purified by silica gel (MeOH/DCM=0-20%) to obtain MFH-3-99-1 (90 mg, yield 58%). LCMS (m/z): 492 [M+H]⁺.

(R)-5-((5-chloro-4-(trifluoromethyl)pyridin-2-ylamino)methyl)-N-(piperidin-3-yl)thiazol-2-amine (MFH-3-106-1)

To a solution of MFH-3-99-1 (90 mg, 0.18 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 392 [M+H]⁺.

(R)—N-(4-(3-(5-((5-chloro-4-(trifluoromethyl)pyridin-2-ylamino)methyl)thiazol-2-ylamino)piperidine-1-carbonyl)phenyl)acrylamide (MFH-3-107-1)

The mixture of MFH-3-106-1 (20 mg, 0.05 mmol), 4-acrylamidobenzoic add (10 mg, 0.05 mmol), HOBT (8 mg, 0.06 mmol) and EDCI (11 mg, 0.06 mmol) in DMF (0.5 ml). Then the reaction mixture was stirred for overnight. The reaction mixture was purified by prep-HPLC (MeOH/H₂O, 0.05% TFA) to provide MFH-3-107-1 (3.8 mg, yield 13%). LCMS (m/z): 565 [M+H]+. ¹H NMR (500 MHz, DMSO) δ 10.31 (s, 1H), 8.28 (s, 1H), 7.68 (s, 3H), 7.36 (d, J=7.2 Hz, 2H), 7.25-6.81 (m, 3H), 6.45 (dd, J=17.0, 10.2 Hz, 1H), 6.28 (dd, J=17.0, 1.9 Hz, 1H), 5.78 (dd, J=10.1, 1.9 Hz, 1H), 4.46 (s, 2H), 3.69 (s, 3H), 3.18 (d, J=11.7 Hz, 2H), 1.96 (s, 1H), 1.75 (s, 1H), 1.55 (m, 2H).

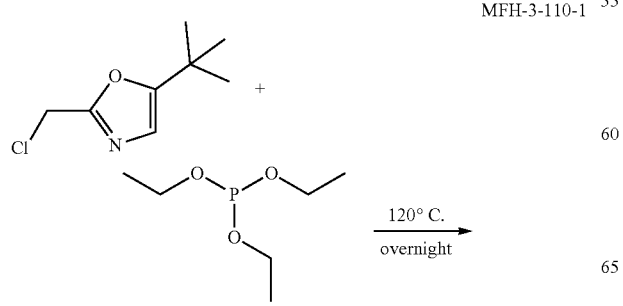

MFH-3-110-1

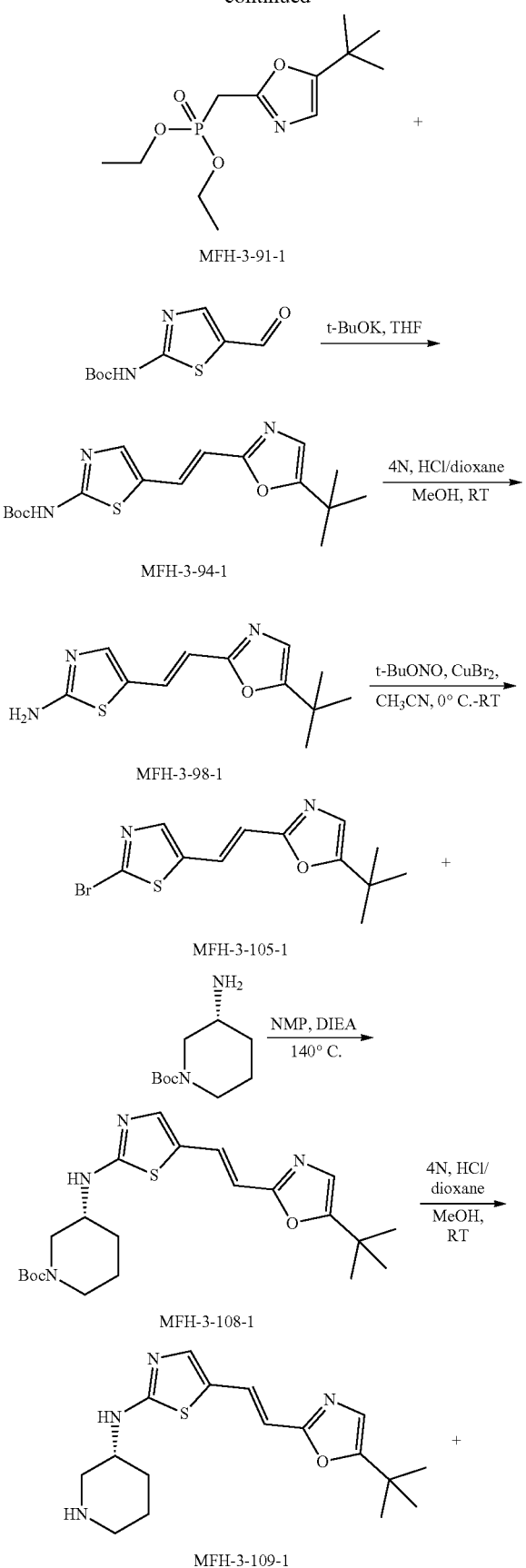

-continued

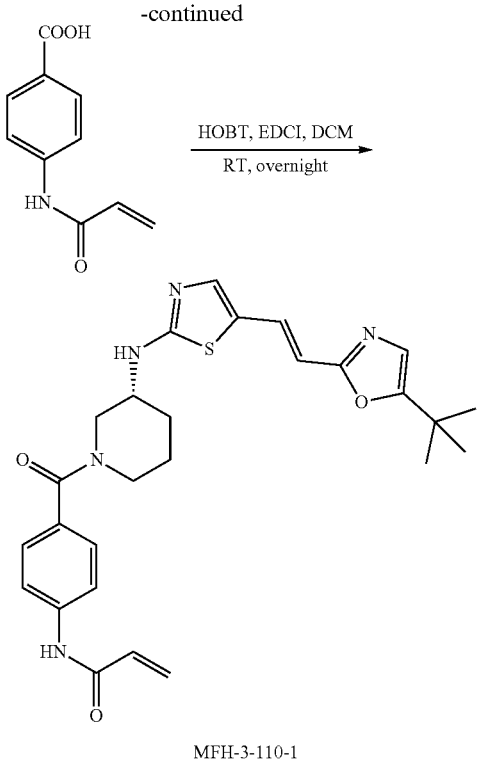

MFH-3-110-1 diethyl (5-tert-butyloxazol-2-yl)methylphosphonate (MFH-3-91-1)

A solution of 5-tert-butyl-2-(chloromethyl)oxazole (800 mg, 4.61 mmol) in triethyl phosphite (3.83 g, 23.04 mmol) was heated at 120° C. for overnight. The solvent was removed under reduced pressure to provide a crude which was directly used in the next step. LCMS (m/z): 276 $[M+H]^+$.

(E)-tert-butyl5-(2-(5-tert-butyloxazol-2-yl)vinyl) thiazol-2-ylcarbamate (MFH-3-94-1)

To a solution of MFH-3-91-1 (500 mg, 1.82 mmol) in THF (5 mL) was added t-BuOK (370 mg, 3.3 mmol) at room temperature. The vial was sealed and stirred at room temperature for 10 min. Then, a solution of tert-butyl 5-formylthiazol-2-ylcarbamate (345 mg, 1.5 mmol) in THF (3 mL) was added. After completion, the reaction mixture was quenched with water. The obtained mixture was extracted with chloroform and iso-propanol (4:1). The organic phase was washed with brine (50 mL×2) and dried over $Na_2SO_4$. After removal of the solvent, the residue was purified by silica gel (MeOH/DCM=0-20%) to obtain MFH-3-94-1 (440 mg, yield 84%). LCMS (m/z): 350 $[M+H]^+$.

(E)-5-(2-(5-tert-butyloxazol-2-yl)vinyl)thiazol-2-amine (MFH-3-98-1)

To a solution of MFH-3-94-1 (220 mg, 0.63 mmol) in methanol (5 mL) was added 4N HCl/dioxane (5 mL). The solution was then stirred for 3 h at room temperature and the solvent was removed under reduced pressure to provide a crude which was directly used in the next step. LCMS (m/z): 250 $[M+H]^+$.

(E)-2-(2-(2-bromothiazol-5-yl)vinyl)-5-tert-butyloxazole (MFH-3-105-1)

To a solution of $CuBr_2$ (172 mg, 0.77 mmol) in acetonitrile (15 mL) at 0° C. was added t-BuONO (79 mg, 0.77 mmol) followed by compound MFH-3-98-1 (160 mg, 0.64 mmol). The mixture was stirred at 0° C. for one hour, then at room temperature for one hour, ethyl acetate was added and the organic mixture washed with hydrochloric acid (20 mL), dried over magnesium sulfate, filtered through a pad of silica gel, and concentrated under reduced pressure. The residue was chromatographed on silica gel to give the MFH-3-105-1 (50 mg, 25%). LCMS (m/z): 314 [M+H]+.

(R,E)-tert-butyl3-(5-(2-(5-tert-butyloxazol-2-yl)vinyl)thiazol-2-ylamino)piperidine-1-carboxylate (MFH-3-108-1)

The mixture of MFH-3-105-1 (50 mg, 0.16 mmol), (R)-tert-butyl 3-aminopiperidine-1-carboxylate (51 mg, 0.26 mmol) and DIEA (41 mg, 0.32 mmol) in NMP (0.5 mL) was stirred at 140° C. for overnight. The residue was extracted with chloroform and iso-propanol (4:1). The organic phase was washed with brine (10 mL×2) and dried over $Na_2SO_4$. After removal of the solvent, the residue was purified by silica gel (MeOH/DCM=0-20%) to obtain MFH-3-108-1 (40 mg, yield 58%). LCMS (m/z): 433 $[M+H]^+$.

(R,E)-5-(2-(5-tert-butyloxazol-2-yl)vinyl)-N-(piperidin-3-yl)thiazol-2-amine (MFH-3-109-1)

To a solution of MFH-3-108-1 (40 g, 0.09 mmol) in methanol (2 mL) was added 4N HCl/dioxane (2 mL). The solution was then stirred for 3 h at room temperature and the solvent was removed under reduced pressure to provide a crude which was directly used in the next step. LCMS (m/z): 333 $[M+H]^+$.

(R,E)-N-(4-(3-(5-(2-(5-tert-butyloxazol-2-yl)vinyl) thiazol-2-ylamino)piperidine-1-carbonyl)phenyl) acrylamide (MFH-3-110-1)

The mixture of MFH-3-109-1 (35 mg, 0.1 mmol), 4-acrylamidobenzoic acid (30 mg, 0.16 mmol), HOBT (21 mg, 0.16 mmol) and EDCI (30 mg, 0.16 mmol) in DMF (0.5 ml). Then the reaction mixture was stirred for overnight. The reaction mixture was purified by prep HPLC (MeOH/$H_2O$, 0.05% TFA) to provide MFH-3-110-1 (5 mg, yield 10%). LCMS (m/z). 506 [M+H]+.

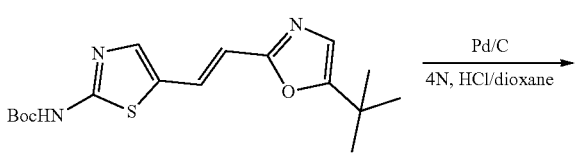

MFH-3-94-1

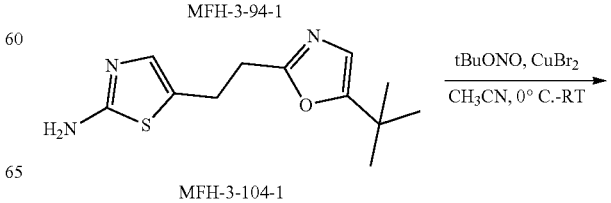

MFH-3-104-1

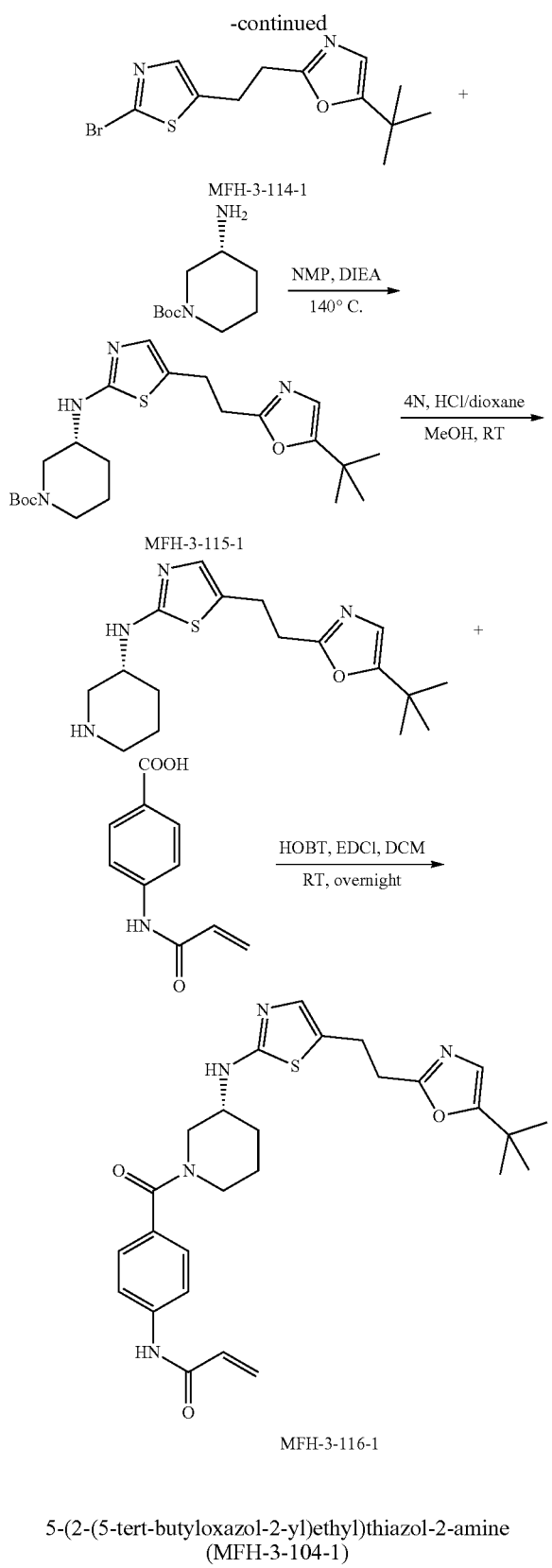

5-(2-(5-tert-butyloxazol-2-yl)ethyl)thiazol-2-amine (MFH-3-104-1)

A mixture of compound MFH-3-94-1 (250 mg, 1 mmol) and 10% Pd/C (20 mg) in MeOH (10 mL) was stirred for 5 h at room temperature under H₂ balloon. The mixture was filtered through celite. The filtrate was added 4N HCl/dioxane (5 mL). The solution was then stirred for 3 h at room temperature and the solvent was removed under reduced pressure to provide a crude which was directly used in the next step. LCMS (m/z): 252 [M+H]⁺.

2-(2-(2-bromothiazol-5-yl)ethyl)-5-tert-butyloxazole (MFH-3-114-1)

To a solution of CuBr₂ (53 mg, 0.24 mmol) in acetonitrile (2 mL) at 0° C. was added t-BuONO (25 mg, 0.24 mmol) followed by compound MFH-3-104-1 (60 mg, 0.24 mmol). The mixture was stirred at 0° C. for one hour, and then was warmed up to room temperature. Ethyl acetate was added and the organic mixture was washed with hydrochloric add (20 mL), dried over magnesium sulfate, filtered through a pad of silica gel, and concentrated in vacuo. The residue was chromatographed on silica gel to give the MFH-3-114-1 (40 mg, 53%). LCMS (m/z): 316 [M+H]+.

(R)-tert-butyl 3-(5-(2-(5-tert-butyloxazol-2-yl)ethyl) thiazol-2-ylamino)piperidine-1-carboxylate (MFH-3-115-1)

The mixture of MFH-3-114-1 (40 mg, 0.13 mmol), (R)-tert-butyl 3-aminopiperidine-1-carboxylate (41 mg, 0.2 mmol) and DIEA (33 mg, 0.25 mmol) in NMP (0.5 mL) was stirred at 140° C. for overnight. The residue was extracted with chloroform and iso-propanol (4.1). The organic phase was washed with brine (10 mL×2) and dried over Na₂SO₄. After removal of the solvent, the residue was purified by silica gel (MeOH/DCM=0-20%) to obtain MFH-3-115-1 (35 mg, yield 63%). LCMS (m/z): 435 [M+H]⁺.

(R)-5-(2-(5-tert-butyloxazol-2-yl)ethyl)-N-(piperidin-3-yl)thiazol-2-amine

To a solution of MFH-3-115-1 (35 mg, 0.08 mmol) in methanol (2 mL) was added 4N HCl/dioxane (2 mL). The solution was then stirred for 3 h at room temperature and the solvent was removed under reduced pressure to provide a crude which was directly used m the next step. LCMS (m/z): 335 [M+H]⁺.

(R)—N-(4-(3-(5-(2-(5-tert-butyloxazol-2-yl)ethyl) thiazol-2-ylamino)piperidine-1-carbonyl)phenyl) acrylamide (MFH-3-116-1)

The mixture of (R)-5-(2-(5-tert-butyloxazol-2-yl)ethyl)-N-(piperidin-3-yl)thiazol-2-amine (23 mg, 0.07 mmol), 4-acrylamidobenzoic acid (15 mg, 0.08 mmol), HOBT (12 mg, 0.09 mmol) and EDCI (17 mg, 0.09 mmol) in DMF (0.5 ml) was stirred for overnight. The reaction mixture was purified by prep-HPLC (MeOH/H₂O, 0.05% TFA) to provide MFH-3-116-1 (5.5 mg, yield 16%). LCMS (m/z): 508 [M+H]+. ¹H NMR (500 MHz, DMSO) δ 10.38 (s, 1H), 8.29 (d, J=7.5 Hz, 1H), 7.82 (d, J=8.8 Hz, 2H), 7.74 (d, J=8.8 Hz, 2H), 6.96 (s, 1H), 6.68 (s, 1H), 6.45 (dd, J=17.0, 10.2 Hz, 1H), 6.29 (dd, J=17.0, 1.9 Hz, 1H), 5.79 (dd, J=10.1, 1.9 Hz, 1H), 3.87 (dd, J=12.3, 4.0 Hz, 1H), 3.75-3.63 (m, 2H), 3.13-2.99 (m, 4H), 2.96 (t, J=6.8 Hz, 2H), 1.88 (m, 2H), 1.63 (m, 2H), 1.22 (s, 9H).

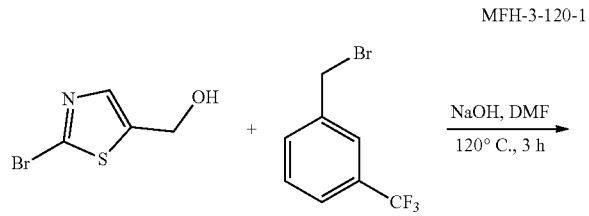

MFH-3-120-1

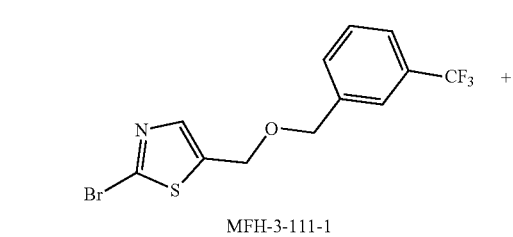

MFH-3-111-1

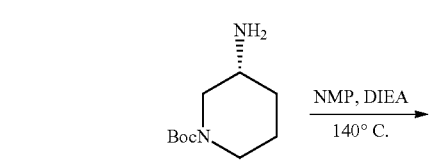

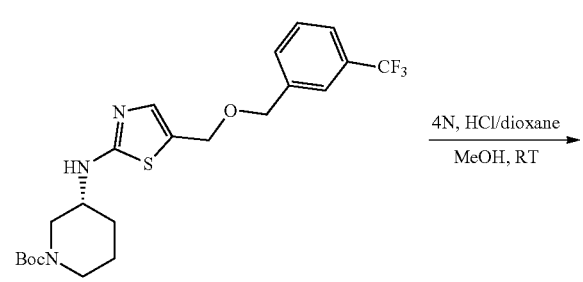

MFH-3-112-1

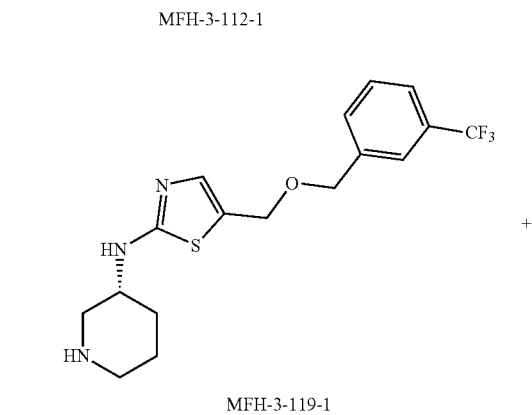

MFH-3-119-1

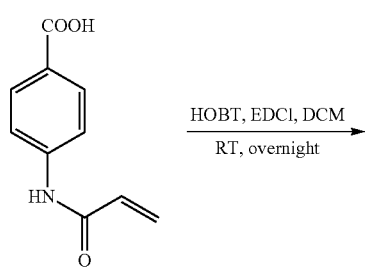

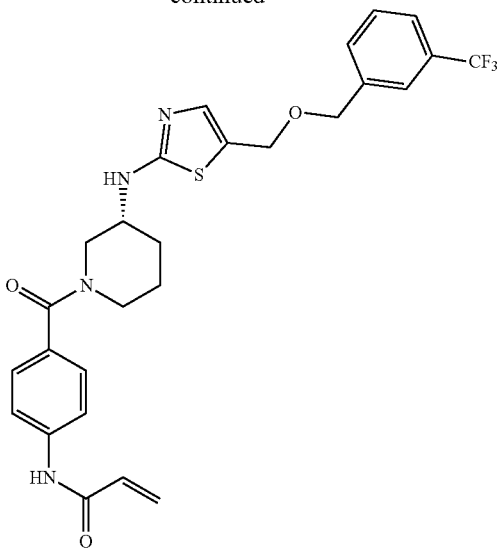

MFH-3-120-1

2-bromo-5-((3-(trifluoromethyl)benzyloxy)methyl)thiazole (MFH-3-111-1)

The mixture of (2-bromothiazol-5-yl)methanol (180 mg, 0.93 mmol), 1-(bromomethyl)-3-(trifluoromethyl)benzene (288 mg, 1.2 mmol) and NaOH (67 mg, 1.67 mmol) in DMF (2 mL) was stirred at 120° C. for 3 h. The residue was extracted with chloroform and iso-propanol (4:1). The organic phase was washed with brine (20 mL×2) and dried over $Na_2SO_4$. After removal of the solvent, the residue was purified by silica gel (PE/EA=0-50%) to obtain MFH-3-111-1 (160 mg, yield 49%). LCMS (m/z): 353 [M+H]$^+$.

(R)-tert-butyl 3-(5-((3-(trifluoromethyl)benzyloxy)methyl)thiazol-2-ylamino)piperidine-1-carboxylate (MFH-3-112-1)

The mixture of MFH-3-111-1 (160 mg, 0.34 mmol), (R)-tert-butyl 3-aminopiperidine-1-carboxylate (109 mg, 0.55 mmol) and DIEA (88 mg, 0.68 mmol) in NMP (1 mL) was stirred at 140° C. for overnight. The residue was extracted with chloroform and iso-propanol (4:1). The organic phase was washed with brine (20 mL×2) and dried over $Na_2SO_4$. After removal of the solvent, the residue was purified by silica gel (MeOH/DCM=0-20%) to obtain MFH-3-112-1 (35 mg, yield 22%). LCMS (m/z): 472 [M+H]$^+$.

(R)—N-(piperidin-3-yl)-5-((3-(trifluoromethyl)benzyloxy)methyl)thiazol-2-amine (MFH-3-119-1)

To a solution of MFH-3-112-1 (35 mg, 0.08 mmol) in methanol (2 mL) was added 4N HCl/dioxane (2 mL). The solution was then stirred for 3 h at room temperature and the solvent was removed under reduced pressure to provide a crude which was directly used in the next step. LCMS (m/z): 372 [M+H]$^+$.

(R)—N-(4-(3-(5-((3-(trifluoromethyl)benzyloxy)methyl)thiazol-2-ylamino)piperidine-1-carbonyl)phenyl)acrylamide (MFH-3-120-1)

The mixture of MFH-3-119-1 (23 mg, 0.06 mmol), 4-acrylamidobenzoic acid (15 mg, 0.08 mmol), HOBT (12 mg, 0.09 mmol) and EDCI (17 mg, 0.09 mmol) in DMF (0.5 ml). Then the reaction mixture was stirred for overnight. The reaction mixture was purified by prep-HPLC (MeOH/H₂O, 0.05% TFA) to provide MFH-3-120-1 (8.7 mg, yield 26%). LCMS (m/z): 545 [M+H]+. ¹H NMR (500 MHz, DMSO) δ 10.32 (s, 1H), 7.72-7.57 (m, 7H), 7.37 (d, J=5.1 Hz, 3H), 6.47-6.40 (m, 1H), 6.27 (dd, J=16.6, 6.9 Hz, 1H), 5.77 (t, J=8.3 Hz, 1H), 4.58 (d, J=8.2 Hz, 2H), 4.56 (s, 2H), 3.78 (s, 3H), 3.20 (d, J=6.7 Hz, 2H), 1.98 (s, 1H), 1.76 (s, 1H), 1.55 (m, 2H).

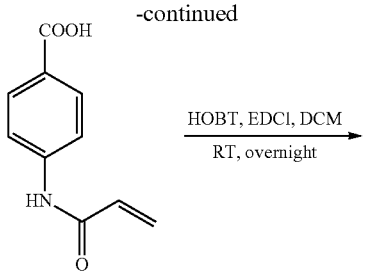

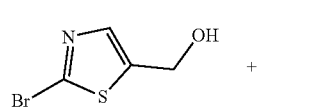

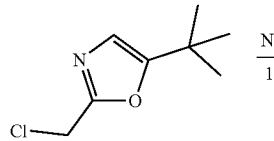

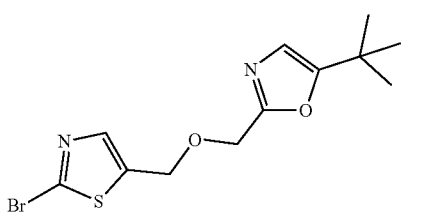

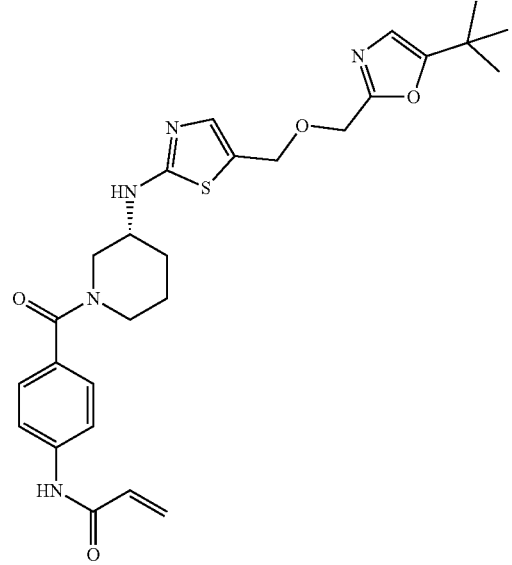

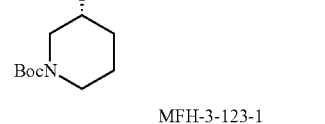

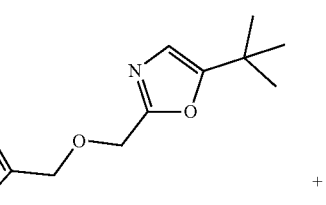

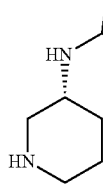

MFH-3-126-1

2-(((2-bromothiazol-5-yl)methoxy)methyl)-5-tert-butyloxazole (MFH-3-121-1)

The mixture of (2-bromothiazol-5-yl)methanol (220 mg, 1.1 mmol), 5-tert-butyl-2-(chloromethyl)oxazole (256 mg, 1.5 mmol) and NaOH (82 mg, 2.04 mmol) in DMF (2 mL) was stirred at 120° C. for 3 h. The residue was extracted with chloroform and iso-propanol (4:1). The organic phase was washed with brine (20 mL) and dried over Na₂SO₄. After removal of the solvent, the residue was purified by silica gel (PE/EA=0-50%) to obtain MFH-3-111-1 (170 mg, yield 45%). LCMS (m/z): 332 [M+H]⁺.

(R)-tert-butyl3-(5-(((5-tert-butyloxazol-2-yl)methoxy)methyl)thiazol-2-ylamino)piperidine-1-carboxylate (MFH-3-123-1)

The mixture of MFH-3-121-1 (170 mg, 0.51 mmol), (R)-tert-butyl 3-aminopiperidine-1-carboxylate (164 mg, 0.82 mmol) and DIEA (133 mg, 1 mmol) in NMP (1 mL) was stirred at 140° C. for overnight. The residue was extracted with chloroform and iso-propanol (4:1). The organic phase was washed with brine (20 mL) and dried over Na₂SO₄. After removal of the solvent, the residue was purified by silica gel (MeOH/DCM=0-20%) to obtain MFH-3-123-1 (50 mg, yield 22%). LCMS (m/z): 451 [M+H]⁺.

(R)-5-(((5-tert-butyloxazol-2-yl)methoxy)methyl)-N-(piperidin-3-yl)thiazol-2-amine (MFH-3-126-1)

To a solution of MFH-3-123-1 (50 mg, 0.11 mmol) in methanol (2 mL) was added 4N HCl/dioxane (2 mL). The solution was then stirred for 3 h at room temperature and the solvent was removed under reduced pressure to provide a crude which was directly used in the next step. LCMS (m/z): 372 [M+H]⁺.

(R)—N-(4-(3-(5-(((5-tert-butyloxazol-2-yl)methoxy)methyl)thiazol-2-ylamino)piperidine-1-carbonyl)phenyl)acrylamide (MFH-3-128-1)

The mixture of MFH-3-126-1 (23 mg, 0.06 mmol), 4-acrylamidobenzoic acid (15 mg, 0.08 mmol), HOBT (12 mg, 0.09 mmol) and EDCI (17 mg, 0.09 mmol) in DMF (0.5 ml) was stirred for overnight. The reaction mixture was purified by prep-HPLC (MeOH/H₂O, 0.05% TFA) to provide MFH-3-128-1 (7 mg, yield 22%). LCMS (m/z): 524 [M+H]+. ¹H NMR (500 MHz, DMSO) δ 10.37 (s, 1H), 8.33 (d, J=38.9 Hz, 1H), 7.84 (d, J=8.5 Hz, 2H), 7.75 (d, J=8.4 Hz, 2H), 7.37 (d, J=8.3 Hz, 1H), 6.89-6.71 (m, 1H), 6.46 (dd, J=16.9, 10.1 Hz, 1H), 6.29 (d, J=17.0 Hz, 1H), 5.80 (d, J=10.0 Hz, 1H), 4.59-4.40 (m, 2H), 4.05 (s, 1H), 3.99-3.85 (m, 2H), 3.33 (dd, J=31.2, 10.4 Hz, 2H), 3.00 (m, 2H), 1.93 (d, J=15.1 Hz, 1H), 1.84 (s, 1H), 1.62 (s, 2H), 1.23 (s, 9H).

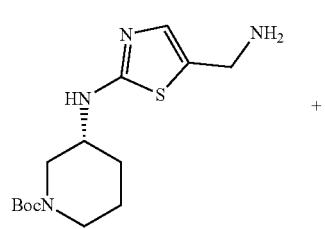

MFH-3-82-1

+

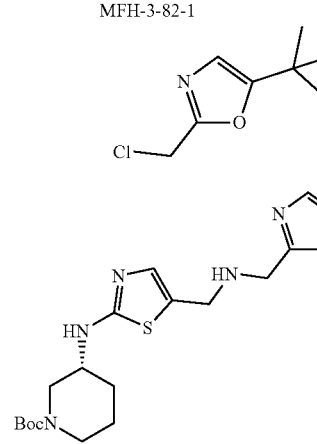

MFH-3-136-1

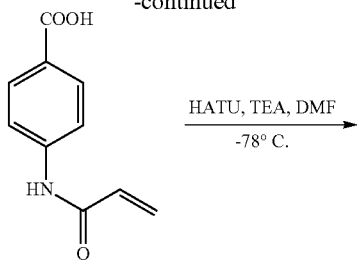

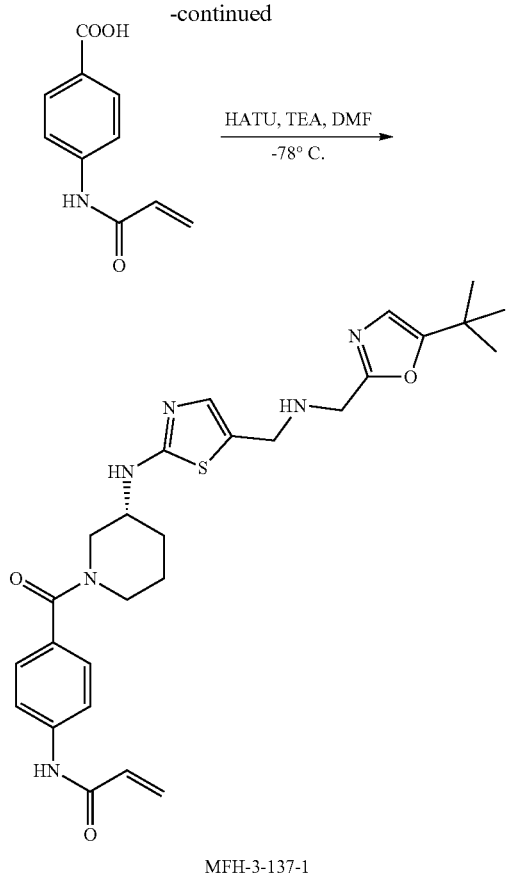

MFH-3-137-1

(R)-tert-butyl 3-(5-(((5-tert-butyloxazol-2-yl)methylamino)methyl)thiazol-2-ylamino)piperidine-1-carboxylate (MFH-3-90-1)

The mixture of MFH-2-82-1 (160 mg, 0.51 mmol), 5-tert-butyl-2-(chloromethyl)oxazole (89 mg, 0.51 mmol) and DIEA (132 mg, 1 mmol) in NMP (1 mL) was stirred at 80° C. for overnight. The solution was extracted with chloroform and iso-propanol (4:1). The organic phase was washed with brine (50 mL×2) and dried over Na₂SO₄. After removal of the solvent, the residue was purified by silica gel (MeOH/DCM=0-20%) to obtain MFH-3-90-1 (133 mg, yield 58%). LCMS (m/z): 450 [M+H]⁺.

(R)-5-(((5-tert-butyloxazol-2-yl)methylamino)methyl)-N-(piperidin-3-yl)thiazol-2-amine (MFH-3-136-1)

To a solution of MFH-3-90-1 (60 mg, 0.13 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 350 [M+H]⁺.

(R)—N-(4-(3-(5-(((5-tert-butyloxazol-2-yl)methylamino)methyl)thiazol-2-ylamino)piperidine-1-carbonyl)phenyl)acrylamide (MFH-3-137-1)

The mixture of MFH-3-136-1 (30 mg, 0.09 mmol), 4-acrylamidobenzoic acid (17 mg, 0.09 mmol) and TEA (9 mg, 0.09 mmol) in DMF (1 ml). The reaction mixture was cooled to −60° C., and HATU (33 mg, 0.09 mmol) was added in the reaction mixture. The reaction mixture was purified by prep-HPLC (MeOH/H₂O, 0.05% TFA) to provide MFH-3-137-1 (18 mg, yield 38%). LCMS (m/z): 523 [M+H]+. ¹H NMR (500 MHz, DMSO) δ 10.31 (s, 1H), 8.79-8.59 (m, 2H), 8.10-7.97 (m, 1H), 7.69 (s, 1H), 7.37 (s, 1H), 7.13 (d, J=6.5 Hz, 1H), 6.96 (dd, J=9.8, 4.5 Hz, 1H), 6.78 (s, 1H), 6.43 (d, J=6.7 Hz, 1H), 6.28 (s, 1H), 5.79 (dd, J=12.2, 4.2 Hz, 1H), 4.31 (s, 2H), 3.86 (s, 2H), 3.72 (s, 2H), 3.43 (d, J=10.6 Hz, 1H), 2.93-2.75 (m, 2H), 2.00 (d J=8.6 Hz, 1H), 1.89 (d, J=22.0 Hz, 1H), 1.59 (m, 2H), 1.23 (s, 9H).

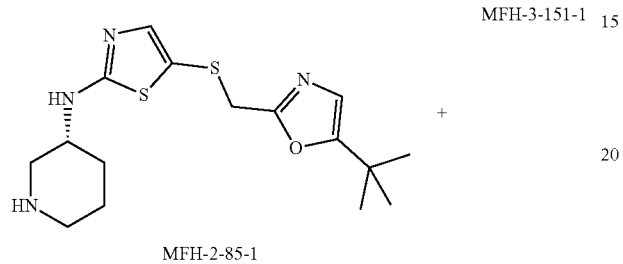

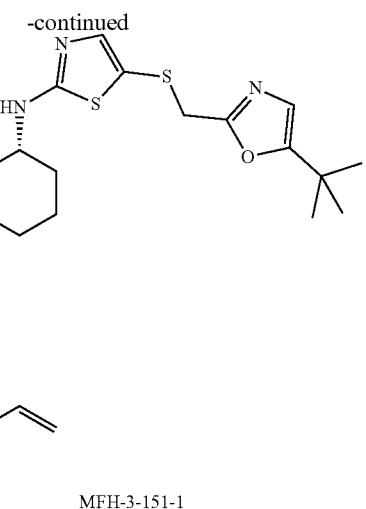

(R)-tert-butyl4-(3-(5-((5-tert-butyloxazol-2-yl)methylthio)thiazol-2-ylamino)piperidin-1-ylsulfonyl)phenylcarbamate (MFH-3-147-1)

The mixture of MFH-2-85-1 (60 mg, 0.17 mmol) and TEA (26 mg, 0.26 mmol) m DCM (1 ml) was cooled to 0° C. and then a solution of tert-butyl 4-(chlorosulfonyl)phenylcarbamate (50 mg, 0.17 mmol) in DCM (1 mL) was added. The reaction mixture was extracted with chloroform and iso-propanol (4:1). The organic phase was washed with brine (50 mL) and dried over Na₂SO₄. After removal of the solvent, the residue was purified by silica gel (MeOH/DCM=0-20%) to obtain MFH-3-147-1 (80 mg, yield 78%). LCMS (m/z): 608 [M+H]⁺.

(R)—N-(1-(4-aminophenylsulfonyl)piperidin-3-yl)-5-((5-tert-butyloxazol-2-yl)methylthio)thiazol-2-amine (MFH-3-148-1)

To a solution of MFH-3-147-1 (80 mg, 0.13 mmol) in methanol (3 mL) was added 4N HCl/dioxane (3 mL). The solution was then stirred for 3 h at room temperature and the solvent was removed under reduced pressure to provide a crude which was directly used m the next step. LCMS (m/z): 507 [M+H]⁺.

(R)—N-(4-(3-(5-((5-tert-butyloxazol-2-yl)methylthio)thiazol-2-ylamino)piperidin-1-ylsulfonyl)phenyl)acrylamide (MFH-3-151-1)

To a solution of MFH-3-148-1 (30 mg, 0.06 mmol) and DIPEA (0.2 mL) in CH₃CN (2 mL) was added acryloyl chloride (7 mg, 0.08 mmol) in DCM (0.2 mL) dropwise. The mixture was then stirred at 0° C. for 1 h. The solution was then concentrated under reduced pressure and the residue was purified by prep-HPLC (MeOH/H₂O, 0.05% TFA) to provide MFH-3-151-1 (8.5 mg, yield 25%). LCMS (m/z): 561 [M+H]+. ¹H NMR (500 MHz, DMSO) δ 10.56 (d, J=22.3 Hz, 1H), 8.00 (d, J=7.3 Hz, 1H), 7.93-7.89 (m, 1H), 7.87 (dd, J=11.3, 4.4 Hz, 1H), 7.83-7.75 (m, 1H), 7.72-7.68 (m, 1H), 6.98 (d, J=2.7 Hz, 1H), 6.75-6.70 (m, 1H), 6.51-6.42 (m, 1H), 6.32 (ddd, J=17.0, 3.9, 1.9 Hz, 1H), 5.83 (ddd, J=10.1, 6.1, 1.9 Hz, 1H), 3.96 (d, J=3.8 Hz, 2H), 3.43-3.34 (m, 1H), 3.25 (d, J=11.8 Hz, 1H), 3.07-2.93 (m, 1H), 2.86 (dd, J=12.6, 9.7 Hz, 1H), 2.32-2.22 (m, 1H), 1.77 (d, J=6.7

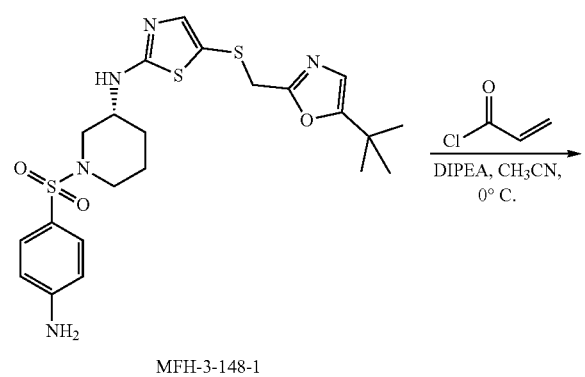

Hz, 1H), 1.67 (d, J=3.5 Hz, 1H), 1.52 (d, J=10.2 Hz, 1H), 1.34 (dd, J=18.1, 10.1 Hz, 1H), 1.24-1.16 (m, 9H).

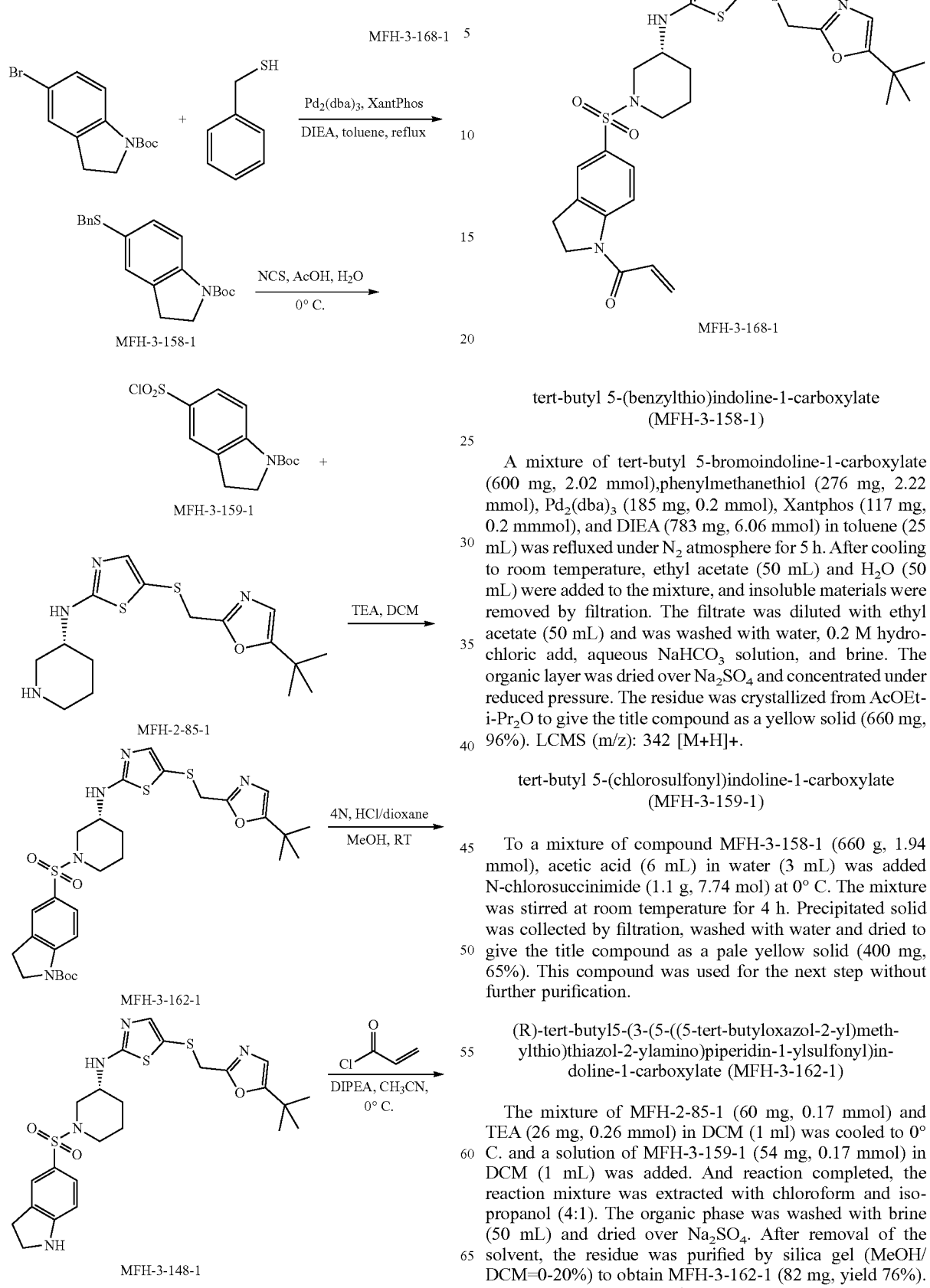

tert-butyl 5-(benzylthio)indoline-1-carboxylate (MFH-3-158-1)

A mixture of tert-butyl 5-bromoindoline-1-carboxylate (600 mg, 2.02 mmol), phenylmethanethiol (276 mg, 2.22 mmol), Pd$_2$(dba)$_3$ (185 mg, 0.2 mmol), Xantphos (117 mg, 0.2 mmmol), and DIEA (783 mg, 6.06 mmol) in toluene (25 mL) was refluxed under N$_2$ atmosphere for 5 h. After cooling to room temperature, ethyl acetate (50 mL) and H$_2$O (50 mL) were added to the mixture, and insoluble materials were removed by filtration. The filtrate was diluted with ethyl acetate (50 mL) and was washed with water, 0.2 M hydrochloric add, aqueous NaHCO$_3$ solution, and brine. The organic layer was dried over Na$_2$SO$_4$ and concentrated under reduced pressure. The residue was crystallized from AcOEt-i-Pr$_2$O to give the title compound as a yellow solid (660 mg, 96%). LCMS (m/z): 342 [M+H]+.

tert-butyl 5-(chlorosulfonyl)indoline-1-carboxylate (MFH-3-159-1)

To a mixture of compound MFH-3-158-1 (660 g, 1.94 mmol), acetic acid (6 mL) in water (3 mL) was added N-chlorosuccinimide (1.1 g, 7.74 mol) at 0° C. The mixture was stirred at room temperature for 4 h. Precipitated solid was collected by filtration, washed with water and dried to give the title compound as a pale yellow solid (400 mg, 65%). This compound was used for the next step without further purification.

(R)-tert-butyl5-(3-(5-((5-tert-butyloxazol-2-yl)methylthio)thiazol-2-ylamino)piperidin-1-ylsulfonyl)indoline-1-carboxylate (MFH-3-162-1)

The mixture of MFH-2-85-1 (60 mg, 0.17 mmol) and TEA (26 mg, 0.26 mmol) in DCM (1 ml) was cooled to 0° C. and a solution of MFH-3-159-1 (54 mg, 0.17 mmol) in DCM (1 mL) was added. And reaction completed, the reaction mixture was extracted with chloroform and isopropanol (4:1). The organic phase was washed with brine (50 mL) and dried over Na$_2$SO$_4$. After removal of the solvent, the residue was purified by silica gel (MeOH/DCM=0-20%) to obtain MFH-3-162-1 (82 mg, yield 76%). LCMS (m/z): 634 [M+H]$^+$.

(R)-5-((5-tert-butyloxazol-2-yl)methylthio)-N-(1-(indolin-5-ylsulfonyl)piperidm-3-yl)thiazol-2-amine (MFH-3-164-1)

To a solution of MFH-3-162-1 (82 mg, 0.13 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 534 [M+H]$^+$.

(R)-1-(5-(3-(5-((5-tert-butyloxazol-2-yl)methylthio)thiazol-2-ylamino)piperidin-1-ylsulfonyl)indolin-1-yl)prop-2-en-1-one (MFH-3-168-1)

To a solution of MFH-3-164-1 (20 mg, 0.04 mmol) and DIPEA (0.1 mL) in CH$_3$CN (2 mL) was added acryloyl chloride (5 mg, 0.05 mmol) in DCM (0.1 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-3-168-1 (5 mg, yield 23%). LCMS (m/z): 588 [M+H]+. $^1$H NMR (500 MHz, DMSO) δ 8.29 (s, 1H), 7.94 (d, J=7.4 Hz, 1H), 7.57 (dd, J=12.2, 3.8 Hz, 2H), 6.96 (s, 1H), 6.81-6.74 (m, 1H), 6.74 (s, 1H), 6.35 (dd, J=16.7, 2.0 Hz, 1H), 5.89 (dd, J=10.3, 2.0 Hz, 1H), 4.29 (t, J=8.7 Hz, 2H), 3.96 (s, 2H), 3.69 (s, 1H), 3.55 (d, J=8.0 Hz, 1H), 3.25 (t, J=8.4 Hz, 3H), 2.31-2.24 (m, 1H), 2.18 (t, J=7.4 Hz, 1H), 1.77 (d, J=6.6 Hz, 2H), 1.49 (dd, J=17.4, 10.0 Hz, 2H), 1.24 (s, 9H).

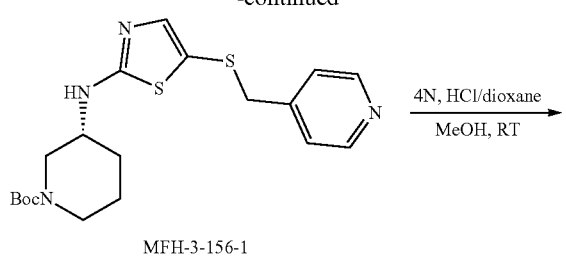

MFH-3-156-1

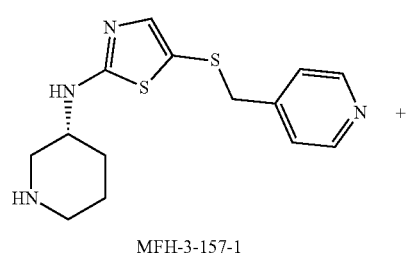

MFH-3-157-1

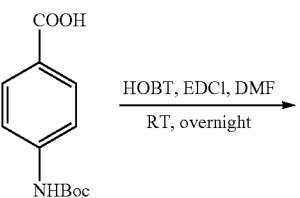

MFH-3-179-1

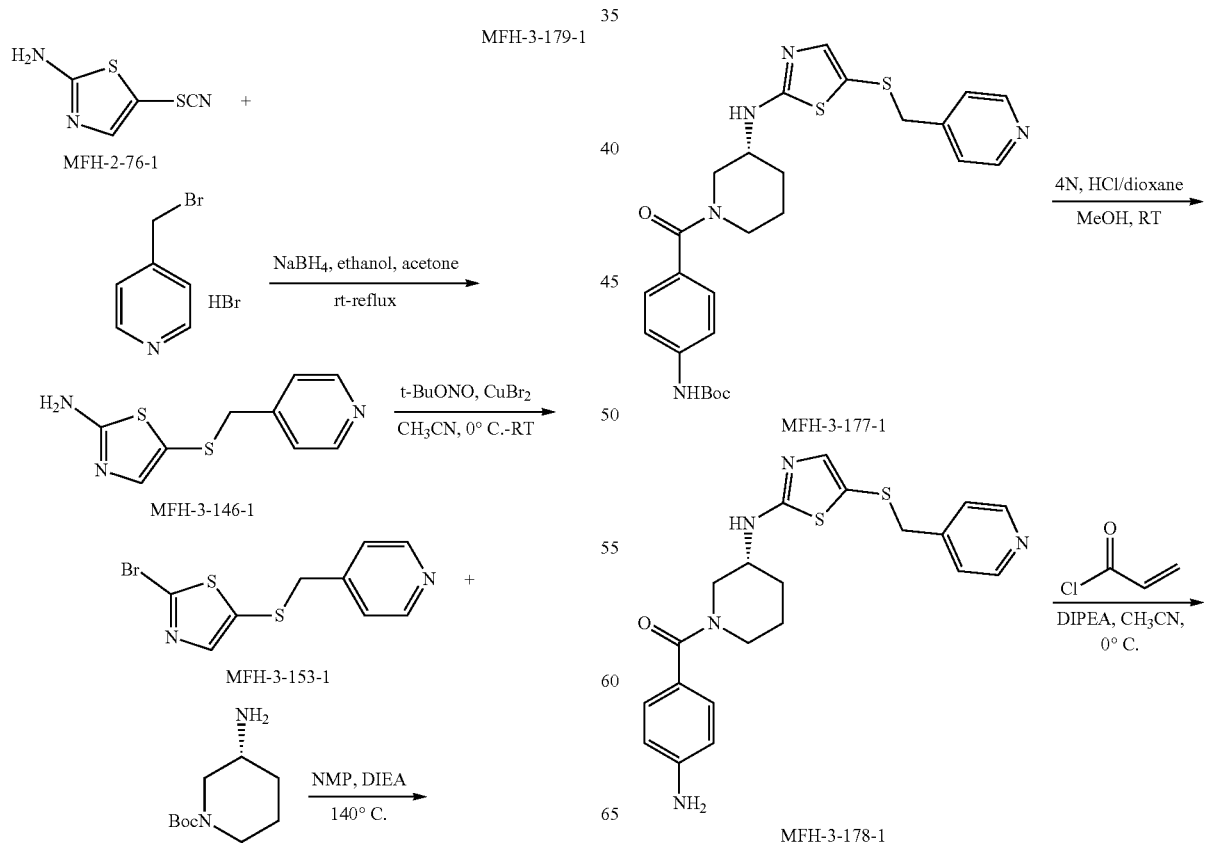

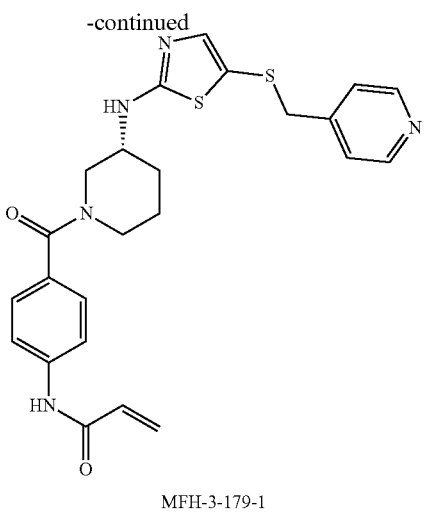

MFH-3-179-1

5-(pyridin-4-ylmethylthio)thiazol-2-amine (MFH-3-146-1)

To a solution of compound MFH-2-76-1 (300 mg, 1.91 mmol) in EtOH (5 ml) was added NaBH$_4$ (144 mg, 3.82 mmol) room temperature. The mixture was stirred for 1 h, and then acetone (3 ml) was slowly introduced. After 1 h, a solution of 4-(bromomethyl)pyridine hydrobromide (483 mg, 1.91 mmol) in EtOH (3 ml) was added. The resulting dark reaction mixture was heated to reflux for 1 h, and was then cooled and concentrated in vacuo. The residue was partitioned between EtOAc and brine. The organic phase was separated, dried. (MgSO$_4$), and concentrated in vacuo to give a crude solid which was triturated with diethyl ether/hexane to provide compound MFH-3-146-1 (240 mg, 56%) as solid LCMS (m/z): 224 [M+H]+.

2-bromo-5-(pyridin-4-ylmethylthio)thiazole (MFH-3-153-1)

To a solution of CuBr$_2$ (288 mg, 1.29 mmol) in acetonitrile (8 mL) at 0° C. was added t-BuONO (133 mg, 1.29 mmol) followed by compound MFH-3-146-1 (240 g, 1.08 mmol). The mixture was stirred at 0° C. for one hour, then at room temperature for one hour. Ethyl acetate was added and the organic mixture washed with hydrochloric acid (20 mL), dried over magnesium sulfate, filtered through a pad of silica gel, and concentrated in vacuo. The residue was chromatographed on silica gel to give the MFH-3-153-1 (130 mg, 42%). LCMS (m/z): 288 [M+H]+.

(R)-tert-butyl3-(5-(pyridin-4-ylmethylthio)thiazol-2-ylamino)piperidine-1-carboxylate (MFH-3-156-1)

The mixture of MFH-3-153-1 (130 mg, 0.45 mmol), (R)-tert-butyl 3-aminopiperidine-1-carboxylate (145 mg, 0.72 mmol) and DIEA (117 mg, 0.91 mmol) in NMP (1 mL) was stirred at 140° C. for overnight. The residue was extracted with chloroform and iso-propanol (4:1). The organic phase was washed with brine (20 mL) and dried over Na$_2$SO$_4$. After removal of the solvent, the residue was purified by silica gel (MeOH/DCM=0-20%) to obtain MFH-3-156-1 (90 mg, yield 49%). LCMS (m/z): 407 [M+H]+.

(R)—N-(piperidin-3-yl)-5-(pyridin-4-ylmethylthio)thiazol-2-amine (MFH-3-157-1)

To a solution of MFH-3-156-1 (90 mg, 0.22 mmol) in methanol (2 mL) was added 4N HCl/dioxane (2 mL). The solution was then stirred for 3 h at room temperature and the solvent was removed under reduced pressure to provide a crude which was directly used in the next step. LCMS (m/z): 307 [M+H]+.

(R)-tert-butyl4-(3-(5-(pyridin-4-ylmethylthio)thiazol-2-ylamino)piperidine-1-carbonyl)phenylcarbamate (MFH-3-177-1)

The mixture of MFH-3-157-1 (60 mg, 0.2 mmol), 4-(tert-butoxycarbonylamino)benzoic acid (15 mg, 0.08 mmol), HOBT (12 mg, 0.09 mmol) and EDCI (60 mg, 0.26 mmol) in DMF (1 ml) was stirred for overnight. The reaction mixture was diluted with chloroform and iso-propanol (4:1). The saturated Na$_2$CO$_3$ was added and the reaction mixture was extracted with chloroform and iso-propanol (4:1), concentrated under reduced pressure and the resulting residue was purified by silica gel column chromatography (MeOH/DCM=0-20%) to give MFH-3-177-1 (90 mg, yield 86%). LCMS (m/z): 526 [M+H]+.

(R)-(4-aminophenyl)(3-(5-(pyridin-4-ylmethylthio)thiazol-2-ylamino)piperidin-1-yl)methanone (MFH-3-178-1)

To a solution of MFH-3-177-1 (90 mg, 0.17 mmol) in methanol (2 mL) was added 4N HCl/dioxane (2 mL). The solution was then stirred for 3 h at room temperature and the solvent was removed under reduced pressure to provide a crude which was directly used in the next step. LCMS (m/z): 426 [M+H]+.

(R)—N-(4-(3-(5-(pyridin-4-ylmethylthio)thiazol-2-ylamino)piperidine-1-carbonyl)phenyl)acrylamide (MFH-3-179-1)

To a solution of MFH-3-178-1 (40 mg, 0.09 mmol) and DIPEA (0.2 mL) in CH$_3$CN (2 mL) was added acryloyl chloride (11 mg, 0.12 mmol) in DCM (0.1 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-3-179-1 (4.4 mg, yield 10%). LCMS (m/z): 480 [M+H]+. $^1$H NMR (500 MHz, DMSO) δ 10.30 (s, 1H), 8.06 (s, 1H), 7.85 (s, 2H), 7.68 (s, 2H), 7.36 (s, 2H), 7.25-7.02 (m, 2H), 6.80 (s, 1H), 6.49-6.37 (m, 1H), 6.27 (d, J=16.9 Hz, 1H), 5.77 (d, J=10.1 Hz, 1H), 4.12 (s, 1H), 3.99 (s, 2H), 3.43-3.31 (m, 2H), 3.14 (d, J=28.5 Hz, 2H), 1.95 (s, 1H), 1.76 (s, 1H), 1.55 (s, 2H).

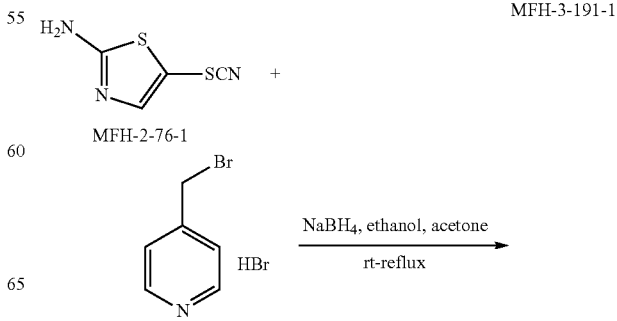

MFH-3-191-1

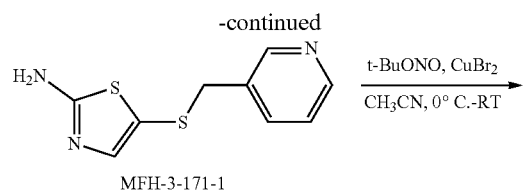

MFH-3-171-1

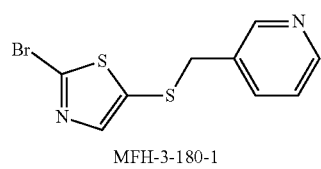

MFH-3-180-1

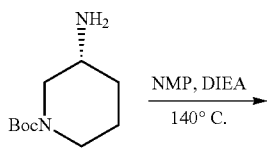

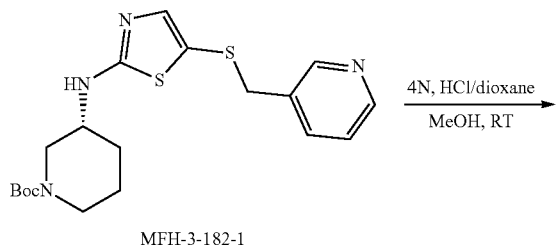

MFH-3-182-1

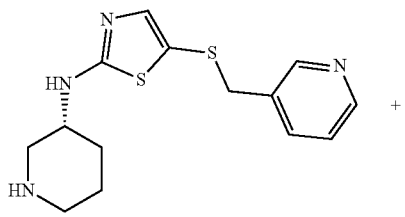

MFH-3-185-1

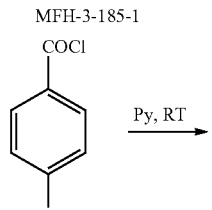

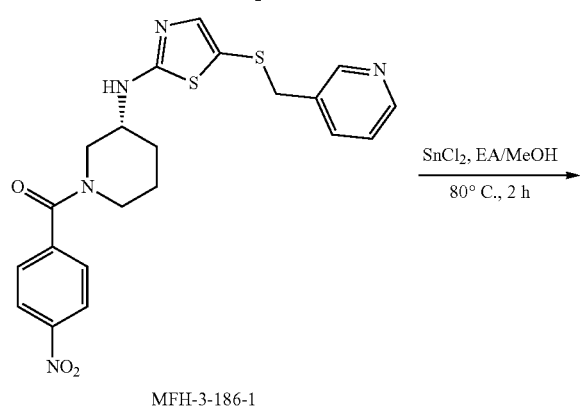

MFH-3-186-1

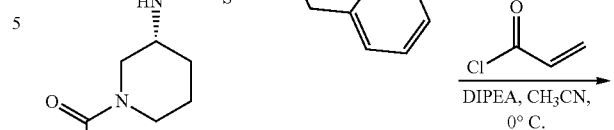

MFH-3-187-1

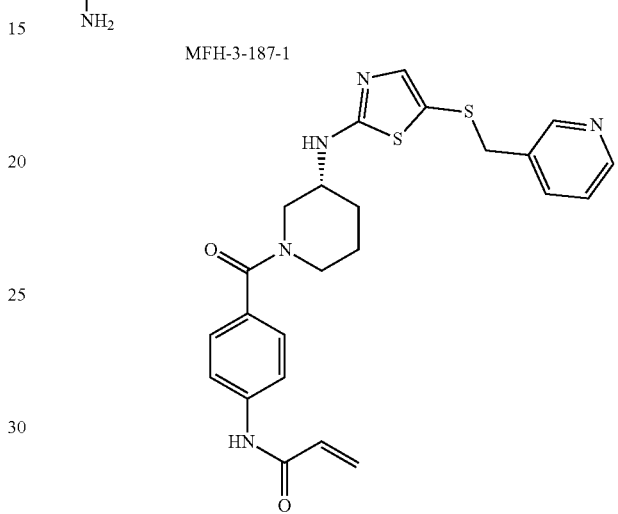

MFH-3-191-1

5-(pyridin-3-ylmethylthio)thiazol-2-amine (MFH-3-171-1)

To a solution of compound MFH-2-76-1 (300 mg, 1.91 mmol) in EtOH (5 ml) was added NaBH$_4$ (144 mg, 3.82 mmol) portionwise at room temperature. The mixture was stirred for 1 h, and then acetone (3 ml) was slowly introduced. After 1 h, a solution of 3-(bromomethyl)pyridine hydrobromide (483 mg, 1.91 mmol) in EtOH (3 mL) was added. The resulting dark reaction mixture was heated to reflux for 1 h, and was then cooled and concentrated in vacuo. The residue was partitioned between EtOAc and brine. The organic phase was separated, dried (MgSO$_4$), and concentrated in vacuo to give a crude solid which was triturated with diethyl ether/hexane to provide compound MFH-3-171-1 (310 mg, 73%) LCMS (m/z): 224 [M+H]+.

2-bromo-5-(pyridin-3-ylmethylthio)thiazole (MFH-3-180-1)

To a solution of CuBr$_2$ (370 mg, 1.66 mmol) in acetonitrile (20 mL) at 0° C. was added t-BuONO (172 mg, 1.66 mmol) followed by compound MFH-3-171-1 (310 mg, 1.39 mmol). The mixture was stirred at 0° C. for one hour, then at room temperature for one hour, ethyl acetate was added and the organic mixture washed with hydrochloric acid (2×50 mL), dried over magnesium sulfate, filtered through a pad of silica gel, and concentrated in vacuo. The residue was chromatographed on silica gel to give the MFH-3-180-1 (288 mg, 72%). LCMS (m/z): 288 [M+H]+.

(R)-tert-butyl3-(5-(pyridin-3-ylmethylthio)thiazol-2-ylamino)piperidine-1-carboxylate (MFH-3-182-1)

The mixture of MFH-3-180-1 (288 mg, 1 mmol), (R)-tert-butyl 3-aminopipendine-1-carboxylate (320 mg, 1.6 mmol) and DIEA (194 mg, 1.5 mmol) in NMP (1 mL) was stirred at 140° C. for overnight. The residue was extracted with chloroform and iso-propanol (4:1). The organic phase was washed with brine (20 mL) and dried over $Na_2SO_4$. After removal of the solvent, the residue was purified by silica gel (MeOH/DCM=0-20%) to obtain MFH-3-182-1 (180 mg, yield 44%). LCMS (m/z): 407 $[M+H]^+$.

(R)—N-(piperidin-3-yl)-5-(pyridin-3-ylmethylthio)thiazol-2-amine (MFH-3-185-1)

To a solution of MFH-3-182-1 (180 mg, 0.44 mmol) in methanol (3 mL) was added 4N HCl/dioxane (3 mL). The solution was then stirred for 3 h at room temperature and the solvent was removed under reduced pressure to provide a crude which was directly used m the next step. LCMS (m/z): 307 $[M+H]^+$.

(R)-(4-nitrophenyl)(3-(5-(pyridin-3-ylmethylthio)thiazol-2-ylamino)piperidin-1-yl)methanone (MFH-3-186-1)

The mixture of MFH-3-185-1 (120 mg, 0.39 mmol), 4-nitrobenzoyl chloride (72 mg, 0.39 mmol) in pyridine (2 mL) was stirred for overnight at room temperature. Then the reaction mixture was concentrated under reduced pressure and the residue was directly used in the next step. LCMS (m/z): 456 $[M+H]^+$.

(R)-(4-aminophenyl)(3-(5-(pyridin-3-ylmethylthio)thiazol-2-ylamino)piperidin-1-yl)methanone (MFH-3-187-1)

To a solution of MFH-3-186-1 (178 mg, 0.39 mmol) in ethyl acetate and methanol (1:1) were added Tin(II) chloride dehydrate (881 mg, 3.9 mmol) and conc. HCl (0.2 mL). After stirring for 3 h at 80° C., the reaction mixture was diluted with chloroform and iso-propanol (4:1), neutralized with saturated NaHCOs and filtered. The filtrate was extracted with chloroform and iso-propanol (4:1), concentrated under reduced pressure and the resulting residue was purified by silica gel column chromatography (MeOH/DCM=0-20%) to give MFH-3-187-1 (20 mg, yield 12%). LCMS (m/z): 426 [M+H]+.

(R)—N-(4-(3-(5-(pyridin-3-ylmethylthio)thiazol-2-ylamino)piperidine-1-carbonyl)phenyl)acrylamide (MFH-3-191-1)

To a solution of MFH-3-187-1 (20 mg, 0.05 mmol) and DIPEA (0.1 mL) in $CH_3CN$ (2 mL) was added acryloyl chloride (6 mg, 0.06 mmol) in DCM (0.5 mL) dropwise. The mixture was then stirred at 0° C. for 1 h. The solution was then concentrated under reduced pressure and the residue was purified by prep-HPLC (MeOH/$H_2O$, 0.05% TFA) to provide MFH-3-191-1 (6 mg, yield 26%). LCMS (m/z): 480 [M+H]+. $^1$H NMR (500 MHz, DMSO) δ 10.30 (s, 1H), 8.58 (d, J=53.1 Hz, 2H), 8.00 (d, J=44.0 Hz, 2H), 7.78-7.62 (m, 2H), 7.40 (d, J=29.7 Hz, 2H), 7.14 (dd, J=67.0, 35.1 Hz, 1H), 6.82 (s, 1H), 6.43 (dd, J=17.4, 10.0 Hz, 1H), 6.28 (t, J=12.8 Hz 1H) 5.84-5.74 (m, 1H), 4.04 (s, 1H), 3.98 (s, 2H), 3.31 (s, 2H), 3.17 (s, 2H), 1.96 (s, 1H), 1.75 (s, 1H), 1.54 (s, 2H).

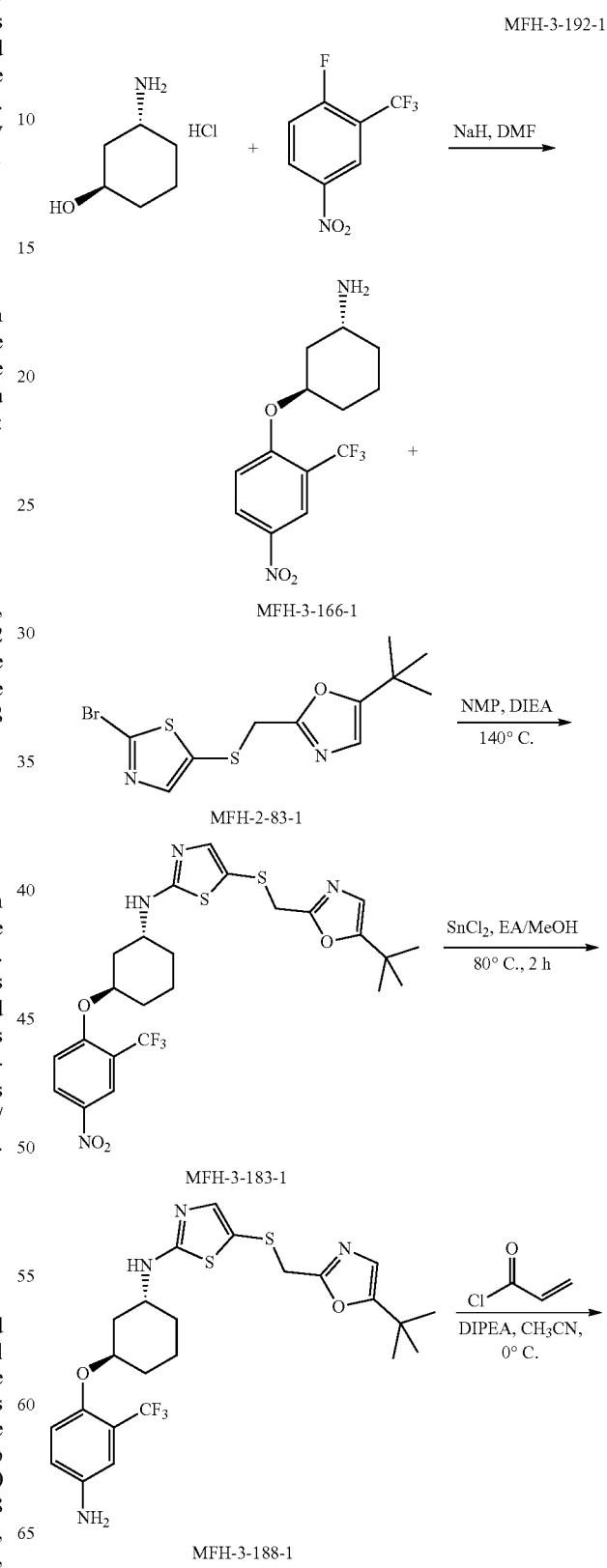

-continued

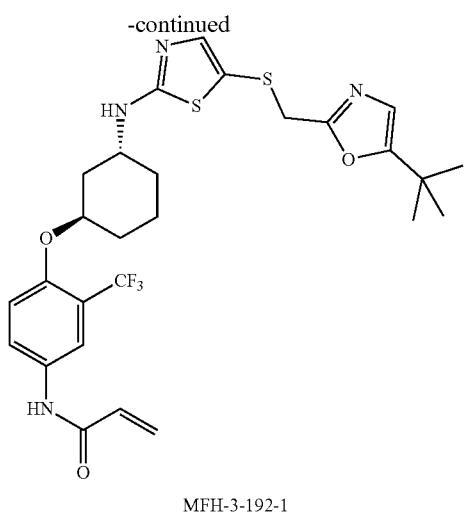

MFH-3-192-1

(1R,3R)-3-(4-nitro-2-(trifluoromethyl)phenoxy)cyclohexanamine (MFH-3-166-1)

To a solution of compound (1R,3R)-3-aminocyclohexanol hydrochloride (120 mg, 0.8 mmol) in absolute DMF (1 ml) was added NaH (130 mg, 3.3 mmol) portionwise at 0° C. The mixture was stirred for 1 h, and then 1-fluoro-4-nitro-2-(trifluoromethyl)benzene (170 mg, 0.8 mmol) was slowly introduced. After 3 h, the water was added slowly. The residue was extracted with chloroform and iso-propanol (4:1). The organic phase was washed with brine (20 mL×2) and dried over $Na_2SO_4$. After removal of the solvent, the residue was purified by silica gel (MeOH/DCM=0-20%) to obtain MFH-3-166-1 (50 mg, yield 20%). LCMS (m/z): 305 $[M+H]^+$.

5-((5-tert-butyloxazol-2-yl)methylthio)-N-((1R,3R)-3-(4-nitro-2-(trifluoromethyl)phenoxy)cyclohexyl)thiazol-2-amine (MFH-3-183-1)

The mixture of MFH-2-83-1 (55 mg, 0.16 mmol), MFH-3-166-1 (50 mg, 0.16 mmol) and DIEA (32 mg, 0.25 mmol) in NMP (0.5 mL) was stirred at 140° C. for overnight. The residue was extracted with chloroform and iso-propanol (4:1). The organic phase was washed with brine (20 mL×2) and dried over $Na_2SO_4$. After removal of the solvent, the residue was purified by silica gel (MeOH/DCM=0-20%) to obtain MFH-3-183-1 (28 mg, yield 31%). LCMS (m/z): 557 $[M+H]^+$.

N-((1R,3R)-3-(4-amino-2-(trifluoromethyl)phenoxy)cyclohexyl)-5-((5-tert-butyloxazol-2-yl)methylthio)thiazol-2-amine (MFH-3-188-1)

To a solution of MFH-3-183-1 (28 mg, 0.05 mmol) in ethyl acetate and methanol (1:1) were added Tin(II) chloride dehydrate (113 mg, 0.5 mmol) and conc. HCl (0.1 mL). After stirring for 3 h at 80° C., the reaction mixture was diluted with chloroform and iso-propanol (4:1), neutralized with saturated $NaHCO_3$ and filtered. The filtrate was extracted with chloroform and iso-propanol (4:1), concentrated under reduced pressure and the resulting residue was purified by silica gel column chromatography (MeOH/DCM=0-20%) to give MFH-3-188-1 (20 mg, yield 75%). LCMS (m/z): 527 [M+H]+.

N-(4-((1R,3R)-3-(5-((5-tert-butyloxazol-2-yl)methylthio)thiazol-2-ylamino)cyclohexyloxy)-3-(trifluoromethyl)phenyl)acrylamide (MFH-3-192-1)

To a solution of MFH-3-188-1 (20 mg, 0.04 mmol) and DIPEA (0.1 mL) in $CH_3CN$ (2 mL) was added acryloyl chloride (5 mg, 0.05 mmol) in DCM (0.1 mL) dropwise. The mixture was then stirred at 0° C. for 1 h. The solution was then concentrated under reduced pressure and the residue was purified by prep-HPLC (MeOH/$H_2O$, 0.05% TFA) to provide MFH-3-192-1 (5.4 mg, yield 24%). LCMS (m/z): 581 [M+H]+. $^1$H NMR (500 MHz, DMSO) δ 10.27 (s, 1H), 8.04 (t, J=5.4 Hz, 2H), 7.82 (dd, J=9.0, 2.5 Hz, 1H), 7.25 (t, J=8.1 Hz, 1H), 6.95 (d, J=5.6 Hz, 1H), 6.70 (d, J=7.3 Hz, 1H), 6.39 (dd, J=17.0, 10.1 Hz, 1H), 6.26 (dd, J=17.0, 2.0 Hz, 1H), 5.77 (dd, J=10.1, 2.0 Hz, 1H), 4.92 (s, 1H), 3.93 (d, J=0.8 Hz, 2H), 2.10 (d, J=14.5 Hz, 1H), 1.93 (d, J=14.3 Hz, 1H), 1.79 (s, 1H), 1.65 (dd, J=22.7, 11.5 Hz, 2H), 1.59 (s, 2H), 1.32 (m, 1H), 1.23 (dd, J=11.2, 6.2 Hz, 1H), 1.17 (s, 9H).

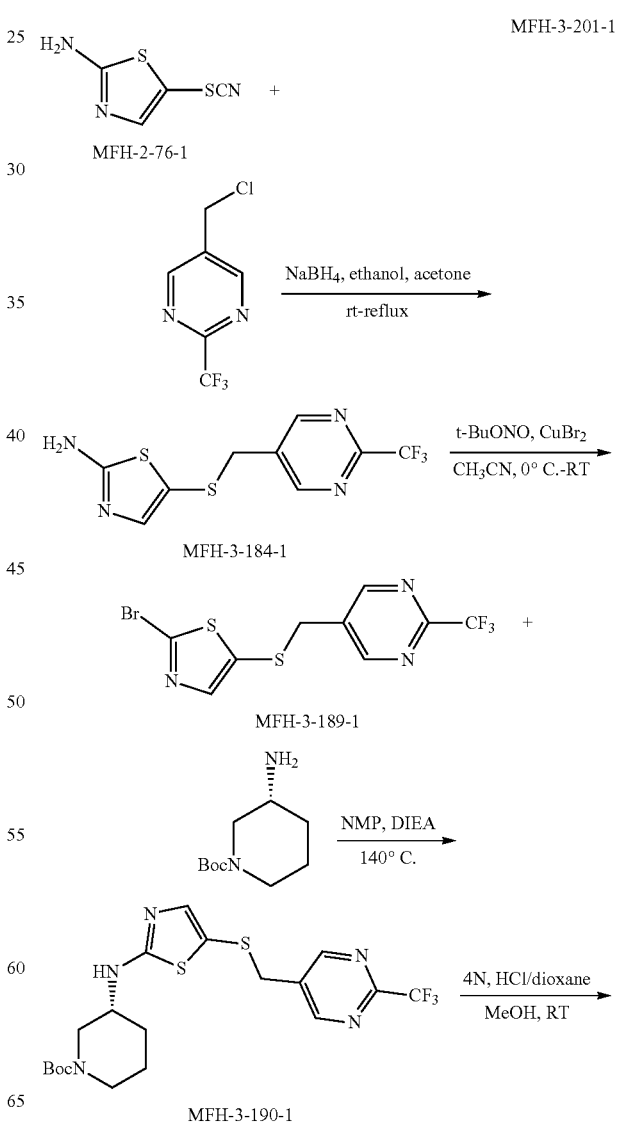

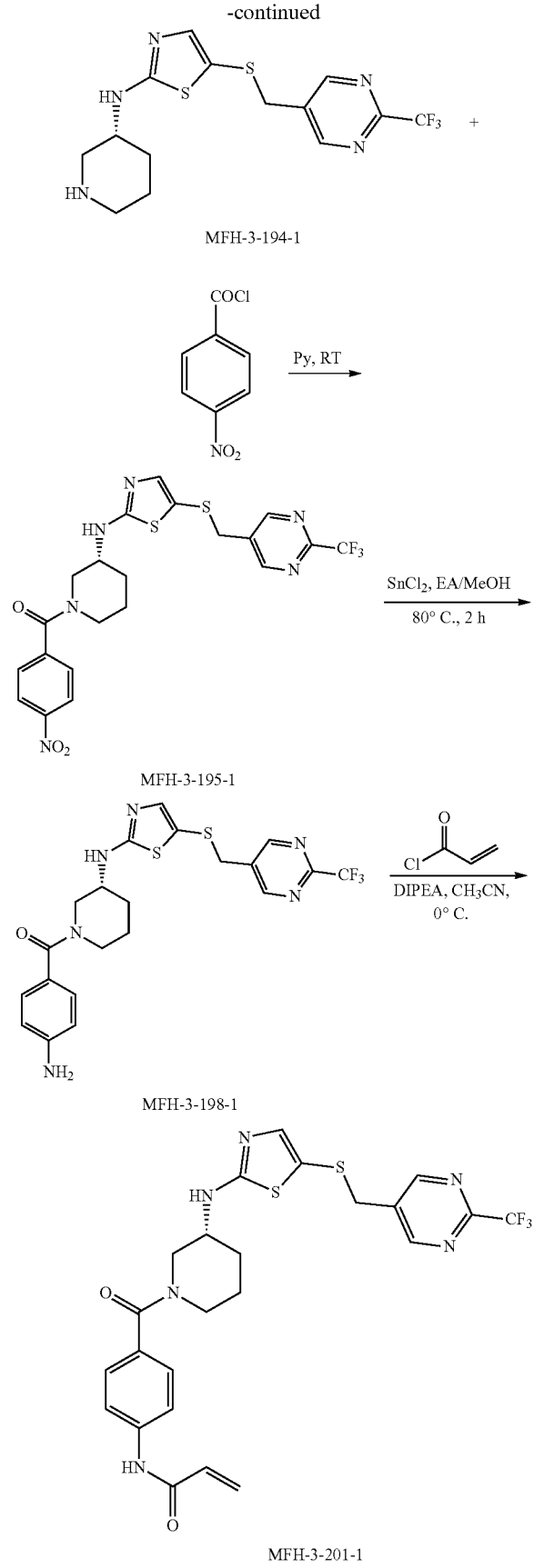

5-((2-(trifluoromethyl)pyrimidin-5-yl)methylthio)thiazol-2-amine (MFH-3-184-1)

To a solution of compound MFH-2-76-1 (300 mg, 1.91 mmol) in absolute EtOH (5 ml) was added NaBH$_4$ (144 mg, 3.82 mmol) at room temperature. The mixture was stirred for 1 h, and then acetone (3 ml) was slowly introduced. After 1 h, a solution of 5-(chloromethyl)-2-(trifluoromethyl)pyrimidine (375 mg, 1.91 mmol) in EtOH (3 ml) was added. The resulting dark reaction mixture was heated to reflux for 1 h, and was then cooled and concentrated in vacuo. The residue was partitioned between EtOAc and brine. The organic phase was separated, dried (MgSO$_4$), and concentrated in vacuo to give a crude solid which was triturated with diethyl ether/hexane to provide compound MFH-3-184-1 (500 mg, 90%) LCMS (m/z): 293 [M+H]+.

2-bromo-5-((2-(trifluoromethyl)pyrimidin-5-yl)methylthio)thiazole (MFH-3-189-1)

To a solution of CuBr$_2$ (458 mg, 2.05 mmol) in acetonitrile (15 mL) at 0° C. was added t-BuONO (211 mg, 2.05 mmol) followed by compound MFH-3-184-1 (500 mg, 1.71 mmol). The mixture was stirred at 0° C. for one hour, then at room temperature for one hour. Ethyl acetate was added and the organic mixture was washed with hydrochloric acid (50 mL), dried over magnesium sulfate, filtered through a pad of silica gel, and concentrated in vacuo. The residue was chromatographed on silica gel to give the MFH-3-189-1 (430 mg, 70%). LCMS (m/z): 357 [M+H]+.

(R)-tert-butyl3-(5-((2-(trifluoromethyl)pyrimidin-5-yl)methylthio)thiazol-2-ylamino)piperidine-1-carboxylate (MFH-3-190-1)

The mixture of MFH-3-189-1 (430 mg, 1.21 mmol), (R)-tert-butyl 3-aminopiperidine-1-carboxylate (362 mg, 1.81 mmol) and DIEA (312 mg, 2.4 mmol) in NMP (1 mL) was stirred at 140° C. for overnight. The residue was extracted with chloroform and iso-propanol (4:1). The organic phase was washed with brine (20 mL) and dried over Na$_2$SO$_4$. After removal of the solvent, the residue was purified by silica gel (MeOH/DCM=0-20%) to obtain MFH-3-190-1 (380 mg, yield 66%). LCMS (m/z): 476 [M+H]$^+$.

(R)—N-(piperidin-3-yl)-5-((2-(trifluoromethyl)pyrimidin-5-yl)methylthio)thiazol-2-amine (MFH-3-194-1)

To a solution of MFH-3-190-1 (380 mg, 0.8 mmol) in methanol (5 mL) was added 4N HCl/dioxane (5 mL). The solution was then stirred for 3 h at room temperature and the solvent was removed under reduced pressure to provide a crude which was directly used in the next step. LCMS (m/z): 376 [M+H]$^+$.

(R)-(4-nitrophenyl)(3-(5-((2-(trifluoromethyl)pyrimidin-5-yl)methylthio)thiazol-2-ylamino)piperidin-1-yl)methanone (MFH-3-195-1)

The mixture of MFH-3-194-1 (230 mg, 0.61 mmol), 4-nitrobenzoyl chloride (113 mg, 0.61 mmol) in pyridine (2 mL) was stirred for overnight at room temperature. Then the reaction mixture was concentrated under reduced pressure and the residue was directly used in the next step. LCMS (m/z): 525 [M+H]$^+$.

(R)-(4-aminophenyl)(3-(5-((2-(trifluoromethyl)pyrimidin-5-yl)methylthio)thiazol-2-ylamino)piperidin-1-yl)methanone (MFH-3-198-1)

To a solution of MFH-3-195-1 (280 mg, 0.53 mmol) in ethyl acetate and methanol (1:1) were added Tin(II) chloride dehydrate (965 mg, 4.27 mmol) and conc. HCl (0.2 mL). After stirring for 3 h at 80° C., the reaction mixture was diluted with chloroform and iso-propanol (4:1), neutralized with saturated NaHCO$_3$ and filtered. The filtrate was extracted with chloroform and iso-propanol (4:1), concentrated under reduced pressure and the resulting residue was purified by silica gel column chromatography (MeOH/DCM=0-20%) to give MFH-3-198-1 (200 mg, yield 76%). LCMS (m/z): 495 [M+H]+.

(R)—N-(4-(3-(5-((2-(trifluoromethyl)pyrimidin-5-yl)methylthio)thiazol-2-ylamino)piperidine-1-carbonyl)phenyl)acrylamide (MFH-3-201-1)

To a solution of MFH-3-198-1 (40 mg, 0.08 mmol) and DIPEA (0.1 mL) in CH$_3$CN (2 mL) was added acryloyl chloride (10 mg, 0.1 mmol) in DCM (0.2 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-3-201-1 (9.8 mg, yield 22%). LCMS (m/z): 549 [M+H]+. $^1$H NMR (500 MHz, DMSO) δ 10.26 (s, 1H), 8.81 (s, 2H), 8.11 (s, 1H), 7.79-7.59 (m, 2H), 7.38 (t, J=13.1 Hz, 2H), 6.99-6.73 (m, 1H), 6.50-6.35 (m, 1H), 6.34-6.17 (m, 1H), 5.80 (m, 1H), 4.01 (s, 2H), 3.81-3.73 (m, 3H), 3.45-3.20 (m, 2H), 1.94 (d, J=18.7 Hz, 1H), 1.78 (m, 1H), 1.54 (s, 2H).

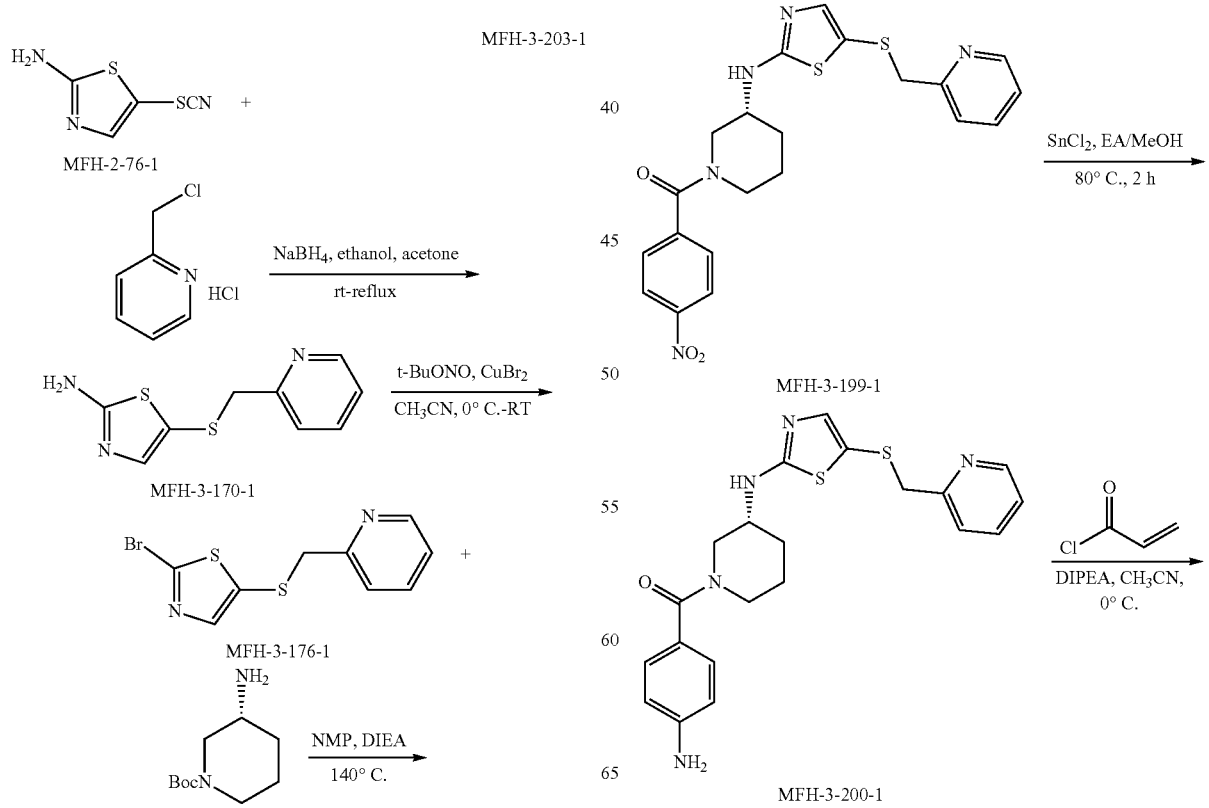

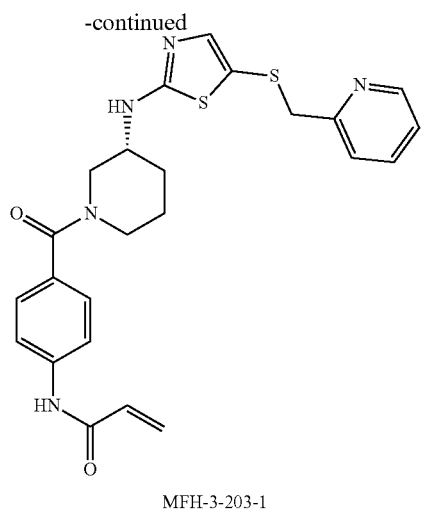

MFH-3-203-1

5-(pyridin-2-ylmethylthio)thiazol-2-amine (MFH-3-170-1)

To a solution of compound MFH-2-76-1 (300 mg, 1.91 mmol) in absolute EtOH (5 ml) was added NaBH$_4$ (144 mg, 3.82 mmol) portionwise at room temperature. The mixture was stirred for 1 h, and then acetone (3 ml) was slowly introduced. After 1 h, a solution of 2-(chloromethyl)pyridine hydrochloride (313 mg, 1.91 mmol) in EtOH (3 ml) was added. The resulting dark reaction mixture was heated to reflux for 1 h, and was then cooled and concentrated in vacuo. The residue was partitioned between EtOAc and brine. The organic phase was separated, dried (MgSO$_4$), and concentrated in vacuo to give a crude solid which was triturated with diethyl ether/hexane to provide compound MFH-3-170-1 (260 mg, 61%) LCMS (m/z): 224 [M+H]+.

2-bromo-5-(pyridin-2-ylmethylthio)thiazole (MFH-3-176-1)

To a solution of CuBr$_2$ (313 mg, 1.4 mmol) in acetonitrile (20 mL) at 0° C. was added t-BuONO (144 mg, 1.4 mmol) followed by compound MFH-3-170-1 (260 mg, 1.16 mmol). The mixture was stirred at 0° C. for one hour, then at room temperature for one hour. Ethyl acetate was added and the organic mixture washed with hydrochloric acid (2×50 mL), dried over magnesium sulfate, filtered through a pad of silica gel, and concentrated in vacuo. The residue was chromatographed on silica gel to give the MFH-3-176-1 (90 mg, 27%). LCMS (m/z): 288 [M+H]+.

(R)-tert-butyl 3-(5-(pyridin-2-ylmethylthio)thiazol-2-ylamino)piperidine-1-carboxylate (MFH-3-196-1)

The mixture of MFH-3-176-1 (180 mg, 0.63 mmol), (R)-tert-butyl 3-aminopiperidine-1-carboxylate (200 mg, 1 mmol) and DIEA (162 mg, 1.3 mmol) in NMP (1 mL) was stirred at 140° C. for overnight. The residue was extracted with chloroform and iso-propanol (4:1). The organic phase was washed with brine (20 mL) and dried over Na$_2$SO$_4$. After removal of the solvent, the residue was purified by silica gel (MeOH/DCM=0-20%) to obtain MFH-3-196-1 (120 mg, yield 47%). LCMS (m/z): 407 [M+H]+.

(R)—N-(piperidin-3-yl)-5-(pyridin-2-ylmethylthio)thiazol-2-amine (MFH-3-197-1)

To a solution of MFH-3-196-1 (120 mg, 0.3 mmol) in methanol (3 mL) was added 4N HCl/dioxane (3 mL). The solution was then stirred for 3 h at room temperature and the solvent was removed under reduced pressure to provide a crude which was directly used m the next step. LCMS (m/z): 307 [M+H]+.

(R)-(4-nitrophenyl)(3-(5-(pyridin-2-ylmethylthio)thiazol-2-ylamino)piperidin-1-yl)methanone (MFH-3-199-1)

The mixture of MFH-3-197-1 (80 mg, 0.26 mmol), 4-nitrobenzoyl chloride (48 mg, 0.26 mmol) in pyridine (2 mL) was stirred for overnight at room temperature. Then the reaction mixture was concentrated under reduced pressure and the residue was directly used in the next step. LCMS (m/z): 456 [M+H]+.

(R)-(4-aminophenyl)(3-(5-(pyridin-2-ylmethylthio)thiazol-2-ylamino)piperidin-1-yl)methanone (MFH-3-200-1)

To a solution of MFH-3-199-1 (118 mg, 0.261 mmol) in ethyl acetate and methanol (1:1) were added Tin(II) chloride dehydrate (472 mg, 2.1 mmol) and conc. HCl (0.2 mL). After stirring for 3 h at 80° C., the reaction mixture was diluted with chloroform and iso-propanol (4:1), neutralized with saturated NaHCO$_3$ and filtered. The filtrate was extracted with chloroform and iso-propanol (4:1), concentrated under reduced pressure and the resulting residue was purified by silica gel column chromatography (MeOH/DCM=0-20%) to give MFH-3-200-1 (60 mg, yield 54%). LCMS (m/z): 426 [M+H]+.

(R)—N-(4-(3-(5-(pyridin-3-ylmethylthio)thiazol-2-ylamino)piperidine-1-carbonyl)phenyl)acrylamide (MFH-3-191-1)

To a solution of MFH-3-187-1 (40 mg, 0.1 mmol) and DIPEA (0.1 mL) in CH$_3$CN (2 mL) was added acryloyl chloride (12 mg, 0.12 mmol) in DCM (0.2 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-3-203-1 (8.4 mg, yield 19%). LCMS (m/z): 480 [M+H]+. $^1$H NMR (500 MHz, DMSO) δ 10.30 (s, 1H), 8.62 (s, 1H), 8.06 (d, J=50.5 Hz, 2H), 7.72 (d, J=21.6 Hz, 2H), 7.51 (s, 2H), 7.37 (s, 2H), 6.86 (s, 1H), 6.44 (dd, J=17.1, 10.2 Hz, 1H), 6.27 (d, J=16.9 Hz, 1H), 5.85-5.74 (m, 1H). 4.04 (s, 1H), 3.98 (s, 2H), 3.31 (s, 2H), 3.17 (s, 2H), 1.96 (s, 1H), 1.75 (s, 1H), 1.54 (s, 2H).

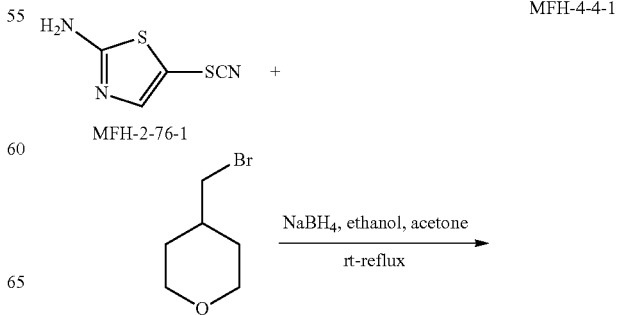

MFH-4-4-1

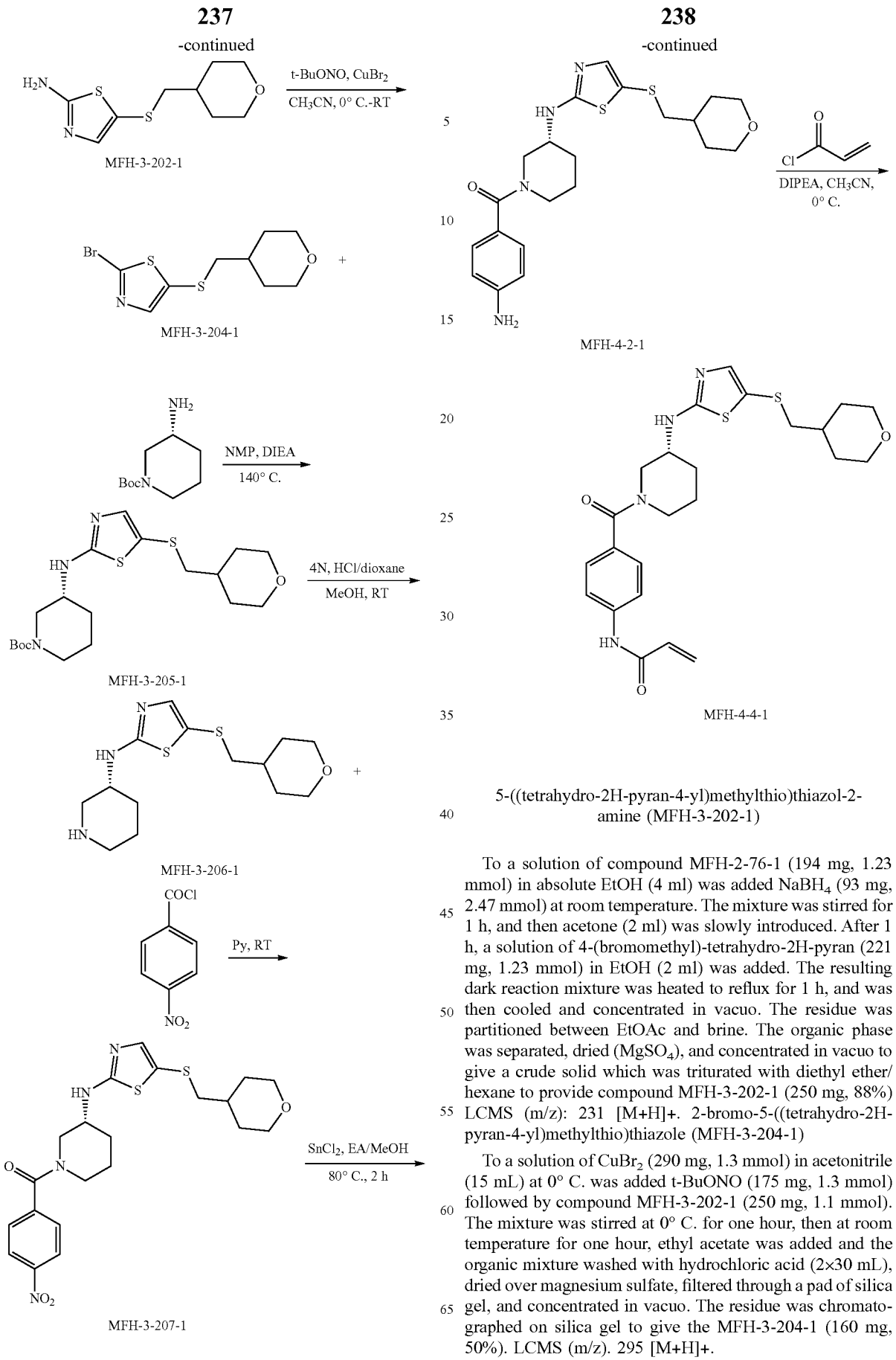

5-((tetrahydro-2H-pyran-4-yl)methylthio)thiazol-2-amine (MFH-3-202-1)

To a solution of compound MFH-2-76-1 (194 mg, 1.23 mmol) in absolute EtOH (4 ml) was added NaBH₄ (93 mg, 2.47 mmol) at room temperature. The mixture was stirred for 1 h, and then acetone (2 ml) was slowly introduced. After 1 h, a solution of 4-(bromomethyl)-tetrahydro-2H-pyran (221 mg, 1.23 mmol) in EtOH (2 ml) was added. The resulting dark reaction mixture was heated to reflux for 1 h, and was then cooled and concentrated in vacuo. The residue was partitioned between EtOAc and brine. The organic phase was separated, dried (MgSO₄), and concentrated in vacuo to give a crude solid which was triturated with diethyl ether/hexane to provide compound MFH-3-202-1 (250 mg, 88%) LCMS (m/z): 231 [M+H]+. 2-bromo-5-((tetrahydro-2H-pyran-4-yl)methylthio)thiazole (MFH-3-204-1)

To a solution of CuBr₂ (290 mg, 1.3 mmol) in acetonitrile (15 mL) at 0° C. was added t-BuONO (175 mg, 1.3 mmol) followed by compound MFH-3-202-1 (250 mg, 1.1 mmol). The mixture was stirred at 0° C. for one hour, then at room temperature for one hour, ethyl acetate was added and the organic mixture washed with hydrochloric acid (2×30 mL), dried over magnesium sulfate, filtered through a pad of silica gel, and concentrated in vacuo. The residue was chromatographed on silica gel to give the MFH-3-204-1 (160 mg, 50%). LCMS (m/z). 295 [M+H]+.

(R)-tert-butyl 3-(5-((tetrahydro-2H-pyran-4-yl)methylthio)thiazol-2-ylamino)piperidine-1-carboxylate (MFH-3-205-1)

The mixture of MFH-3-204-1 (160 mg, 0.54 mmol), (R)-tert-butyl 3-aminopiperidine-1-carboxylate (174 mg, 0.87 mmol) and DIEA (112 mg, 0.87 mmol) in NMP (0.5 mL) was stirred at 140° C. for overnight. The residue was extracted with chloroform and iso-propanol (4:1). The organic phase was washed with brine (20 mL×2) and dried over Na$_2$SO$_4$. After removal of the solvent, the residue was purified by silica gel (MeOH/DCM=0-20%) to obtain MFH-3-205-1 (120 mg, yield 53%). LCMS (m/z): 414 [M+H]$^+$.

(R)—N-(piperidin-3-yl)-5-((tetrahydro-2H-pyran-4-yl)methylthio)thiazol-2-amine (MFH-3-206-1)

To a solution of MFH-3-205-1 (120 mg, 0.3 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 314 [M+H]$^+$.

(R)-(4-nitrophenyl)(3-(5-((tetrahydro-2H-pyran-4-yl)methylthio)thiazol-2-ylamino)piperidin-1-yl)methanone (MFH-3-207-1)

The mixture of MFH-3-206-1 (80 mg, 0.26 mmol), 4-nitrobenzoyl chloride (48 mg, 0.26 mmol) in pyridine (2 mL) was stirred for overnight at room temperature. Then the reaction mixture was concentrated under reduced pressure and the residue was directly used in the next step. LCMS (m/z): 463 [M+H]$^+$.

(R)-(4-aminophenyl)(3-(5-((tetrahydro-2H-pyran-4-yl)methylthio)thiazol-2-ylamino)piperidin-1-yl)methanone (MFH-4-2-1)

To a solution of MFH-3-207-1 (120 mg, 0.26 mmol) in ethyl acetate and methanol (1:1) were added Tin(II) chloride dehydrate (472 mg, 2.1 mmol) and conc. HCl (0.2 mL). After stirring for 3 h at 80° C., the reaction mixture was diluted with chloroform and iso-propanol (4:1), neutralized with saturated NaHCO$_3$ and filtered. The filtrate was extracted with chloroform and iso-propanol (4:1), concentrated under reduced pressure and the resulting residue was purified by silica gel column chromatography (MeOH/DCM=0-20%) to give MFH-4-2-1 (60 mg, yield 54%). LCMS (m/z): 433 [M+H]+.

(R)—N-(4-(3-(5-((tetrahydro-2H-pyran-4-yl)methylthio)thiazol-2-ylamino)piperidine-1-carbonyl)phenyl)acrylamide (MFH-4-4-1)

To a solution of MFH-4-2-1 (30 mg, 0.07 mmol) and DIPEA (0.1 mL) in CH$_3$CN (2 mL) was added acryloyl chloride (8 mg, 0.09 mmol) in DCM (0.1 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-4-4-1 (4.6 mg, yield 13%). LCMS (m/z): 487 [M+H]+. $^1$H NMR (500 MHz, DMSO) δ 10.32 (d, J=28.3 Hz, 1H), 8.07 (s, 1H), 7.77-7.62 (m, 2H), 7.40 (dd, J=32.0, 7.9 Hz, 2H), 7.15-6.93 (m, 1H), 6.45 (dd, J=17.0, 10.1 Hz, 1H), 6.28 (dd, J=17.0, 1.9 Hz, 1H), 5.79 (dd, J=10.1, 1.9 Hz, 1H), 3.83 (d, J=9.4 Hz, 2H), 3.62 (s, 4H), 3.24 (t, J=11.1 Hz, 2H), 3.11 (s, 1H), 2.58 (d, J=6.4 Hz, 1H), 1.98 (d, J=12.6 Hz, 1H), 1.77 (s, 1H), 1.70 (d, J=11.6 Hz, 2H), 1.57 (m, 3H), 1.21 (m, 3H).

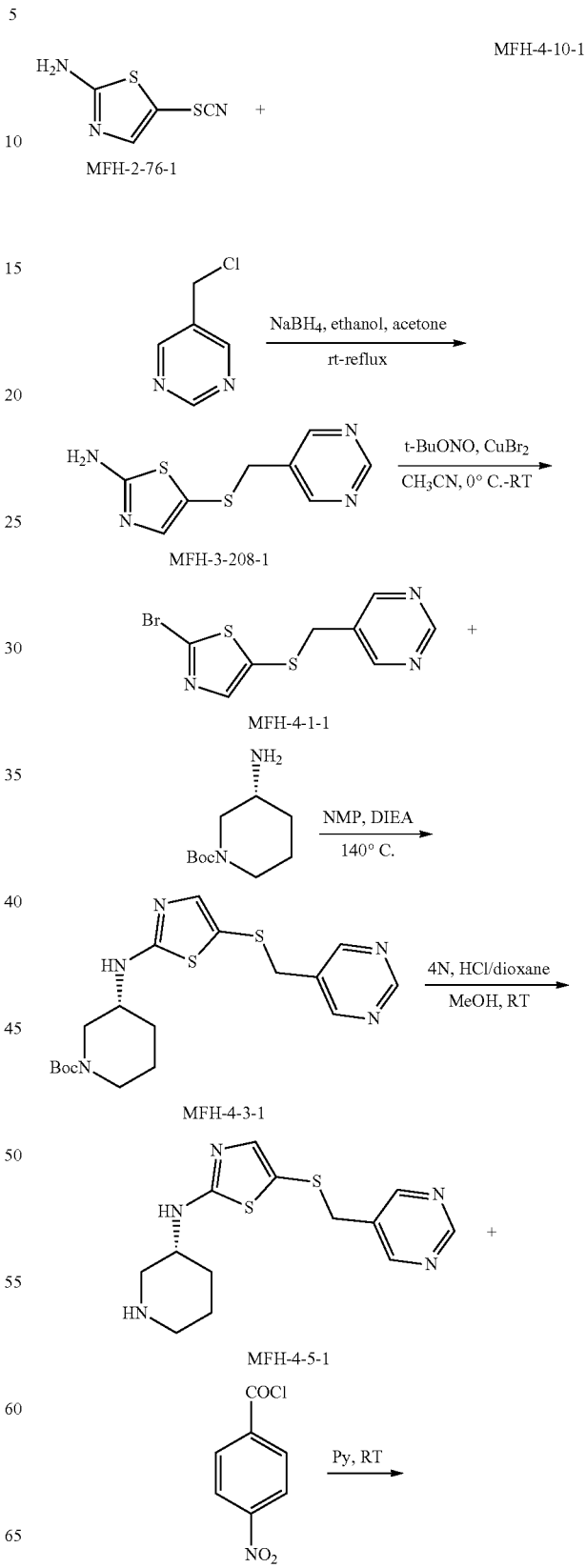

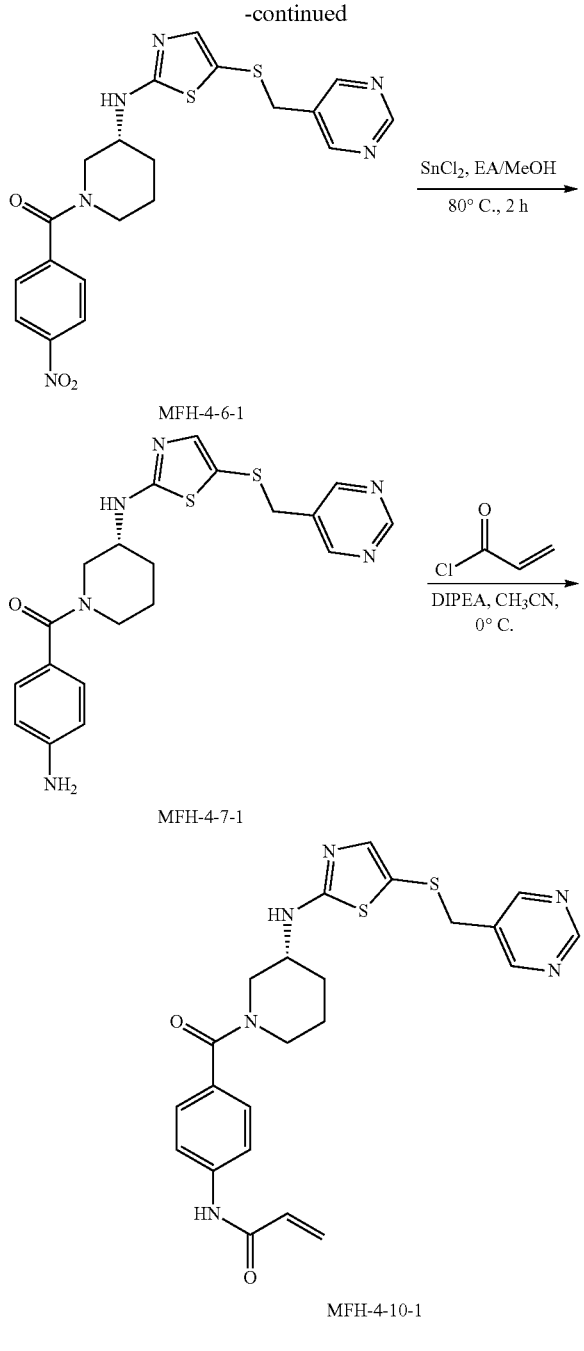

5-(pyrimidin-5-ylmethylthio)thiazol-2-amine (MFH-3-208-1)

To a solution of compound MFH-2-76-1 (230 mg, 1.46 mmol) in absolute EtOH (5 ml) was added NaBH$_4$ (166 mg, 4.38 mmol) at room temperature. The mixture was stirred for 1 h, and then acetone (3 ml) was slowly introduced. After 1 h, a solution of 5-(chloromethyl)pyrimidine (241 mg, 1.46 mmol) in EtOH (3 ml) was added. The resulting dark reaction mixture was heated to reflux for 1 h, and was then cooled and concentrated in vacuo. The residue was partitioned between EtOAc and brine. The organic phase was separated, dried (MgSO$_4$), and concentrated in vacuo to give a crude solid which was triturated with diethyl ether/hexane to provide compound MFH-3-208-1 (180 mg, 55%) LCMS (m/z): 225 [M+H]+.

2-bromo-5-(pyrimidin-5-ylmethylthio)thiazole (MFH-4-1-1)

To a solution of CuBr$_2$ (215 mg, 0.96 mmol) in acetonitrile (15 mL) at 0° C. was added t-BuONO (99 mg, 0.96 mmol) followed by compound MFH-3-208-1 (180 mg, 0.8 mmol). The mixture was stirred at 0° C. for one hour, then at room temperature for one hour, ethyl acetate was added and the organic mixture washed with hydrochloric acid (2×50 mL), dried over magnesium sulfate, filtered through a pad of silica gel, and concentrated in vacuo. The residue was chromatographed on silica gel to give the MFH-4-1-1 (90 mg, 39%). LCMS (m/z): 289 [M+H]+.

(R)-tert-butyl3-(5-(pyrimidin-5-ylmethylthio)thiazol-2-ylamino)piperidine-1-carboxylate (MFH-4-3-1)

The mixture of MFH-4-1-1 (90 mg, 0.31 mmol), (R)-tert-butyl 3-aminopiperidine-1-carboxylate (100 mg, 0.5 mmol) and DIEA (65 mg, 0.5 mmol) in NMP (1 mL) was stirred at 140° C. for overnight. The residue was extracted with chloroform and iso-propanol (4:1). The organic phase was washed with brine (20 mL×2) and dried over Na$_2$SO$_4$. After removal of the solvent, the residue was purified by silica gel (MeOH/DCM=0-20%) to obtain MFH-4-3-1 (66 mg, yield 52%). LCMS (m/z): 408 [M+H]$^+$.

(R)—N-(piperidin-3-yl)-5-(pyrimidin-5-ylmethylthio)thiazol-2-amine (MFH-4-5-1)

To a solution of MFH-4-3-1 (66 mg, 0.16 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 308 [M+H]$^+$.

(R)-(4-nitrophenyl)(3-(5-(pyrimidin-5-ylmethylthio)thiazol-2-ylamino)piperidin-1-yl)methanone (MFH-4-6-1)

The mixture of MFH-4-5-1 (50 mg, 0.16 mmol), 4-nitrobenzoyl chloride (30 mg, 0.16 mmol) in pyridine (2 mL) was stirred for overnight at room temperature. Then the reaction mixture was concentrated under reduced pressure and the residue was directly used in the next step. LCMS (m/z): 457 [M+H]$^+$.

(R)-(4-aminophenyl)(3-(5-(pyrimidin-5-ylmethylthio)thiazol-2-ylamino)piperidin-1-yl)methanone (MFH-4-7-1)

To a solution of MFH-4-6-1 (74 mg, 0.16 mmol) in ethyl acetate and methanol (1:1) were added Tin(II) chloride dehydrate (292 mg, 1.3 mmol) and conc. HCl (0.1 mL). After stirring for 3 h at 80° C., the reaction mixture was diluted with chloroform and iso-propanol (4:1), neutralized with saturated NaHCO$_3$ and filtered. The filtrate was extracted with chloroform and iso-propanol (4:1), concentrated under reduced pressure and the resulting residue was purified by silica gel column chromatography (MeOH/DCM=0-20%) to give MFH-4-7-1 (15 mg, yield 22%). LCMS (m/z): 427 [M+H]+.

(R)—N-(4-(3-(5-(pyrimidin-5-ylmethylthio)thiazol-2-ylamino)piperidine-1-carbonyl)phenyl)acrylamide (MFH-4-10-1)

To a solution of MFH-4-7-1 (15 mg, 0.04 mmol) and DIPEA (0.1 mL) in CH$_3$CN (2 mL) was added acryloyl chloride (4 mg, 0.05 mmol) in DCM (0.1 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-4-10-1 (2.2 mg, yield 13%). LCMS (m/z): 481 [M+H]+. $^1$H NMR (500 MHz, DMSO) δ 10.26 (s, 1H), 9.07 (s, 1H) 8.81 (s, 2H), 8.11 (s, 1H), 7.79-7.59 (m, 2H), 7.38 (t, J=13.1 Hz, 2H), 6.99-6.73 (m, 1H), 6.50-6.35 (m, 1H), 6.34-6.17 (m, 1H), 5.80 (ddd, J=23.3, 10.0, 2.6 Hz, 1H), 4.01 (s, 2H), 3.81-3.73 (m, 3H), 3.45-3.20 (m, 2H), 1.94 (d, J=18.7 Hz, 1H), 1.78 (m, 1H), 1.54 (s, 2H).

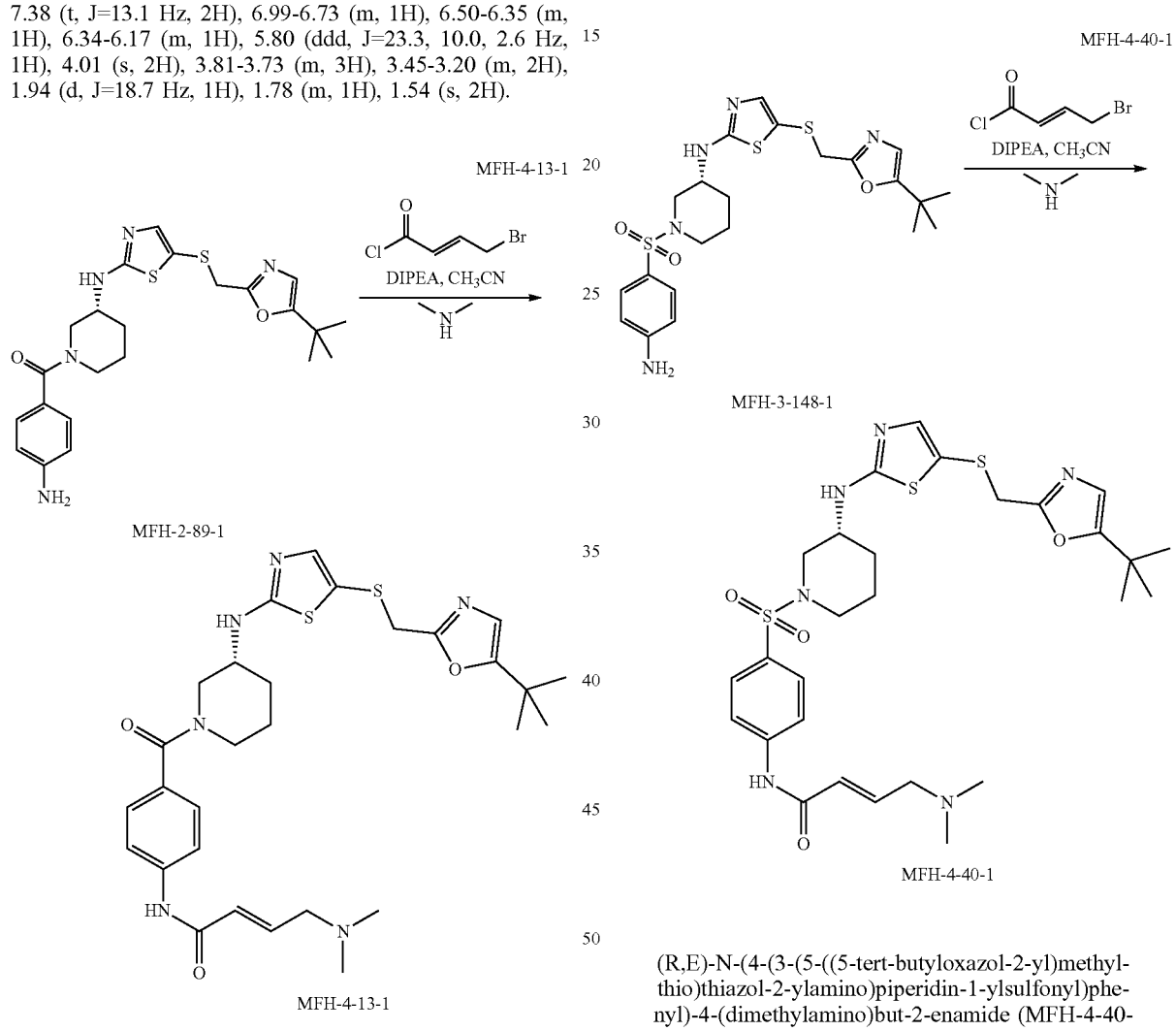

(R,E)-N-(4-(3-(5-((5-tert-butyloxazol-2-yl)methylthio)thiazol-2-ylamino)piperidine-1-carbonyl)phenyl)-4-(dimethylamino)but-2-enamide (MFH-4-13-1)

To a solution of (E)-4-bromobut-2-enoic acid (17 mg, 0.1 mmol) in SOCl$_2$ (0.2 mL). The mixture was stirred at 70° C. for 1 h under N$_2$ atmosphere. The mixture was cooled to room temperature and then was concentrated under reduced pressure. The residue was diluted with dichloromethane and the resulted solution was added dropwise to a solution of MFH-2-20-1 (37 mg, 0.08 mmol) and DIPEA (0.2 mL) in CH$_3$CN (2 mL) at 0° C. After stirring for 1 h at 0° C., a solution of dimethylamine in THF (2 mol/L, 0.1 ml, 0.2 mmol) was added and the reaction mixture was stirred at room temperature for 1 h. The removal of the solvent under reduced pressure provided the residue which was purified by HPLC (MeOH/H$_2$O, 0.05% TFA) to obtain MFH-4-13-1 (18 mg, yield 39%). LCMS (m/z): 583 [M+H]$^+$; $^1$H NMR (500 MHz, DMSO) δ 10.18 (s, 1H), 7.96 (s, 1H), 7.66 (s, 2H), 7.34 (d, J=6.9 Hz, 2H), 6.84 (s, 1H), 6.80-6.65 (m, 2H), 6.27 (d, J=15.4 Hz, 1H), 3.94 (s, 2H), 3.79 (s, 1H), 3.65 (s, 2H), 3.14 (m, 2H), 3.06 (d, J=5.8, 2H), 2.18 (s, 6H), 1.95 (s, 1H), 1.75 (s, 1H), 1.51 (d, J=9.0 Hz, 2H), 1.17 (s, 9H).

(R,E)-N-(4-(3-(5-((5-tert-butyloxazol-2-yl)methylthio)thiazol-2-ylamino)piperidin-1-ylsulfonyl)phenyl)-4-(dimethylamino)but-2-enamide (MFH-4-40-1)

To a solution of (E)-4-bromobut-2-enoic acid (12 mg, 0.07 mmol) in SOCl$_2$ (0.2 mL). The mixture was stirred at 70° C. for 1 h under N$_2$ atmosphere. The mixture was cooled to room temperature and then was concentrated under reduced pressure. The residue was diluted with dichloromethane and the resulted solution was added dropwise to a solution of MFH-4-40-1 (25 mg, 0.05 mmol) and DIPEA (0.2 mL) in CH$_3$CN (2 mL) at 0° C. After stirring for 1 h at 0° C., a solution of dimethylamine in THF (2 mol/L, 0.05 ml, 0.1 mmol) was added and the reaction mixture was stirred at room temperature for 1 h. The removal of the solvent under reduced pressure provided the residue which was purified by HPLC (MeOH/H₂O, 0.05% TFA) to obtain MFH-4-40-1 (20 mg, yield 66%). LCMS (m/z): 619 [M+H]⁺; ¹H NMR (500 MHz, DMSO) δ 10.76 (s, 1H), 7.98 (d, J=7.2 Hz, 1H), 7.90 (dd, J=6.5, 4.7 Hz, 2H), 7.70 (dd, J=6.6, 4.8 Hz, 2H), 6.97 (d, J=2.7 Hz, 1H), 6.83-6.75 (m, 1H), 6.72 (d, J=8.8 Hz, 1H), 6.48 (d, J=15.3 Hz, 1H), 3.96 (s, 2H), 3.71 (s, 2H), 3.53 (d, J=9.9 Hz, 2H), 3.24 (d, J=11.2 Hz, 1H), 3.17 (s, 2H), 2.81 (s, 6H), 2.34-2.22 (m, 1H), 1.84-1.70 (m, 2H), 1.52 (dd, J=10.1, 4.0 Hz, 1H), 1.22 (s, 9H).

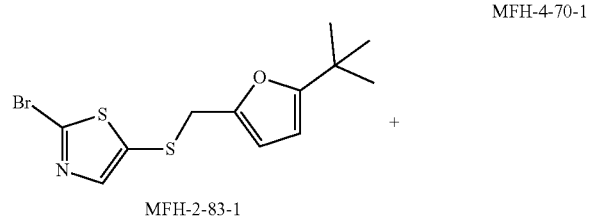

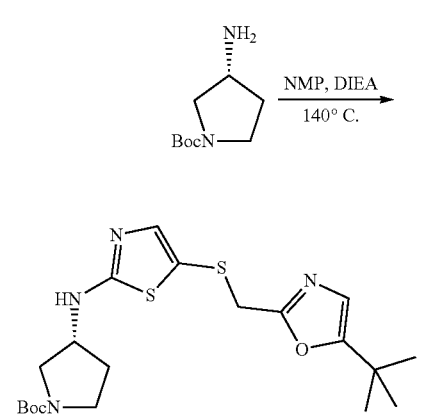

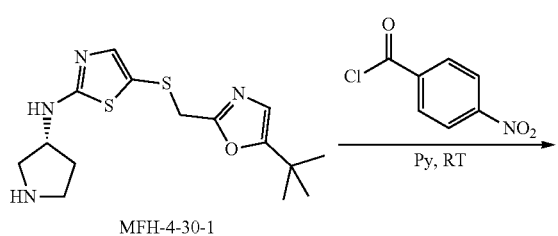

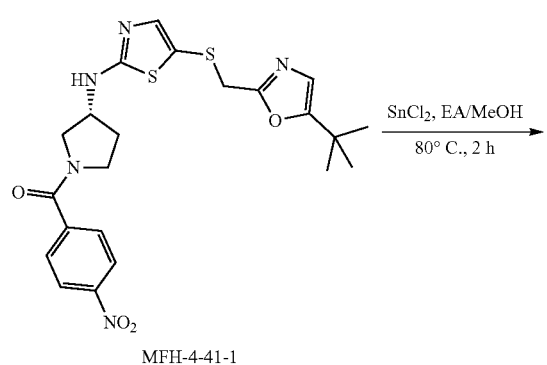

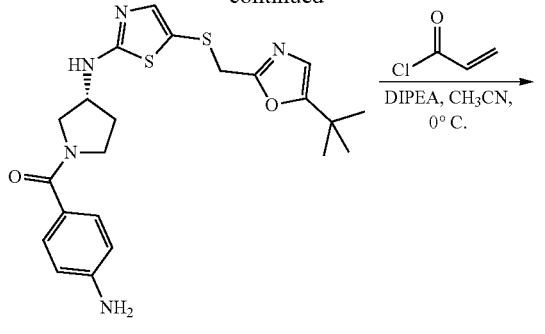

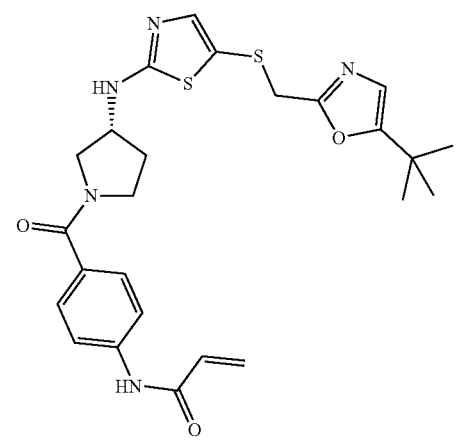

(R)-tert-butyl 3-(5-(((5-tert-butyloxazol-2-yl)methyl-thio)thiazol-2-ylamino)pyrrolidine-1-carboxylate (MFH-4-30-1)

The mixture of MFH-2-83-1 (150 mg, 0.45 mmol), (R)-tert-butyl 3-aminopyrrolidine-1-carboxylate (134 mg, 0.72 mmol) and DIEA (116 mg, 0.9 mmol) in NMP (1 mL) was stirred at 140° C. for overnight. The residue was extracted with chloroform and iso-propanol (4:1). The organic phase was washed with brine (30 mL×2) and dried over Na₂SO₄. After removal of the solvent, the residue was purified by silica gel (MeOH/DCM=0-20%) to obtain MFH-4-30-1 (110 mg, yield 56%). LCMS (m/z): 439 [M+H]⁺.

(R)-5-((5-tert-butyloxazol-2-yl)methylthio)-N-(pyrrolidin-3-yl)thiazol-2-amine (MFH-4-39-1)

To a solution of MFH-4-30-1 (110 mg, 0.25 mmol) in methanol (3 mL) was added 4N HCl/dioxane (3 mL). The solution was then stirred for 3 h at room temperature and the solvent was removed under reduced pressure to provide a crude which was directly used in the next step. LCMS (m/z): 339 [M+H]⁺.

(R)-(3-(5-((5-tert-butyloxazol-2-yl)methylthio)thiazol-2-ylamino)pyrrolidin-1-yl)(4-nitrophenyl)methanone (MFH-4-41-1)

The mixture of MFH-4-39-1 (80 mg, 0.24 mmol), 4-nitrobenzoyl chloride (53 mg, 0.28 mmol) in pyridine (2 mL) was stirred for overnight at room temperature. Then the reaction mixture was concentrated under reduced pressure and the residue was directly used in the next step. LCMS (m/z): 488 [M+H]$^+$.

(R)-(4-aminophenyl)(3-(5-((5-tert-butyloxazol-2-yl)methylthio)thiazol-2-ylamino)pyrrolidin-1-yl)methanone (MFH-4-44-1)

To a solution of MFH-4-41-1 (117 mg, 0.24 mmol) in ethyl acetate and methanol (1:1) were added Tin(II) chloride dehydrate (427 mg, 1.9 mmol) and conc. HCl (0.1 mL). After stirring for 3 h at 80° C., the reaction mixture was diluted with chloroform and iso-propanol (4:1), neutralized with saturated NaHCO$_3$ and filtered. The filtrate was extracted with chloroform and iso-propanol (4:1), concentrated under reduced pressure and the resulting residue was purified by silica gel column chromatography (MeOH/DCM=0-20%) to give MFH-4-44-1 (90 mg, yield 83%). LCMS (m/z): 458 [M+H]+.

(R)—N-(4-(3-(5-((5-tert-butyloxazol-2-yl)methylthio)thiazol-2-ylamino)pyrrolidine-1-carbonyl)phenyl)acrylamide (MFH-4-70-1)

To a solution of MFH-4-44-1 (22 mg, 0.05 mmol) and DIPEA (0.2 mL) in CH$_3$CN (2 mL) was added acryloyl chloride (5 mg, 0.06 mmol) in DCM (0.1 mL) dropwise. The mixture was then stirred at 0° C. for 1 h. The solution was then concentrated under reduced pressure and the residue was purified by prep-HPLC (MeOH/H$_2$O, 0.05% TFA) to provide MFH-4-70-1 (13.4 mg, yield 54%). LCMS (m/z): 512 [M+H]+. $^1$H NMR (500 MHz, DMSO) δ 10.33 (s, 1H), 8.38-8.21 (m, 1H), 7.73 (d, J=8.3 Hz, 2H), 7.52 (t, J=8.6 Hz, 2H), 7.04-6.85 (m, 1H), 6.77-6.65 (m, 1H), 6.45 (dd, J=17.0, 10.1 Hz, 1H), 6.29 (d, J=16.9 Hz, 1H), 5.84-5.75 (m, 1H), 3.96 (d, J=24.0 Hz, 2H), 3.82-3.72 (m, 1H), 3.57 (ddd, J=25.0, 12.1, 7.0 Hz, 3H), 3.33 (d, J=7.5 Hz, 1H), 2.15 (dt, J=30.0, 14.1 Hz, 1H), 1.92 (m, 1H), 1.23-1.12 (m, 9H).

-continued

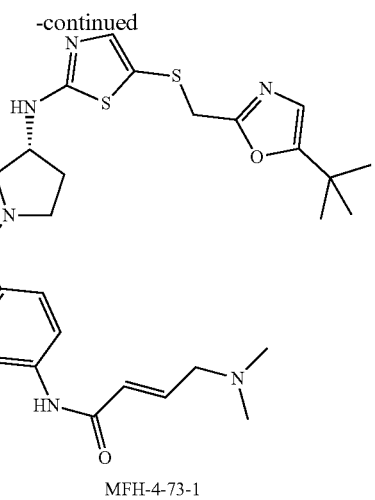

MFH-4-73-1

(R,E)-N-(4-(3-(5-((5-tert-butyloxazol-2-yl)methylthio)thiazol-2-ylamino)pyrrolidine-1-carbonyl)phenyl)-4-(dimethylamino)but-2-enamide (MFH-4-73-1)

To a solution of (E)-4-bromobut-2-enoic acid (15 mg, 0.09 mmol) in SOCl$_2$ (0.2 mL). The mixture was stirred at 70° C. for 1 h under N$_2$ atmosphere. The mixture was cooled to room temperature and then was concentrated under reduced pressure. The residue was diluted with dichloromethane and the resulted solution was added dropwise to a solution of MFH-4-40-1 (30 mg, 0.07 mmol) and DIPEA (0.2 mL) in CH$_3$CN (2 mL) at 0° C. After stirring for 1 h at 0° C., a solution of dimethylamine in THF (2 mol/L, 0.1 ml, 0.2 mmol) was added and the reaction mixture was stirred at room temperature for 1 h. The removal of the solvent under reduced pressure provided the residue which was purified by HPLC (MeOH/H$_2$O, 0.05% TFA) to obtain MFH-4-73-1 (23 mg, yield 61%). LCMS (m/z): 569 [M+H]$^+$; $^1$H NMR (500 MHz, DMSO) δ 10.52 (s, 1H), 8.30-8.19 (m, 1H), 7.73 (d, J=8.3 Hz, 2H), 7.53 (t, J=8.4 Hz, 2H), 7.03-6.85 (m, 1H), 6.78 (dd, J=15.1, 7.4 Hz, 1H), 6.75-6.65 (m, 1H), 6.48 (d, J=15.3 Hz, 1H), 3.97 (s, 2H), 3.93 (s, 2H), 3.81-3.71 (m, 1H), 3.65-3.42 (m, 3H), 3.32 (dd, J=10.0, 2.5 Hz, 1H), 2.81 (d, J=2.5 Hz, 6H), 2.21-2.10 (m, 1H), 1.99-1.85 (m, 1H), 1.23-1.12 (m, 9H).

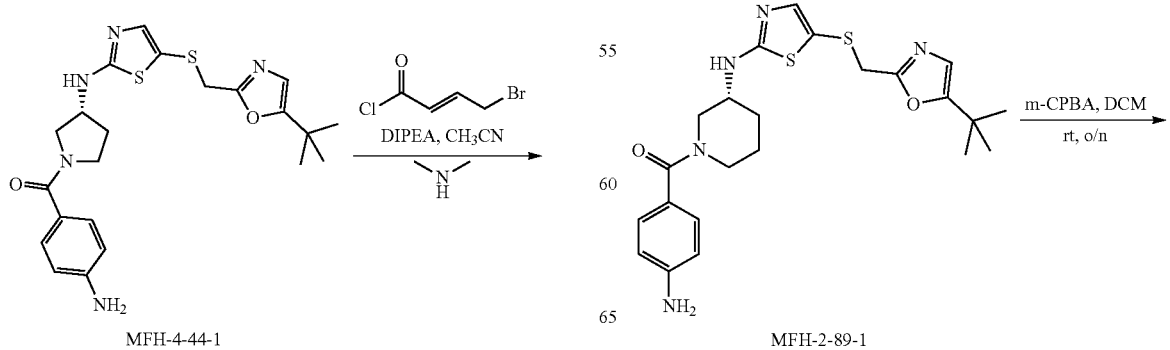

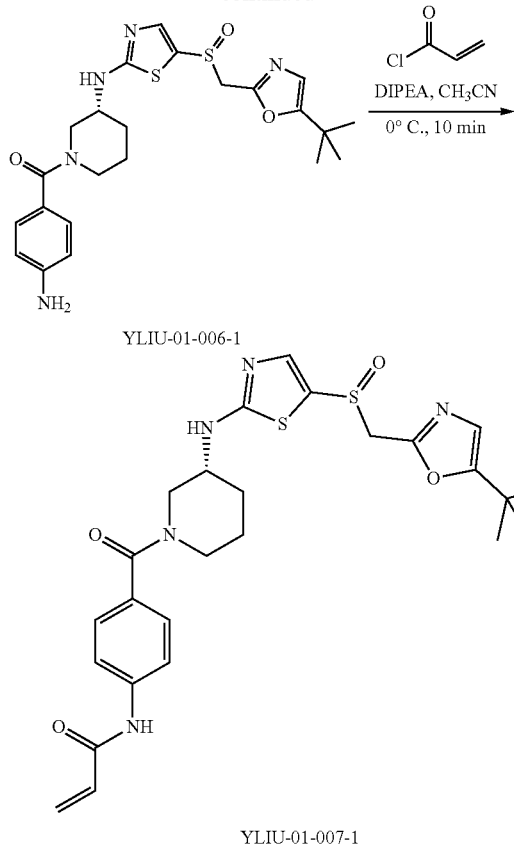

YLIU-01-006-1

YLIU-01-007-1

(4-aminophenyl)((3R)-3-((5-(((5-(tert-butyl)oxazol-2-yl)methyl)sulfinyl)thiazol-2-yl)amino)piperidin-1-yl)methanone (YLIU-01-006-1)

To a solution of MFH-2-89-1 (30 mg, 0.064 mmol) in DCM (2 mL) was added m-CPBA (12 mg, 0.07 mmol), the reaction mixture was stirred at rt overnight. Then diluted with DCM, washed with NaHCO$_3$ aq.(sat.), concentrated and purified with silica gel column (eluted with MeOH in DCM 0% to 15%) to give the title compound (20 mg, 64%) as a brown oil. LCMS (m/z): 488 [M+H]+.

N-(4-((3R)-3-((5-(((5-(tert-butyl)oxazol-2-yl)methyl)sulfinyl)thiazol-2-yl)amino)piperidine-1-carbonyl)phenyl)acrylamide (YLIU-01-007-1)

To a solution of YLIU-01-006-1 (20 mg, 0.04 mmol) in MeCN (2 mL) was added DIPEA (25 mg, 0.2 mmol). At 0° C., acryloyl chloride (4 mg, 0.044 mmol) was added dropwise. Monitored with LCMS, when the reaction was completed, Na$_2$CO$_3$ aq.(sat.) was added, the resulting mixture was extracted with DCM/i-PrOH (4/1) (20 mL). The combined organic layer was concentrated and purified with Prep-HPLC (MeOH/H$_2$O, 0.05% TFA) to give the title compound (8 mg, 36.9%) as white solid. LCMS (m/z): 542 [M+H]+.
1H NMR (500 MHz, DMSO) δ 10.18 (s, 1H), 8.45 (s, 1H), 7.71-7.48 (m, 2H), 7.39-7.10 (m, 3H), 6.68 (s, 1H), 6.42-6.24 (m, 1H), 6.23-6.06 (m, 1H), 5.77-5.57 (m, 1H), 4.62-4.44 (m, 2H), 4.42-4.20 (m, 2H), 3.56 (m, 3H), 2.02-1.68 (m, 2H), 1.57-1.32 (m, 2H), 0.99 (s, 9H).

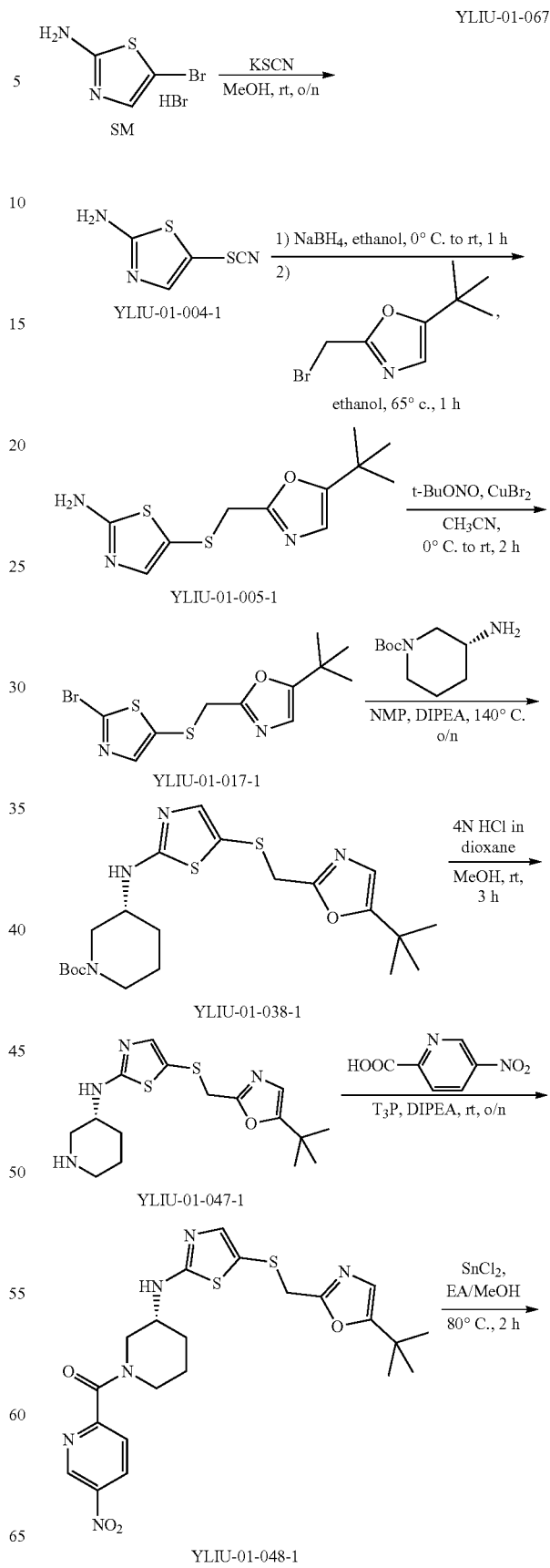

-continued

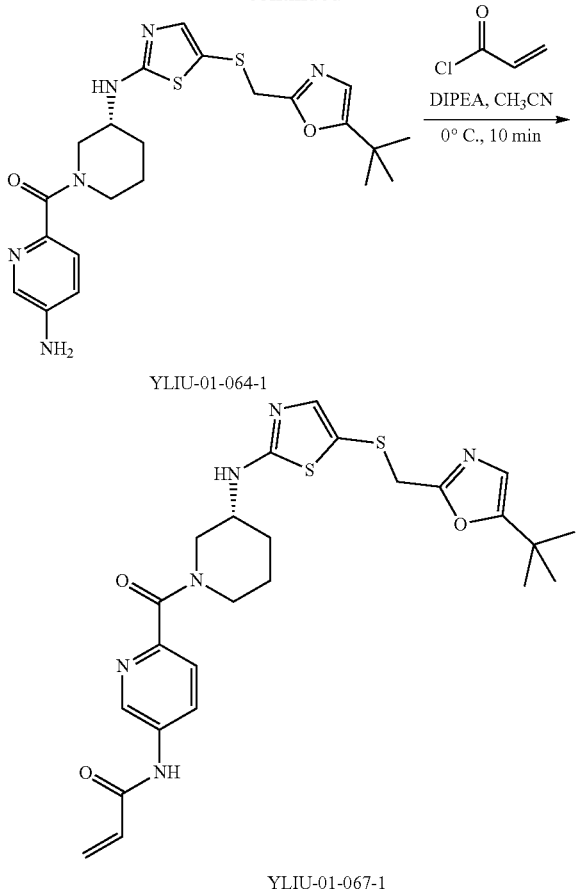

5-Thiocyanatothiazol-2-amine (YLIU-01-004-1)

A mixture of 2-amino-5-bromothiazole hydrobromide (7.8 g, 30 mmol) and potassium thiocyanate (20.46 g, 210.93 mmol) in methanol (230 mL) was stirred at room temperature for 48 h. Methanol was evaporated and water (30 ml) was added. The pH of the aqueous solution was adjusted to pH=12 with 10% NaOH aq and precipitate formed. The solid was collected by filtration to yield compound YLIU-01-004-1 (3.3 g, 70%) as a brownish solid. LCMS (m/z): 158 [M+H]+.

5-((5-tert-Butyloxazol-2-yl)methylthio)thiazol-2-amine (YLIU-01-005-1)

To a solution of compound YLIU-01-004-1 (156 mg, 1 mmol) in absolute EtOH (3 ml) was added NaBH$_4$ (76 mg, 2 mmol) portionwise at 0° C. The mixture was stirred at rt for 1 h, and then acetone (2 ml) was slowly introduced. After 1 h, a solution of 2-(bromomethyl)-5-(tert-butyl)oxazole (240 mg, 1.1 mmol) in EtOH (2 ml) was added. The resulting dark reaction mixture was heated to 65° C. for 1 h, and was then cooled and concentrated in vacuo. The residue was partitioned between EtOAc and brine. The organic phase was separated, dried (MgSO4), concentrated and purified with silica gel column (eluted with MeOH in DCM 0% to 10%) to provide the title compound (120 mg, 44%) as a brown solid. LCMS (m/z): 270 [M+H]+.

2-(((2-bromothiazol-5-yl)thio)methyl)-5-(tert-butyl) oxazole (YLIU-01-017-1)

To a solution of CuBr$_2$ (2.32 g, 10 mmol) in acetonitrile (50 mL) at 0° C. was added t-BuONO (1.1 g, 10 mmol) followed by compound YLIU-01-004-1 (1.66 g, 6.13 mmol). The mixture was stirred at 0° C. for 1 h, then at room temperature for 1 h. Ethyl acetate was added and the organic layer was washed with hydrochloric acid (2×50 mL), dried over magnesium sulfate, filtered through a pad of silica gel, and concentrated in vacuo. The residue was purified on silica gel column to give the YLIU-01-017-1 (690 mg, 33%) as orange oil. LCMS (m/z): 333 [M+H]+.

tert-butyl (R)-3-((5-(((5-(tert-butyl)oxazol-2-yl) methyl)thio)thiazol-2-yl)amino) piperidine-1-carboxylate (YLIU-01-038-1)

A mixture of YLIU-01-017-1 (150 mg, 0.45 mmol), tert-butyl (R)-3-aminopiperidine-1-carboxylate (180 mg, 0.9 mmol), DIPEA (0.24 mL, 1.35 mmol) in NMP (3 mL) was heated to 140° C. overnight. The solution was diluted with water (20 mL) and extracted with chloroform and iso-propanol (4:1). The organic phase was washed with brine (50 mL×2) and dried over Na$_2$SO$_4$, filtered and concentrated. The residue was purified by silica gel column (MeOH/DCM, 0-20%) to give YLIU-01-038-1 (150 mg, 73%). LCMS (m/z). 453 [M+H]+.

(R)-5-(((5-(tert-butyl)oxazol-2-yl)methyl)thio)-N-(piperidin-3-yl)thiazol-2-amine (YLIU-01-047-1)

To a mixture of compound YLIU-01-038-1 (150 mg, 0.33 mmol) in methanol (2 mL) was added 4N HCl/dioxane (2 mL) and the resulted solution was stirred at rt for 3 h. The mixture was concentrated under reduced pressure to give the title compound as HCl salt, which was directly used in the next step. LCMS (m/z): 353 [M+H]$^+$.

(R)-(3-((5-(((5-(tert-butyl)oxazol-2-yl)methyl)thio) thiazol-2-yl)amino)piperidin-1-yl)(5-nitropyridin-2-yl)methanone (YLIU-01-048-1)

To a mixture of YLIU-01-047-1 (50 mg, 0.12 mmol), 5-nitropicolinic acid (23 mg, 0.14 mmol) and DIPEA (78 mg, 0.6 mmol) in DCM (2 mL) was added T$_3$P (50% solution in EA, 230 mg, 0.36 mmol) dropwise at rt. The reaction mixture was stirred at rt overnight. The solution was diluted with DCM (20 mL) and washed with brine (50 mL×2) and dried over Na$_2$SO$_4$ filtered and concentrated. The residue was purified by silica gel column (MeOH/DCM, 0-20%) to give the title compound (46 mg, 76%) as yellow solid. LCMS (m/z): 503 [M+H]$^+$.

(R)-(5-aminopyridin-2-yl)(3-((5-(((5-(tert-butyl) oxazol-2-yl)methyl)thio)thiazol-2-yl)amino)piperidin-1-yl)methanone (YLIU-01-064-1)

To a solution of YLIU-01-048-1 (46 mg, 0.091 mmol) in ethyl acetate and methanol (2 mL, 1:1) was added Tin(II) chloride (138 mg, 0.73 mmol) at rt. After stirring for 2 h at 80° C., the reaction mixture was diluted with chloroform and iso-propanol (4:1), neutralized with saturated NaHCO$_3$ aq. and filtered. The filtrate was extracted with chloroform and iso-propanol (4:1). The combined organic layer was concentrated under reduced pressure and the resulting residue was purified by silica gel column chromatography (MeOH/

DCM=0-20%) to give YLIU-01-064-1 (16 mg, 37%) as yellow solid. LCMS (m/z): 473 [M+H]+.

(R)—N-(6-(3-((5-(((5-(tert-butyl)oxazol-2-yl)methyl)thio)thiazol-2-yl)amino)piperidine-1-carbonyl)pyridin-3-yl)acrylamide (YLIU-01-067-1)

To a solution of YLIU-01-064-1 (16 mg, 0.034 mmol) and DIPEA (13 mg, 0.1 mmol) in MeCN (2 mL) was added acryloyl chloride (4 mg, 0.044 mmol) dropwise at 0° C. Monitored with LCMS, when the reaction was completed, Na$_2$CO$_3$ aq.(sat.) was added, the resulting mixture was extracted with DCM/i-PrOH (4/1) (20 mL×2). The combined organic layer was concentrated and purified with Prep-HPLC (MeOH/H$_2$O, 0.05% TFA) to give the title compound (1.3 mg, 7.27%) as white solid. LCMS (m/z): 527 [M+H]+.

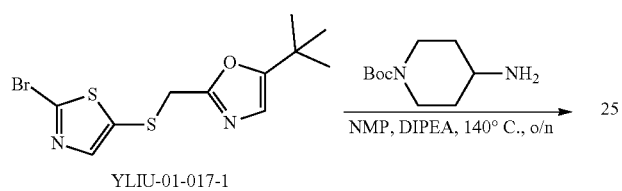

YLIU-01-017-1

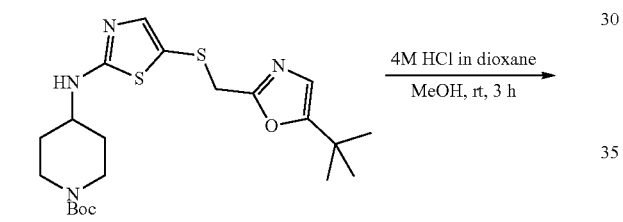

YLIU-01-062-1

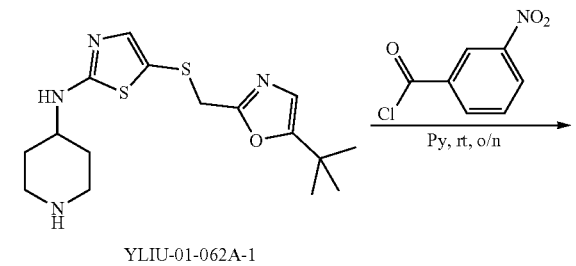

YLIU-01-062A-1

YLIU-01-068-1

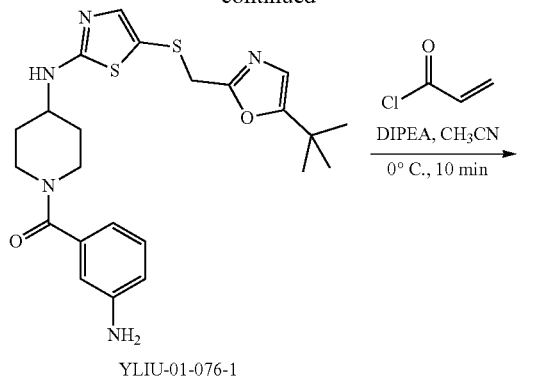

YLIU-01-076-1

YLIU-01-078-1 tert-butyl 4-((5-(((5-(tert-butyl)oxazol-2-yl)methyl)thio)thiazol-2-yl)amino) piperidine-1-carboxylate (YLIU-01-062-1)

A mixture of YLIU-01-017-1 (150 mg, 0.45 mmol), tert-butyl 4-aminopiperidine-1-carboxylate (180 mg, 0.9 mmol), DIPEA (0.24 mL, 1.35 mmol) in NMP (3 mL) was heated to 140° C. overnight. The solution was diluted with water (20 mL) and extracted with chloroform and isopropanol (4:1). The organic phase was washed with brine (50 mL×2) and dried over Na$_2$SO$_4$, filtered and concentrated. The residue was purified by silica gel column (MeOH/DCM, 0-20%) to give YLIU-01-062-1 (150 mg, 73%). LCMS (m/z): 453 [M+H]+.

5-(((5-(tert-butyl)oxazol-2-yl)methyl)thio)-N-(piperidin-4-yl)thiazol-2-amine (YLIU-01-062A-1)

To a mixture of compound YLIU-01-062-1 (150 mg, 0.33 mmol) in methanol (2 mL) was added 4N HCl/dioxane (2 mL) and the resulted solution was stirred at rt for 3 h. The mixture was concentrated under reduced pressure to give the title compound as HCl salt, which was directly used in the next step. LCMS (m/z): 353 [M+H]$^+$.

(4-((5-(((5-(tert-butyl)oxazol-2-yl)methyl)thio)thiazol-2-yl)amino)piperidin-1-yl)(3-nitrophenyl)methanone (YLIU-01-068-1)

The mixture of YLIU-01-062A-1 (330 mg, 0.89 mmol), 3-nitrobenzoyl chloride (330 mg, 1.78 mmol) in pyridine (2 mL) was stirred at rt overnight. Then the reaction mixture was concentrated under reduced pressure and the residue was purified by silica gel column (MeOH/DCM, 0-20%) to give YLIU-01-068-1 (320 mg, 72%) as yellow solid. LCMS (m/z): 502 [M+H]+.

(3-aminophenyl)(4-((5-(((5-(tert-butyl)oxazol-2-yl)methyl)thio)thiazol-2-yl)amino)piperidin-1-yl)methanone (YLIU-01-076-1)

To a solution of YLIU-01-068-1 (100 mg, 0.2 mmol) in MeOH (3 mL) was added Pd/C (10%, 20 mg) and N₂H₄—H₂O (0.1 mL). The reaction mixture was stirred at 80° C. overnight, then filtered through Celite. The filtrate was concentrated and purified by Prep-HPLC (MeOH/H₂O, 0.05% TFA) to give the title compound (27 mg, 29%) as yellow oil. LCMS (m/z): 472 [M+H]+.

N-(3-(4-((5-(((5-(tert-butyl)oxazol-2-yl)methyl)thio)thiazol-2-yl)amino)piperidine-1-carbonyl)phenyl)acrylamide (YLIU-01-078-1)

To a solution of YLIU-01-076-1 (20 mg, 0.042 mmol) and DIPEA (17 mg, 0.13 mmol) in MeCN (2 mL) was added acryloyl chloride (4.2 mg, 0.046 mmol) dropwise at 0° C. Monitored with LCMS, when the reaction was completed, Na₂CO₃ aq.(sat.) was added, the resulting mixture was extracted with DCM/i-PrOH (4/1) (20 mL×2). The combined organic layer was concentrated and purified with Prep-HPLC (MeOH/H₂O, 0.05% TFA) to give the title compound (1.4 mg, 6.3%) as white solid. LCMS (m/z): 526 [M+H]+.

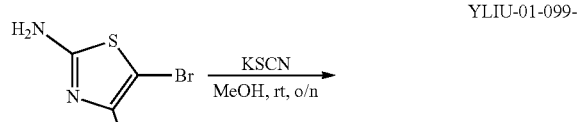

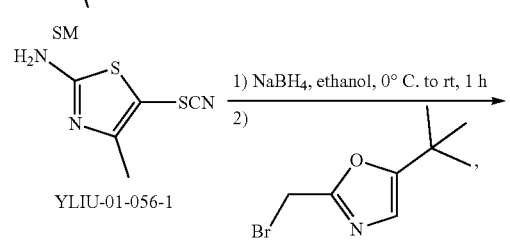

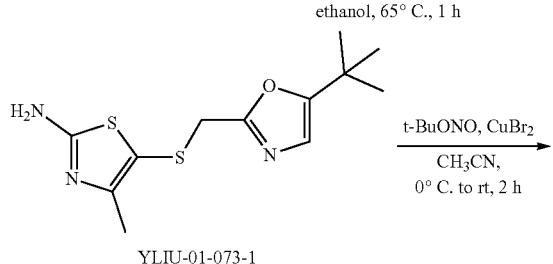

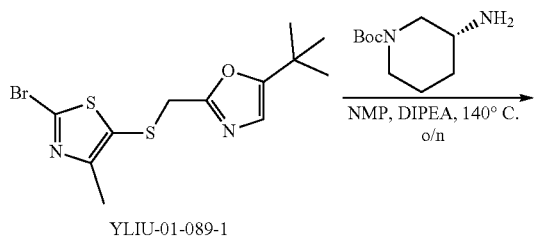

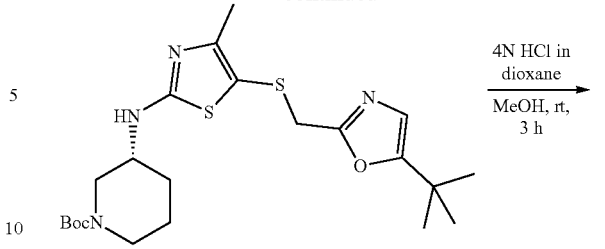

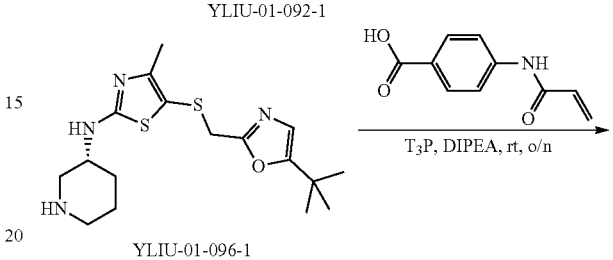

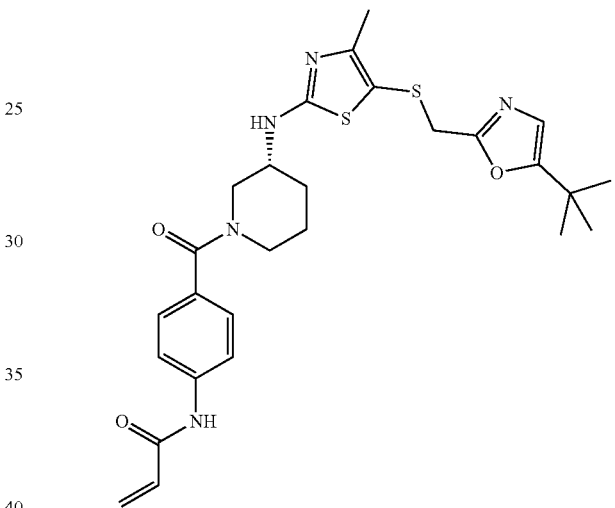

4-methyl-5-thiocyanatothiazol-2-amine (YLIU-01-056-1)

A mixture of 2-amino-5-bromothiazole hydrobromide (580 mg, 3 mmol) and potassium thiocyanate (2.9 g, 30 mmol) in methanol (20 mL) was stirred at room temperature for 48 h. Methanol was evaporated and water (3 ml) was added. The pH of the aqueous solution was adjusted to pH=12 with 10% NaOH aq and precipitate formed. The solid was collected by filtration to yield compound YLIU-01-056-1 (480 mg, 93%) as a brownish solid. LCMS (m/z): 172 [M+H]+.

5-(((5-(tert-butyl)oxazol-2-yl)methyl)thio)-4-methylthiazol-2-amine (YLIU-01-073-1)

To a solution of compound YLIU-01-056-1 (171 mg, 1 mmol) in absolute EtOH (3 ml) was added NaBH₄ (76 mg, 2 mmol) portionwise at 0° C. The mixture was stirred at rt for 1 h, and then acetone (2 ml) was slowly introduced. After 1 h, a solution of 2-(bromomethyl)-5-(tert-butyl)oxazole (240 mg, 1.1 mmol) in EtOH (2 ml) was added. The resulting dark reaction mixture was heated to 65° C. for 1 h, and was then cooled and concentrated in vacuo. The residue was partitioned between EtOAc and brine. The organic phase was separated, dried (MgSO4), concentrated and purified with silica gel column (eluted with MeOH in DCM 0% to 10%) to provide the title compound (314 mg, >100%) as a brown oil. LCMS (m/z): 284 [M+H]+.

2-(((2-bromo-4-methylthiazol-5-yl)thio)methyl)-5-(tert-butyl)-4-methyloxazole (YLIU-01-089-1)

To a solution of CuBr$_2$ (423 mg, 1.9 mmol) in acetonitrile (10 mL) at 0° C. was added t-BuONO (200 mg, 1.9 mmol) followed by compound YLIU-01-073-1 (314 mg, 1.1 mmol). The mixture was stirred at 0° C. for 1 h, then at room temperature for 1 h. Ethyl acetate was added and the organic layer was washed with hydrochloric acid (2×50 mL), dried over magnesium sulfate, filtered through a pad of silica gel, and concentrated in vacuo. The residue was purified on silica gel column to give the YLIU-01-089-1 (140 mg, 37%) as orange oil. LCMS (m/z): 347 [M+H]+.

tert-butyl (R)-3-((5-(((5-(tert-butyl)oxazol-2-yl)methyl)thio)-4-methylthiazol-2-yl) amino)piperidine-1-carboxylate (YLIU-01-092-1)

A mixture of YLIU-01-089-1 (140 mg, 0.4 mmol), tert-butyl (R)-3-aminopiperidine-1-carboxylate (160 mg, 0.8 mmol), DIPEA (0.22 mL, 1.2 mmol) in NMP (3 mL) was heated to 140° C. overnight. The solution was diluted with water (20 mL) and extracted with chloroform and iso-propanol (4:1). The organic phase was washed with brine (50 mL×2) and dried over Na$_2$SO$_4$, filtered and concentrated. The residue was purified by silica gel column (MeOH/DCM, 0-20%) to give YLIU-01-092-1 (220 mg, >100%). LCMS (m/z): 467 [M+H]+.

(R)-5-(((5-(tert-butyl)oxazol-2-yl)methyl)thio)-4-methyl-N-(piperidin-3-yl)thiazol-2-amine (YLIU-01-096-1)

To a mixture of compound YLIU-01-092-1 (220 mg, 0.47 mmol) in methanol (2 mL) was added 4N HCl/dioxane (2 mL) and the resulted solution was stirred at rt for 3 h. The mixture was concentrated and the residue was purified by Prep-HPLC (MeOH/H$_2$O, 0.05% TFA) to give the title compound (88 mg, 51%) as yellow solid. LCMS (m/z): 367 [M+H]+.

(R)—N-(4-(3-((5-(((5-(tert-butyl)oxazol-2-yl)methyl)thio)-4-methylthiazol-2-yl)amino)piperidine-1-carbonyl)phenyl)acrylamide (YLIU-01-099-1)

To a mixture of YLIU-01-096-1 (22 mg, 0.06 mmol), 4-acrylamidobenzoic acid (14 mg, 0.072 mmol) and DIPEA (39 mg, 0.3 mmol) in DCM (2 mL) was added T$_3$P (50% solution in EA, 57 mg, 0.18 mmol) dropwise at rt. The reaction mixture was stirred at rt overnight. The solution was diluted with DCM (20 mL) and washed with brine (50 mL×2) and dried over Na$_2$SO$_4$, filtered and concentrated. The residue was purified by Prep-HPLC (MeOH/H$_2$O, 0.05% TFA) to give the title compound (17.1 mg, 53%) as yellow solid. LCMS (m/z): 540 [M+H]$^+$.
1H NMR (500 MHz, DMSO) δ 10.28 (s, 1H), 8.44-7.89 (m, 1H), 7.81-7.57 (m, 2H), 7.36 (m, 2H), 6.81-6.60 (m, 1H), 6.51-6.36 (m, 1H), 6.32-6.20 (m, 1H), 5.88-5.67 (m, 1H), 3.87 (m, 3H), 3.63 (s, 2H), 3.12 (m, 2H), 1.90 (m, 2H), 1.63-1.39 (m, 5H), 1.19 (s, 9H).

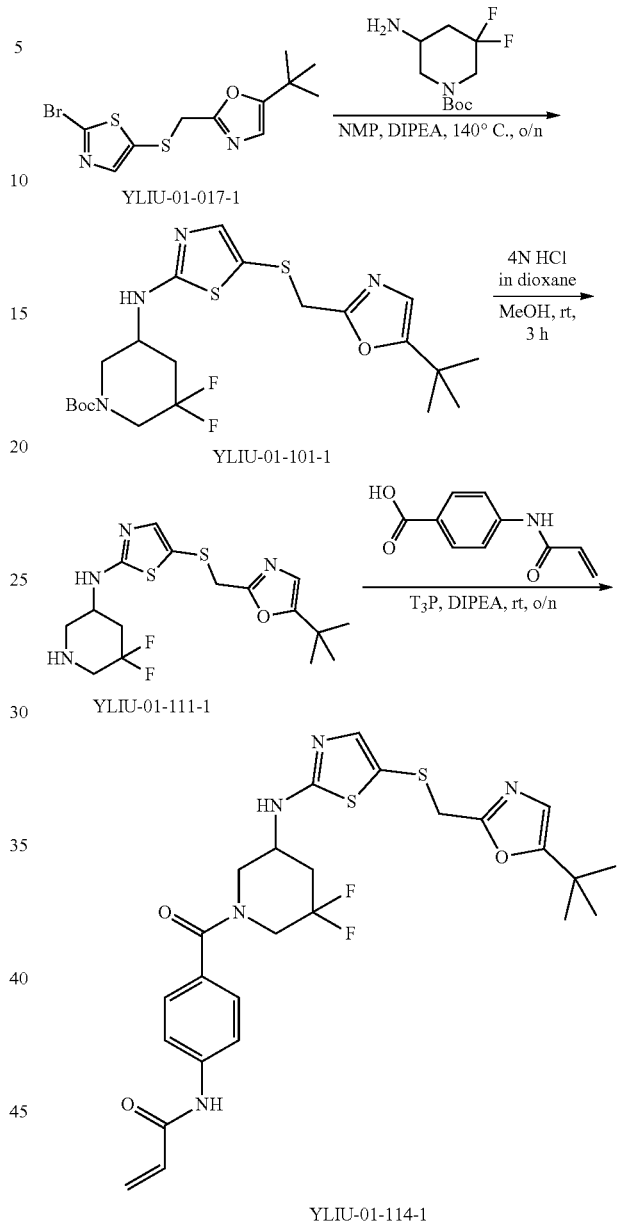

tert-butyl 5-((5-(((5-(tert-butyl)oxazol-2-yl)methyl)thio)thiazol-2-yl)amino)-3,3-difluoropiperidine-1-carboxylate (YLIU-01-101-1)

A mixture of YLIU-01-017-1 (130 mg, 0.4 mmol), tert-butyl 5-amino-3,3-difluoropiperidine-1-carboxylate (350 mg, 1.5 mmol), DIPEA (0.36 mL, 1.8 mmol) in NMP (3 mL) was heated to 140° C. overnight. The solution was diluted with water (20 mL) and extracted with chloroform and iso-propanol (4:1). The organic phase was washed with brine (50 mL×2) and dried over Na$_2$SO$_4$, filtered and concentrated. The residue was purified by silica gel column (MeOH/DCM, 0-20%) to give YLIU-01-101-1 (12 mg, 6%). LCMS (m/z): 489 [M+H]+.

5-(((5-(tert-butyl)oxazol-2-yl)methyl)thio)-N-(5,5-difluoropiperidin-3-yl)thiazol-2-amine (YLIU-01-111-1)

To a mixture of compound YLIU-01-101-1 (12 mg, 0.024 mmol) in methanol (2 mL) was added 4N HCl/dioxane (2 mL) and the resulted solution was stirred at rt for 3 h. The mixture was concentrated and the crude product was used into next step directly as HCl salt. LCMS (m/z): 389 [M+H]+.

N-(4-(5-(((5-(tert-butyl)oxazol-2-yl)methyl)thio)thiazol-2-yl)amino)-3,3-difluoropiperidine-1-carbonyl)phenyl)acrylamide (YLIU-01-114-1)

To a mixture of YLIU-01-111-1 (10 mg, crude HCl salt), 4-acrylamidobenzoic acid (6 mg, 0.03 mmol) and DIPEA (16 mg, 0.12 mmol) in DCM (2 mL) was added T$_3$P (50% solution in EA, 46 mg, 0.07 mmol) dropwise at rt. The reaction mixture was stirred at rt overnight. The solution was diluted with DCM (20 mL) and washed with brine (50 mL×2) and dried over Na$_2$SO$_4$, filtered and concentrated. The residue was purified by Prep-HPLC (MeOH/H$_2$O, 0.05% TFA) to give the title compound (2.5 mg, 19%) as yellow solid. LCMS (m/z): 562 [M+H]+.
1H NMR (500 MHz, DMSO) δ 10.35 (s, 1H), 8.10 (s, 1H), 7.74 (d, J=8.3 Hz, 2H), 7.42 (d, J=8.6 Hz, 2H), 7.08-6.83 (m, 1H), 6.72 (m, 1H), 6.45 (m, 1H), 6.29 (m, 1H), 5.80 (m, 1H), 3.97 (s, 2H), 3.65-3.44 (m, 3H), 3.22-2.90 (m, 2H), 2.08 (m, 2H), 1.21 (s, 9H).

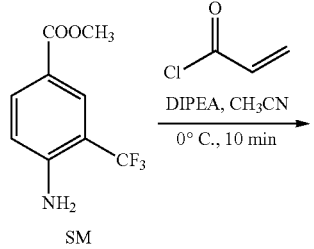

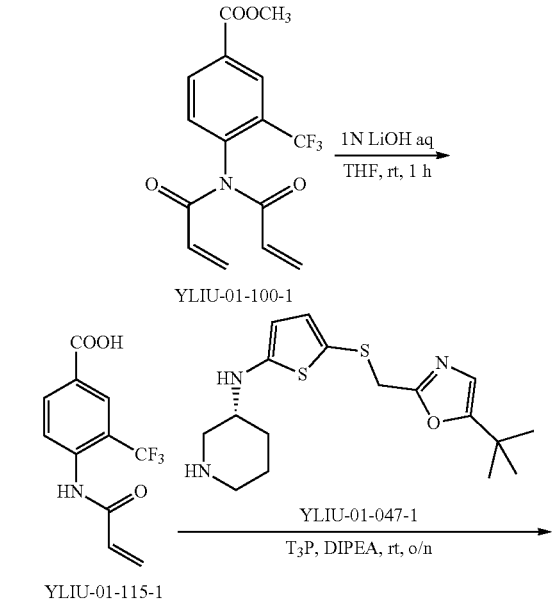

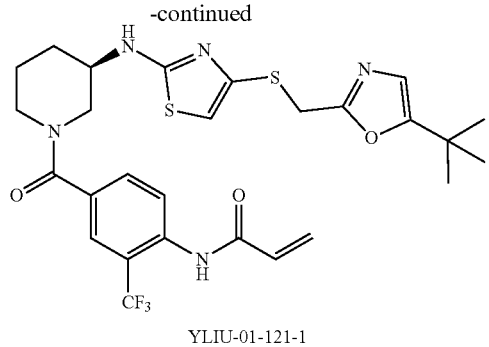

YLIU-01-121-1

Methyl 4-(N-acryloylacrylamido)-3-(trifluoromethyl)benzoate (YLIU-01-100-1)

To a solution of methyl 4-amino-3-(trifluoromethyl)benzoate (220 mg, 1 mmol) and DIPEA (390 mg, 3 mmol) in MeCN (5 mL) was added acryloyl chloride (108 mg, 1.2 mmol) dropwise at 0° C. The reaction was stirred at rt for 1 h, then Na$_2$CO$_3$ aq.(sat.) was added, the resulting mixture was extracted with DCM (20 mL×2). The combined organic layer was concentrated and purified with SGC (Hexane/EA=4/1) to give YLIU-01-100-1 (114 mg, 35%) as white solid. LCMS (m/z): 328 [M+H]+.

4-acrylamido-3-(trifluoromethyl)benzoic acid (YLIU-01-115-1)

To a solution of YLIU-01-100-1 (114 mg, 0.35 mmol) in THF (4 mL) was added 1N LiOH aq. (4 mL). The reaction mixture was stirred at rt for 1 h, then adjusted PH<7 with 4N HCl aq. The resulting mixture was extracted with EA (20 mL×3), washed with brine (50 mL×2) and dried over Na$_2$SO$_4$, filtered and concentrated to give the desire product (110 mg, >100%) as a white solid. LCMS (m/z): 260 [M+H]+.

(R)—N-(4-(3-((4-(((5-(tert-butyl)oxazol-2-yl)methyl)thio)thiazol-2-yl)amino)piperidine-1-carbonyl)-2-(trifluoromethyl)phenyl)acrylamide (YLIU-01-121-1)

To a mixture of YLIU-01-047-1 (20 mg, 0.057 mmol), YLIU-01-115-1 (18 mg, 0.068 mmol) and DIPEA (37 mg, 0.285 mmol) in DCM (2 mL) was added T$_3$P (50% solution in EA, 108 mg, 0.17 mmol) dropwise at rt. The reaction mixture was stirred at rt overnight. The solution was diluted with DCM (20 mL) and washed with brine (50 mL×2) and dried over Na$_2$SO$_4$, filtered and concentrated. The residue was purified by Prep-HPLC (MeOH/H$_2$O, 0.05% TFA) to give the title compound (17.8 mg, 53%) as yellow solid. LCMS (m/z): 594 [M+H]$^+$. $^1$H NMR (500 MHz, DMSO) δ 9.87 (m, 1H), 8.15 (m, 1H), 7.72 (m, 3H), 7.08-6.66 (m, 2H), 6.64-6.50 (m, 1H), 6.29 (m, 1H), 5.93-5.70 (m, 1H), 3.94 (m, 2H), 3.72 (m, 2H), 3.40 (m, 1H), 3.15 (m, 2H), 2.07-1.66 (m, 2H), 1.64-1.35 (m, 2H), 1.14 (s, 9H).

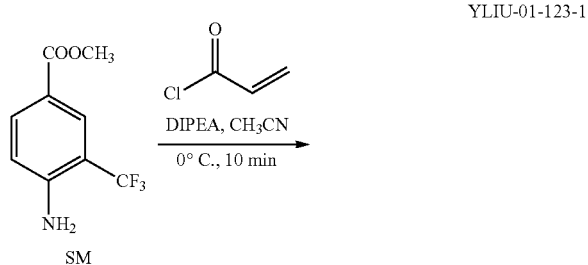

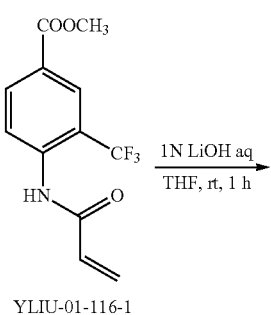

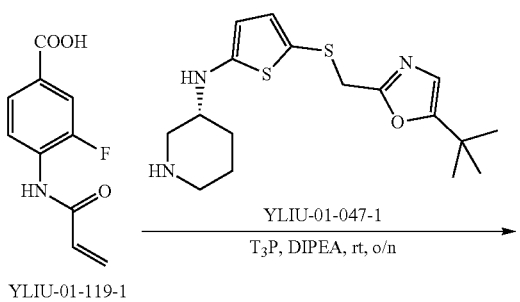

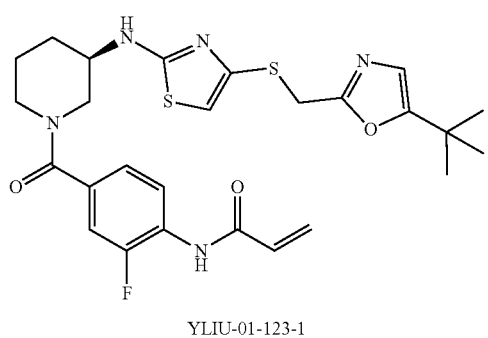

methyl 4-acrylamido-3-fluorobenzoate (YLIU-01-116-1)

To a solution of methyl 4-amino-3-fluorobenzoate (500 mg, 3 mmol) and DIPEA (1.65 mL, 9 mmol) in MeCN (5 mL) was added acryloyl chloride (320 mg, 3.6 mmol) dropwise at 0° C. The reaction was stirred at rt for 1 h, then Na$_2$CO$_3$ aq.(sat.) was added, the resulting mixture was extracted with DCM (20 mL×2). The combined organic layer was concentrated and recrystallized from EA to give YLIU-01-116-1 (190 mg, 28%) as white solid. LCMS (m/z): 224 [M+H]+.

4-acrylamido-3-fluorobenzoic acid (YLIU-01-119-1)

To a solution of YLIU-01-116-1 (190 mg, 0.85 mmol) in THF/water (4 mL/4 mL) was added LiOH (204 mg, 8.5 mmol). The reaction mixture was stirred at rt for 1 h, then adjusted PH<7 with 4N HCl aq. The resulting mixture was extracted with EA (20 mL×3), washed with brine (50 mL×2) and dried over Na$_2$SO$_4$, filtered and concentrated to give the desire product (110 mg, 61%) as a white solid. LCMS (m/z): 210 [M+H]+.

(R)—N-(4-(3-((4-(((5-(tert-butyl)oxazol-2-yl)methyl)thio)thiazol-2-yl)amino)piperidine-1-carbonyl)-2-fluorophenyl)acrylamide (YLIU-01-123-1)

To a mixture of YLIU-01-047-1 (20 mg, 0.057 mmol), YLIU-01-115-1 (15 mg, 0.068 mmol) and DIPEA (37 mg, 0.285 mmol) in DCM (2 mL) was added T$_3$P (50% solution in EA, 108 mg, 0.17 mmol) dropwise at rt. The reaction mixture was stirred at rt overnight. The solution was diluted with DCM (20 mL) and washed with brine (50 mL×2) and dried over Na$_2$SO$_4$, filtered and concentrated. The residue was purified by Prep-HPLC (MeOH/H$_2$O, 0.05% TFA) to give the title compound (23.8 mg, 77%) as yellow solid. LCMS (m/z): 544 [M+H]$^+$. $^1$H NMR (500 MHz, DMSO) δ 10.06 (s, 1H), 8.05 (m, 2H), 7.44-6.97 (m, 2H), 6.74-6.53 (m, 3H), 6.36-6.21 (m, 1H), 5.80 (m, 1H), 3.69 (s, 2H), 3.53 (m, 3H), 3.31-3.01 (m, 2H), 1.86 (m, 2H), 1.51 (m, 2H), 1.16 (s, 9H).

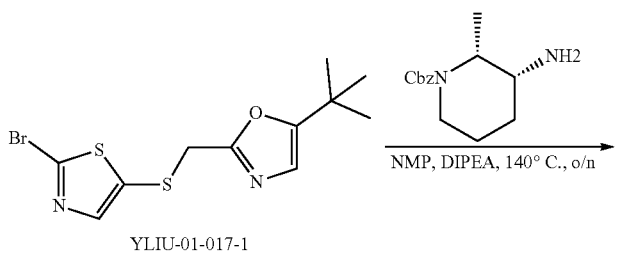

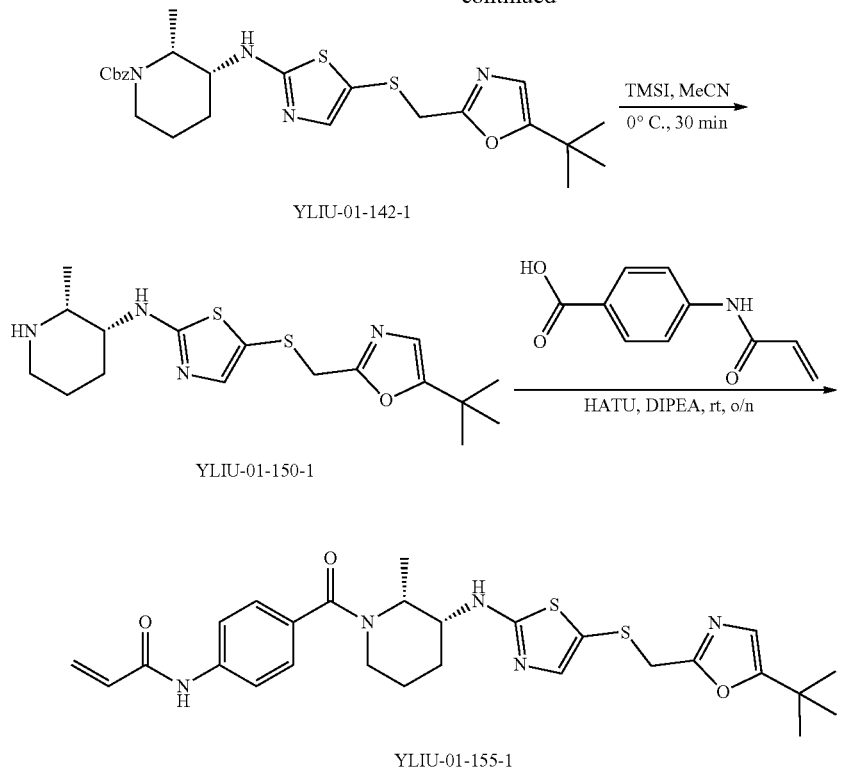

benzyl (2R,3R)-3-((5-(((5-(tert-butyl)oxazol-2-yl)methyl)thio)thiazol-2-yl)amino)-2-methylpiperidine-1-carboxylate (YLIU-01-142-1)

A mixture of YLIU-01-017-1 (80 mg, 0.24 mmol), benzyl (2R,3R)-3-amino-2-methyl piperidine-1-carboxylate (300 mg, 1.2 mmol), DIPEA (0.42 mL, 2.4 mmol) in NMP (3 mL) was heated to 140° C. overnight. The solution was diluted with water (20 mL) and extracted with chloroform and iso-propanol (4:1). The organic phase was washed with brine (50 mL×2) and dried over Na$_2$SO$_4$, filtered and concentrated. The residue was purified by silica gel column (MeOH/DCM, 0-20%) to give YLIU-01-142-1 (70 mg, 58%) as yellow solid. LCMS (m/z): 501 [M+H]+.

5-(((5-(tert-butyl)oxazol-2-yl)methyl)thio)-N-((2R,3R)-2-methylpiperidin-3-yl)thiazol-2-amine (YLIU-01-150-1)

To a mixture of compound YLIU-01-142-1 (70 mg, 0.14 mmol) in MeCN (4 mL) was added TMSI (280 mg, 1.4 mmol) and the resulted solution was stirred at 0° C. for 30 min. The reaction was quenched with water and the resulting solution was purified by Prep-HPLC (MeOH/H$_2$O, 0.05% TFA) to give the title compound (34 mg, 66%) as yellow solid. LCMS (m/z): 367 [M+H]+.

N-(4-((2R,3R)-3-((5-(((5-(tert-butyl)oxazol-2-yl)methyl)thio)thiazol-2-yl)amino)-2-methylpiperidine-1-carbonyl)phenyl)acrylamide (YLIU-01-155-1)

To a mixture of YLIU-01-150-1 (17 mg, 0.046 mmol), 4-acrylamidobenzoic acid (10 mg, 0.055 mmol) and DIPEA (0.04 mL, 0.23 mmol) in DMF (2 mL) was added HATU (35 mg, 0.093 mmol) at rt. The reaction mixture was stirred at rt overnight. The solution was diluted with DCM (20 mL) and washed with brine (50 mL×2) and dried over Na$_2$SO$_4$, filtered and concentrated. The residue was purified by Prep-HPLC (MeOH/H$_2$O, 0.05% TFA) to give the title compound (8.2 mg, 33%) as yellow solid. LCMS (m/z): 540 [M+H]$^+$.

1H NMR (500 MHz, DMSO) δ 10.30 (s, 1H), 8.02 (s, 1H), 7.72 (d, J=8.6 Hz, 2H), 7.38 (d, J=8.3 Hz, 2H), 6.79 (m, 2H), 6.45 (dd, J=17.0, 10.2 Hz, 1H), 6.28 (dd, J=17.0, 1.9 Hz, 1H), 5.79 (dd, J=10.1, 1.9 Hz, 1H), 3.79 (m, 4H), 3.08 (m, 2H), 1.84-1.38 (m, 4H), 1.19 (s, 9H), 1.04 (s, 3H).

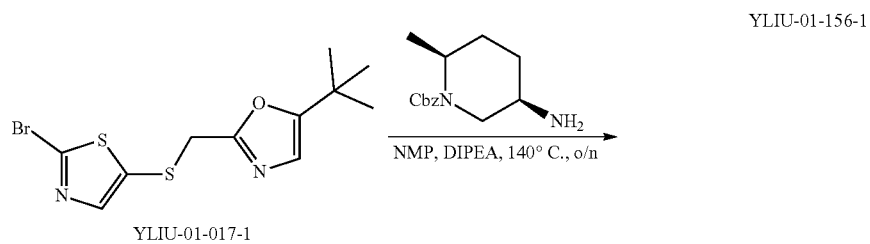

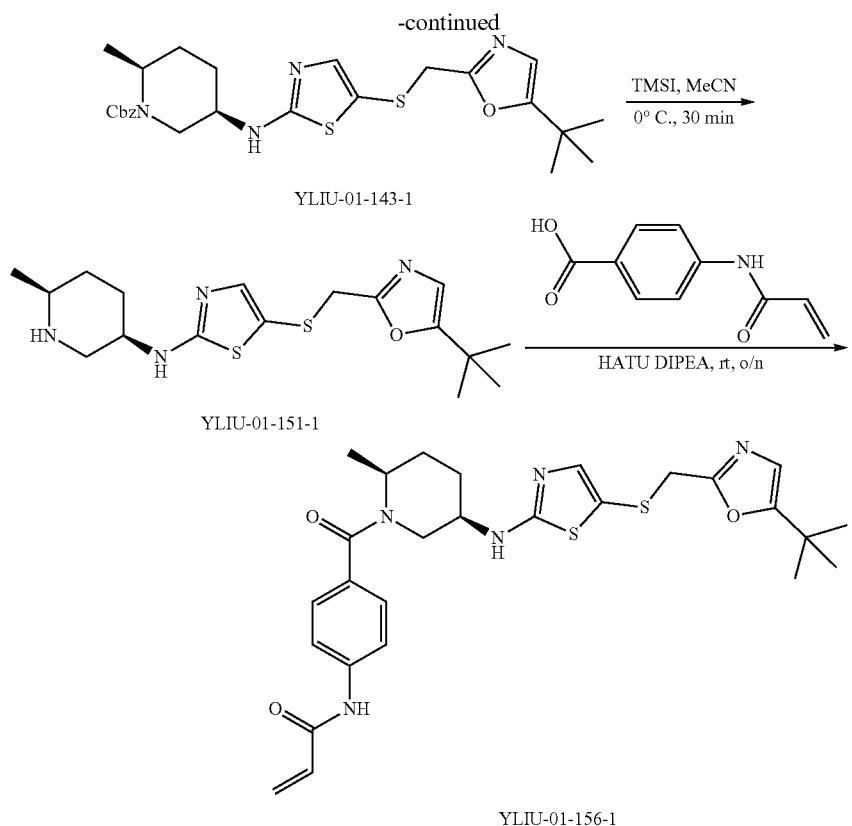

benzyl (2S,5R)-5-(((5-(((5-(tert-butyl)oxazol-2-yl)methyl)thio)thiazol-2-yl)amino)-2-methylpiperidine-1-carboxylate (YLIU-01-143-1)

A mixture of YLIU-01-017-1 (80 mg, 0.24 mmol), benzyl (2S,5R)-5-amino-2-methyl piperidine-1-carboxylate (300 mg, 1.2 mmol), DIPEA (0.42 mL, 2.4 mmol) in NMP (3 mL) was heated to 140° C. overnight. The solution was diluted with water (20 mL) and extracted with chloroform and iso-propanol (4:1). The organic phase was washed with brine (50 mL×2) and dried over $Na_2SO_4$, filtered and concentrated. The residue was purified by silica gel column (MeOH/DCM, 0-20%) to give YLIU-01-143-1 (50 mg, 42%) as yellow solid. LCMS (m/z): 501 [M+H]+.

5-(((5-(tert-butyl)oxazol-2-yl)methyl)thio)-N-((3R,6S)-6-methylpiperidin-3-yl)thiazol-2-amine (YLIU-01-151-1)

To a mixture of compound YLIU-01-143-1 (50 mg, 0.1 mmol) in MeCN (4 mL) was added TMSI (200 mg, 1 mmol) and the resulted solution was stirred at 0° C. for 30 min. The reaction was quenched with water and the resulting solution was purified by Prep-HPLC (MeOH/$H_2O$, 0.05% TFA) to give the title compound (20 mg, 54%) as yellow solid. LCMS (m/z): 367 [M+H]+.

N-(4-((2S,5R)-5-((5-(((5-(tert-butyl)oxazol-2-yl)methyl)thio)thiazol-2-yl)amino)-2-methylpiperidine-1-carbonyl)phenyl)acrylamide (YLIU-01-156-1)

To a mixture of YLIU-01-151-1 (20 mg, 0.054 mmol), 4-acrylamidobenzoic acid (12.5 mg, 0.065 mmol) and DIPEA (0.05 mL, 0.27 mmol) in DMF (2 mL) was added HATU (41 mg, 0.108 mmol) at rt. The reaction mixture was stirred at rt overnight. The solution was diluted with DCM (20 mL) and washed with brine (50 mL×2) and dried over $Na_2SO_4$, filtered and concentrated. The residue was purified by Prep-HPLC (MeOH/H2O, 0.05% TFA) to give the title compound (11 mg, 38%) as yellow solid. LCMS (m/z): 540 [M+H]+. 1H NMR (500 MHz, DMSO) δ 10.30 (s, 1H), 8.03 (s, 1H), 7.73 (d, J=8.6 Hz, 2H), 7.39 (d, J=8.6 Hz, 2H), 6.97 (m, 1H), 6.71 (s, 1H), 6.45 (dd, J=17.0, 10.1 Hz, 1H), 6.28 (dd, J=17.0, 1.9 Hz, 1H), 5.79 (dd, J=10.1, 1.9 Hz, 1H), 3.95 (m, 2H), 3.57 (m, 2H), 3.34-3.02 (m, 1H), 2.68 (m, 1H), 1.71 (m, 4H), 1.35-0.88 (m, 12H).

Synthesis of B1

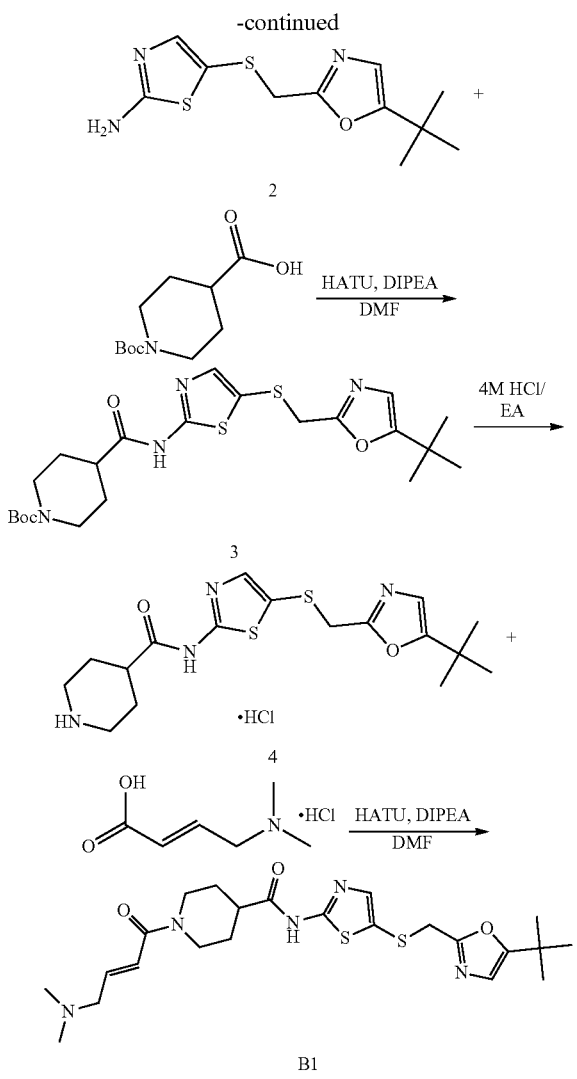

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 hours and then concentrated under vacuum. The residue was diluted with H$_2$O (150 mL). The pH of the solution was adjusted to 10 with 10% Na$_2$CO$_3$. The precipitate was filtered and washed with water to obtain (1.8 g, 58%) of the title compound (1) as a brown solid. MS m/z 158.95 [M+H]$^+$.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added NaBH$_4$ (0.87 g, 2.3 mmol) portionwise at room temperature. The resulting mixture was stirred for 1 hour, and then acetone (20 ml) was slowly introduced. After 1 hours, a solution of 5-(tert-butyl)-2-(chloromethyl)oxazole (2.19 g, 12.6 mmol) in EtOH (10 ml) was added, and the resulting mixture was cooled, concentrated in vacuo, and then partitioned between EtOAc and brine, dried (Na$_2$SO$_4$), and concentrated. The residue was purified by an silica gel column to afford (2.1 g, 68%) of the title compound (2) as a pale red-brown solid. MS m/z 270.06 [M+H]$^+$.

tert-butyl 4-((5-(((5-(tert-butyl)oxazol-2-yl)methyl)thio)thiazol-2-yl)carbamoyl)piperidine-1-carboxylate (3)

To a solution of 5-(((5-(tert-butyl)oxazol-2-yl)methyl)thio)thiazol-2-amine (186 mg, 0.69 mmol), 1-(tert-butoxycarbonyl)piperidine-4-carboxylic acid (229 mg, 0.94 mmol), DMAP (42.8 mg, 0.35 mmol), and triethylamine (0.2 ml, 1.4 mmol) in DMF (1 mL) and DCM (2 ml) was added EDAC (267 mg, 1.4 mmol) at room temperature. The reaction mixture was stirred for 1.5 hours, diluted with EtOAc, washed with water and brine, dried (Na$_2$SO$_4$), and concentrated. The residue was purified by an silica gel column to afford (226 mg, 83%) of the title compound (3) as a white solid. MS m/z 481.18[M+H]$^+$.

N-(5-(((5-(tert-butyl)oxazol-2-yl)methyl)thio)thiazol-2-yl)piperidine-4-carboxamide hydrochloride (4)

To a solution of tert-butyl 4-((5-(((5-(tert-butyl)oxazol-2-yl)methyl)thio)thiazol-2-yl)carbamoyl)piperidine-1-carboxylate (117 mg, 0.24 mmol) in 4 M HCl EtOAc (5 mL). The resulting mixture was stirred at room temperature for 30 min. Then it was concentrated under vacuum to afford (100 mg, 100%) of the title compound (4) as a white solid, which was used without further purification. MS m/z 381.14 [M+H]$^+$.

(E)-N-(5-(((5-(tert-butyl)oxazol-2-yl)methyl)thio)thiazol-2-yl)-1-(4-(dimethylamino)but-2-enoyl)piperidine-4-carboxamide (B1)

To a solution of N-(5-(((5-(tert-butyl)oxazol-2-yl)methyl)thio)thiazol-2-yl)piperidine-4-carboxamide hydrochloride (100 mg, 0.24 mmol) in DMF (1 mL) was added HATU (110 mg, 0.29 mmol), (E)-4-(dimethylamino)but-2-enoic acid hydrochloride (45 mg, 0.27 mmol) and DIPEA (125 mg, 0.96 mmol). The resulting mixture was stirred at room temperature for 1 hour. Then it was diluted with EtOAc (100 mL), washed with water and brine, dried (Na$_2$SO$_4$), and concentrated. The residue was purified by an silica gel column to afford (6 mg, 5.1%) of the title compound as a yellow solid. MS m/z 492.21 [M+H]$^+$. $^1$H NMR (400 MHz, DMSO-d$_6$) δ 12.42 (s, 1H), 10.66 (s, 2H), 7.77 (s, 2H), 7.40 (s, 3H), 6.83 (s, 1H), 6.72 (s, 1H), 6.51 (d, J=15.1 Hz, 1H), 4.52-4.17 (m, 1H), 4.07 (s, 2H), 3.63 (s, 1H), 3.08 (s, 2H), 2.77 (s, 6H), 2.02 (s, 2H), 1.72 (s, 3H), 1.46 (s, 2H), 1.19 (s, 9H).

Synthesis of B2

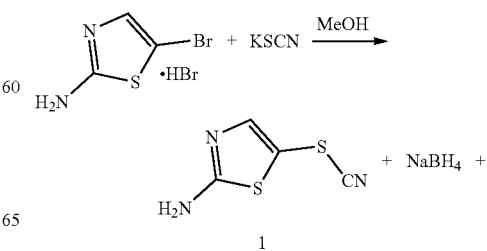

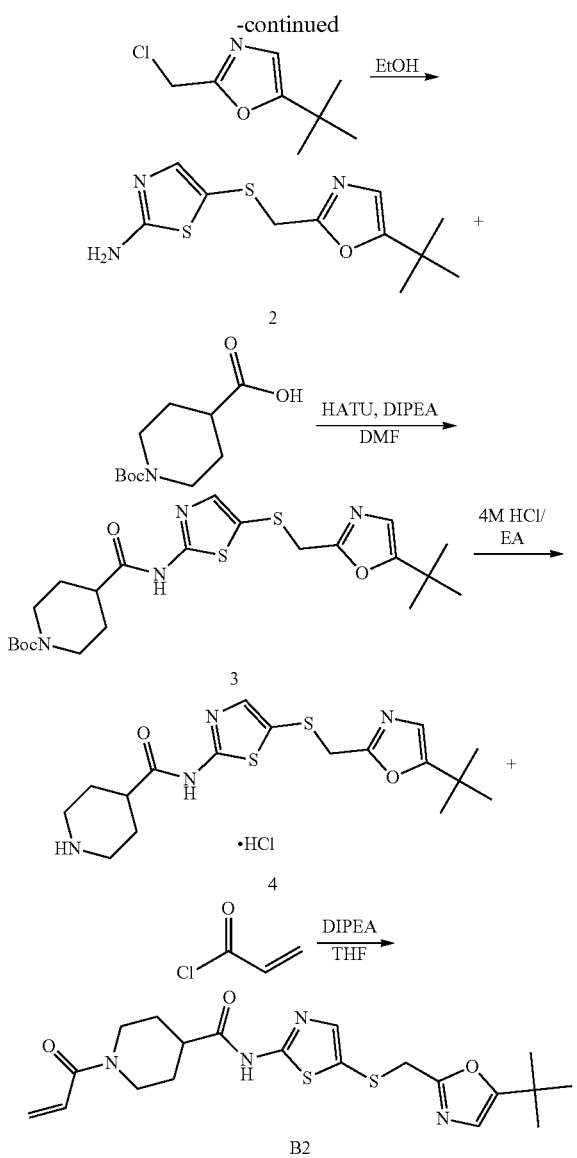

in EtOH (10 ml) was added, and the resulting mixture was cooled, concentrated in vacuo, and then partitioned between EtOAc and brine, dried (Na₂SO₄), and concentrated. The residue was purified by an silica gel column to afford (2.1 g, 68%) of the title compound (2) as a pale red-brown solid. MS m/z 270.06 [M+H]⁺.

tert-butyl 4-((5-(((5-(tert-butyl)oxazol-2-yl)methyl)
thio)thiazol-2-yl)carbamoyl)piperidine-1-carboxylate
(3)

To a solution of 5-(((5-(tert-butyl)oxazol-2-yl)methyl) thio)thiazol-2-amine (186 mg, 0.69 mmol), 1-(tert-butoxycarbonyl)piperidine-4-carboxylic acid (229 mg, 0.94 mmol), DMAP (42.8 mg, 0.35 mmol), and triethylamine (0.2 ml, 1.4 mmol) in DMF (1 mL) and DCM (2 ml) was added ED AC (267 mg, 1.4 mmol) at room temperature. The reaction mixture was stirred for 1.5 hours, diluted with EtOAc, washed with water and brine, dried (Na₂SO₄), and concentrated. The residue was purified by an silica gel column to afford (226 mg, 83%) of the title compound (3) as a white solid. MS m/z 481.18[M+H]⁺.

N-(5-(((5-(tert-butyl)oxazol-2-yl)methyl)thio)thi-
azol-2-yl)piperidine-4-carboxamide hydrochloride
(4)

To a solution of tert-butyl 4-((5-(((5-(tert-butyl)oxazol-2-yl)methyl)thio)thiazol-2-yl)carbamoyl)piperidine-1-carboxylate (20 mg, 0.047 mmol) in 4 M HCl EtOAc (3 mL). The resulting mixture was stirred at room temperature for 30 min. Then it was concentrated under vacuum to afford (100 mg, 100%) of the title compound (4) as a white solid, which was used without further purification. MS m/z 381.14 [M+H]⁺.

1-acryloyl-N-(5-(((5-(tert-butyl)oxazol-2-yl)methyl)
thio)thiazol-2-yl)piperidine-4-carboxamide (B2)

To a solution of N-(5-(((5-(tert-butyl)oxazol-2-yl)methyl) thio)thiazol-2-yl)piperidine-4-carboxamide hydrochloride (20 mg, 0.05 mmol) in THF (5 mL) was added DIPEA (17 mg, 0.15 mmol) and acryloyl chloride (43 mg, 0.05 mmol) at 0° C. for 1 hour. The resulting mixture was stirred at room temperature for 2 hours. Then it was concentrated and purified by an silica gel column to afford (11 mg, 50.7%) of the title compound as a slightly white solid. MS m/z 435.15 [M+H]⁺. ¹H NMR (400 MHz, CDCl₃) δ 11.64 (s, 1H), 7.29 (s, 1H), 6.58 (q, J=11.0 Hz, 2H), 6.28 (d, J=16.7 Hz, 1H), 5.71 (d, J=10.6 Hz, 1H), 4.58 (d, J=12.1 Hz, 1H), 4.09 (dd, J=17.6, 10.2 Hz, 1H), 3.96 (s, 2H), 3.21 (s, 1H), 2.90 (s, 1H), 2.68 (t, J=10.4 Hz, 1H), 1.95 (d, J=12.0 Hz, 2H), 1.82 (s, 2H), 1.24 (s, 9H).

Synthesis of B3

5-thiocyanatothiazol-2-amine (1)

To a solution of 5-bromothiazol-2-amine hydrobromide (5.2 g, 20 mmol) in Methanol (100 mL) was added KSCN (19.5 g, 200 mmol) at room temperature. The resulting mixture was stirred for 20 hours and then concentrated under vacuum. The residue was diluted with H₂O (150 mL). The pH of the solution was adjusted to 10 with 10% Na₂CO₃. The precipitate was filtered and washed with water to obtain (1.8 g, 58%) of the title compound (1) as a brown solid. MS m/z 158.95 [M+H]⁺.

5-(((5-(tert-butyl)oxazol-2-yl)methyl)thio)thiazol-2-
amine (2)

To a solution of 5-thiocyanatothiazol-2-amine (1.8 g, 11.46 mmol) in absolute EtOH (50 mL) was added NaBH₄ (0.87 g, 2.3 mmol) portionwise at room temperature. The resulting mixture was stirred for 1 hour, and then acetone (20 ml) was slowly introduced. After 1 hour, a solution of 5-(tert-butyl)-2-(chloromethyl)oxazole (2.19 g, 12.6 mmol)

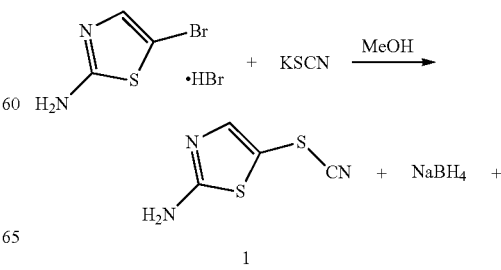

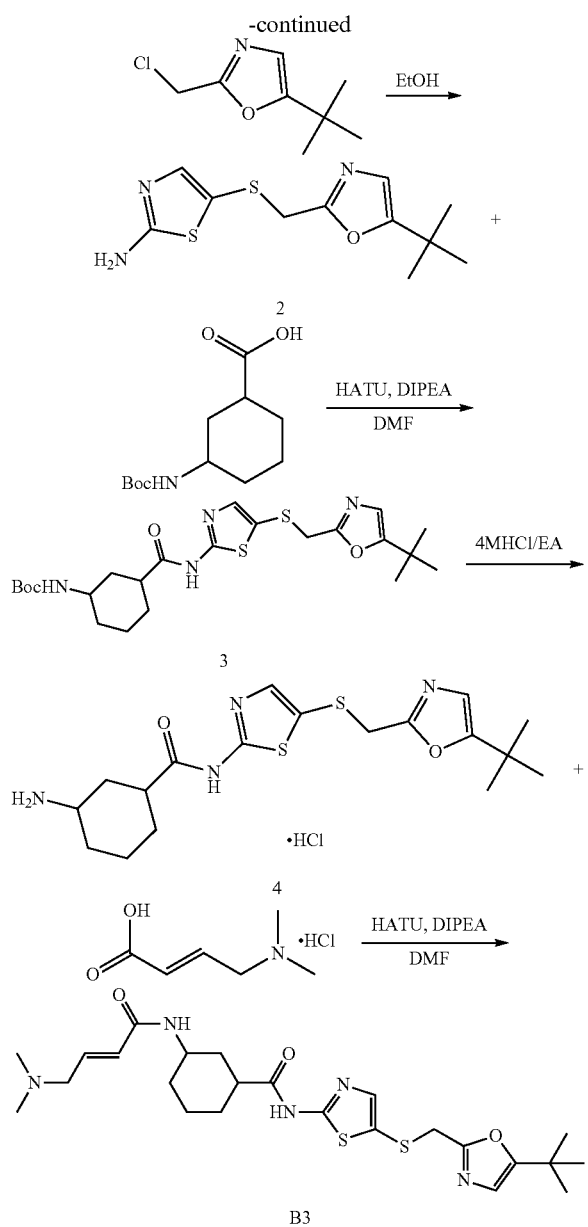

resulting mixture was stirred for 1 hour, and then acetone (20 ml) was slowly introduced. After 1 hour, a solution of 5-(tert-butyl)-2-(chloromethyl)oxazole (2.19 g, 12.6 mmol) in EtOH (10 ml) was added, and the resulting mixture was cooled, concentrated in vacuo, and then partitioned between EtOAc and brine, dried ($Na_2SO_4$), and concentrated. The residue was purified by an silica gel column to afford (2.1 g, 68%) of the title compound (2) as a pale red-brown solid. MS m/z 270.06 $[M+H]^+$.

tert-butyl (3-((5-(((5-(tert-butyl)oxazol-2-yl)methyl) thio)thiazol-2-yl)carbamoyl)cyclohexyl)carbamate (3)

To a solution of 5-(((5-(tert-butyl)oxazol-2-yl)methyl) thio)thiazol-2-amine (160 mg, 0.6 mmol) in DMF (2 mL) was added HATU (456 mg, 1.2 mmol), 3-((tert-butoxycarbonyl)amino)cyclohexane-1-carboxylic acid (292 mg, 1.2 mmol), and DIPEA (143 mg, 2.4 mmol). The resulting mixture was stirred at room temperature for 1 hour. Then it was diluted with EtOAc (150 mL), washed with water and brine, dried ($Na_2SO_4$), and concentrated. The residue was purified by an silica gel column to afford (210 mg, 70%) of the title compound (3) as a white solid. MS m/z 495.20$[M+H]^+$.

3-amino-N-(5-(((5-(tert-butyl)oxazol-2-yl)methyl) thio)thiazol-2-yl)cyclohexane-1-carboxamide hydrochloride (4)

To a solution of tert-butyl (3-((5-(((5-(tert-butyl)oxazol-2-yl)methyl)thio)thiazol-2-yl)carbamoyl)cyclohexyl)carbamate (210 mg, 0.424 mmol) in 4 M HCl EtOAc (5 mL). The resulting mixture was stirred at room temperature for 30 min. Then it was concentrated under vacuum to afford (182 mg, 99%) of the title compound (4) as a white solid, which was used without further purification. MS m/z 395.15 $[M+H]^+$.

(E)-N-(5-(((5-(tert-butyl)oxazol-2-yl)methyl)thio) thiazol-2-yl)-3-(4-(dimethylamino)but-2-enamido) cyclohexane-1-carboxamide (B3)

To a solution of 3-amino-N-(5-(((5-(tert-butyl)oxazol-2-yl)methyl)thio)thiazol-2-yl)cyclohexane-1-carboxamide hydrochloride (130 mg, 0.3 mmol) in DMF (1 mL) was added HATU (228 mg, 0.6 mmol), (E)-4-(dimethylamino) but-2-enoic acid hydrochloride (100 mg, 0.6 mmol), and DIPEA (0.214 ml, 1.2 mmol). The resulting mixture was stirred at room temperature for 1 hour. Then it was diluted with EtOAc (100 mL), washed with water and brine, dried ($Na_2SO_4$), and concentrated. The residue was purified by an silica gel column to afford (48 mg, 33%) of the title compound as a white solid. MS m/z 506.26$[M+H]^+$. $^1$H NMR (400 MHz, DMSO-$d_6$) δ 12.27 (s, 1H), 8.00 (d, J=8.0 Hz, 1H), 7.39 (s, 1H), 6.73 (s, 1H), 6.54 (d, J=16.2 Hz, 1H), 6.01 (d, J=15.7 Hz, 1H), 4.06 (s, 2H), 3.63 (d, J=26.0 Hz, 2H), 3.03 (s, 2H), 2.60 (s, 1H), 2.17 (s, 6H), 1.91 (d, J=11.2 Hz, 1H), 1.79 (s, 3H), 1.30 (s, 4H), 1.18 (s, 9H).

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 hours and then concentrated under vacuum. The residue was diluted with $H_2O$ (150 mL). The pH of the solution was adjusted to 10 with 10% $Na_2CO_3$. The precipitate was filtered and washed with water to obtain (1.8 g, 58%) of the title compound (1) as a brown solid. MS m/z 158.95 $[M+H]^+$.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added $NaBH_4$ (0.87 g, 2.3 mmol) portionwise at room temperature. The Synthesis of B4
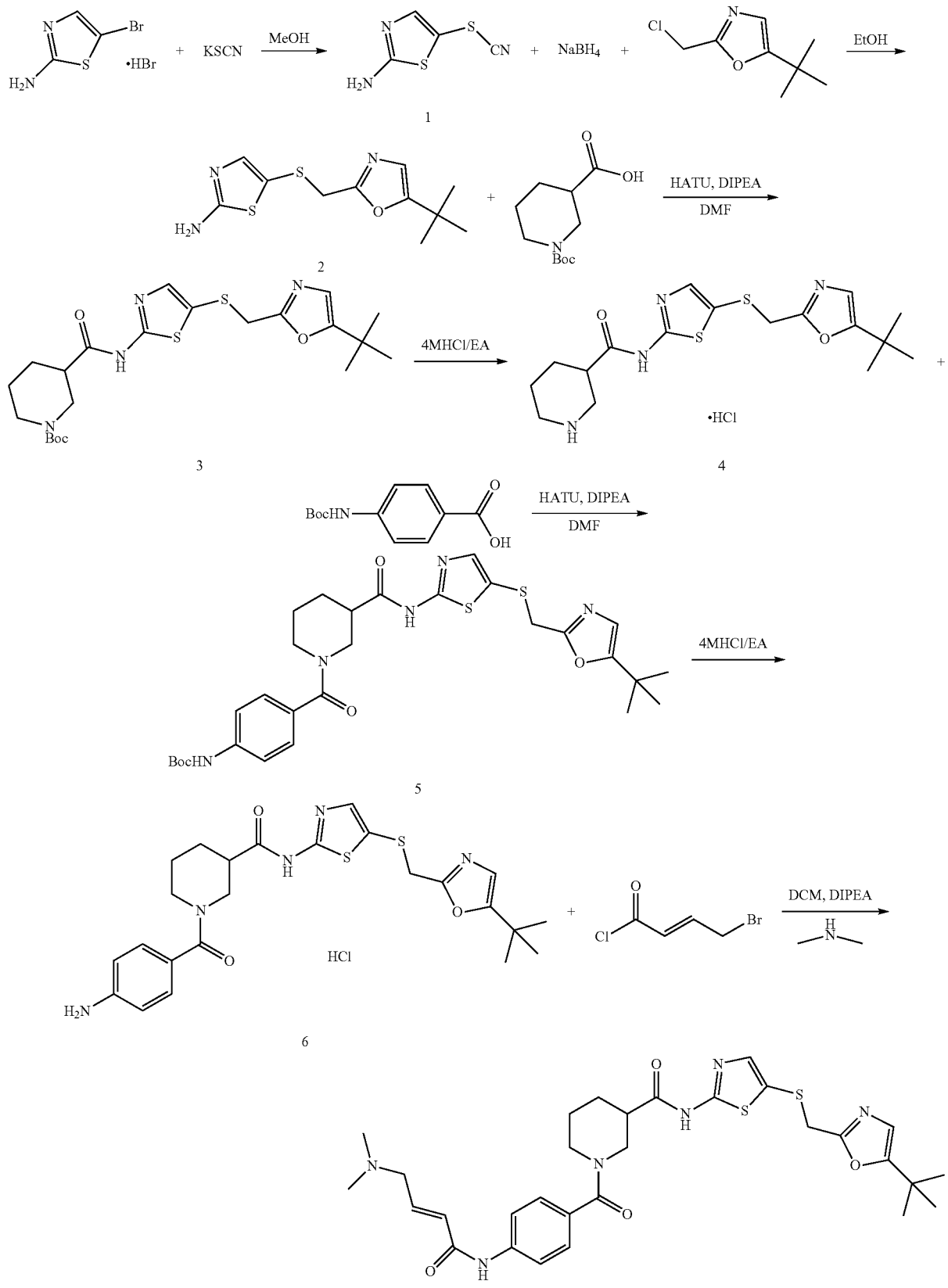

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 hours and then concentrated under vacuum. The residue was diluted with $H_2O$ (150 mL). The pH of the solution was adjusted to 10 with 10% $Na_2CO_3$. The precipitate was filtered and washed with water to obtain (1.8 g, 58%) of the title compound (1) as a brown solid. MS m/z 158.95 [M+H]$^+$.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added $NaBH_4$ (0.87 g, 2.3 mmol) portionwise at room temperature. The resulting mixture was stirred for 1 hour, and then acetone (20 ml) was slowly introduced. After 1 hour, a solution of 5-(tert-butyl)-2-(chloromethyl)oxazole (2.19 g, 12.6 mmol) in EtOH (10 ml) was added, and the resulting mixture was cooled, concentrated in vacuo, and then partitioned between EtOAc and brine, dried ($Na_2SO_4$), and concentrated. The residue was purified by an silica gel column to afford (2.1 g, 68%) of the title compound (2) as a pale red-brown solid. MS m/z 270.06 [M+H]$^+$.

tert-butyl 3-((5-(((5-(tert-butyl)oxazol-2-yl)methyl)thio)thiazol-2-yl)carbamoyl)piperidine-1-carboxylate (3)

To a solution of 5-(((5-(tert-butyl)oxazol-2-yl)methyl)thio)thiazol-2-amine (200 mg, 0.74 mmol) in DMF (2 mL) was added HATU (562 mg, 1.5 mmol), 1-(tert-butoxycarbonyl)piperidine-3-carboxylic acid (343 mg, 1.5 mmol), and DIPEA (0.54 ml, 3 mmol). The resulting mixture was stirred at room temperature for 1 hour. Then it was diluted with EtOAc (150 mL), washed with water and brine, dried ($Na_2SO_4$), and concentrated. The residue was purified by an silica gel column to afford (260 mg, 73%) of the title compound (3) as a white solid. MS m/z 481.19[M+H]$^+$.

N-(5-(((5-(tert-butyl)oxazol-2-yl)methyl)thio)thiazol-2-yl)piperidine-3-carboxamide hydrochloride (4)

To a solution of tert-butyl 3-((5-(((5-(tert-butyl)oxazol-2-yl)methyl)thio)thiazol-2-yl)carbamoyl)piperidine-1-carboxylate (260 mg, 0.54 mmol) in 4 M HCl EtOAc (5 mL). The resulting mixture was stirred at room temperature for 30 min. Then it was concentrated under vacuum to afford (180 mg, 80%) of the title compound (4) as a white solid, which was used without further purification. MS m/z 381.14 [M+H]$^+$.

tert-butyl (4-(3-((5-(((5-(tert-butyl)oxazol-2-yl)methyl)thio)thiazol-2-yl)carbamoyl)piperidine-1-carbonyl)phenyl)carbamate (5)

To a solution of N-(5-(((5-(tert-butyl)oxazol-2-yl)methyl)thio)thiazol-2-yl)piperidine-3-carboxamide hydrochloride (180 mg, 0.43 mmol) in DMF (2 mL) was added HATU (329 mg, 0.86 mmol), 4-((tert-butoxycarbonyl)amino)benzoic acid (205 mg, 0.86 mmol), and DIPEA (0.38 ml, 2.15 mmol). The resulting mixture was stirred at room temperature for 1 hour. Then it was diluted with EtOAc (100 mL), washed with water and brine, dried ($Na_2SO_4$), and concentrated. The residue was purified by an silica gel column to afford (80 mg, 31%) of the title compound (5) as a white solid. MS m/z 600.23[M+H]$^+$.

1-(4-aminobenzoyl)-N-(5-(((5-(tert-butyl)oxazol-2-yl)methyl)thio)thiazol-2-yl)piperidine-3-carboxamide hydrochloride (6)

To a solution of tert-butyl (4-(3-((5-(((5-(tert-butyl)oxazol-2-yl)methyl)thio)thiazol-2-yl)carbamoyl)piperidine-1-carbonyl)phenyl)carbamate (80 mg, 0.133 mmol) in 4 M HCl EtOAc (3 mL). The resulting mixture was stirred at room temperature for 30 min. Then it was concentrated under vacuum to afford (65 mg, 91%) of the title compound (6) as a white solid, which was used without further purification. MS m/z 381.14 [M+H]$^+$.

(E)-N-(5-(((5-(tert-butyl)oxazol-2-yl)methyl)thio)thiazol-2-yl)-1-(4-(4-(dimethylamino)but-2-enamido)benzoyl)piperidine-3-carboxamide (B4)

To a solution of 1-(4-aminobenzoyl)-N-(5-(((5-(tert-butyl)oxazol-2-yl)methyl)thio)thiazol-2-yl)piperidine-3-carboxamide hydrochloride (0.60 g, 0.112 mmol) in DCM (5 mL) was added DIPEA (0.2 ml, 1.34 mmol) and (E)-4-bromobut-2-enoyl chloride (22.5 mg, 0.134 mmol) at 0° C. for 3 min. Then it was added 4.0 M dimethylamine in THF (2 mL). The resulting mixture was stirred at room temperature for 2 hours. Then it was concentrated and purified by an silica gel column to afford (8 mg, 11.7%) of the title compound as a slightly white solid. MS m/z 611.24 [M+H]$^+$. $^1$H NMR (400 MHz, DMSO-d$_6$) δ 12.42 (s, 1H), 10.66 (s, 2H), 7.77 (s, 2H), 7.40 (s, 3H), 6.83 (s, 1H), 6.72 (s, 1H), 6.51 (d, J=15.1 Hz, 1H), 4.52-4.17 (m, 1H), 4.07 (s, 2H), 3.63 (s, 1H), 3.08 (s, 2H), 2.77 (s, 6H), 2.02 (s, 2H), 1.72 (s, 3H), 1.46 (s, 2H), 1.19 (s, 9H).

Synthesis of B5

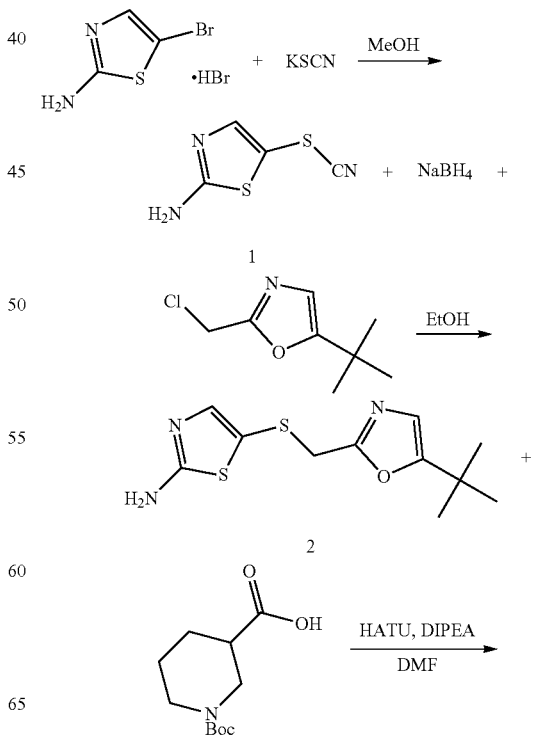

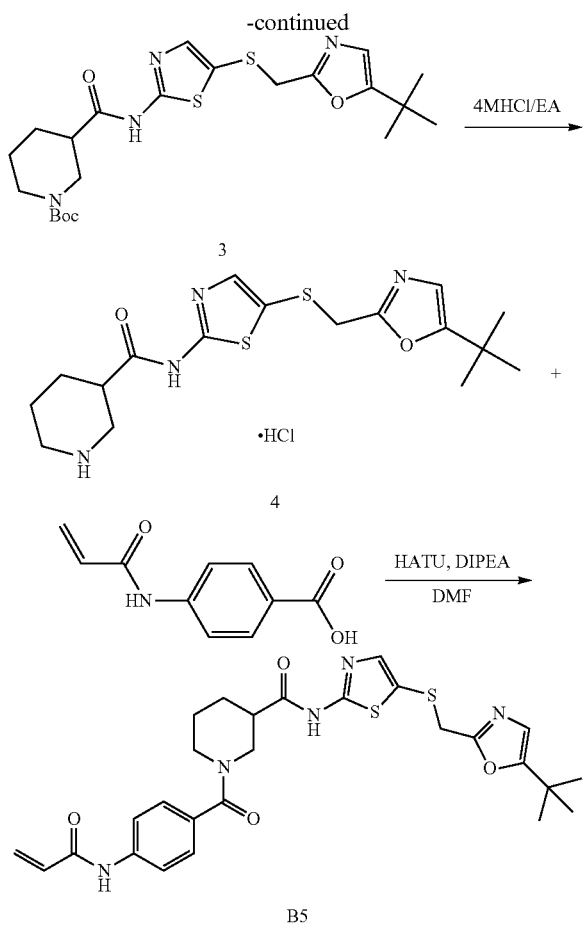

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 hours and then concentrated under vacuum. The residue was diluted with $H_2O$ (150 mL). The pH of the solution was adjusted to 10 with 10% $Na_2CO_3$. The precipitate was filtered and washed with water to obtain (1.8 g, 58%) of the title compound (1) as a brown solid. MS m/z 158.95 $[M+H]^+$.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added $NaBH_4$ (0.87 g, 2.3 mmol) portionwise at room temperature. The resulting mixture was stirred for 1 hour, and then acetone (20 ml) was slowly introduced. After 1 hour, a solution of 5-(tert-butyl)-2-(chloromethyl)oxazole (2.19 g, 12.6 mmol) in EtOH (10 ml) was added, and the resulting mixture was cooled, concentrated in vacuo, and then partitioned between EtOAc and brine, dried ($Na_2SO_4$), and concentrated. The residue was purified by an silica gel column to afford (2.1 g, 68%) of the title compound (2) as a pale red-brown solid. MS m/z 270.06 $[M+H]^+$.

tert-butyl 3-((5-(((5-(tert-butyl)oxazol-2-yl)methyl)thio)thiazol-2-yl)carbamoyl)piperidine-1-carboxylate (3)

To a solution of 5-(((5-(tert-butyl)oxazol-2-yl)methyl)thio)thiazol-2-amine (65 mg, 0.24 mmol) in DMF (2 mL) was added HATU (183 mg, 0.48 mmol), 1-(tert-butoxycarbonyl)piperidine-3-carboxylic acid (83 mg, 0.36 mmol) and DIPEA (126 mg, 0.96 mmol). The resulting mixture was stirred at room temperature for 1 hour. Then it was diluted with EtOAc (100 mL), washed with water and brine, dried ($Na_2SO_4$), and concentrated. The residue was purified by an silica gel column to afford (23 mg, 20%) of the title compound (3) as a white solid. MS m/z 481.19$[M+H]^+$.

N-(5-(((5-(tert-butyl)oxazol-2-yl)methyl)thio)thiazol-2-yl)piperidine-3-carboxamide hydrochloride (4)

To a solution of tert-butyl 3-((5-(((5-(tert-butyl)oxazol-2-yl)methyl)thio)thiazol-2-yl)carbamoyl)piperidine-1-carboxylate (23 mg, 0.048 mmol) in 4 M HCl EtOAc (2 mL). The resulting mixture was stirred at room temperature for 30 min. Then it was concentrated under vacuum to afford (16 mg, 80%) of the title compound (4) as a white solid, which was used without further purification. MS m/z 381.14 $[M+H]+$.

1-(4-acrylamidobenzoyl)-N-(5-(((5-(tert-butyl)oxazol-2-yl)methyl)thio)thiazol-2-yl)piperidine-3-carboxamide (B5)

To a solution of N-(5-(((5-(tert-butyl)oxazol-2-yl)methyl)thio)thiazol-2-yl)piperidine-3-carboxamide hydrochloride (50 mg, 0.12 mmol) in DMF (1 mL) was added HATU (92 mg, 0.24 mmol), 4-acrylamidobenzoic acid (46 mg, 0.24 mmol), and DIPEA (0.22 ml, 1.2 mmol). The resulting mixture was stirred at room temperature for 1 hour. Then it was diluted with EtOAc (100 mL), washed with water and brine, dried ($Na_2SO_4$), and concentrated. The residue was purified by an silica gel column to afford (8 mg, 12%) of the title compound as a white solid. MS m/z 554.21 $[M+H]^+$. $^1H$ NMR (400 MHz, DMSO-$d_6$) δ 12.37 (s, 1H), 7.73 (d, J=7.8 Hz, 2H), 7.55-7.22 (m, 3H), 6.71 (s, 1H), 6.44 (dd, J=16.9, 10.3 Hz, 1H), 6.28 (d, J=16.8 Hz, 1H), 5.78 (d, J=9.9 Hz, 1H), 4.05 (s, 2H), 3.67 (s, 1H), 3.05 (s, 2H), 2.69 (s, 1H), 1.97 (s, 1H), 1.70 (d, J=12.1 Hz, 2H), 1.44 (s, 1H), 1.23 (s, 2H), 1.12 (s, 9H).

Synthesis of B6

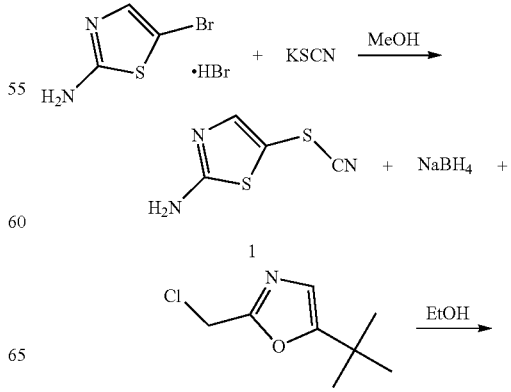

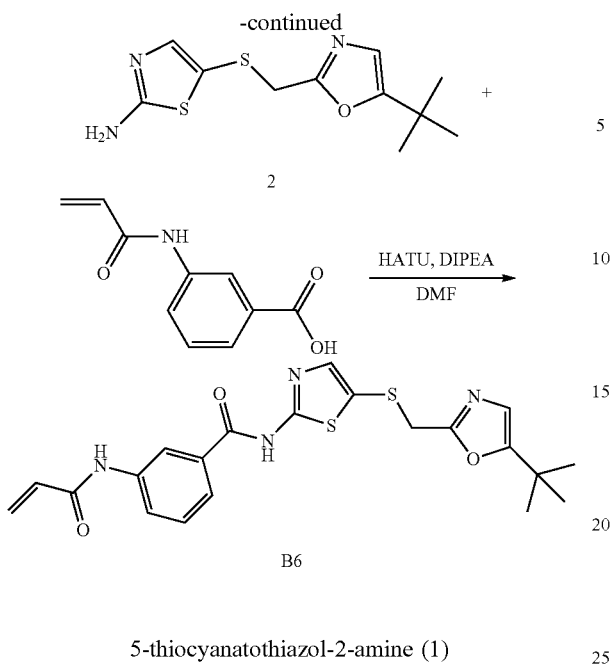

1H), 6.44 (d, J=16.8 Hz, 1H), 6.32 (dd, J=16.8, 10.0 Hz, 1H), 5.76 (d, J=10.0 Hz, 1H), 3.95 (s, 2H), 1.23 (s, 9H).

Synthesis of B7

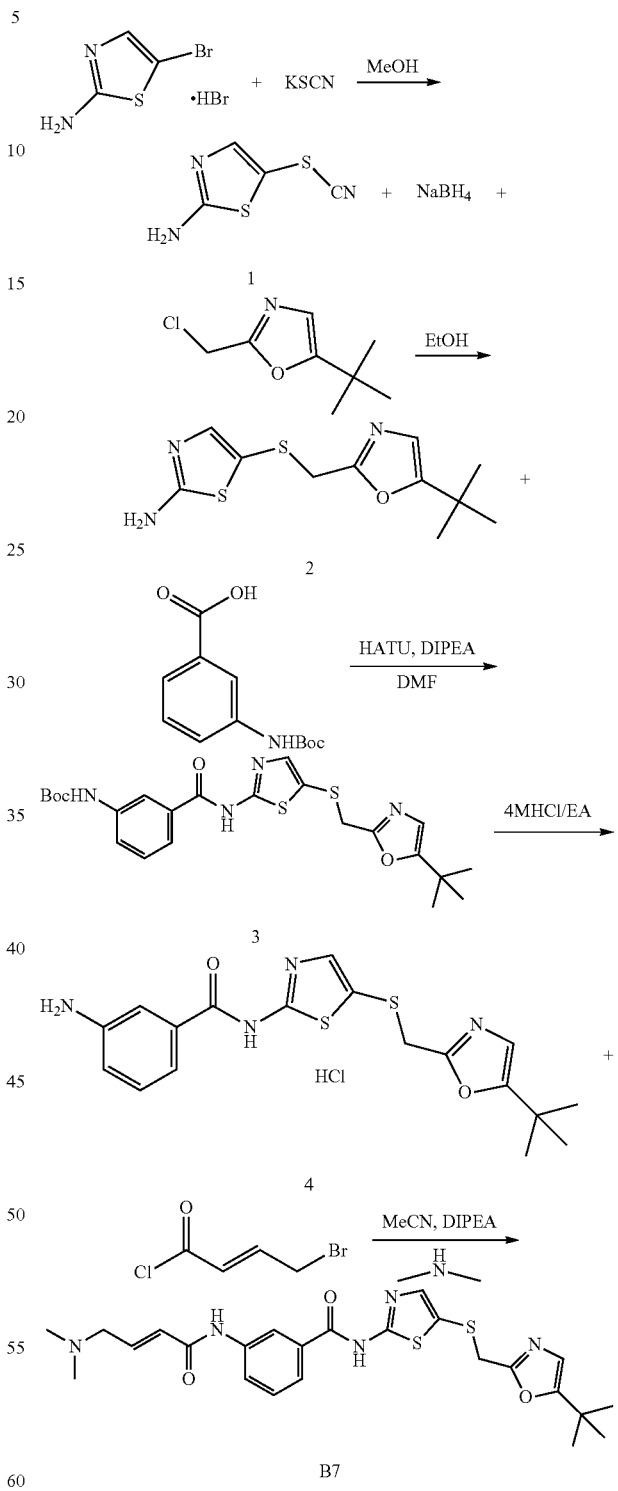

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 hours and then concentrated under vacuum. The residue was diluted with $H_2O$ (150 mL). The pH of the solution was adjusted to 10 with 10% $Na_2CO_3$. The precipitate was filtered and washed with water to obtain (1.8 g, 58%) of the title compound (1) as a brown solid. MS m/z 158.95 $[M+H]^+$.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added $NaBH_4$ (0.87 g, 2.3 mmol) portionwise at room temperature. The resulting mixture was stirred for 1 hour, and then acetone (20 ml) was slowly introduced. After 1 hour, a solution of 5-(tert-butyl)-2-(chloromethyl)oxazole (2.19 g, 12.6 mmol) in EtOH (10 ml) was added, and the resulting mixture was cooled, concentrated in vacuo, and then partitioned between EtOAc and brine, dried ($Na_2SO_4$), and concentrated. The residue was purified by an silica gel column to afford (2.1 g, 68%) of the title compound (2) as a pale red-brown solid. MS m/z 270.06 $[M+H]^+$.

3-acrylamido-N-(5-(((5-(tert-butyl)oxazol-2-yl)methyl)thio)thiazol-2-yl)benzamide (B6)

To a solution of 5-(((5-(tert-butyl)oxazol-2-yl)methyl)thio)thiazol-2-amine (54 mg, 0.2 mmol) in DMF (1 mL) was added HATU (160 mg, 0.42 mmol), 3-acrylamidobenzoic acid (60 mg, 0.31 mmol), and DIPEA (52 mg, 0.4 mmol). The resulting mixture was stirred at room temperature for 1 hour. Then it was diluted with EtOAc (100 mL), washed with water and brine, dried ($Na_2SO_4$), and concentrated. The residue was purified by an silica gel column to afford (7 mg, 8%) of the title compound as a white solid. MS m/z 443.12$[M+H]^+$. $^1H$ NMR (400 MHz, $CDCl_3$) δ 12.36 (s, 1H), 9.08 (s, 1H), 8.24-7.99 (m, 2H), 7.90 (s, 1H), 7.63 (d, J=7.6 Hz, 1H), 7.41 (t, J=7.9 Hz, 1H), 6.95 (s, 1H), 6.55 (s,

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 hours and then concentrated under vacuum. The residue was diluted with H₂O (150 mL). The pH of the solution was adjusted to 10 with 10% Na₂CO₃. The precipitate was filtered and washed with water to obtain (1.8 g, 58%) of the title compound (1) as a brown solid. MS m/z 158.95 [M+H]⁺.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added NaBH₄ (0.87 g, 2.3 mmol) portionwise at room temperature. The resulting mixture was stirred for 1 hour, and then acetone (20 ml) was slowly introduced. After 1 hour, a solution of 5-(tert-butyl)-2-(chloromethyl)oxazole (2.19 g, 12.6 mmol) in EtOH (10 ml) was added, and the resulting mixture was cooled, concentrated in vacuo, and then partitioned between EtOAc and brine, dried (Na₂SO₄), and concentrated. The residue was purified by an silica gel column to afford (2.1 g, 68%) of the title compound (2) as a pale red-brown solid. MS m/z 270.06 [M+H]⁺.

tert-butyl (3-((5-(((5-(tert-butyl)oxazol-2-yl)methyl)thio)thiazol-2-yl)carbamoyl)phenyl)carbamate (3)

To a solution of 5-(((5-(tert-butyl)oxazol-2-yl)methyl)thio)thiazol-2-amine (404 mg, 1.5 mmol) in DMF (2 mL) was added HATU (1.14 g, 3 mmol), 3-((tert-butoxycarbonyl)amino)benzoic acid (573 mg, 3 mmol), and DIPEA (1.05 ml, 6 mmol). The resulting mixture was stirred at room temperature for 1 hour. Then it was diluted with EtOAc (200 mL), washed with water and brine, dried (Na₂SO₄), and concentrated. The residue was purified by an silica gel column to afford (490 mg, 67%) of the title compound (3) as a white solid. MS m/z 489.15[M+H]⁺.

3-amino-N-(5-(((5-(tert-butyl)oxazol-2-yl)methyl)thio)thiazol-2-yl)benzamide hydrochloride (4)

To a solution of tert-butyl (3-((5-(((5-(tert-butyl)oxazol-2-yl)methyl)thio)thiazol-2-yl)carbamoyl)phenyl)carbamate (245 mg, 0.5 mmol) in 4 M HCl EtOAc (5 mL). The resulting mixture was stirred at room temperature for 30 min. Then it was concentrated under vacuum to afford (212 mg, 100%) of the title compound (4) as a white solid, which was used without further purification. MS m/z 389.11 [M+H]⁺.

(E)-N-(5-(((5-(tert-butyl)oxazol-2-yl)methyl)thio)thiazol-2-yl)-3-(4-(dimethylamino)but-2-enamido)benzamide (B7)

To a solution of 3-amino-N-(5-(((5-(tert-butyl)oxazol-2-yl)methyl)thio)thiazol-2-yl)benzamide hydrochloride (83 mg, 0.195 mmol) in MeCN (5 mL) was added DIPEA (77.6 mg, 0.6 mmol), and (E)-4-bromobut-2-enoyl chloride (40.26 mg, 0.22 mmol) at 0° C. for 3 min. Then it was added 4.0 M dimethylamine in THF (1 mL). The resulting mixture was stirred at room temperature for 2 hours. Then it was concentrated and purified by an silica gel column to afford (7 mg, 7.2%) of the title compound as a slightly yellow solid. MS m/z 500.18 [M+H]⁺. ¹H NMR (400 MHz, CDCl₃) δ 8.82 (s, 1H), 8.01 (d, J=16.7 Hz, 2H), 7.64 (s, 1H), 7.42 (s, 1H), 7.10 (s, 1H), 7.00 (s, 1H), 6.58 (s, 1H), 6.24 (d, J=13.7 Hz, 1H), 3.96 (s, 2H), 3.16 (s, 2H), 2.31 (s, 6H), 1.26 (s, 9H).

Synthesis of B8

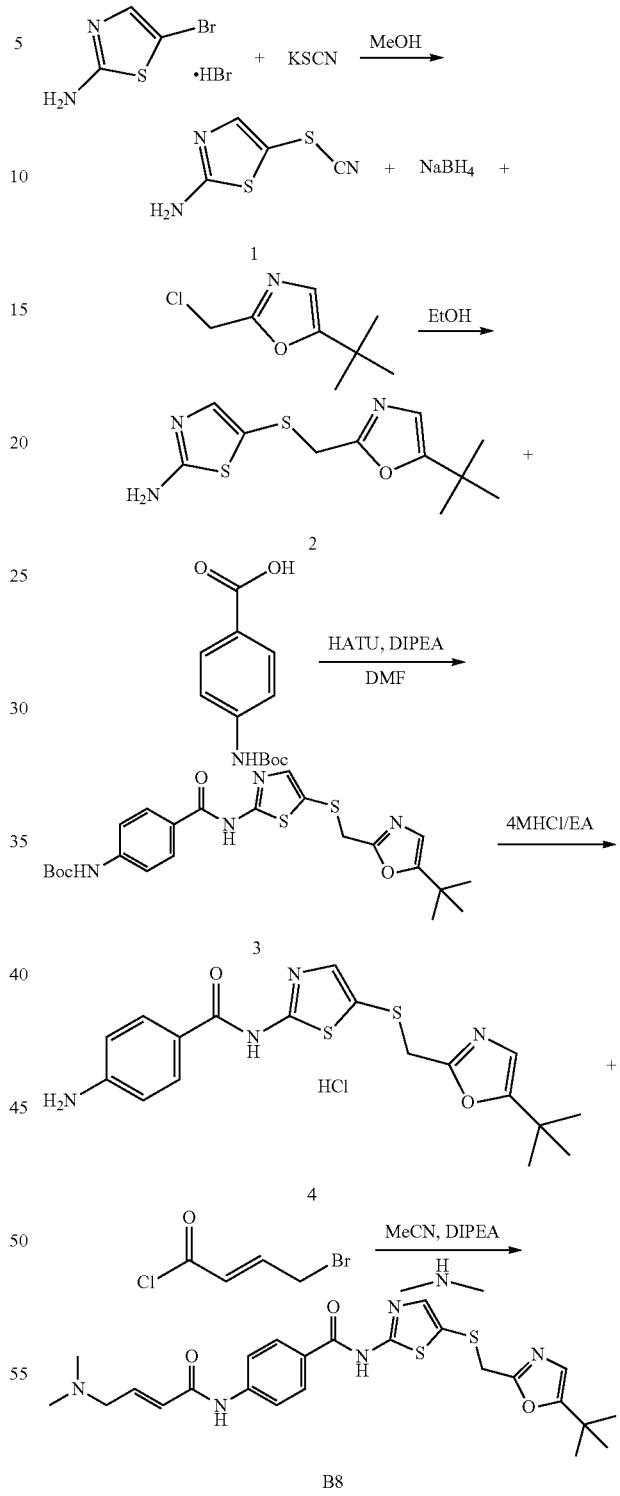

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 h and then concentrated under vacuum. The residue was diluted with H$_2$O (150 mL). The pH of the solution was adjusted to 10 with 10% Na$_2$CO$_3$. The precipitate was filtered and washed with water to obtain (1.8 g, 58%) of the title compound (1) as a brown solid. MS m/z 158.95 [M+H]$^+$.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added NaBH$_4$ (0.87 g, 2.3 mmol) portionwise at room temperature. The resulting mixture was stirred for 1 hour, and then acetone (20 mL) was slowly introduced. After 1 hour, a solution of 5-(tert-butyl)-2-(chloromethyl)oxazole (2.19 g, 12.6 mmol) in EtOH (10 mL) was added, and the resulting mixture was cooled, concentrated in vacuo, and then partitioned between EtOAc and brine, dried (Na$_2$SO$_4$), and concentrated. The residue was purified by an silica gel column to afford (2.1 g, 68%) of the title compound (2) as a pale red-brown solid. MS m/z 270.06 [M+H]$^+$.

tert-butyl (4-((5-(((5-(tert-butyl)oxazol-2-yl)methyl) thio)thiazol-2-yl)carbamoyl)phenyl)carbamate (3)

To a solution of 5-(((5-(tert-butyl)oxazol-2-yl)methyl) thio)thiazol-2-amine (220 mg, 0.82 mmol) in DMF (1 mL) was added HATU (623 mg, 1.64 mmol), 4-((tert-butoxycarbonyl)amino)benzoic acid (390 mg, 1.64 mmol) and DIPEA (0.6 ml, 3.28 mmol). The resulting mixture was stirred at room temperature for 1 hour. Then it was diluted with EtOAc (150 mL), washed with water and brine, dried (Na$_2$SO$_4$), and concentrated. The residue was purified by an silica gel column to afford (200 mg, 50%) of the title compound (3) as a white solid. MS m/z 489.15[M+H]$^+$.

4-amino-N-(5-(((5-(tert-butyl)oxazol-2-yl)methyl) thio)thiazol-2-yl)benzamide hydrochloride (4)

To a solution of tert-butyl (4-((5-(((5-(tert-butyl)oxazol-2-yl)methyl)thio)thiazol-2-yl)carbamoyl)phenyl)carbamate (200 mg, 0.41 mmol) in 4 M HCl EtOAc (5 mL). The resulting mixture was stirred at room temperature for 30 min. Then it was concentrated under vacuum to afford (174 mg, 100%) of the title compound (4) as a white solid, which was used without further purification. MS m/z 389.11 [M+H]$^+$.

(E)-N-(5-(((5-(tert-butyl)oxazol-2-yl)methyl)thio) thiazol-2-yl)-4-(4-(dimethylamino)but-2-enamido) benzamide (B8)

To a solution of 4-amino-N-(5-(((5-(tert-butyl)oxazol-2-yl)methyl)thio)thiazol-2-yl)benzamide hydrochloride (75 mg, 0.177 mmol) in MeCN (5 mL) was added DIPEA (0.3 ml, 2.6 mmol) and (E)-4-bromobut-2-enoyl chloride (46.85 mg, 0.256 mmol) at 0° C. for 3 min. Then it was added 4.0 M dimethylamine in THF (1 mL). The resulting mixture was stirred at room temperature for 2 hours. Then it was concentrated and purified by an silica gel column to afford (7 mg, 8%) of the title compound as a slightly yellow solid. MS m/z 500.18 [M+H]$^+$. $^1$H NMR (400 MHz, CDCl$_3$) δ 8.57 (s, 1H), 7.90 (d, J=7.3 Hz, 2H), 7.76 (s, 2H), 7.19 (s, 1H), 7.05 (s, 1H), 6.61 (s, 1H), 6.23 (d, J=15.5 Hz, 1H), 3.98 (s, 2H), 3.18 (s, 2H), 2.34 (s, 6H), 1.27 (s, 9H).
Synthesis of B9

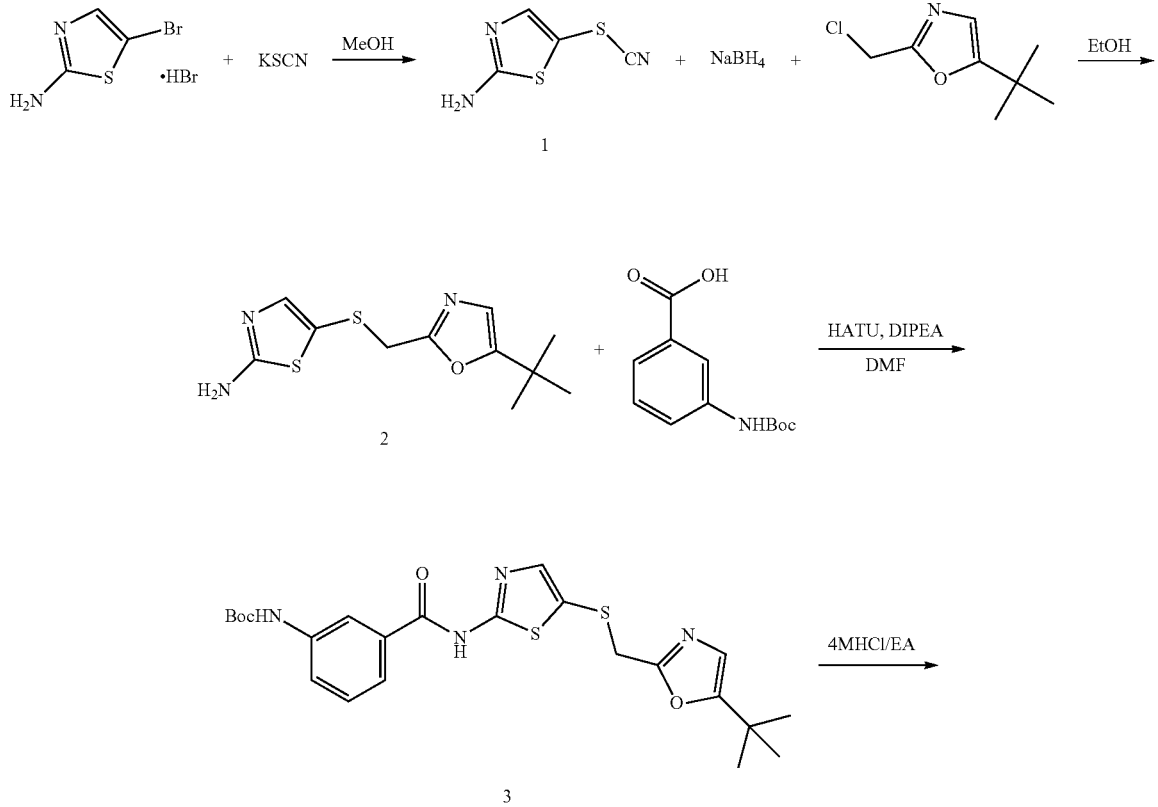

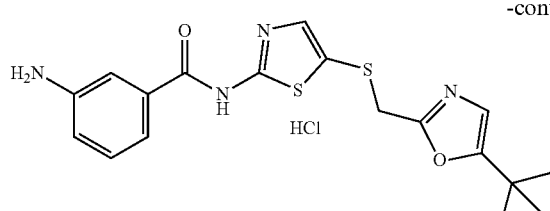

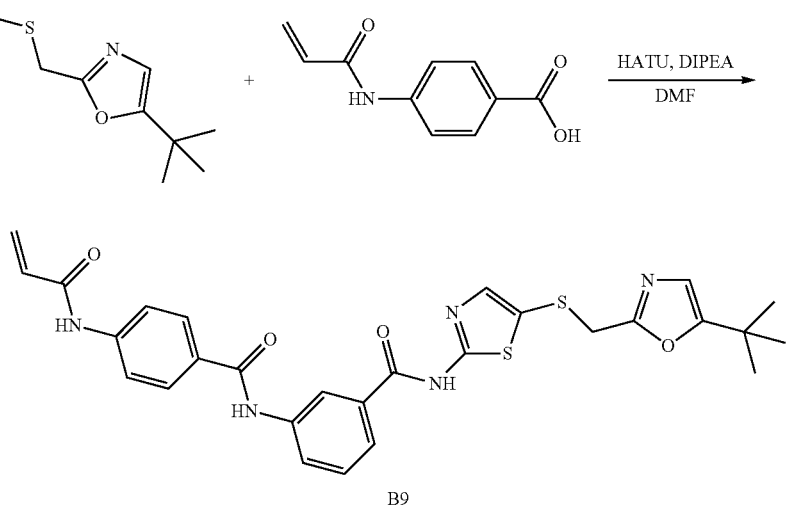

5-thiocyanatothiazol-2-amine (1)

To a solution of 5-bromothiazol-2-amine hydrobromide (5.2 g, 20 mmol) in methanol (100 mL) was added KSCN (19.5 g, 200 mmol) at room temperature. The resulting mixture was stirred for 20 h and then concentrated under vacuum. The residue was diluted with H$_2$O (150 mL). The pH of the solution was adjusted to 10 with 10% Na$_2$CO$_3$. The precipitate was filtered and washed with water to obtain (1.8 g, 58%) of the title compound (1) as a brown solid. MS m/z 158.95 [M+H]$^+$.

5-(((5-(tert-butyl)oxazol-2-yl)methyl)thio)thiazol-2-amine (2)

To a solution of 5-thiocyanatothiazol-2-amine (1.8 g, 11.46 mmol) in absolute EtOH (50 mL) was added NaBH$_4$ (0.87 g, 2.3 mmol) portionwise at room temperature. The resulting mixture was stirred for 1 hour, and then acetone (20 mL) was slowly introduced. After 1 hour, a solution of 5-(tert-butyl)-2-(chloromethyl)oxazole (2.19 g, 12.6 mmol) in EtOH (10 mL) was added, and the resulting mixture was cooled, concentrated in vacuo, and then partitioned between EtOAc and brine, dried (Na$_2$SO$_4$), and concentrated. The residue was purified by an silica gel column to afford (2.1 g, 68%) of the title compound (2) as a pale red-brown solid. MS m/z 270.06 [M+H]$^+$.

tert-butyl (3-((5-(((5-(tert-butyl)oxazol-2-yl)methyl)thio)thiazol-2-yl)carbamoyl)phenyl)carbamate (3)

To a solution of 5-(((5-(tert-butyl)oxazol-2-yl)methyl)thio)thiazol-2-amine (404 mg, 1.5 mmol) in DMF (2 mL) was added HATU (1.14 g, 3 mmol), 3-((tert-butoxycarbonyl)amino)benzoic acid (573 mg, 3 mmol), and DIPEA (1.05 ml, 6 mmol). The resulting mixture was stirred at room temperature for 1 hour. Then it was diluted with EtOAc (200 mL), washed with water and brine, dried (Na$_2$SO$_4$), and concentrated. The residue was purified by an silica gel column to afford (490 mg, 67%) of the title compound (3) as a white solid. MS m/z 489.15 [M+H]$^+$.

3-amino-N-(5-(((5-(tert-butyl)oxazol-2-yl)methyl)thio)thiazol-2-yl)benzamide hydrochloride (4)

To a solution of tert-butyl (3-((5-(((5-(tert-butyl)oxazol-2-yl)methyl)thio)thiazol-2-yl)carbamoyl)phenyl)carbamate (245 mg, 0.5 mmol) in 4 M HCl EtOAc (5 mL). The resulting mixture was stirred at room temperature for 30 min. Then it was concentrated under vacuum to afford (212 mg, 100%) of the title compound (4) as a white solid, which was used without further purification. MS m/z 389.11 [M+H]$^+$.

3-(4-acrylamidobenzamido)-N-(5-(((5-(tert-butyl)oxazol-2-yl)methyl)thio)thiazol-2-yl)benzamide (B9)

To a solution of 3-amino-N-(5-(((5-(tert-butyl)oxazol-2-yl)methyl)thio)thiazol-2-yl)benzamide hydrochloride (212 mg, 0.5 mmol) in DMF (2 mL) was added HATU (380 mg, 1 mmol), 4-acrylamidobenzoic acid (191 mg, 1 mmol), and DIPEA (0.5 ml, 3 mmol). The resulting mixture was stirred at room temperature for 1 hour. Then it was diluted with EtOAc (200 mL), washed with water and brine, dried (Na$_2$SO$_4$), and concentrated. The residue was purified by an silica gel column to afford (93 mg, 34%) of the title compound as a white solid. MS m/z 562.18[M+H]$^+$. $^1$H NMR (400 MHz, DMSO-d$_6$) δ 12.83 (s, 1H), 10.47 (s, 1H), 10.40 (s, 1H), 8.46 (s, 1H), 8.00 (dd, J=15, 5.0 Hz, 3H), 7.83 (d, J=15.0 Hz, 3H), 7.52 (d, J=5.0 Hz, 2H), 6.75 (s, 1H), 6.46 (d, J=6.3 Hz, 1H), 6.31 (d, J=6.5 Hz, 1H), 5.82 (d, J=15.0 Hz, 1H), 4.12 (s, 2H), 1.22 (s, 9H).

Synthesis of B12

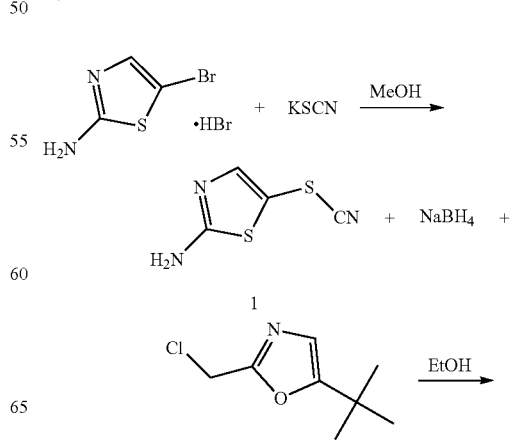

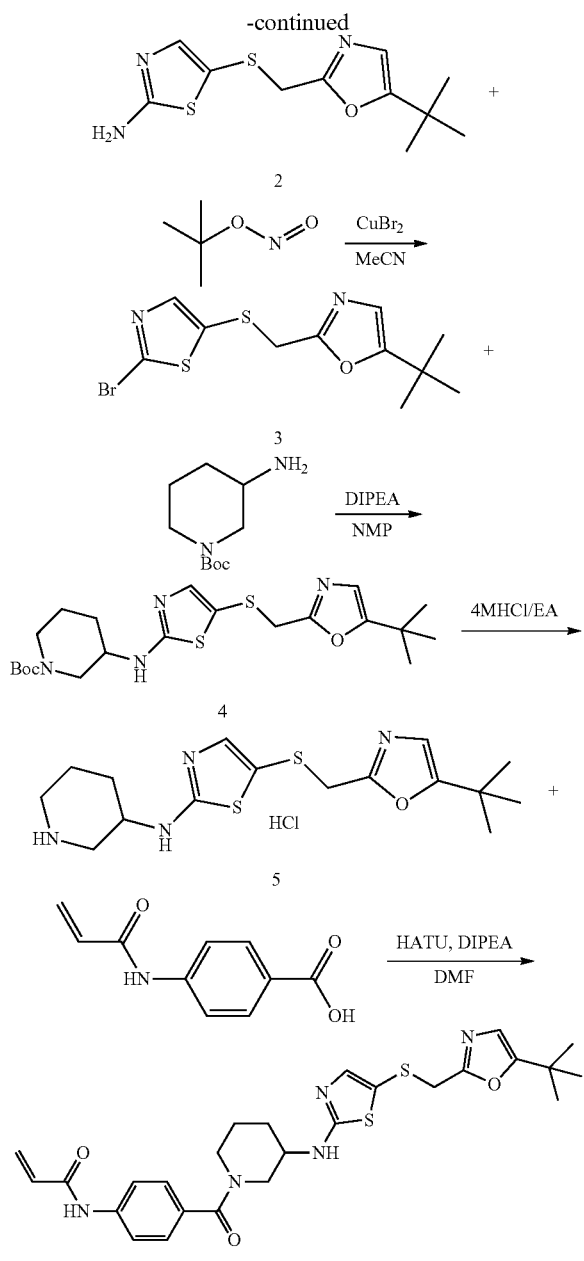

5-thiocyanatothiazol-2-amine (1)

To a solution of 5-bromothiazol-2-amine hydrobromide (26 g, 100 mmol) in methanol (500 mL) was added KSCN (50 g, 500 mmol) at room temperature. The resulting mixture was stirred for 20 hours and then concentrated under vacuum. The residue was diluted with H$_2$O (300 mL). The pH of the solution was adjusted to 10 with 10% Na$_2$CO$_3$. The precipitate was filtered and washed with water to obtain (8 g, 51%) of the title compound (1) as a brown solid. MS m/z 158.95 [M+H]$^+$.

5-(((5-(tert-butyl)oxazol-2-yl)methyl)thio)thiazol-2-amine (2)

To a solution of 5-thiocyanatothiazol-2-amine (2 g, 13 mmol) in absolute EtOH (50 mL) was added NaBH$_4$ (1 g, 26 mmol) portionwise at room temperature. The resulting mixture was stirred for 1 hour, and then acetone (20 mL) was slowly introduced. After 1 hour, a solution of 5-(tert-butyl)-2-(chloromethyl)oxazole (2.71 g, 15.6 mmol) in EtOH (10 mL) was added, and the resulting mixture was cooled, concentrated in vacuo, and then partitioned between EtOAc and brine, dried (Na$_2$SO$_4$), and concentrated. The residue was purified by an silica gel column to afford (2.8 g, 80%) of the title compound (2) as a pale red-brown solid. MS m/z 270.06 [M+H]$^+$.

2-(((2-bromothiazol-5-yl)thio)methyl)-5-(tert-butyl)oxazole (3)

To a solution of 5-(((5-(tert-butyl)oxazol-2-yl)methyl)thio)thiazol-2-amine (404 mg, 1.5 mmol) in MeCN (10 mL) was added tert-butyl nitrite (239 mg, 2.25 mmol) at 0° C. The resulting mixture was stirred for 10 min, and then CuBr$_2$ (402 mg, 1.8 mmol) was introduced. The resulting mixture was stirred at room temperature for 3 hours, the resulting mixture was concentrated in vacuo. The residue was purified by an silica gel column to afford (143 mg, 29%) of the title compound (3) as a pale yellow oil. MS m/z 333.96 [M+H]$^+$.

tert-butyl 3-((5-(((5-(tert-butyl)oxazol-2-yl)methyl)thio)thiazol-2-yl)amino)piperidine-1-carboxylate (4)

To a solution of 2-(((2-bromothiazol-5-yl)thio)methyl)-5-(tert-butyl)oxazole (80 mg, 0.22 mmol) in NMP (0.1 mL) was added tert-butyl 3-aminopiperidine-1-carboxylate (80 mg, 0.4 mmol) and DIPEA (0.084 ml, 0.48 mmol). The resulting mixture was heated at 140° C. for 8 hours. Then it was diluted with EtOAc (150 mL) at room temperature, washed with water and brine, dried (Na$_2$SO$_4$), and concentrated. The residue was purified by an silica gel column to afford (30 mg, 28%) of the title compound (4) as a slightly yellow solid. MS m/z 453.20 [M+H]$^+$.

5-(((5-(tert-butyl)oxazol-2-yl)methyl)thio)-N-(piperidin-3-yl)thiazol-2-amine hydrochloride (5)

To a solution of tert-butyl 3-((5-(((5-(tert-butyl)oxazol-2-yl)methyl)thio)thiazol-2-yl)amino)piperidine-1-carboxylate (38 mg, 0.084 mmol) in 4 M HCl EtOAc (5 mL). The resulting mixture was stirred at room temperature for 30 min. Then it was concentrated under vacuum to afford (35 mg, 98%) of the title compound (5) as a white solid, which was used without further purification. MS m/z 353.14 [M+H]$^+$.

N-(4-(3-((5-(((5-(tert-butyl)oxazol-2-yl)methyl)thio)thiazol-2-yl)amino)piperidine-1-carbonyl)phenyl)acrylamide (B12)

To a solution of 5-(((5-(tert-butyl)oxazol-2-yl)methyl)thio)-N-(piperidin-3-yl)thiazol-2-amine hydrochloride (35 mg, 0.082 mmol) in DMF (0.5 mL) was added HATU (62.4 mg, 0.164 mmol), 4-acrylamidobenzoic acid (31.5 mg, 0.164 mmol), and DIPEA (42.6 mg, 0.33 mmol). The resulting mixture was stirred at room temperature for 1 hour. Then it was diluted with EtOAc (70 mL), washed with water and brine, dried (Na$_2$SO$_4$), and concentrated. The residue was purified by an silica gel column to afford (5 mg, 12%) of the title compound as a white solid. MS m/z 526.21 [M+H]$^+$. $^1$H NMR (400 MHz, CDCl$_3$) δ 9.83 (s, 1H), 7.59 (d, J=7.2 Hz, 2H), 7.29 (s, 2H), 6.86 (s, 1H), 6.66 (s, 1H), 6.56 (s, 1H), 6.44 (d, J=16.9 Hz, 1H), 6.26 (s, 1H), 5.72 (s, 1H), 4.03 (s, 1H), 3.84 (s, 2H), 3.55 (s, 1H), 3.46 (d, J=31.2 Hz, 2H), 2.03 (s, 3H), 1.84 (s, 2H), 1.32 (s, 9H).

Synthesis of B15

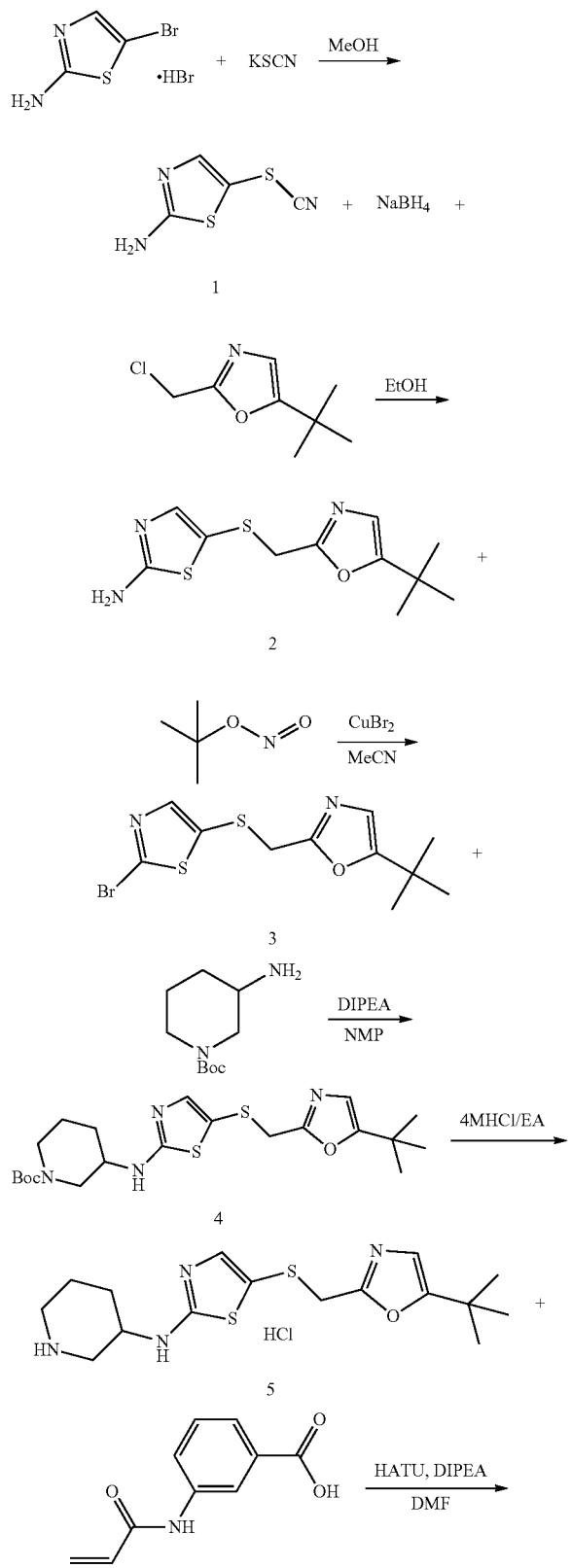

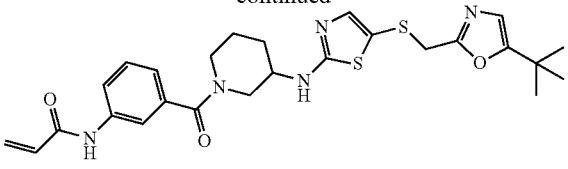

B15

5-thiocyanatothiazol-2-amine (1)

To a solution of 5-bromothiazol-2-amine hydrobromide (26 g, 100 mmol) in methanol (500 mL) was added KSCN (50 g, 500 mmol) at room temperature. The resulting mixture was stirred for 20 h and then concentrated under vacuum. The residue was diluted with $H_2O$ (300 mL). The pH of the solution was adjusted to 10 with 10% $Na_2CO_3$. The precipitate was filtered and washed with water to obtain (8 g, 51%) of the title compound (1) as a brown solid. MS m/z 158.95 $[M+H]^+$.

5-(((5-(tert-butyl)oxazol-2-yl)methyl)thio)thiazol-2-amine (2)

To a solution of 5-thiocyanatothiazol-2-amine (2 g, 13 mmol) in absolute EtOH (50 mL) was added $NaBH_4$ (1 g, 26 mmol) portionwise at room temperature. The resulting mixture was stirred for 1 hour, and then acetone (20 mL) was slowly introduced. After 1 hour, a solution of 5-(tert-butyl)-2-(chloromethyl)oxazole (2.71 g, 15.6 mmol) in EtOH (10 mL) was added, and the resulting mixture was cooled, concentrated in vacuo, and then partitioned between EtOAc and brine, dried ($Na_2SO_4$), and concentrated. The residue was purified by an silica gel column to afford (2.8 g, 80%) of the title compound (2) as a pale red-brown solid. MS m/z 270.06 $[M+H]^+$.

2-(((2-bromothiazol-5-yl)thio)methyl)-5-(tert-butyl)oxazole (3)

To a solution of 5-(((5-(tert-butyl)oxazol-2-yl)methyl)thio)thiazol-2-amine (2.02 g, 7.5 mmol) in MeCN (50 mL) was added tert-butyl nitrite (1.2 g, 11.7 mmol) at 0° C. The resulting mixture was stirred for 10 min, and then $CuBr_2$ (2.01 mg, 9 mmol) was introduced. The resulting mixture was stirred at room temperature for 3 hours, the resulting mixture was concentrated in vacuo. The residue was purified by an silica gel column to afford (0.6 g, 24%) of the title compound (3) as a pale yellow oil. MS m/z 333.96 $[M+H]^+$.

tert-butyl 3-((5-(((5-(tert-butyl)oxazol-2-yl)methyl)thio)thiazol-2-yl)amino)piperidine-1-carboxylate (4)

To a solution of 2-(((2-bromothiazol-5-yl)thio)methyl)-5-(tert-butyl)oxazole (0.6 g, 1.8 mmol) in NMP (0.6 mL) was added tert-butyl 3-aminopiperidine-1-carboxylate (0.72 mg, 3.6 mmol) and DIPEA (0.65 ml, 3.6 mmol). The resulting mixture was heated at 140° C. for 8 hours. Then it was diluted with EtOAc (200 mL) at room temperature, washed with water and brine, dried ($Na_2SO_4$), and concentrated. The residue was purified by an silica gel column to afford (150 mg, 18.5%) of the title compound (4) as a slightly yellow solid. MS m/z 453.20 $[M+H]^+$.

5-(((5-(tert-butyl)oxazol-2-yl)methyl)thio)-N-(piperidin-3-yl)thiazol-2-amine hydrochloride (5)

To a solution of tert-butyl 3-((5-(((5-(tert-butyl)oxazol-2-yl)methyl)thio)thiazol-2-yl)amino)piperidine-1-carboxylate (150 mg, 0.33 mmol) in 4 M HCl EtOAc (5 mL). The resulting mixture was stirred at room temperature for 30 min. Then it was concentrated under vacuum to afford (130 mg, 93%) of the title compound (5) as a white solid, which was used without further purification. MS m/z 353.14 [M+H]+.

N-(3-(3-((5-(((5-(tert-butyl)oxazol-2-yl)methyl)thio)thiazol-2-yl)amino)piperidine-1-carbonyl)phenyl)acrylamide (B12)

To a solution of 5-(((5-(tert-butyl)oxazol-2-yl)methyl)thio)-N-(piperidin-3-yl)thiazol-2-amine hydrochloride (55 mg, 0.13 mmol) in DMF (0.5 mL) was added HATU (99 mg, 0.26 mmol), 3-acrylamidobenzoic acid (49.7 mg, 0.26 mmol), and DIPEA (67 mg, 0.52 mmol). The resulting mixture was stirred at room temperature for 1 hour. Then it was diluted with EtOAc (70 mL), washed with water and brine, dried (Na$_2$SO$_4$), and concentrated. The residue was purified by an silica gel column to afford (12 mg, 18%) of the title compound as a white solid. MS m/z 526.21 [M+H]+. $^1$H NMR (400 MHz, CDCl$_3$) δ 9.41 (s, 1H), 7.85 (s, 1H), 7.57 (s, 1H), 7.07 (s, 1H), 6.86 (s, 1H), 6.64 (s, 1H), 6.45 (d, J=17.1 Hz, 1H), 6.41-6.20 (m, 1H), 5.73 (s, 1H), 5.55 (s, 1H), 4.03-3.80 (m, 2H), 3.71 (s, 1H), 3.56 (s, 2H), 2.04 (s, 2H), 1.85 (s, 4H), 1.29 (s, 9H).

Synthesis of B16

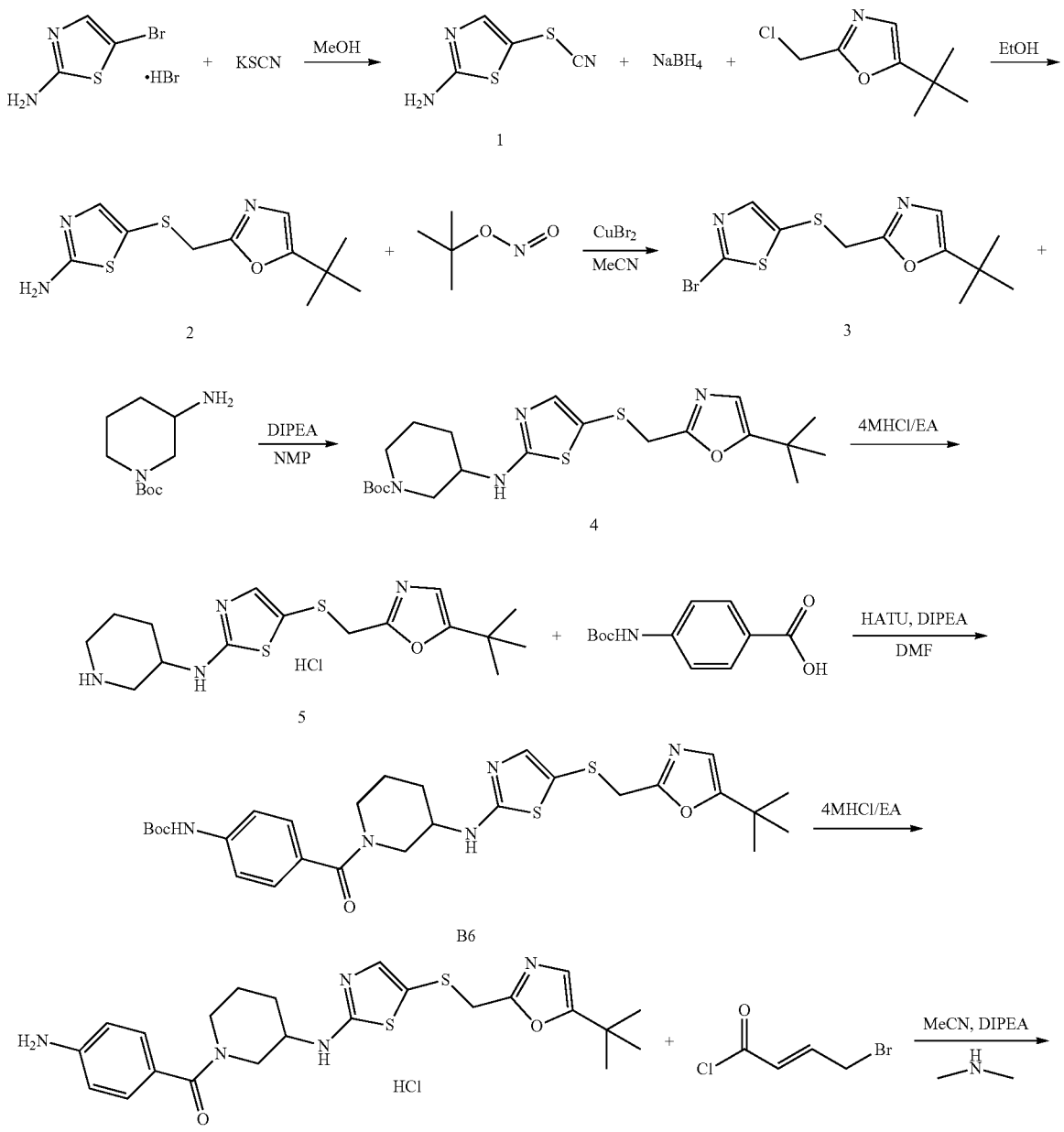

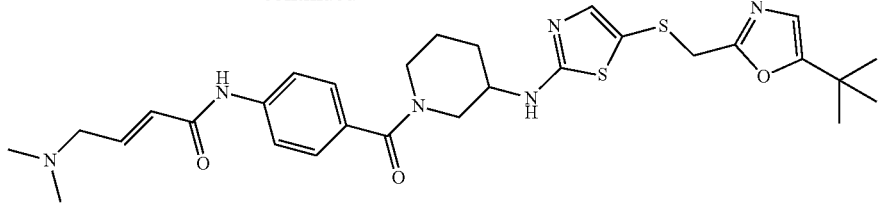

B16

5-thiocyanatothiazol-2-amine (1)

To a solution of 5-bromothiazol-2-amine hydrobromide (26 g, 100 mmol) in methanol (500 mL) was added KSCN (50 g, 500 mmol) at room temperature. The resulting mixture was stirred for 20 hours and then concentrated under vacuum. The residue was diluted with H$_2$O (300 mL). The pH of the solution was adjusted to 10 with 10% Na$_2$CO$_3$. The precipitate was filtered and washed with water to obtain (8 g, 51%) of the title compound (1) as a brown solid. MS m/z 158.95 [M+H]$^+$.

5-(((5-(tert-butyl)oxazol-2-yl)methyl)thio)thiazol-2-amine (2)

To a solution of 5-thiocyanatothiazol-2-amine (2 g, 13 mmol) in absolute EtOH (50 mL) was added NaBH$_4$ (1 g, 26 mmol) portionwise at room temperature. The resulting mixture was stirred for 1 hour, and then acetone (20 mL) was slowly introduced. After 1 hour, a solution of 5-(tert-butyl)-2-(chloromethyl)oxazole (2.71 g, 15.6 mmol) in EtOH (10 mL) was added, and the resulting mixture was cooled, concentrated in vacuo, and then partitioned between EtOAc and brine, dried (Na$_2$SO$_4$), and concentrated. The residue was purified by an silica gel column to afford (2.8 g, 80%) of the title compound (2) as a pale red-brown solid. MS m/z 270.06 [M+H]$^+$.

2-(((2-bromothiazol-5-yl)thio)methyl)-5-(tert-butyl)oxazole (3)

To a solution of 5-(((5-(tert-butyl)oxazol-2-yl)methyl)thio)thiazol-2-amine (2.02 g, 7.5 mmol) in MeCN (50 mL) was added tert-butyl nitrite (1.2 g, 11.7 mmol) at 0° C. The resulting mixture was stirred for 10 min, and then CuBr$_2$ (2.01 mg, 9 mmol) was introduced. The resulting mixture was stirred at room temperature for 3 hours, the resulting mixture was concentrated in vacuo. The residue was purified by an silica gel column to afford (0.6 g, 24%) of the title compound (3) as a pale yellow oil. MS m/z 333.96 [M+H]$^+$.

tert-butyl 3-((5-(((5-(tert-butyl)oxazol-2-yl)methyl)thio)thiazol-2-yl)amino)piperidine-1-carboxylate (4)

To a solution of 2-(((2-bromothiazol-5-yl)thio)methyl)-5-(tert-butyl)oxazole (0.6 g, 1.8 mmol) in NMP (0.6 mL) was added tert-butyl 3-aminopiperidine-1-carboxylate (0.72 mg, 3.6 mmol) and DIPEA (0.65 ml, 3.6 mmol). The resulting mixture was heated at 140° C. for 8 hours. Then it was diluted with EtOAc (200 mL) at room temperature, washed with water and brine, dried (Na$_2$SO$_4$), and concentrated. The residue was purified by an silica gel column to afford (150 mg, 18.5%) of the title compound (4) as a slightly yellow solid. MS m/z 453.20 [M+H]$^+$.

5-(((5-(tert-butyl)oxazol-2-yl)methyl)thio)-N-(piperidin-3-yl)thiazol-2-amine hydrochloride (5)

To a solution of tert-butyl 3-((5-(((5-(tert-butyl)oxazol-2-yl)methyl)thio)thiazol-2-yl)amino)piperidine-1-carboxylate (150 mg, 0.33 mmol) in 4 M HCl EtOAc (5 mL). The resulting mixture was stirred at room temperature for 30 min. Then it was concentrated under vacuum to afford (130 mg, 93%) of the title compound (5) as a white solid, which was used without further purification. MS m/z 353.14 [M+H]$^+$.

tert-butyl (4-(3-((5-(((5-(tert-butyl)oxazol-2-yl)methyl)thio)thiazol-2-yl)amino)piperidine-1-carbonyl)phenyl)carbamate (6)

To a solution of 5-(((5-(tert-butyl)oxazol-2-yl)methyl)thio)-N-(piperidin-3-yl)thiazol-2-amine hydrochloride (65 mg, 0.153 mmol) in DMF (0.5 mL) was added HATU (118 mg, 0.31 mmol), 4-((tert-butoxycarbonyl)amino)benzoic acid (72 mg, 0.31 mmol), and DIPEA (79 mg, 0.612 mmol). The resulting mixture was stirred at room temperature for 1 hour. Then it was diluted with EtOAc (70 mL), washed with water and brine, dried (Na$_2$SO$_4$), and concentrated. The residue was purified by an silica gel column to afford (40 mg, 43%) of the title compound (6) as a white solid. MS m/z 572.22[M+H]$^+$.

(4-aminophenyl)(3-((5-(((5-(tert-butyl)oxazol-2-yl)methyl)thio)thiazol-2-yl)amino)piperidin-1-yl)methanone hydrochloride (7)

To a solution of tert-butyl (4-(3-((5-(((5-(tert-butyl)oxazol-2-yl)methyl)thio)thiazol-2-yl)amino)piperidine-1-carbonyl)phenyl)carbamate (40 mg, 0.07 mmol) in 4 M HCl EtOAc (1 mL). The resulting mixture was stirred at room temperature for 30 min. Then it was concentrated under vacuum to afford (35 mg, 93%) of the title compound (7) as a white solid, which was used without further purification. MS m/z 472.18 [M+H]$^+$.

(E)-N-(4-(3-((5-(((5-(tert-butyl)oxazol-2-yl)methyl)thio)thiazol-2-yl)amino)piperidine-1-carbonyl)phenyl)-4-(dimethylamino)but-2-enamide (B16)

To a solution of (4-aminophenyl)(3-((5-(((5-(tert-butyl)oxazol-2-yl)methyl)thio)thiazol-2-yl)amino)piperidin-1-yl)methanone hydrochloride (50 mg, 0.1 mmol) in MeCN (5 mL) was added DIPEA (65 mg, 0.5 mmol) and (E)-4-bromobut-2-enoyl chloride (22 mg, 0.12 mmol) at 0° C. for 3 min. Then it was added 4.0 M dimethylamine in THF (1 mL). The resulting mixture was stirred at room temperature for 2 hours. Then it was concentrated and purified by an silica gel column to afford (10 mg, 17%) of the title compound as a white solid. MS m/z 500.18 [M+H]$^+$. $^1$H NMR (400 MHz, MeOD) δ 7.72 (s, 2H), 7.41 (s, 2H), 7.01-6.88 (m, 1H), 6.74 (d, J=22.4 Hz, 2H), 3.94 (s, 2H), 3.86-3.68 (m, 4H), 3.50 (s, 1H), 3.27 (d, J=6.6 Hz, 2H), 2.44 (s, 6H), 2.23 (d, J=21.3 Hz, 1H), 2.13 (d, J=20.0 Hz, 1H), 1.98 (s, 2H), 1.72 (s, 2H), 1.45-1.40 (m, 9H).

Synthesis of B17

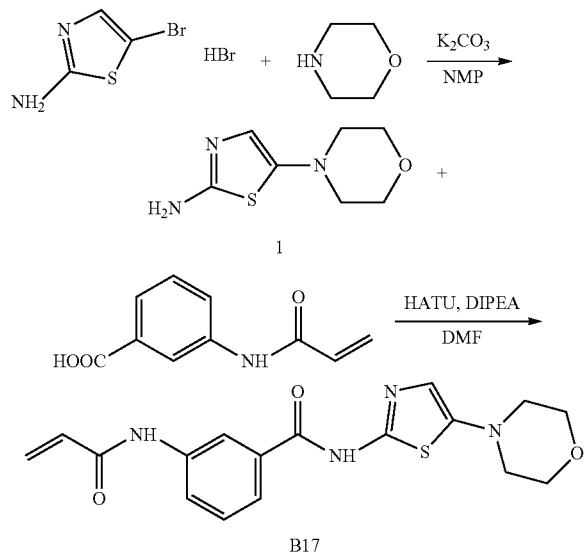

5-morpholinothiazol-2-amine (1)

To a mixture of 5-bromothiazol-2-amine hydrobromide (2.6 g, 10 mmol) and powdered potassium carbonate (2.77 g, 20 mmol) in NMP (5 mL) was added morpholine (1.73 mL, 20 mmol) under argon atmosphere and heated at 60° C. for 3 hours. Reaction mixture was cooled to room temperature and poured over ice cold water (100 mL), extracted with EtOAc (3×100 mL), washed with brine, dried over anhydrous sodium sulfate, filtered and concentrated under reduced pressure. The residue was purified by an silica gel column to afford (420 mg, 45.4%) of the title compound (1) as a brown solid. MS m/z 186.07[M+H]$^+$.

3-acrylamido-N-(5-morpholinothiazol-2-yl)benzamide (B17)

To a solution of 5-morpholinothiazol-2-amine (90 mg, 0.5 mmol) in DMF (0.5 mL) was added HATU (380 mg, 1 mmol), 3-acrylamidobenzoic acid (191 mg, 1 mmol), and DIPEA (129 mg, 1 mmol). The resulting mixture was stirred at room temperature for 1 hour. Then it was diluted with EtOAc (100 mL), washed with water and brine, dried (Na$_2$SO$_4$), and concentrated. The residue was purified by an silica gel column to afford (36 mg, 21%) of the title compound as a yellow solid. MS m/z 359.14 [M+H]$^+$. $^1$H NMR (400 MHz, DMSO-d$_6$) δ 12.30 (s, 1H), 10.37 (s, 1H), 8.29 (s, 1H), 7.91 (d, J=7.2 Hz, 1H), 7.78 (d, J=7.0 Hz, 1H), 7.49 (d, J=6.9 Hz, 1H), 6.78 (s, 1H), 6.47 (dd, J=15.8, 10.4 Hz, 1H), 6.31 (d, J=16.8 Hz, 1H), 5.81 (d, J=9.8 Hz, 1H), 3.75 (s, 4H), 3.05 (s, 4H).

Synthesis of B18

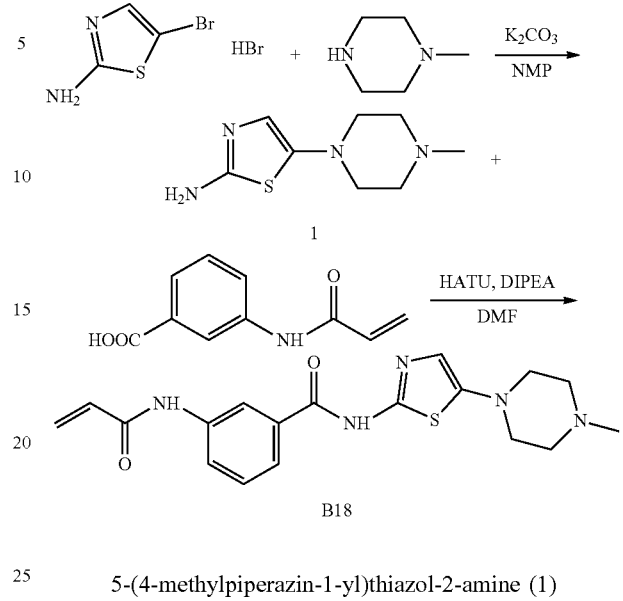

5-(4-methylpiperazin-1-yl)thiazol-2-amine (1)

To a mixture of 5-bromothiazol-2-amine hydrobromide (2.6 g, 10 mmol) and powdered potassium carbonate (2.77 g, 20 mmol) in NMP (5 mL) was added 1-methylpiperazine (2.25 mL, 20 mmol) under argon atmosphere and heated at 60° C. for 3 hours. Reaction mixture was filtered and concentrated under reduced pressure. The residue was purified by an silica gel column to afford (340 mg, 34.3%) of the title compound (1) as a brown solid. MS m/z 199.10 [M+H]$^+$.

3-acrylamido-N-(5-(4-methylpiperazin-1-yl)thiazol-2-yl)benzamide (B18)

To a solution of 5-(4-methylpiperazin-1-yl)thiazol-2-amine (99 mg, 0.5 mmol) in DMF (0.5 mL) was added HATU (380 mg, 1 mmol), 3-acrylamidobenzoic acid (191 mg, 1 mmol), and DIPEA (129 mg, 1 mmol). The resulting mixture was stirred at room temperature for 1 hour. Then it was purified by an silica gel column to afford (41 mg, 22%) of the title compound as a yellow solid. MS m/z 372.17 [M+H]$^+$. $^1$H NMR (400 MHz, DMSO-d$_6$) δ 12.22 (s, 1H), 10.35 (s, 1H), 8.28 (s, 1H), 7.91 (d, J=6.9 Hz, 1H), 7.78 (d, J=6.7 Hz, 1H), 7.47 (t, J=7.7 Hz, 1H), 6.71 (s, 1H), 6.47 (dd, J=16.8, 10.1 Hz, 1H), 6.31 (d, J=17.0 Hz, 1H), 5.88-5.68 (m, 1H), 3.06 (s, 4H), 2.47 (s, 4H), 2.22 (s, 3H).

Synthesis of B19

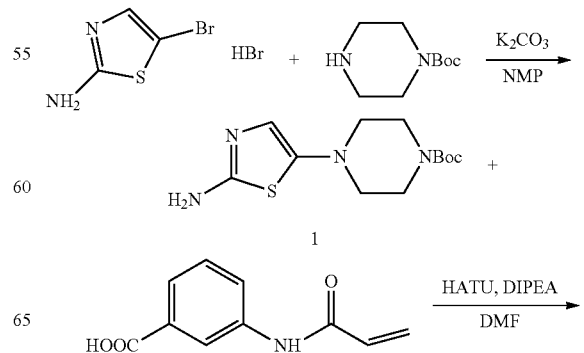

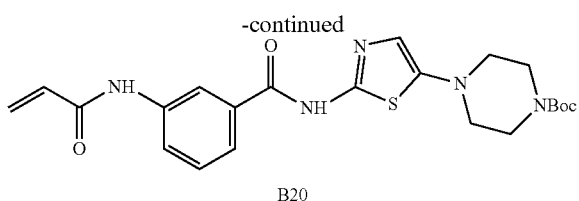

B20

5-(4-ethylpiperazin-1-yl)thiazol-2-amine (1)

To a mixture of 5-bromothiazol-2-amine hydrobromide (2.6 g, 10 mmol) and powdered potassium carbonate (2.77 g, 20 mmol) in NMP (5 mL) was added 1-ethylpiperazine (2.28 mL, 20 mmol) under argon atmosphere and heated at 60° C. for 3 hours. Reaction mixture was filtered and concentrated under reduced pressure. The residue was purified by an silica gel column to afford (382 mg, 36%) of the title compound (1) as a brown solid. MS m/z 213.11 [M+H]$^+$.

3-acrylamido-N-(5-(4-methylpiperazin-1-yl)thiazol-2-yl)benzamide (B19)

To a solution of 5-(4-ethylpiperazin-1-yl)thiazol-2-amine (106 mg, 0.5 mmol) in DMF (0.5 mL) was added HATU (380 mg, 1 mmol), 3-acrylamidobenzoic acid (191 mg, 1 mmol) and DIPEA (129 mg, 1 mmol). The resulting mixture was stirred at room temperature for 1 hour. Then it was purified by an silica gel column to afford (20 mg, 10.3%) of the title compound as a yellow solid. MS m/z 386.20 [M+H]$^+$. $^1$H NMR (400 MHz, DMSO-d$_6$) δ 12.23 (s, 1H), 10.35 (s, 1H), 8.29 (s, 1H), 7.91 (d, J=7.0 Hz, 1H), 7.79 (d, J=6.8 Hz, 1H), 7.49 (d, J=7.3 Hz, 1H), 6.72 (s, 1H), 6.58-6.43 (m, 1H), 6.31 (d, J=17.2 Hz, 1H), 5.81 (d, J=10.0 Hz, 1H), 3.07 (s, 4H), 2.52 (s, 4H), 2.38 (d, J=6.3 Hz, 2H), 1.03 (s, 3H).

Synthesis of B20

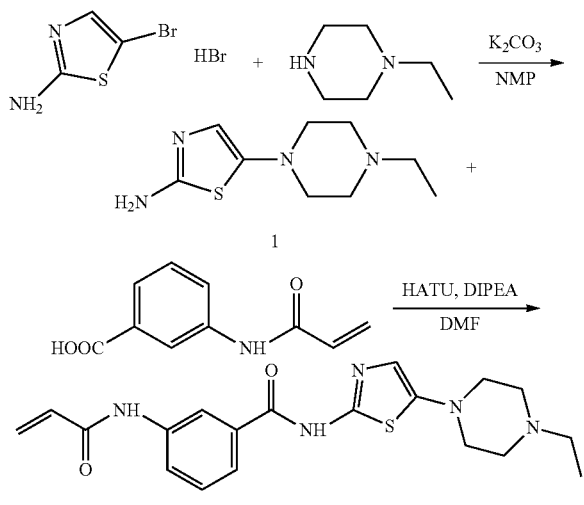

tert-butyl 4-(2-aminothiazol-5-yl)piperazine-1-carboxylate (1)

To a mixture of 5-bromothiazol-2-amine hydrobromide (2.6 g, 10 mmol) and powdered potassium carbonate (2.77 g, 20 mmol) in NMP (5 mL) was added tert-butyl piperazine-1-carboxylate (3.72 g, 20 mmol) under argon atmosphere and heated at 60° C. for 3 hours. Reaction mixture was cooled to room temperature and poured over ice cold water (100 mL), extracted with EtOAc (3×100 mL), washed with brine, dried over anhydrous sodium sulfate, filtered and concentrated under reduced pressure. The residue was purified by an silica gel column to afford (600 mg, 42.3%) of the title compound (1) as a brown solid. MS m/z 285.13[M+H]$^+$.

tert-butyl 4-(2-(3-acrylamidobenzamido)thiazol-5-yl)piperazine-1-carboxylate (B20)

To a solution of tert-butyl 4-(2-aminothiazol-5-yl)piperazine-1-carboxylate (142 mg, 0.5 mmol) in DMF (0.5 mL) was added HATU (380 mg, 1 mmol), 3-acrylamidobenzoic acid (191 mg, 1 mmol), and DIPEA (129 mg, 1 mmol). The resulting mixture was stirred at room temperature for 1 hour. Then it was diluted with EtOAc (100 mL), washed with water and brine, dried (Na$_2$SO$_4$), and concentrated. The residue was purified by an silica gel column to afford (31 mg, 13%) of the title compound as a yellow solid. MS m/z 458.25 [M+H]$^+$. $^1$H NMR (400 MHz, DMSO-d$_6$) δ 12.29 (s, 1H), 10.35 (s, 1H), 8.29 (s, 1H), 7.91 (d, J=7.5 Hz, 1H), 7.79 (d, J=7.4 Hz, 1H), 7.48 (t, J=7.9 Hz, 1H), 6.79 (s, 1H), 6.57-6.40 (m, 1H), 6.31 (d, J=16.6 Hz, 1H), 5.85-5.68 (m, 2H), 3.49 (s, 4H), 3.03 (s, 4H), 1.43 (s, 9H).

Synthesis of B22

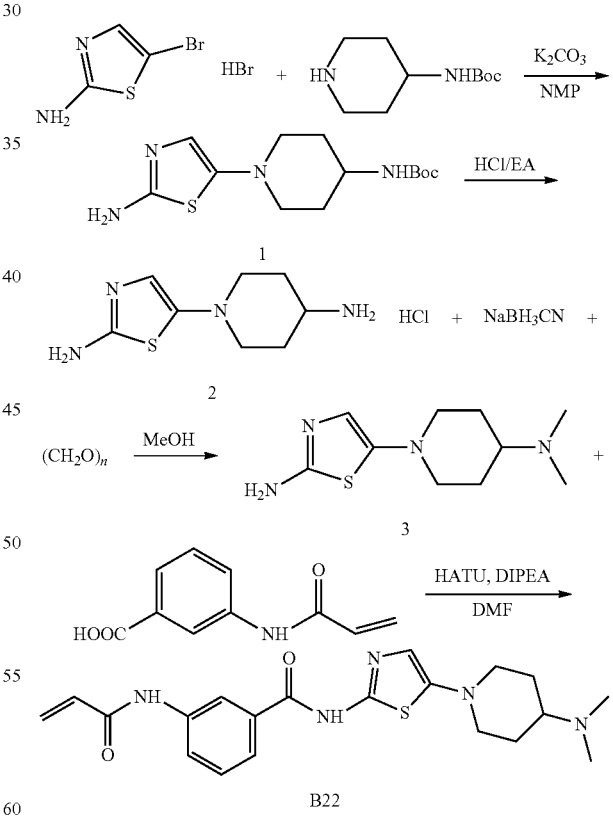

tert-butyl 1-(2-aminothiazol-5-yl)piperidin-4-ylcarbamate (1)

To a mixture of 5-bromothiazol-2-amine hydrobromide (2.6 g, 10 mmol) and powdered potassium carbonate (2.77 g, 20 mmol) in NMP (5 mL) was added tert-butyl piperidin-4-ylcarbamate (4.0 g, 20 mmol) under argon atmosphere and heated at 60° C. for 3 hours. Reaction mixture was cooled to room temperature and poured over ice cold water (100 mL), extracted with EtOAc (3×100 mL), washed with brine, dried over anhydrous sodium sulfate, filtered and concentrated under reduced pressure. The residue was purified by an silica gel column to afford (400 mg, 13.4%) of the title compound (1) as a brown solid. MS m/z 299.15[M+H]$^+$.

5-(4-aminopiperidin-1-yl)thiazol-2-amine (2)

To a solution of tert-butyl 1-(2-aminothiazol-5-yl)piperidin-4-ylcarbamate (200 mg, 0.67 mmol) in 4 M HCl EtOAc (4 mL). The resulting mixture was stirred at room temperature for 30 min. Then it was diluted with EtOAc (100 mL). The pH of the solution was adjusted to 7 with 1 M NaOH. The organics washed with water and brine, dried ($Na_2SO_4$), and concentrated to afford (120 mg, 90%) of the title compound (2) as a slightly brown solid. MS m/z 199.10 [M+H]$^+$.

5-(4-(dimethylamino)piperidin-1-yl)thiazol-2-amine (3)

To a solution of 5-(4-aminopiperidin-1-yl)thiazol-2-amine (120 mg, 0.61 mmol) in MeOH (5 mL) was added paraformaldehyde (90 mg, 3 mmol), AcOH (1 drop), and $NaBH_3CN$ (251 mg, 4 mmol). The resulting mixture was stirred at room temperature for 15 hours. Then it was concentrated under reduced pressure. The residue was purified by an silica gel column to afford (9 mg, 5.8%) of the title compound (3) as a brown solid. MS m/z 227.15[M+H]$^+$.

3-acrylamido-N-(5-(4-(dimethylamino)piperidin-1-yl)thiazol-2-yl)benzamide (B22)

To a solution of 5-(4-(dimethylamino)piperidin-1-yl)thiazol-2-amine (100 mg, 0.442 mmol) in DMF (0.5 mL) was added HATU (335 mg, 0.884 mmol), 3-acrylamidobenzoic acid (169 mg, 0.884 mmol), and DIPEA (228 mg, 1.768 mmol). The resulting mixture was stirred at room temperature for 1 hour. Then it was purified by an silica gel column to afford (35 mg, 17.5%) of the title compound as a yellow solid. MS m/z 400.20 [M+H]$^+$. $^1$H NMR (400 MHz, DMSO-$d_6$) δ 12.21 (s, 1H), 10.36 (s, 1H), 8.27 (s, 1H), 7.89 (s, 1H), 7.76 (s, 1H), 7.46 (s, 1H), 6.69 (s, 1H), 6.52-6.40 (m, 1H), 6.30 (d, J=17.1 Hz, 1H), 5.79 (d, J=9.6 Hz, 1H), 3.42 (d, J=9.5 Hz, 2H), 2.74 (t, 7=11.1 Hz, 2H), 2.19 (s, 7H), 1.82 (d, J=11.2 Hz, 2H), 1.54 (d, J=10.9 Hz, 2H).

Structure-Activity Analyses for Selected Compounds

Select compounds described herein were evaluated for structure-activity analyses. Exemplary results are shown in Table 1.

TABLE 1

| | | | | | |
|---|---|---|---|---|---|
| IC$_{50}$ values of exemplary compounds described herein. | | | | | |
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
| 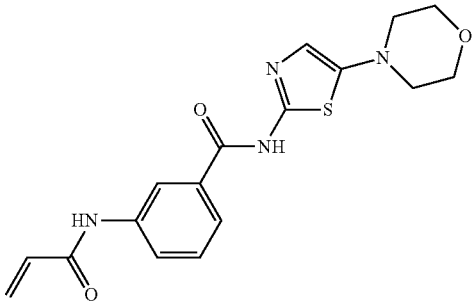<br>THZ-CE-B-17 | >10,000 | >10,000 | >10,000 | >10,000 | >10,000 |
| 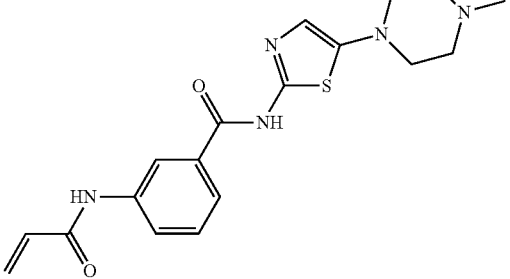<br>THZ-CE-B-18 | >10,000 | >10,000 | >10,000 | >10,000 | >10,000 |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 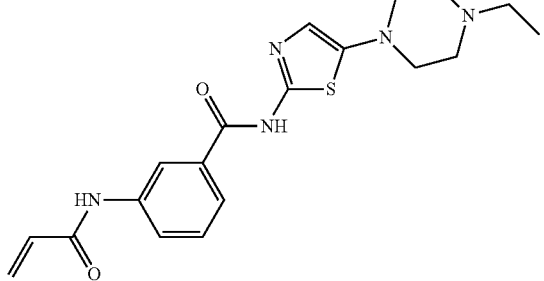 THZ-CE-B-19 | >10,000 | >10,000 | >10,000 | >10,000 | >10,000 |
| 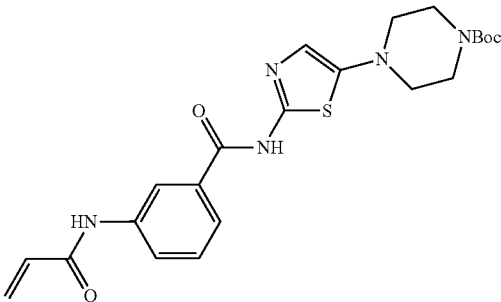 THZ-CE-B-20 | >10,000 | >10,000 | >10,000 | >10,000 | >10,000 |
| 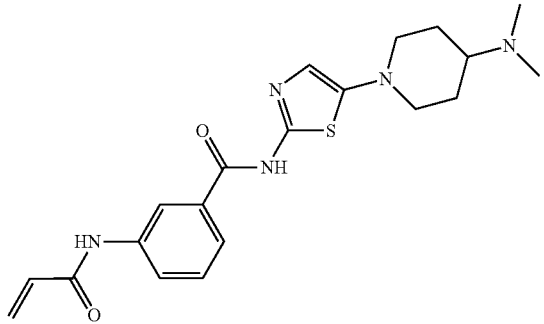 THZ-CE-B-22 | >10,000 | >10,000 | >10,000 | >10,000 | >10,000 |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 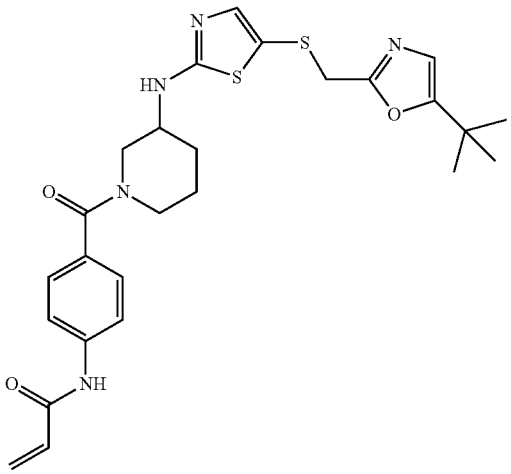 MFH-2-90-1 | 120 | 6020 | 114 | 8 | 308 |
| 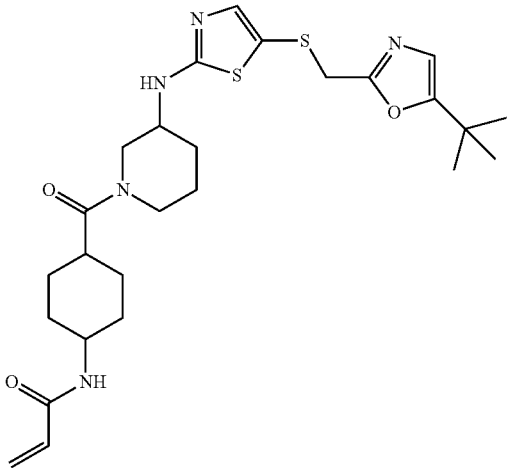 MFH-2-95-1 | 185 | 5550 | 22 | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 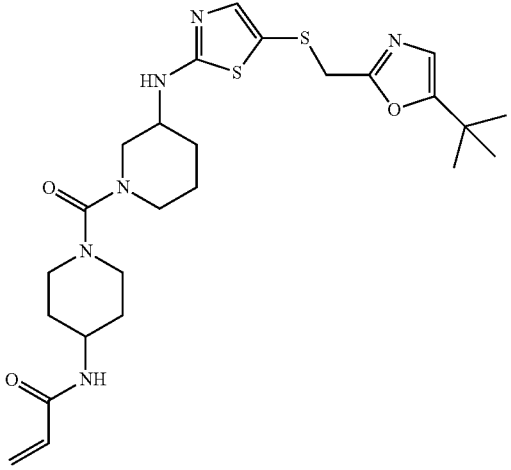  MFH-2-104-1 | 174 | 6170 | 182 | | |
| 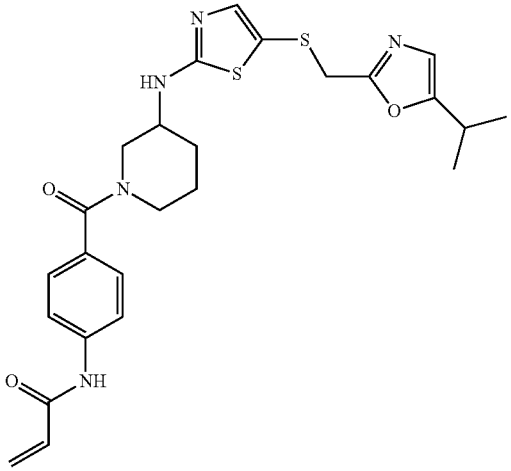  MFH-2-92-1 | >10,000 | >10,000 | >10,000 | | |
| 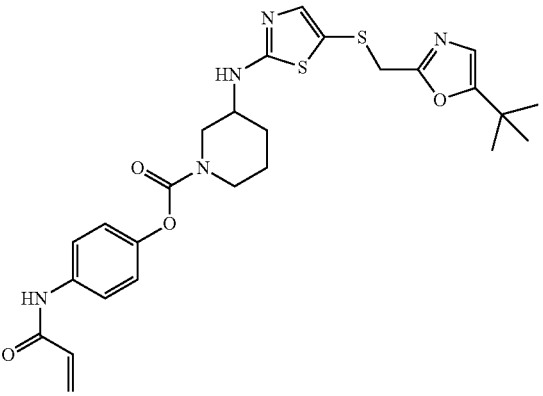  MFH-102-1 | 24.6 | 362 | 20.4 | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 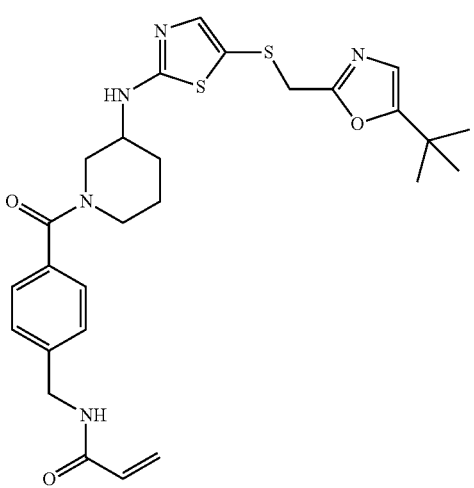 MFH-2-98-1 | 267 | 9230 | 212 | | |
| 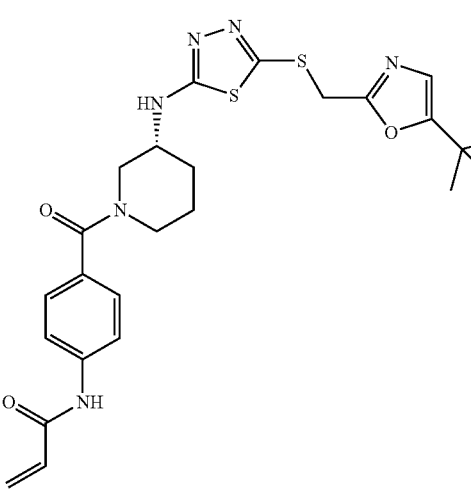 MFH-3-25-1 | >10,000 | >10,000 | >10,000 | >10,000 | >10,000 |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/CDK13 CS HAP1 IC$_{50}$ (nM) |
|---|---|---|---|---|---|
| 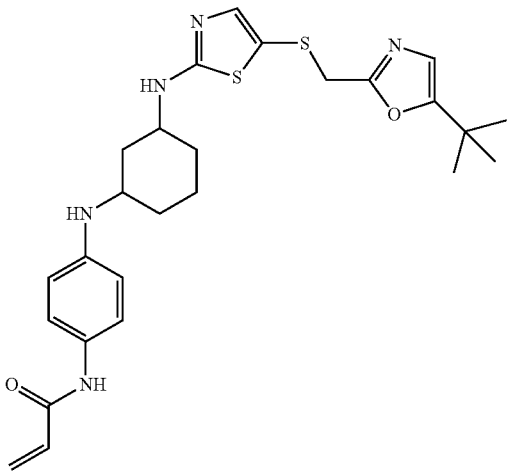 MFH-3-35-1 | 15.7 | 557 | 30.9 | | |
| 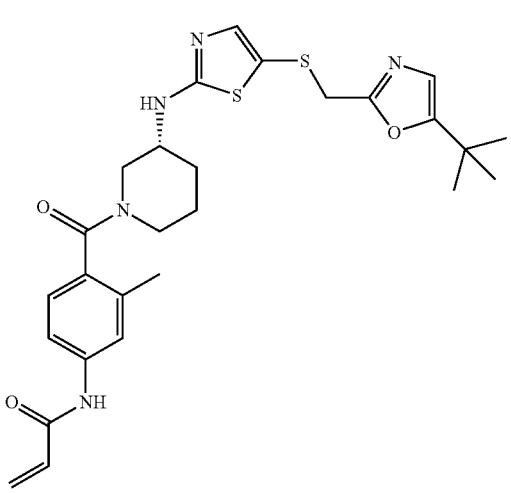 MFH-3-75-1 | | | | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/CDK13 CS HAP1 IC$_{50}$ (nM) |
|---|---|---|---|---|---|
| 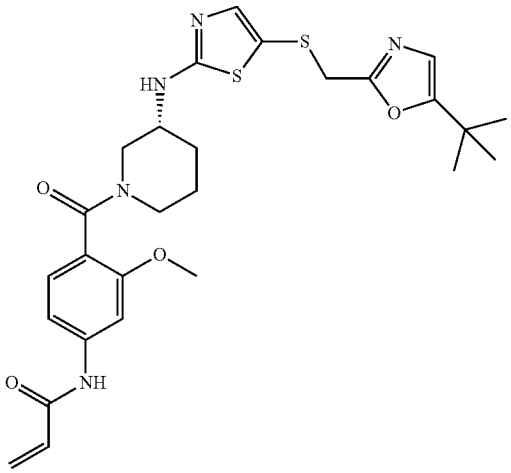 MFH-3-81-1 | 126 | >10,000 | 164 | | |
| 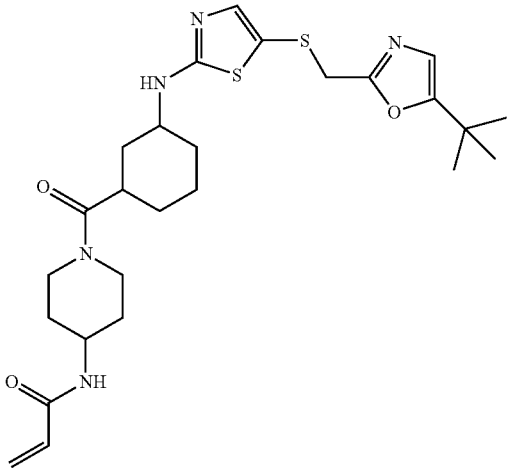 MFH-3-88-1 | 93.5 | 4400 | 199 | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 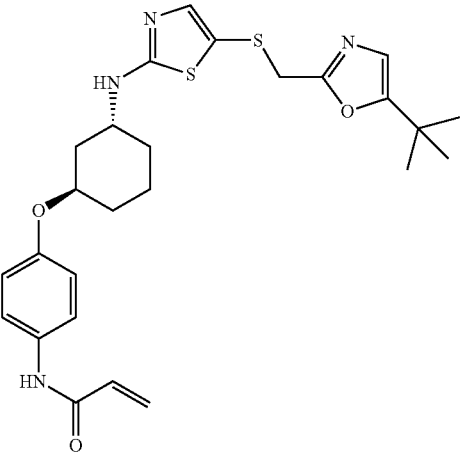 MFH-3-103-1 | 334 | 1280 | 66.5 | 119 | 591 |
| 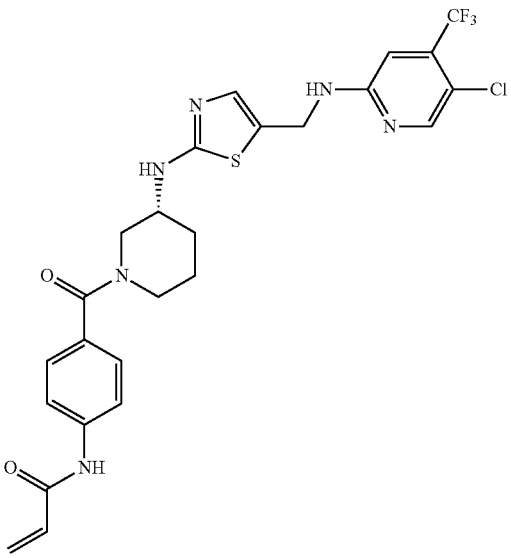 MFH-3-107-1 | >1,000 | >10,000 | >10,000 | >10,000 | >10,000 |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/CDK13 CS HAP1 IC$_{50}$ (nM) |
|---|---|---|---|---|---|
| 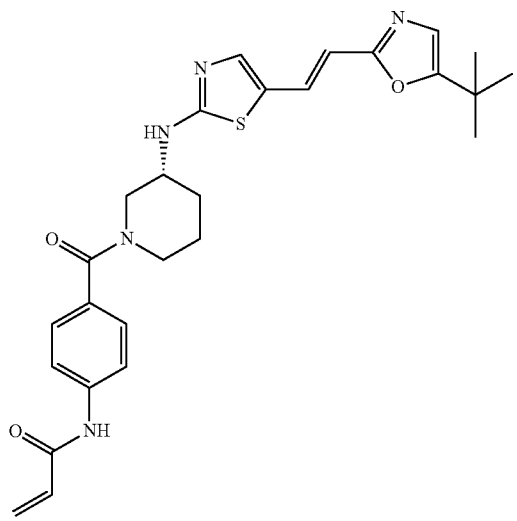 MFH-3-110-1 | 22.9 | 3400 | 15.1 | | |
| 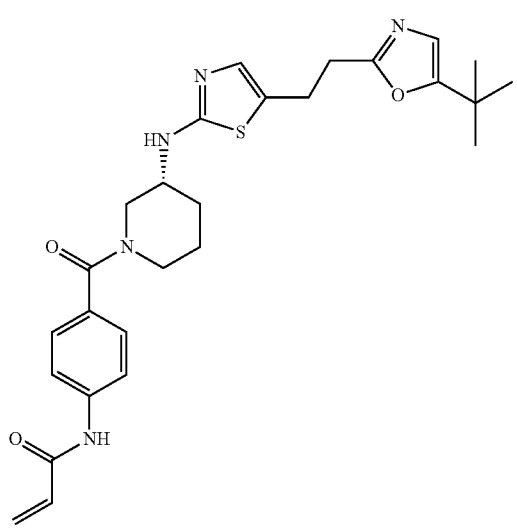 MFH-3-116-1 | >10,000 | >10,000 | >10,000 | >10,000 | >10,000 |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/CDK13 CS HAP1 IC$_{50}$ (nM) |
|---|---|---|---|---|---|
| 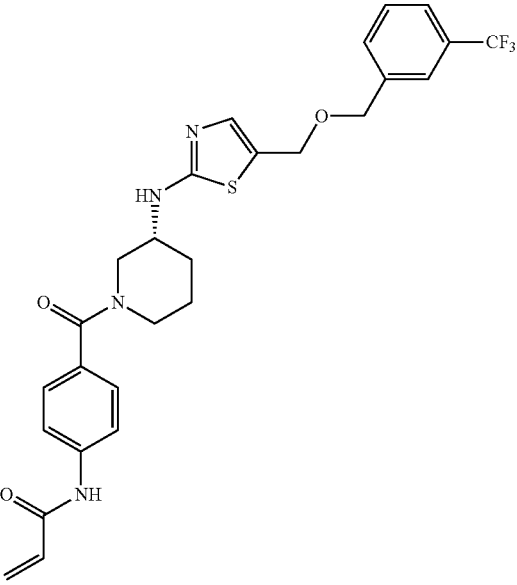 MFH-3-120-01 | >1,000 | >10,000 | >10,000 | >10,000 | >10,000 |
| 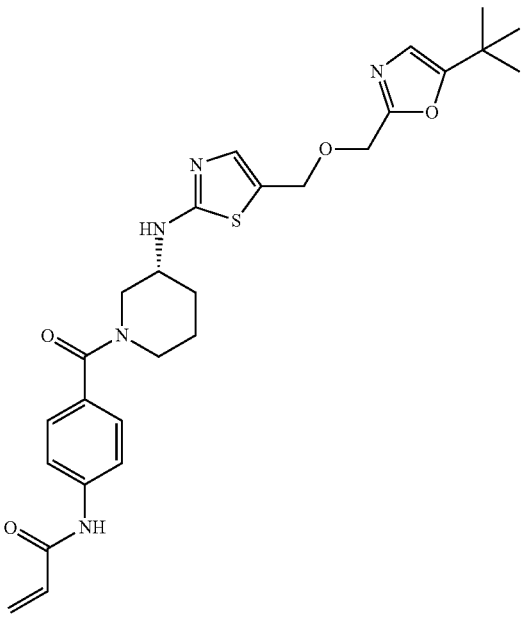 MFH-3-128-1 | >1,000 | >10,000 | >10,000 | >10,000 | >10,000 |

TABLE 1-continued

IC$_{50}$ values of exemplary compounds described herein.

| Compound | CDK2 (nM) | CDK7 (nM) | CDK9 (nM) | CDK12/CDK13 WT HAP1 IC$_{50}$ (nM) | CDK12/CDK13 CS HAP1 IC$_{50}$ (nM) |
|---|---|---|---|---|---|
| MFH-3-137-1 | 3170 | 8870 | 7140 | >10,000 | >10,000 |
| MFH-3-151-1 | 264 | 224 | 197 | 197 | 1096 |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 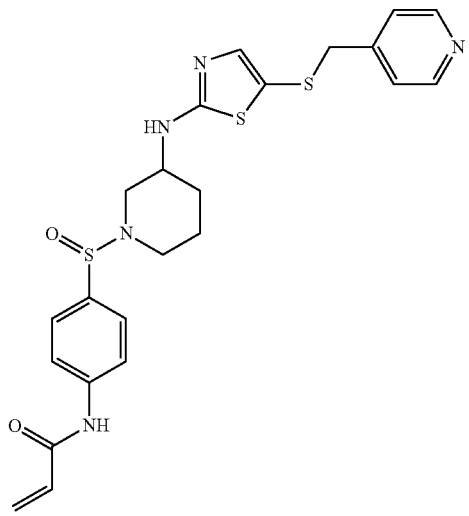 MFH-3-179-1 | >1,000 | >1,000 | >1,000 | | |
| 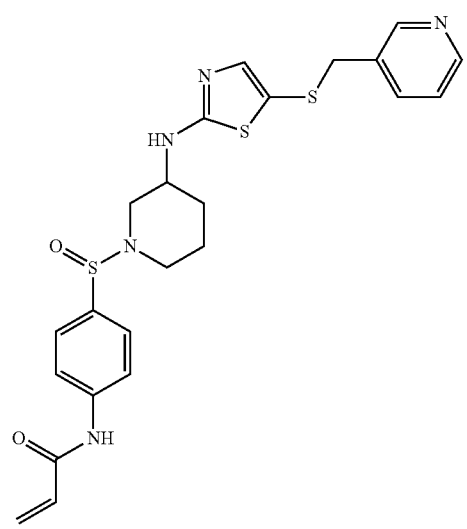 MFH-3-191-1 | >1,000 | >1,000 | >1,000 | | |

TABLE 1-continued

IC₅₀ values of exemplary compounds described herein.

| Compound | CDK2 (nM) | CDK7 (nM) | CDK9 (nM) | WT HAP1 IC₅₀ (nM) | CDK12/ CDK13 CS HAP1 IC₅₀ (nM) |
|---|---|---|---|---|---|
| MFH-3-203-1 | >370 | 2870 | 1000 | | |
| MFH-3-201-1 | >1,000 | >1,000 | >1,000 | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/CDK13 CS HAP1 IC$_{50}$ (nM) |
|---|---|---|---|---|---|
| 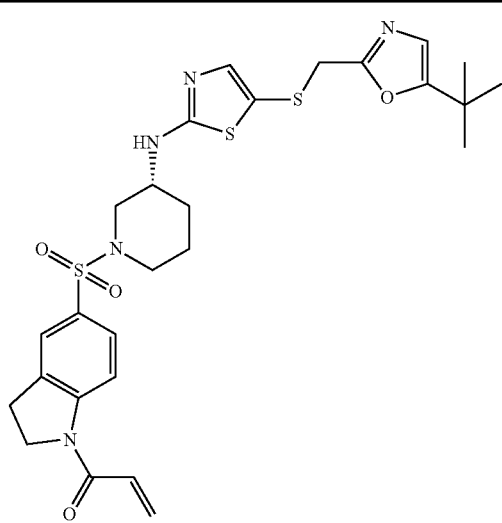 MFH-3-168-1 | 124 | 447 | 1570 | | |
| 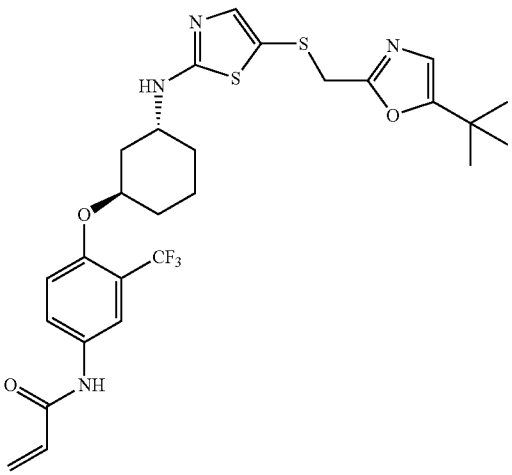 MFH-3-192-1 | 251 | 498 | 298 | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 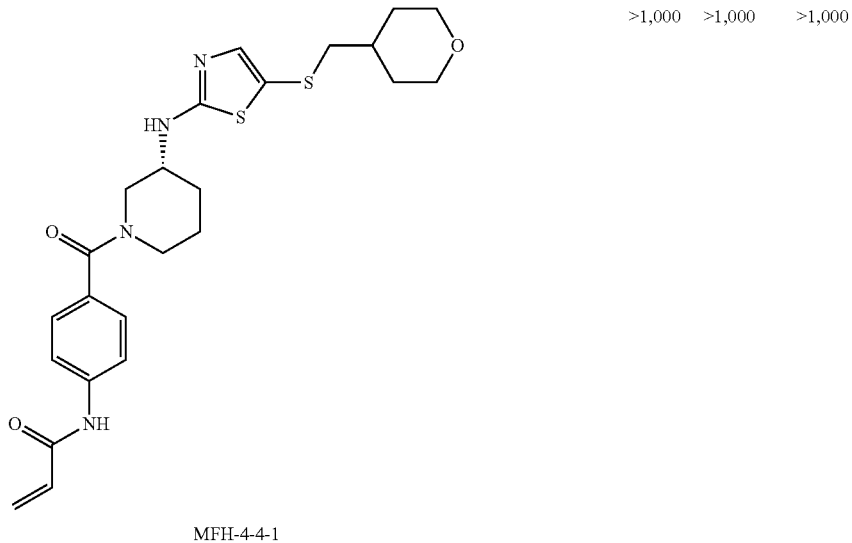<br>MFH-4-4-1 | >1,000 | >1,000 | >1,000 | | |
| 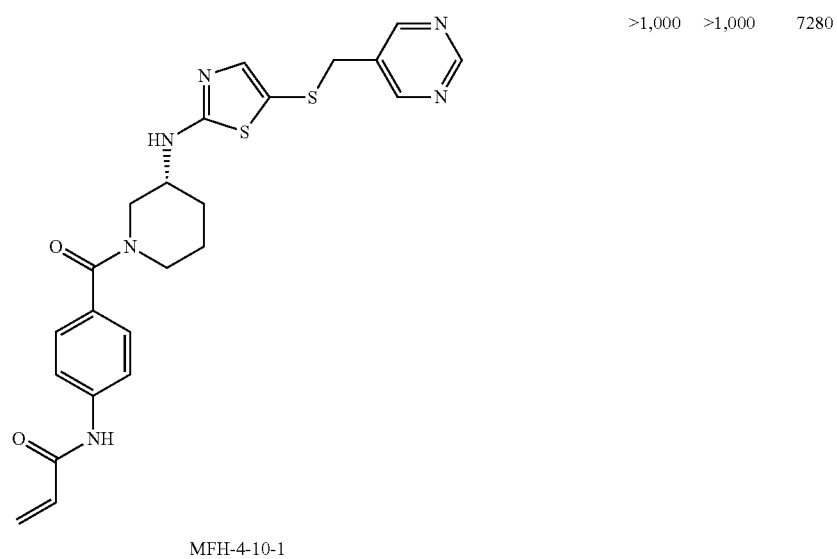<br>MFH-4-10-1 | >1,000 | >1,000 | 7280 | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/CDK13 CS HAP1 IC$_{50}$ (nM) |
|---|---|---|---|---|---|
| 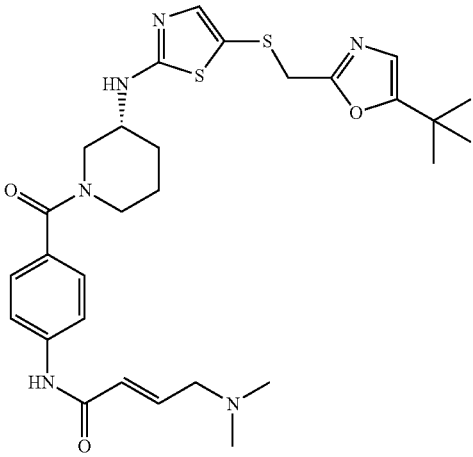 MFH-4-13-1 | 92.3 | 5000 | 65 | | |
| 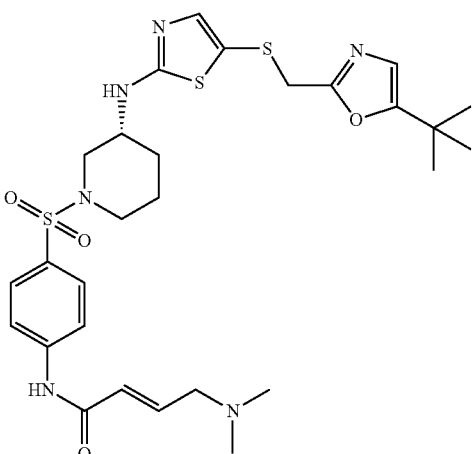 MFH-4-40-1 | 689 | 158 | 474 | | |
| 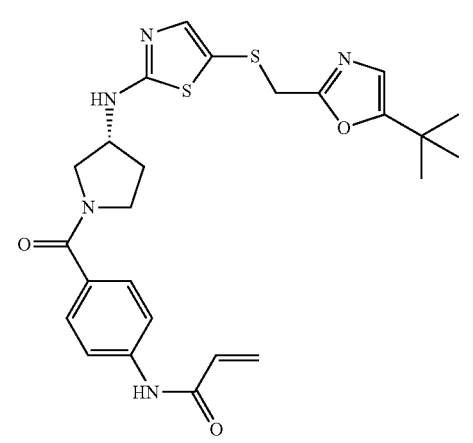 MFH-4-70-1 | 9.86 | 242 | 33 | | |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 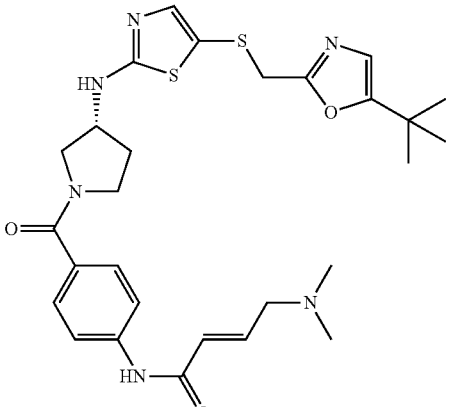 MFH-4-73-1 | 11.9 | 230 | 54.5 | | |
| 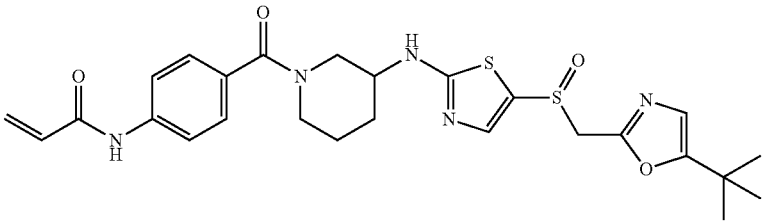 YLIU-01-007-1 | | | | 10,000 | 10,000 |
| 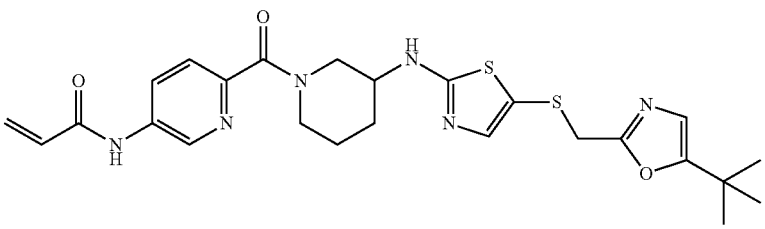 YLIU-01-067-1 | | | | 122 | 2111 |
| 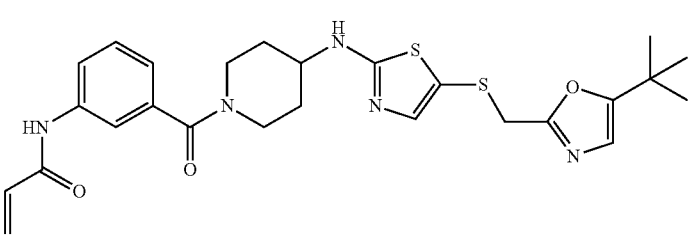 YLIU-01-078-1 | | | | 1539 | 3331 |

TABLE 1-continued
IC$_{50}$ values of exemplary compounds described herein.
| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 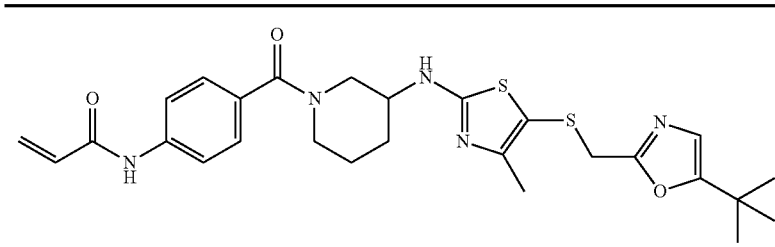 YLIU-01-099-1 | | | | 7480 | 10,000 |
| 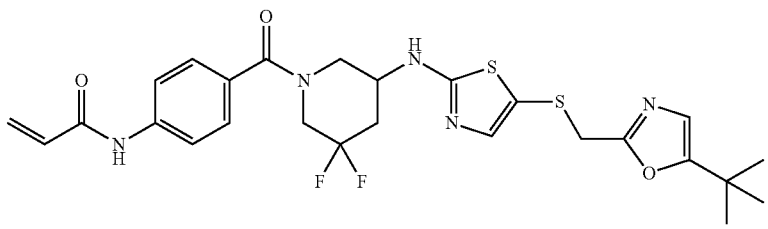 YLIU-01-114-1 | | | | 1180 | 4960 |
| 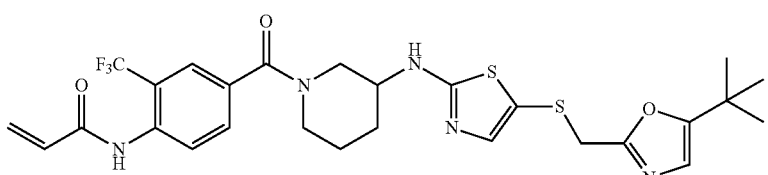 YLIU-01-121-1 | | | | 412 | 944 |
| 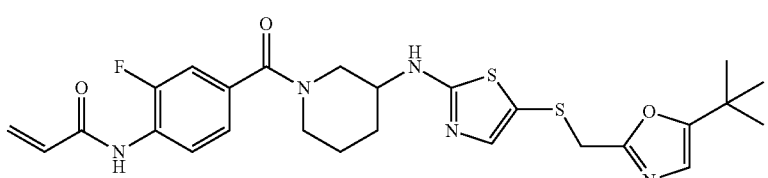 YLIU-01-123-1 | | | | 61 | 618 |
| 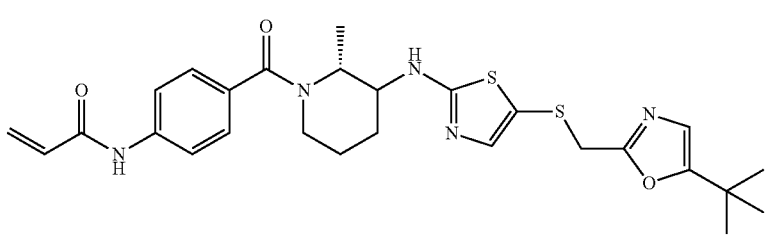 YLIU-01-155-1 | | | | | |

TABLE 1-continued

IC$_{50}$ values of exemplary compounds described herein.

| Compound | CDK2 (nM) | CDK7 (nM) | CDK9 (nM) | WT HAP1 IC$_{50}$ (nM) | CDK12/ CDK13 CS HAP1 IC$_{50}$ (nM) |
|---|---|---|---|---|---|
| 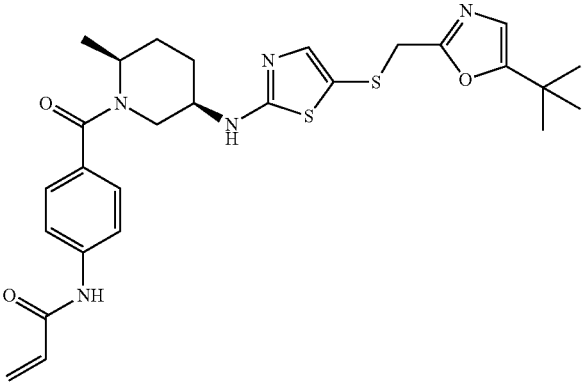 YLIU-01-156-1 | | | | | |

Genome Editing:

With regard to the exemplary results for cellular assays shown in Table 1 above, genome editing was performed as follows. The CRISPR/Cas9 system was used to mutate the endogenous CDK12 and CDK13 loci to encode for CDK12 C1039S and CDK13 C1017S, both are putative CDK12/13 inhibitor-refractory mutants. Target-specific oligonucleotides were cloned into pX330, which carries a codon-optimized version of Cas9 and was further modified to express GFP for identifying transfectants. Cells were co-transfected (X-tremeGENE 9 (Roche)) with 1) pX330 expressing Cas9 and CDK12-targeting guide RNAs and 2) a pUC57-AMP construct bearing 1500 bp of modified CDK12 reference genome that is centered around the CRISPR targeting site in CDK12. Two days after transfection, cells were sorted using GFP as a marker of transfected cells and cells were re-plated for five days. Cells were then re-plated at low density to facilitate the isolation of individual clones. Individual clones were isolated, expanded, and PCR genotyped using mutant specific PCR primers. Following initial PCR screening, individual clones were Sanger sequenced to confirm the presence of the desired mutation. Western blot confirmed the presence of intact CDK12 kinase. The process was sequentially repeated this time with Cas9/sgRNA constructs to target and replace the CDK13 genetic loci. Subsequent experiments were conducted using a CDK12 C1039S/CDK13 C1017S clone and a WT control clone that was carried through the entirety of the CRISPR protocol but that was verified by Sanger sequencing to be WT for CDK12 and CDK13. The genomic sequence complementary to the CDK12-directed guide RNA that was cloned into pX330 and used in the genome editing experiments is: GGCAGGATTGCCATGAGTTG. The genomic sequence complementary to the CDK13-directed guide RNA that was cloned into pX330 and used in the genome editing experiments is: GGCAAGAT TGTCATGAGTTA. The reference genome sequence used as a repair template for CDK12 and CDK13 CRISPR was edited to 1) introduce DNA coding for serine, 2) introduce mutations to either remove the PAM site (NGG) targeted by CRISPR/Cas9 or introduce sufficient wobble mutations such that the guide RNA could not recognize the repair template and thus could not be cut by CRISPR/Cas9, and 3) introduce mutations that could allow for mutant and WT-specific PCR amplification.

HAP1 Cell Proliferation Assay:

With regard to the exemplary results shown in Table 1 above, the HAP1 cell proliferation assay was performed as follows. HAP1 WT and double mutants cells were seeded at a density of 12,000 cells/well in 96-well plates. Twenty-four hours cells were then treated with the indicated compounds in a 10-pt dose escalation format from 1 nM to 10 μM or DMSO control for 72 hrs. After 72 hrs, cells were assayed using CellTiter-Glo Luminescent Cell Viability Assay (Promega) to determine cell viability by measuring the amount of ATP present in each sample cell population, which is an indicator of cell metabolic activity. Results are graphed as fraction of the DMSO control at 72 hrs. All data points were performed in biological triplicate.

HAP1 cells expressing putative inhibitor-refractory mutations in CDK12 (C1039S) and CDK13 (C1017S) show up to 20-fold less sensitivity to exemplary compounds as compared to control WT HAP1 cells. This result indicates that a substantial portion of intracellular compound activity comes from covalent inhibition of CDK12 and/or CDK13 and mutation of the targeted cysteines (C1039 in CDK12 and 0017 in CDK13) to less nucleophilic serines is sufficient to rescue a substantial portion of anti-proliferative activity.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I'):

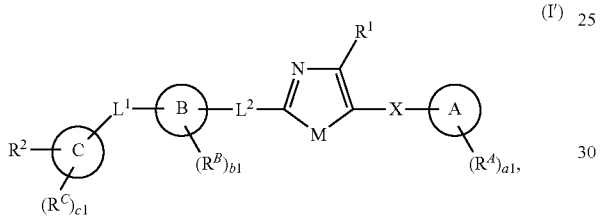

or a pharmaceutically acceptable salt thereof, wherein:
$R^1$ is hydrogen, halogen, or optionally substituted alkyl;
M is O, S, or $NR^M$;
$R^M$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group;
Ring A is optionally substituted monocyclic carbocyclyl, optionally substituted monocyclic heterocyclyl, optionally substituted phenyl, or optionally substituted monocyclic heteroaryl;
Ring B is

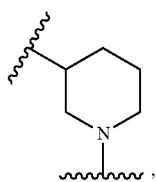

attached to $L^1$ via the ring nitrogen of Ring B;
Ring C is optionally substituted monocyclic $C_{3-10}$ carbocyclyl, optionally substituted 5-6 membered monocyclic heterocyclyl having ring carbon atoms and 1-4 ring heteroatoms, wherein each heteroatom is independently selected from nitrogen, oxygen, and sulfur, optionally substituted phenyl, or optionally substituted 5-10 membered, monocyclic or bicyclic heteroaryl having ring carbon atoms and 1-4 ring heteroatoms,
wherein each heteroatom is independently selected from nitrogen, oxygen, and sulfur;

each instance of $R^A$, $R^B$, and $R^C$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^a$, $-N(R^a)_2$, $-SR^a$, $-CN$, $-SCN$, $-NO_2$, $-N_3$, or optionally substituted acyl;

each instance of $R^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

each of a1, b1, and c1 is independently 0, 1, 2, 3, 4, 5, or 6, as valency permits;

$L^1$ is $-CH_2-$, $^{lc}-S(=O)_2-^{lb}$, $-O-$, $-S-$, $-NR^{L1}-$, $-C(=O)-$, $^{lc}-NR^{L1}C(=O)-^{lb}$, $^{lc}-C(=O)NR^{L1}-^{lb}$, $^{lc}-OC(=O)-^{lb}$, or $^{lc}-C(=O)O-^{lb}$; wherein $^{lb}$ indicates the point of attachment is to Ring B; and $^{lc}$ indicates the point of attachment is to Ring C;

$L^2$ is $-O-$, $-S-$, $-NR^{L2}-$, $^{lb}-NR^{L2}C(=O)-^{lm}$, $^{lb}-C(=O)NR^{L2}-^{lm}$; wherein $^{lb}$ indicates the point of attachment is to Ring B; and $^{lm}$ indicates the point of attachment is to the heteroaryl ring with M;

X is $^{xm}-CH_2CH_2-^{xa}$, $^{xm}-CH=CH-^{xa}$, $^{xm}-CH_2-NR^{LX}-^{xa}$, $^{xm}-CH_2-O-CH_2-^{xa}$, $^{xm}-CH_2-NR^{LX}-CH_2-^{xa}$, $-O-$, $-S-$, $-NR^{LX}-$, $^{xm}-O-CH_2-^{xa}$, $^{xm}-S-CH_2-^{xa}$, $^{xm}-S-C(=O)CH_2-^{xa}$, or $^{xm}-NR^{LX}-CH_2-^{xa}$; wherein $^{xa}$ indicates the point of attachment is to Ring A; and $^{xm}$ indicates the point of attachment is to the heteroaryl ring with M;

each of $R^{L1}$, $R^{L2}$, and $R^{LX}$ is independently hydrogen, optionally substituted $C_{1-6}$ alkyl, or a nitrogen protecting group;

R² is any of Formulae (i-1)-(i-41):
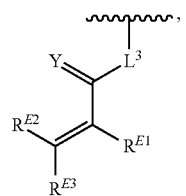 (i-1)
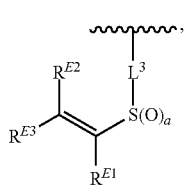 (i-2)
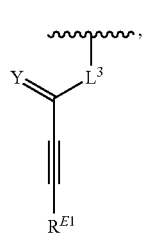 (i-3)
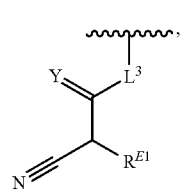 (i-4)
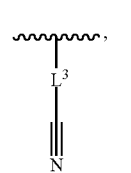 (i-5)
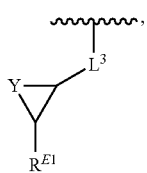 (i-6)
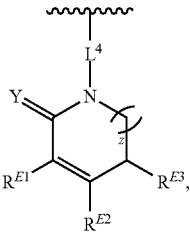 (i-7)
-continued
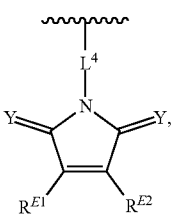 (i-8)
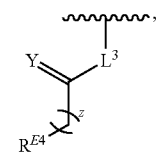 (i-9)
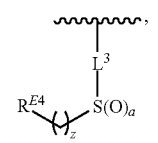 (i-10)
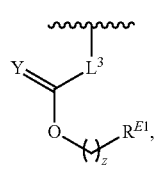 (i-11)
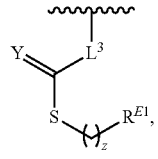 (i-12)
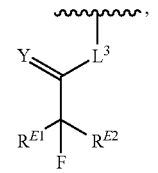 (i-13)
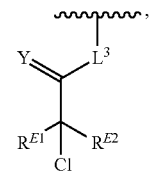 (i-14)
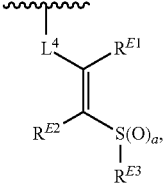 (i-15)

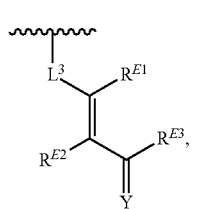 (i-16)
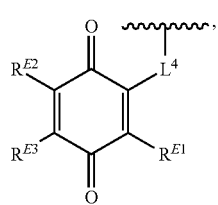 (i-17)
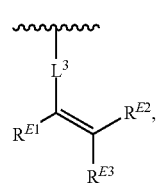 (i-18)
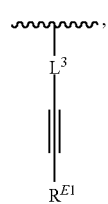 (i-19)
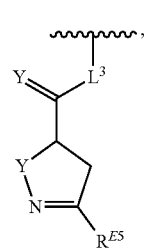 (i-20)
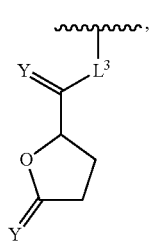 (i-21)
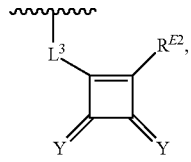 (i-22)
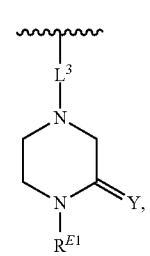 (i-23)
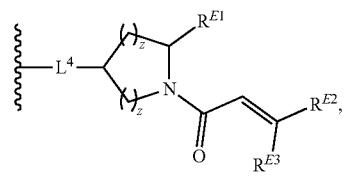 (i-24)
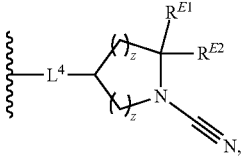 (i-25)
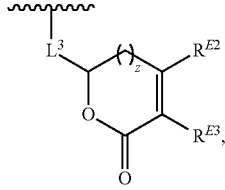 (i-26)
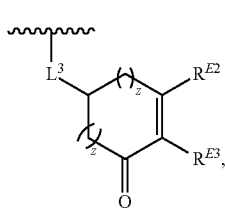 (i-27)
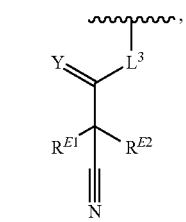 (i-28)
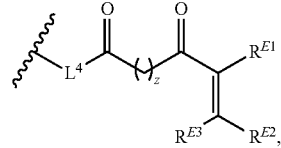 (i-29)
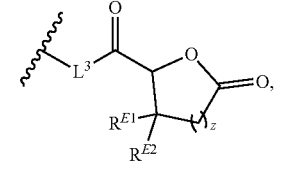 (i-30)

-continued (i-31)

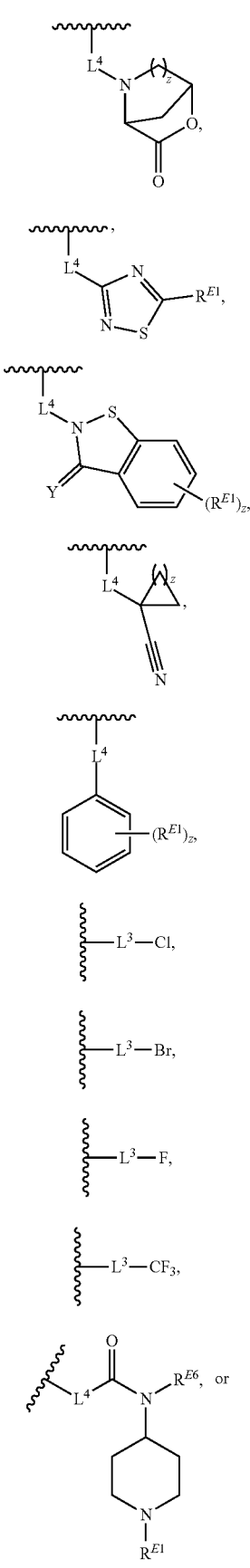

(i-32)

(i-33)

(i-34)

(i-35)

(i-36)

(i-37)

(i-38)

(i-39)

(i-40)

-continued (i-41)

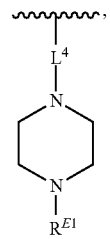

wherein:
L$^3$ is a bond or an optionally substituted C$_1$—$_4$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, optionally substituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring;

or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, optionally substituted C$_{1-6}$ alkyl, or a nitrogen protecting group;

each instance of Y is independently O, S, or NR$^{E7}$, wherein R$^{E7}$ is hydrogen, optionally substituted C$_{1-6}$ alkyl, or a nitrogen protecting group;

a is 1 or 2; and each instance of z is independently 0, 1, 2, 3, 4, 5, or 6, as valency permits;

wherein the oxygen protecting group is —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, or —P(=O)(N(R$^{bb}$)$_2$)$_2$;

wherein the nitrogen protecting group is —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, aralkyl, heteroaralkyl, C$_{2-10}$ alkenyl, C$_{2-10}$ alkynyl, C$_{3-10}$ carbocyclyl, 3-14 membered heterocyclyl, C$_{6-14}$ aryl, or 5-14 membered heteroaryl group, wherein each alkyl, alkenyl, alkynyl, carbocyclyl, heterocyclyl, aralkyl, heteroaralkyl, aryl, and heteroaryl is independently substituted with 0, 1, 2, 3, 4, or 5 R$^{dd}$ groups;

wherein the sulfur protecting group is —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, or —P(=O)(N(R$^{bb}$)$_2$)$_2$;

wherein when any one of the groups referred to above is substituted with one or more substituents at a carbon atom, the one or more substituents at the carbon atom are independently selected from the substituents in Group (i);

when any one of the groups referred to above is substituted with one or more substituents at a nitrogen atom, the one or more substituents at the nitrogen atom are independently selected from the substituents in Group (ii);

Group (i) consists of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

Group (ii) consists of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

wherein:

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R^ff)$_2$, —OC(=O)N(R^ff)$_2$, —NR^ff C(=O) R^ee, —NR^ff CO$_2$R^ee, —NR^ff C(=O)N(R^ff)$_2$, —C(=NR^ff)OR^ee, —OC(=NR^ff)R^ee, —OC(=NR^ff) OR^ee, —C(=NR^ff)N(R^ff)$_2$, —OC(=NR^ff)N(R^ff)$_2$, —NR^ff C(=NR^ff)N(R^ff)$_2$, —NR^ff SO$_2$R^ee, —SO$_2$N(R^ff)$_2$, —SO$_2$R^ee, —SO$_2$OR^ee, —OSO$_2$R^ee, —S(=O)R^ee, —Si(R^ee)$_3$, —OSi(R^ee)$_3$, —C(=S)N(R^ff)$_2$, —C(=O)SR^ee, —C(=S)SR^ee, —SC(=S)SR^ee, —P(=O)(OR^ee)$_2$, —P(=O)(R^ee)$_2$, —OP(=O)(R^ee)$_2$, —OP(=O)(OR^ee)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R^gg groups, or two geminal R^dd substituents can be joined to form =O or =S; wherein X$^-$ is a counterion;

each instance of R^ee is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R^gg groups;

each instance of R^ff is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R^ff groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R^gg groups; and each instance of R^gg is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R^gg substituents can be joined to form =O or =S; wherein X$^-$ is a counterion; and wherein the compound is not

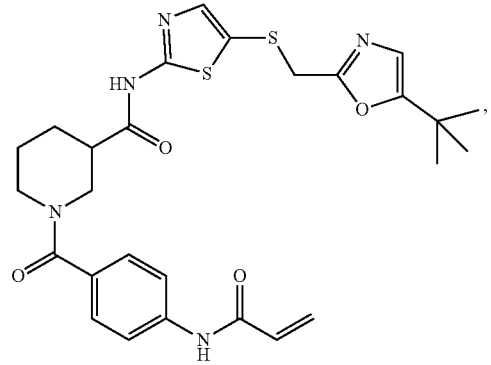 [SMILES: C=CC(=O)Nc1ccc(C(=O)N2CCCC(C(=O)Nc3ncc(SCc4ncc(C(C)(C)C)o4)s3)C2)cc1]

or a pharmaceutically acceptable salt thereof.

2. The compound of claim 1, wherein the compound is of the formula:

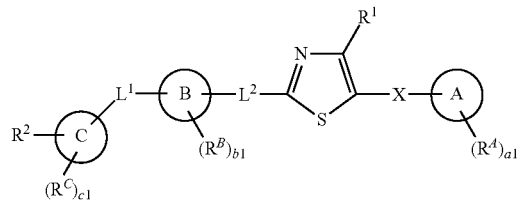

or a pharmaceutically acceptable salt thereof.

3. The compound of claim 1, wherein the compound is of Formula (I-ii), (I-ii-a), (I-ii-b), (I-ii-c), or (I'-i):

(I-ii)

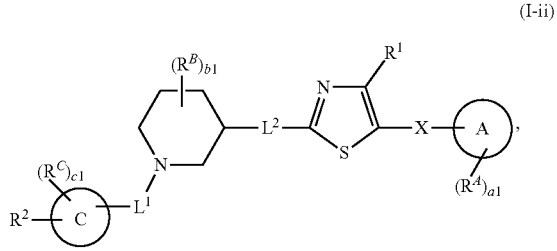

(I-ii-a)

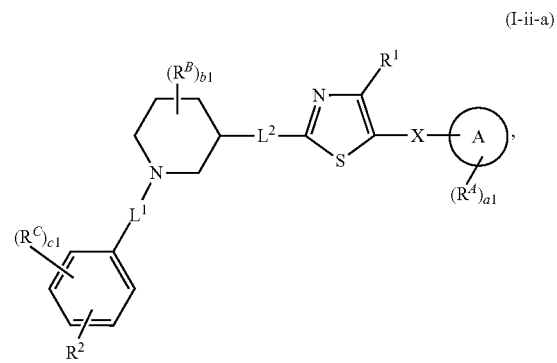

-continued

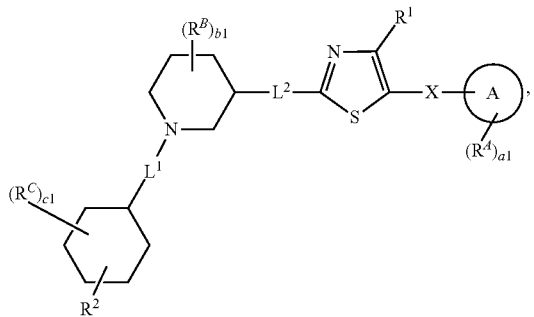
(I-ii-b)

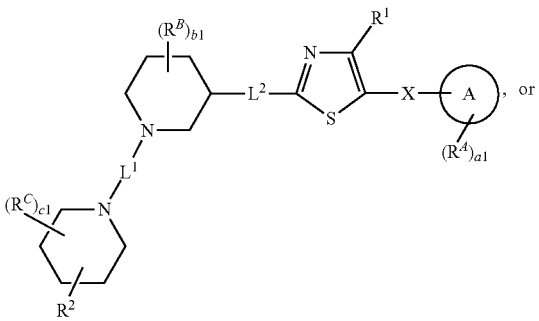
(I-ii-c), or

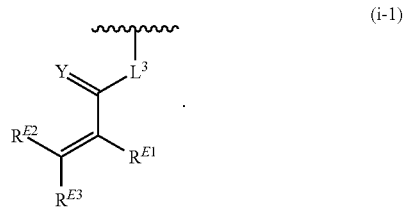
(I'-i)

or a pharmaceutically acceptable salt thereof.

4. The compound of claim 1, or a pharmaceutically acceptable salt thereof, wherein Ring C is optionally substituted phenyl or optionally substituted 5-10 membered monocyclic or bicyclic heteroaryl having ring carbon atoms and 1-4 ring heteroatoms wherein each heteroatom is independently selected from nitrogen, oxygen, and sulfur.

5. The compound of claim 1, or a pharmaceutically acceptable salt thereof, wherein Ring A is optionally substituted monocyclic heteroaryl.

6. The compound of claim 1 or a pharmaceutically acceptable salt thereof, wherein Ring A is optionally substituted phenyl.

7. The compound of claim 1, or a pharmaceutically acceptable salt thereof, wherein Ring A is optionally substituted monocyclic carbocyclyl.

8. The compound of claim 1, or a pharmaceutically acceptable salt thereof, wherein Ring A is optionally substituted monocyclic heterocyclyl.

9. The compound of claim 1, or a pharmaceutically acceptable salt thereof, wherein Ring A is optionally substituted 6-membered heteroaryl.

10. The compound of claim 1, or a pharmaceutically acceptable salt thereof, wherein $L^1$ is —CH$_2$— or $^{Ic}$—S($=$O)$_2^{Ib}$.

11. The compound of claim 1, or a pharmaceutically acceptable salt thereof, wherein $R^2$ is of Formula (i-1):

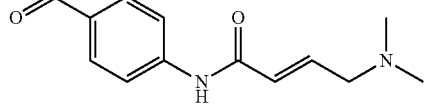
(i-1)

12. The compound of claim 1, wherein the compound is of one of the following formulae:

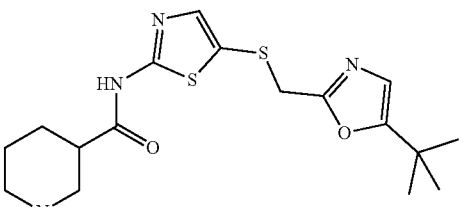

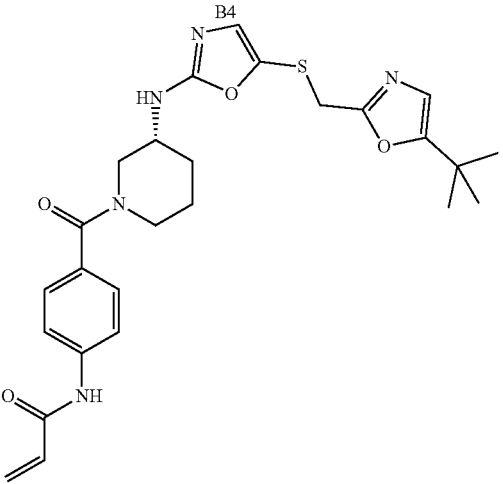

369
-continued
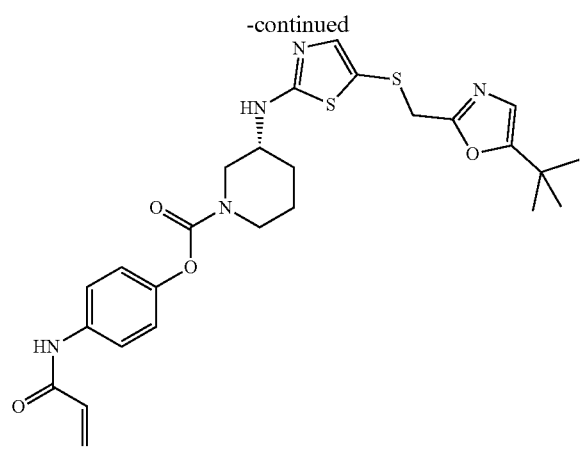
B12
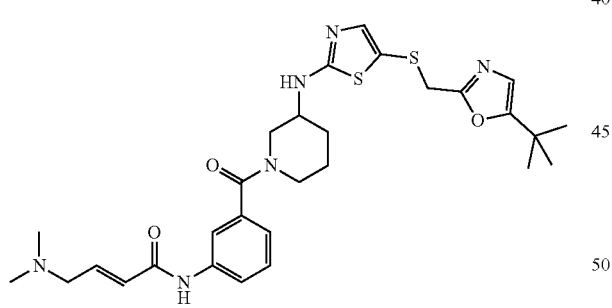
B16
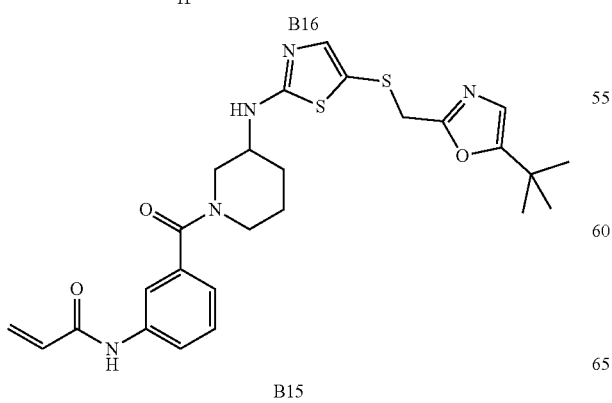
B15
370
-continued
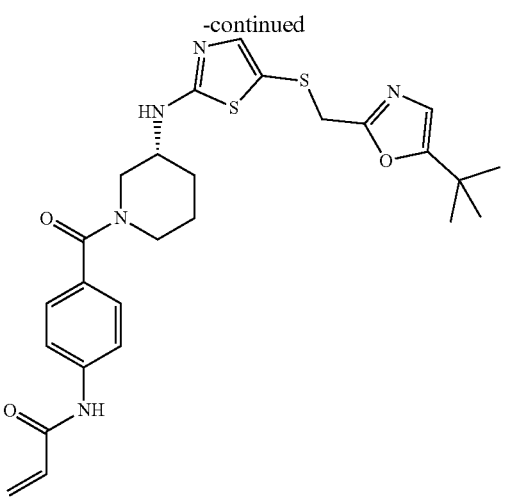
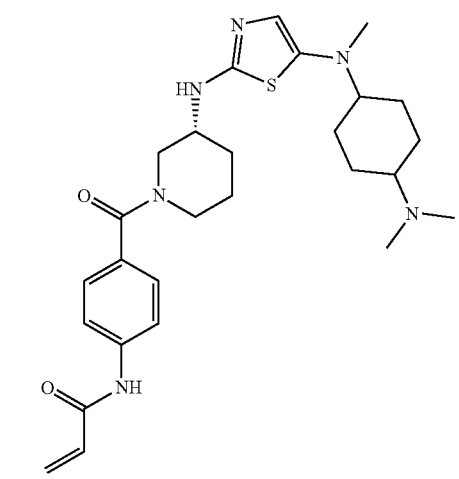

371
-continued
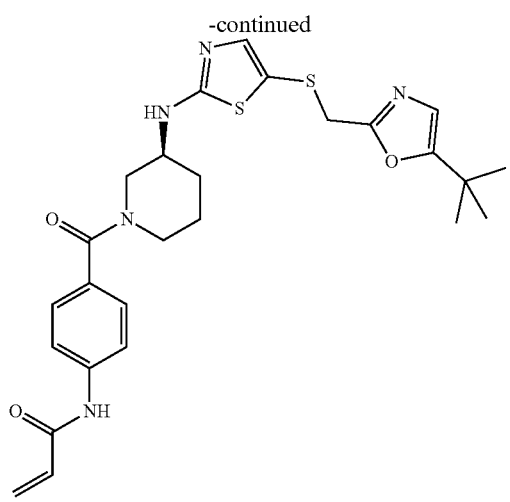
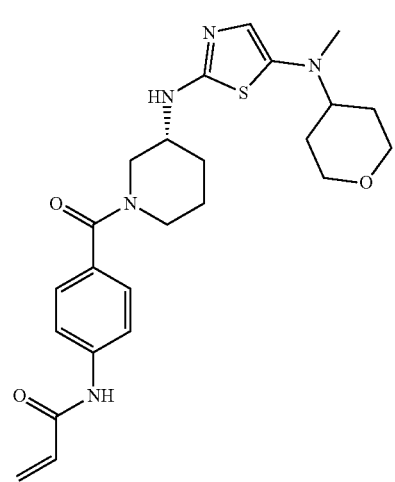
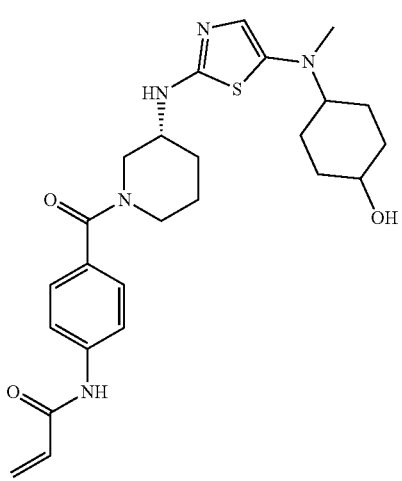
372
-continued
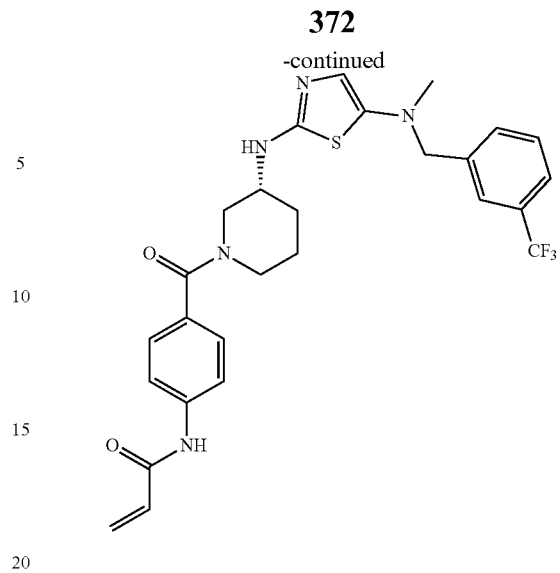
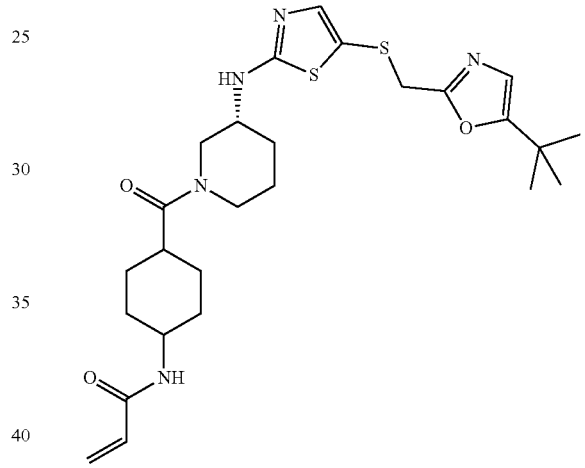
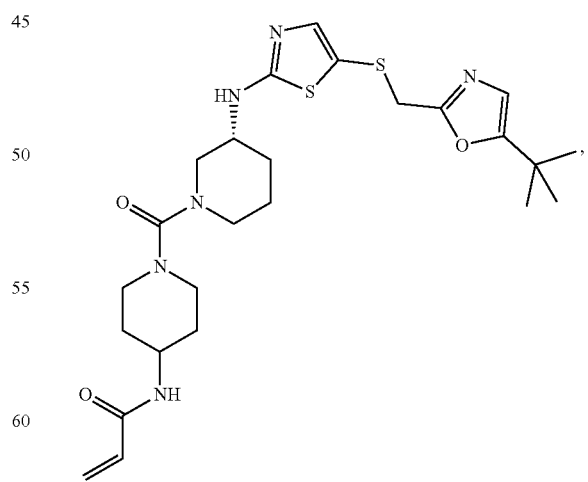
or a pharmaceutically acceptable salt thereof.
13. The compound of claim 1, wherein the compound is of one of the following formulae:

373                                              374
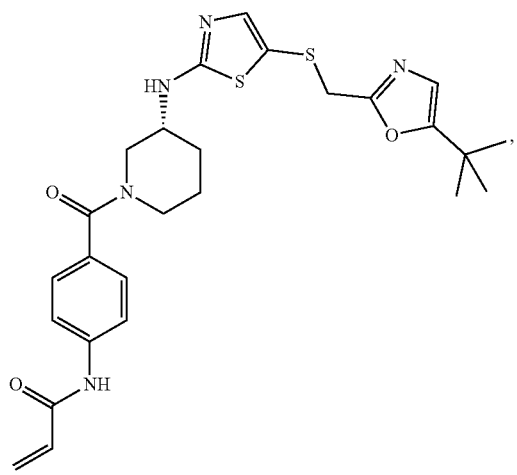
MFH-2-90-1
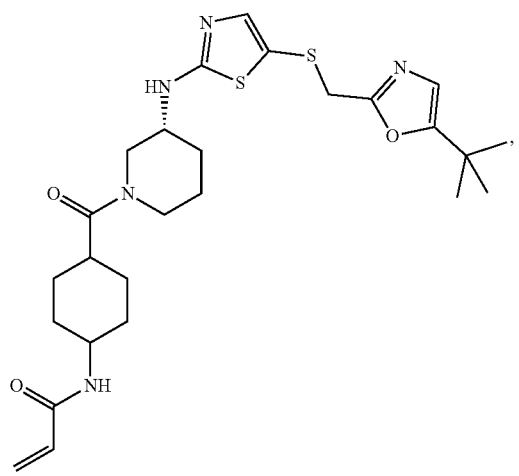 [SMILES: C=CC(=O)NC1CCN(C(=O)N2CCC[C@@H](Nc3ncc(SCc4ncc(C(C)(C)C)o4)s3)C2)CC1]
MFH-2-95-1
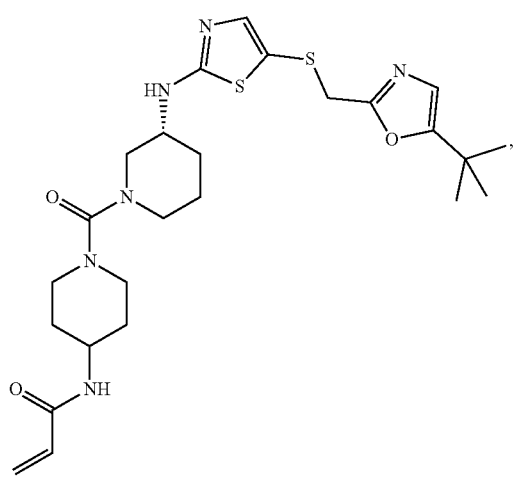
MFH-2-104-1
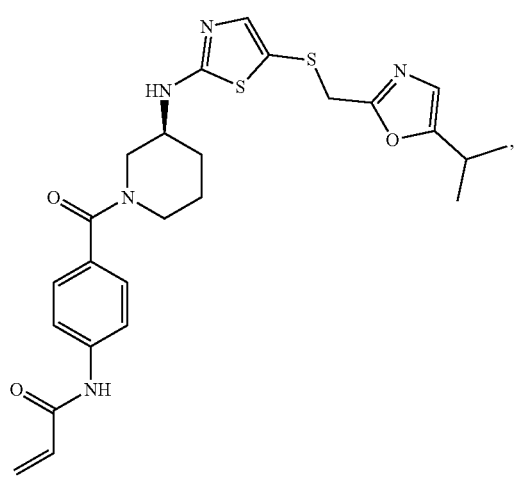
MFH-2-92-1
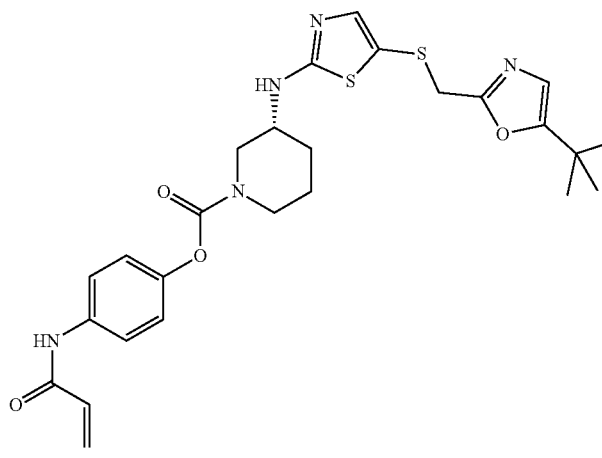
MFH-2-102-1
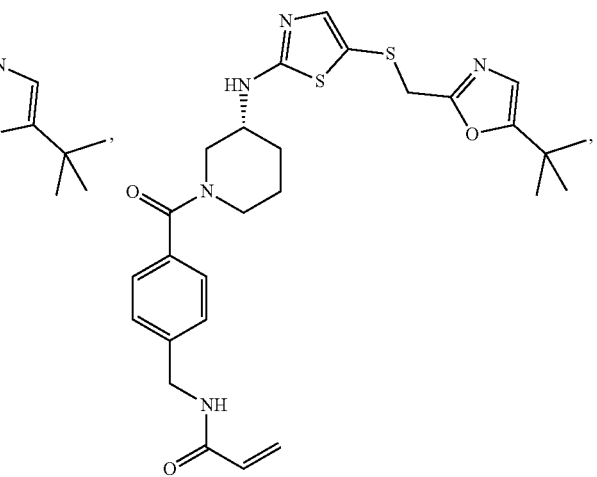
MFH-2-98-1

-continued
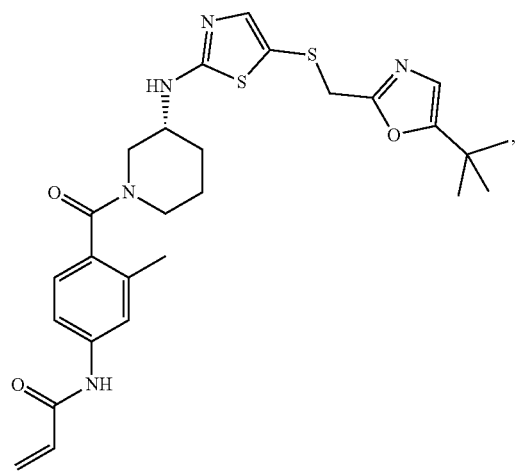
MFH-3-75-1
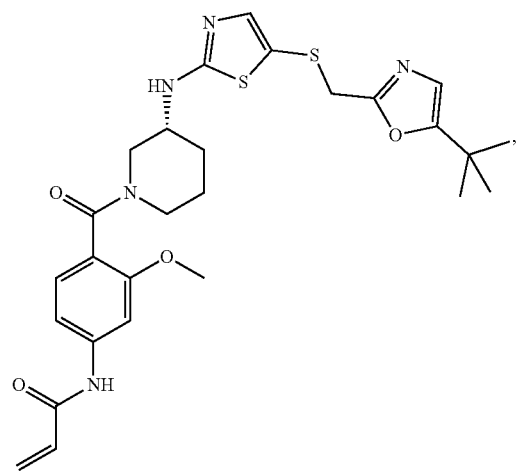
MFH-3-81-1
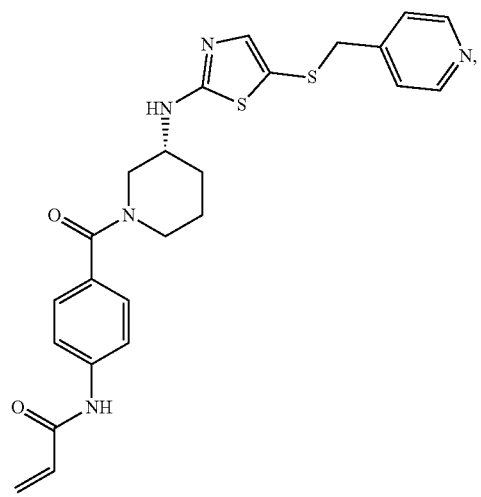
MFH-3-179-1
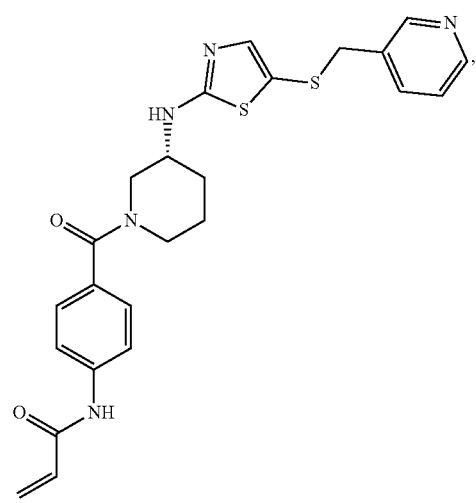
MFH-3-191-1
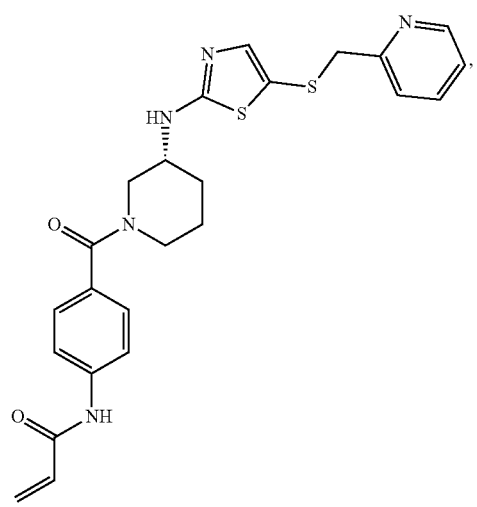
MFH-3-203-1
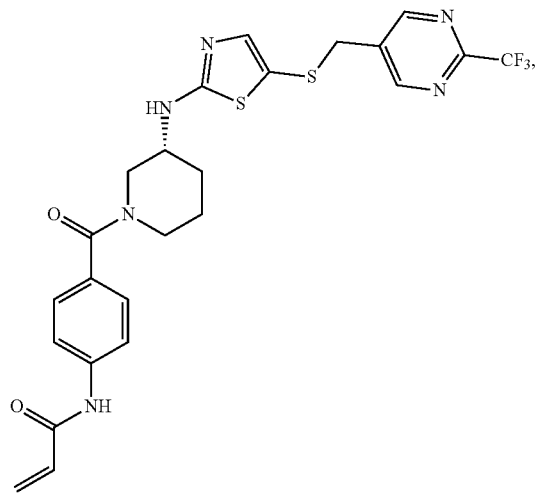
MFH-3-201-1

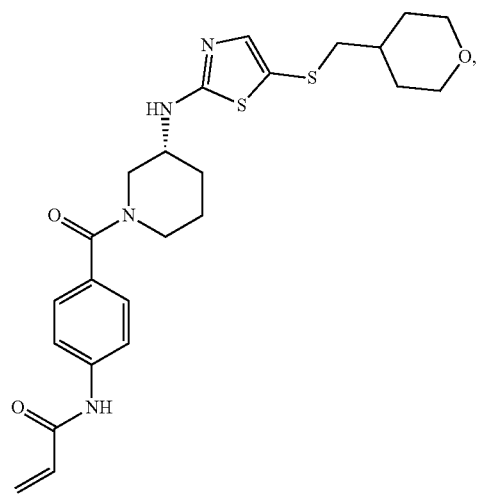
MFH-4-4-1
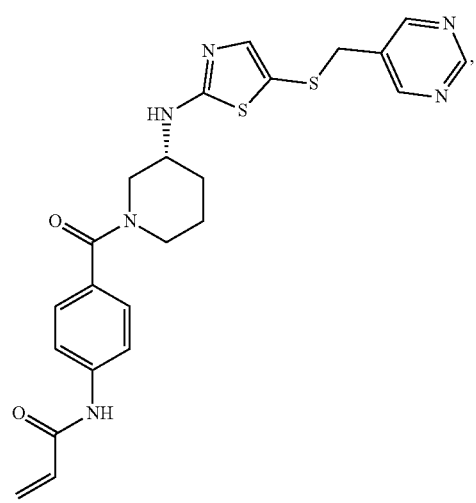
MFH-4-10-1
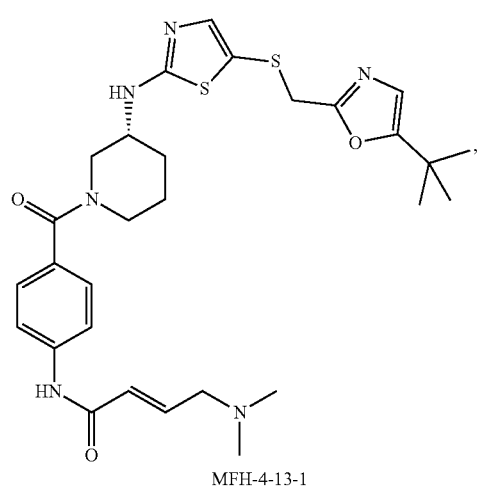
MFH-4-13-1
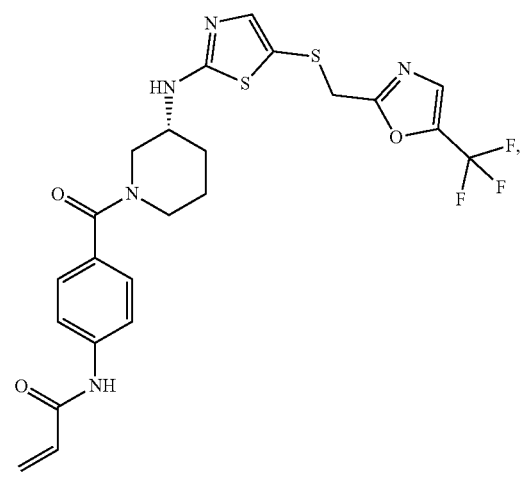
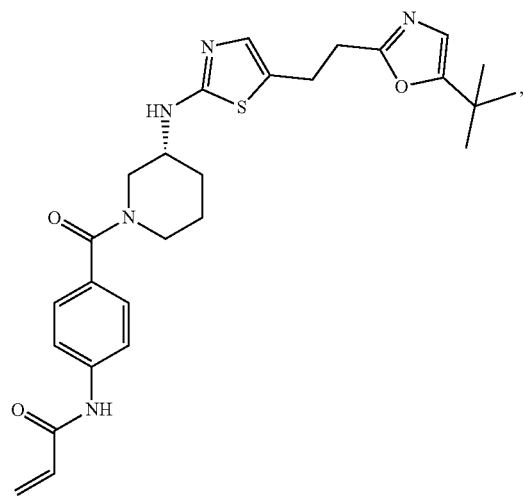
MFH-3-116-1

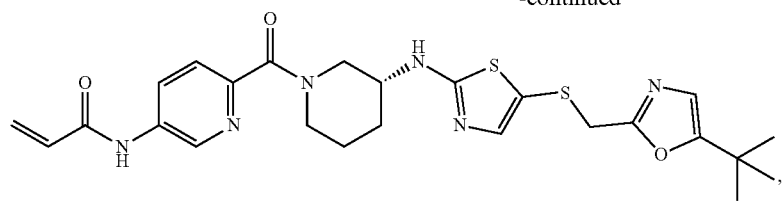
YLIU-01-057-1
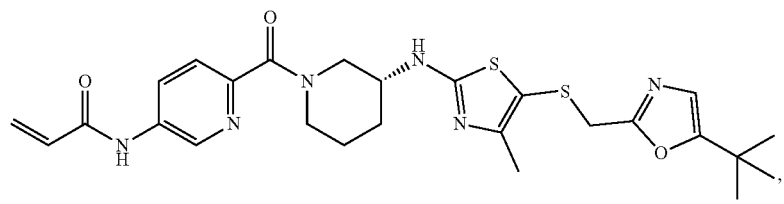
YLIU-01-099-1
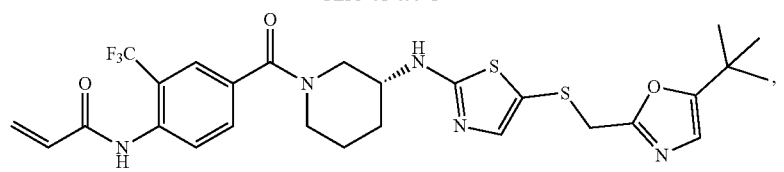
YLIU-01-121-1
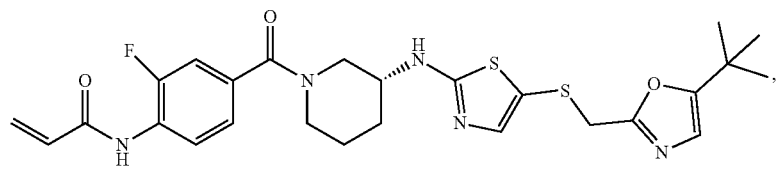
YLIU-01-123-1
or a pharmaceutically acceptable salt thereof.
14. The compound of claim 1, wherein the compound is of one of the following formulae:
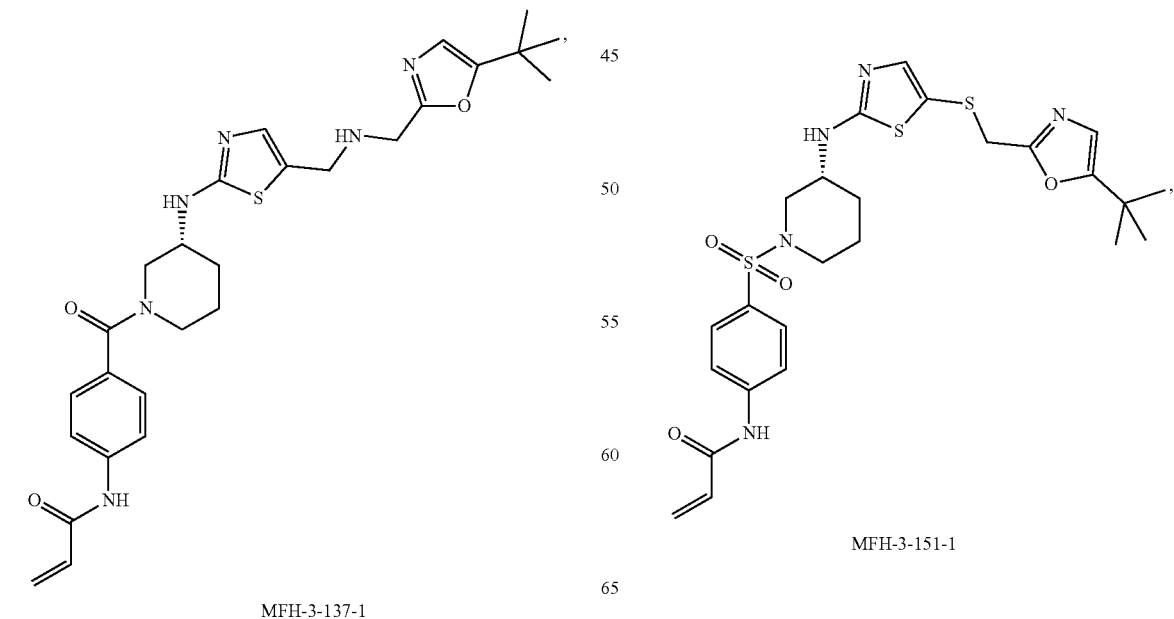
MFH-3-137-1
MFH-3-151-1

381
-continued

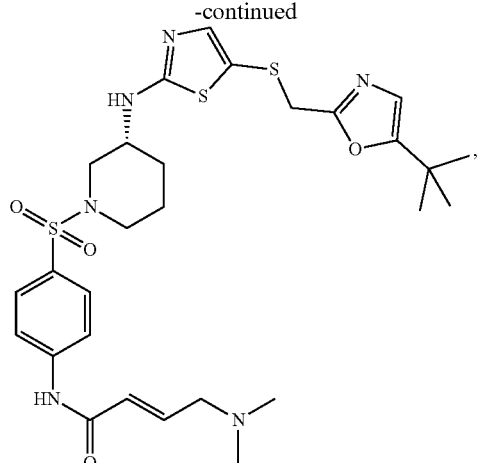

MFH-4-40-1

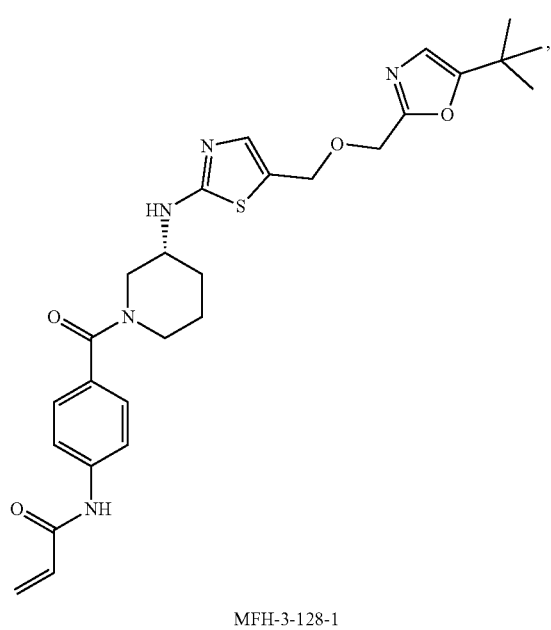

MFH-3-128-1

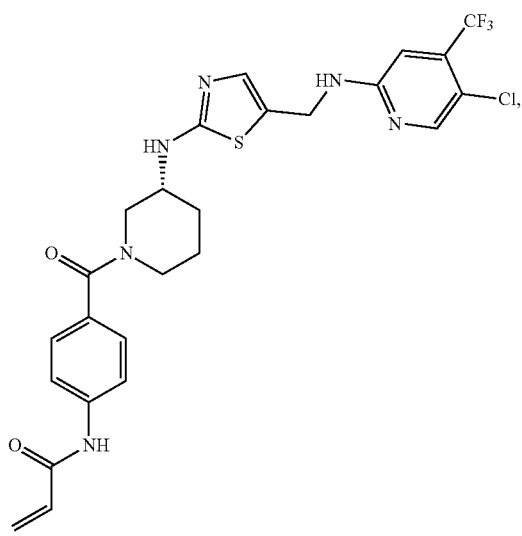

MFH-3-107-1

382
-continued

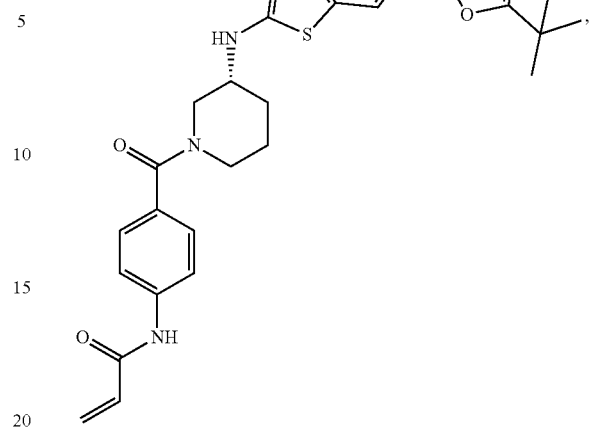

MFH-3-110-1

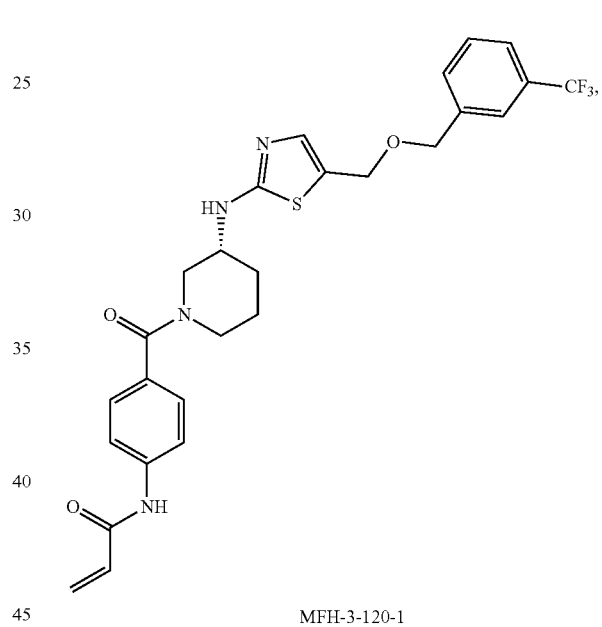

MFH-3-120-1 or a pharmaceutically acceptable salt thereof.

15. A pharmaceutical composition comprising a compound of claim 1, or a pharmaceutically acceptable salt thereof, and optionally a pharmaceutically acceptable excipient.

16. A method of treating a proliferative disease in a subject in need thereof, the method comprising administering to the subject a therapeutically effective amount of a compound of claim 1, or a pharmaceutically acceptable salt thereof.

17. A method of inhibiting the activity of a cyclin-dependent kinase (CDK) in a biological sample or subject, the method comprising administering to the subject or contacting the biological sample with a therapeutically effective amount of a compound of claim 1, or a pharmaceutically acceptable salt thereof.

18. The compound of claim 1, or a pharmaceutically acceptable salt thereof, wherein Ring A is of the formula:

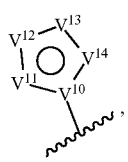

(x-i)

wherein:
each of $V^{10}$, $V^{11}$, $V^{12}$, $V^{13}$, and $V^{14}$ is independently be O, S, N, $NR^{A1}$, C, or $CR^{A2}$, as valency permits;
each instance of $R^{A1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, and a nitrogen protecting group;
each instance of $R^{A2}$ is independently selected from the group consisting of hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —$OR^{A2a}$, —$N(R^{A2a})_2$, and —$SR^{A2a}$; and
each occurrence of $R^{A2a}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two $R^{A2a}$ groups are joined to form a substituted or unsubstituted heterocyclic ring.

19. A compound of formula:

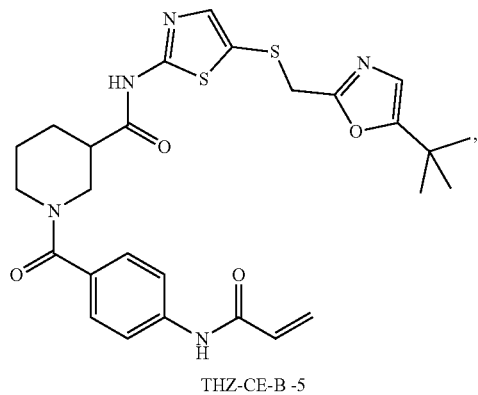

THZ-CE-B-5

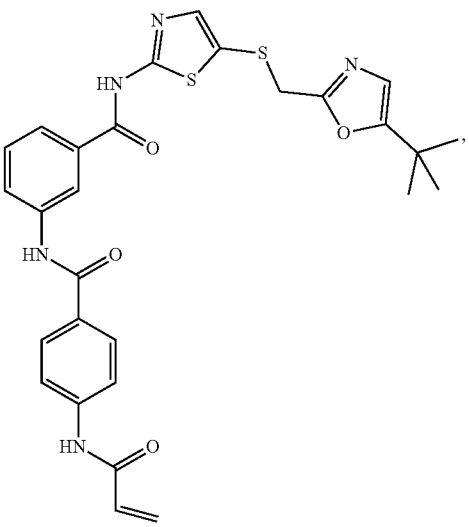

B9

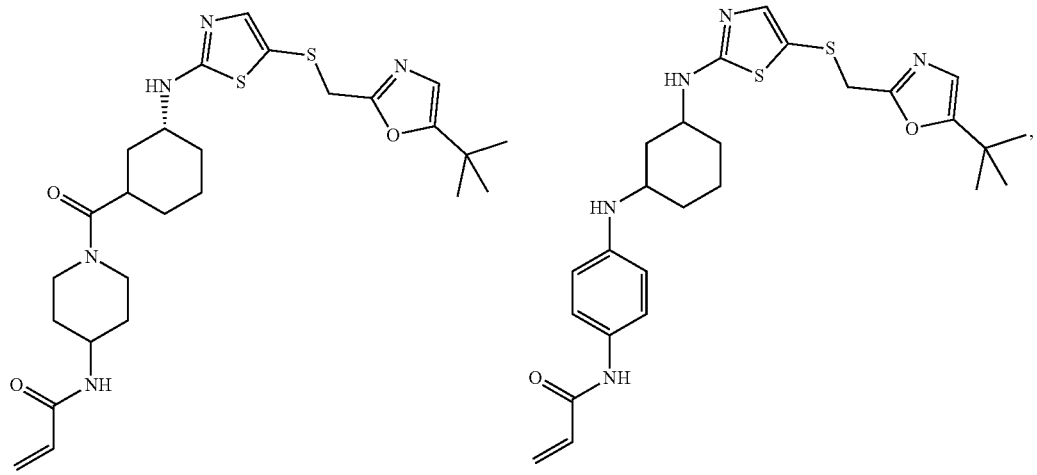

-continued
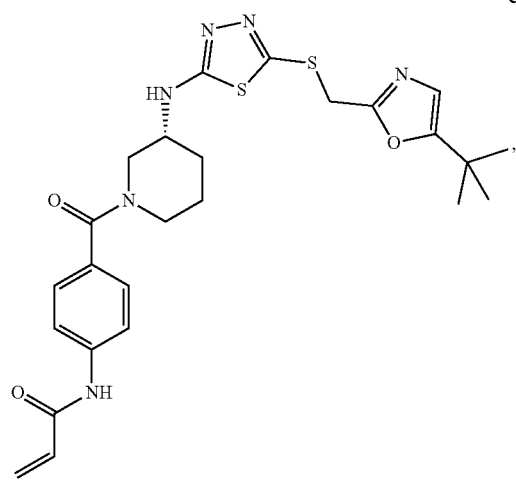
MFH-3-25-1
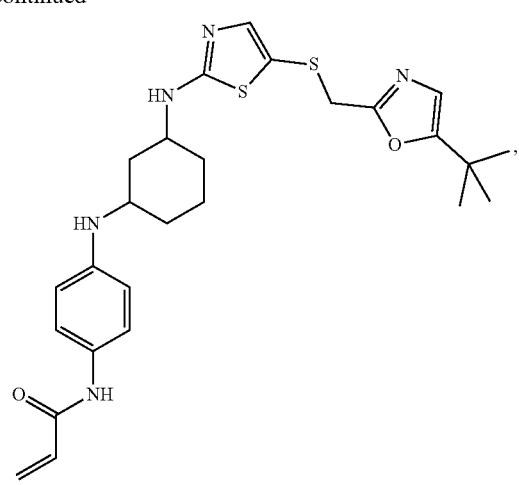
MFH-3-35-1
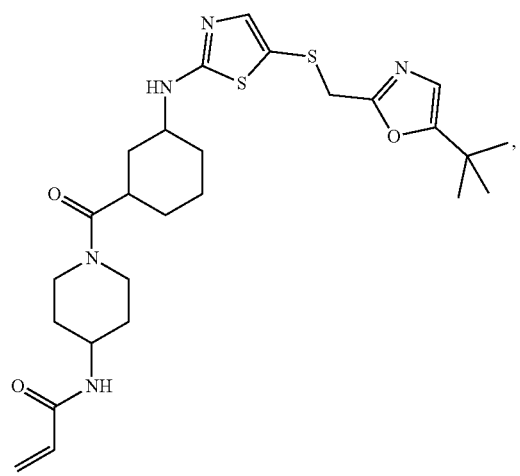
MFH-3-88-1
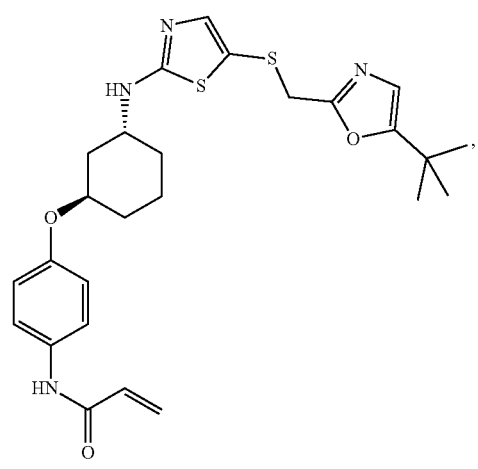
MFH-3-103-1
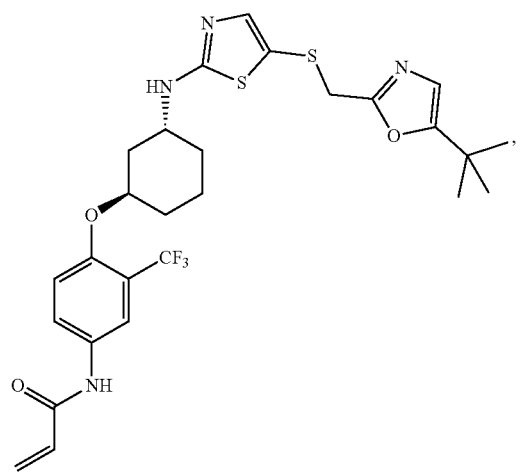
MFH-3-192-1
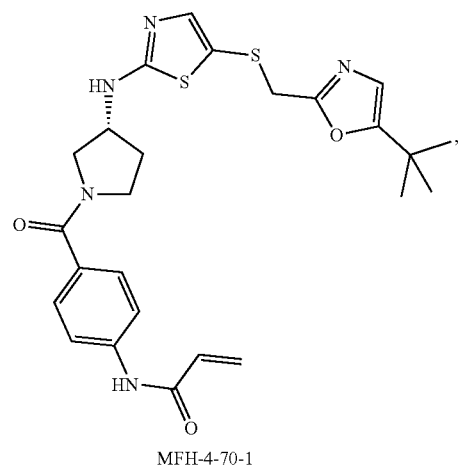
MFH-4-70-1

387
388
-continued
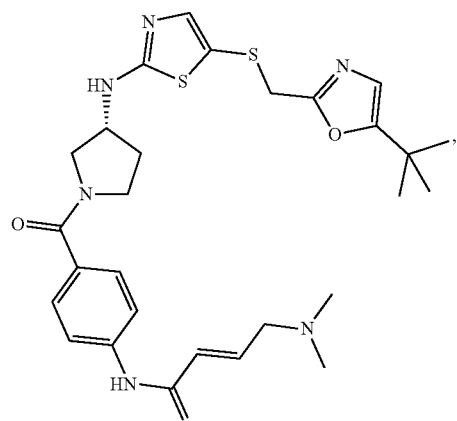
MFH-4-73-1
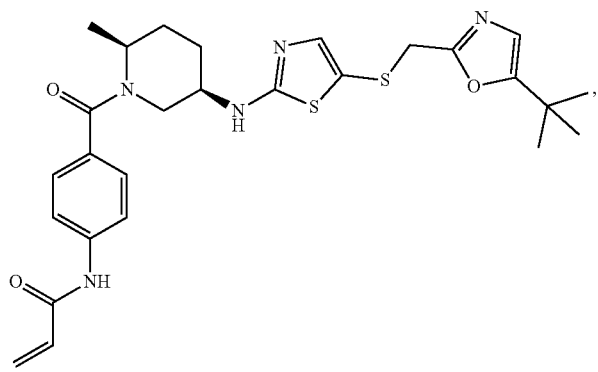
YLIU-01-156-1
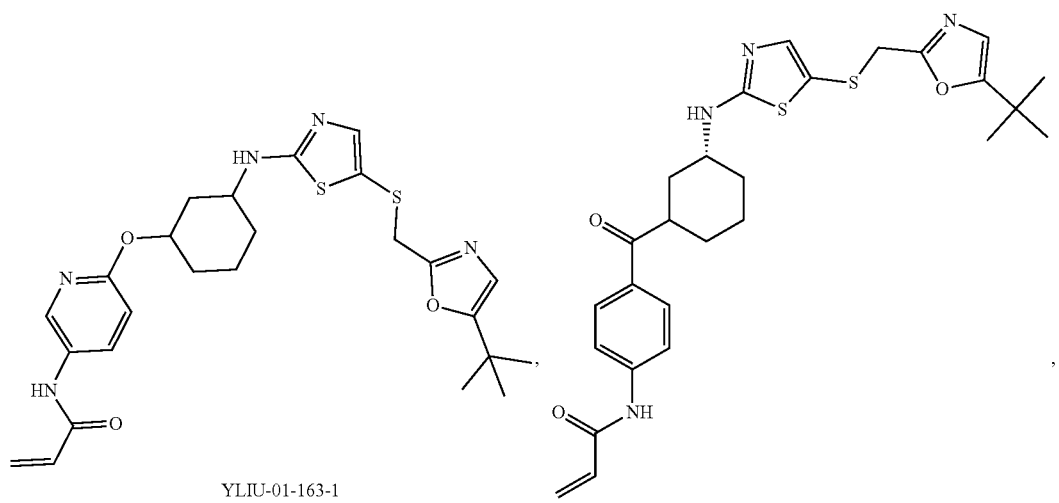
YLIU-01-163-1
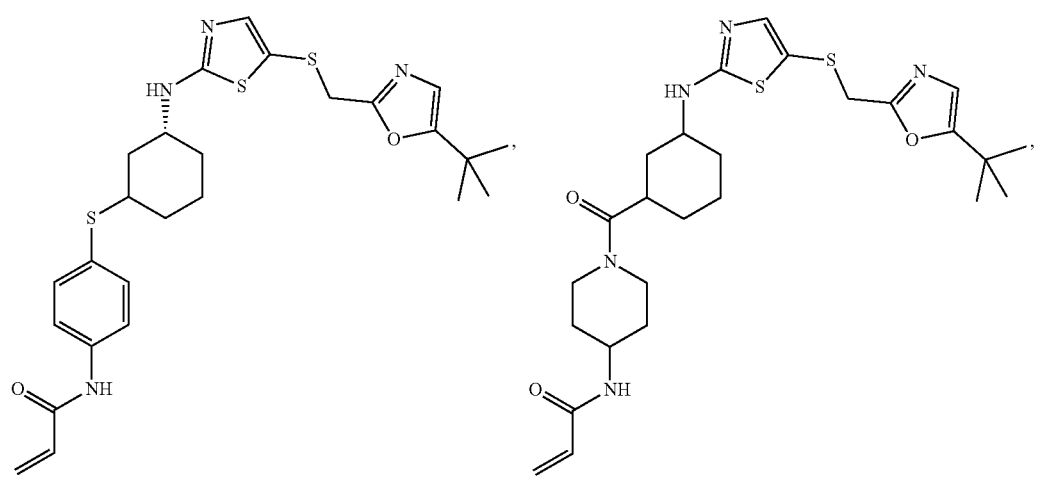
MFH-3-68-1

-continued
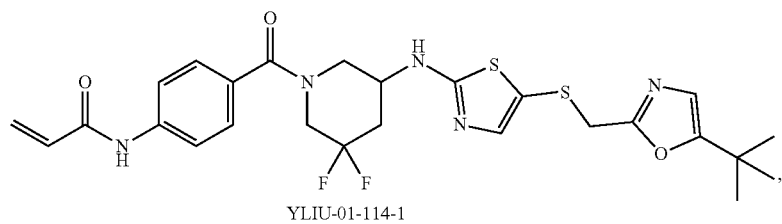
YLIU-01-114-1
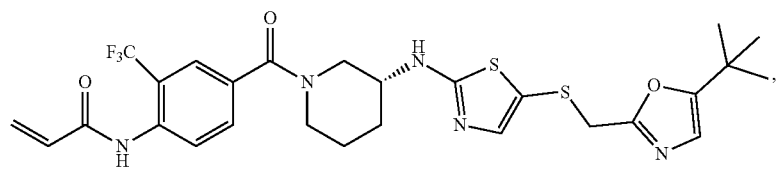
YLIU-01-121-1
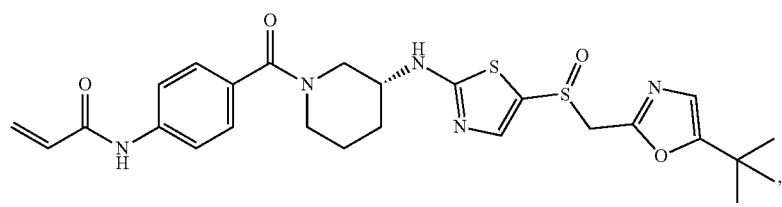
YLIU-01-007-1
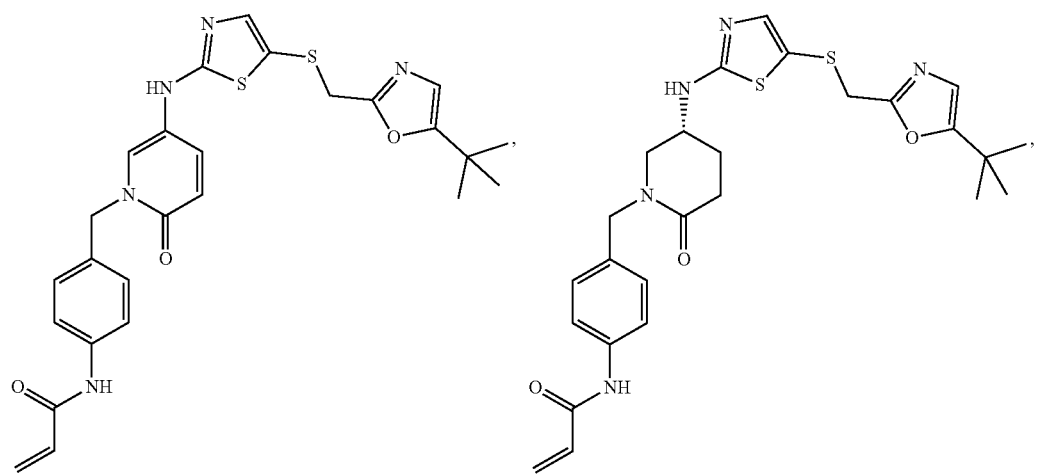

391
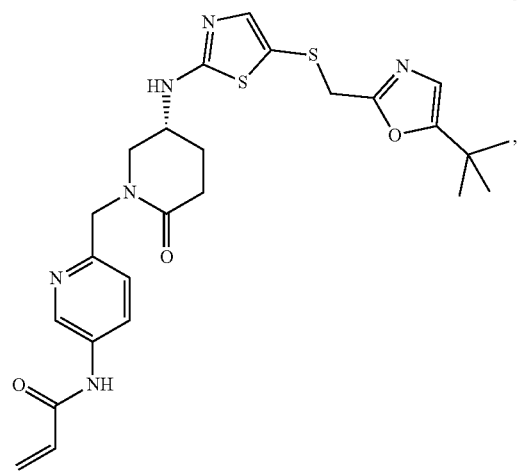
392
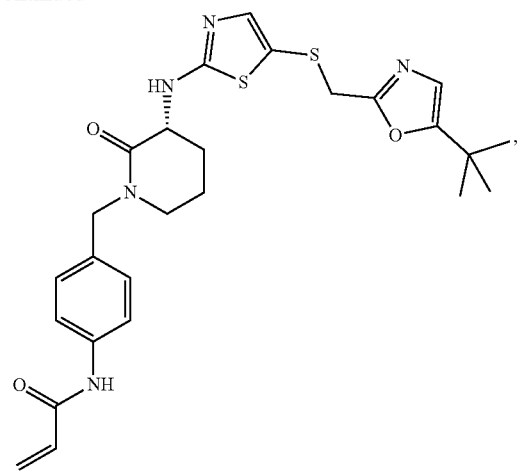
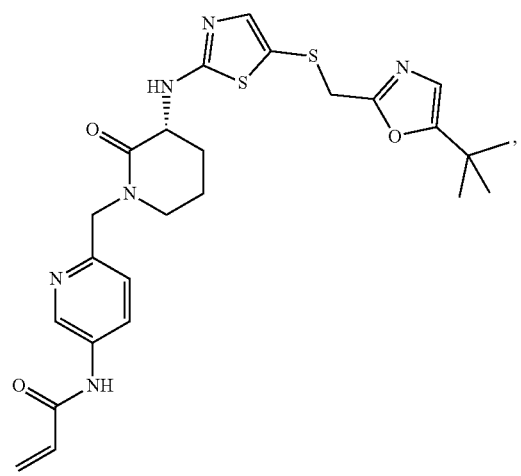
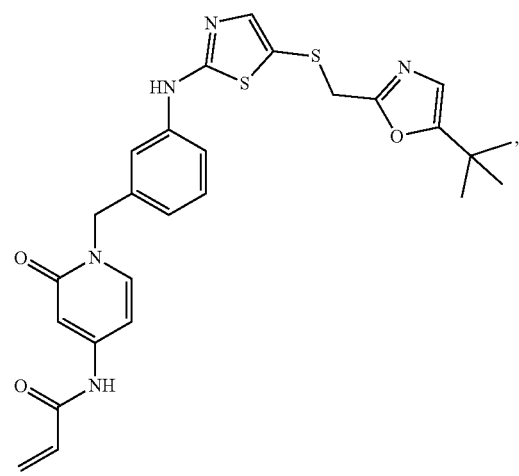
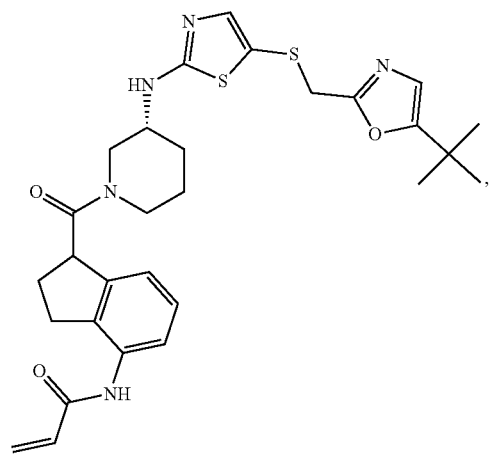
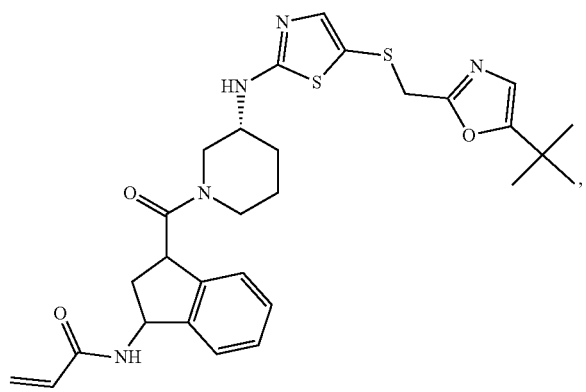

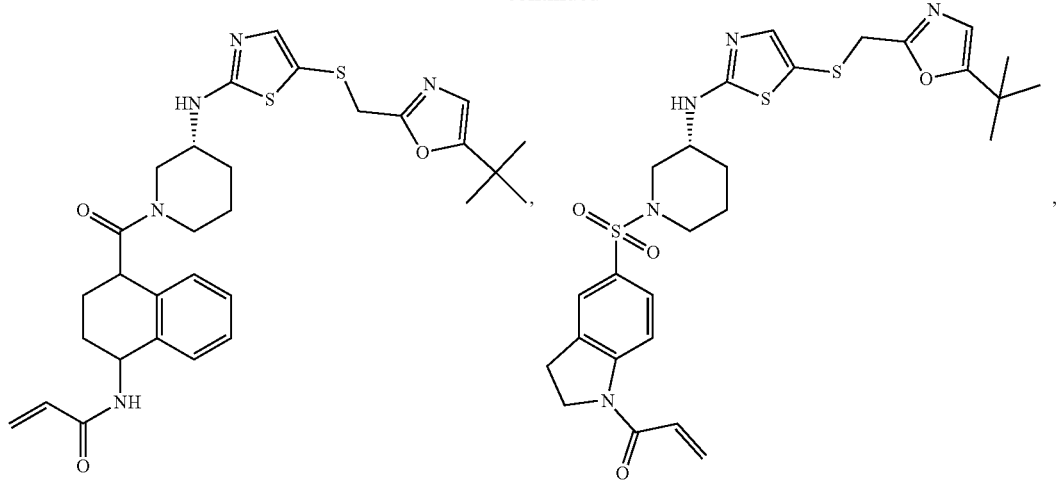

or a pharmaceutically acceptable salt thereof.

20. The compound of claim 1, or a pharmaceutically acceptable salt thereof, wherein Ring A is of the formula:

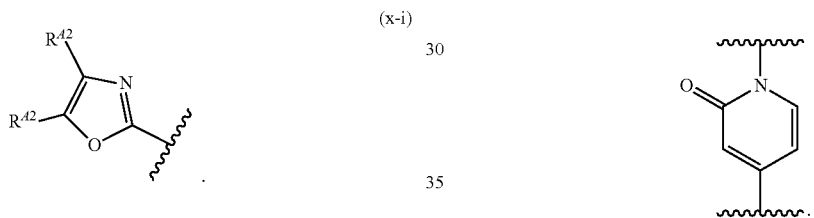

(x-i)

21. The compound of claim 1, or a pharmaceutically acceptable salt thereof, wherein Ring A is of the formula:

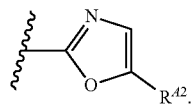

22. The compound of claim 1, or a pharmaceutically acceptable salt thereof, wherein Ring C is phenyl.

23. The compound of claim 1, or a pharmaceutically acceptable salt thereof, wherein Ring C is:

24. The compound of claim 1, or a pharmaceutically acceptable salt thereof, wherein $L^1$ is —C(=O)—.

25. The compound of claim 1, or a pharmaceutically acceptable salt thereof, wherein $L^2$ is —NR$^{L2}$—.

26. The compound of claim 1, or a pharmaceutically acceptable salt thereof, wherein $L^2$ is $^{lb}$—C(=O)NR$^{L2}$—$^{lm}$.

* * * * *

UNITED STATES PATENT AND TRADEMARK OFFICE
CERTIFICATE OF CORRECTION

| | |
|---|---|
| PATENT NO. | : 11,142,507 B2 |
| APPLICATION NO. | : 15/758982 |
| DATED | : October 12, 2021 |
| INVENTOR(S) | : Gray et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 440 days.

Signed and Sealed this
Eleventh Day of October, 2022

*Katherine Kelly Vidal*

Katherine Kelly Vidal
*Director of the United States Patent and Trademark Office*